(12) United States Patent
Kipnis et al.

(10) Patent No.: US 12,352,767 B2
(45) Date of Patent: Jul. 8, 2025

(54) METHOD OF TREATING COGNITIVE DECLINE ASSOCIATED WITH NEUROLOGICAL DISEASES BASED ON A DECREASE IN FLT4 EXPRESSION OR ACTIVITY

(71) Applicant: University of Virginia Patent Foundation, Charlottesville, VA (US)

(72) Inventors: Jonathan Kipnis, Charlottesville, VA (US); Sandro Da Mesquita, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1131 days.

(21) Appl. No.: 17/260,023

(22) PCT Filed: Jul. 15, 2019

(86) PCT No.: PCT/US2019/041882
§ 371 (c)(1),
(2) Date: Jan. 13, 2021

(87) PCT Pub. No.: WO2020/018461
PCT Pub. Date: Jan. 23, 2020

(65) Prior Publication Data
US 2021/0311076 A1     Oct. 7, 2021

Related U.S. Application Data

(60) Provisional application No. 62/865,035, filed on Jun. 21, 2019, provisional application No. 62/778,801, filed on Dec. 12, 2018, provisional application No. 62/698,859, filed on Jul. 16, 2018.

(51) Int. Cl.
*G01N 33/68* (2006.01)

(52) U.S. Cl.
CPC ..... *G01N 33/6896* (2013.01); *G01N 2500/10* (2013.01); *G01N 2800/2821* (2013.01); *G01N 2800/50* (2013.01); *G01N 2800/52* (2013.01); *G01N 2800/60* (2013.01)

(58) Field of Classification Search
CPC .......... G01N 33/6896; G01N 2500/10; G01N 2800/2821; G01N 2800/50; G01N 2800/52; G01N 2800/60
See application file for complete search history.

(56) References Cited

U.S. PATENT DOCUMENTS

| | | |
|---|---|---|
| 2013/0190388 A1 | 7/2013 | Bastiani et al. |
| 2016/0011213 A1 | 1/2016 | Tofaris |
| 2016/0090599 A1 | 3/2016 | Collard et al. |

FOREIGN PATENT DOCUMENTS

| | | |
|---|---|---|
| WO | 2014/059052 A1 | 4/2014 |
| WO | 2015/035190 A1 | 3/2015 |
| WO | 2015/143062 A1 | 9/2015 |
| WO | 2017/210343 A1 | 12/2017 |

OTHER PUBLICATIONS

Ding X-B, et al. (Mar. 2021) Nat Med. 27(3):411-418. (doi: 10.1038/s41591-020-01198-1. Epub Jan. 18, 2021).*
Chaudhry DA and Dore S (Mar. 2009) American Journal of Alzheimer's Disease & Other Dementias. 24(1):46-51.*
Stopa et al.(2018) Fluids Barriers CNS. 15:18. 7 pages. (https://doi.org/10.1186/s12987-018-0102-9).*
https://presse.inserm.fr/en/vegf-c-an-indispensable-growth-factor-for-producing-new-neurons/55765/.*
Cruz-Monteagudo et al., Efficient and biologically relevant consensus strategy for Parkinson's disease gene prioritization. BMC Med Genomics. Mar. 9, 2016;9:1-25.
Jacobs et al., Identification of Dlk1, Ptpru and Klhl1 as novel Nurr1 target genes in meso-diencephalic dopamine neurons. Development. Jul. 2009;136(14):2363-73.
International Search Report and Written Opinion for Application No. PCT/US2019/041882, dated Nov. 27, 2019, 26 pages.

* cited by examiner

*Primary Examiner* — Robert S Landsman
(74) *Attorney, Agent, or Firm* — McCarter & English, LLP; Marcie B. Clarke, Esq.

(57) ABSTRACT

In some embodiments herein, methods, compositions, and uses for countering the effects of aberrant meningeal lymphatic drainage and/or modulating lymphatic vessels of the central nervous system are described. In some embodiments, methods, compositions, or uses for treating, preventing, or ameliorating symptoms of a neurodegenerative disease associated with aberrant meningeal lymphatic drainage are described. Modulating lymphatic vessels, or countering the effects of aberrant meningeal lymphatic drainage, in accordance with some embodiments, are used to diagnose, treat, prevent, or ameliorate symptoms of neurodegenerative diseases such as Alzheimer's disease (AD) and dementia. Methods of diagnosing and monitoring the progression of neurological diseases are also provided.

13 Claims, 78 Drawing Sheets

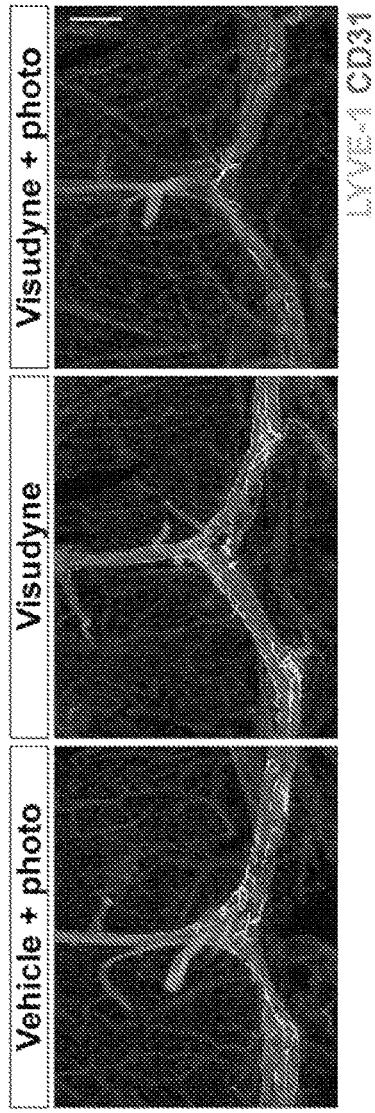
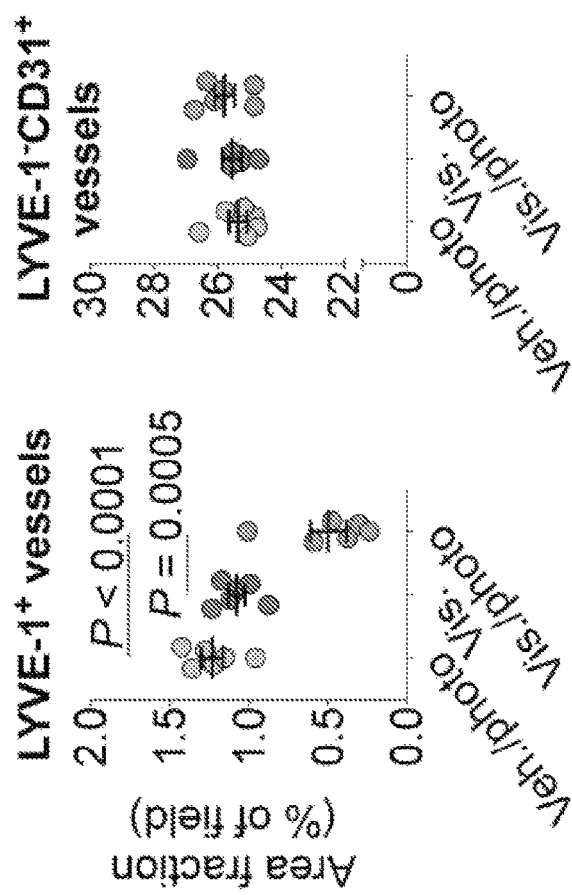
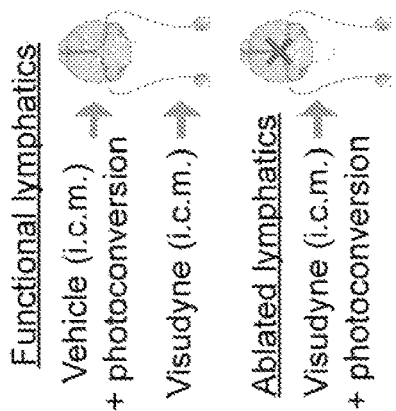

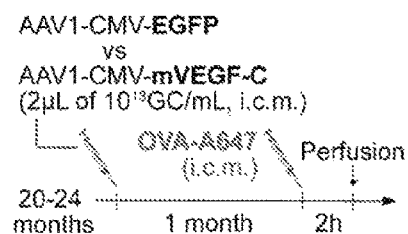
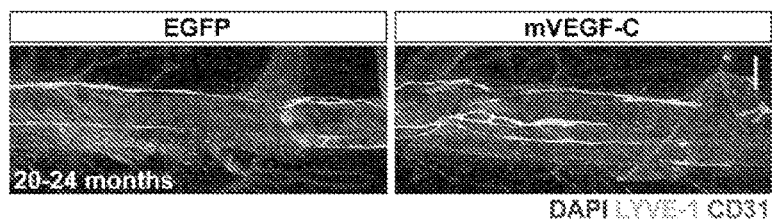
FIG. 2E  FIG. 2F
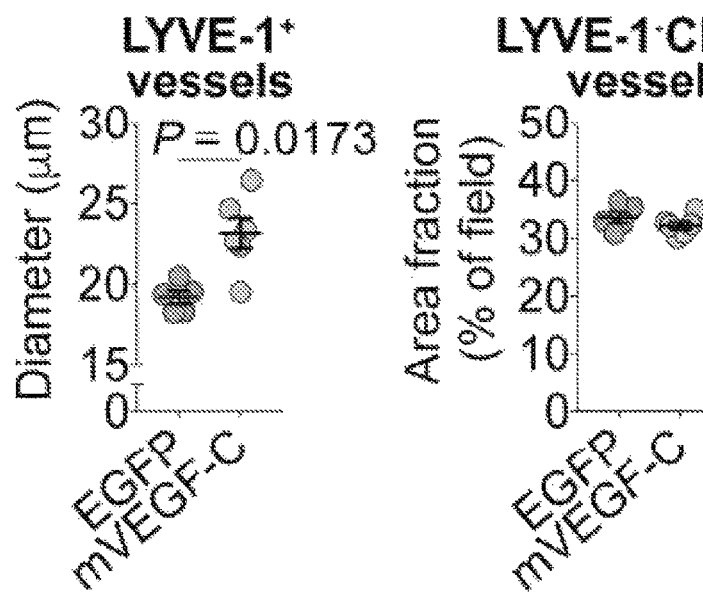
FIG. 2G  FIG. 2H

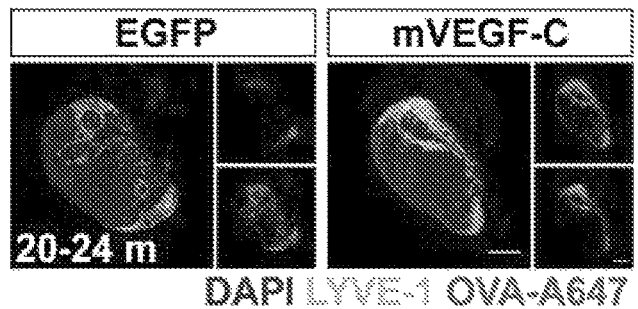
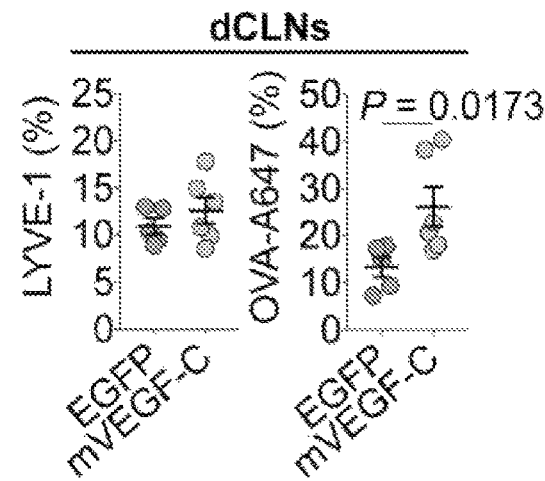
FIG. 2I  FIG. 2J
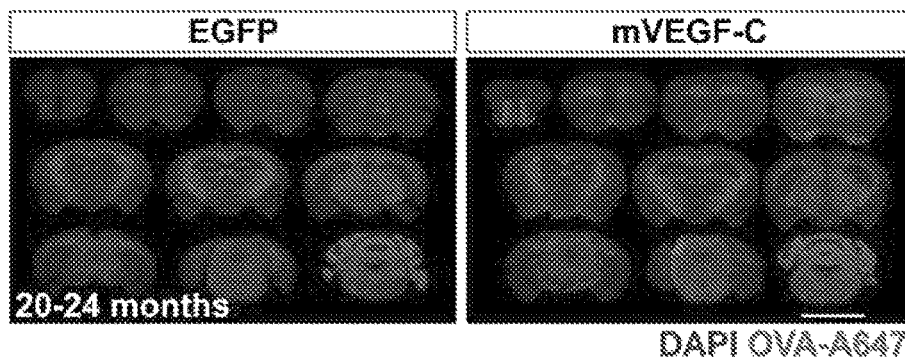
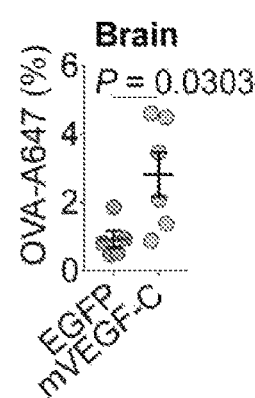
FIG. 2K  FIG. 2L

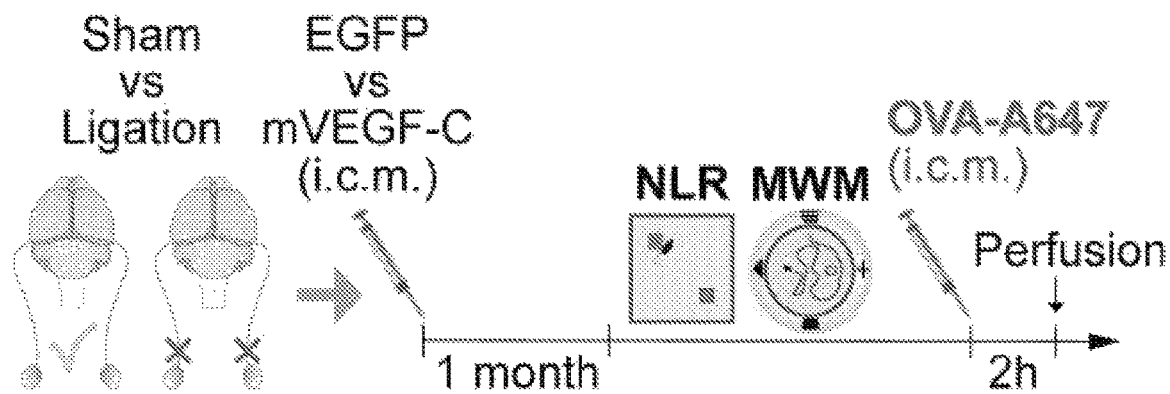
FIG. 2M
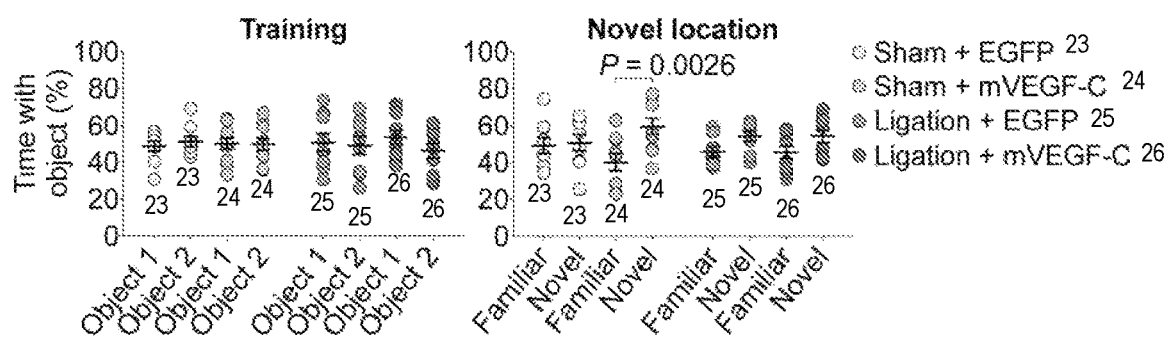
FIG. 2N  FIG. 2O

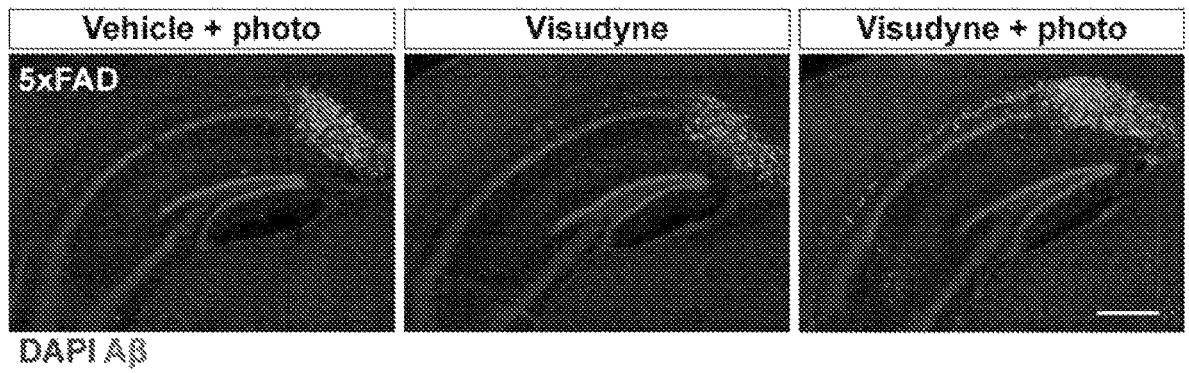
FIG. 3D
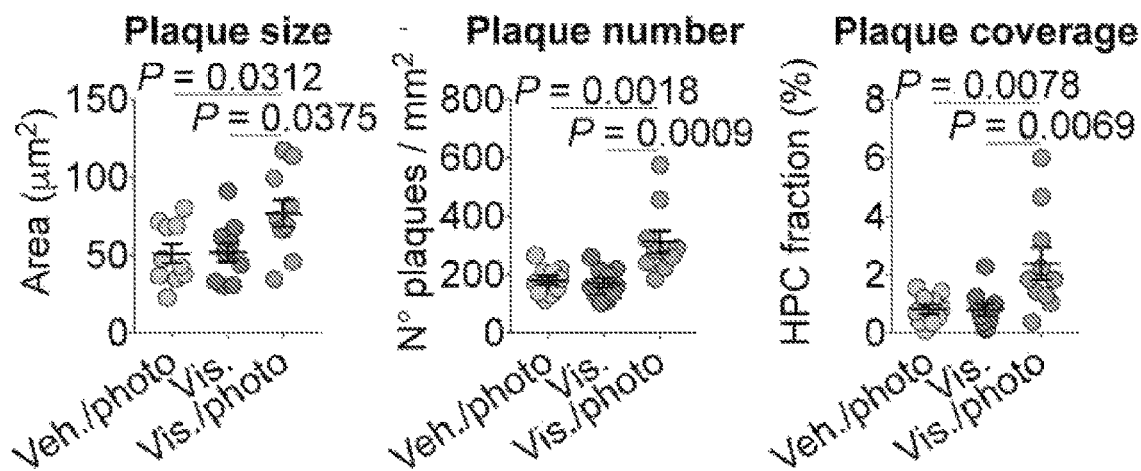
FIG. 3E  FIG. 3F  FIG. 3G

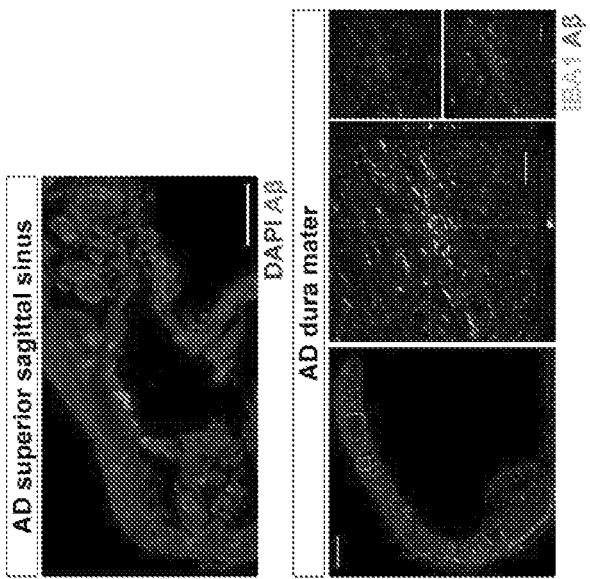
FIG. 3H  FIG. 3I  FIG. 3J
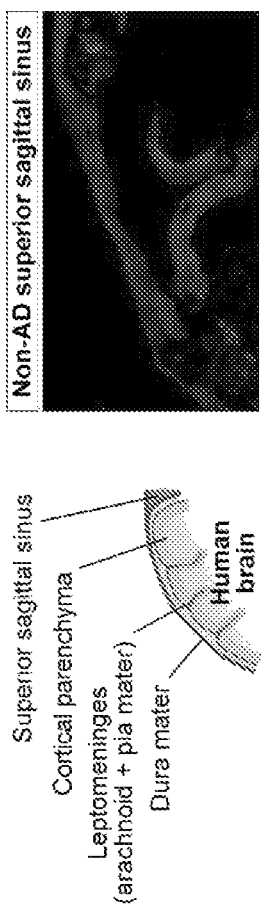
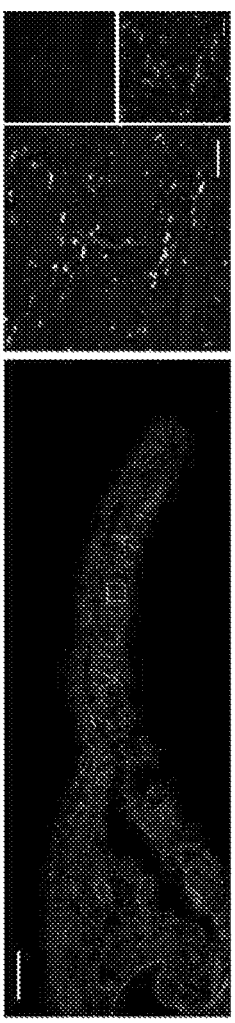
FIG. 3K  FIG. 3L

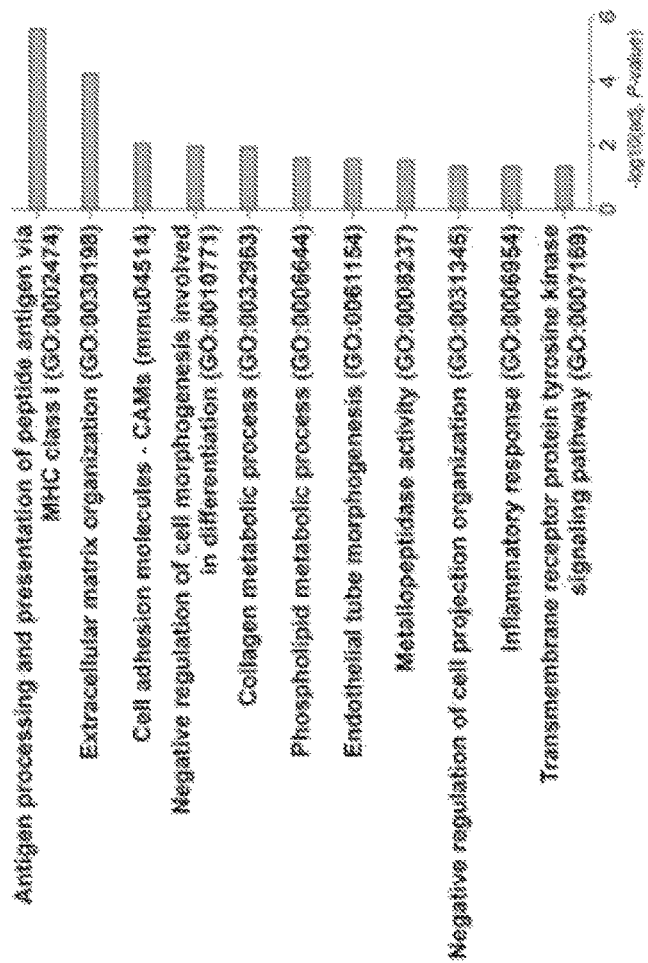
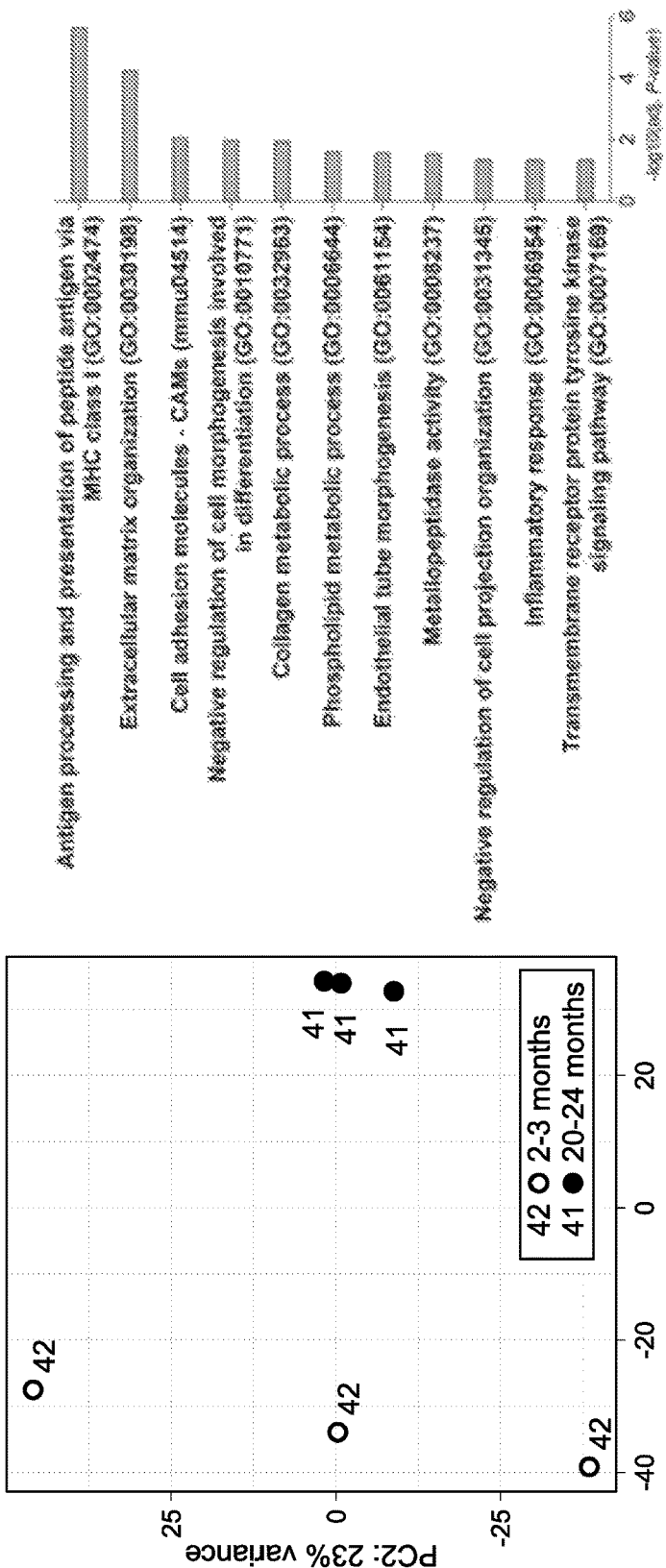
FIG. 4B
FIG. 4A

Top 20 hit genes predicted to explain changes in transcriptome of meningeal LECs from old mice

| # | name | description |
|---|---|---|
| 1 | IFNB1 | Interferons, interferon, beta 1, fibroblast |
| 2 | CD40 | Tumour necrosis factor (TNF) receptor family, CD40 molecule, TNF receptor superfamily member 5 |
| 3 | IFNG | Interferons, interferon, gamma |
| 4 | LYN | Src family, v-yes-1 Yamaguchi sarcoma viral related oncogene homolog |
| 5 | IMPDH2 | Oxidoreductases, IMP (inosine 5'-monophosphate) dehydrogenase 2 |
| 6 | NUP88 | nucleoporin 88kDa |
| 7 | ADA | Adenosine turnover, adenosine deaminase |
| 8 | IRF2 | interferon regulatory factor 2 |
| 9 | ZNF114 | Zinc fingers, C2H2-type, zinc finger protein 114 |
| 10 | TCF7L2 | transcription factor 7-like 2 (T-cell specific, HMG-box) |
| 11 | DYRK2 | Dyrk2 subfamily, dual-specificity tyrosine-(Y)-phosphorylation regulated kinase 2 |
| 12 | TACC3 | transforming, acidic coiled-coil containing protein 3 |
| 13 | GPR87 | GPCR/ Class A: Orphans, G protein-coupled receptor 87 |
| 14 | ALDH3B1 | Aldehyde dehydrogenases, aldehyde dehydrogenase 3 family, member B1 |
| 15 | ARPC1B | Actin related protein 2/3 complex subunits, actin related protein 2/3 complex, subunit 1B, 41kDa |
| 16 | RELB | NFkappaB transcription factor family, v-rel reticuloendotheliosis viral oncogene homolog B |
| 17 | TMEM154 | transmembrane protein 154 |
| 18 | SPDEF | ETS Transcription Factors, SAM pointed domain containing ets transcription factor |
| 19 | SMAD7 | SMADs, SMAD family member 7 |
| 20 | MTFR1 | mitochondrial fission regulator 1 |

FIG. 4C

Top 10 compounds predicted to revert gene signature in meningeal LECs of old mice

| Compound | Cell line | Dose (μM) | Time (h) | Regulated molecules/genes (up↑, down↓) |
|---|---|---|---|---|
| (R)-Haraclenol | A375 | 10 | 6 | TP53BP1↓, RB1↓, HPRT1↓, STAT3↓, HMGA2↓, NET1↓, TERC↓, AATF↓, MIR210↓, IKBKB↑, NOTCH3↓, PPARGC1A↓, E2F8↓, GTF2I↓, IL17RC↓, ELAVL1↓, CHEK2↓, LMO3↓, ZXDC↓ |
| Pifithrin-beta, p53 inhibitor | A375 | 10 | 6 | RPS24↑, HNRNPU-AS1↑, PDE1C↓, HNF4A↓, PINK1↓, AKAP12↓, HSF1↓, NDEL1↓, RB1↓, IL1RN↓, MYB↓, AKT1↓, PRKCZ↓, ATF6↓, CLPP↓, MYB↓, RAP1A↓, FOXA1↓, GOLGA8A↑ |
| Iocetamic acid (Cholebrine) | PC3 | 10 | 24 | RPS6KA3↓, MALAT1↑, MYC↓, EWSR1↓, FLI1↓, GRN↓, SOX3↓, PDE1C↓, SRBB2↓, CROSHA↓, NOTCH3↓, CLDN2↓, MIR210↓, NFE2L2↓, EPCAM↑ |
| Indolphenanthridine | VCAP | 10 | 6 | MYC↓, SYK↓, YY2↓, FLI1↓, EWSR1↓, YY1↑, IRF1↑, SMC3↓ |
| NF-κB Activation Inhibitor II (JSH-23) | NCIH596 | 6 | 6 | MIR221↑, TFAP2C↓, EWSR1↓, IRF1↑, FLI1↓, CXCL5↓, ATM↓, TGFBR2↓, ATF6↓, MAPK14↓, VAMP7↓, CHEK2↓, PARK2↓, CHEK1↓, CLDN2↓, PIK3CB↑ |
| Noscapine KCR-24 (Terbanol) | HCC515 | 10 | 6 | MIR210↑, MALAT1↑, HSF1↓, NFE2L2↓, NET1↓, PDE1C↓, MET↓, FOXP1↓, TNIK↓, TP53INP2↑, ZNF322↓, ERBB2↓, BRAF↓, MIR29A↓, SNCA↓, HIRA↓, TP53↓ |
| Secnidazole (Flagentyl) | VCAP | 10 | 24 | NOTCH3↑, RPS24↑, NET1↓, SYNCRIP↑, ZNF750↓, FGFR3↓, HNF4A↓, ZXDC↓, TMEM173↓, IRF1↑, RELA↓, CBFB↓, EPHA4↓, TRIM33↓, MAPK14↓ |
| C₁₇H₁₆BrN₃O₂ | PHH | 10 | 24 | PARK7↓, ATM↓, SMAD3↓, TREM2↓, CSTB↓, RBBP8↓, YY2↓, CEBPA↓, IL1B↓, GFAP↑, DROSHA↓, PARP3↓, RB1↓, IGF1↓, TGM2↓, PTEN↓, PRMT8↑ |
| Piretanide (Tauliz) | A549 | 10 | 24 | SYK↓, RPS24↑, HNRNPU-AS1↑, BRMS1↓, NR3C3↓, HSF1↓, GRN↓, PIK3CA↓, MITOH↓, XLPS↓, SOX2↓, SOD2↓ |
| Ciprofibrate (Lipanor) | PC3 | 10 | 24 | CHEK2↓, ATM↓, CHEK1↓, ATR↓, ATM↓, NOTCH3↓, SRBB2↓, SYK↓, MAP3K7↓, PRNP↓, PARK2↓, PIK3CB↑, ETS1↓, MYC↑, EMX2↓, NFE2L2↓, HSF1↓ |

FIG. 4D

FIG. 5I
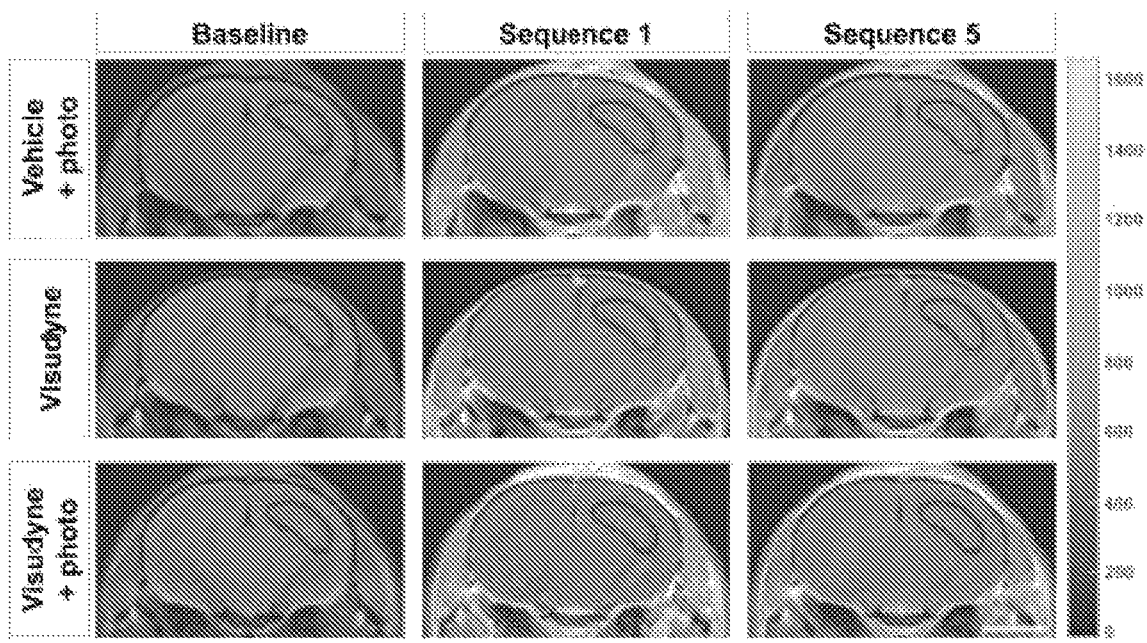
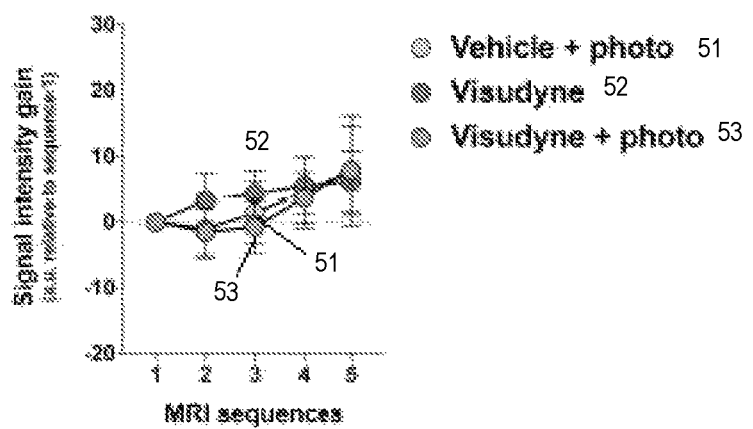
FIG. 5J

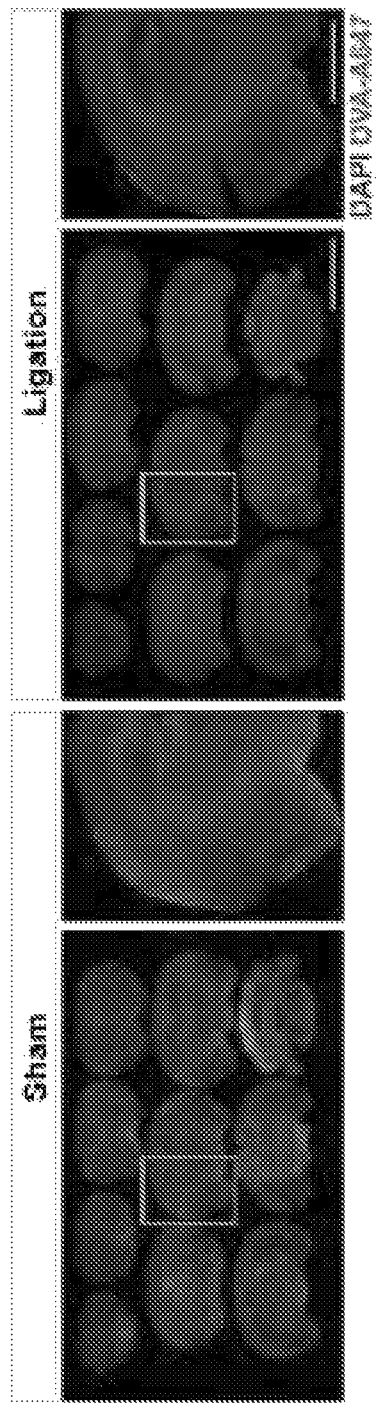
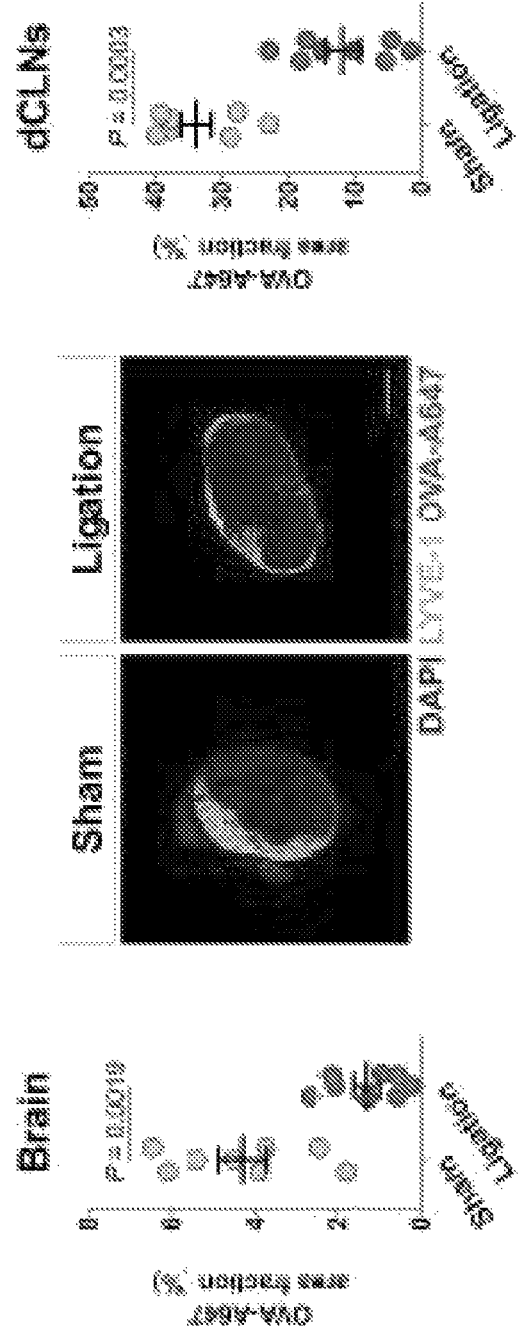
FIG. 7A
FIG. 7B
FIG. 7C
FIG. 7D

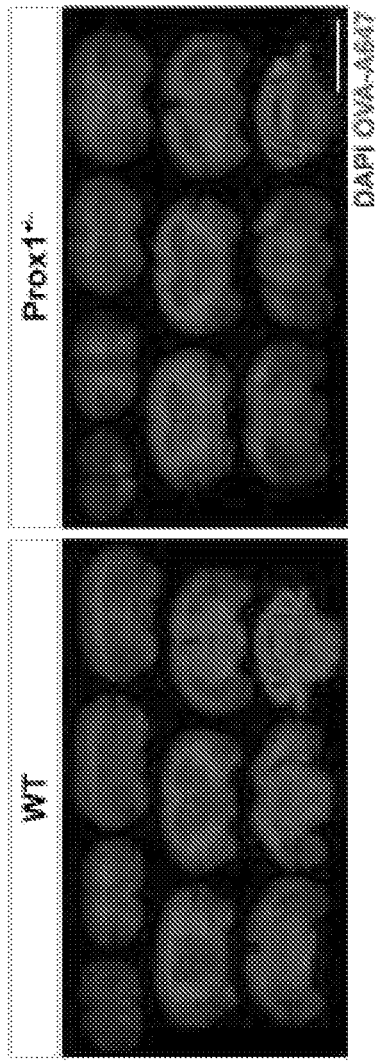
FIG. 7F
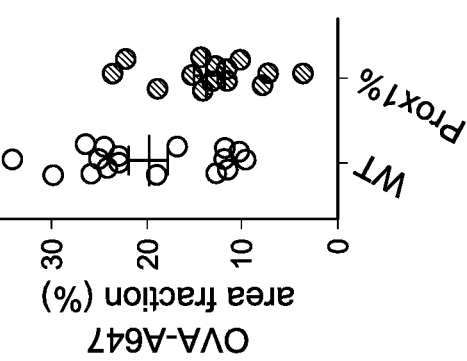
FIG. 7I
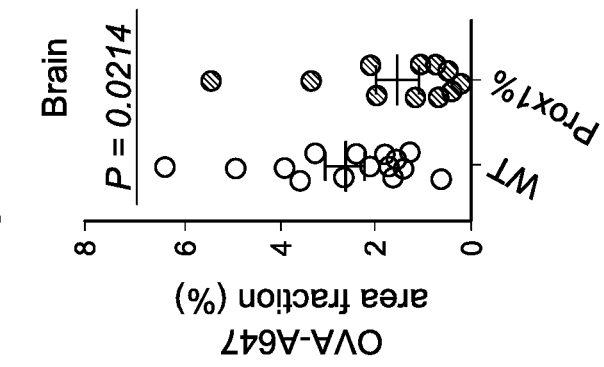
FIG. 7H
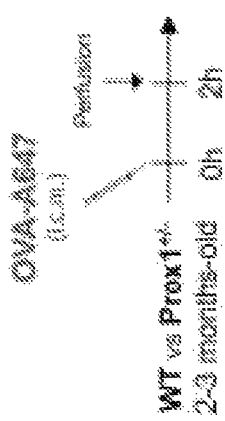
FIG. 7E
FIG. 7G

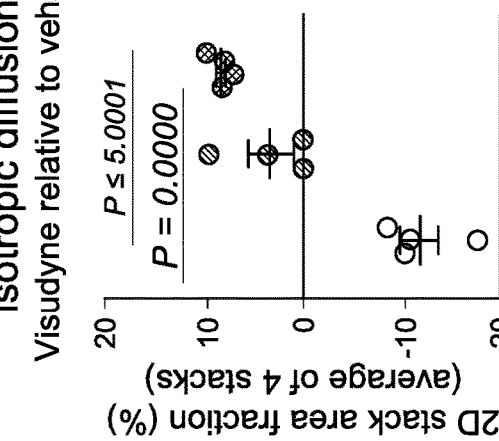
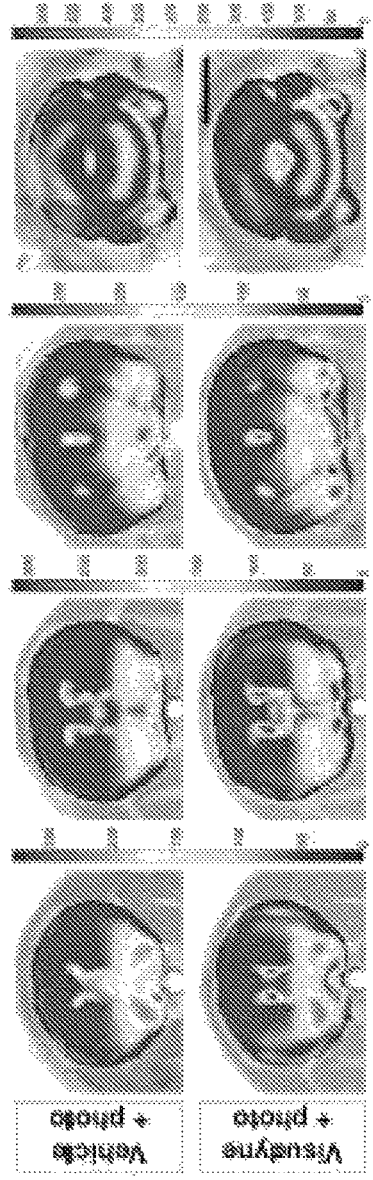
FIG. 7N
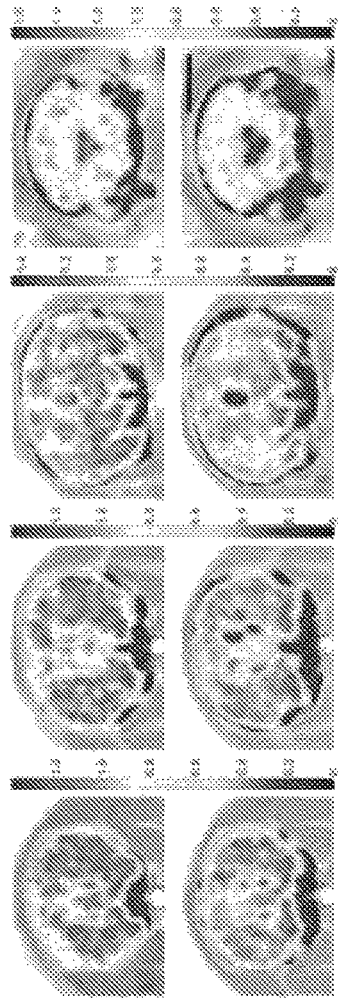
FIG. 7O
FIG. 7P

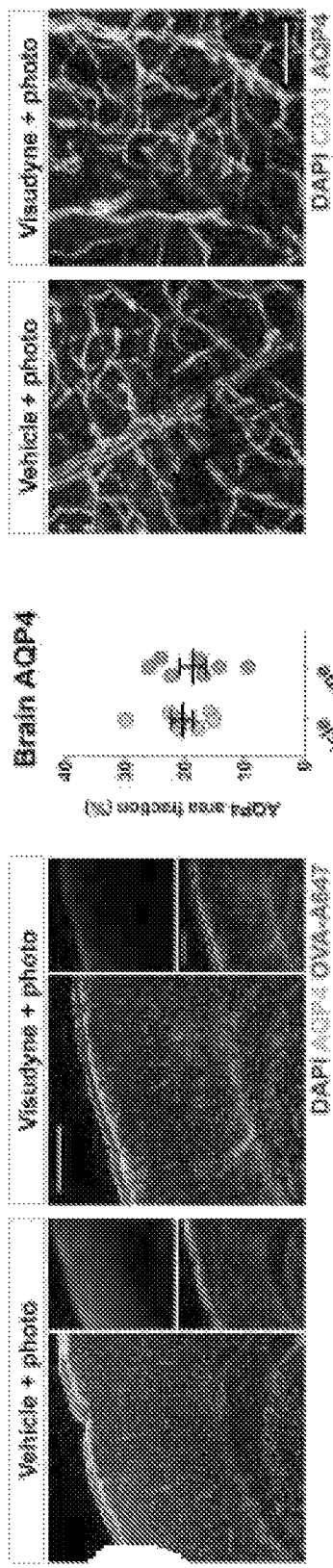
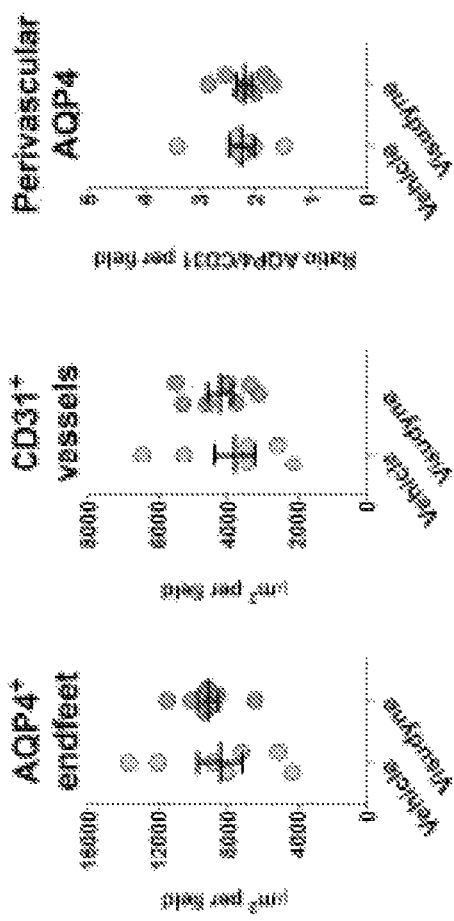
FIG. 7Q
FIG. 7R
FIG. 7S
FIG. 7T
FIG. 7U
FIG. 7V

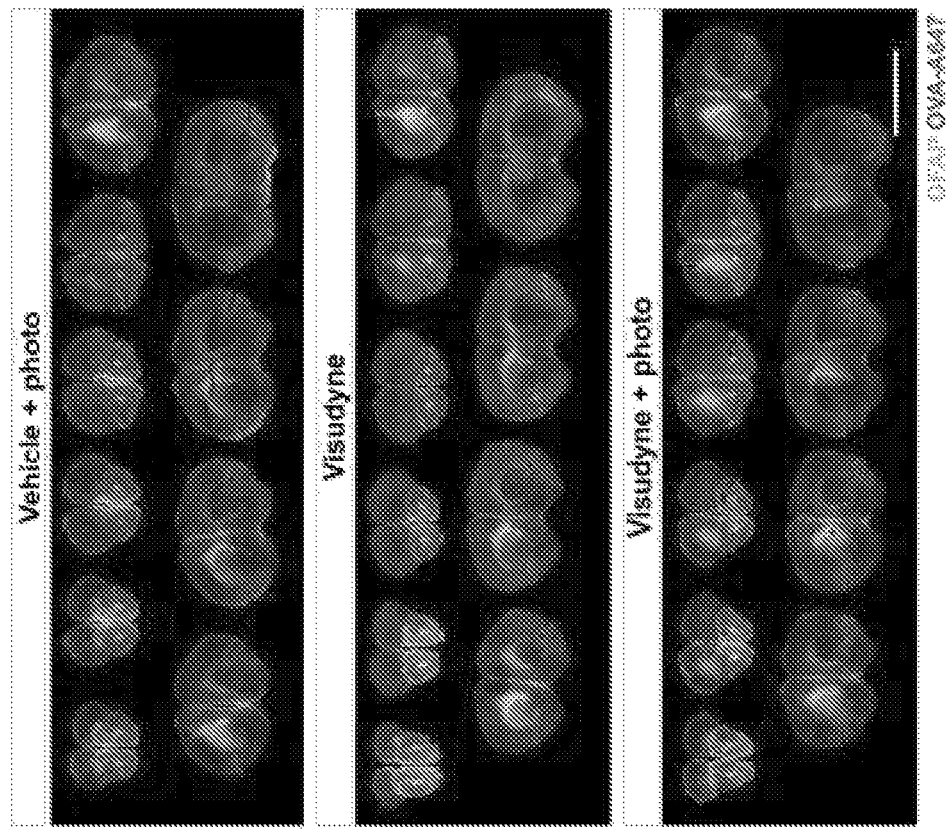
FIG. 8B
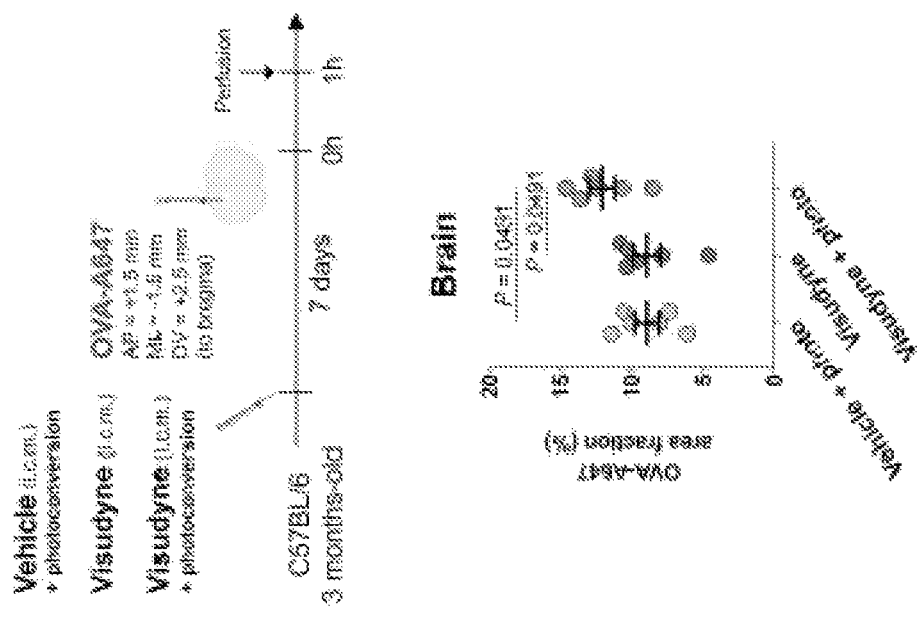
FIG. 8A
FIG. 8C

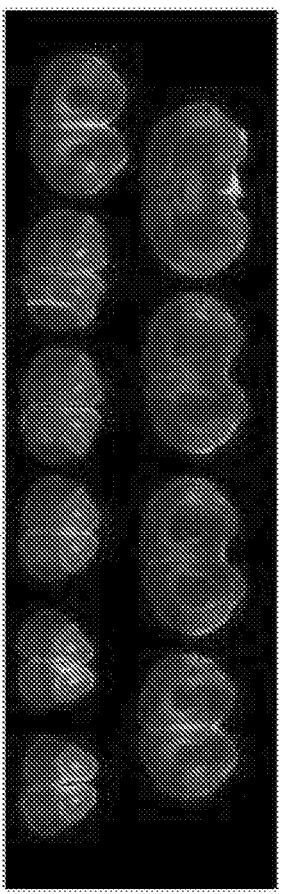
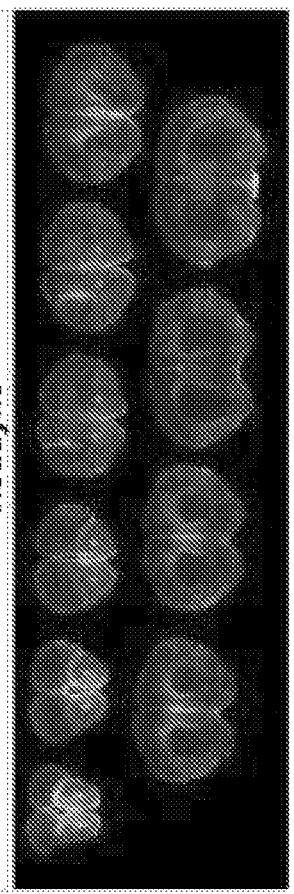
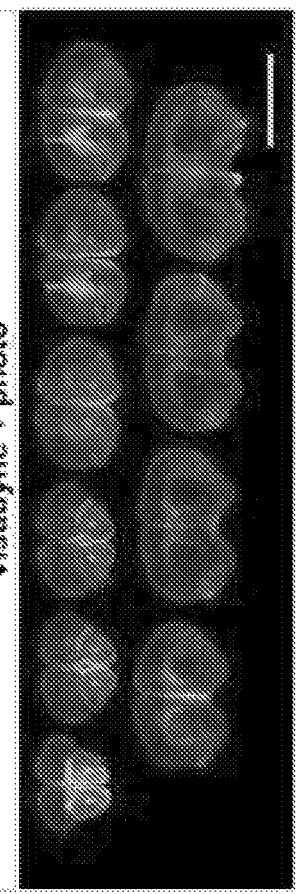
FIG. 8E
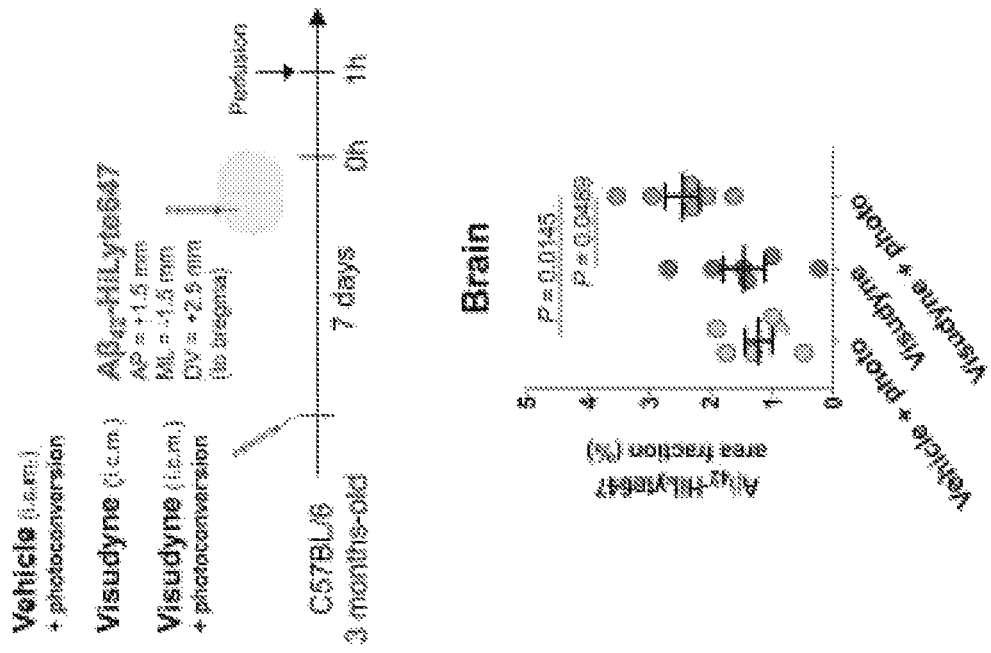
FIG. 8D
FIG. 8F

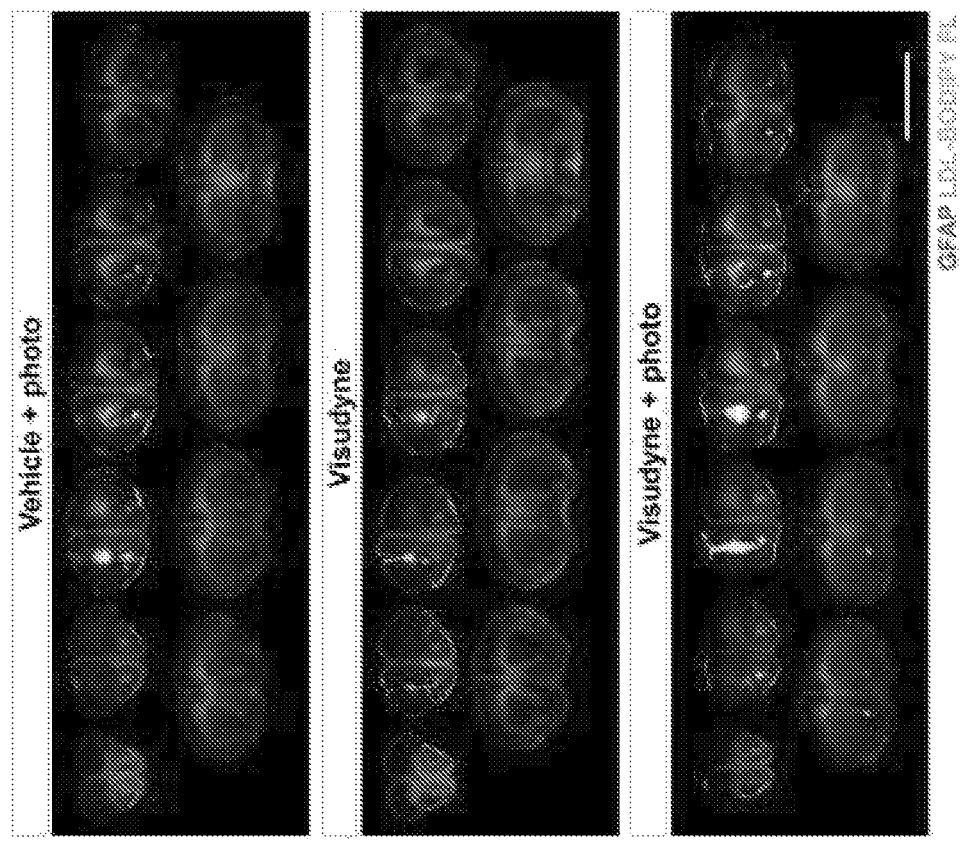
FIG. 8G
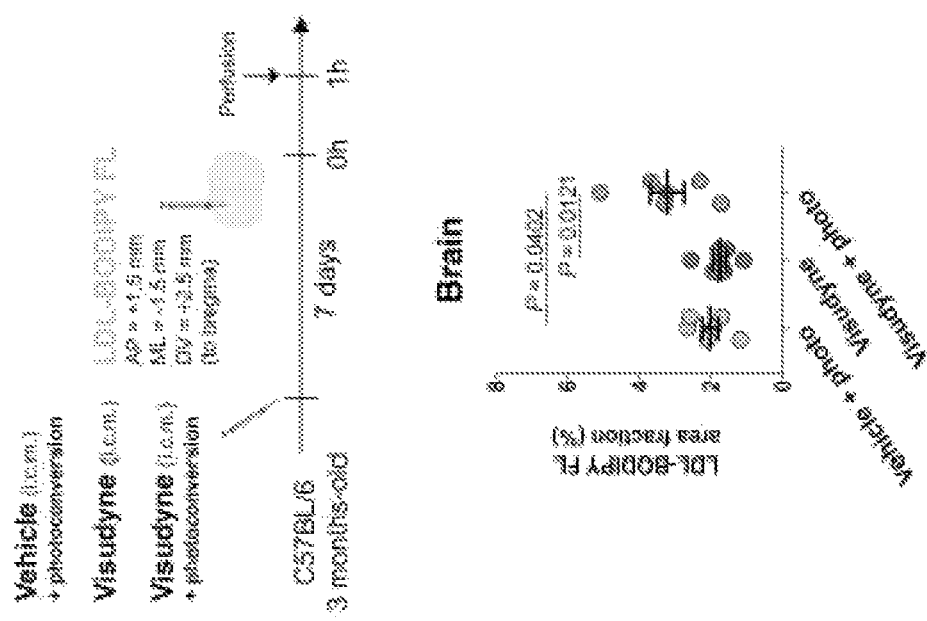
FIG. 8H
FIG. 8I

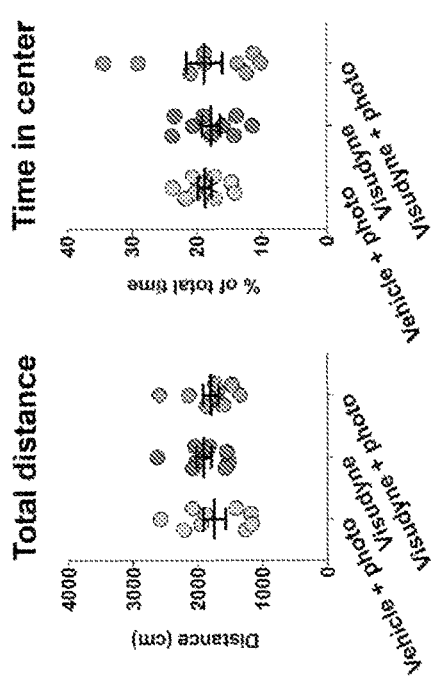
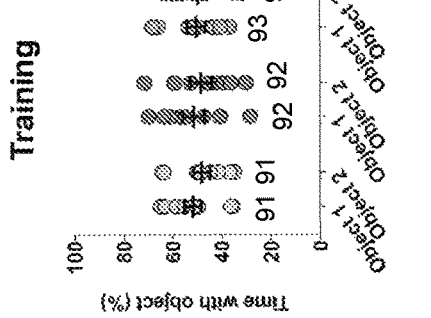
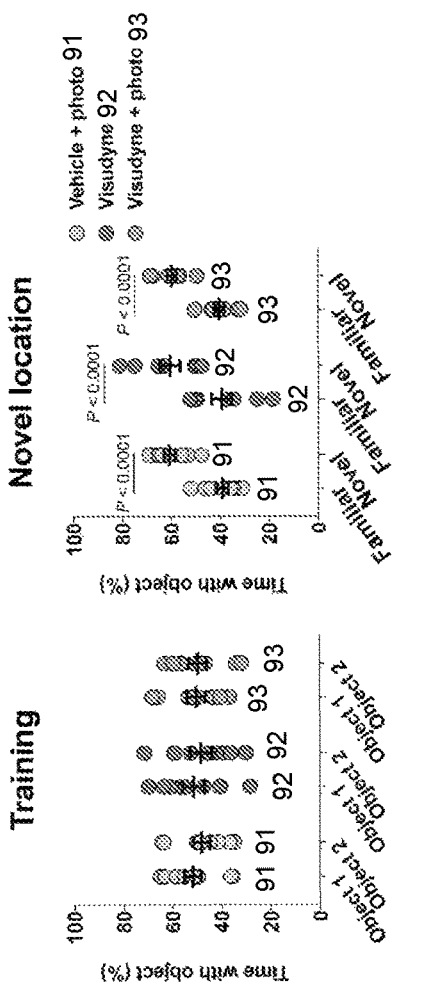
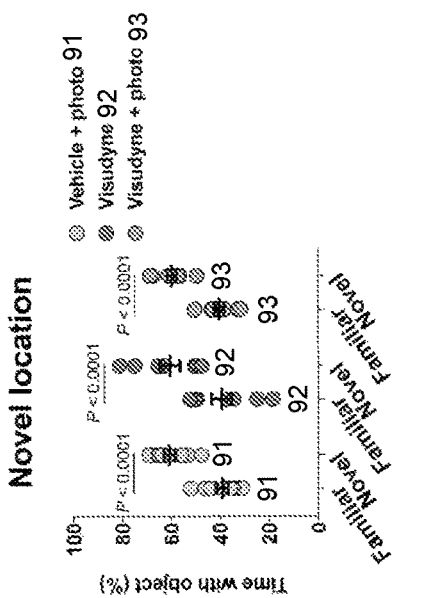
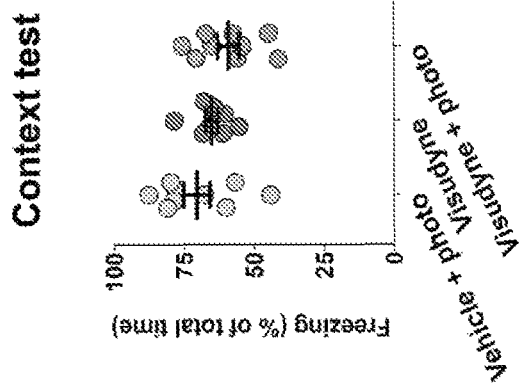
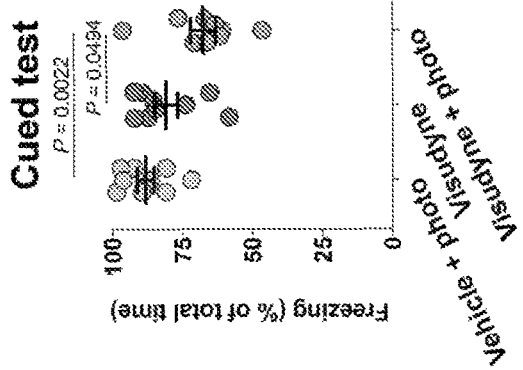
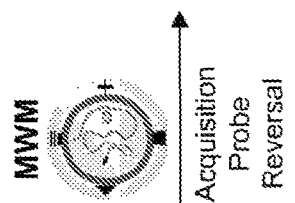
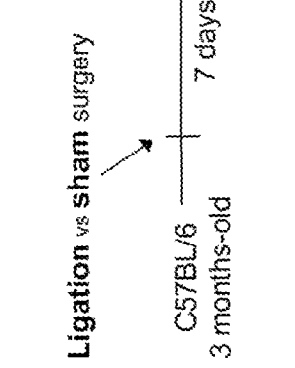
FIG. 9A
FIG. 9B
FIG. 9C
FIG. 9D
FIG. 9E
FIG. 9F
FIG. 9G

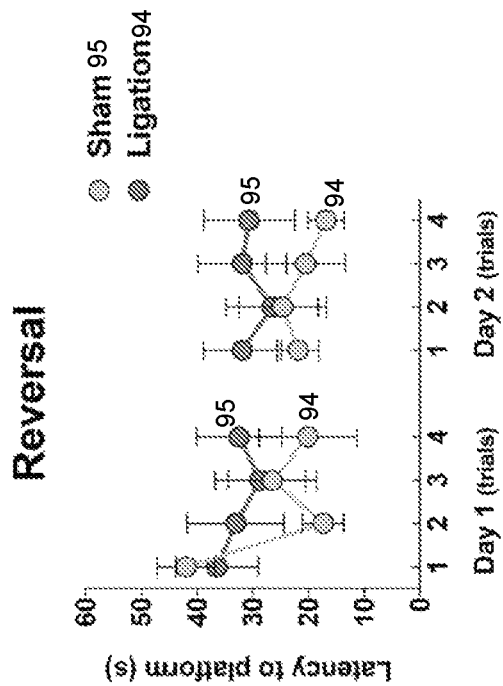
FIG. 9I
FIG. 9J
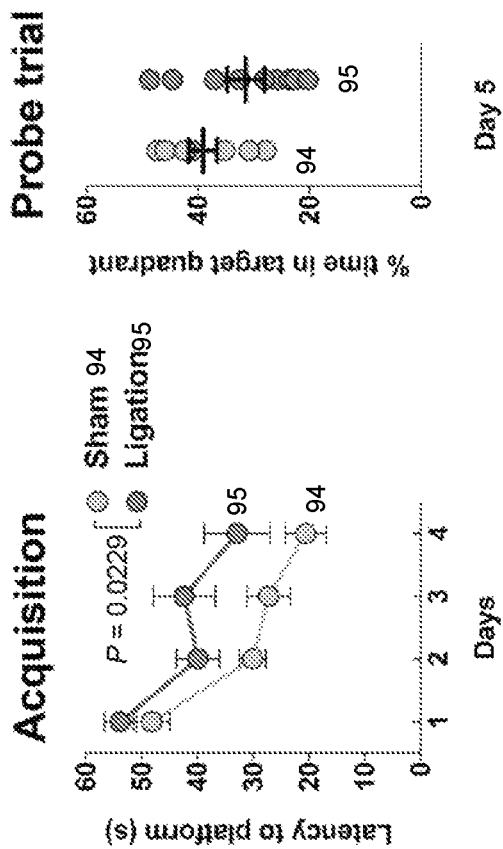
FIG. 9H

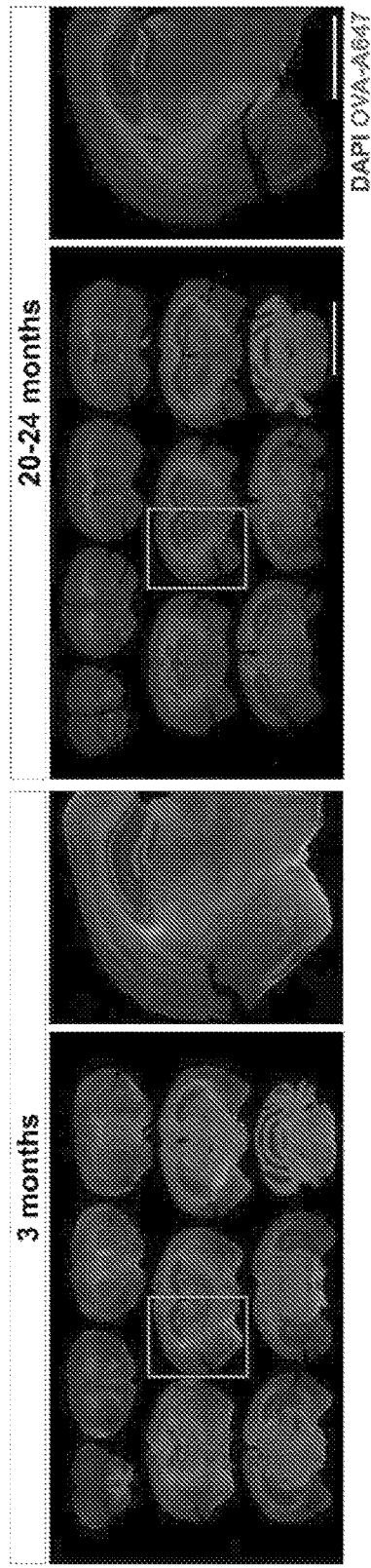
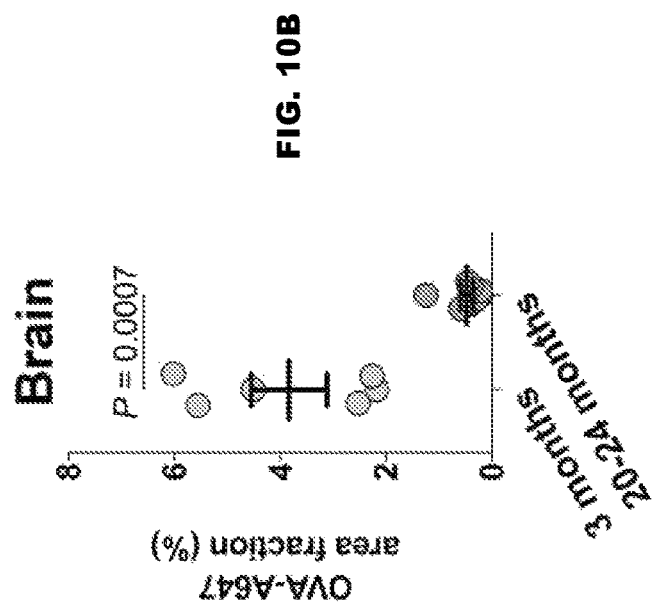
FIG. 10A
FIG. 10B

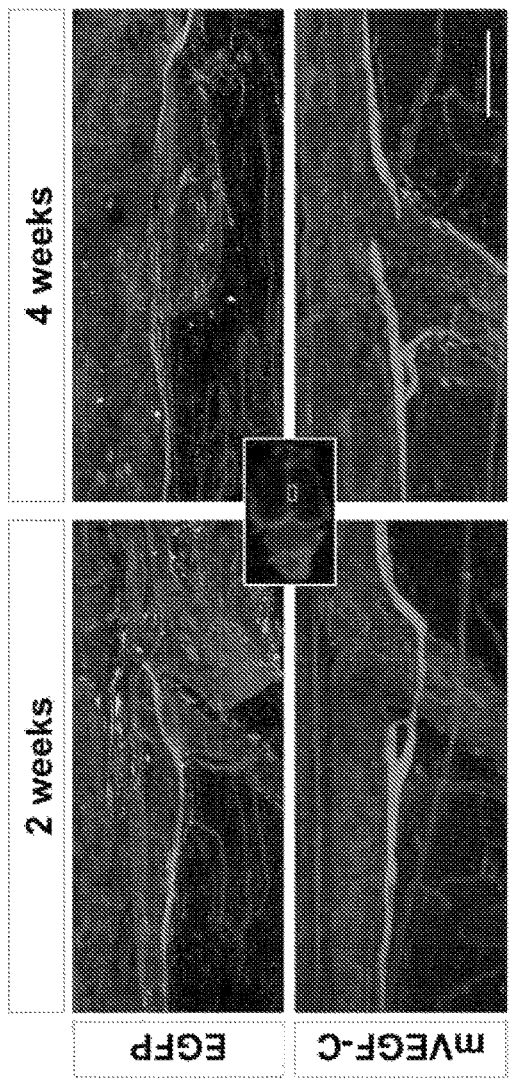
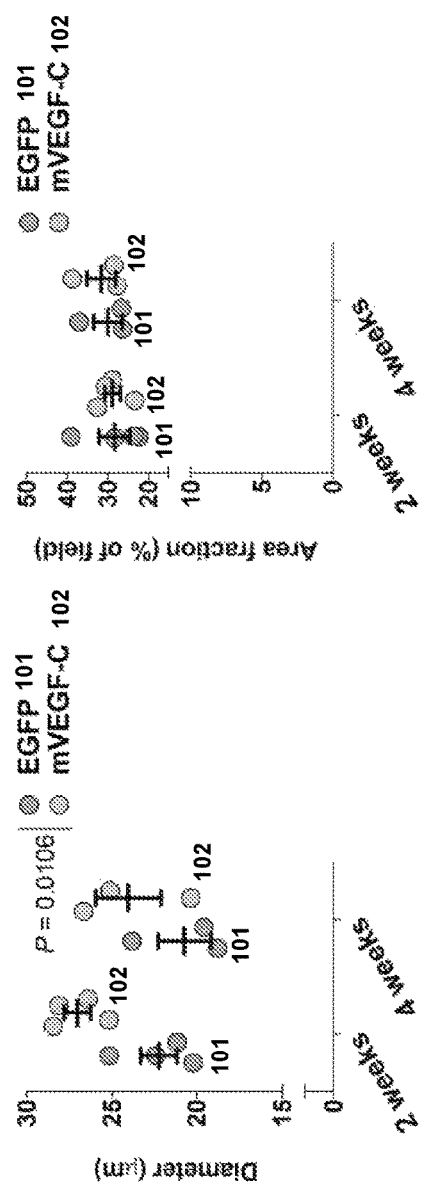
FIG. 10K
FIG. 10L
FIG. 10M

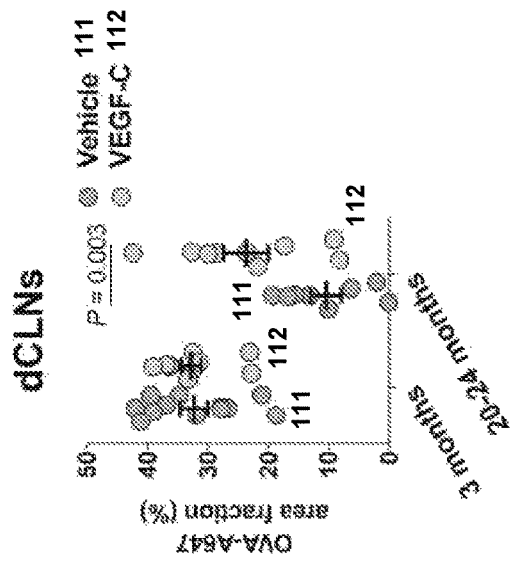
FIG. 11E
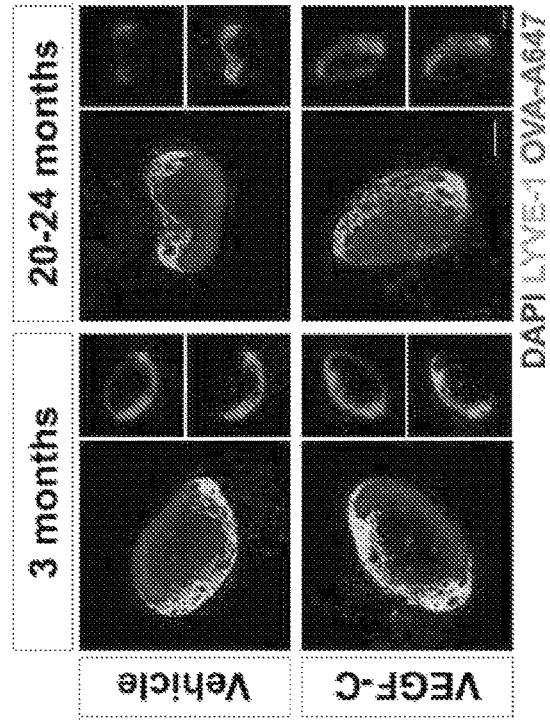
FIG. 11D
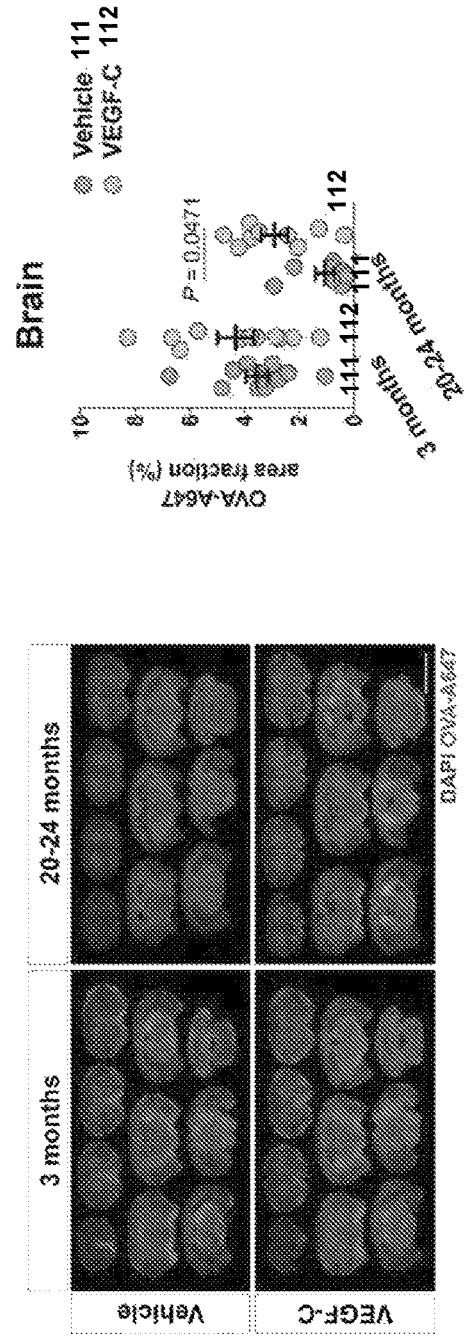
FIG. 11G
FIG. 11F

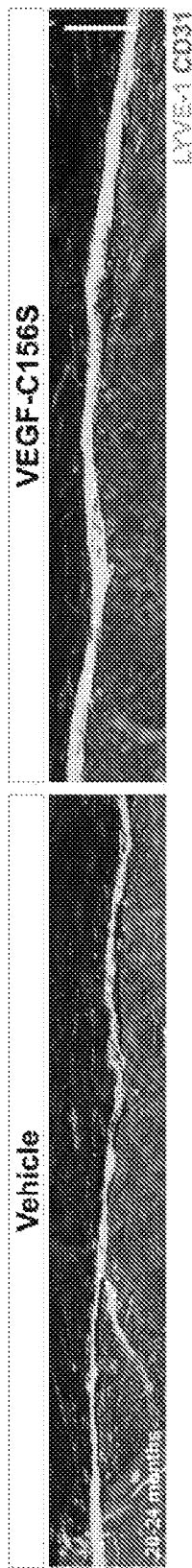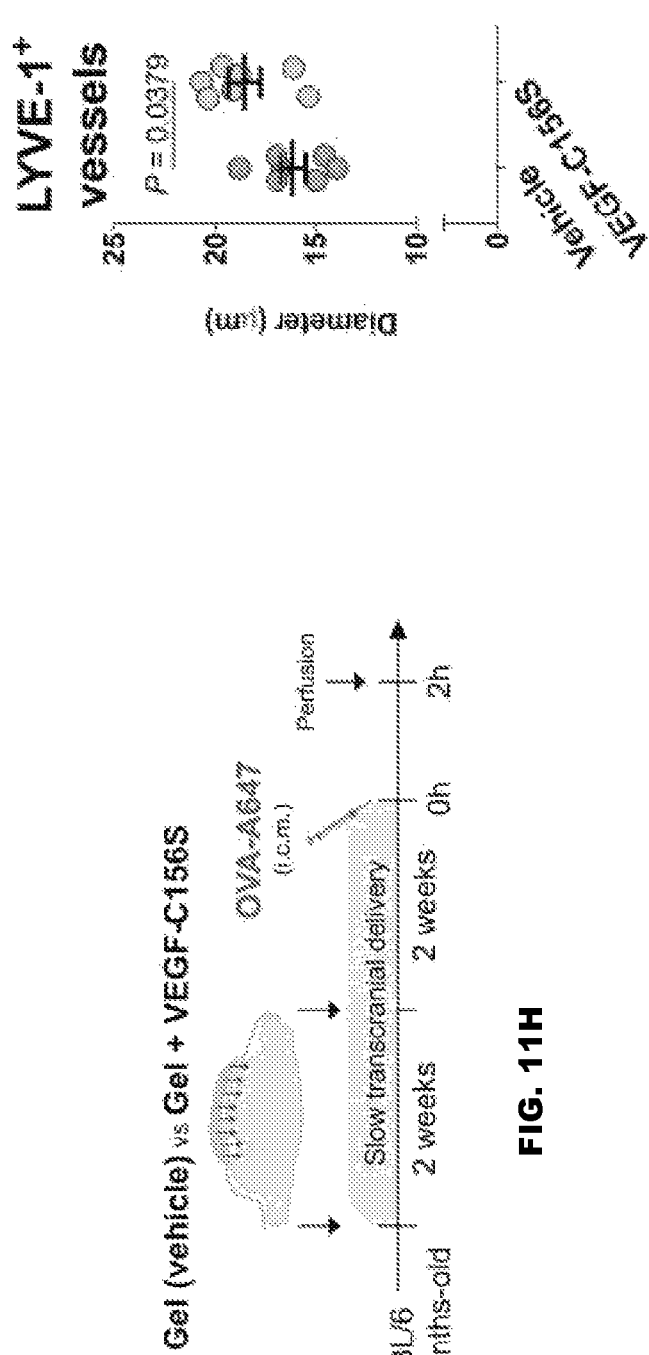
FIG. 11I
FIG. 11J
FIG. 11H

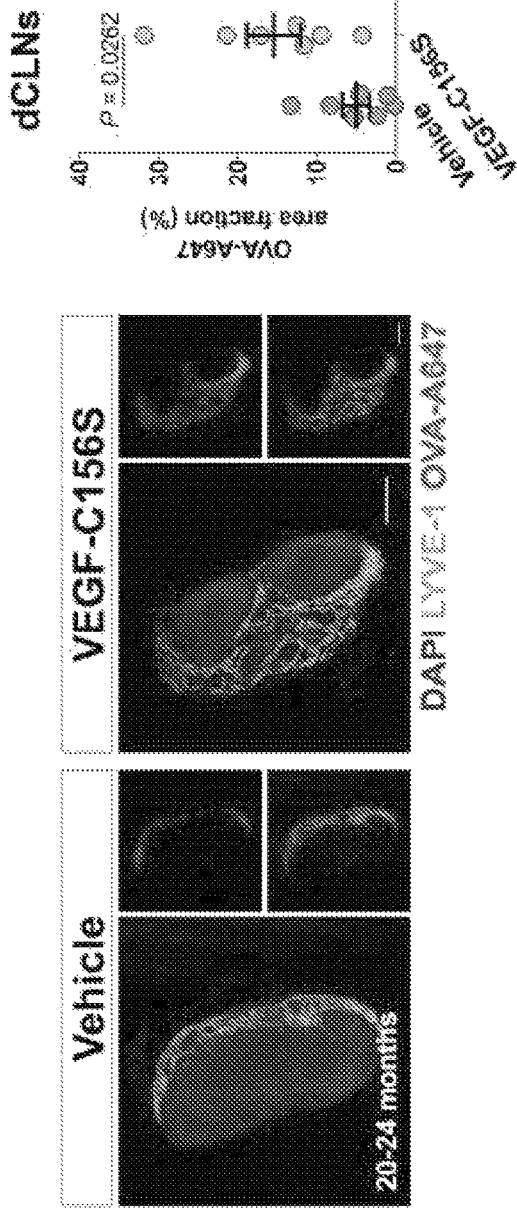
FIG. 11K
FIG. 11L
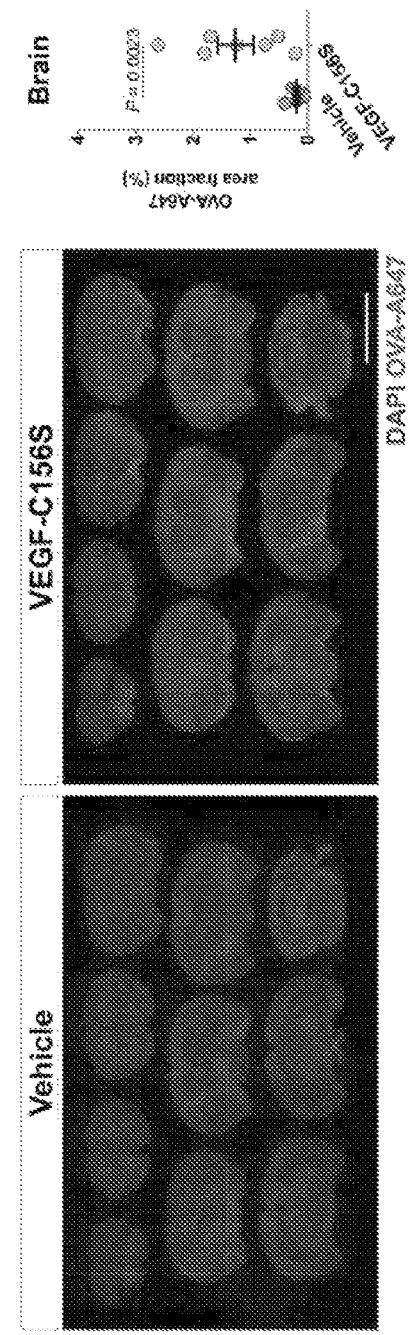
FIG. 11M
FIG. 11N

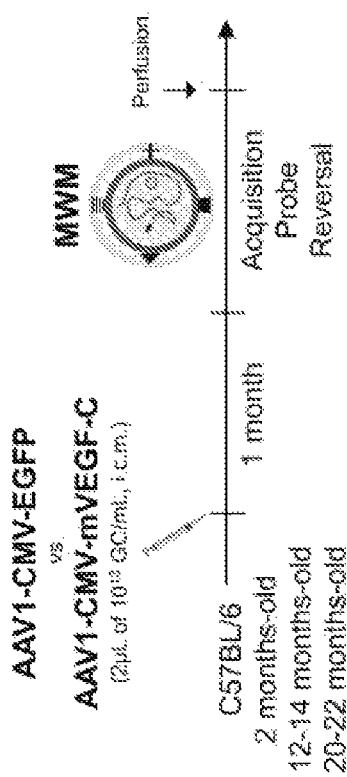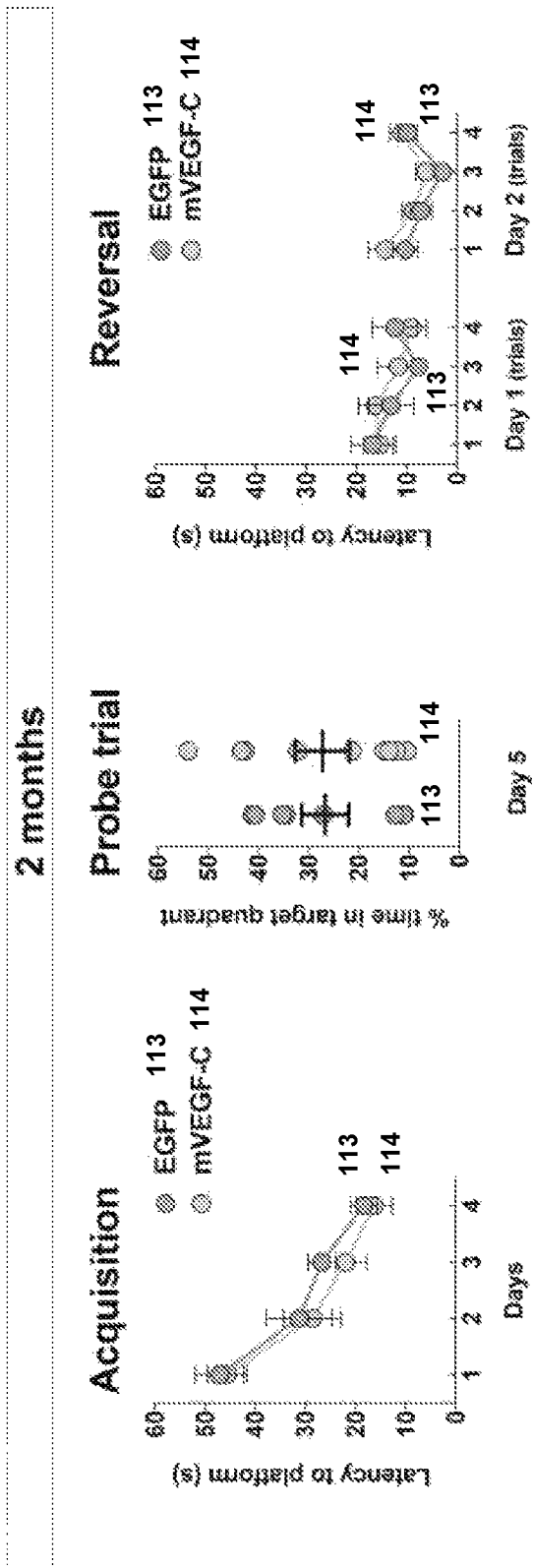
FIG. 11P
FIG. 11O

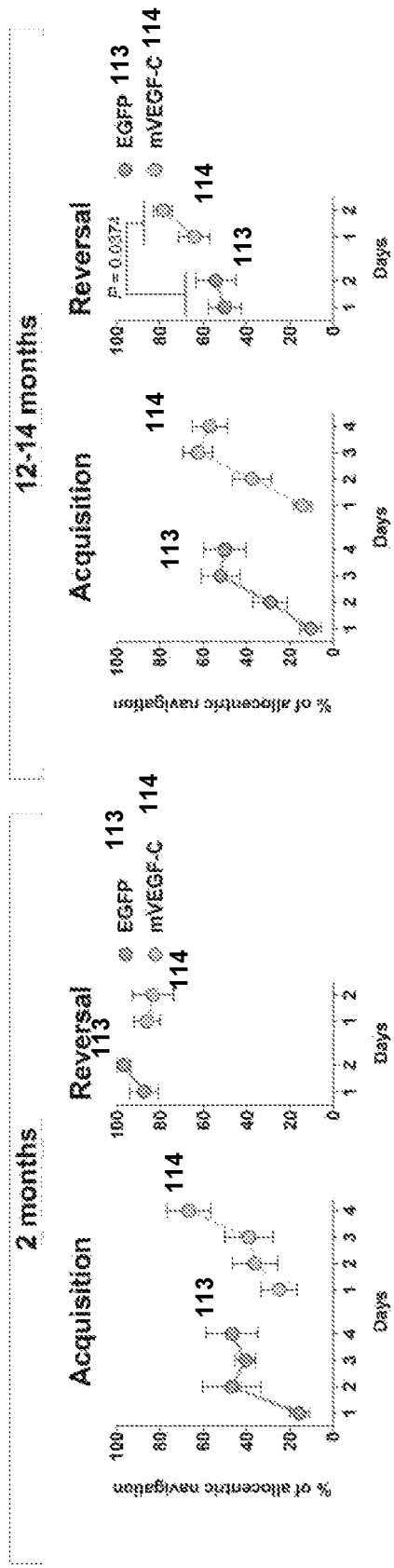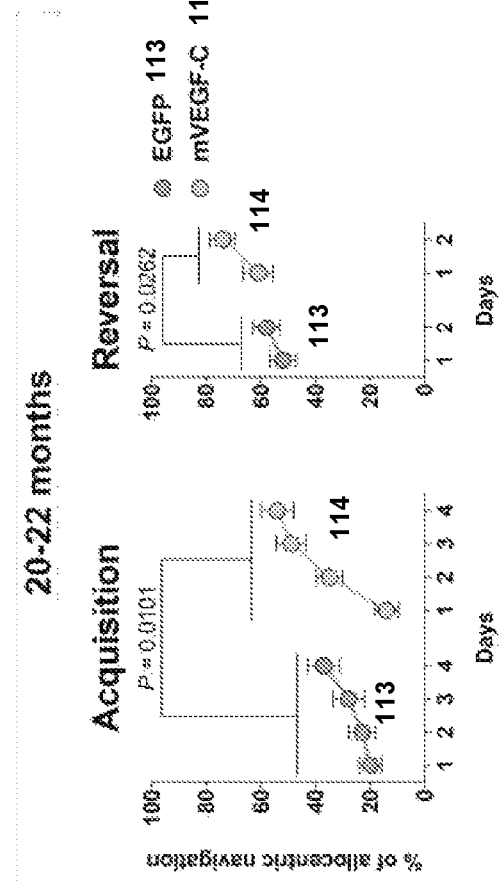
FIG. 11S
FIG. 11T
FIG. 11U

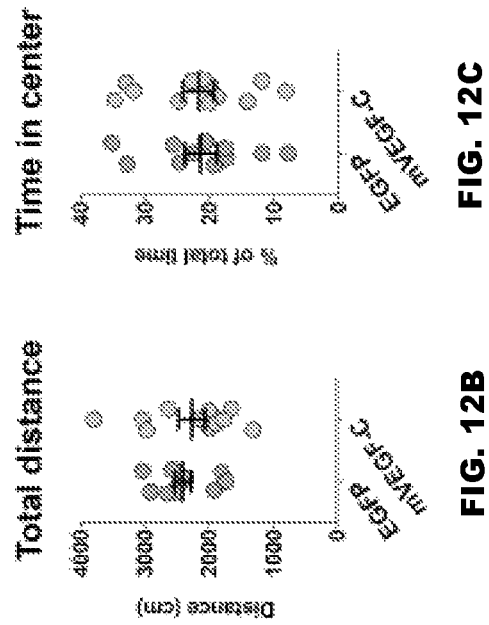
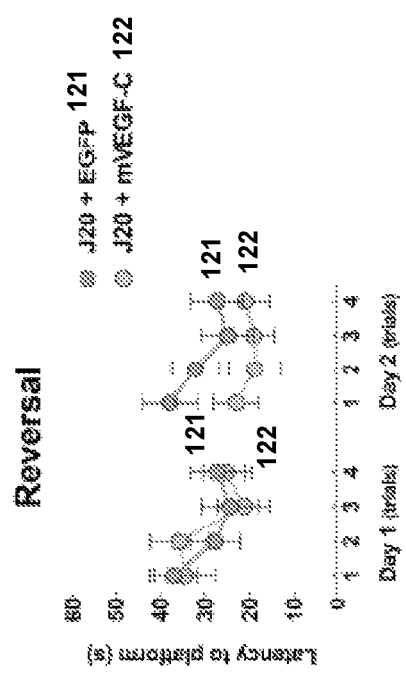
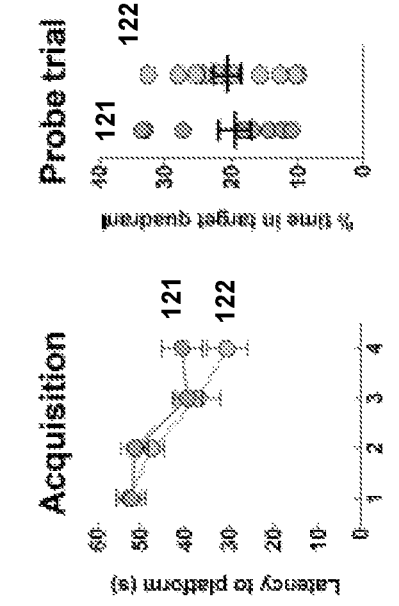
FIG. 12A
FIG. 12B
FIG. 12C
FIG. 12D
FIG. 12E
FIG. 12F

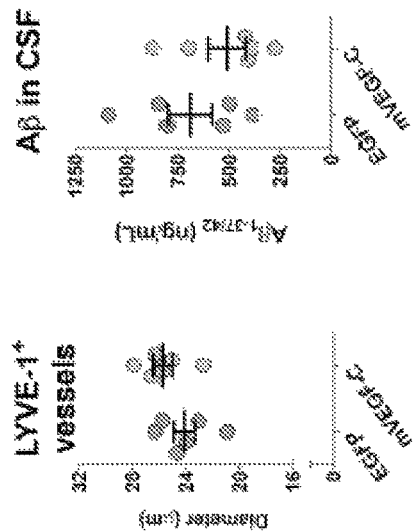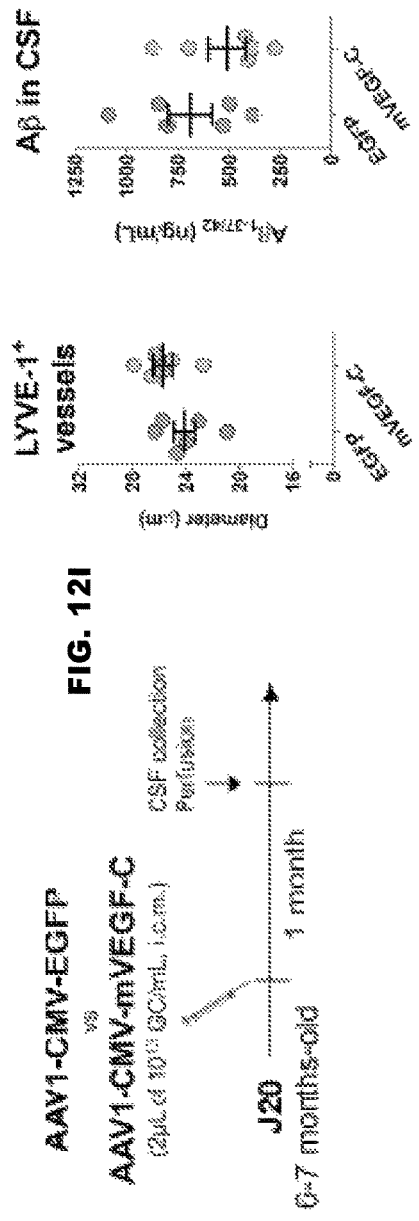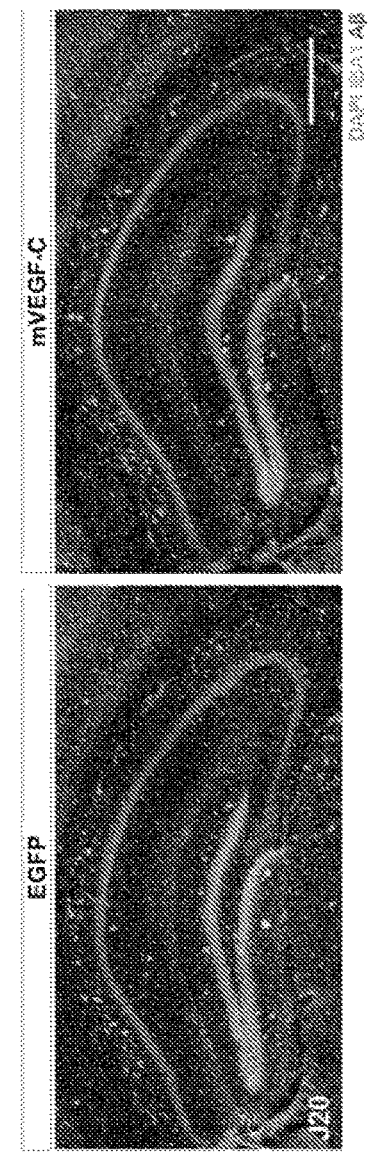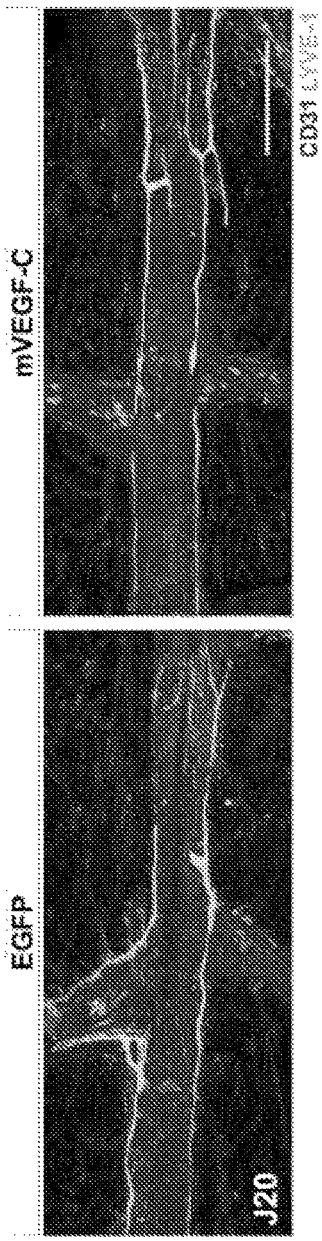

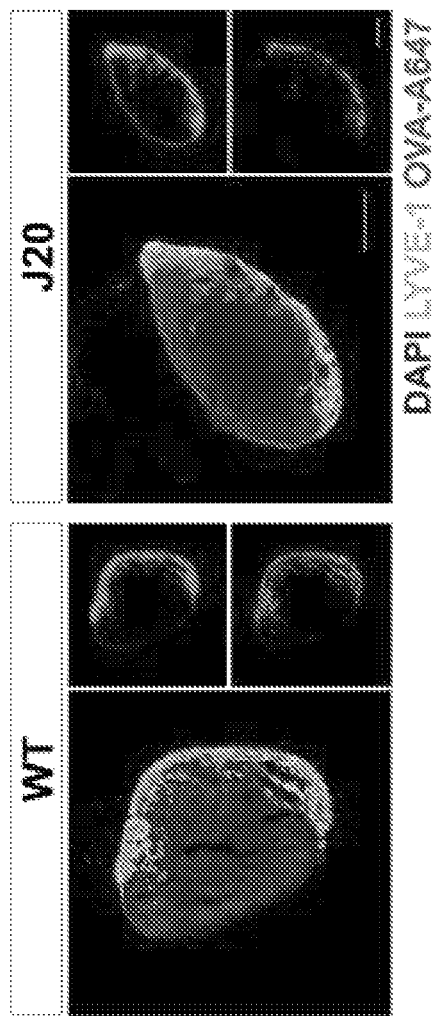
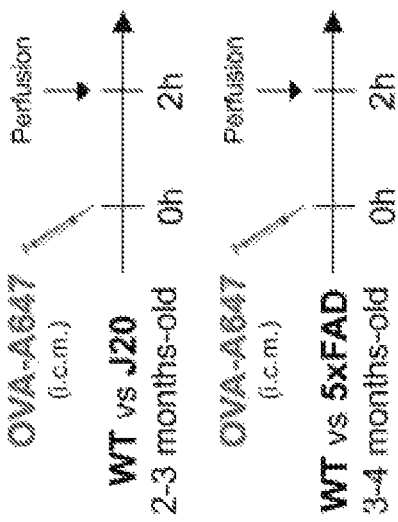
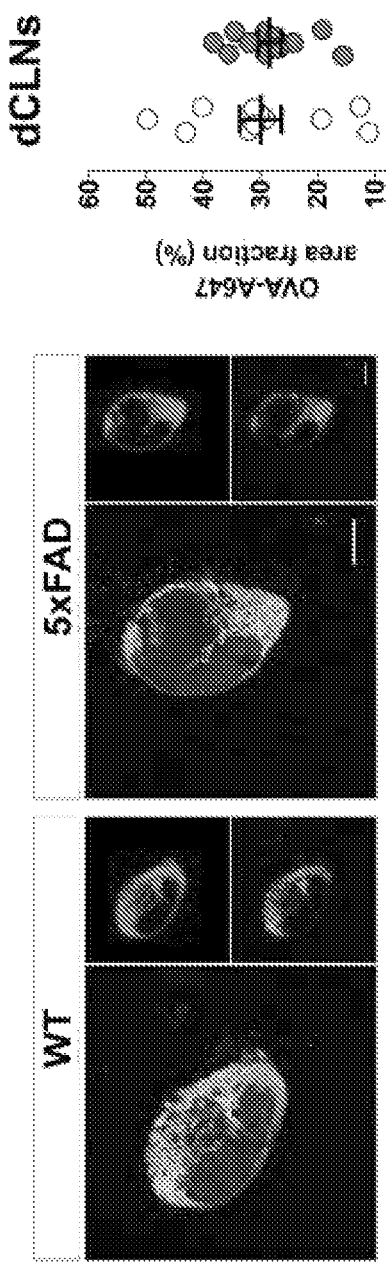
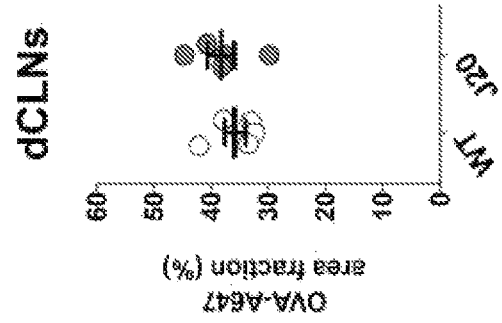
FIG. 12O
FIG. 12P
FIG. 12Q
FIG. 12R
FIG. 12S

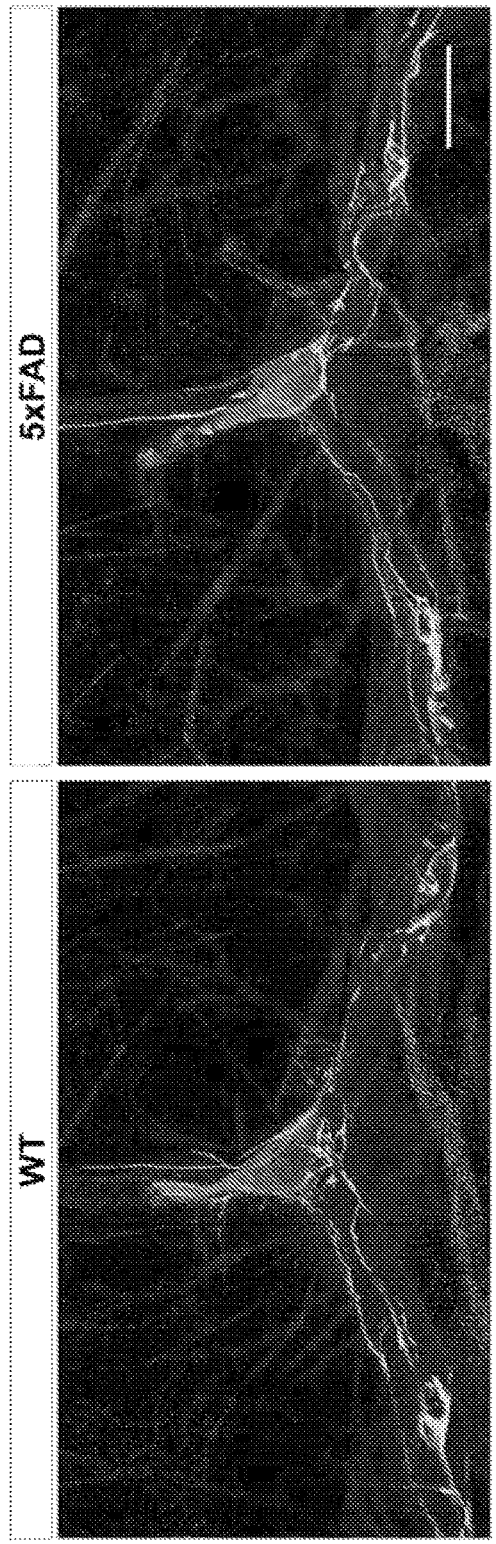
FIG. 12T
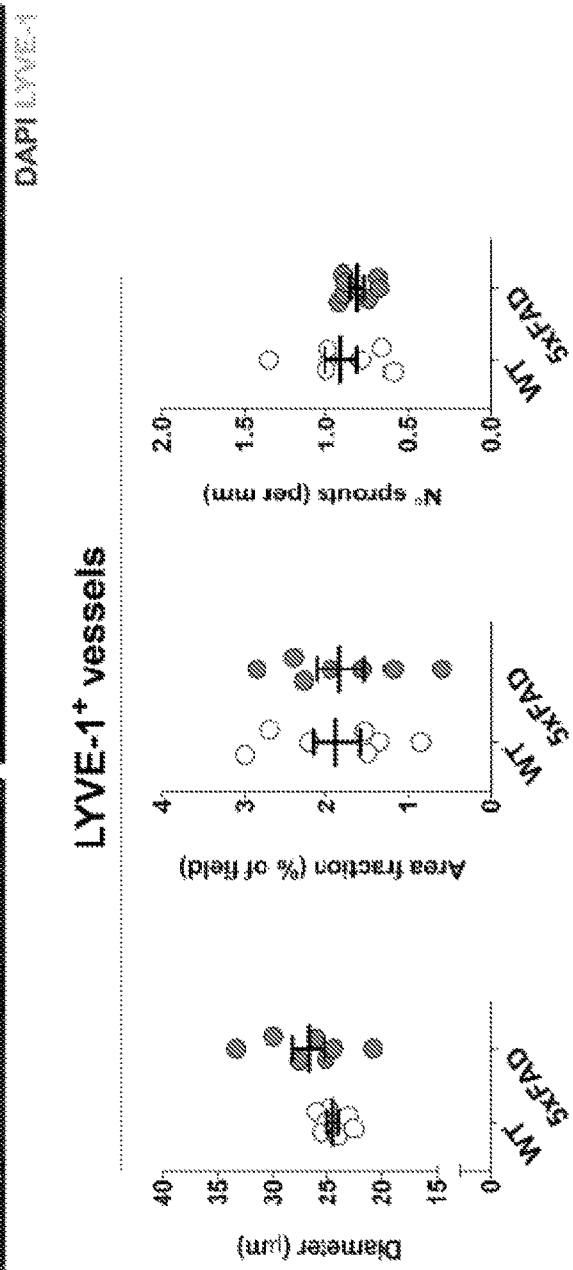
FIG. 12U
FIG. 12V
FIG. 12W

FIG. 13A
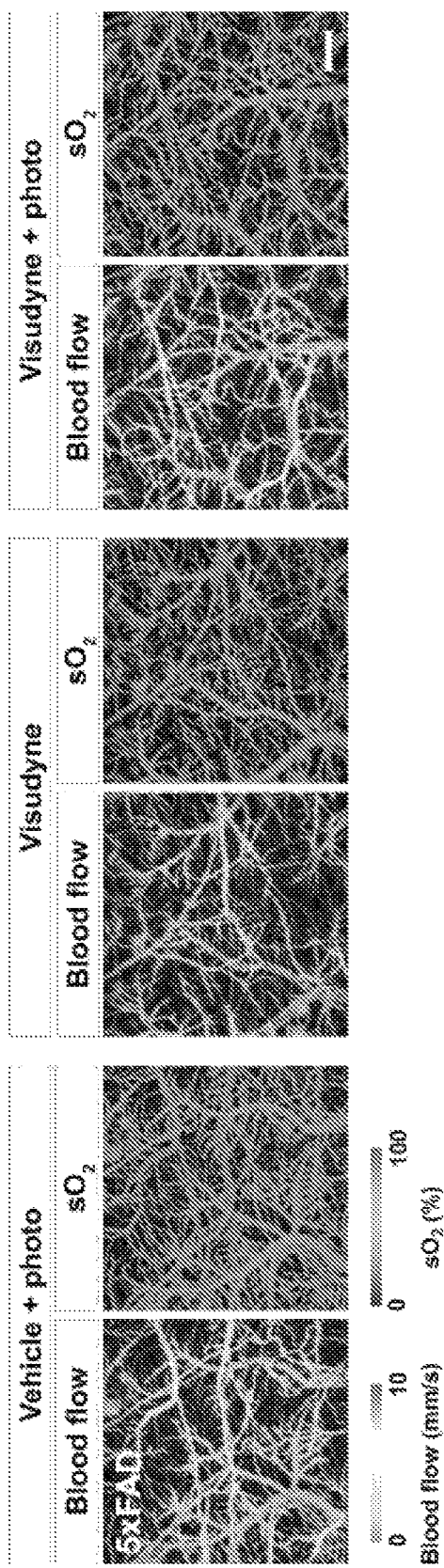
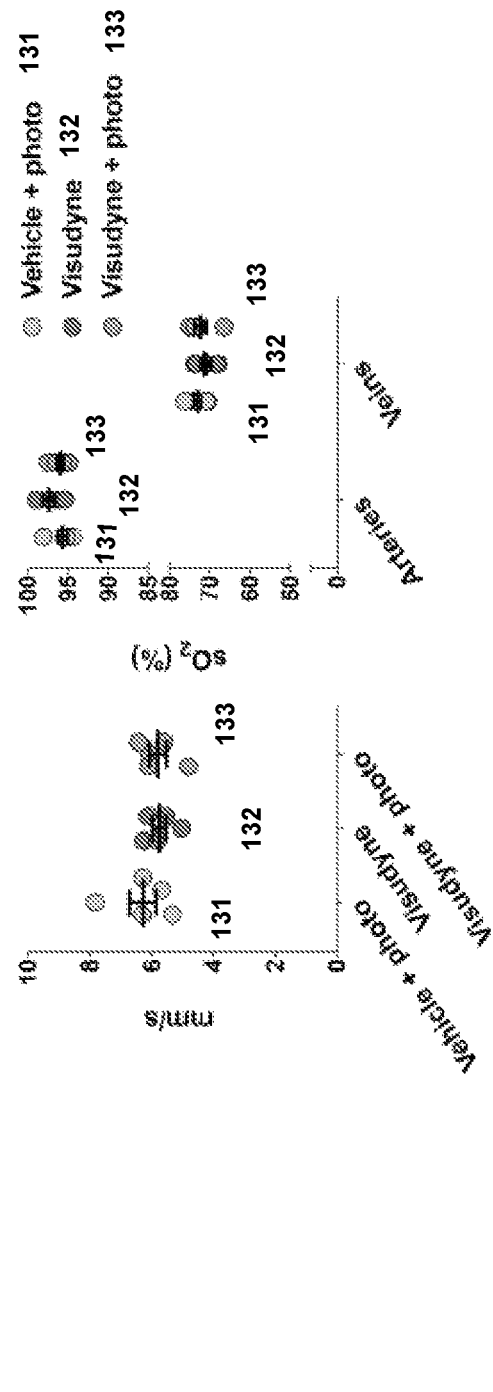
FIG. 13B
FIG. 13C

FIG. 13H
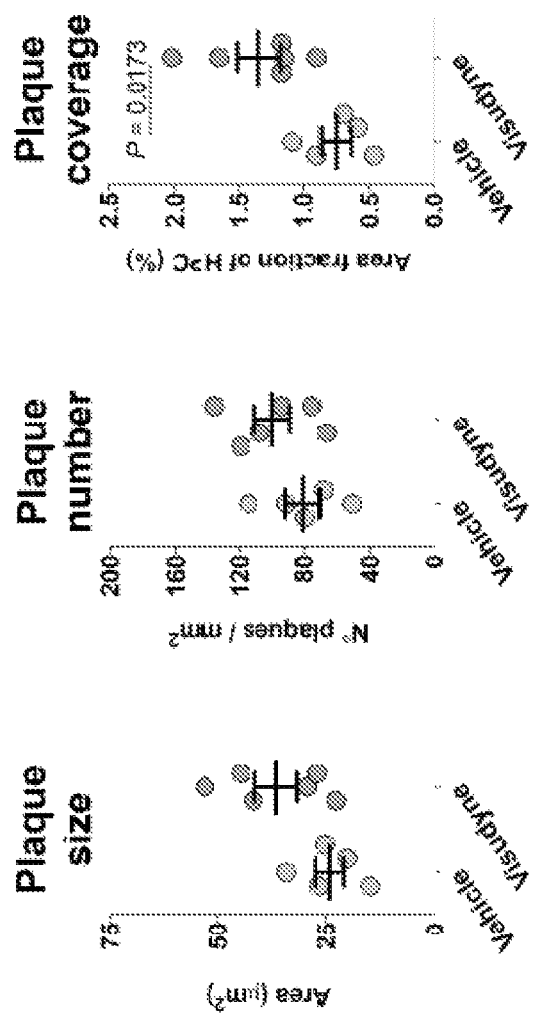
FIG. 13K
FIG. 13J
FIG. 13I

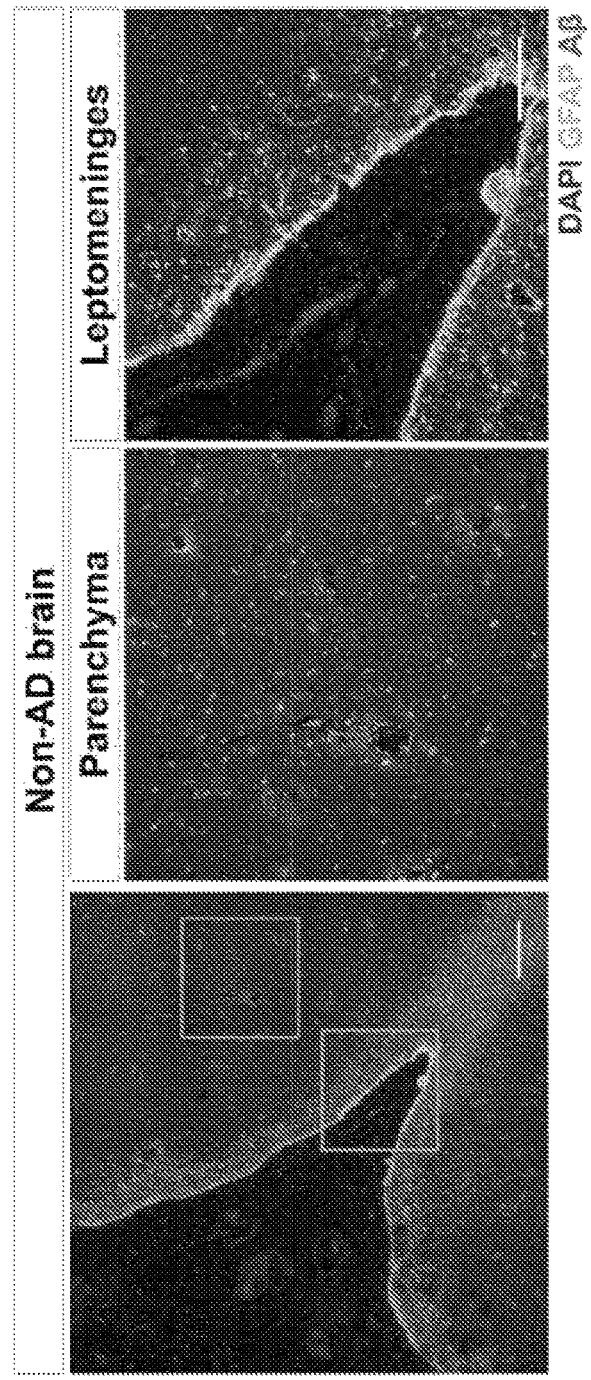
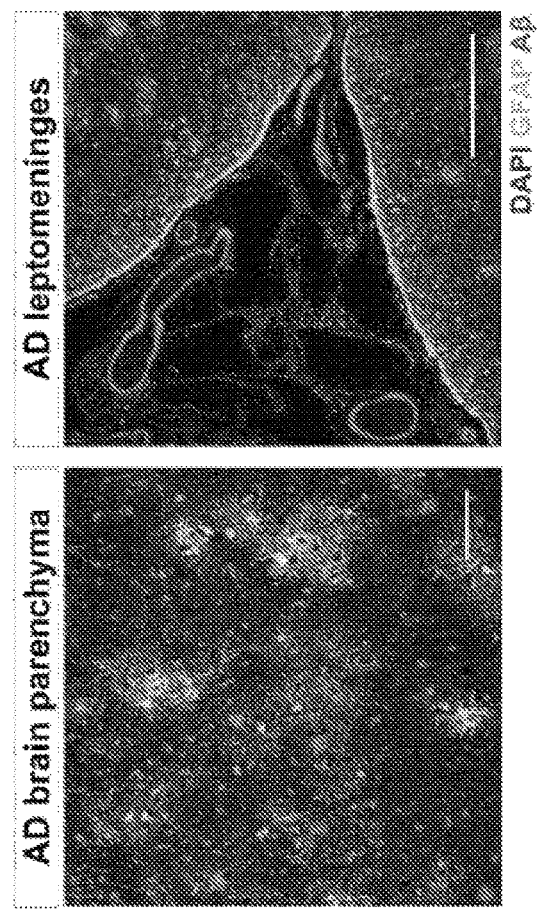
FIG. 13L
FIG. 13M

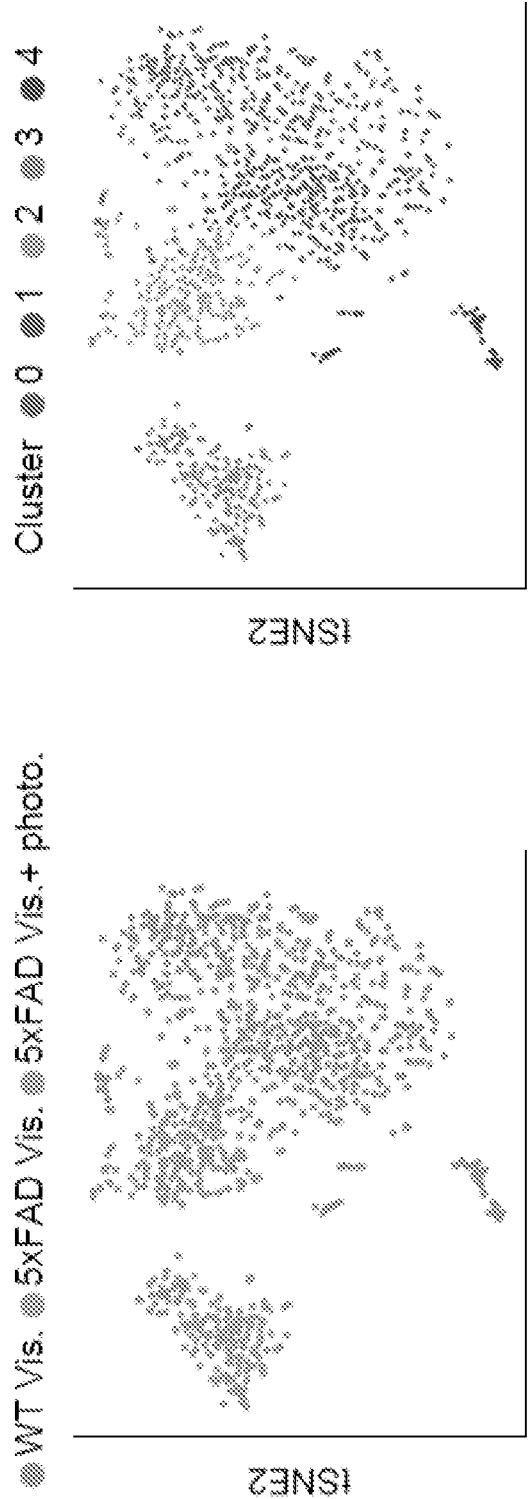
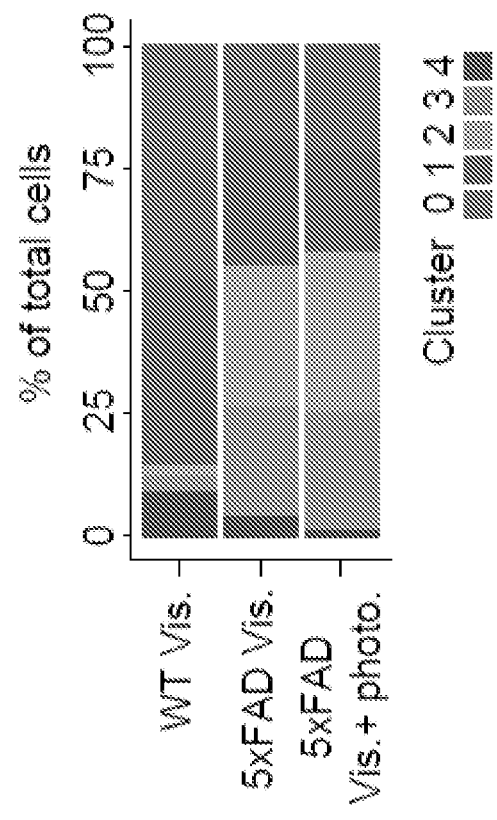
FIG. 14A
FIG. 14B
FIG. 14C

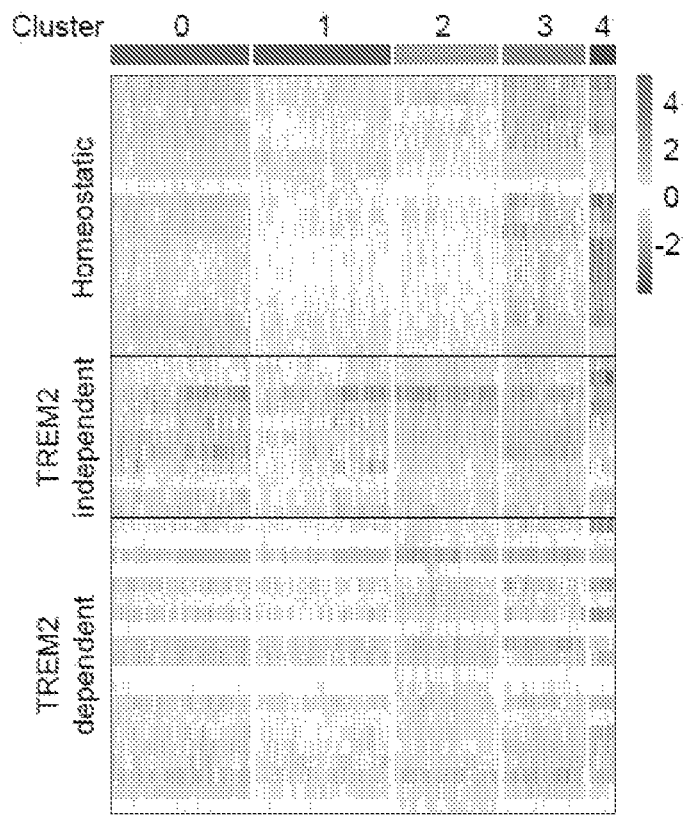
FIG. 14D
FIG. 14E
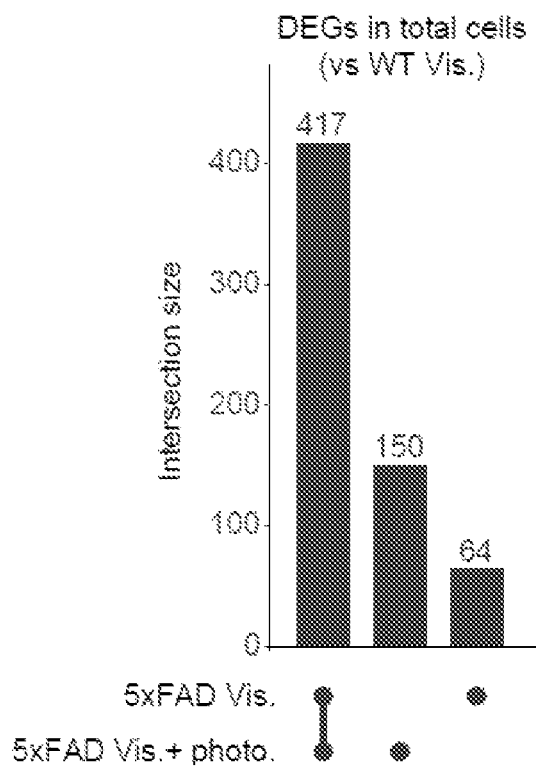
FIG. 14F
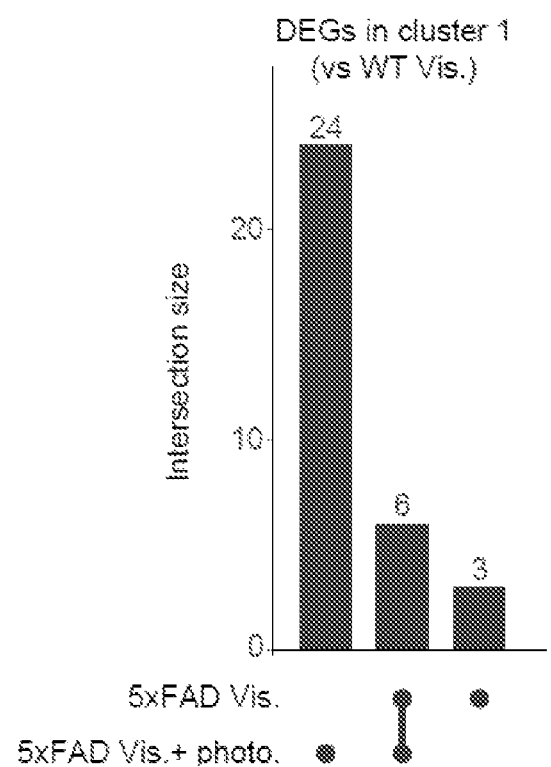

FIG. 15E   FIG. 15F   FIG. 15G

METHOD OF TREATING COGNITIVE DECLINE ASSOCIATED WITH NEUROLOGICAL DISEASES BASED ON A DECREASE IN FLT4 EXPRESSION OR ACTIVITY

INCORPORATION BY REFERENCE TO ANY PRIORITY APPLICATIONS

The present application is a 35 U.S.C. § 371 national stage filing of International Application No. PCT/US2019/041882, filed Jul. 15, 2019, which in turn claims the benefit of U.S. Provisional Application No. 62/698,859, filed Jul. 16, 2018, U.S. Provisional App-Application No. 62/778,801, filed Dec. 12, 2018, and U.S. Provisional Application No. 62/865,035, filed Jun. 21, 2019. The entire contents of each of the foregoing applications are incorporated by reference herein.

STATEMENT REGARDING FEDERALLY SPONSORED R&D

This invention was made with government support under grant Nos. AG034113 and AG057496 awarded by the National Institutes of Health. The government has certain rights in the invention.

BACKGROUND

Neurological diseases impact millions of people worldwide, and include degenerative and inflammatory neurological diseases. Among degenerative neurological diseases, Alzheimer's Disease (AD) is the most prevalent form of dementia worldwide (Andrieu et al., 2015) and is distinctively characterized by early and marked cognitive impairment (Andrieu et al., 2015; Ballard et al., 2011). The vast majority (>98%) of AD cases are sporadic (Blennow et al., 2006), and in such cases the etiology of the amyloid pathology is poorly understood (Benilova et al., 2012; Blennow et al., 2006). This is in contrast to familial AD, where rare hereditary dominant mutations in amyloid precursor protein (APP) or in presenilins 1 and 2 drive the uncontrolled formation of amyloid-beta (Hardy and Selkoe, 2002). The brain's pathological hallmarks of AD are intracellular neurofibrillary tangles and extracellular amyloid plaques, the latter being a product of the amyloidogenic processing of APP and the resulting deposition of amyloid-beta in the brain parenchyma (Benilova et al., 2012; Hardy and Selkoe, 2002; Ittner and Götz, 2011). Increasing aggregation of diffusible amyloid-beta peptides from the ISF and the CSF into toxic oligomeric intermediates and their accumulation in the brain parenchyma (Hong et al., 2011; Iliff et al., 2012) are believed to be precipitating factors for different neuroinflammatory abnormalities (Guillot-Sestier et al., 2015; Hong et al., 2016; Matarin et al., 2015), such as the formation of neurofibrillary tangles (Ittner and Götz, 2011) and the pronounced neuronal dysfunction (Palop et al., 2007; Sun et al., 2009; Walsh et al., 2002) in the AD brain.

Organs generally function less effectively with age. For example, skin becomes less elastic, muscle tone is lost, and heart function declines. Aging is a substantial risk factor for numerous neurological diseases, including neurodegenerative diseases.

FIELD

Several embodiments herein relate generally to compositions, methods, and uses related to the diagnosing, treating, preventing, or ameliorating symptoms of neurodegenerative diseases such as Alzheimer's disease (AD). Several embodiments herein also relate generally to compositions, methods, and uses for diagnosing and monitoring the progression of neurological diseases are also provided.

SUMMARY

Disclosed herein include methods and compositions for determining whether a subject is afflicted with a neurological disease or at risk for developing a neurological disease. In some embodiments, the method comprises a) obtaining a biological sample from the subject; b) determining the copy number, level of expression, or level of activity of one or more targets listed in Table 2 and/or Table 4 and/or Table 6 and/or Table 7, in the subject sample; and c) comparing the copy number, level of expression, or level of activity of the one or more targets detected in steps b) to the copy number, level of expression, or level of activity of the one or more targets in a control. In some such embodiments, a significant increase and/or decrease in the copy number, level of expression, or level of activity of the one or more targets in the subject sample relative to the control copy number, level of expression, or level of activity of the one or more targets indicates that the subject is afflicted with a neurological disease or is at risk for developing a neurological disease.

Disclosed herein include methods and compositions for determining whether a subject afflicted with a neurological disease or at risk for developing a neurological disease resulting from or characterized by an aberrant decrease in meningeal lymphatic drainage. In some embodiments, the method comprises a) obtaining a biological sample from the subject; b) determining the copy number, level of expression, or level of activity of one or more targets listed in Table 2 and/or Table 4 and/or Table 6 and/or Table 7, in the subject sample; and c) comparing the copy number, level of expression, or level of activity of the one or more targets detected in steps b) to the copy number, level of expression, or level of activity of the one or more targets in a control. In some such embodiments, a significant increase and/or decrease in the copy number, level of expression, or level of activity of the one or more targets in the subject sample relative to the control copy number, level of expression, or level of activity of the one or more targets indicates that the subject afflicted with a neurological disease or at risk for developing a neurological disease resulting from or characterized by an aberrant decrease in meningeal lymphatic drainage.

Disclosed herein include methods and compositions for monitoring the progression of a neurological disease in a subject. In some embodiments, the method comprises a) detecting in a subject sample at a first point in time the copy number, level of expression, or level of activity of one or more targets listed in Table 2 and/or Table 4 and/or Table 6 and/or Table 7; b) repeating step a) at a subsequent point in time; and c) comparing the copy number, level of expression, or level of activity of the one or more targets detected in steps a) and b) to monitor the progression of the neurological disease.

Disclosed herein include methods and compositions for determining the efficacy of a test compound for treating a neurological disease in a subject. In some embodiments, the method comprises a) determining the copy number, level of expression, or level of activity of one or more targets listed in Table 2 and/or Table 4 and/or Table 6 and/or Table 7, in a first sample obtained from the subject and exposed to the test compound; b) determining the copy number, level of expression, or level of activity of the one or more targets in a second sample obtained from the subject, wherein the second sample is not exposed to the test compound, and c) comparing the copy number, level of expression, or level of activity of the one or more targets in the first and second samples. In some such embodiments, a significantly modulated copy number, level of expression, or level of activity of the target, relative to the second sample, is an indication that the test compound is efficacious for treating the neurological disease in the subject.

Disclosed herein include methods and compositions for identifying a compound which treats a neurological disease. In some embodiments, the method comprises a) contacting a cell with a test compound; and b) determining the effect of the test compound on the copy number, level of expression, or level of activity of the one or more targets listed in Table 2 and/or Table 4 and/or Table 6 and/or Table 7 in the cell to thereby identify a compound which treats a neurological disease.

Disclosed herein include methods and compositions for treating a subject afflicted with a neurological disease. In some embodiments, the method comprises administering an agent that: i) decreases the copy number, level of expression, or level of activity of one or more targets upregulated in Table 2 and/or Table 4 and/or Table 6 and/or Table 7, and/or ii) increases the copy number, level of expression, or level of activity of one or more targets downregulated in Table 2 and/or Table 4 and/or Table 6 and/or Table 7, such that the neurological disease is treated.

Disclosed herein include methods and compositions for increasing flow of fluid in the central nervous system of a subject. In some embodiments, the method comprises determining the subject to be in need of increased fluid flow in the central nervous system; and administering to a meningeal space of the subject in need an effective amount of an agent that: i) decreases the copy number, level of expression, or level of activity of one or more targets upregulated in Table 2 and/or Table 4 and/or Table 6 and/or Table 7, and/or ii) increases the copy number, level of expression, or level of activity of one or more targets downregulated in Table 2 and/or Table 4 and/or Table 6 and/or Table 7, thereby increasing fluid flow in the central nervous system of the subject.

Disclosed herein include methods and compositions for reducing the accumulation of, or reducing a quantity of, accumulated amyloid-beta plaques in a subject having a neurodegenerative disease or a risk factor therefor. In some embodiments, the method comprises determining the subject to have the neurodegenerative disease or the risk factor; and administering to a meningeal space of the subject in need an effective amount of an agent that: i) decreases the copy number, level of expression, or level of activity of one or more targets upregulated in Table 2 and/or Table 4 and/or Table 6 and/or Table 7, and/or ii) increases the copy number, level of expression, or level of activity of one or more targets downregulated in Table 2 and/or Table 4 and/or Table 6 and/or Table 7, thereby reducing the quantity of accumulated amyloid-beta plaques in the subject.

Disclosed herein include methods and compositions for increasing clearance of molecules from a central nervous system (CNS) of a subject. In some embodiments, the method comprises administering to a meningeal space of the subject in need an effective amount of an agent that: i) decreases the copy number, level of expression, or level of activity of one or more targets upregulated in Table 2 and/or Table 4 and/or Table 6 and/or Table 7, and/or ii) increases the copy number, level of expression, or level of activity of one or more targets downregulated in Table 2 and/or Table 4 and/or Table 6 and/or Table 7, thereby increasing clearance of molecules from the CNS of the subject.

Disclosed herein include methods and compositions for treating a subject afflicted with a neurological disease. In some embodiments, the method comprises administering to the hippocampus of the subject in need an effective amount of an agent that: i) decreases the copy number, level of expression, or level of activity of one or more targets upregulated in Table 2 and/or Table 4 and/or Table 6 and/or Table 7, and/or ii) increases the copy number, level of expression, or level of activity of one or more targets downregulated in Table 2 and/or Table 4 and/or Table 6 and/or Table 7, such that the neurological disease is treated. In some embodiments, the method comprises administering to the hippocampus of the subject in need an effective amount of an agent that: i) decreases the copy number, level of expression, or level of activity of one or more targets upregulated in Table 2 and/or Table 4, and/or ii) increases the copy number, level of expression, or level of activity of one or more targets downregulated in Table 2 and/or Table 4 such that the neurological disease is treated. In some embodiments, the method comprises administering to the hippocampus of the subject in need an effective amount of an agent that: i) decreases the copy number, level of expression, or level of activity of one or more targets upregulated in Table 6 and/or Table 7, and/or ii) increases the copy number, level of expression, or level of activity of one or more targets downregulated in Table 6 and/or Table 7, such that the neurological disease is treated.

In some embodiments, the copy number, level of expression, or level of activity of the one or more targets comprises the copy number, level of expression, or level of activity of the one or more targets in the hippocampus. In some embodiments, the copy number, level of expression, or level of activity of the one or more targets comprises the copy number, level of expression, or level of activity of the one or more targets in lymphatic endothelial cells (LECs) and/or microglia. By way of example, microglia can be identified as Ly6G$^{neg}$CD45$^+$CD11b$^+$ brain myeloid cells. Impaired meningeal lymphatic function has been observed herein to affect microglial gene expression in AD background, as shown in Example 9 (See, e.g., differentially expressed genes listed Tables 6-7 and FIGS. 5G and 5I). Without being limited by theory, it is contemplated that changes in gene expression of microglia in 5×FAD mice with meningeal lymphatic ablation may represent changes in gene expression associated with a risk of AD, when there is a presence of AD, and/or when an AD phenotype or prognosis becomes more severe. In accordance with some embodiments, the changes in gene expression depicted in Tables 6 and/or 7 may be indicative of a risk for a neurological disease (e.g., a proteinopathy such as AD), a presence of a neurological disease (e.g., a proteinopathy such as AD), or a severity of a neurological disease (e.g., a proteinopathy such as AD). Without being limited by theory, it is contemplated that targets with altered microglial expression in 5×FAB mice with meningeal lymphatic ablation may represent therapeutic targets. For example, a therapeutic agent may reverse one or more of the indicated changes in gene expression (for example, by upregulating a target that is downregulated, or downregulating a target that is upregulated as depicted in Table 6 and/or 7) in microglia of 5×FAD mice suffering from meningeal lymphatic dysfunction.

In some embodiments, the one or more targets are downregulated in Table 2. In some embodiments, the one or more targets are downregulated in Table 4. In some embodiments, the one or more targets are downregulated in Table 6 and/or Table 7. It is noted that for the targets disclosed in Tables 2 and 4, Ensembl and Entrez ID numbers are provided, and for Tables 6 and 7, Entrez numbers are provided. The corresponding nucleic acid sequence can be retrieved, for example, from the world wide web at www dot ncbi dot nlm dot nih dot gov (for Entrez ID's) and from www dot ensembl dot org (for Ensembl ID's). Due to the size, Tables 2 and 4 are provided in the appendix below. In some embodiments, the one or more targets are upregulated in Table 2. In some embodiments, the one or more targets are upregulated in Table 4. In some embodiments, the one or more targets are upregulated in Table 6 and/or Table 7. In some embodiments, the one or more targets are downregulated at least 1.5-fold. In some embodiments, the one or more targets are downregulated at least 2-fold. In some embodiments, the one or more targets are downregulated at least 4-fold. In some embodiments, the one or more targets are upregulated at least 1.5-fold. In some embodiments, the one or more targets are upregulated at least 2-fold. In some embodiments, the one or more targets are upregulated at least 4-fold. In some embodiments, the one or more targets comprises one or more of the following: Met, Sorbs2, Nlgn1, ND2, Adam10, Bmpr2, Fmr1, Ptk2b, Nrgn, Adora1, Cnih2, Camk2b, Homer3, Erc2, Arrb2, Rab8a, Bcr, Dvl, Rgs14, Palm, Neurl1a, Atp1a1, Grin1, Cdk5, Dmtn, Actb, Prkcg, Arhgef2, Arfgap1, Shank3, Cryab, Dgki, Syndig1, Slc17a7, Dlg4, Nsmf, Clstn3, Src, Kcnab2, and Itpr1. In some embodiments, the one or more targets comprises one or more of the following: ND1, ND4L, Ndufb4, Ndufab1, Ndufc1, Ndufc2, Ndufb6, Ndufa13, Ndufa8, Ndufs5, Ndufs8, Ndufv1, Ndufa3, Ndufa11, Ndufs6, Ndufv3, Park7, Ndufa2, Ndufb8, Ndufb10, Ndufb11, Ndufa9, Ndufs2, Ndufb9, Ndufs3, and Ndufb3. In some embodiments, the one or more targets comprises one or more of the following: ND1, CYTB, ND2, ND4, ND5, Oprk1, Pmpcb, Nfatc3, Akt2, Uqcr10, Uqcrh, Bloc1s1, Cox8a, Pygb, Sirt3, Ogdhl, Prelid1, Slc25a25, Hk1, Prkaca, Park7, Pfkm, Aco2, Eif6, Ndutfb8, Mdh2, Gsk3a, Uqcrcl, Akt1, Mt3, Aldoa, Pkm, Tpi1, Idh3g, Gpi1, Ndufv1, Gpd1, Gapdh, Cox4i1, and Pfkl. In some embodiments, the one or more targets comprises one or more of the following: Nr4a3, Cpeb2, Oxr1, Sirt1, Ncoa7, Bcl2, Stk26, Hif1a, Cd36, Met, Prkcd, Etv5, Kdm6b, Prdx2, Nup93, Sod1, Apex1, Prdx5, Sirt2, Trp53, Ppif, Scly, Gpx1, G6pdx, Stat6, Parp1, Trap1, Sesn2, Mapt, Hsf1, Tldc1, Kcnc2, Src, Rps3, Mt3, Txn2, Stk25, Lonp1, Park7, and Psap. In some embodiments, the one or more targets comprises one or more of the following: App, Reln, Calb1, Nog, Pafahib1, Ap1s2, Oprk1, Cnr1, Neto1, Grin2b, Egfr, Ptprz1, Kras, Petn, Slc17a7, Apbb1, Atp1a3, Slc8a2, Ppp1r1b, Dcdc2a, Dgki, Asic1, Comt, Rin1, Serpinf1, Pdelb, Cdk5, Btbd9, Jph3, Grin1, Cntn2, Ephb2, Ncam1, Crtc1, Thra, Rgs14, Ehmt2, B4galt2, Shank3, and Shc3. In some embodiments, the one or more targets comprises one or more of the following: Ngf, Ror1, Myoc, Errfi1, Ctnnb1, Arid5b, Fgf1, Dll1, Pik3r2, Fst14, Ndrg4, Adra2c, Adamtsl2, Ntrk2, Lrig2, Epha7, Tsc1, Col1a1, Rbm4, Pag1, Prkcd, Btk, Cdk5r1, Csf1r, Syk, Adamts3, Fam20c, Ofd1, and Fgfr3. In some embodiments, the one or more targets comprises one or more of the following: IFNB1, CD40, IFNG, LYN, IMPDH2, NUP88, ADA, IRF2, ZNF114, TCF7L2, DYRK2, TACC3, GPR87, ALDH3B1, ARCPCiB, RELB, TMEM154, SPDEF, SMAD7, and MTFR1. In some embodiments, the one or more targets comprises one or more of the following: Serinc3, Hexb, Lgmn, Rtp4, Lpl, HS-Q7, Axl, Ctdnep1, Fabp5, Nampt, Tfdp1, Hspb11, Tyrobp, Tpt1, Fth1, Eef1a1, Lgals3 bp, Ifitm3, Atp5h, Fau, Ftl1, H2-K1, Tmsb4x, and Uba52. In some embodiments, the one or more targets comprises one or more of the following: Serinc 3, Hexb, and Lgmn. In some embodiments, the one or more targets comprises one or more of the following: Rtp4, Lpl, HS-Q7, Axl, Ctdnep1, Fabp5, Nampt, Tfdp1, Hspb11, Tyrobp, Tpt1, Fth1, Eef1a1, Lgals3 bp, Ifitm3, Atp5h, Fau, Ftl1, H2-K1, Tmsb4x, and Uba52. In some embodiments, the one or more targets comprises one or more of the following: Lgmn, Hexb, Hexa, Rnaset2b, Cd63, Grn, Lamp1, Fuca1, Hck, Gusb, Ctsl, Cd68, Ctsb, Ctsd, Ctsz, Milr1, Aga, Rnf19b, Cat, PIbd2, Laptm4a, Tmbim1, Atraid, Shkbp1, Atp13a2, Ggh, Rptor, Ctsf, LMbrd1, Pla2g15, Scarb2, Ctsa, Hsp90ab1, Lamp2, Unc93b1, Hspa8, Asah1, Ctsc, Itm2c, and Fuca2.

In some embodiments, the one or more targets are listed in Table 2 and the one or more targets are associated with one or more of the categories listed in Table 3. In some embodiments, the one or more targets are listed in Table 4 and the one or more targets are associated with one or more of the categories listed in Table 5. In some embodiments, the one or more targets are listed in Table 6. In some embodiments, the one or more targets are listed in Table 7. In some embodiments, the one or more targets are listed in Table 6 and/or Table 7 and the one or more targets are associated with one or more of the categories listed in FIG. 5H. In some embodiments, the one or more targets comprises two or more targets. In some embodiments, the one or more targets comprises four or more targets. In some embodiments, the one or more targets comprises six or more targets. In some embodiments, the control is an unaffected subject or member of the same species to which the subject belongs. In some embodiments, the sample consists of or comprises fluid cerebral spinal fluid (CSF), interstitial fluid (ISF), or both, obtained from the subject. In some embodiments, the copy number is assessed by microarray, quantitative PCR (qPCR), high-throughput sequencing, comparative genomic hybridization (CGH), or fluorescent in situ hybridization (FISH). In some embodiments, the expression level of the one or more targets is assessed by detecting the presence in the samples of a polynucleotide molecule encoding the target or a portion of the polynucleotide molecule. In some embodiments, the polynucleotide molecule is a mRNA, cDNA, or functional variants or fragments thereof and, optionally, wherein the step of detecting further comprises amplifying the polynucleotide molecule. In some embodiments, the expression level of the one or more targets is assessed by annealing a nucleic acid probe with the sample of the polynucleotide encoding the one or more targets or a portion of the polynucleotide molecule under stringent hybridization conditions. In some embodiments, the expression level of the target is assessed by detecting the presence in the samples of a protein of the target, a polypeptide, or protein fragment thereof comprising the protein In some embodiments, the presence of the protein, polypeptide or protein fragment thereof is detected using a reagent which specifically binds with the protein, polypeptide or protein fragment thereof. In some embodiments, the reagent is selected from the group consisting of an antibody, an antibody derivative, and an antibody fragment. In some embodiments, the activity level of the target is assessed by determining the magnitude of modulation of the activity or expression level of downstream targets of the one or more targets. In some embodiments, an at least twenty percent increase or an at least twenty percent decrease between the copy number, level of expression, or level of activity of the one or more targets in the subject sample at a first point in time relative to the copy number, level of expression, or level of activity of the one or more targets in the subject sample at a subsequent point in time indicates progression of the neurological disease; or wherein less than a twenty percent increase or less than a twenty percent decrease between the copy number, level of expression, or level of activity of the one or more targets in the subject sample at a first point in time relative to the copy number, level of expression, or level of activity of the one or more targets in the subject sample at a subsequent point in time indicates a lack of significant progression of the neurological disease. In some embodiments, between the first point in time and the subsequent point in time, the subject has undergone treatment to modulate one or more targets listed in Table 2 and/or Table 4 and/or Table 6 and/or Table 7. In some embodiments, between the first point in time and the subsequent point in time, the subject has undergone treatment to modulate one or more targets listed in Table 2 and/or Table 4. In some embodiments, between the first point in time and the subsequent point in time, the subject has undergone treatment to modulate one or more targets listed in Table 6 and/or Table 7.

In some embodiments, the methods provided herein further comprise treating the subject with one or more modulators of one or more targets listed in Table 2 and/or Table 4 and/or Table 6 and/or Table 7. In some embodiments, the methods provided herein further comprise treating the subject with one or more modulators of one or more targets listed in Table 2 and/or Table 4. In some embodiments, the methods provided herein further comprise treating the subject with one or more modulators of one or more targets listed in Table 6 and/or Table 7. In some embodiments, the agent is a nucleic acid encoding one or more targets downregulated in Table 2 and/or Table 4 Table 6 and/or Table 7. In some embodiments, the agent is an antibody against one or more targets upregulated in Table 2 and/or Table 4 and/or Table 6 and/or Table 7. In some embodiments, the agent is a small molecule inhibitor of one or more targets upregulated in Table 2 and/or Table 4 and/or Table 6 and/or Table 7. In some embodiments, the agent is a small molecule activator of one or more targets downregulated in Table 2 and/or Table 4 and/or Table 6 and/or Table 7. In some embodiments, the agent is an inhibitor of one or more targets upregulated in Table 2 and/or Table 4 and/or Table 6 and/or Table 7 selected from the group consisting of a small molecule, antisense nucleic acid, interfering RNA, shRNA, siRNA, aptamer, ribozyme, and dominant-negative protein binding partner. In some embodiments, the diameter of the meningeal lymphatic vessel is increased by at least 20%. In some embodiments, the central nervous system of the subject comprises amyloid-beta plaques, and wherein increasing the fluid flow reduces the quantity of amyloid-beta plaques. In some embodiments, increasing the meningeal lymphatic drainage reduces the quantity of accumulated amyloid-beta plaques by at least 5%. In some embodiments, at least some of the accumulated amyloid-beta plaques are in the meninges of the subject's brain.

In some embodiments, the subject has the risk factor for the neurodegenerative disease. In some embodiments, the method further comprises determining the subject to have the risk factor for the neurodegenerative disease. In some embodiments, the risk factor comprises a risk factor for Alzheimer's disease selected from the group consisting of: diploidy for apolipoprotein-E-epsilon-4 (apo-E-epsilon-4), a variant in apo-J, a variant in phosphatidylinositol-binding clathrin assembly protein (PICALM), a variant in complement receptor 1 (CR3), a variant in CD33 (Siglec-3), or a variant in triggering receptor expressed on myeloid cells 2 (TREM2), age, familial AD, a symptom of dementia, or a combination of any of the listed risk factors.

In some embodiments, for any method or composition for use described herein, the agent is administered selectively to the meningeal space of the subject. In some embodiments, the agent is administered to the subject by a route selected from the group consisting of: intrathecal administration, nasal administration, transcranial administration, contact cerebral spinal fluid (CSF) of the subject, pumping into CSF of the subject, implantation into the skull or brain, contacting a thinned skull or skull portion of the subject with the agent, expression in the subject of a nucleic acid encoding one or more of the targets listed in Table 2 and/or Table 4 and/or Table 6 and/or Table 7, or a combination of any of the listed routes. In some embodiments, for any method or composition for use described herein, the effective amount of the agent is administered to the subject after determining the subject to have the risk factor for the neurodegenerative disease. In some embodiments, for any method or composition for use described herein, the effective amount of the agent is administered to the subject after determining whether a subject is afflicted with a neurological disease or at risk for developing a neurological disease according to the diagnostic methods disclosed herein. In some embodiments, for any method or composition for use described herein, the effective amount of the agent is administered to the subject after determining the subject to have the neurodegenerative disease. In some embodiments, for any method or composition for use described herein, the neurological disease is a neurodegenerative disease. In some embodiments, the neurodegenerative disease is selected from the group consisting of: Alzheimer's disease (AD), dementia, age-related dementia, Parkinson's disease (PD), cerebral edema, amyotrophic lateral sclerosis (ALS), Pediatric Autoimmune Neuropsychiatric Disorders Associated with Streptococcal Infections (PANDAS), meningitis, hemorrhagic stroke, autism spectrum disorder (ASD), brain tumor, and epilepsy. In some embodiments, for any method or composition for use described herein, the neurodegenerative disease is selected from the group consisting of: AD (such as familial AD and/or sporadic AD), PD, cerebral edema, ALS, PANDAS, meningitis, hemorrhagic stroke, ASD, brain tumor (such as glioblastoma), epilepsy, Down's syndrome, hereditary cerebral hemorrhage with amyloidosis-Dutch type (HCHWA-D), Familial Danish/British dementia, dementia with Lewy bodies (DLB), Lewy body (LB) variant of AD, multiple system atrophy (MSA), familial encephalopathy with neuroserpin inclusion bodies (FENIB), frontotemporal dementia (FTD), Huntington's disease (HD), Kennedy disease/spinobulbar muscular atrophy (SBMA), dentatorubropallidoluysian atrophy (DRPLA); spinocerebellar ataxia (SCA) type I, SCA2, SCA3 (Machado-Joseph disease), SCA6, SCA7, SCA17, Creutzfeldt-Jakob disease (CJD) (such as familial CJD), Kuru, Gerstmann-Straussler-Scheinker syndrome (GSS), fatal familial insomnia (FFI), corticobasal degeneration (CBD), progressive supranuclear palsy (PSP), cerebral amyloid angiopathy (CAA), multiple sclerosis (MS), AIDS-related dementia complex, or a combination of two or more of any of the listed items. In some embodiments, for any method or composition for use described herein the neurodegenerative disease is selected from the group consisting of: AD (such as familial AD and/or sporadic AD), PD, cerebral edema, ALS, PANDAS, meningitis, hemorrhagic stroke, ASD, brain tumor (such as glioblastoma), epilepsy, Down's syndrome, hereditary cerebral hemorrhage with amyloidosis-Dutch type (HCHWA-D), Familial Danish/British dementia, dementia with Lewy bodies (DLB), Lewy body (LB) variant of AD, multiple system atrophy (MSA), familial encephalopathy with neuroserpin inclusion bodies (FENIB), frontotemporal dementia (FTD), Huntington's disease (HD), Kennedy disease/spinobulbar muscular atrophy (SBMA), dentatorubropallidoluysian atrophy (DRPLA); spinocerebellar ataxia (SCA) type I, SCA2, SCA3 (Machado-Joseph disease), SCA6, SCA7, SCA17, Creutzfeldt-Jakob disease (CJD) (such as familial CJD), Kuru, Gerstmann-Straussler-Scheinker syndrome (GSS), fatal familial insomnia (FFI), corticobasal degeneration (CBD), progressive supranuclear palsy (PSP), cerebral amyloid angiopathy (CAA), AIDS-related dementia complex, or a combination of two or more of any of the listed items. In some embodiments, for any method or composition for use described herein the neurodegenerative disease is selected from the group consisting of AD (such as familial AD and/or sporadic AD), dementia, age-related dementia, PD, cerebral edema, ALS, PANDAS, meningitis, hemorrhagic stroke, ASD, epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, for any method or composition for use described herein, the neurodegenerative disease comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, for any method or composition for use described herein, the neurodegenerative disease comprises, consists essentially of, or consists of prion disease. In some embodiments, for any method or composition for use described herein, the neurodegenerative disease comprises, consists essentially of, or consists of a non-human prion disease such as scrapie, chronic wasting disease, or Bovine Spongiform Encephalopathy (BSE).

In some embodiments, the administration of the agent counteracts an effect of a decrease in fluid flow in the central nervous system. In some embodiments, the administration of the agent increases fluid flow in the central nervous system. In some embodiments, the amount of agent increases the diameter of a meningeal lymphatic vessel of the subject. In some embodiments, the fluid comprises lymphatic fluid, cerebral spinal fluid (CSF), and/or interstitial fluid (ISF).

In some embodiments, compositions are provided. In some embodiments, the composition comprises a compound identified by a method disclosed herein which treats a neurological disease. In some embodiments, the composition comprises an agent that decreases the copy number, level of expression, or level of activity of one or more targets upregulated in Table 2 and/or Table 4 and/or Table 6 and/or Table 7. In some embodiments, the composition comprises an agent that increases the copy number, level of expression, or level of activity of one or more targets downregulated in Table 2 and/or Table 4 and/or Table 6 and/or Table 7. In some embodiments pharmaceutical compositions are provided, comprising one or more compounds or agents disclosed herein.

The compositions and related methods summarized above and set forth in further detail below describe certain actions taken by a practitioner; however, it should be understood that they can also include the instruction of those actions by another party. Thus, actions such as "administering a viral vector" include "instructing the administration of a viral vector."

BRIEF DESCRIPTION OF THE FIGURES

FIGS. 1A-O show that impairing meningeal lymphatics affects brain CSF influx and ISF diffusion, worsens cognitive function and changes hippocampal gene expression profile. Seven days after lymphatic ablation mice were injected with 5 µL of ovalbumin-Alexa647 (OVA-A647) into the cisterna magna (i.c.m.) (FIG. 1A). Representative images of meningeal whole-mounts stained for LYVE-1/CD31 (scale bar, 1 mm) showing loss of meningeal vessel staining (FIG. 1B). Quantification of area fraction (%) occupied by LYVE-1+ lymphatic vessels (FIG. 1C) and LYVE-1$^-$CD31$^+$ blood vessels (FIG. 1D). Representative brain sections showing 4',6-diamidino-2-phenylindole (DAPI) and OVA-A647 (scale bar, 5 mm; inset scale bar, 1 mm) (FIG. 1E). Quantification of OVA-A647 area fraction (FIG. 1F). Data in FIGS. 1C, 1D, and 1F are is presented as mean±s.e.m., n=6 per group; one-way ANOVA with Bonferroni's post-hoc test was used in FIGS. 1C-D and 1F; FIGS. 1A-F are representative of 2 independent experiments; significant differences between vehicle/photoconversion and Visudyne/photoconversion were replicated in 5 independent experiments. Gadolinium (Gd) was injected (i.c.m.) and T1-weighted magnetic resonance imaging (MRI) acquisition was performed 7 days after meningeal lymphatic ablation (FIG. 1G). Representative images of sequence 1 and of Gd intensity gain in subsequent sequences (hippocampus delineated in red; scale bar, 3 mm) (FIG. 1H). Quantification of the Gd signal intensity gain over 16 sequences (relative to sequence 1) in hippocampus (FIG. 1I). Data in FIG. 1I are presented as mean s.e.m., n=4 per group; repeated measures two-way ANOVA with Bonferroni's post-hoc test; Figures G-I are representative of 2 independent experiments. Meningeal lymphatic ablation was performed twice and two weeks after the last intervention, open field (OF), novel location recognition (NLR), contextual fear conditioning (CFC) and Morris water maze (MWM) behavioral tests were performed (FIG. 1J) (See also FIGS. 9A-V for OF, NLR and CFC). Latency to platform (acquisition) (FIG. 1K). Time spent (%) in the target quadrant (probe) (FIG. 1L). Latency to platform (reversal) (FIG. 1M). Allocentric navigation strategies (%) used in the MWM acquisition (FIG. 1N) and reversal (FIG. 1O). Data in FIGS. 1K-M and FIGS. 1N-O are presented as mean±s.e.m., n=9 per group; repeated measures two-way ANOVA with Bonferroni's post-hoc test was used in FIGS. 1K, 1M, 1N, and 1O; one-way ANOVA with Bonferroni's post-hoc test was used in FIG. 1L; significant differences between vehicle/photoconversion and Visudyne/photoconversion were replicated in 3 independent experiments.

in FIGS. 2A-C, P-values were corrected for multiple hypothesis testing with the Benjamini-Hochberg false discovery rate procedure; in FIGS. 2C-D functional enrichment of differential expressed genes performed using gene sets from GO and KEGG and determined with Fisher's exact test. Old mice were injected (i.c.m.) with 2 µL of AAV1-CMV-EGFP (EGFP) or AAV1-CMV-mVEGF-C (mVEGF-C), at $10^{13}$ genome copies (GC)/mL. One month later, OVA-A647 was injected i.c.m (FIG. 2A). Insets of the superior sagittal sinus showing DAPI/LYVE-1/CD31 (scale bar, 200 µm) (FIG. 2F). Quantification of diameter (FIG. 2G) of LYVE-1+ lymphatic vessels and of area fraction (%) (FIG. 2H) of LYVE-1$^-$CD31$^+$ blood vessels. Representative sections of deep cervical lymph nodes (dCLNs) showing DAPI/LYVE-1/OVA-A647 (scale bar, 200 µm) (FIG. 2I). Quantification of LYVE-1 and OVA-A647 area fraction in dCLNs (FIG. 2J). Representative brain coronal sections showing DAPI/OVA-A647 (scale bar, 5 mm) (FIG. 2K). Quantification of OVA-A647 area fraction in brain sections (FIG. 2L). Data in FIGS. 2G, 2H, 2J, and 2L are presented as mean±s.e.m., n=5 in EGFP, n=6 in mVEGF-C; two-tailed Mann-Whitney test was used in FIGS. 2G, 2H, 2J, and 2L; FIGS. 2E=L are representative of 2 independent experiments. Old mice were injected with EGFP or mVEGF-C viruses (i.c.m.) after ligation of the lymphatics afferent to the dCLNs or sham surger. One month later, learning and memory was assessed in the NLR and MWM tests and mice were injected (i.c.m.) with OVA-A647 (FIG. 2M). Time with the object (%) was assessed in the NLR (FIG. 2N) training and (FIG. 2O) novel location tasks. Latency to platform (acquisition) (FIG. 2P). Time spent (%) in the target quadrant (probe) (FIG. 2Q). Latency to platform (reversal) (FIG. 2R). Representative sections of dCLNs showing DAPI/ LYVE-1/OVA-A647 (scale bar, 200 µm) (FIG. 2S). Quantification of OVA-A647 area fraction in dCLNs (FIG. 2T). Data in FIGS. 2N-R and 2T are presented as mean±s.e.m., n=9 in sham+EGFP and ligation+EGFP, n=10 in sham+ mVEGF-C and ligation+mVEGF-C; two-way ANOVA with Bonferroni's post-hoc test was used in FIGS. 2N, 2O, 2Q, and 2T; repeated measures two-way ANOVA with Bonferroni's post-hoc test was used in FIGS. 2P and 2R; FIGS. 2M-T refer to results from 2 independent experiments.

FIGS. 3A-L show the ablation of meningeal lymphatics aggravating amyloid pathology in AD transgenic mice. Young-adult 5×FAD mice were submitted to meningeal lymphatic ablation or control procedures. Procedures were repeated 3 weeks later and amyloid pathology was assessed 6 weeks after initial treatment (FIG. 3A). Staining for CD31/LYVE-1/Aβ in meninges (scale bar, 2 mm; inset scale bar, 500 µm) (FIG. 3B). Orthogonal view of IBA$^+$ macrophages clustering around an amyloid plaque in meninges of a 5×FAD with ablated lymphatics (scale bar, 200 µm) (FIG. 3C). Representative images of DAPI/Aβ in the hippocampus of 5×FAD mice from each group (scale bar, 500 µm) (FIG. 3D). Quantification of amyloid plaque size (FIG. 3E), number (FIG. 3F) and coverage (FIG. 3G) in the hippocampus of 5×FAD mice. Data in FIGS. 3E-G are presented as mean±s.e.m., n=10 per group; one-way ANOVA with Bonferroni's post-hoc test was used in FIGS. 3E-G; FIGS. 3A-G are representative of 2 independent experiments. Staining for amyloid pathology (FIG. 3H) was performed in human non-AD and AD brains and different meningeal layers (See also FIGS. 9A-M). Meningeal superior sagittal sinus tissue of non-AD (FIG. 3I) or AD (FIG. 3J) patients stained with DAPI/Aβ (scale bar, 2 mm). Meningeal dura mater tissue of non-AD (FIG. 3K) or AD (FIG. 3L) patients, stained for IBA1/Aβ (scale bars, 1 mm; orthogonal view inset scale bars, 50 µm). Data in FIGS. 3H-L refer to results of n=8 non-AD samples and n=9 AD samples and is representative of 2 independent experiments.

FIGS. 4A-D depicts data related to CMap analysis of the meningeal LEC transcriptome of old mice. PCA plot of transcripts from RNA-seq of lymphatic endothelial cells (LECs) sorted from the meninges of young-adult (2-3 months-old) and old (20-24 months-old) mice (FIG. 4A). Functional enrichment of differentially expressed genes revealed changes in gene sets important for the properties of LECs and the function of the lymphatic vessels (FIG. 4B). Running a list of significantly altered genes, 134 upregulated and 150 downregulated, on the Connectivity Map software (CMap, LINCS L1000 small molecule assay, Broad Institute Cambridge MA) revealed target genes that may predict some of the altered functional pathways in meningeal LECs from old mice (FIG. 4C). Running the same genes in the L1000CDS$^2$ tool, which also uses the LINCS L1000 small molecule expression profile dataset (developed by the Ma'ayan Lab, Icahn School of Medicine at Mount Sinai) disclosed candidate compounds/drugs, many of them FDA-approved and commercially available, that are predicted to revert, at least in part, the observed gene expression differences observed in old meningeal LECs (FIG. 4D).

FIGS. 5A-M shows ablation of meningeal lymphatics leading to decreased CSF macromolecule drainage without affecting meningeal/brain blood vasculature or brain ventricular volume. FIG. 5A shows seven days after meningeal lymphatic ablation, a volume of 5 µL of fluorescent oval-bumin-Alexa647 (OVA-A647) was injected intra-cisterna magna (i.c.m.), into the CSF, and drainage of tracer into the deep cervical lymph nodes (dCLNs) was assessed 2 h later. Representative images of OVA-A647 (red) drained into the dCLNs stained for LYVE-1 (green) and with DAPI (blue; scale bar, 200 µm). FIG. 5B shows quantification of OVA-A647 area fraction (%) in the dCLNs showed significantly less amount of tracer in the Visudyne/photoconversion group than in control groups (mean±s.e.m., n=6 per group; one-way ANOVA with Bonferroni's post-hoc test; FIGS. 5A and 5B are representative of 2 independent experiments; significant differences between vehicle/photoconversion and Visudyne/photoconversion groups were observed in a total of 5 independent experiments). FIG. 5C shows seven days after meningeal lymphatic ablation, mice from the 3 groups were submitted to magnetic resonance venography (MRV) or angiography (MRA) and 24 h later to T2-weighted MRI to assess blood-brain barrier integrity after i.v. injection of the contrast agent gadolinium (Gd) at a dose of 0.3 mmol/ Kg. FIG. 5D shows representative 3D reconstructions of intracranial veins and arteries of mice from each group (scale bar, 5 mm). FIGS. 5E-H show no significant changes between groups were observed for venous vessel volume (FIG. 5E), superior sagittal sinus (SSS) diameter (FIG. 5F), arterial vessel volume (FIG. 5G) and basilar artery diameter (FIG. 5H) (mean±s.e.m., n=5 in vehicle/photoconversion and in Visudyne/photoconversion, n=4 in Visudyne; one-way ANOVA with Bonferroni's post-hoc test). Using the Lymph4D software, it was possible to measure changes in signal intensity gain in MRI sequences 1-5 (relative to baseline) in the hippocampus of mice from each group (scale bar, 3 mm) (FIG. 5I). Quantification of the signal intensity gain (relative to baseline) in the hippocampus over 5 MRI acquisition sequences showed no differences between groups (mean±s.e.m., n=5 in vehicle/photoconversion and in Visudyne/photoconversion, n=4 in Visudyne; repeated measures two-way ANOVA with Bonferroni's post-hoc test) (FIG. 5J). Mice were subjected to T2-weighted MRI to assess volume changes in brain ventricles 7 days after injection of vehicle or Visudyne and photoconversion (FIG. 5K). Representative images of 3D reconstruction of brain ventricles of mice from the two groups (scale bar, 1 mm) (FIG. 5L). No differences were detected in the volume of the brain ventricles after meningeal lymphatic ablation (mean±s.e.m., n=5 per group; two-tailed Mann-Whitney test) (FIG. 5M).

FIGS. 6A-B are representative of 2 independent experiments.

FIGS. 8A-I show ablation of meningeal lymphatic vessels impairs efflux of macromolecules from the brain. Seven days after meningeal lymphatic ablation, 1 μL of fluorescent OVA-A647 (0.5 mg/mL in artificial CSF) was stereotaxically injected (coordinates from bregma, AP=+1.5 mm, ML=-1.5 mm, DV=+2.5 mm) into the brain parenchyma (FIG. 8A). Representative brain sections rostral and caudal to the injection site, stained for glial fibrillary acidic protein (GFAP, in green), demonstrating OVA-A647 (red) coverage of the brain parenchyma in the Visudyne/photoconversion group and the control groups (scale bar, 5 mm) (FIG. 8A). Quantification of OVA-A647 area fraction (%) in the injected brain hemisphere showing a significantly higher level in the Visudyne/photoconversion group, when compared to both control groups (mean±s.e.m., n=6 per group; one-way ANOVA with Bonferroni's post-hoc test) (FIG. 8C). Seven days after meningeal lymphatic ablation, 1 μL of fluorescent Aβ$_{42}$-HiLyte647 (0.05 μg/mL in artificial CSF)

was stereotaxically injected (coordinates from bregma, AP=+1.5 mm, ML=−1.5 mm, DV=+2.5 mm) into the brain parenchyma (FIG. 8D). Representative brain sections rostral and caudal to the injection site, stained for GFAP (green), demonstrating Aβ$_{42}$-HiLyte647 (red) coverage of the brain parenchyma in the Visudyne/photoconversion group and the control groups (scale bar, 5 mm) (FIG. 8E). Quantification of Aβ$_{42}$-HiLyte647 area fraction (%) in the injected brain hemisphere showing a significantly higher level in the Visudyne/photoconversion group, when compared to both control groups (mean±s.e.m., n=6 per group; one-way ANOVA with Bonferroni's post-hoc test) (FIG. 8F). Seven days after meningeal lymphatic ablation, 1 μL of fluorescent low density lipoprotein (LDL)-BODIPY FL (0.1 mg/mL in artificial CSF) was stereotaxically injected (coordinates from bregma, AP=+1.5 mm, ML=−1.5 mm, DV=+2.5 mm) into the brain parenchyma (FIG. 8G). Representative brain sections rostral and caudal to the injection site, stained for GFAP (red), demonstrating LDL-BODIPY FL (green) coverage of the brain parenchyma in the Visudyne/photoconversion group and the control groups (scale bar, 5 mm) (FIG. 8H). Quantification of LDL-BODIPY FL area fraction (%) in the injected brain hemisphere showing a significantly higher level in the Visudyne/photoconversion group, when compared to both control groups (mean s.e.m., n=6 per group; one-way ANOVA with Bonferroni's post-hoc test) (FIG. 8I).

Figure 9L:
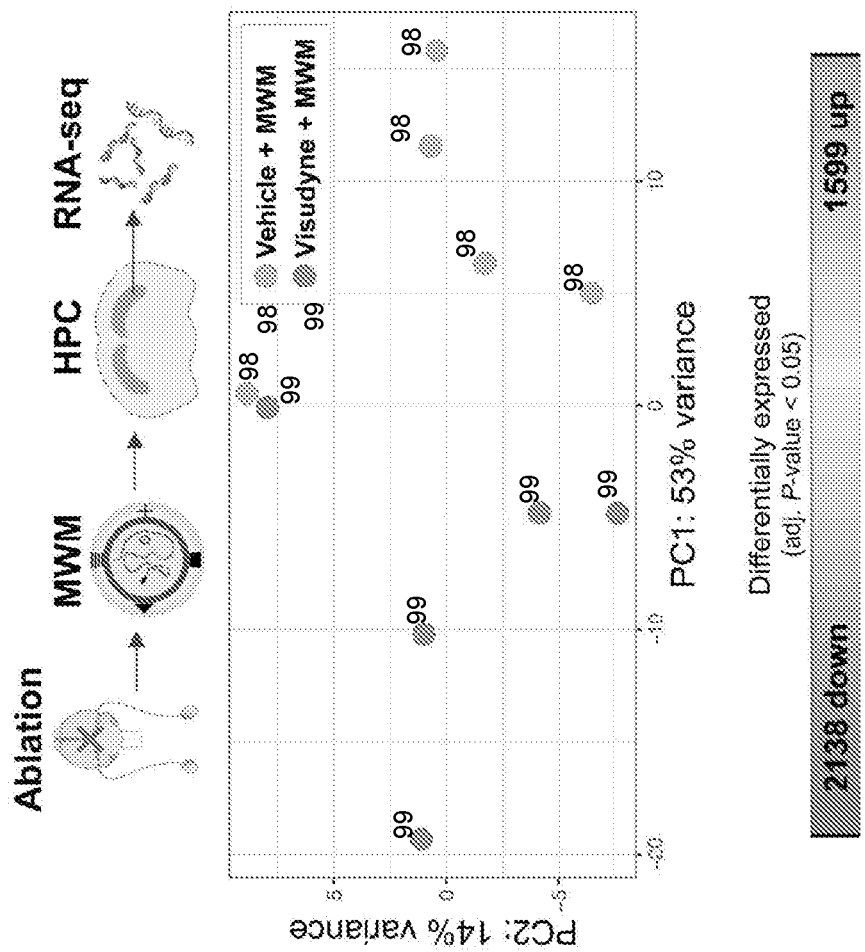
Figure 9K:
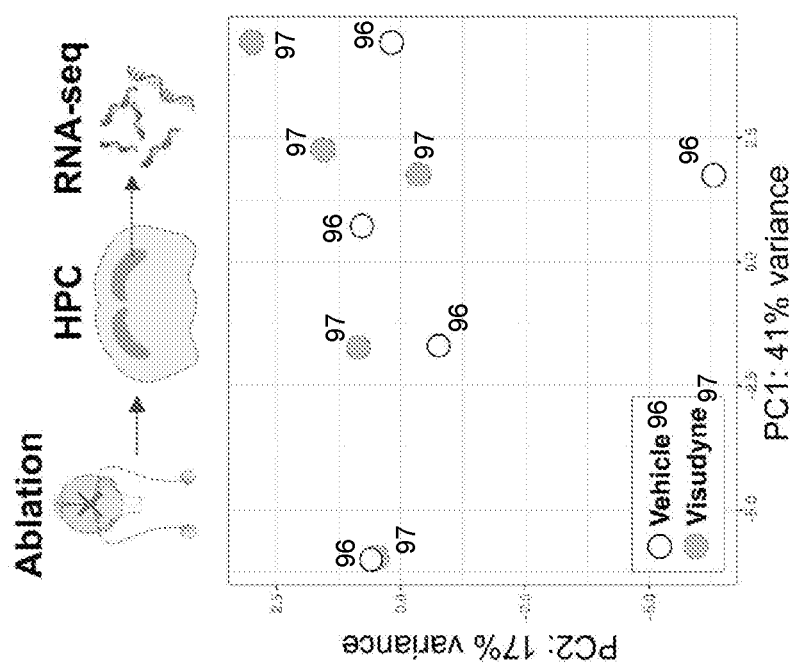
Figure 9M:
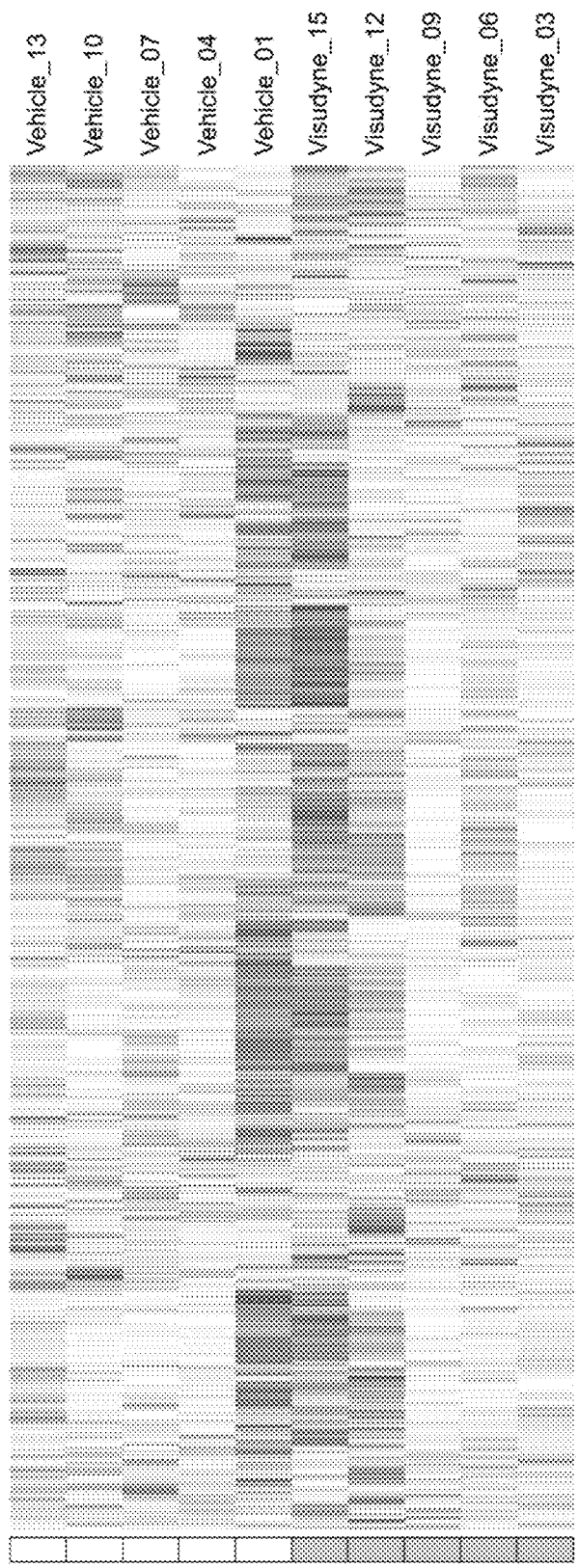
Figure 9N:
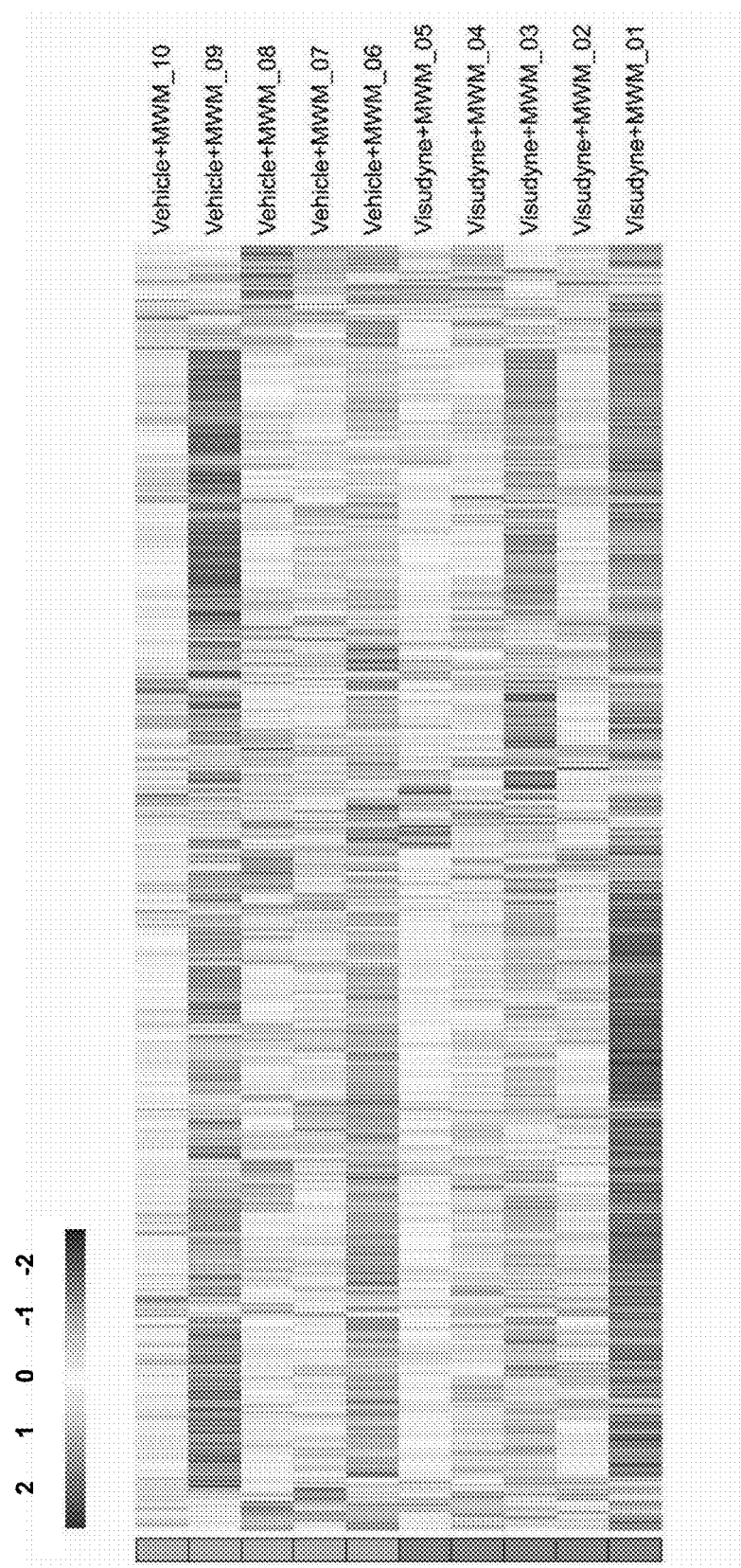
Figures 9O, 9P:
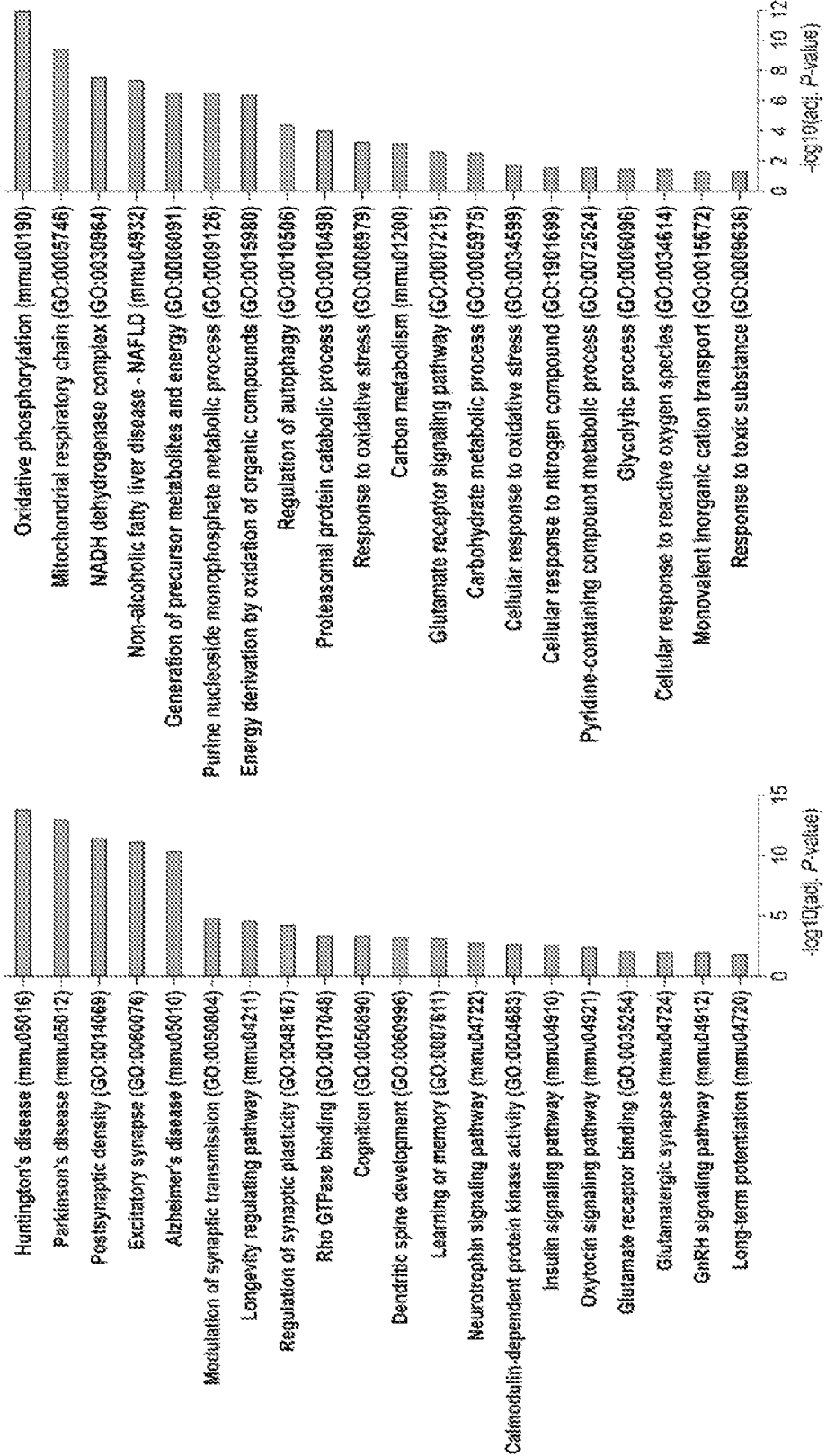
Figure 9Q:
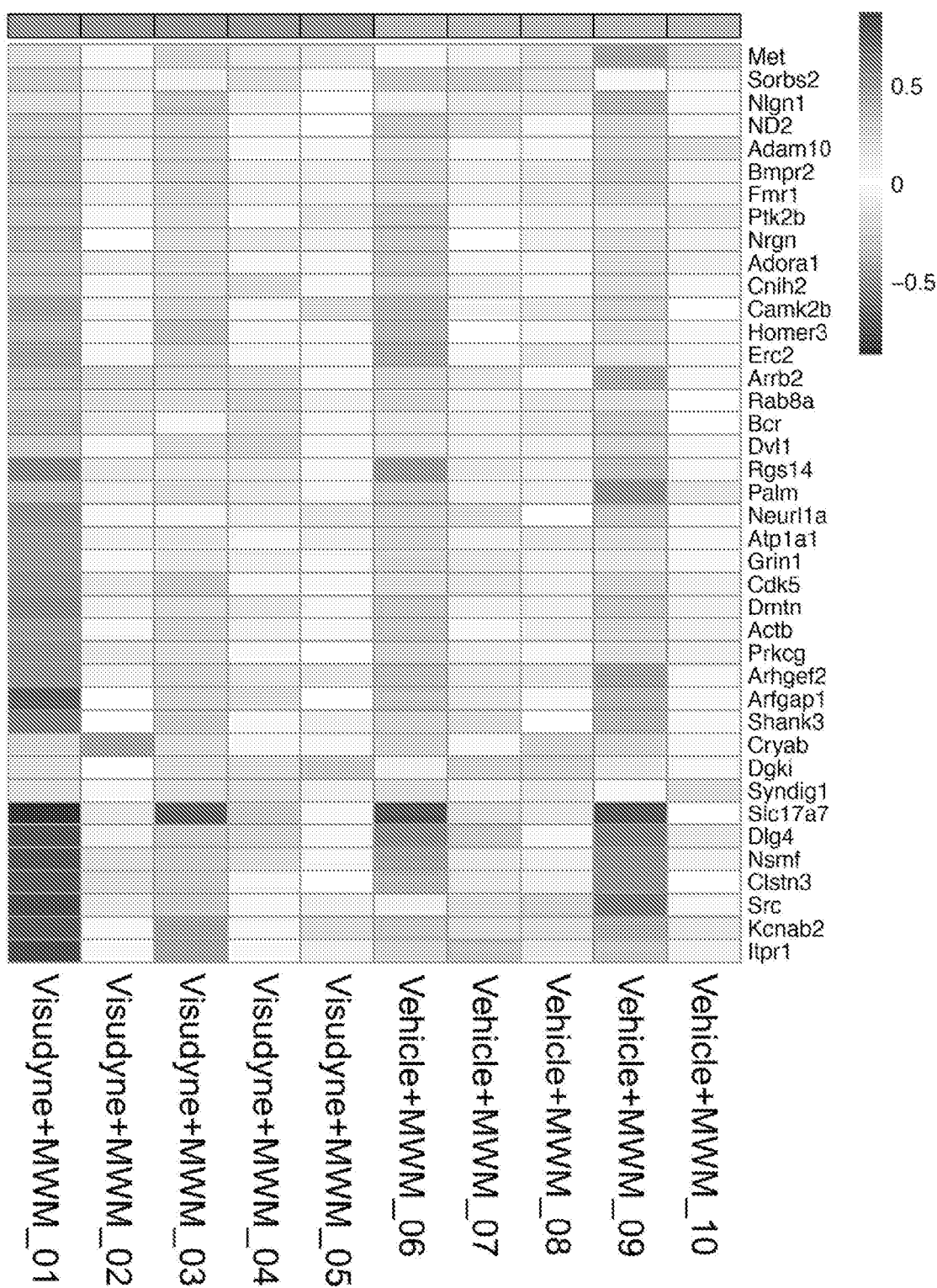
Figure 9R:
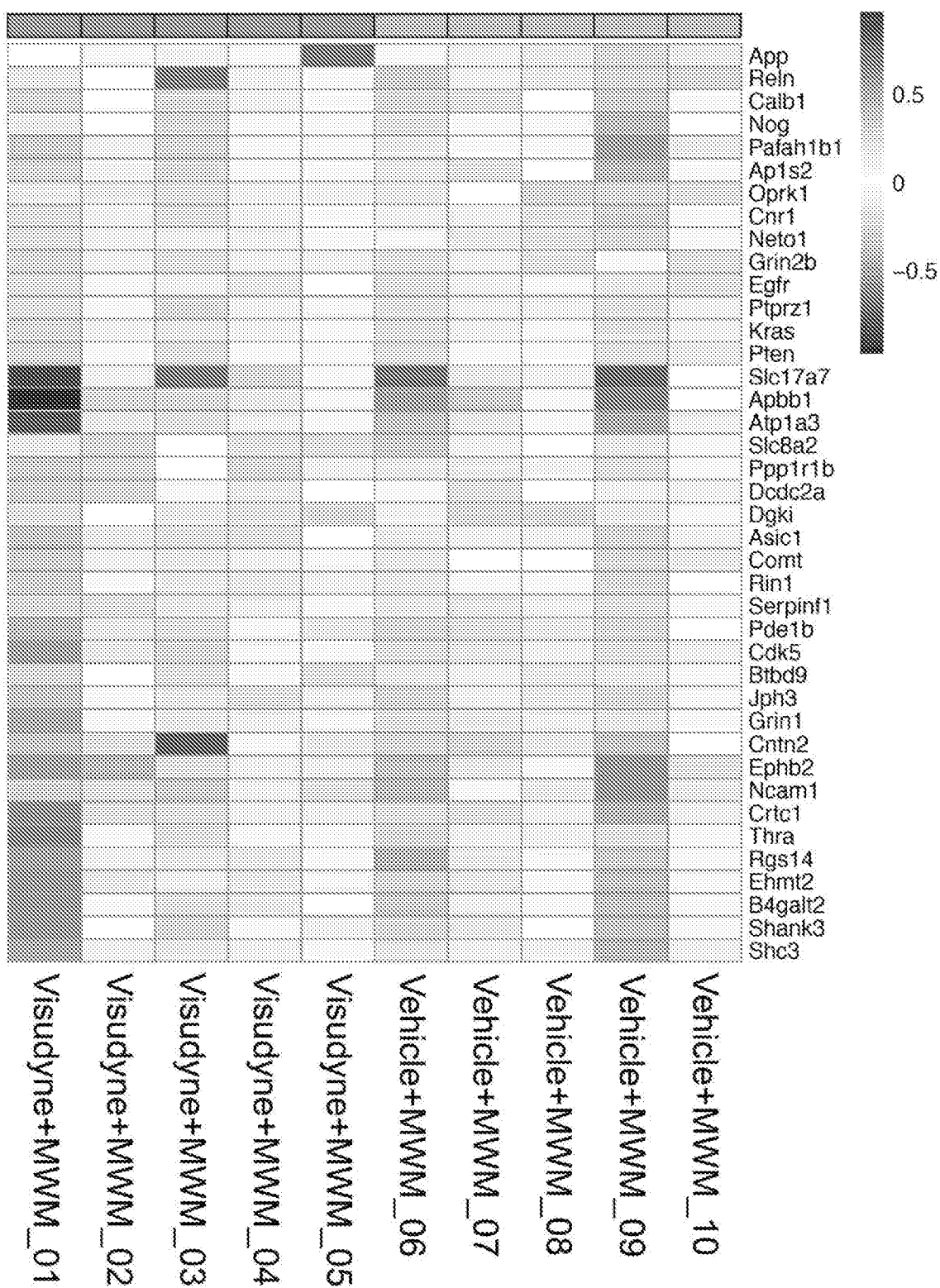
Figure 9S:
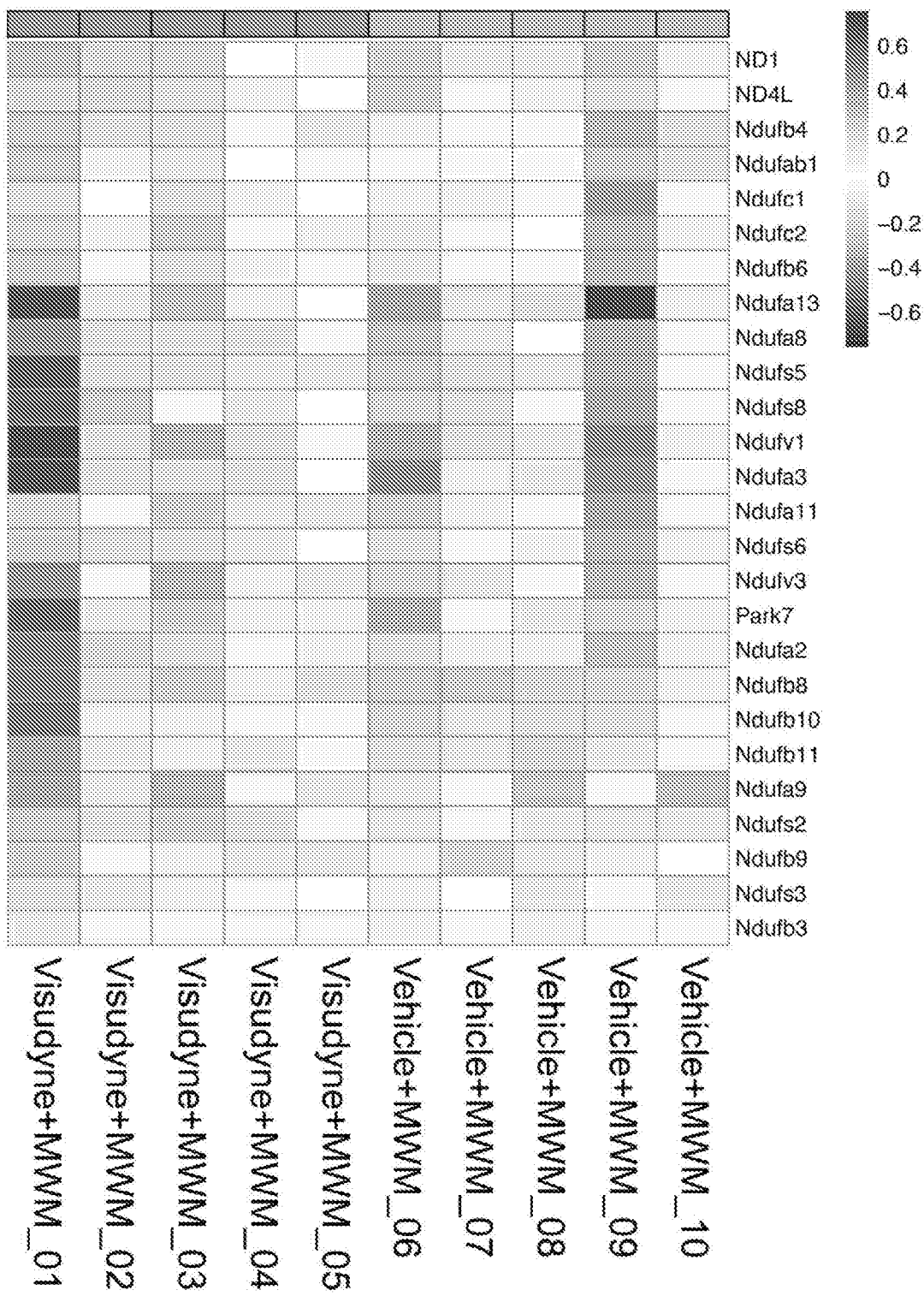
Figure 9T:
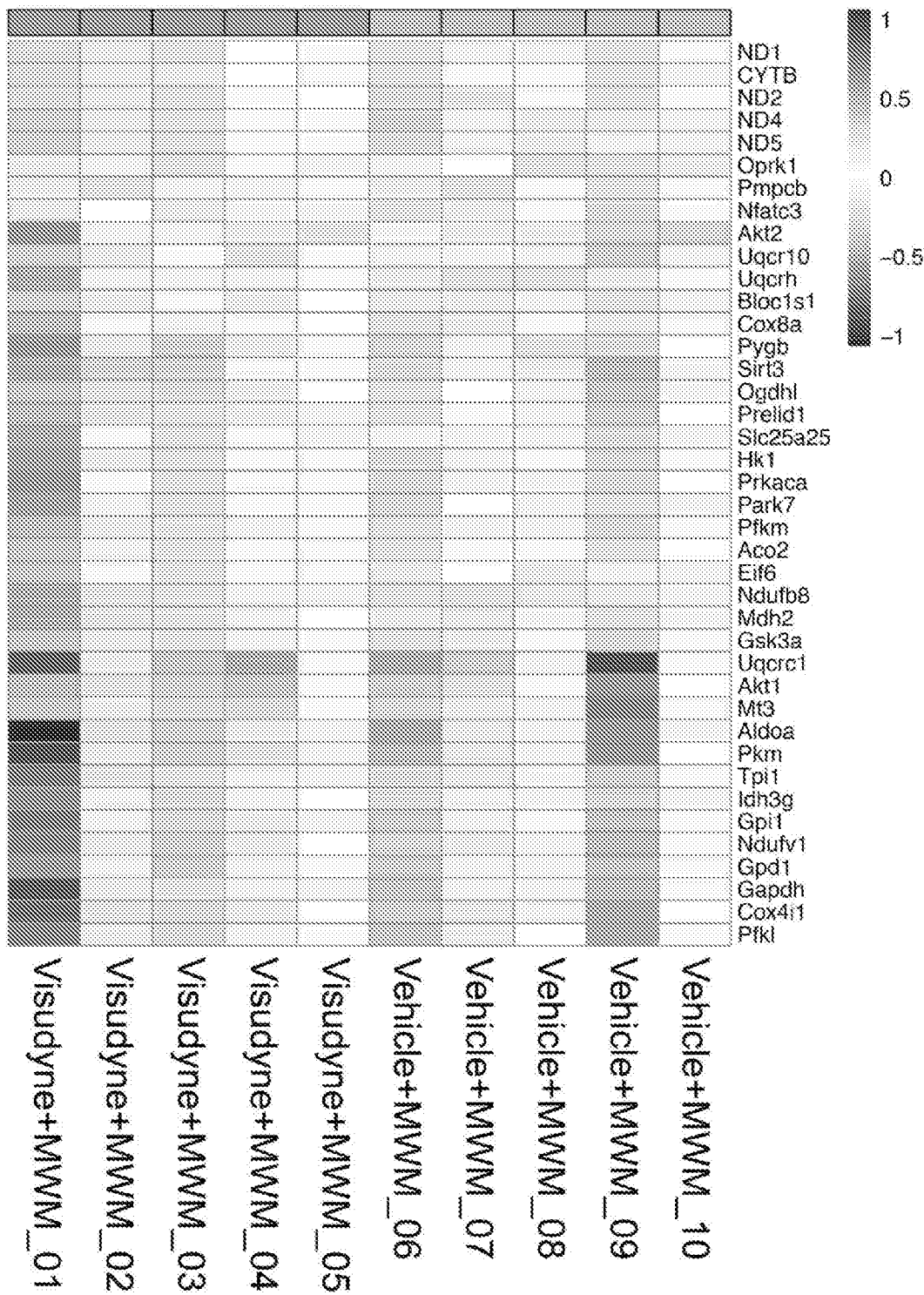
Figure 9U:
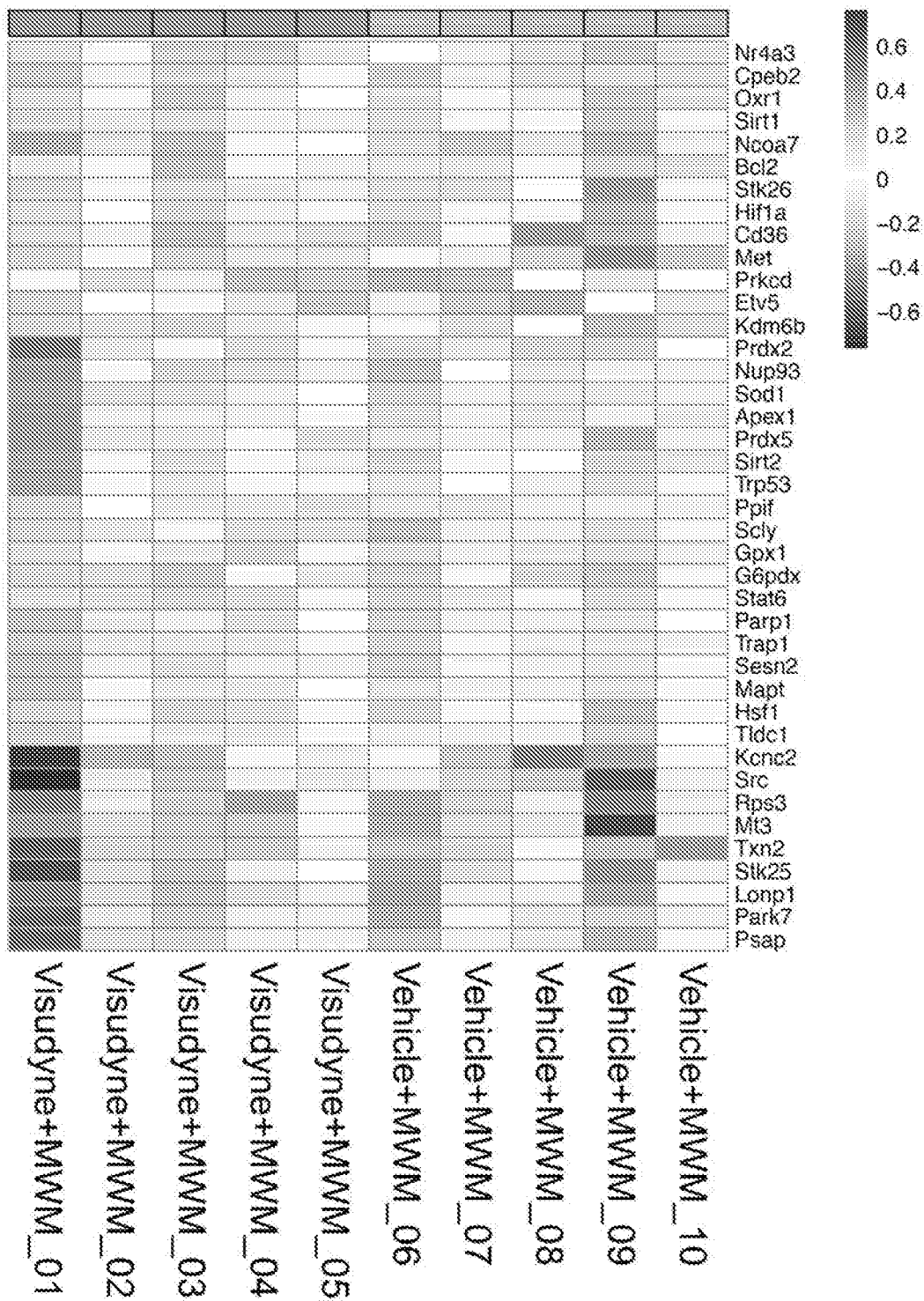
Figure 9V:
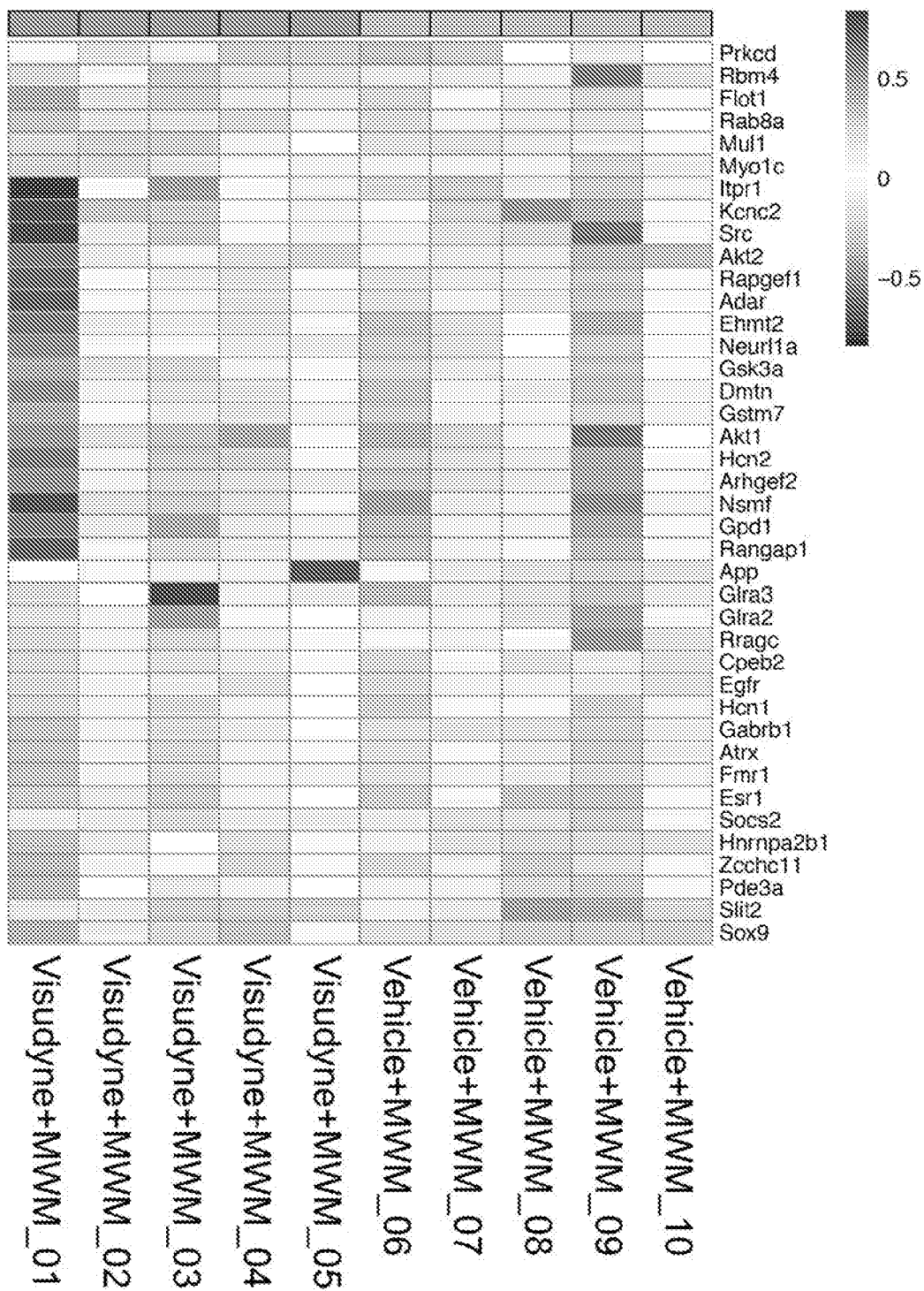

FIGS. 9A-V depict cognitive deficits and hippocampal RNA-seq analysis after impairing meningeal lymphatic function. No differences in (FIG. 9A) total distance and in (FIG. 9B) time in center of the open field arena were observed between vehicle/photoconversion, Visudyne and Visudyne/photoconversion groups (mean s.e.m., n=9 per group; one-way ANOVA with Bonferroni's post-hoc test). Performance of mice from the 3 groups was also identical both in the (FIG. 9C) training and in the (FIG. 9D) novel location task of the novel location recognition paradigm (mean±s.e.m., n=9 per group; two-way ANOVA with Bonferroni's post-hoc test). Mice performance in the contextual fear conditioning paradigm showed no differences between groups in the (FIG. 9E) context test, but a statistically significant difference in the (FIG. 9F) cued test (mean±s.e.m., n=9 per group; one-way ANOVA with Bonferroni's post-hoc test). The cognitive performance of adult mice was assessed in the Morris water maze (MWM) test, one week after sham surgery or surgical ligation of the lymphatics afferent to the dCLNs (FIG. 9G). Ligated mice presented a significant increase in the (FIG. 9H) latency to platform during acquisition, when compared to sham-operated mice. No significant differences between groups were observed in the (FIG. 9I) % of time spent in the target quadrant in the probe trial or in the (FIG. 9J) reversal (mean±s.e.m., n=8 in sham, n=9 in ligation; repeated measures two-way ANOVA with Bonferroni's post-hoc test was used in FIGS. 9H and 9J; two-tailed Mann-Whitney test was used in FIG. 9I). Vehicle or Visudyne injection with photoconversion were performed twice within two weeks interval. Total RNA was extracted from the hippocampus of mice from both groups and sequenced (RNA-seq) (FIG. 9K). RNA-seq principal component (PC) analysis did not show a differential clustering of samples from vehicle and Visudyne groups. Heatmap showing relative expression levels of genes in vehicle/photoconversion and in Visudyne/photoconversion samples (FIG. 9L). After meningeal lymphatic ablation (twice within two weeks interval) and MWM performance, total RNA was extracted from the hippocampus of mice from vehicle/photoconversion or Visudyne/ photoconversion groups and sequenced. RNA-seq principal component (PC) analysis demonstrating a differential clustering of samples from vehicle and Visudyne groups. A total of 2138 genes were down-regulated and 1599 genes were up-regulated in the hippocampus after meningeal lymphatic ablation and MWM performance (Table 2) (FIG. 9M). Heatmap (FIG. 9N) showing relative expression levels of genes in vehicle/photoconversion and in Visudyne/photoconversion samples (color scale bar values represent standardized r log-transformed values across samples for FIGS. 9L and 9N). Neurological disease, neuronal activity and synaptic plasticity related GO and KEGG terms enriched upon Visudyne treatment, as measured by the −log 10(adj. P-value) (FIG. 9O). GO and KEGG terms related with metabolite generation and processing, glycolysis and mitochondrial respiration and oxidative stress that were enriched, as measured by the −log 10(adj. P-value), upon Visudyne treatment and MWM performance (FIG. 9P). Heatmap showing relative expression levels of genes involved in two of the significantly altered GO terms related to excitatory synapse (FIG. 9Q) and Learning or memory (FIG. 9R). Heatmaps showing relative expression levels of genes involved in four of the significantly altered GO terms related to NADH dehydrogenase complex (FIG. 9S), Generation of precursor metabolites and energy (FIG. 9T), Cellular response to oxidative stress (FIG. 9U) and Cellular response to nitrogen compound (FIG. 9V). Datasets in FIGS. 9K-V all consist of n=5 per group; in FIGS. 9K and 9M P-values were corrected for multiple hypothesis testing with the Benjamini-Hochberg false discovery rate procedure; in FIG. 9L and FIGS. 9N-V functional enrichment of differential expressed genes was performed using gene sets from GO and KEGG and determined with Fisher's exact test; color scale bar values in FIG. 9N and FIG. 9Q-V represent standardized r log-transformed values across samples.

Figure 10C:
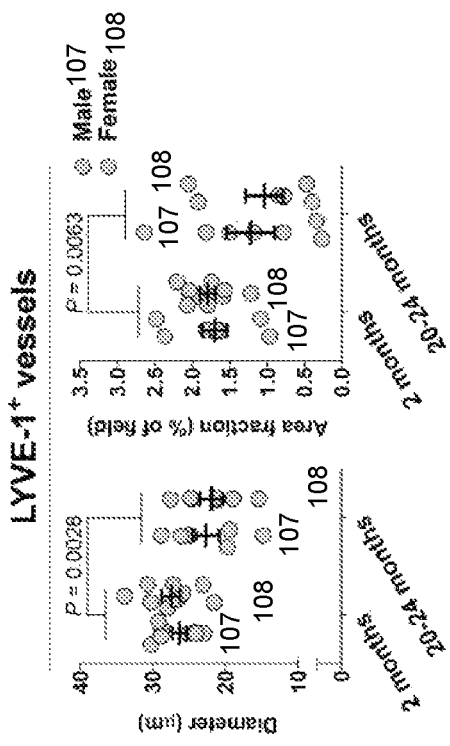
Figure 10E:
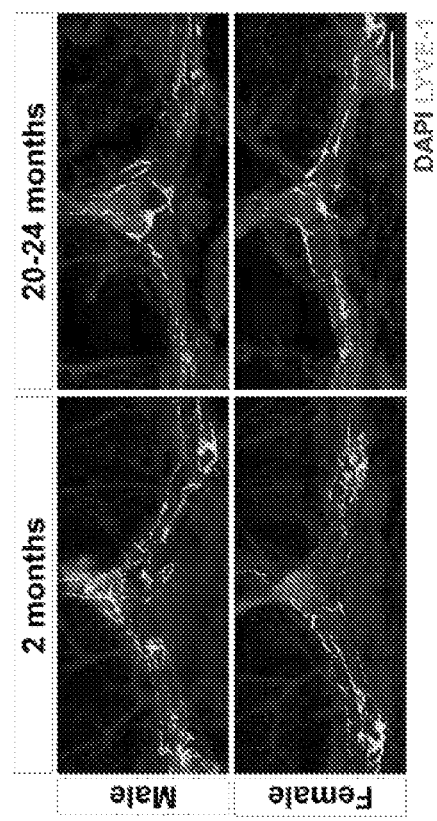
Figure 10D:
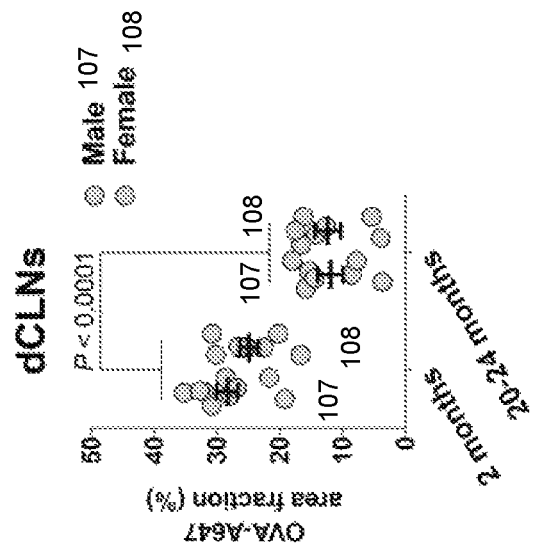
Figure 10F:
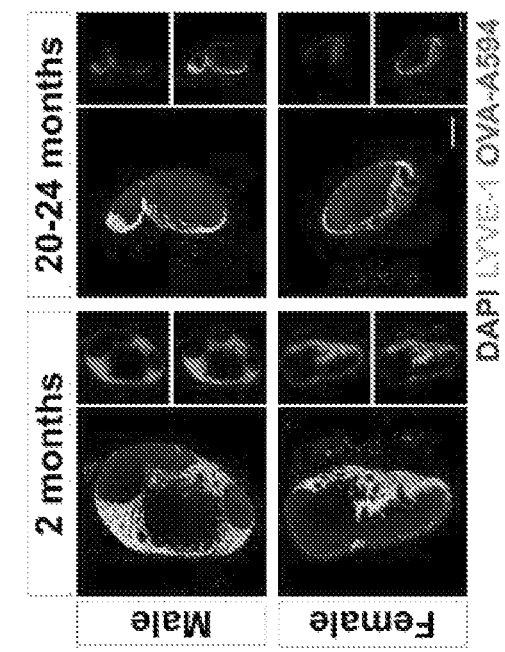
Figure 10G:
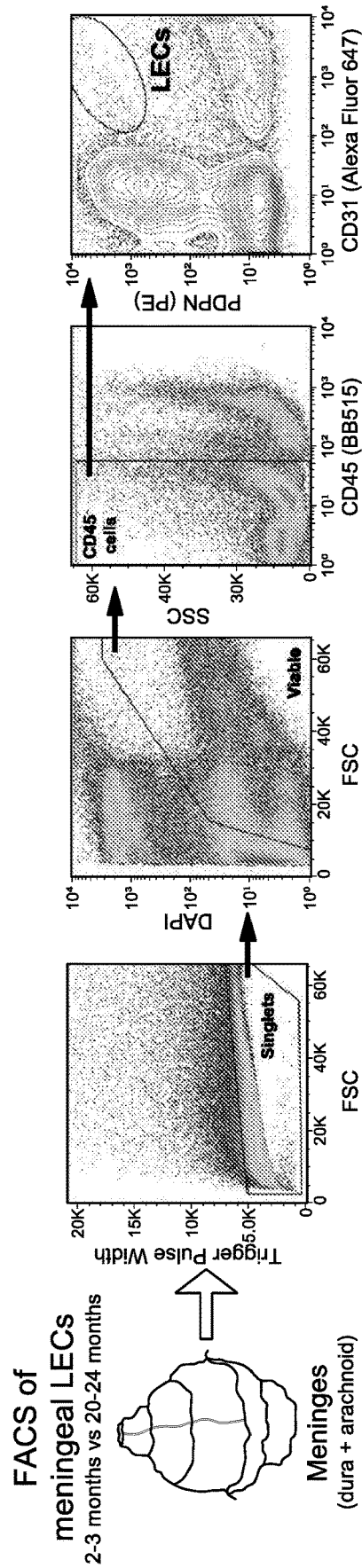
Figure 10H:
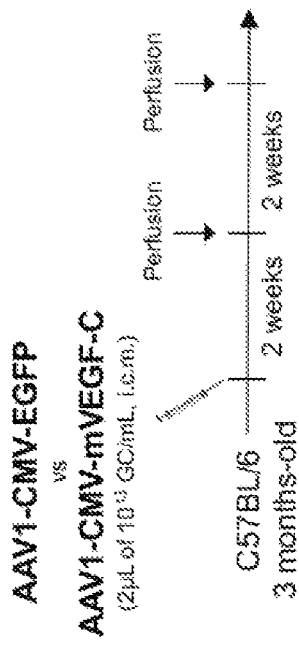
Figure 10I:
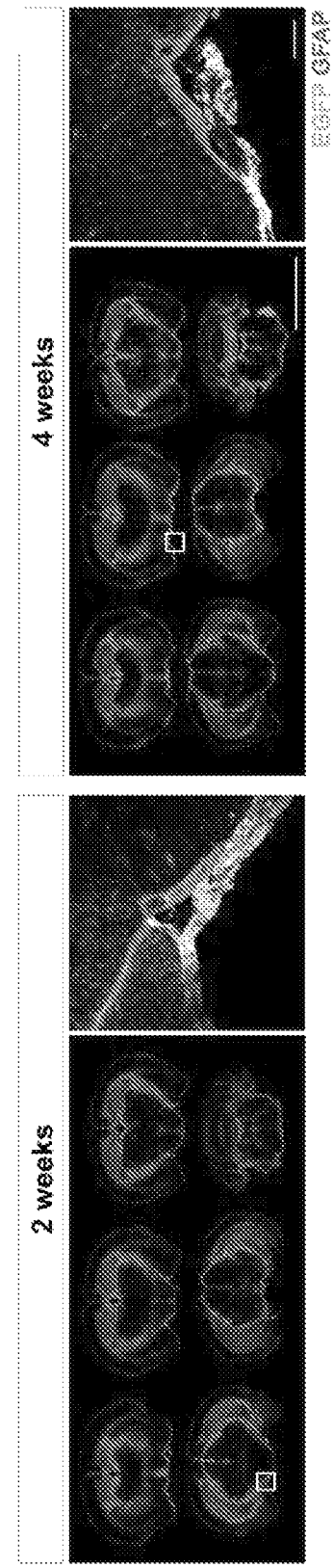
Figure 10J:
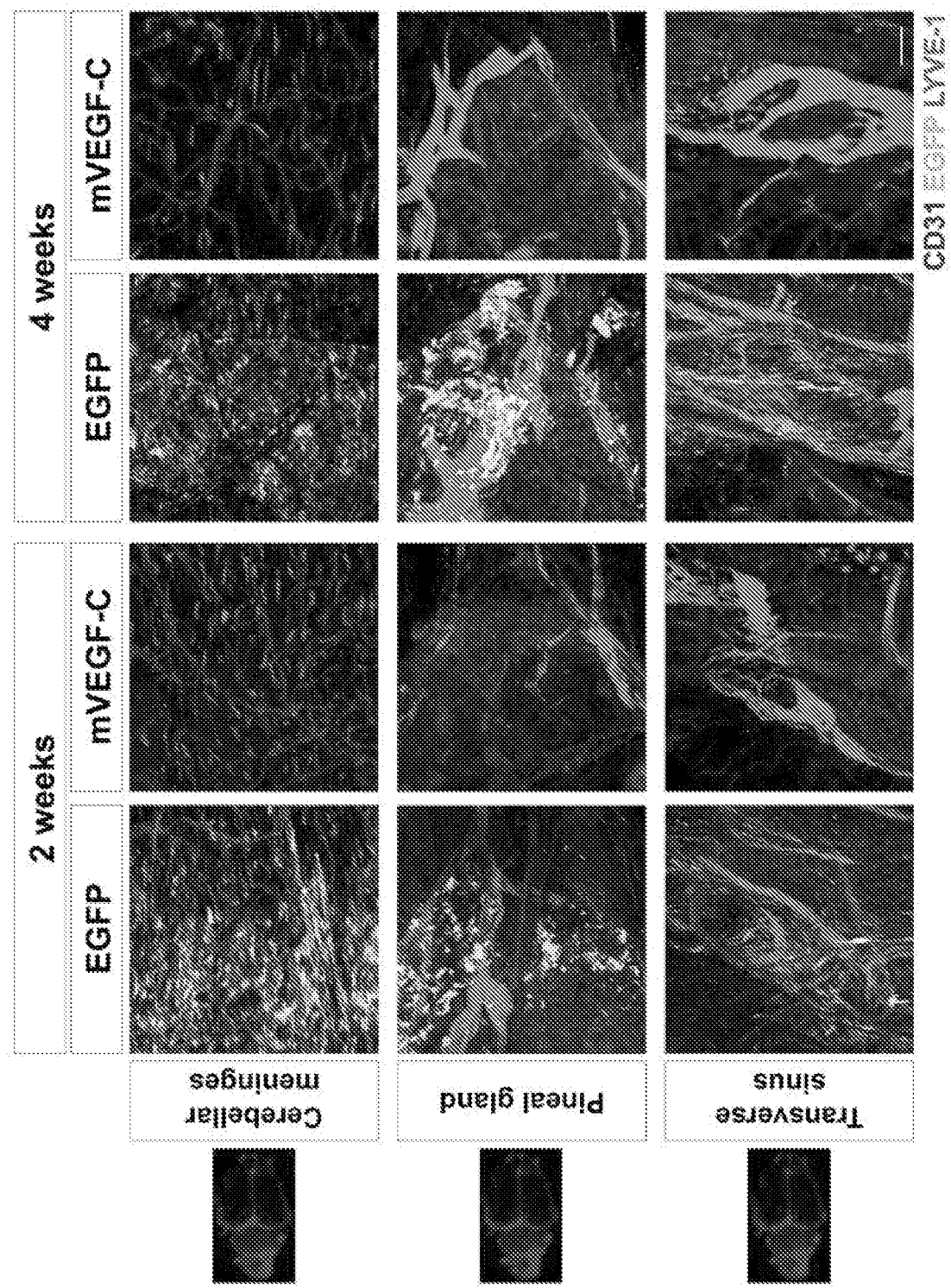
Figure 10N:
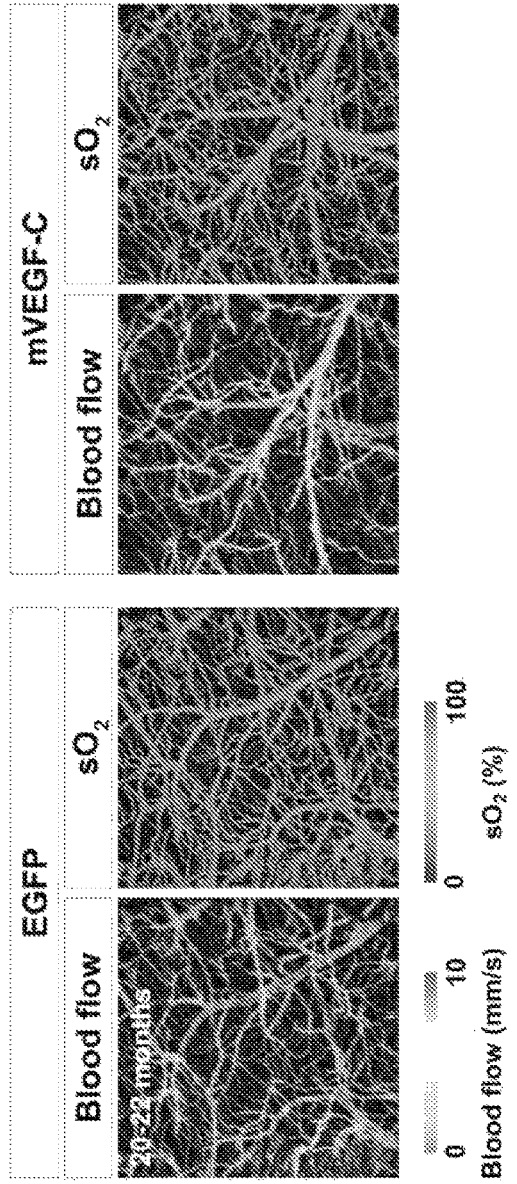
Figure 10P:
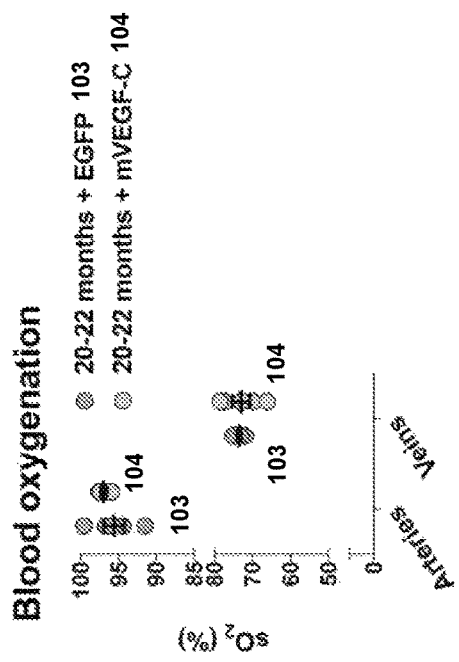
Figure 10O:
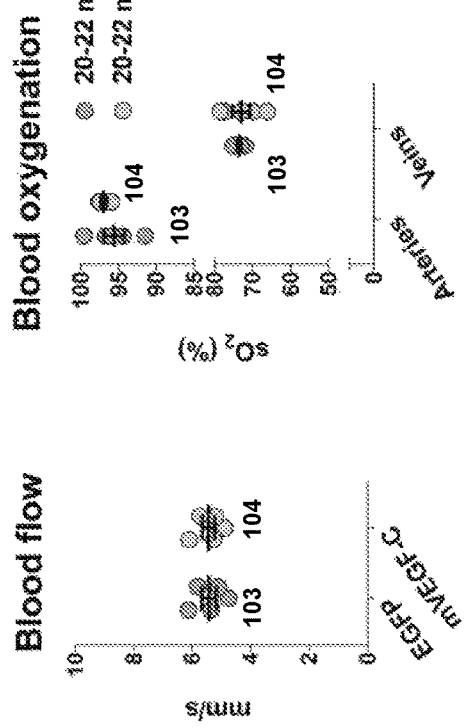
Figure 10Q:
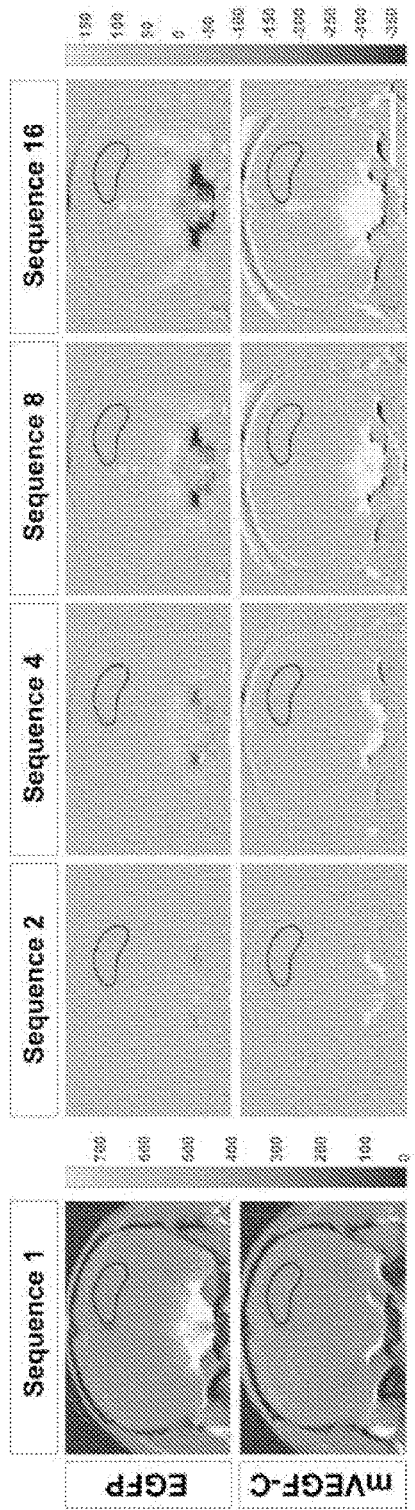
Figure 10R:
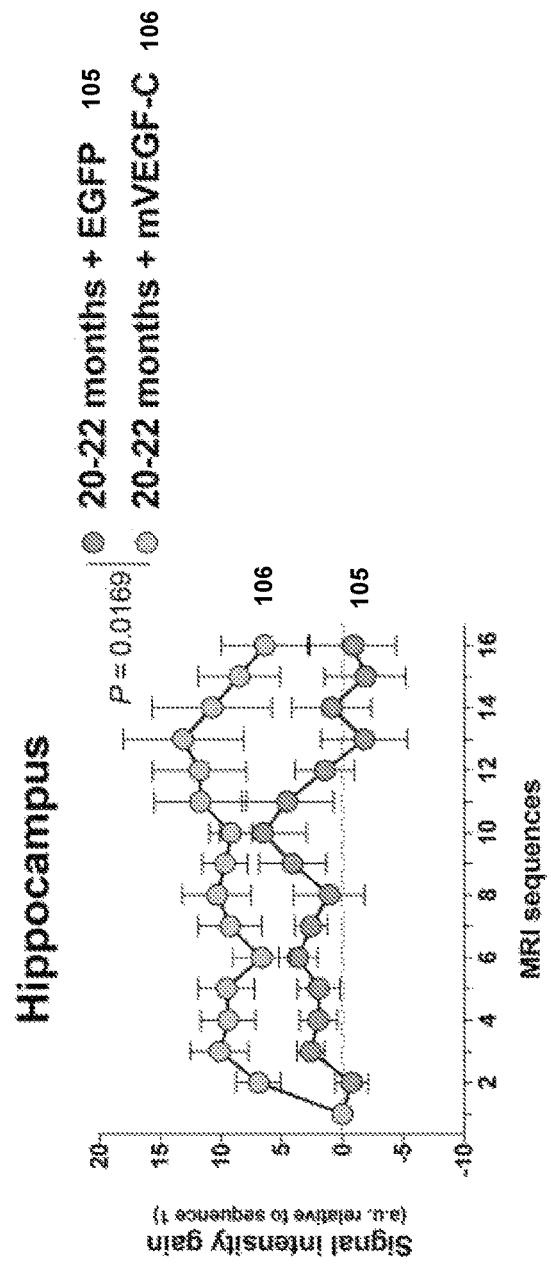

FIGS. 10A-R depict a characterization of meningeal lymphatics in young and old mice and improvement of lymphatic function by viral-mediated expression of mVEGF-C. OVA-A647 was injected into the CSF (i.c.m.) of young-adult (3 months of age) and old (20-24 months of age) mice. Representative brain sections stained with DAPI (blue) showing degree of OVA-A647 (red) influx into the parenchyma (scale bar, 5 mm; inset scale bar, 2 mm) (FIG. 10A). Quantification of OVA-A647 area fraction (%) in brain sections (mean±s.e.m., n=6 in 3 months, n=8 in 20-24 months; two-tailed Mann-Whitney test; representative of 2 independent experiments) (FIG. 10B). Representative images of DAPI (blue) and LYVE-1 (green) staining in meningeal whole-mounts of young-adult (2 months-old) and old (20-24 months-old) male and female mice (scale bar, 1 mm) (FIG. 10C). Measurement of LYVE-1$^+$ vessel diameter and area fraction showed a significant decrease in both parameters in old mice, when compared to young-adults, in both females and males (FIG. 10D). Representative images of DAPI (blue) and LYVE-1 (green) staining in dCLNs 2 h after injection of OVA-A594 (red) into the CSF of young-adult and old mice from both genders (scale bar, 200 μm) (FIG. 10E). Quantification of OVA-A594 area fraction (%) in the dCLNs of mice from different ages and genders showed a significant decrease in 20-24 months-old female and male mice (FIG. 10F). Data in FIGS. 10D and 10F are presented as mean±s.e.m., n=9 per group at 2 months, n=7 per group at 20-24 months for male and female; two-way ANOVA with Bonferroni's post-hoc test was used in FIGS. 10D and 10F; data were pooled from 2 independent experiments. Representative dot and contour plots showing the gating strategy used to isolate meningeal lymphatic endothelial cells (LECs) by fluorescence-activated cell sorting (FACS) from the meninges of young-adult and old mice (n=3 per group, pooled from 2 independent experiments) (FIG. 10G). Adult mice were injected i.c.m. with 2 μL of AAV1-CMV-EGFP (EGFP) or AAV1-CMV-mVEGF-C (mVEGF-C), both at $10^{13}$ genome copies (GC)/mL, and transcardially perfused with saline 2 or 4 weeks later (FIG. 10H). Representative brain coronal sections of mice showing EGFP$^+$ infected cells (green) in the pia mater, surrounding the GFAP$^+$ glia limitans (red) of the brain parenchyma, at 2 and 4 weeks post injection (scale bar, 5 mm; inset scale bar, 200 μm) (FIG. 10I). Representative insets from meningeal whole-mounts stained for CD31 (blue), EGFP (green) and LYVE-1 (red; scale bar, 200 μm). Green cells are observed in the cerebellar meninges, pineal gland and transverse sinus in the EGFP group at 2 and 4 weeks, but not in the same regions of the meninges in the mVEGF-C group (FIG. 10J). Representative images of LYVE-1+ lymphatic vessels (red) and LYVE-1$^-$CD31$^+$ blood vessels (blue) in the superior sagittal sinus of mice treated with either EGFP or mVEGF-C, for 2 or 4 weeks (scale bar, 200 μm) (FIG. 10K). Mice treated with AAV1 expressing mVEGF-C presented a significant increase in lymphatic vessel diameter (FIG. 10L), but not in coverage by blood vessels (FIG. 10M). Data in FIGS. 10L and 10M are presented as mean±s.e.m., n=4 per group at 2 weeks, n=3 per group at 4 weeks; two-way ANOVA with Bonferroni's post-hoc test was used in FIGS. 10L and 10M; data in FIGS. 10H-10M are representative of 2 independent experiments. Representative images of blood flow (mm/s) and arterial and venous blood oxygenation (% of $sO_2$) readings obtained by Photoacoustic imaging of brain/meningeal vasculature of old mice (20-22 months-old) treated for 1 month with EGFP or mVEGF-C virus (both at $10^{13}$ GC/mL) (FIG. 10N). The different treatments did not affect blood flow (FIG. 10N) or blood oxygenation (FIG. 10P) in the brain/meninges of old mice (mean±s.e.m., n=5 per group; two-tailed Mann-Whitney test was used in FIG. 10N and two-way ANOVA with Bonferroni's post-hoc test was used in FIG. 10P; data results from a single experiment). Old mice (20-22 months-old) were injected i.c.m. with 2 μL of viral vectors expressing EGFP or mVEGF-C. One month later, T1-weighted MRI acquisition was performed after i.c.m. injection of 5 μL of gadolinium (25 mM in saline). Using the Lymph4D software, it was possible to measure the rate of contrast agent influx into the delineated brain hippocampal region of mice from both groups (scale bar, 3 mm). Images in sequence 2 and subsequent were obtained by subtraction of sequence 1 (FIG. 10Q). Quantification of the signal intensity gain (relative to sequence 1) in the hippocampus revealed a significant increase in the mVEGF-C group, when compared to EGFP (mean±s.e.m., n=4 per group; repeated measures two-way ANOVA with Bonferroni's post-hoc; data was pooled from 2 independent experiments) (FIG. 10R).

Figure 11A:
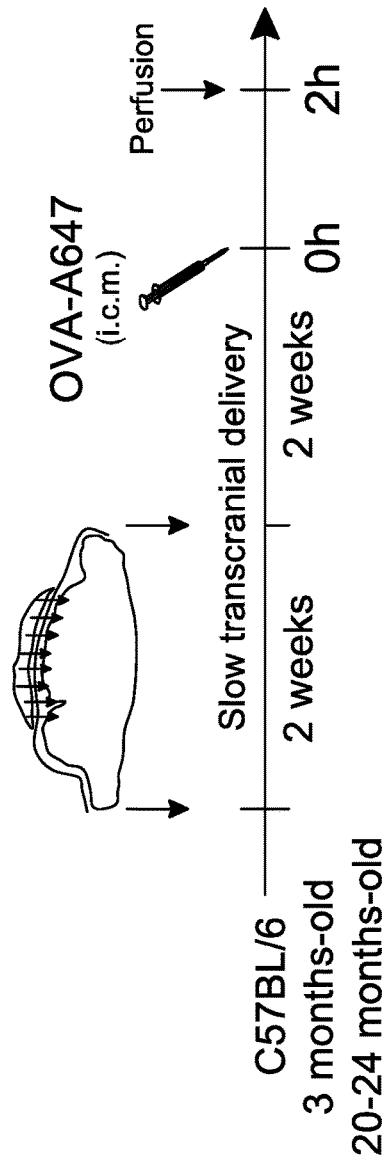
Figure 11C:
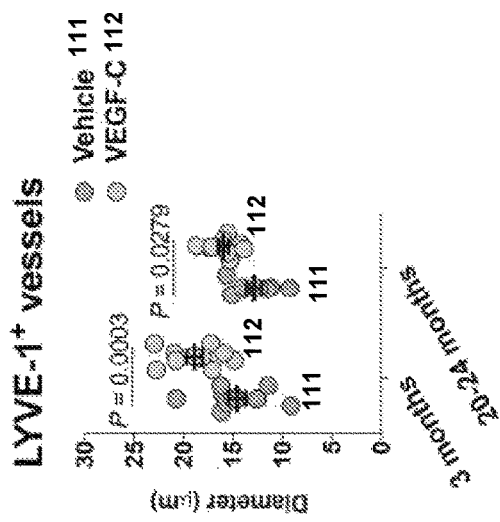
Figure 11B:
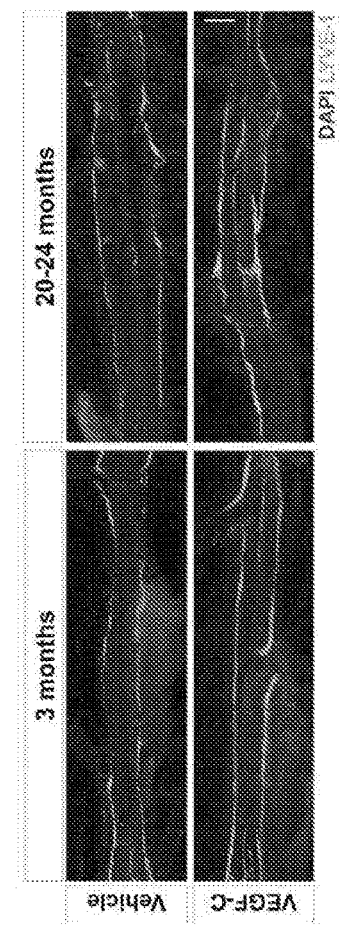
Figure 11Q:
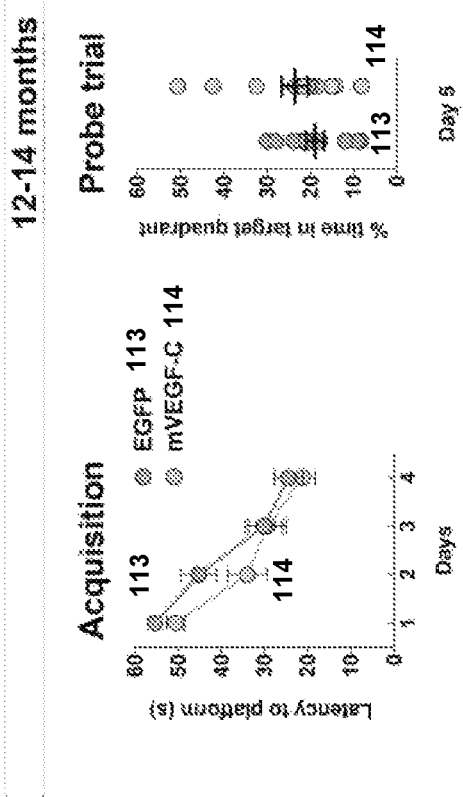
Figure 11R:
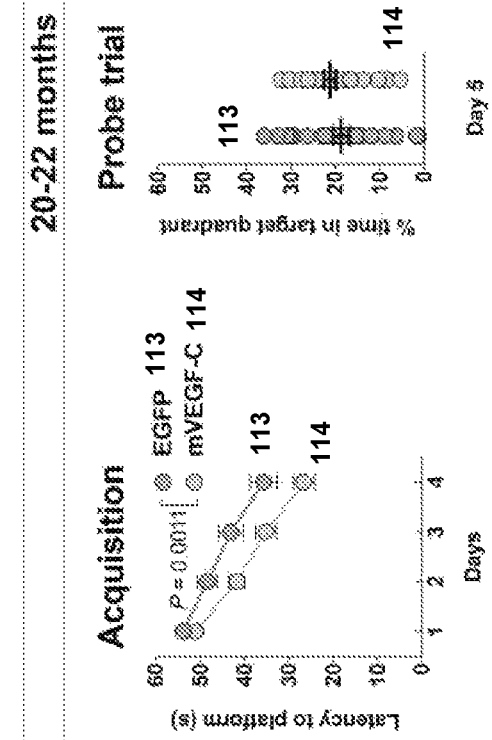

FIGS. 11A-U show treatment with VEGF-C improves meningeal lymphatic function, brain perfusion by CSF macromolecules and cognitive performance in old mice. Hydrogel alone (vehicle) or containing recombinant human VEGF-C (200 ng/mL) was applied on top of a thinned skull surface of adult (3 months-old) and old mice (20-24 months-old). Gels were re-applied two weeks later. Four weeks after the initial treatment, 5 μL of OVA-A647 (in artificial CSF) was injected into the CSF (i.c.m.) and mice were transcardially perfused 2 h later (FIG. 11A). Representative images of DAPI (blue) staining and LYVE-1$^+$ vessels (in green) in the superior sagittal sinus after transcranial delivery of VEGF-C (scale bar, 50 μm) (FIG. 11B). Treatment with VEGF-C resulted in significant increase of lymphatic vessel diameter in the superior sagittal sinus in both adult and old mice (FIG. 11C). Representative sections of dCLNs stained with DAPI (blue) and for LYVE-1 (green) showing drained OVA-A647 (red; scale bar, 200 μm) (FIG. 11D). Quantification of OVA-A647 (red) area fraction (%) in the dCLNs showed increased drainage in old mice treated with VEGF-C, when compared to vehicle-treated age-matched mice (FIG. 11E). Representative brain sections stained with DAPI (blue) showing OVA-A647 (red) influx into the brain parenchyma (scale bar, 5 mm) (FIG. 11F). Influx of OVA-A647 into the brain parenchyma of old mice was significantly increased after transcranial delivery of VEGF-C (FIG. 11G). Data in FIGS. 11C, 11E, and 11G are presented as mean±s.e.m., n=12 in vehicle at 3 months, n=11 in VEGF-C at 3 months, n=8 in vehicle at 20-24 months and n=9 in VEGF-C at 20-24 months; two-way ANOVA with Bonferroni's post-hoc test was used in FIGS. 11C, 11E, and 11G; data in FIGS. 11A-G were pooled from 2 independent experiments. Hydrogel alone (vehicle) or containing recombinant human VEGF-C156S (200 ng/mL) was applied on top of a thinned skull surface of old mice. Gels were re-applied two weeks later (FIG. 11H). Whole-mounts of brain meninges were stained for LYVE-1 (green) and CD31 (red). Images show insets of lymphatic vessels near the superior sagittal sinus (scale bar, 100 μm) (FIG. 11I). Old mice that received VEGF-C156S treatment showed increased diameter of LYVE-1$^+$ vessels in the superior sagittal sinus (FIG. 11J). Representative sections of dCLNs stained with DAPI (blue) and for LYVE-1 (green) showing levels of OVA-A647 (red) drained from the CSF (scale bar, 200 μm) (FIG. 11K). Quantification of OVA-A647 area fraction (%) in the dCLNs showed a significant increase in VEGF-C156S group when compared to vehicle (FIG. 11L). Representative images of OVA-A647 (red) in brain sections also stained with DAPI (blue; scale bar, 5 mm) (FIG. 11M). Quantification of OVA-A647 area fraction (%) in brain sections showed a significant increase in brain influx of the tracer in old mice treated with VEGF-C156S (FIG. 11N). Data in FIGS. 11J, 11L, and 11N are presented as mean±s.e.m., n=7 mice per group; two-tailed Mann-Whitney test was used in FIGS. 11J, 11L and 11N; data in FIGS. 11H-11N were pooled from 2 independent experiments. Young-adult (2 months), middle-aged (12-14 months) or old (20-22 months) mice were injected with viral vectors expressing EGFP or mVEGF-C. One month after injection, learning and memory was assessed using the MWM test (FIG. 11O). Injection of mVEGF-C virus in young-adult mice did not alter their performance in the acquisition, probe trial or reversal of the MWM (mean±s.e.m., n=8 in EGFP and n=9 in mVEGF-C; repeated measures two-way ANOVA with Bonferroni's post-hoc test was used in the acquisition and reversal; two-tailed Mann-Whitney test was used in the probe trial; data was obtained in a single experiment) (FIG. 11P). Injection of mVEGF-C virus in middle-aged mice did not alter their performance in the acquisition and in the probe trial, but significantly improved their performance in the reversal (mean±s.e.m., n=12 in EGFP and n=14 in mVEGF-C; repeated measures two-way ANOVA with Bonferroni's post-hoc test was used in the acquisition and reversal, two-tailed Mann-Whitney test was used in the probe trial; data was pooled from 2 independent experiments) (FIG. 11Q). Injection of mVEGF-C virus in old mice did not alter their performance in the probe trial, but significantly improved their performance in the acquisition and in the reversal (mean±s.e.m., n=25 in EGFP and n=25 in mVEGF-C; repeated measures two-way ANOVA with Bonferroni's post-hoc test was used in the acquisition and reversal; two-tailed Mann-Whitney test was used in the probe trial; data was pooled from 3 independent experiments) (FIG. 11R). Treatment of young-adult mice (FIG. 11S) with mVEGF-C did not affect the % of allocentric navigation strategies used in the MWM. The % of allocentric navigation strategies was significantly higher in middle-aged mice (FIG. 11T) treated with mVEGF-C during the reversal and in (FIG. 11U) old mice treated with mVEGF-C during the acquisition and reversal, when compared to their age-matched EGFP-treated counterparts. Data in FIGS. 11S-U are presented as mean±s.e.m.; n=8 in EGFP and n=9 in mVEGF-C at 2 months in FIG. 11S; n=12 in EGFP and n=14 in mVEGF-C at 12-14 months in FIG. 11T; n=25 per group at 20-22 months in FIG. 11U; repeated measures two-way ANOVA with Bonferroni's post-hoc test was used in FIGS. 11S-U; data in FIG. 11S were obtained from a single experiment, data in FIG. 11T were pooled from 2 independent experiments and data in FIG. 11U were pooled from 3 independent experiments.

Figure 12N:
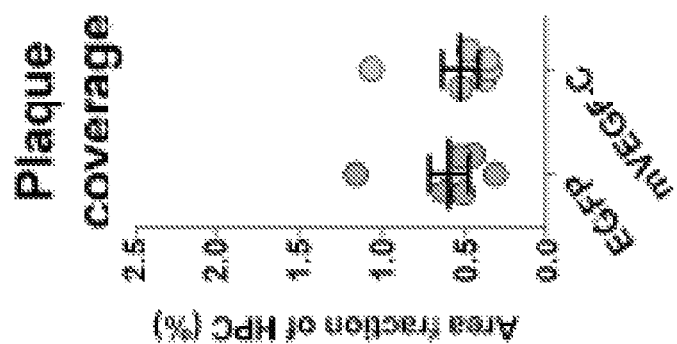
Figure 12M:
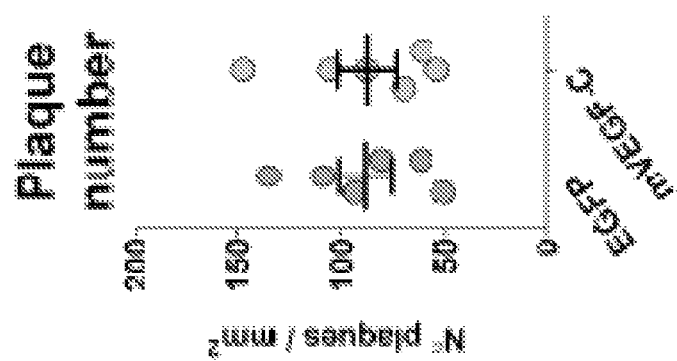
Figure 12L:
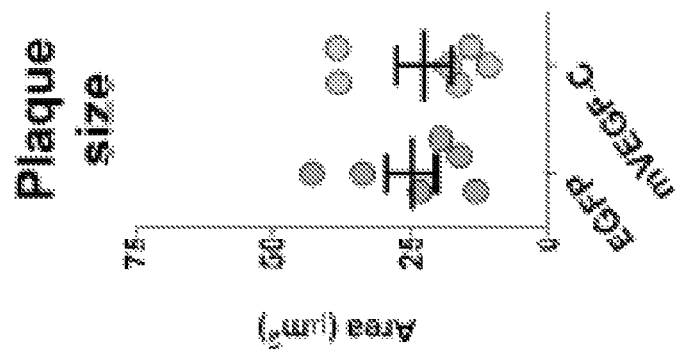

FIGS. 12A-W show expression of mVEGF-C in the meninges of J20 mice does not ameliorate lymphatic drainage or brain amyloid pathology. J20 mice were injected i.c.m. with 2 μL of AAV1-CMV-EGFP or AAV1-CMV-mVEGF-C ($10^{13}$ GC/mL) at 6-7 months. One month after injection, the mice were tested in the open field (OF) and in the MWM (FIG. 12A). Total distance and % of time in the center of the OF arena was not ameliorated by treatment of J20 mice with mVEGF-C (FIGS. 12B-C). No statistically significant differences were observed in the acquisition (FIG. 12D), in the probe trial (FIG. 12E) or in the reversal (FIG. 12F) of the MWM test after 1 month of mVEGF-C. Data in FIGS. 12B-F are presented as mean±s.e.m., n=11 in EGFP, n=12 in mVEGF-C; two-tailed Mann-Whitney test was used in FIGS. 12B, 12C, and 12E and repeated measures two-way ANOVA with Bonferroni's post-hoc test was used in FIGS. 12D and 12F; data results from a single experiment. J20 mice were treated with EGFP or mVEGF-C and, 1 month later, CSF, meninges and brain were collected for analysis (FIG. 12G). Representative images of DAPI (blue) and LYVE-1+ lymphatic vessels (green) in the superior sagittal sinus of mice treated with either EGFP or mVEGF-C (scale bar, 500 μm) (FIG. 12H). AAV1-mediated expression of mVEGF-C did not affect meningeal lymphatic vessel diameter (FIG. 12I). Levels of Aβ in the CSF measured by ELISA remained unaltered after mVEGF-C treatment (FIG. 12J). Representative images of dorsal hippocampus (scale bar, 500 μm) of J20 mice of EGFP or mVEGF-C groups stained with DAPI (cyan) and for IBA1 (green) and Aβ (red) (FIG. 12K). No changes were observed in amyloid plaque size (FIG. 12L), number (FIG. 12M) or coverage (FIG. 12N) between the groups. Data in FIGS. 12I, 12J and 12L-N are presented as mean±s.e.m., n=6 per group; two-tailed Mann-Whitney test was used in FIGS. 12I, 12J and 12L-N; data in FIGS. 12G-N represent results from a single experiment. J20 mice (2-3 months-old) and 5xFAD mice (3-4 months-old), and respective age-matched WT littermate controls, were injected with fluorescent OVA-A647 (i.c.m.) in order to measure drainage into the dCLNs (FIG. 12O). Representative images of DAPI (blue) and LYVE-1 (green) staining in dCLNs of WT and J20 mice (scale bar, 200 μm) 2 h after injection of OVA-A647 (red) (FIG. 12P). Quantification of OVA-A647 area fraction (%) in the dCLNs shows equal levels of tracer in mice from both genotypes (mean±s.e.m., n=5 per group; two-tailed Mann-Whitney test; representative of 2 independent experiments) (FIG. 12Q). Representative images of DAPI (blue) and LYVE-1 (green) staining in dCLNs of WT and 5xFAD mice (scale bar, 200 μm) 2 h after injection of OVA-A594 (red) (FIG. 12R). Quantification of OVA-A594 area fraction (%) in the dCLNs shows equal levels of tracer in mice from both genotypes (mean±s.e.m., n=11 per group; two-tailed Mann-Whitney test; data was pooled from 2 independent experiments) (FIG. 12S). Representative images of DAPI (blue) and LYVE-1 (green) staining in meningeal whole-mounts of WT and 5xFAD mice at 3-4 months (scale bar, 1 mm) (FIG. 12T). Measurement of LYVE-1$^+$ vessel diameter, area fraction and number of sprouts (per mm of vessel) showed no differences between genotypes (mean±s.e.m., n=7 per group; two-tailed Mann-Whitney test; data was pooled from 2 independent experiments) (FIG. 12U).

Figure 13D:
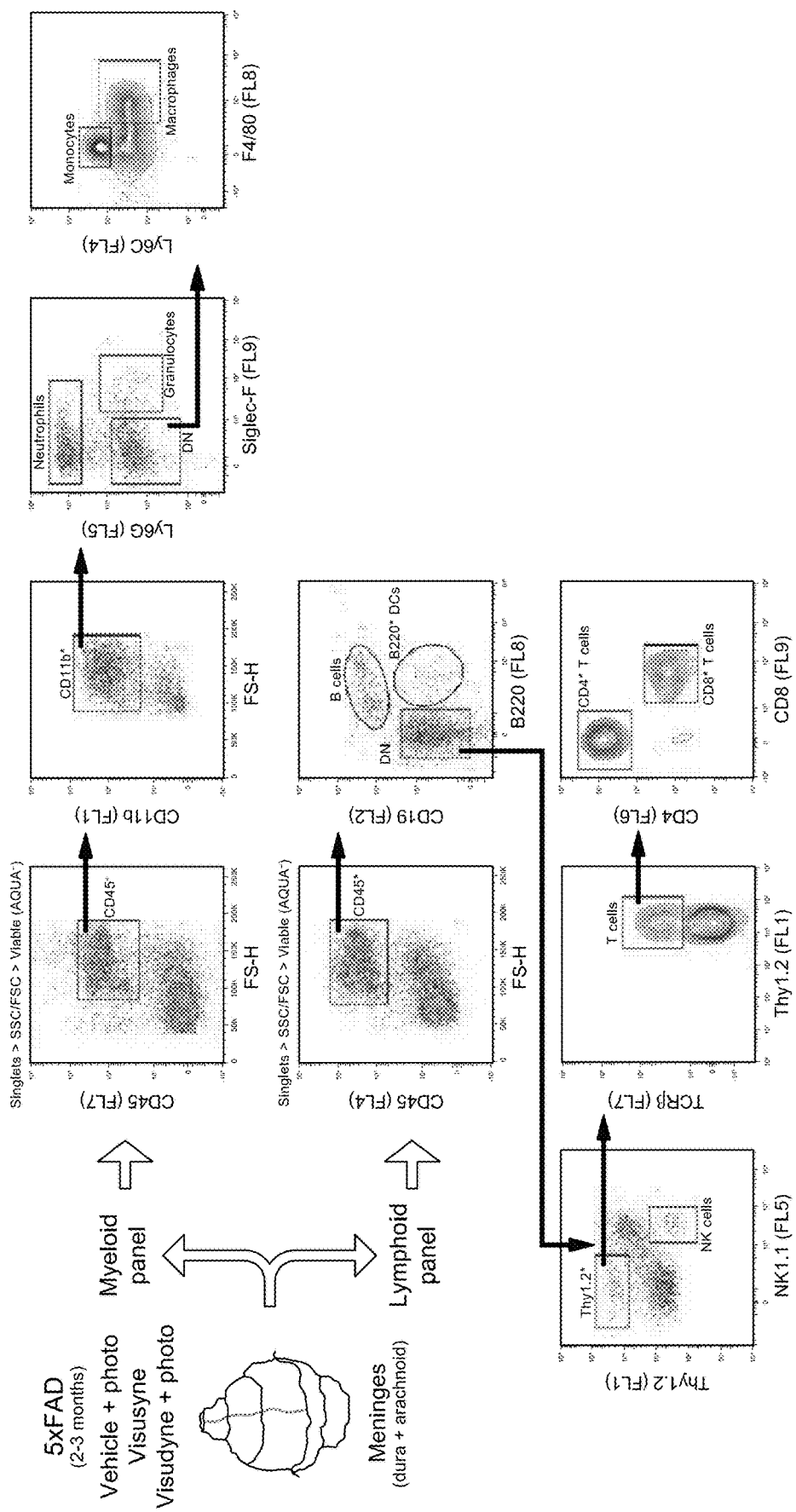
Figure 13E:
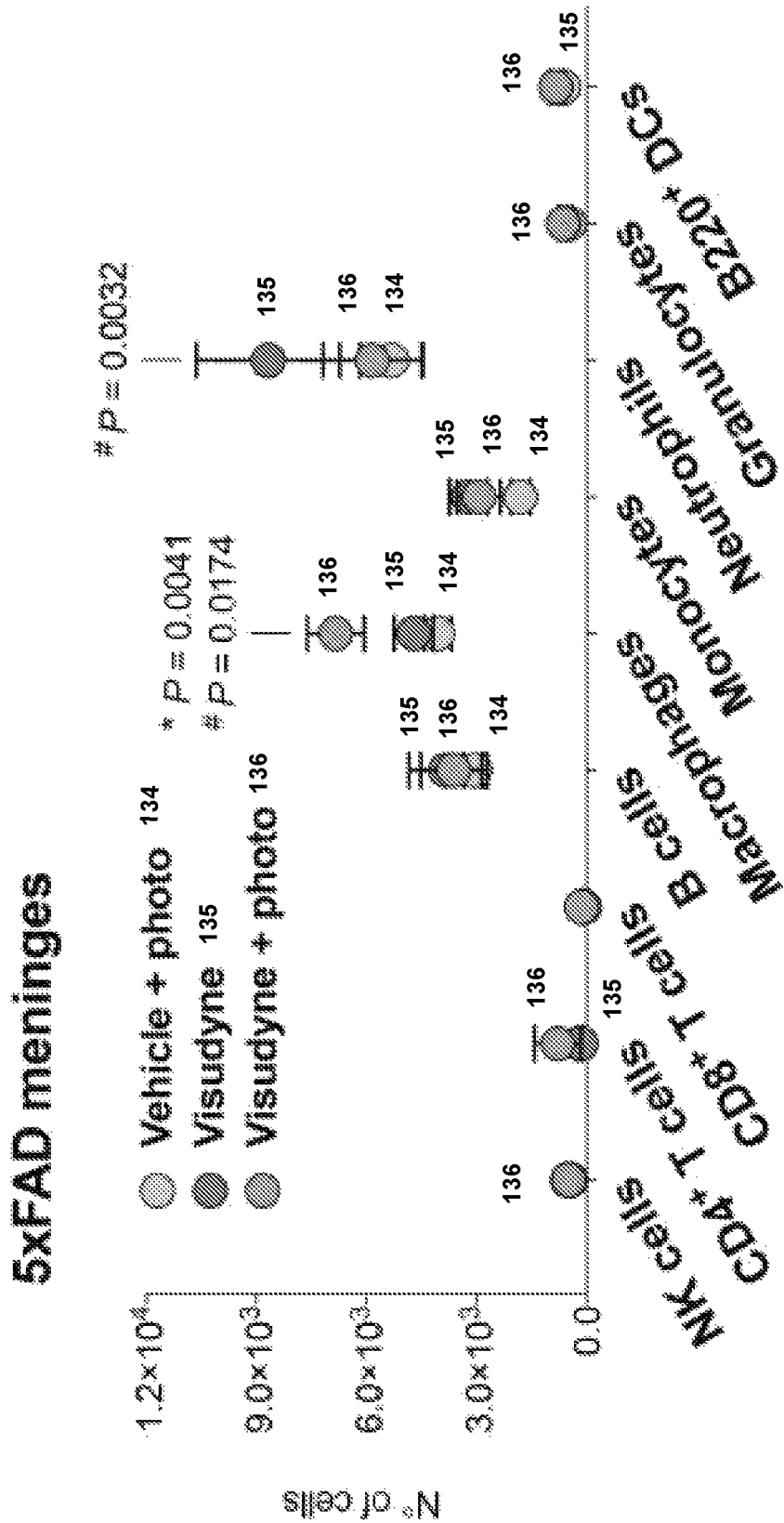
Figure 13F:
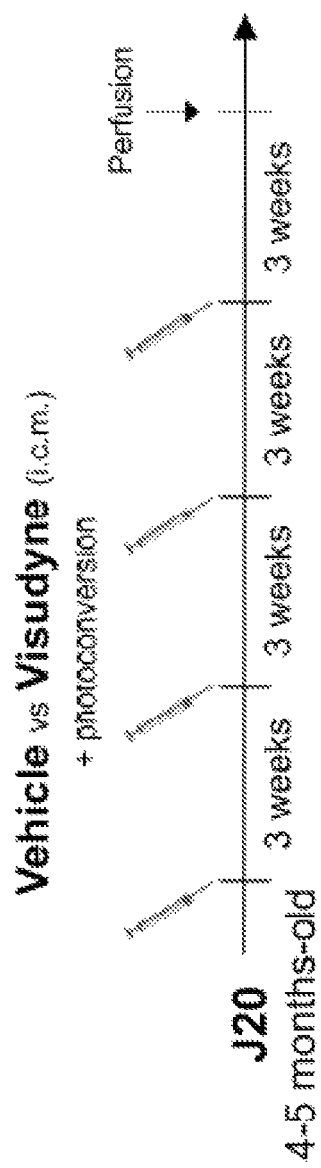
Figure 13G:
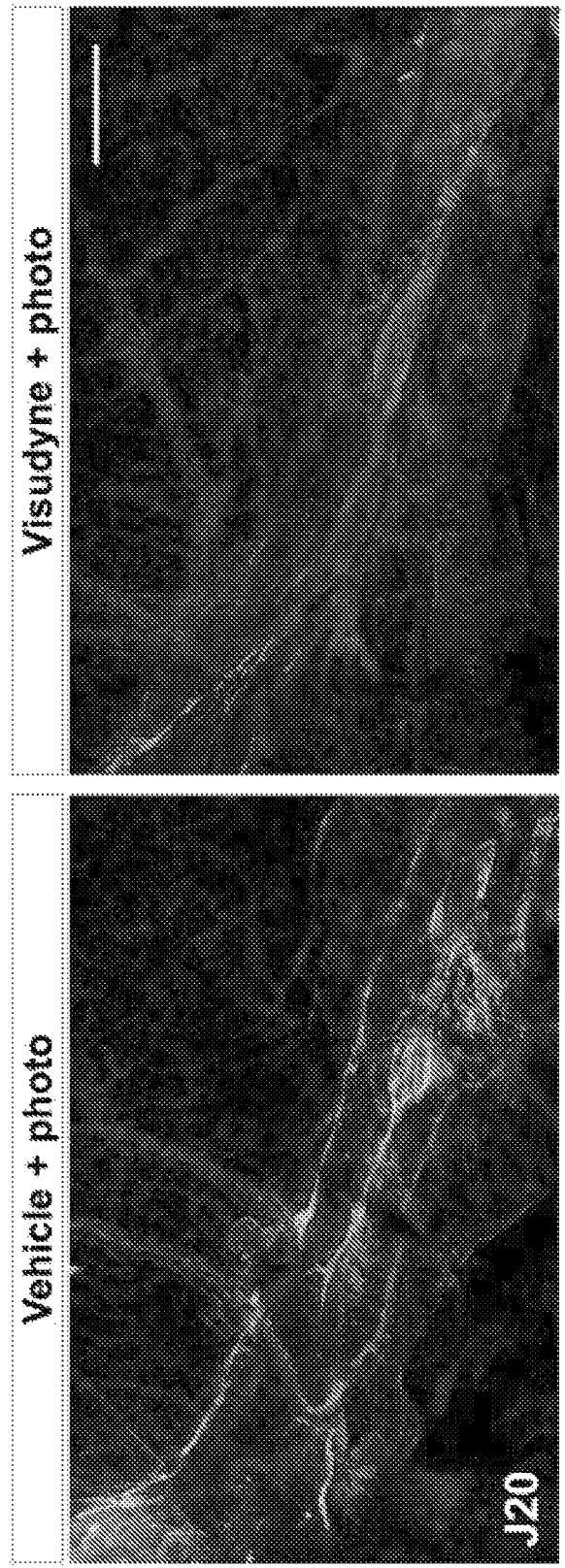

FIGS. 13A-M show meningeal lymphatic ablation in AD transgenic mice worsens amyloid pathology without affecting blood vessel function. Representative images of blood flow (mm/s) and arterial and venous blood oxygenation (% of $sO_2$) readings obtained by Photoacoustic imaging of brain/meningeal vasculature of 5xFAD mice one week after vehicle/photoconversion, Visudyne or Visudyne/photoconversion (FIG. 13A). The different treatments did not affect blood flow (FIG. 13B) or blood oxygenation (FIG. 13C) in the brain/meninges of 5xFAD mice (mean±s.e.m., n=5 per group; one-way ANOVA with Bonferroni's post-hoc test was used in (FIG. 13B) and two-way ANOVA with Bonferroni's post-hoc test was used in (FIG. 13C); data results from a single experiment. Representative flow cytometry dot and contour plots showing the gating strategies used to determine the frequency of specific immune cell populations, using a myeloid or lymphoid panel of markers, in the meninges of 5xFAD after prolonged (1.5 months) meningeal lymphatic ablation (FIG. 13D). Analysis of specific immune cell populations in the meninges of 5xFAD mice from the different groups showed a significant increase in macrophages in the Visudyne/photoconversion group when compared to the control groups (FIG. 13E). A significant increase in neutrophils was observed in Visudyne group, but not in vehicle/photoconversion group, when compared to Visudyne/photoconversion group (mean±s.e.m., n=5 per group; two-way ANOVA with Holm-Sidak's post-hoc test; *vs vehicle/photoconversion; #vs Visudyne; data results from a single experiment). 4-5 months-old J20 mice were submitted to meningeal lymphatic ablation by injection (i.c.m.) of Visudyne or vehicle as a control, followed by a photoconversion step. This procedure was repeated every 3 weeks, for a total of 3 months, to achieve prolonged meningeal lymphatic ablation (FIG. 13F). Staining with DAPI (blue) and for LYVE-1 (green) and Aβ (red) in meningeal whole-mounts of J20 mice showing marked amyloid deposition in mice from the Visudyne group (scale bar, 500 μm) (FIG. 13G). Representative brain sections of J20 mice at 7-8 months stained with DAPI (cyan) and for Aβ (red; scale bar, 500 μm) showing degree of amyloid deposition after meningeal lymphatic ablation (FIG. 13H). Quantification of amyloid plaque size (FIG. 13I), number (FIG. 13J) and coverage (FIG. 13K) in the dorsal hippocampus of J20 mice showed a statistically significant increase in coverage in the Visudyne group, when compared to vehicle. Data in FIGS. 3I-K are presented as mean±s.e.m., n=5 in vehicle, n=6 in Visudyne; two-tailed Mann-Whitney test was used in FIGS. 13I-K; experiments in FIGS. 13F-K were performed once. Sections of human brain cortex, containing meningeal layers (leptomeninges) attached, from non-AD brain (FIG. 13L) (scale bar, 500 μm; inset scale bar, 200 μm) and AD brain (FIG. 13M) (left image scale bar, 100 μm; right image scale bar, 500 μm) were stained with DAPI (blue), for the astrocyte marker GFAP (green) and for Aβ (red). Data in FIGS. 13L and 13M represent results of n=8 non-AD samples and n=9 AD samples and are representative of 2 independent experiments.

Figure 14G:
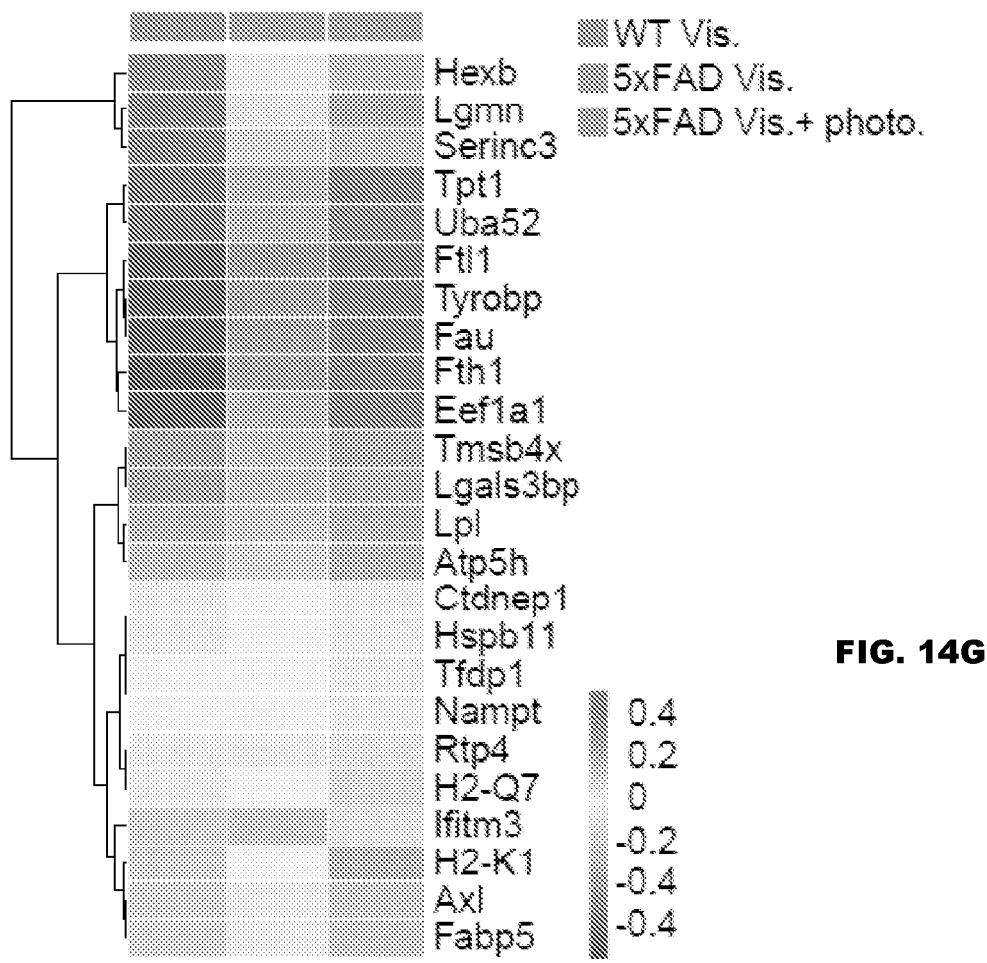
Figure 14H:
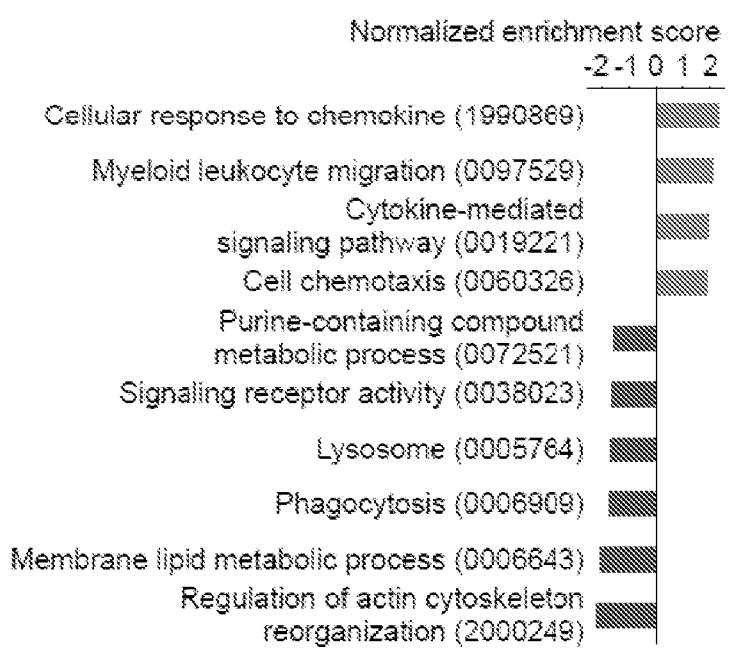
Figure 14I:
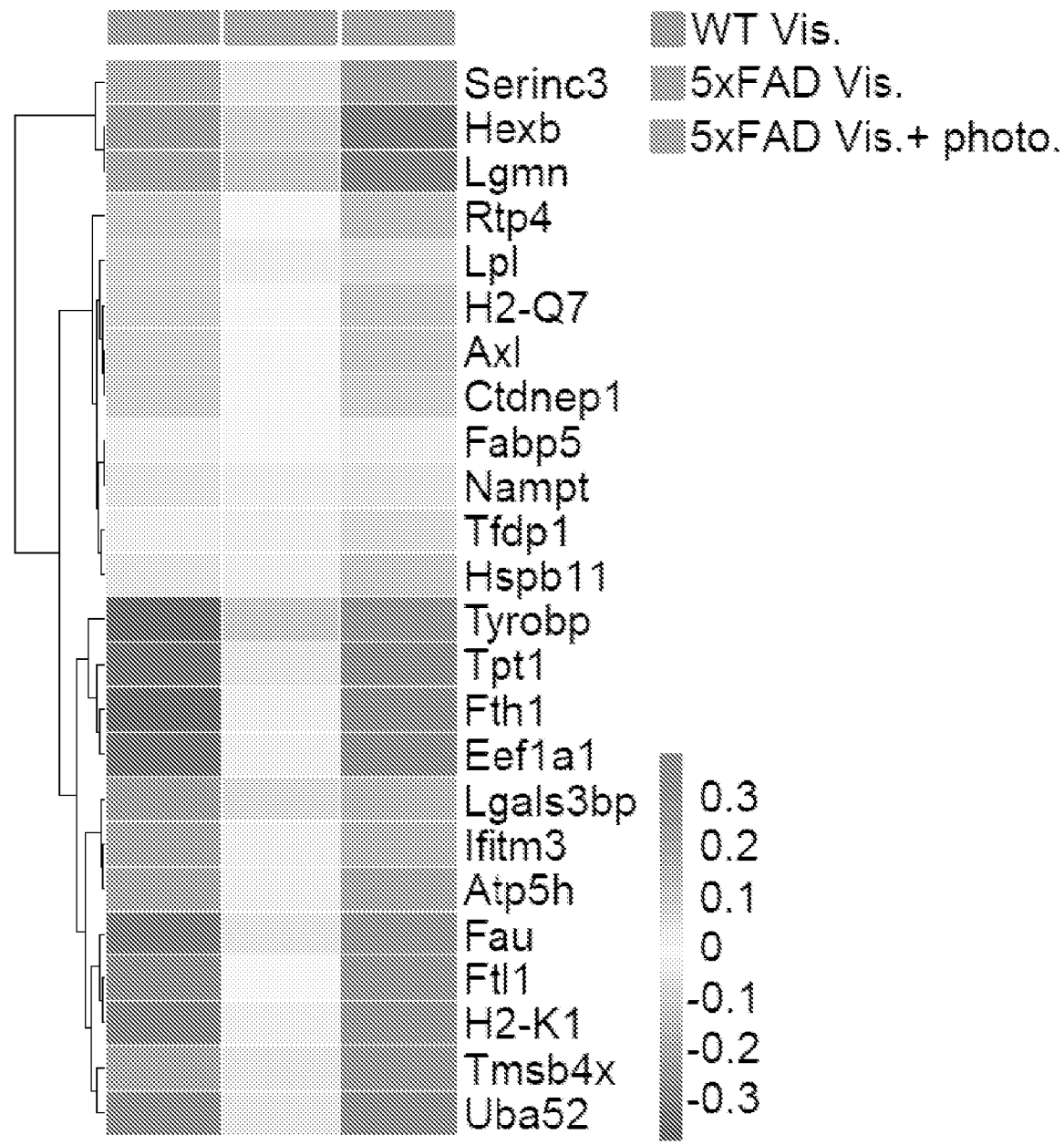

FIGS. 14A-1 are a series of graphs depicting that meningeal lymphatic dysfunction in 5xFAD mice lead to unique changes in the microglial transcriptome. Single cell RNA-seq of brain myeloid cells from 4 months old wild type (WT) and 5xFAD mice were injected with Visudyne alone (Vis., functional meningeal lymphatics) or injected with Visudyne and subjected to transcranial photoconversion (Vis.+photo., ablated meningeal lymphatics). Meningeal lymphatic ablation step was performed twice within a span of 3 weeks and brain myeloid cells were isolated 3 weeks after the last step. Data were obtained from sorted live $Ly6G^{neg}CD45^{+}CD11b^{+}$ brain myeloid cells pooled from 3 mice per group (FIGS. 14A-B). Unsupervised clustering of brain myeloid single cells using t-distributed Stochastic Neighbor Embedding (t-SNE) plotted by group (FIG. 14A) or by distinct cell cluster (FIG. 14B). Frequency of cells from each cluster within the total 354, 487 and 308 cells from WT Vis., 5xFAD Vis. and 5xFAD Vis.+photo. groups, respectively (FIG. 14C). Genes involved in the acquisition of the disease-associated microglia phenotype, depicting the homeostatic, TREM2-independent and TREM2-dependent signatures within each cell were depicted in a heatmap (FIG. 14D). Cells are grouped by cluster and genes are grouped by signature (FIG. 14D). Upset plots were generated for all cells (FIG. 14E) or cluster 1 cells (FIG. 14F) showing the overlap in differentially expressed genes for comparisons between 5xFAD Vis. or 5xFAD Vis.+photo. and WT Vis. A heatmap with 24 genes whose expression is significantly different between 5xFAD Vis.+photo. and WT Vis., but not significantly different between 5xFAD Vis. and WT Vis., in cluster 1 is depicted in FIG. 14G. Expression values are averaged across cells within each group. Normalized enrichment score for GSEA pathways were obtained by Fisher's exact test with Benjamini-Hochberg corrections for the 24 differentially expressed genes in cluster 1 is shown in FIG. 14H. Enrichment analysis was performed in R using the clusterProfiler package. Depicted in FIG. 14I is a heatmap showing the mean-centered average log normalized expression of each gene contributing to the core-enrichment of the "Lysosome" GSEA pathway. Expression values are averaged across cells within each group. All scales show mean-centered, log-normalized expression values.

Figure 6B:
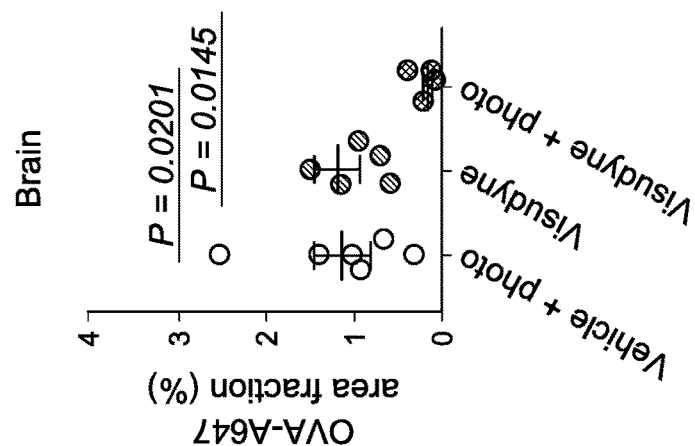
FIGS. 6A-B depict data related to assessment of CSF drainage and brain influx. Representative brain sections stained with DAPI (blue) showing OVA-A647 (red) influx into the brain parenchyma of mice from Visudyne/photoconversion and control groups (scale bar, 5 mm; inset scale bar, 1 mm) (FIG. 6A). Quantification of OVA-A647 area fraction (%) in brain sections showing a significant decrease in the Visudyne/photoconversion group when compared to control groups (FIG. 6B). Data in is presented as mean±s.e.m., n=6 per group; one-way ANOVA with Bonferroni's post-hoc test was used in FIG. 6B.
Figure 6A:
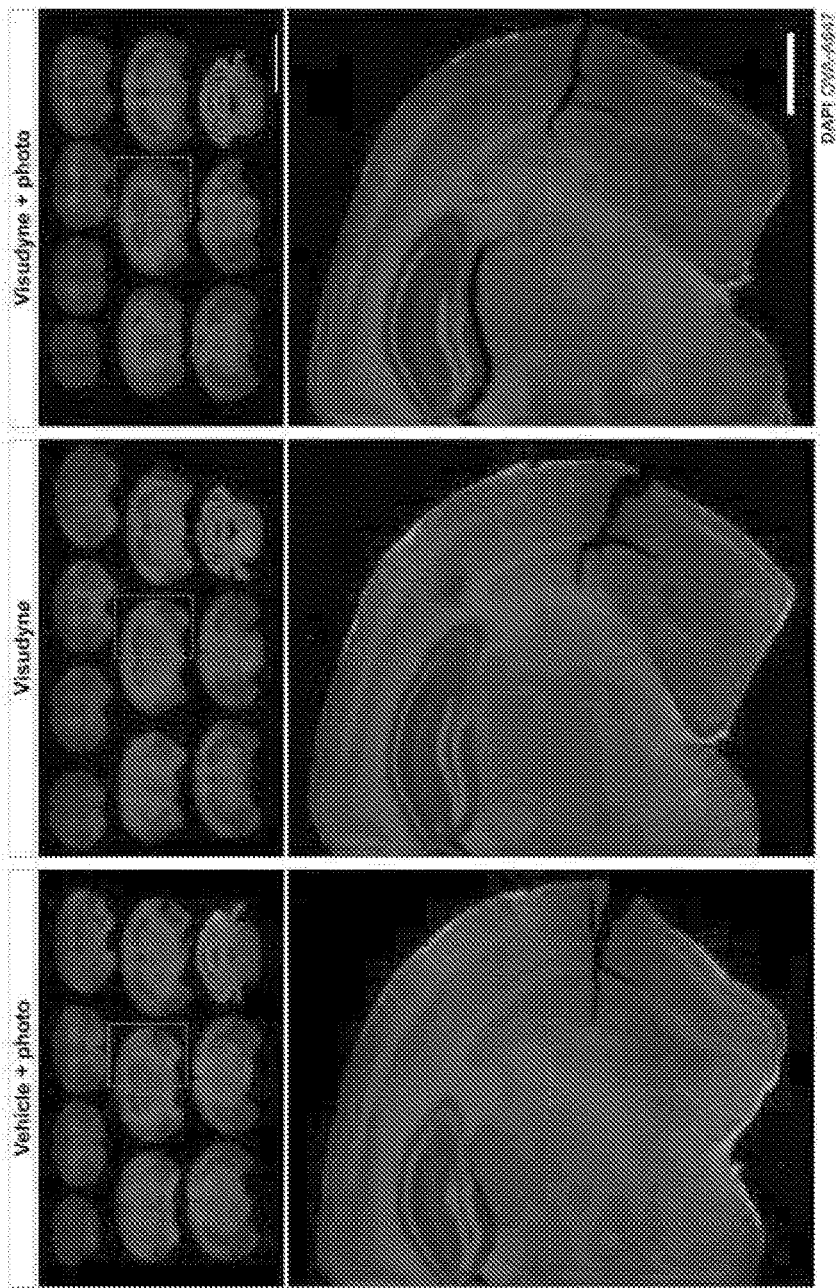
Figure 15A:
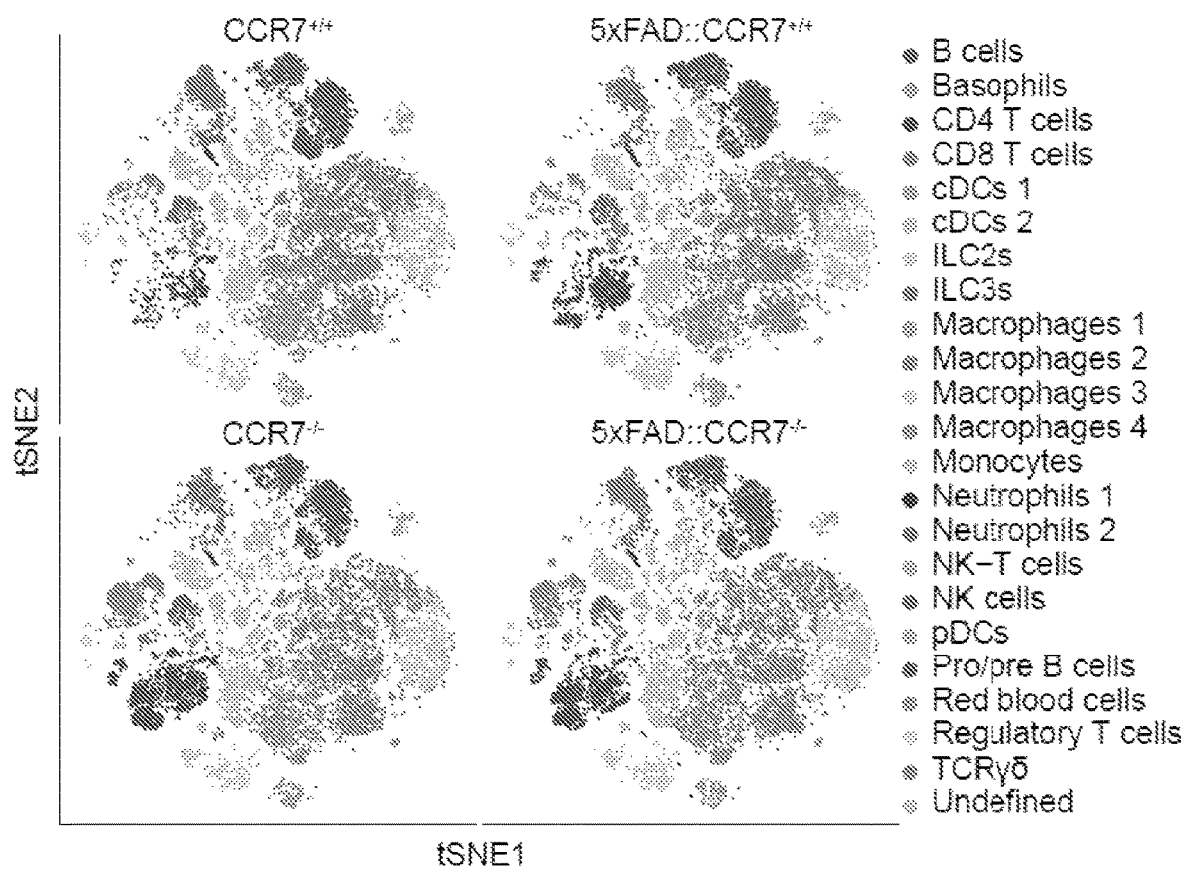
Figure 15B:
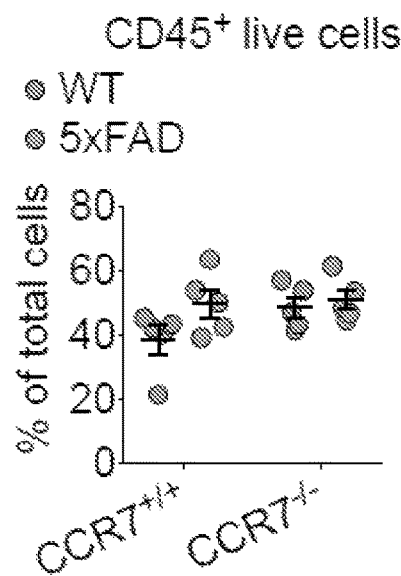
Figure 15C:
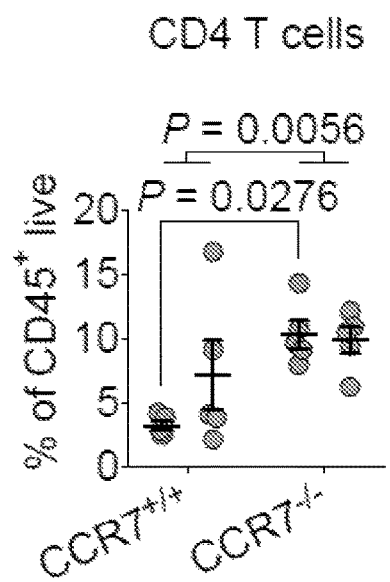
Figure 15D:
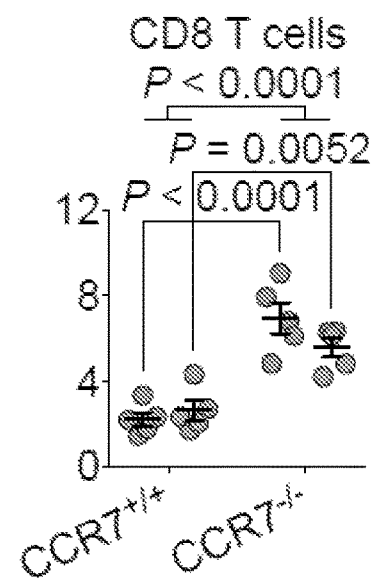
Figure 15H:
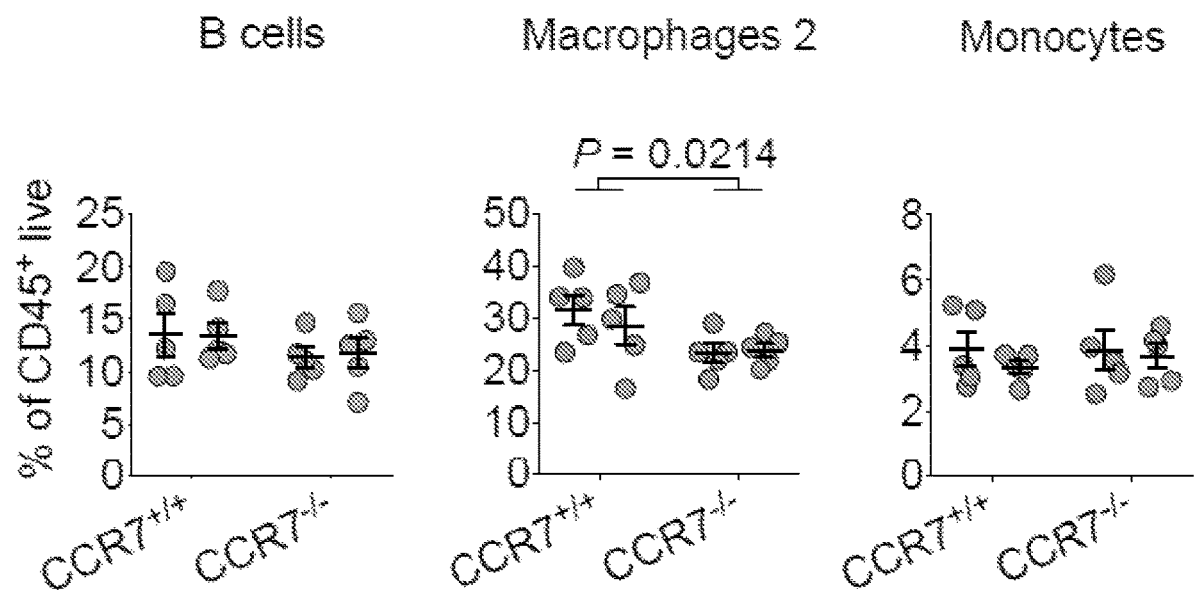
Figure 15H:
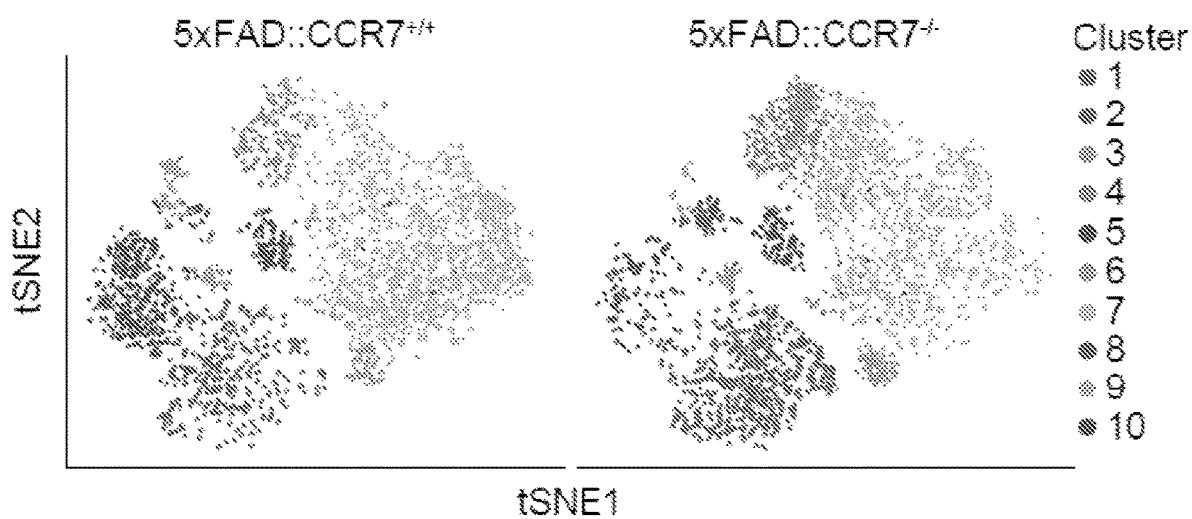
Figures 15I, 15J, 15K, 15L:
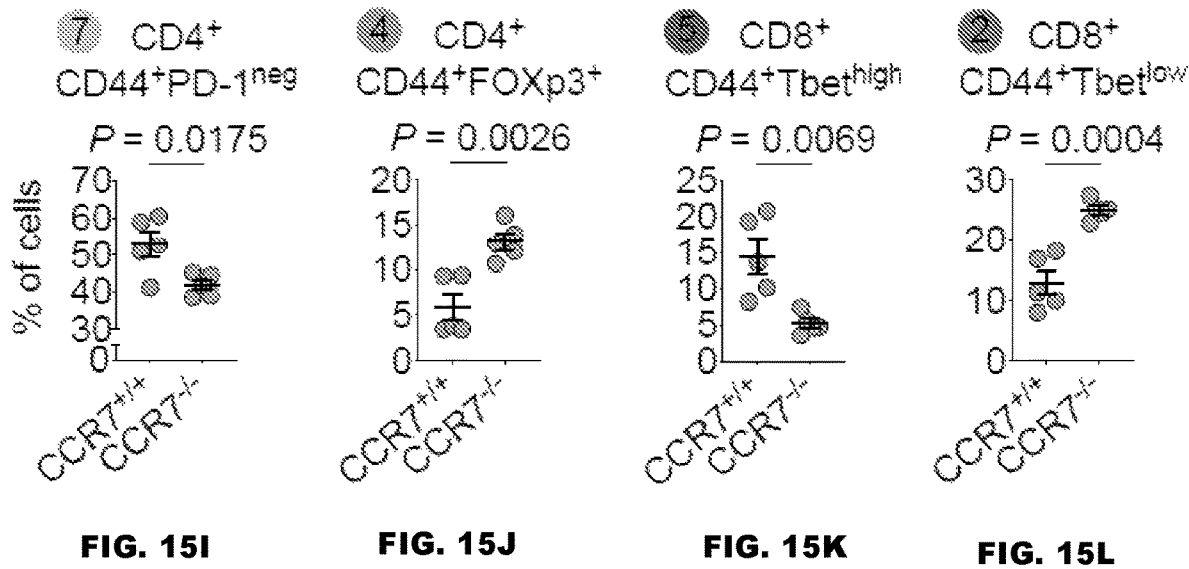
Figure 15M:
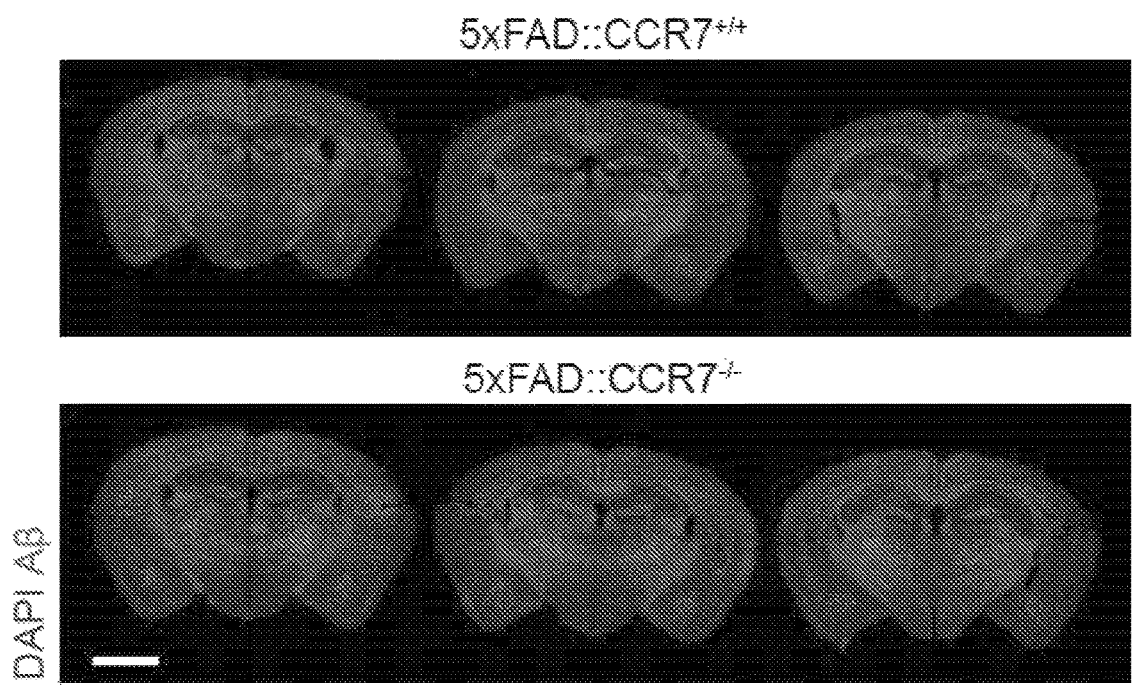
Figure 15N:
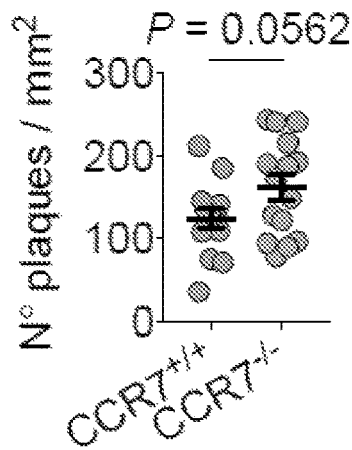
Figure 15O:
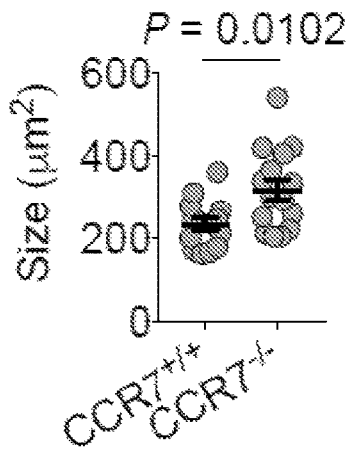
Figure 15P:
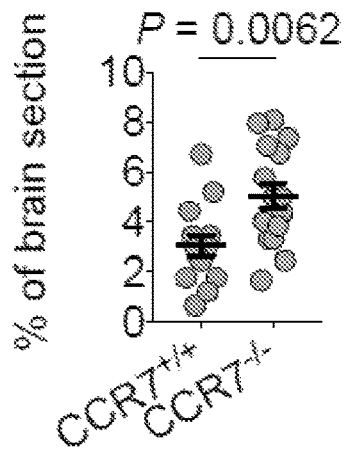
Figure 15Q:
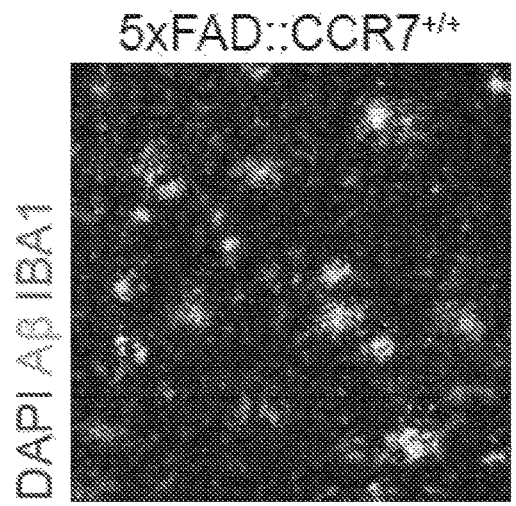
Figure 15Q:
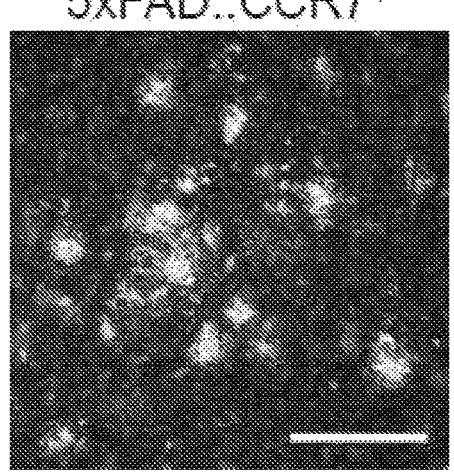
Figure 15R:
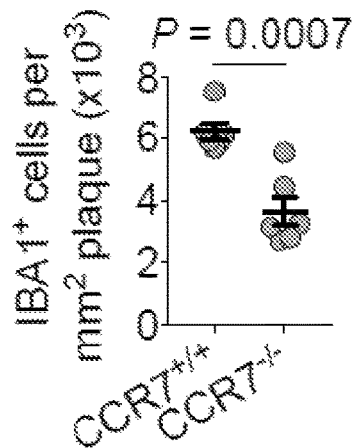
Figure 15S:
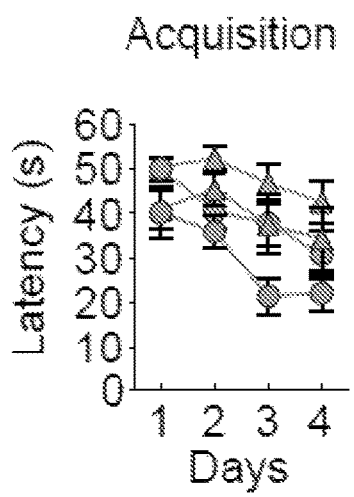
Figure 15T:
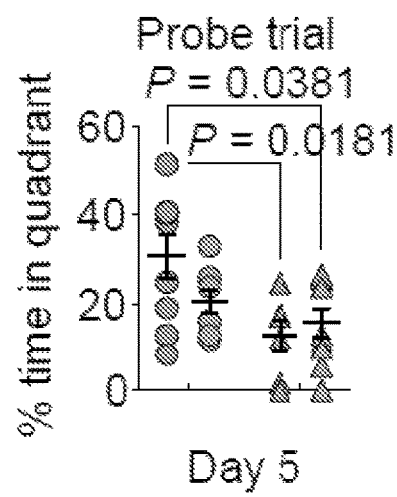
Figure 15U:
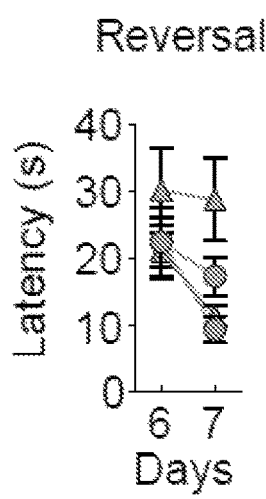

FIGS. 15A-U are a series of graphs and images depicting abnormal accumulation of meningeal T cells aggravates brain amyloid pathology, affects microglial response and worsens cognitive performance in 5xFAD mice. CyTOF assessment of meningeal immune cell populations from WT and 5xFAD mice on $CCR7^{+/+}$ or CCR7 backgrounds (littermates at 4-5 months of age) are depicted in FIG. 15A. Frequencies of total $CD45^{+}$ live leukocytes and of specific leukocyte population clusters within total CD45 live are depicted in FIGS. 15B-G. No significant changes were observed in the frequency of meningeal leukocytes between the groups (FIG. 15B). Deficiency in CCR7 resulted in a significant increase in the frequency of CD4 (FIG. 15C) and of CD8 (FIG. 15D) T cells and a significant decrease in macrophage 2($CD11b^{+}F4/80^{+}CD64^{+}$) population in both WT and 5xFAD mice (FIG. 15F). No changes were observed in B cells (FIG. 15E) and infiltrating monocytes ($CD11b^{+}F4/80e9CD64^{neg/low}Ly6C^{high}$) (FIG. 15G). Results in FIGS. 15B-G are presented as mean s.e.m.; n=5 per group; Two-way ANOVA with Sidak's multiple comparison test. tSNE plots obtained by re-clustering the meningeal $CD4^{+}$ and $CD8^{+}$ T cell populations using Flowsome and a 10 cluster-restricting condition are depicted in FIG. 15H. After removal of remnant contaminating macrophages and dendritic cells a total of four distinct clusters of $CD4^{+}$ T cells (4, 6, 7 and 10) and six distinct clusters of $CD8^{+}$ T cells (1, 2, 3, 5, 8 and 9) were identified (FIGS. 15J-L), There was a significant decrease in $CD4^{+}CD44^{+}PD-1^{neg}$ (FIG. 15I) and $CD8^{+}CD44^{+}Tbet^{high}$ (FIG. 15K) and a significant increase in $CD4^{+}CD44^{+}FOXp3^{+}$ (FIG. 15J) and $CD8^{+}CD44^{+}Tbet^{low}$ (FIG. 15L) cell frequency. Results in FIG. 15I-L are presented as mean±s.e.m.; n=5 per group; Unpaired Student's T test. Representative images of brain sections of male $CCR7^{+/+}$ or $CCR7^{-/-}$ 5xFAD mice stained for Aβ (red) and with DAPI (blue); scale bar, 2 mm (FIG. 15M). Also quantified were number of plaques per $mm^2$ (FIG. 15N), plaque average size (in $\mu m^2$) (FIG. 15O), and coverage (% area of section) (FIG. 15P). Representative images of brain cortex stained for Aβ (green) and IBA1 (red) and with DAPI (blue); scale bar, 100 μm were obtained (FIG. 15Q). Quantification of IBA1+ cells clustered around plaques (FIG. 15R). Results in FIG. 15N-P and FIG. 15R are presented as mean±s.e.m.; in n-p, n=14 in $5xFAD::CCR7^{+/+}$ and n=15 in $5xFAD::CCR7^{-/-}$ groups pooled from 2 independent experiments; in r, n=6 per group representative of 2 independent experiments; Unpaired Student's T test. FIGS. 15S-U depict performance in the MWM acquisition (FIG. 15S), probe trial (FIG. 15T) and reversal (FIG. 15U) revealed statistically significant differences between $WT::CCR7^{+/+}$ and $5xFAD::CCR7^{-/-}$ at days 3 and 4 of the acquisition, in the probe trial and in the 2nd day of reversal (day 6 of the test). Statistically significant differences were also observed between $WT::CCR7^{+/+}$ and $WT::CCR7^{-/-}$ mice in the probe trial. Results in FIG. 15S-U are presented as mean s.e.m.; n=9 in $WT::CCR7^{+/+}$ and in $5xFAD::CCR7^{-/-}$, n=7 in $WT::CCR7^{-/-}$, n=8 in $5xFAD::CCR7^{+/+}$ groups; Repeated measures Two-way ANOVA with Sidak's multiple comparison test in FIGS. 15S and 6U; Two-way ANOVA with Sidak's multiple comparison test in FIG. 15T.

DETAILED DESCRIPTION

Traditionally, the central nervous system was viewed as being immune privileged, and was believed to lack a classical lymphatic drainage system. As described herein, a lymphatic system is present in meningeal spaces, and functions in draining macromolecules, immune cells, and debris from the central nervous system (CNS). Moreover, it has been discovered herein that modulating drainage by the meningeal lymphatic drainage can affect certain diseases of the brain and central nervous system. In particular, as described in several embodiments herein, reducing drainage by meningeal lymphatic vessels can reduce the flow in fluids of the CNS such as, cerebral spinal fluid (CSF) and interstitial fluid (ISF), and can exacerbate symptoms of neurodegenerative diseases characterized by increases in concentration and/or accumulations of molecules in the central nervous system, for example, Alzheimer's disease (AD).

Differential gene expression caused by and/or related to changes in meningeal lymphatic flow, for example in aged animals or in animals subjected to lymphatic ablation to mimic disease states, has led to the identification of molecular targets that play a role in causing, or are influenced by, a reduction in meningeal lymphatic drainage. These targets can be modulated to improve meningeal lymphatic flow and/or to counter the effects of reduced meningeal lymphatic flow. Modulating these targets that are related to or influenced by meningeal lymphatic flow can alleviate symptoms of AD, including cognitive symptoms, and accumulation of amyloid-beta plaques. Accordingly, in some embodiments, methods, compositions, and uses for diagnosing, treating, preventing, inhibiting, or ameliorating symptoms of neurodegenerative diseases associated with increased concentration and/or the accumulation of macromolecules, cells, and debris in the CNS (for example, AD, which is associated with the accumulation of amyloid-beta plaques) are described. In some embodiments, the methods, compositions, and uses can increase drainage by meningeal lymphatic vessel, and thus increase flow in CSF and ISF. In some embodiments, the methods, compositions, and uses can counteract a change in expression and/or activity of one or more molecular targets caused by abnormal (e.g. reduced) meningeal lymphatic drainage. Several embodiments herein are particularly advantageous because they include one, several or all of the following benefits: (i) counteracting a change in expression and/or activity of one or more molecular targets caused by abnormal (e.g. reduced) meningeal lymphatic drainage; (ii) increased flow in the CNS; (iii) decreased accumulation of macromolecules, cells, or debris in the CNS (for example, decreased accumulation of amyloid-beta); and (iv) maintenance of or improvement in cognitive function (for example memory function) in a subject suffering from, suspected of having, and/or at risk for dementia (such as in a neurodegenerative disease such as AD).

Flow and Flow Modulators

As used herein "flow" shall be given its ordinary meaning and shall also refer to a rate of perfusion through an area of the central nervous system of a subject. Flow in some embodiments, can be measured as a rate at which a label or tracer in CSF perfuses through a particular area of the central nervous system. As such, flow can be compared between two subjects or two sets of conditions by ascertaining how quickly an injected label or tracer perfuses throughout a particular area or volume of the brain and/or other portion of the CNS.

As used herein, "flow modulators" shall be given its ordinary meaning and shall also broadly refer to classes of compositions that can increase or decrease the passage of substances into and out of meningeal lymphatic vessels, and thus can modulate flow in CSF and ISF, and/or, can modulate immune cell migration within, into, and out of the meningeal lymphatic vessels, and/or can counteract the effects of decreased flow with or without restoring flow.

As shown herein, increasing the passage of substances into and out of meningeal lymphatic vessels can increase flow in CSF and ISF. Without being limited by theory, it is contemplated, according to several embodiments herein, that removal of macromolecules through meningeal lymphatic vessels can keep their concentrations low in the CSF, allowing a gradient to clear macromolecules from the parenchyma. As such, the higher the rate of drainage of molecules by meningeal lymphatic vessels, the higher the rate of flow of molecules in the CNS (e.g., in CSF and ISF). Furthermore, the higher the rate of fluid flow and drainage in the CNS, the higher the rate of clearance and/or the lower the concentration of cells, macromolecules, waste, and debris form the CNS. In some embodiments, flow modulators increase the diameter of meningeal lymphatic vessels, which increases drainage, resulting in increased flow in the CSF and ISF. In some embodiments, flow modulators counteract the effects (e.g., changes in the hippocampal transcriptome) of decreased flow with or without restoring flow. In some embodiments, flow modulators increase the number of meningeal lymphatic vessels, thus increasing net drainage, resulting in increased flow in the CSF and ISF. Examples of suitable flow modulators for increasing flow (for example by increasing meningeal lymphatic vessel diameter) and/or for counteracting the effects of decreased flow with or without restoring flow, in accordance with various embodiments herein include, but are not limited to, agents that modulate the copy number, level of expression, or level of activity of one or more targets listed in Table 2 and/or Table 4 and/or Table 6 and/or Table 7, and functional fragments, variants, analogs, and mimetics of these molecules.

In methods, uses, or compositions of some embodiments, a flow modulator (e.g., agents that modulate the copy number, level of expression, or level of activity of one or more targets listed in Table 2 and/or Table 4 and/or Table 6 and/or Table 7) comprises or consists essentially of a polypeptide or protein that comprises a modification, for example a glycosylation, PEGylation, or the like.

In some embodiments, a composition or composition for use in accordance with methods and uses described herein comprises or consists essentially of one or more flow modulators (e.g., agents that modulate the copy number, level of expression, or level of activity of one or more targets listed in Table 2 and/or Table 4 and/or Table 6 and/or Table 7), and a pharmaceutically acceptable diluent or carrier. Examples of suitable pharmaceutically acceptable carriers and formulations are described in "Remington: The Science and Practice of Pharmacy" 22nd Revised Edition, Pharmaceutical Press, Philadelphia, 2012, which is hereby incorporated by reference in its entirety. In some embodiments, the composition comprises or consists essentially of a unit dose of a flow modulator effective for increasing flow of CNS fluids, increasing clearance of molecules in the CNS, reducing a quantity of accumulated amyloid-beta plaques, reducing immune cell migration, counteracting the effects of decreased flow with or without restoring flow, or reducing inflammation in accordance with methods or uses as described herein. In some embodiments, the composition comprises, or consists essentially of a single unit dose of flow modulator effective for increasing flow, increasing clearance reducing accumulate amyloid-beta plaques, counteracting the effects of decreased flow with or without restoring flow, reducing immune cell migration, or reducing inflammation. In some embodiments, the effective amount of flow modulator is about 0.00015 mg/kg to about 1.5 mg/kg (including any other amount or range contemplated as a therapeutically effective amount of a compound as disclosed herein), is less than about 1.5 mg/kg (including any other range contemplated as a therapeutically effective amount of a compound as disclosed herein), or is greater than 0.00015 mg/kg (including any other range contemplated as a therapeutically effective amount of a compound as disclosed herein).

Routes of Administration

Flow modulators in accordance with methods, compositions for use, or uses of embodiments herein can be administered to a subject using any of a number of suitable routes of administration, provided that the route of administration administers the flow modulator to the meningeal space of a subject. It is noted that many compounds do not readily cross the blood-brain barrier, and as such, some routes of administration such as intravenous will not necessarily deliver the flow modulator to the meningeal space (unless the flow modulator can readily cross the blood-brain barrier). By "administering to the meningeal space of a subject," as used herein (including variations of this root term), it is not necessarily required that a flow modulator be administered directly to the meningeal space, but rather, this term encompasses administering a flow modulator directly and/or indirectly to the meningeal space. It is contemplated that administering the flow modulator so that it is in fluid communication with the meningeal space of the subject in accordance with some embodiments herein (typically by administering the flow modulator on the "brain" side of the blood-brain barrier), the flow modulator will be administered to the meningeal space. Accordingly, in some embodiments, the flow modulator is not administered systemically. In some embodiments, the flow modulator is not administered systemically, but rather is administered to a fluid, tissue, or organ in fluid communication with the meningeal space, and on the brain side of the blood-brain barrier. In some embodiments, the flow modulator is not administered systemically, but rather is administered to the CNS. In some embodiments, the flow modulator is administered to the CNS, but is not administered to any organ or tissue outside of the CNS. In some embodiments, the flow modulator is not administered to the blood. In some embodiments, the flow modulator is not administered to a tumor, or to the vasculature of a tumor.

In some embodiments, the flow modulator is administered nasally. For example, the flow modulator can be provided in a nasal spray, or can be contacted directly with a nasal mucous membrane.

In some embodiments, the flow modulator is administered through contacting with CSF of the subject. For example, the flow modulator can be directly injected into CSF of a patient (for example into a ventricle of the brain). Suitable apparatuses for injection can include a syringe, or a pump that is inserted or implanted in the subject and in fluid communication with CSF. In some embodiments, a composition comprising or consisting essentially of the flow modulator, for example a slow-release gel, is implanted in a subject so that it is in fluid communication with CSF of the subject, and thus contacts the CSF.

In some embodiments, the flow modulator is administered transcranially. For example, a composition comprising or consisting essentially of the flow modulator such as a gel can be placed on an outer portion of the subject's skull, and can pass through the subject's skull. In some embodiments, the flow modulator is contacted with a thinned portion of the subject's skull to facilitate transcranial delivery.

In some embodiments, the flow modulator is administered by expressing a nucleic acid encoding the flow modulator in the subject. A vector comprising or consisting essentially of the nucleic acid, for example a viral vector such as a retroviral vector, lentiviral vector, or adenoviral vector, or adeno-associated viral vector (AAV) can be administered to a subject as described herein, for example via injection or inhalation. In some embodiments, expression of the nucleic acid is induced in the subject, for example via a drug or optical regulator of transcription.

In some embodiments, the flow modulator (e.g. agents that modulate the copy number, level of expression, or level of activity of one or more targets listed in Table 2 and/or Table 4 and/or Table 6 and/or Table 7) is administered selectively to the meningeal space of the subject, or is for use in administration selectively to the meningeal space of the subject. As used herein administered "selectively" and variations of the root term indicate that the flow modulator is administered preferentially to the indicated target (e.g. meningeal space) compared to other tissues or organs on the same side of the blood brain barrier. As such, direct injection to meningeal spaces of the brain would represent "selective" administration, whereas administration to CSF in general via a spinal injection would not. In some embodiments, the flow modulator is administered selectively to the meningeal space, and not to portions of the CNS outside of the meningeal space, nor to any tissues or organs outside of the CNS. In some embodiments, the flow modulator is administered selectively to the CNS, and not to tissue or organs outside of the CNS such as the peripheral nervous system, muscles, the gastrointestinal system, musculature, or vasculature.

For any of the routes of administration listed herein in accordance with methods, uses, and compositions herein, it is contemplated that a flow modulator can be administered in a single administration, or in two or more administrations, which can be separated by a period of time. For example, in some embodiments, the flow modulator as described herein can be administered via a route of administration as described herein hourly, daily, every other day, every three days, every four days, every five days, every six days, weekly, biweekly, monthly, bimonthly, and the like, or a range defined by any two of the preceding values. In some embodiments, the flow administration is administered in a single administration, but not in any additional administrations.

Some embodiments include methods of making a composition or medicament comprising or consisting essentially of a flow modulator as described herein suitable for administration according to a route of administration as described herein. For example, in some embodiments, a composition comprising or consisting essentially of an agonist of a target disclosed herein is prepared for nasal administration, administration to the CSF, or transcranial administration. For example, in some embodiments, a composition comprising or consisting essentially of an antagonist of a target disclosed herein is prepared for nasal administration, administration by contacting with CSF, or transcranial administration.

Neurodegenerative Diseases

Methods, uses, and compositions in accordance with some embodiments herein can be useful for diagnosing, treating, preventing, inhibiting, ameliorating, or reducing the symptoms of one or more neurological diseases, or compositions for use in these methods. In some embodiments, the neurological diseases are neurodegenerative diseases. These diseases can occur in subjects, for example humans, as well as non-human animals, such as non-human mammals, and non-human primates in some embodiments.

In some embodiments, neurodegenerative, neurodevelopmental, neuroinflammatory, or neuropsychiatric diseases associated with accumulation of macromolecules, cells, and debris in the CNS are treated, prevented, inhibited, or reduced by methods, uses, or compositions that increase flow, drainage, and/or clearance in meningeal lymphatic vessels. In some embodiments, neurodegenerative, neurodevelopmental, neuroinflammatory, or neuropsychiatric diseases associated with accumulation of macromolecules, cells, and debris in the CNS are treated, prevented, inhibited, or reduced by methods, uses, or compositions that counteract the effects (e.g., changes in the hippocampal transcriptome) of decreased flow with or without restoring flow. In some embodiments, neurodegenerative diseases associated with accumulation of macromolecules, cells, and debris in the CNS are treated, prevented, inhibited, or reduced. Examples of neurodegenerative diseases include AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, MS, AIDS-related dementia complex, or a combination of two or more of the listed items. By way of example, neurodegenerative diseases can include AD, dementia, age-related dementia, PD, cerebral edema, ALS, PANDAS, meningitis, hemorrhagic stroke, ASD, brain tumor, and epilepsy. In some embodiments, the neurodegenerative disease comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, the neurodegenerative disease comprises, consists essentially of, or consists of prion disease. In some embodiments, the neurodegenerative disease comprises, consists essentially of, or consists of a non-human prion disease such as scrapie, chronic wasting disease, or BSE.

In some embodiments, the neurodegenerative disease can be prevented, treated, or ameliorated prophylactically. Accordingly, a subject having one or more risk factors for the neurodegenerative disease can be determined to be in need of receiving a method, use, or composition described herein. For example, a subject may have accumulated amyloid-beta plaques in their CNS, and may benefit from increased flow, increased drainage, increased clearance and/or reduction of amyloid-beta plaques, even if they do not yet have an AD diagnosis based on cognitive symptoms.

A number of risk factors for AD are suitable as risk factors in accordance with methods, compositions, and uses of some embodiments herein, for example familial AD, a genetic marker for AD, or a symptom of AD such as early dementia. The foremost risk factor for sporadic AD is age. However, increased risk of this form of AD has also been attributed to diverse genetic abnormalities. One of them is diploidy for apolipoprotein-E4 (Apo-E4), widely viewed as a major genetic risk factor promoting both early onset of amyloid-beta aggregation and defective amyloid-beta clearance from the brain (Deane et al., 2008; Zlokovic, 2013). Other genetic variants that significantly increase the risk for sporadic AD are Apo-J (or clusterin), phosphatidylinositol-binding clathrin assembly protein (PICALM), complement receptor 1 (CR1), CD33 or Siglec-3, and triggering receptor expressed on myeloid cells 2 (TREM2). All of these proteins, interestingly, have been implicated in different mechanisms of amyloid-beta removal from the brain (Bertram et al., 2008; Guerreiro et al., 2013; Harold et al., 2009; Lambert et al., 2009, 2013; Naj et al., 2011). In some embodiments, the risk factor for AD is selected from the group consisting of at least one of the following: diploidy for apolipoprotein-E-epsilon-4 (apo-E-epsilon-4), a variant in apo-J, a variant in phosphatidylinositol-binding clathrin assembly protein (PICALM), a variant in complement receptor 1 (CR3), a variant in CD33 (Siglee-3), or a variant in triggering receptor expressed on myeloid cells 2 (TREM2), age, or a symptom of dementia.

Novel Targets

A "target," "marker," or "biomarker" includes a nucleic acid or polypeptide whose altered level of expression in a tissue or cell from its expression level in a control e.g, normal or healthy tissue or cell) is associated with a disease state, such as a neurological disease (e.g., AD, dementia, PD). A "marker nucleic acid" is a nucleic acid (e.g., mRNA, cDNA, mature miRNA, pre-miRNA, pri-miRNA, miRNA*, anti-miRNA, or a miRNA binding site, or a variant thereof and other classes of small RNAs known to a skilled artisan) encoded by or corresponding to a marker of the disclosure. Such marker nucleic acids include DNA (e.g., cDNA) comprising the entire or a partial sequence of any of the nucleic acid sequences set forth in Table 2 and/or Table 4 and/or Table 6 and/or Table 7 and/or the Examples or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" includes a protein encoded by or corresponding to a marker of the disclosure. A marker protein comprises the entire or a partial sequence of any of the sequences set forth in Table 2 and/or Table 4 and/or Table 6 and/or Table 7 and/or the Examples or the Examples. The terms "protein" and "polypeptide" are used interchangeably. In some embodiments, specific combinations of targets are preferred. For example, a combination or subgroup of one or more of the targets selected from the group shown in Tables 2 and/or Table 4 and/or Table 6 and/or Table 7. In some embodiments, the one or more targets are associated with one or more of the categories listed in Table 3 and/or Table 5 and/or FIG. 14H.

In some embodiments, the one or more targets comprises one or more of the following: Met, Sorbs2, Nlgn1, ND2, Adam10, Bmpr2, Fmr1, Ptk2b, Nrgn, Adora1, Cnih2, Camk2b, Homer3, Erc2, Arrb2, Rab8a, Bcr, Dvl, Rgs14, Palm, Neurl1a, Atp1a1, Grin1, Cdk5, Dmtn, Actb, Prkcg, Arhgef2, Arfgap1, Shank3, Cryab, Dgki, Syndig1, Slc17a7, Dlg4, Nsmf, Clstn3, Src, Kcnab2, Itpr1. In some embodiments, the one or more targets comprises one or more of the following: App, Reln, Calb1, Nog, Pafah1b1, Ap1 s2, Oprk1, Cnr1, Neto1, Grin2b, Egfr, Ptprz1, Kras, Petn, Slc17a7, Apbb1, Atp1a3, Slc8a2, Ppp1 r1b, Dcdc2a, Dgki, Asic1, Comt, Rin1, Serpinf1, Pde1b, Cdk5, Btbd9, Jph3, Grin1, Cntn2, Ephb2, Ncam1, Crtc1, Thra, Rgs14, Ehmt2, B4galt2, Shank3, Shc3. In some embodiments, the one or more targets comprises one or more of the following: Ngf, Ror1, Myoc, Errfi1, Ctnnb1, Arid5b, Fgf1, Dll1, Pik3r2, Fst14, Ndrg4, Adra2c, Adamts12, Ntrk2, Lrig2, Epha7, Tsc1, Col1a1, Rbm4, Pag1, Prkcd, Btk, Cdk5r1, Csf1r, Syk, Adamts3, Fam20c, Ofd1, Fgfr3. In some embodiments, the one or more targets comprises one or more of the following: ND1, ND4L, Ndufb4, Ndufab1, Ndufc1, Ndufc2, Ndufb6, Ndufa13, Ndufa8, Ndufs5, Ndufs8, Ndufv1, Ndufa3, Ndufa11, Ndufs6, Ndufv3, Park7, Ndufa2, Ndufb8, Ndufb10, Ndufb11, Ndufa9, Ndufs2, Ndufb9, Ndufs3, and Ndufb3. In some embodiments, the one or more targets comprises one or more of the following: ND1, CYTB, ND2, ND4, ND5, Oprk1, Pmpcb, Nfatc3, Akt2, Uqcr10, Uqcrh, Bloc1s1, Cox8a, Pygb, Sirt3, Ogdhl, Prelid1, Slc25a25, Hk1, Prkaca, Park7, Pfkm, Aco2, Eif6, Ndutfb8, Mdh2, Gsk3a, Uqcrcl, Akt1, Mt3, Aldoa, Pkm, Tpi1, Idh3g, Gpi1, Ndufv1, Gpd1, Gapdh, Cox4i1, and Pfkl. In some embodiments, the one or more targets comprises one or more of the following: Nr4a3, Cpeb2, Oxr1, Sirt1, Ncoa7, Bcl2, Stk26, Hif1a, Cd36, Met, Prkcd, Etv5, Kdm6b, Prdx2, Nup93, Sod1, Apex1, Prdx5, Sirt2, Trp53, Ppif, Scly, Gpx1, G6pdx, Stat6, Parp1, Trap1, Sesn2, Mapt, Hsf1, Tldc1, Kcnc2, Src, Rps3, Mt3, Txn2, Stk25, Lonp1, Park7, and Psap. In some embodiments, the one or more targets comprises one or more of the following: IFNB1, CD40, IFNG, LYN, IMPDH2, NUP88, ADA, IRF2, ZNF114, TCF7L2, DYRK2, TACC3, GPR87, ALDH3B1, ARCPCIB, RELB, TMEM154, SPDEF, SMAD7, and MTFR1.

Agents and Compositions

Novel agents and compositions are provided herein and can be used for the diagnosis, prognosis, prevention, and treatment of neurological diseases (e.g., AD, dementia, and/or Parkinson's disease). Such agents and compositions can detect and/or modulate, e.g., up- or down-regulate, expression and/or activity of gene products or fragments thereof encoded by targets of the disclosure, including the targets listed in Tables 2 and/or Table 4 and/or Table 6 and/or Table 7 and/or the Examples. Exemplary agents include antibodies, small molecules, peptides, peptidomimetics, natural ligands, and derivatives of natural ligands, that can either bind and/or activate or inhibit protein targets of the disclosure, including the targets listed in Table 2 and/or Table 4 and/or Table 6 and/or Table 7 and/or the Examples, or fragments thereof; RNA interference, antisense, nucleic acid aptamers, etc. that can downregulate the expression and or activity of the targets of the disclosure, including the targets listed in Tables 2 and/or Table 4 and/or Table 6 and/or Table 7 and/or the Examples, or fragments thereof. In some embodiments, any of the agents or compositions described herein is for medical use.

Nucleic Acids

In some embodiments, isolated nucleic acid molecules that specifically hybridize with or encode one or more targets listed in Tables 2 and/or Table 4 and/or Table 6 and/or Table 7 and/or the Examples or biologically active portions thereof are presented. As used herein, the term "nucleic acid molecule" has its ordinary meaning as understood in the art in view of the specification, and includes DNA molecules (e.g. cDNA or genomic DNA) and RNA molecules (e.g., mRNA) and analogs of the DNA or RNA generated using nucleotide analogs. The nucleic acid molecule can be single-stranded or double-stranded. An "isolated" nucleic acid molecule is one which is separated from other nucleic acid molecules which are present in the natural source of the nucleic acid. In some embodiments, an "isolated" nucleic acid is free of sequences which naturally flank the nucleic acid (e.g., sequences located at the 5' and 3' ends of the nucleic acid) in the genomic DNA of the organism from which the nucleic acid is derived. For example, in various embodiments, the isolated nucleic acid molecules corresponding to the one or more targets listed in Table 2 and/or Table 4 and/or Table 6 and/or Table 7 and/or the Examples can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., blood, ISF, CSF), or a range defined by any two of the preceding values. Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present disclosure, e.g., a nucleic acid molecule having the nucleotide sequence of one or more targets listed in Table 2 and/or Table 4 and/or Table 6 and/or Table 7 and/or the Examples or a nucleotide sequence which is at least about 50%, at least about 60%, at least about 70%, at least about 80%, at least about 90%, and at least about 95% or more (e.g., about 98%) homologous to the nucleotide sequence of one or more targets listed in Table 2 and/or Table 4 and/or Table 6 and/or Table 7 and/or the Examples or a portion thereof (e.g., at least 20, 40, 60, 80, 100, 200, 300, 400, 450, 500, or more nucleotides, or a range defined by any two of the preceding values), can be isolated using standard molecular biology techniques and the sequence information provided herein. For example, a human cDNA can be isolated from a human cell line (from Stratagene, La Jolla, CA, or Clontech, Palo Alto, CA) using all or portion of the nucleic acid molecule, or fragment thereof, as a hybridization probe and standard hybridization techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, NY, 1989). Moreover, a nucleic acid molecule encompassing all or a portion of the nucleotide sequence of one or more targets listed in Table 2 and/or Table 4 and/or Table 6 and/or Table 7 and/or the Examples or a nucleotide sequence which is at least about 50%, in some embodiments at least about 60%, in some embodiments at least about 70%, in some embodiments at least about 80%, in some embodiments at least about 90%, and in some embodiments at least about 95% or more (or a range defined by any two of the preceding values) homologous to the nucleotide sequence, or fragment thereof, can be isolated by the polymerase chain reaction using oligonucleotide primers designed based upon the sequence of the one or more targets listed in Table 2 and/or Table 4 and/or Table 6 and/or Table 7 and/or the Examples, or fragment thereof, or the homologous nucleotide sequence. Synthetic oligonucleotide primers for PCR amplification can be designed according to well-known methods in the art. A nucleic acid of the disclosure can be amplified using in some embodiments, cDNA or, in some embodiments, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequence of one or more targets listed in Table 2 and/or Table 4 and/or Table 6 and/or Table 7 and/or the Examples can be prepared by standard synthetic techniques, e.g., using an automated DNA synthesizer.

Probes based on the nucleotide sequences of one or more targets listed in Table 2 and/or Table 4 and/or Table 6 and/or Table 7 and/or the Examples can be used to detect transcripts or genomic sequences encoding the same or homologous proteins. In some embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which express one or more targets listed in Table 2 and/or Table 4 and/or Table 6 and/or Table 7 and/or the Examples, such as by measuring a level of nucleic acid in a sample of cells from a subject, e.g., detecting mRNA levels of one or more targets listed in Table 2 and/or Table 4 and/or Table 6 and/or Table 7 and/or the Examples.

Nucleic acid molecules encoding proteins corresponding to one or more targets listed in Table 2 and/or Table 4 and/or Table 6 and/or Table 7 and/or the Examples from different species are also contemplated. For example, rat or monkey cDNA can be identified based on the nucleotide sequence of a human and/or mouse sequence and such sequences are well known in the art. In some embodiments, the nucleic acid molecule(s) of the disclosure encodes a protein or portion thereof which includes an amino acid sequence which is sufficiently homologous to an amino acid sequence of one or more targets listed in Table 2 and/or Table 4 and/or Table 6 and/or Table 7 and/or the Examples, such that the protein or portion thereof modulates (e.g., enhance), one or more of the following biological activities: a) binding to the target; b) modulating the copy number of the target; c) modulating the expression level of the target; and d) modulating the activity level of the target.

As used herein, the language "sufficiently homologous" has its ordinary meaning as understood in the art in view of the specification, and includes proteins or portions thereof which have amino acid sequences which include a minimum number of identical or equivalent [e.g., an amino acid residue which has a similar side chain as an amino acid residue in one or more targets listed in Table 2 and/or Table 4 and/or Table 6 and/or Table 7 and/or the Examples, or fragment thereof) amino acid residues to an amino acid sequence of the target, or fragment thereof, such that the protein or portion thereof modulates (e.g., enhance) one or more of the following biological activities: a) binding to the target; b) modulating the copy number of the target; c) modulating the expression level of the target; and d) modulating the activity level of the target.

In some embodiments, the protein is at least about 50%, at least about 60%, at least about 70%, 75%, 80%, 85%, 90%, 91%, 92%, 93%, 94%, 95%, 96%, 97%, 98%, 99% or more, or a range defined by any of the proceeding values, homologous to the entire amino acid sequence of the target, or a fragment thereof.

Portions of proteins encoded by nucleic acid molecules of the one or more targets listed in Table 2 and/or Table 4 and/or Table 6 and/or Table 7 and/or the Examples are in some embodiments biologically active portions of the protein. As used herein, the term "biologically active portion" has its ordinary meaning as understood in the art in view of the specification, and includes one or more targets listed in Table 2 and/or Table 4 and/or Table 6 and/or Table 7 and/or the Examples is intended to include a portion, e.g., a domain/motif, that has one or more of the biological activities of the full-length protein.

Standard binding assays, e.g., immunoprecipitations and yeast two-hybrid assays, as described herein, or functional assays, e.g., RNAi or overexpression experiments, can be performed to determine the ability of the protein or a biologically active fragment thereof to maintain a biological activity of the full-length protein.

The disclosure further encompasses nucleic acid molecules that differ from the nucleotide sequence of the one or more targets listed in Table 2 and/or Table 4 and/or Table 6 and/or Table 7 and/or the Examples, or fragment thereof due to degeneracy of the genetic code and thus encode the same protein as that encoded by the nucleotide sequence, or fragment thereof. In some embodiments, an isolated nucleic acid molecule of the disclosure has a nucleotide sequence encoding a protein having an amino acid sequence of one or more targets listed in Table 2 and/or Table 4 and/or Table 6 and/or Table 7 and/or the Examples, or fragment thereof, or a protein having an amino acid sequence which is at least about 70%, 75%, 80%, 85%, 90%, 91%, 92%, 93%, 94%, 95%, 96%, 97%, 98%, 99% or more, or a range defined by any two of the preceding values, homologous to the amino acid sequence of the one or more targets listed in Table 2 and/or Table 4 and/or Table 6 and/or Table 7 and/or the Examples, or fragment thereof. In some embodiments, a nucleic acid encoding a polypeptide consists of nucleic acid sequence encoding a portion of a full-length fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length, or a range defined by any two of the preceding values.

It will be appreciated by those skilled in the art that DNA sequence polymorphisms that lead to changes in the amino acid sequences of the one or more targets listed in Table 2 and/or Table 4 and/or Table 6 and/or Table 7 and/or the Examples may exist within a population (e.g., a mammalian and or human population). Such genetic polymorphisms may exist among individuals within a population due to natural allelic variation. As used herein, the terms "gene" and "recombinant gene" have their ordinary meaning as understood in the art in view of the specification, and include nucleic acid molecules comprising an open reading frame encoding one or more targets listed in Table 2 and/or Table 4 and/or Table 6 and/or Table 7 and/or the Examples, in some embodiments a mammalian, e.g., human, protein. Such natural allelic variations can typically result in 1-5% variance in the nucleotide sequence of the one or more targets listed in Table 2 and/or Table 4 and/or Table 6 and/or Table 7 and/or the Examples. Any and all such nucleotide variations and resulting amino acid polymorphisms in the one or more targets listed in Table 2 and/or Table 4 and/or Table 6 and/or Table 7 and/or the Examples that are the result of natural allelic variation and that do not alter the functional activity of the one or more targets listed in Table 2 and/or Table 4 and/or Table 6 and/or Table 7 and/or the Examples are intended to be within the scope of the disclosure. Moreover, nucleic acid molecules encoding one or more targets listed in Table 2 and/or Table 4 and/or Table 6 and/or Table 7 and/or the Examples from other species.

In addition to naturally-occurring allelic variants of the one or more targets listed in Table 2 and/or Table 4 and/or Table 6 and/or Table 7 and/or the Examples sequence that may exist in the population, the skilled artisan will further appreciate that changes can be introduced by mutation into the nucleotide sequence, or fragment thereof, thereby leading to changes in the amino acid sequence of the encoded one or more targets listed in Table 2 and/or Table 4 and/or Table 6 and/or Table 7 and/or the Examples, without altering the functional ability of the one or more targets listed in Table 2 and/or Table 4 and/or Table 6 and/or Table 7 and/or the Examples. For example, nucleotide substitutions leading to amino acid substitutions at "non-essential" amino acid residues can be made in the sequence, or fragment thereof. A "non-essential" amino acid residue is a residue that can be altered from the wild-type sequence of the one or more targets listed in Table 2 and/or Table 4 and/or Table 6 and/or Table 7 and/or the Examples without altering the activity of the one or more targets listed in Table 2 and/or Table 4 and/or Table 6 and/or Table 7 and/or the Examples, whereas an "essential" amino acid residue is required for the activity of the one or more targets listed in Table 2 and/or Table 4 and/or Table 6 and/or Table 7 and/or the Examples. Other amino acid residues, however, (e.g., those that are not conserved or only semi-conserved between mouse and human) may not be essential for activity and thus are likely to be amenable to alteration without altering the activity of the one or more targets listed in Table 2 and/or Table 4 and/or Table 6 and/or Table 7 and/or the Examples.

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

An isolated nucleic acid molecule encoding a protein homologous to one or more targets listed in Table 2 and/or Table 4 and/or Table 6 and/or Table 7 and/or the Examples, or fragment thereof, can be created by introducing one or more nucleotide substitutions, additions or deletions into the nucleotide sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. In some embodiments, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in one or more targets listed in Table 2 and/or Table 4 and/or Table 6 and/or Table 7 and/or the Examples is in some embodiments replaced with another amino acid residue from the same side chain family. In some embodiments, mutations can be introduced randomly along all or part of the coding sequence of the one or more targets listed in Table 2 and/or Table 4 and/or Table 6 and/or Table 7 and/or the Examples, such as by saturation mutagenesis, and the resultant mutants can be screened for an activity described herein to identify mutants that retain desired activity. Following mutagenesis, the encoded protein can be expressed recombinantly according to well-known methods in the art and the activity of the protein can be determined using, for example, assays described herein.

The levels of one or more targets listed in Table 2 and/or Table 4 and/or Table 6 and/or Table 7 and/or the Examples levels may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In some embodiments, the levels of one or more targets listed in Table 2 and/or Table 4 and/or Table 6 and/or Table 7 and/or the Examples levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, in some embodiments, can be a qualitative assessment of the level of gene expression, in particular in comparison with a control level. The type of level being detected will be clear from the context.

In some embodiments, the mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al, ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides, or a range defined by any two of the preceding values, in length and sufficient to specifically hybridize under stringent conditions to a mRNA or genomic DNA encoding one or more targets listed in Table 2 and/or Table 4 and/or Table 6 and/or Table 7 and/or the Examples. Other suitable probes for use in the diagnostic assays of the disclosure are described herein. Hybridization of an mRNA with the probe indicates that one or more targets listed in Table 2 and/or Table 4 and/or Table 6 and/or Table 7 and/or the Examples is being expressed.

In one format, the mRNA is immobilized on a solid surface and contacted with a probe, for example by running the isolated mRNA on an agarose gel and transferring the mRNA from the gel to a membrane, such as nitrocellulose. In some embodiments, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the one or more targets listed in Table 2 and/or Table 4 and/or Table 6 and/or Table 7 and/or the Examples mRNA expression levels.

In some embodiments the method of determining mRNA expression level in a sample involves the process of nucleic acid amplification, e.g., by RT-PCR (the experimental embodiment set forth in Mullis, 1987, U.S. Pat. No. 4,683, 202), ligase chain reaction (Barany, 1991, Proc. Natl. Acad. Sci. USA, 88:189-193), self-sustained sequence replication (Guatelli et al, 1990, Proc. Natl. Acad. Sci. USA 87:1874-1878), transcriptional amplification system (Kwoh et al., 1989, Proc. Natl. Acad. Sci. USA 86: 1173-1177), Q-Beta Replicase (Lizardi et al., 1988, Bio/Technology 6: 1197), rolling circle replication {Lizardi et al, U.S. Pat. No. 5,854, 033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers have their ordinary meaning as understood in the art in view of the specification, and include a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared and processed using known histological methods. The sample is then immobilized on a support, typically a glass slide, and then contacted with a probe that can hybridize to the one or more targets listed in Table 2 and/or Table 4 and/or Table 6 and/or Table 7 and/or the Examples mRNA.

In addition to, or instead of, making determinations based on the absolute expression level, determinations may be based on the normalized expression level of one or more targets listed in Table 2 and/or Table 4 and/or Table 6 and/or Table 7 and/or the Examples. Expression levels are normalized by correcting the absolute expression level by comparing its expression to the expression of a non-target gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a protein corresponding to one or more targets listed in Table 2 and/or Table 4 and/or Table 6 and/or Table 7 and/or the Examples can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express the target of interest.

Polypeptides and Antibodies

The present disclosure further provides soluble, purified and/or isolated polypeptide forms of one or more targets listed in Table 2 and/or Table 4 and/or Table 6 and/or Table 7 and/or the Examples, or fragments thereof. In addition, it is to be understood that any and all attributes of the polypeptides described herein, such as percentage identities, polypeptide lengths, polypeptide fragments, biological activities, antibodies, etc. can be combined in any order or combination with respect to any target listed in Table 2 and/or Table 4 and/or Table 6 and/or Table 7 and/or the Examples and combinations thereof.

In one aspect, a polypeptide may comprise a full-length amino acid sequence corresponding to one or more targets listed in Table 2 and/or Table 4 and/or Table 6 and/or Table 7 and/or the Examples or a full-length amino acid sequence with 1 to about 20 conservative amino acid substitutions. An amino acid sequence of any described herein can also be at least 50, 55, 60, 65, 70, 75, 80, 85, 90, 91, 92, 93, 94, 95, 96, 97, 98, 99, or 99.5%, or a range defined by any two of the preceding values, identical to the full-length sequence of one or more targets listed in Table 2 and/or Table 4 and/or Table 6 and/or Table 7 and/or the Examples, which is either described herein, well known in the art, or a fragment thereof. In some embodiments, the present disclosure contemplates a composition comprising an isolated polypeptide corresponding to one or more targets listed in Table 2 and/or Table 4 and/or Table 6 and/or Table 7 and/or the Examples polypeptide and less than about 25% in some embodiments, or 15% in some embodiments, or 5% in some embodiments, or a range defined by any two of the preceding values, contaminating biological macromolecules or polypeptides.

The present disclosure further provides compositions related to producing, detecting, characterizing, or modulating the level or activity of such polypeptides, or fragment thereof, such as nucleic acids, vectors, host cells, and the like. Such compositions may serve as compounds that modulate the expression and/or activity of one or more targets listed in Table 2 and/or Table 4 and/or Table 6 and/or Table 7 and/or the Examples.

An isolated polypeptide or a fragment thereof (or a nucleic acid encoding such a polypeptide) corresponding to one or more targets of the disclosure, including the targets listed in Table 2 and/or Table 4 and/or Table 6 and/or Table 7 and/or the Examples or fragments thereof, can be used as an immunogen to generate antibodies that bind to said immunogen, using standard techniques for polyclonal and monoclonal antibody preparation according to well-known methods in the art. An antigenic peptide comprises at least 8 amino acid residues and encompasses an epitope present in the respective full length molecule such that an antibody raised against the peptide forms a specific immune complex with the respective full length molecule. In some embodiments the antigenic peptide comprises at least 10 amino acid residues. In some embodiments such epitopes can be specific for a given polypeptide molecule from one species, such as mouse or human (e.g., an antigenic peptide that spans a region of the polypeptide molecule that is not conserved across species is used as immunogen; such non-conserved residues can be determined using an alignment such as that provided herein).

For example, a polypeptide immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) Nature 256:495-497) (see also Brown et al. (1981) J. Immunol. 127:539-46; Brown et al. (1980) J. Biol. Chem. 255:4980-83; Yeh et al. (1976) Proc. Natl. Acad. Sci. 76:2927-31; Yeh et al. (1982) Int. J. Cancer 29:269-75), the more recent human B cell hybridoma technique (Kozbor et al. (1 83) Immunol. Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well known (see generally Kenneth, R. H. in Monoclonal Antibodies: A New Dimension In Biological Analyses, Plenum Publishing Corp., New York, New York (1980); Lerner, E. A. (1981) Yale J. Biol. Med. 54:387-402; Gefter, M. L. et al. (1977) Somatic Cell Genet. 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, in some embodiments specifically.

Any of the many well-known protocols used for fusing lymphocytes and immortalized cell lines can be applied for the purpose of generating a monoclonal antibody against one or more targets of the disclosure, including the targets listed in Table 2 and/or Table 4 and/or Table 6 and/or Table 7 and/or the Examples, or a fragment thereof (see, e.g., Galfre, G. et al. (1 77) Nature 266:550-52; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present disclosure with an immortalized mouse cell line. In some embodiments immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NSI/I-Ag4-1, P3-x63-Ag8.653 or Sp2/0-Agl4 myeloma lines. These myeloma lines are available from the American Type Culture Collection (ATCC), Rockville, MD. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the disclosure are detected by screening the hybridoma culture supernatants for antibodies that bind a given polypeptide, e.g., using a standard ELISA assay. As an alternative to preparing monoclonal antibody-secreting hybridomas, a monoclonal antibody specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available.

Additionally, recombinant polypeptide antibodies, such as chimeric and humanized monoclonal antibodies, comprising both human and non-human portions, which can be made using standard recombinant DNA techniques, are within the scope of the disclosure. Such chimeric and humanized monoclonal antibodies can be produced by recombinant DNA techniques known in the art. In addition, humanized antibodies can be made according to standard protocols such as those disclosed in U.S. Pat. No. 5,565,332. In some embodiments, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art.

Additionally, fully human antibodies could be made against targets of the disclosure, including the targets listed in Table 2 and/or Table 4 and/or Table 6 and/or Table 7 and/or the Examples, or fragments thereof. Fully human antibodies can be made in mice that are transgenic for human immunoglobulin genes, e.g., according to Hogan, et al., "Manipulating the Mouse Embryo: A Laboratory Manuel," Cold Spring Harbor Laboratory, which is herein incorporated by reference in its entirety. Briefly, transgenic mice are immunized with purified immunogen. Spleen cells are harvested and fused to myeloma cells to produce hybridomas. Hybridomas are selected based on their ability to produce antibodies which bind to the immunogen. Fully human antibodies would reduce the immunogenicity of such antibodies in a human.

In some embodiments, an antibody for use in the instant disclosure is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al (1985) Nature 314:628, and Perez et al. (1985) Nature 316:354) and hybridoma technology (Staerz and Bevan (1986) Proc. Natl. Acad. Sci. USA, 83:1453, and Staerz and Bevan (1986) Immunol. Today 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more targets of the disclosure, including one or more targets listed in Table 2 and/or Table 4 and/or Table 6 and/or Table 7 and/or the Examples, or a fragment thereof. In some embodiments, the bispecific antibody could specifically bind to both a polypeptide or a fragment thereof and its natural binding partner(s) or a fragment(s) thereof.

Expression Vectors

In some embodiments, expression vectors, containing a nucleic acid encoding a target listed in Table 2 and/or Table 4 and/or Table 6 and/or Table 7, or a fragment thereof, or an ortholog thereof. As used herein, the term "vector" has its ordinary meaning as understood in the art in view of the specification, and includes a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein, in some embodiments, as "expression vectors". In general, expression vectors of utility in recombinant DNA techniques are often in the form of plasmids. In the present specification, "plasmid" and "vector" can be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions. In some embodiments, adenoviral vectors comprising a target nucleic acid molecule are provided.

The recombinant expression vectors disclosed herein comprise, in some embodiments, a nucleic acid in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the disclosure can be introduced into host cells to thereby produce proteins or peptides, including fusion proteins or peptides, encoded by nucleic acids as described herein.

The recombinant expression vectors of the disclosure can be designed for expression of the desired target in prokaryotic or eukaryotic cells or human or non-human hosts. For example, a target can be expressed in bacterial cells such as E. coli, insect cells (using baculovirus expression vectors) yeast cells or mammalian cells. Suitable host cells are discussed further in Goeddel, Gene Expression Technology". Methods in Enzymolog 185, Academic Press, San Diego, CA (1990). In some embodiments, the recombinant expression vector can be transcribed and translated in vitro, for example using T7 promoter regulatory sequences and T7 polymerase. In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. In some embodiments, the viral vector comprises a strong eukaryotic promoter operably linked to the polynucleotide e.g., a cytomegalovirus (CMV) promoter.

In some embodiments vectors include viral vectors, fusion proteins and chemical conjugates. Retroviral vectors include Moloney murine leukemia viruses and HIV-based viruses. In some embodiments the HIV-based viral vector comprises at least two vectors wherein the gag and pol genes are from an HIV genome and the env gene is from another virus. DNA viral vectors are employed in some embodiments. These vectors include pox vectors such as orthopox or avipox vectors, herpesvirus vectors such as a herpes simplex I virus (HSV) vector, Adenovirus Vectors and Adeno-associated Virus Vectors.

Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations Peptides and Peptide Mimetics In some embodiments, peptides or peptide mimetics can be used to antagonize or promote the activity of one or more targets of the disclosure, including one or more targets listed in Table 2 and/or Table 4 and/or Table 6 and/or Table 7 and/or the Examples, or a fragment(s) thereof. In some embodiments, variants of one or more targets listed in Table 2 and/or Table 4 and/or Table 6 and/or Table 7 and/or the Examples which function as a modulating agent for the respective full length protein, can be identified by screening combinatorial libraries of mutants, e.g., truncation mutants, for antagonist activity. In some embodiments, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) Tetrahedron 39:3; Itakura et al (1984) Annu. Rev. Bioche. 53:323; Itakura et al. (1984) Science 198: 1056; Ike et al. (1983) Nucleic Acid Res. 11:477.

In addition, libraries of fragments of a polypeptide coding sequence can be used to generate a variegated population of polypeptide fragments for screening and subsequent selection of variants of a given polypeptide. In some embodiments, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S 1 nuclease, and ligating the resulting fragment library into an expression vector. By this method, an expression library can be derived which encodes N-terminal, C-terminal and internal fragments of various sizes of the polypeptide. Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) Proc. Natl. Acad. Sci. USA 89:7811-7815; Delagrave et al. (1993) Protein Eng. 6(3):327-331). In some embodiments, cell based assays can be exploited to analyze a variegated polypeptide library. For example, a library of expression vectors can be transfected into a cell line which ordinarily synthesizes one or more targets of the disclosure, including one or more targets listed in Table 2 and/or Table 4 and/or Table 6 and/or Table 7 and/or the Examples, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or in some embodiments, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) Annu. Rev. Biochem. 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. In some embodiments, such peptides can be synthesized by chemical methods. Methods for expression of heterologous proteins in recombinant hosts, chemical synthesis of polypeptides, and in vitro translation are well known in the art and are described further in Maniatis et al. Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1 87), Academic Press, Inc., San Diego, Calif.; Merrifield, J. (1969) J. Am. Chem. Soc. 91:501; Chaiken I. M. (1981) CRC Crit. Rev. Biochem. 1 1: 255; Kaiser et al. (1989) Science 243: 187; Merrifield, B. (1986) Science 232:342; Kent, S. B. H. (1988) rnK. Rev. Biochem. 57:957; and Offord, R. E. (1980) Semisynthetic Proteins, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In some embodiments, either the carboxy-terminus or the ammo-terminus, or both, are chemically modified. The most common modifications of the terminal amino and carboxyl groups are acetylation and amidation, respectively. Amino-terminal modifications such as acylation {e.g., acetylation) or alkylation (e.g., methylation) and carboxy-terminal-modifications such as amidation, as well as other terminal modifications, including cyclization, can be incorporated into various embodiments of the disclosure. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient. Peptidomimetics (Fauchere, J. (1986) Adv. Drug Res. 15:29; Veber and Freidinger (1985) TINS p. 392; and Evans et al. (1987) J. Med. Chem. 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (e.g., a polypeptide that has a biological or pharmacological activity), but have one or more peptide linkages optionally replaced by a linkage selected from the group consisting of: —CH2NH—, —CH2S—, —CH2-CH2-, —CH═CH— (cis and trans), —COCH2-, —CH(OH)CH2-, and —CH2SO—, by methods known in the art and further described in the following references: Spatola, A. F. in "Chemistry and Biochemistry of Amino Acids, Peptides, and Proteins" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) Trends Pharm. Sci. pp. 463-468 (general review); Hudson, D. et al. (1979) Int. J. Pept. Prot. Res. 14: 177-185 (—CH2NH—, CH2CH2-); Spatola, A. F. et al. (1986) Life Sci. 38: 1243-1249 (—CH2-S); Hann, M. M. (1982) J. Chem. Soc. Perkin Trans./. 307-314 (—CH═CH—, cis and trans); Almquist, R. G. et al. (190) J Med.

Chem. 23:1392-1398 (—COCH2-); Jennings-White, C. et al. (1982) Tetrahedron Lett. 23:2533 (—COCH2-); Szelke, M. et al. European Appln. EP 45665 (1 82) CA: 97:39405 (1982) (—CH(OH)CH2-); Holladay, M. W. et al. (1983) Tetrahedron Lett. (1983) 24:4401-4404 (—C(OH)CH2-); and Hruby, V. J. (1982) Life Sci. (1982) 31: 189-199 (—CH2-S—); each of which is incorporated herein by reference. In some embodiments the non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g, an amide group), to non-interfering position(s) on the peptidomimetic that are predicted by quantitative structure-activity data and or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

Small Molecules

Also encompassed by the present disclosure are small molecules which can modulate (either enhance or inhibit) interactions, e.g., between targets listed in Table 2 and/or Table 4 and/or Table 6 and/or Table 7 and/or the Examples and their natural binding partners, or inhibit activity. The small molecules of the present disclosure can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J Med. Chem. 37:1233.

Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner USP '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. USA 87:6378-6382); (Felici (1991) J. Mol. Biol. 222:301-310); (Ladner supra.). Compounds can be screened in cell based or non-cell based assays. Compounds can be screened in pools (e.g., multiple compounds in each testing sample) or as individual compounds.

Chimeric and Fusion Proteins

The disclosure also relates to chimeric or fusion proteins of the targets of the disclosure, including the targets listed in Table 2 and/or Table 4 and/or Table 6 and/or Table 7 and/or the Examples, or fragments thereof. As used herein, a "chimeric protein" or "fusion protein" have their ordinary meaning as understood in the art in view of the specification, and include one or more targets of the disclosure, including one or more targets listed in Table 2 and/or Table 4 and/or Table 6 and/or Table 7 and/or the Examples, or a fragment thereof, operatively linked to another polypeptide having an amino acid sequence corresponding to a protein which is not substantially homologous to the respective target. In some embodiments, the fusion protein comprises at least one biologically active portion of one or more targets of the disclosure, including one or more targets listed in Table 2 and/or Table 4 and/or Table 6 and/or Table 7 and/or the Examples, or fragments thereof. Within the fusion protein, the term "operatively linked" is intended to indicate that the target sequences and the non-target sequences are fused in-frame to each other in such a way as to preserve functions exhibited when expressed independently of the fusion. The "another" sequences can be fused to the N-terminus or C-terminus of the target sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In some embodiments, the first peptide consists of a portion of a biologically active molecule (e.g., the extracellular portion of the polypeptide or the ligand binding portion). The second peptide can include an immunoglobulin constant region, for example, a human Cyl domain or Cy4 domain {e.g., the hinge, CH2 and CH3 regions of human IgOy 1, or human IgCy4, see e.g., Capon et al. U.S. Pat. Nos. 5,116,964; 5,580,756; 5,844,095 and the like, incorporated herein by reference). Such constant regions may retain regions which mediate effector function {e.g., Fc receptor binding) or may be altered to reduce effector function. A resulting fusion protein may have altered solubility, binding affinity, stability and/or valency (e.g., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. In some embodiments, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

In some embodiments, a fusion protein of the disclosure is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In some embodiments, the fusion gene can be synthesized by conventional techniques including automated DNA synthesizers. In some embodiments, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1 92). In some embodiments, the fusion protein contains a heterologous signal sequence at its N-terminus. In certain host cells (e.g., mammalian host cells), expression and/or secretion of a polypeptide can be increased through use of a heterologous signal sequence.

The fusion proteins of the disclosure can be used as immunogens to produce antibodies in a subject. Such antibodies may be used to purify the respective natural polypeptides from which the fusion proteins were generated, or in screening assays to identify polypeptides which inhibit the interactions between one or more targets polypeptide or a fragment thereof and its natural binding partners) or a fragments) thereof.

Small Nucleic Acids and Antisense Oligonucleotides

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-mi RNA, a miRNA binding site, a variant and/or functional variant thereof, cellular mRNAs or a fragments thereof). In some embodiments, expression of the small nucleic acids or antisense oligonucleotides or derivatives thereof in a cell can enhance or upregulate one or more biological activities associated with the corresponding wild-type, naturally occurring, or synthetic small nucleic acids. In some embodiments, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more targets of the disclosure, including one or more targets listed in Table 2 and/or Table 4 and/or Table 6 and/or Table 7 and/or the Examples, or fragment(s) thereof. In some embodiments, the small nucleic acids or antisense oligonucleotides or derivatives thereof are small RNAs (e.g., microRNAs) or complements of small RNAs. In some embodiments, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10, or a range defined by any two of the preceding values, nucleotides in length. In some embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In some embodiments, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well known in the art that modifications can be made to the sequence of a miRNA or a pre-miRNA without disrupting miRNA activity. As used herein, the term "functional variant" have their ordinary meaning as understood in the art in view of the specification, and include a miRNA sequence refers to an oligonucleotide sequence that varies from the natural miRNA sequence, but retains one or more functional characteristics of the miRNA (e.g., specific miRNA target inhibition). In some embodiments, a functional variant of a miRNA sequence retains all of the functional characteristics of the miRNA. In some embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99%, or a range defined by any two of the preceding values, identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more, or a range defined by any two of the preceding values, nucleobases, or that the functional variant hybridizes to the complement of the miRNA or precursor thereof under stringent hybridization conditions. Accordingly, in some embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the disclosure may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin. In some embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). In some embodiments, the small nucleic acid molecules can produce RNA which encodes mR A, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol. 20:497-500; Paddison et al. (2002), Genes Dev. 16:948-958; Lee et I. (2002), Nat. Biotechnol. 20:500-505; and Paul et al. (2002), Nat. Biotechnol. 20:505-508, the entire disclosures of which are herein incorporated by reference.

In some embodiments, small nucleic acids and/or antisense constructs are oligonucleotide probes that are generated ex vivo and which, when introduced into the cell, results in hybridization with cellular nucleic acids. Such oligonucleotide probes are in some embodiments modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264, 564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to targets listed in Table 2 and/or Table 4 and/or Table 6 and/or Table 7 and/or the Examples). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, R. (1994) Nature 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10, or a range defined by any two of the preceding values, nucleotides in length.

Regardless of the choice of target sequence, in some embodiments in vitro studies are first performed to quantitate the ability of the antisense oligonucleotide to inhibit gene expression. In some embodiments these studies utilize controls that distinguish between antisense gene inhibition and nonspecific biological effects of oligonucleotides. In some embodiment these studies compare levels of the target nucleic acid or protein with that of an internal control nucleic acid or protein. Additionally, it is envisioned that results obtained using the antisense oligonucleotide are compared with those obtained using a control oligonucleotide. In some embodiments the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides {e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1 87) Proc. Natl. Acad. Sci. 84:648-652; PCT Publication No. WO88/ 09810, published Dec. 15, 1988) or the blood-brain barrier (see, e.g., PCT Publication No. WO89/10134, published Apr. 25, 1988), hybridization-triggered cleavage agents. (See, e.g., Rrol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxyiethyl) uracil, 5-carboxymethylaminomethyl-2-thiouridine, 5-carboxymemylaminomethyluracil, dihydrouracil, beta-D-galactosylqueosine, inosine, N6-isopcntenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-memoxyarnmomemyl-2-tMouraciL beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In some embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In some embodiments, a conjugate group is attached directly to the oligonucleotide. In some embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1—C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the S'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a S'-phosphoramidate, a 5'-phosphorothioate, a 5'-amino, a bridging and/or non-bridging 5-phosphoramidate, a phosphorothioate, and a 5-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In some embodiments, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are a-anomeric oligonucleotides. An ot-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-O-methylribonucleotide (Inoue et al. (1 87) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Bioscarch, Applied Biosy stems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, 111., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically. In some embodiments, small nucleic acids and/or antisense oligonucleotides may comprise or be generated from double stranded small interfering RNAs (siRNAs), in which sequences fully complementary to cellular nucleic acids (e.g., mRNAs) sequences mediate degradation or in which sequences incompletely complementary to cellular nucleic acids (e.g., mRNAs) mediate translational repression when expressed within cells. In some embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene, in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. In some embodiments, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™

Ribozymes

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver e/o/. (1990) Science 247: 1222-1225 and U.S. Pat. No. 5,093,246). While ribozymes that cleave mRNA at site specific recognition sequences can be used to destroy cellular mRNAs, the use of hammerhead ribozymes is employed in some embodiments.

Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; e.g., to increase efficiency and minimize the intracellular accumulation of non-functional mR A transcripts.

The ribozymes of the methods and compositions presented herein also include RNA endoribonucleases (which have their ordinary meaning as understood in the art in view of the specification, and include "Cech-type ribozymes") such as the one which occurs naturally in *Tetrahymena thermophila* (known as the IVS, or L-1 IVS RNA) and which has been extensively described by Thomas Cech and collaborators (Zaug, et al. (1984) Science 224:574-578; Zaug, et al (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). In some embodiments, the method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are in some embodiments single stranded and composed of deoxyribonucleotides. The base composition of these oligonucleotides should promote triple helix formation via Hoogsteen base pairing rules, which generally require sizable stretches of either purines or pyrrolidines to be present on one strand of a duplex.

Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex. In some embodiments, the potential sequences that can be targeted for triple helix formation may be increased by creating a so called "switchback" nucleic acid molecule. Switchback molecules are synthesized in an alternating 5'-3\ 3'-5' manner, such that they base pair with first one strand of a duplex and then the other, eliminating the necessity for a sizable stretch of either purines or pyrimidines to be present on one strand of a duplex.

Small Nucleic Acid Preparation

Small nucleic acids (e g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxy-ribonucleotides and oligoribonucleotides well known in the art such as for example solid phase phosphoramidite chemical synthesis. In some embodiments, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. In some embodiments, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g, a heterologous peptide), e.g., that serves as a means of protein detection. Non-limiting examples of label peptide or polypeptide moieties useful for detection include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art.

Methods of Selecting Agents and Compositions

Another aspect of the disclosure relates to methods of selecting agents (e.g., antibodies, fusion proteins, peptides, small molecules, or small nucleic acids) which bind to, upregulate, downregulate, or modulate one or more targets of the disclosure listed in Table 2 and/or Table 4 and/or Table 6 and/or Table 7 and/or the Examples. Such methods can use screening assays, including cell based and non-cell based assays. In some embodiments, the disclosure relates to assays for screening candidate or test compounds which bind to or modulate the expression or activity level of, one or more targets of the disclosure, including one or more targets listed in Table 2 and/or Table 4 and/or Table 6 and/or Table 7 and/or the Examples, or a fragment thereof. Such compounds include, without limitation, antibodies, proteins, fusion proteins, nucleic acid molecules, and small molecules.

In some embodiments, an assay is a cell-based assay, comprising contacting a cell expressing one or more targets of the disclosure, including one or more targets listed in Table 2 and/or Table 4 and/or Table 6 and/or Table 7 and/or the Examples, or a fragment thereof, with a test compound and determining the ability of the test compound to modulate (e.g., stimulate or inhibit) the level of interaction between the target and its natural binding partners as measured by direct binding or by measuring a parameter of a neurological disease or disorder.

For example, in a direct binding assay, the target polypeptide, a binding partner polypeptide of the target, or a fragment(s) thereof, can be coupled with a radioisotope or enzymatic label such that binding of the target polypeptide or a fragment thereof to its natural binding partners) or a fragment(s) thereof can be determined by detecting the labeled molecule in a complex. For example, the target polypeptide, a binding partner polypeptide of the target, or a fragment(s) thereof, can be labeled with $^{125}$I, $^{35}$S, $^{7}$C, or $^{3}$H, either directly or indirectly, and the radioisotope detected by direct counting of radioemission or by scintillation counting. In some embodiments, the polypeptides of interest a can be enzymatically labeled with, for example, horseradish peroxidase, alkaline phosphatase, or luciferase, and the enzymatic label detected by determination of conversion of an appropriate substrate to product.

It is also within the scope of this disclosure to determine the ability of a compound to modulate the interactions between one or more targets of the disclosure, including one or more targets listed in Table 2 and/or Table 4 and/or Table 6 and/or Table 7 and/or the Examples, or a fragment thereof, and its natural binding partner(s) or a fragments) thereof, without the labeling of any of the interactants (e.g., using a micropbysiometer as described in McConnell, H. M. et al. (1992) Science 257: 1906-1912). As used herein, a "microphysiometer" (e.g., Cytosensor) has its ordinary meaning as understood in the art in view of the specification, and includes an analytical instrument that measures the rate at which a cell acidifies its environment using a light-addressable potentiometric sensor (LAPS). Changes in this acidification rate can be used as an indicator of the interaction between compound and receptor.

In some embodiments, determining the ability of the blocking agents (e.g., antibodies, fusion proteins, peptides, nucleic acid molecules, or small molecules) to antagonize the interaction between a given set of polypeptides can be accomplished by determining the activity of one or more members of the set of interacting molecules. For example, the activity of one or more targets of the disclosure, including one or more targets listed in Table 2 and/or Table 4 and/or Table 6 and/or Table 7 and/or the Examples, or a fragment thereof, can be determined by detecting induction of cytokine or chemokine response, detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by the target or a fragment thereof (e.g., modulations of biological pathways identified herein, such as modulated proliferation, apoptosis, cell cycle, and/or ligand-receptor binding activity).

In some embodiments, an assay of the present disclosure is a cell-free assay in which one or more targets of the disclosure, including one or more targets listed in Table 2 and/or Table 4 and/or Table 6 and/or Table 7 and/or the Examples or a fragment thereof, e.g., a biologically active fragment thereof, is contacted with a test compound, and the ability of the test compound to bind to the polypeptide, or biologically active portion thereof, is determined. Binding of the test compound to the target or a fragment thereof, can be determined either directly or indirectly as described above. Determining the ability of the target or a fragment thereof to bind to its natural binding partner(s) or a fragment(s) thereof can also be accomplished using a technology such as real-time Biomolecular Interaction Analysis (BIA) (Sjolander, S. and Urbaniczky, C. (1991) Anal. Chem. 63:2338-2345 and Szabo et al. (1995) Curr. Opin. Struct. Biol. 5:699-705). As used herein, "BIA" has its ordinary meaning as understood in the art in view of the specification, and includes a technology for studying biospecific interactions in real time, without labeling any of the interactants (e.g., BIAcore). Changes in the optical phenomenon of surface plasmon resonance (SPR) can be used as an indication of real-time reactions between biological polypeptides. One or more targets polypeptide or a fragment thereof can be immobilized on a BIAcore chip and multiple agents, e.g., blocking antibodies, fusion proteins, peptides, or small molecules, can be tested for binding to the immobilized target polypeptide or fragment thereof. An example of using the BIA technology is described by Fitz et al. (1997) Oncogene 15:613.

The cell-free assays of the present disclosure are amenable to use of both soluble and/or membrane-bound forms of proteins. In the case of cell-free assays in which a membrane-bound form protein is used it may be desirable to utilize a solubilizing agent such that the membrane-bound form of the protein is maintained in solution. Examples of such solubilizing agents include non-ionic detergents such as n-octylghicoside, n-dodecylglucoside, n-dodecylmaltoside, octanoyl-N-methylglucamide, decanoyl-N-methylglucamide, Triton® X-100, Triton® X-I 14, Thesit®, Isotridecypoly(ethylene glycol ether)$_n$, 3-[(3-cholamidopropyl) dimethylammino]-1-propane sulfonate (CHAPS), 3-[(3- cholamidopropyl)dimemylamminio]-2-hydroxy-I-propane sulfonate (CHAPSO), or N-dodecyl=N,N-dimethyl-3-ammonio-1-propane sulfonate.

In one or more embodiments of the above described assay methods, it may be desirable to immobilize either the target polypeptide, the natural binding partner(s) polypeptide of the target, or fragments thereof, to facilitate separation of complexed from uncomplexed forms of one or both of the proteins, as well as to accommodate automation of the assay. Binding of a test compound in the assay can be accomplished in any vessel suitable for containing the reactants. Examples of such vessels include microtiter plates, test tubes, and micro-centrifuge tubes. In some embodiments, a fusion protein can be provided which adds a domain that allows one or both of the proteins to be bound to a matrix. For example, glutathione-S-transferase-base fusion proteins, can be adsorbed onto glutathione Sepharose® beads (Sigma Chemical, St. Louis, MO) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. In some embodiments, the complexes can be dissociated from the matrix, and the level of binding or activity determined using standard techniques.

In an alternative embodiment, determining the ability of the test compound to modulate the activity of one or more targets of the disclosure, including one or more targets listed in Table 2 and/or Table 4 and/or Table 6 and/or Table 7 and/or the Examples, or a fragment thereof, or of natural binding partner(s) thereof can be accomplished by determining the ability of the test compound to modulate the expression or activity of a gene, e.g., nucleic acid, or gene product, e.g., polypeptide, that functions downstream of the interaction. For example, inflammation (e.g., cytokine and chemokine) responses can be determined, the activity of the interactor polypeptide on an appropriate target can be determined, or the binding of the interactor to an appropriate target can be determined as previously described.

In some embodiment, modulators of one or more targets of the disclosure, including one or more targets listed in Table 2 and/or Table 4 and/or Table 6 and/or Table 7 and/or the Examples, or a fragment thereof, are identified in a method wherein a cell is contacted with a candidate compound and the expression or activity level of the target is determined. The level of expression of target mRNA or polypeptide or fragments thereof in the presence of the candidate compound is compared to the level of expression of target mRNA or polypeptide or fragments thereof in the absence of the candidate compound. The candidate compound can then be identified as a modulator of target expression based on this comparison. For example, when expression of target mRNA or polypeptide or fragments thereof is greater (e.g., statistically significantly greater) in the presence of the candidate compound than in its absence, the candidate compound is identified as a stimulator of target expression. In some embodiments, when expression of target mRNA or polypeptide or fragments thereof is reduced (e.g., statistically significantly less) in the presence of the candidate compound than in its absence, the candidate compound is identified as an inhibitor of target expression. The expression level of target mRNA or polypeptide or fragments thereof in the cells can be determined by methods described herein for detecting target mRNA or polypeptide or fragments thereof.

In some embodiments, a target of the disclosure, including one or more targets listed in Table 2 and/or Table 4 and/or Table 6 and/or Table 7 and/or the Examples, or a fragment thereof, can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8: 1693-1696; and Brent WO94/10300), to identify other polypeptides which bind to or interact with the target or fragments thereof and are involved in activity of the targets. Such target-binding proteins are also likely to be involved in the propagation of signals by the target polypeptides or target natural binding partner(s) as, for example, downstream elements of one or more targets—mediated signaling pathway. The two-hybrid system is based on the modular nature of most transcription factors, which consist of separable DNA-binding and activation domains. Briefly, the assay utilizes two different DNA constructs. In one construct, the gene that codes for one or more targets polypeptide is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming one or more targets—dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with one or more targets polypeptide of the disclosure, including one or more targets listed in Table 2 and/or Table 4 and/or Table 6 and/or Table 7 and/or the Examples or a fragment thereof.

In some embodiments, the disclosure pertains to a combination of two or more of the assays described herein. For example, a modulating agent can be identified using a cell-based or a cell-free assay, and the ability of the agent to modulate the activity of one or more targets polypeptide or a fragment thereof can be confirmed in vivo, e.g., in an animal such as an animal model for cellular transformation and/or tumorigenesis.

This disclosure further pertains to novel agents identified by the above-described screening assays. Accordingly, it is within the scope of this disclosure to further use an agent identified as described herein in an appropriate animal model. For example, an agent identified as described herein can be used in an animal model to determine the efficacy, toxicity, or side effects of treatment with such an agent. In some embodiments, an agent identified as described herein can be used in an animal model to determine the mechanism of action of such an agent. Furthermore, this disclosure pertains to uses of novel agents identified by the above-described screening assays for treatments as described herein.

USES AND METHODS OF THE DISCLOSURE

The targets of the disclosure described herein, including the targets listed in Table 2 and/or Table 4 and/or Table 6 and/or Table 7 and/or the Examples or fragments thereof, can be used in one or more of the following methods: a) screening assays; b) predictive medicine (e.g., diagnostic assays, prognostic assays, and monitoring of clinical trials); and c) methods of treatment (e.g., therapeutic and prophylactic, e.g., by up- or down-modulating the copy number, level of expression, and/or level of activity of the one or more targets).

The targets described herein or agents that modulate the expression and/or activity of such targets can be used, for example, to (a) express one or more targets of the disclosure, including one or more targets listed in Table 2 and/or Table 4 and/or Table 6 and/or Table 7 and/or the Examples or a fragment thereof (e.g., via a recombinant expression vector in a host cell in gene therapy applications or synthetic nucleic acid molecule), (b) detect target mRNA or a fragment thereof (e.g., in a biological sample) or a genetic alteration in one or more targets gene, and/or (c) modulate target activity, as described further below. The targets or modulatory agents thereof can be used to treat conditions or disorders characterized by insufficient or excessive production of one or more targets polypeptide or fragment thereof or production of target polypeptide inhibitors. In addition, the target polypeptides or fragments thereof can be used to screen for naturally occurring target binding partner(s), to screen for drugs or compounds which modulate target activity, as well as to treat conditions or disorders characterized by insufficient or excessive production of target polypeptide or a fragment thereof or production of target polypeptide forms which have decreased, aberrant or unwanted activity compared to target wild-type polypeptides or fragments thereof (e.g., a neurological disease or disorder). Neurological diseases or disorders include, but are not limited to Alzheimer's disease (AD), dementia, age-related dementia, Parkinson's disease, cerebral edema, amyotrophic lateral sclerosis (ALS), Pediatric Autoimmune Neuropsychiatric Disorders Associated with Streptococcal Infections (PANDAS), meningitis, hemorrhagic stroke, autism spectrum disorder (ASD), brain tumor, and epilepsy. In some embodiments, the neurological disease or disorder is AD, dementia, or PD.

In some embodiments, the methods provided herein do not comprise administering a VEGFR3 agonist or Fibroblast Growth Factor 2 (FGF2). In some embodiments the target is not VEGF-c.

Screening Assays

In one aspect, the present disclosure relates to a method for preventing in a subject, a disease or condition associated with an unwanted, more than desirable, or less than desirable, expression and/or activity of one or more targets described herein. Subjects at risk for a disease that would benefit from treatment with the claimed agents or methods (e.g., a neurological disease or disorder) can be identified, for example, by any one or combination of diagnostic or prognostic assays known in the art and described herein (see, for example, agents and assays described in Methods of Selecting Agents and Compositions). In some embodiments, methods for preventing or reducing the likelihood of a neurological disease or disorder are provided. Neurological diseases or disorders include, but are not limited to AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, MS, AIDS-related dementia complex, or a combination of two or more of the listed items. By way of example, neurological diseases or disorders can include (but are not limited to) AD, dementia, age-related dementia, Parkinson's disease, cerebral edema, ALS, PANDAS, meningitis, hemorrhagic stroke, ASD, brain tumor, and epilepsy. In some embodiments, the neurological disease or disorder is AD, dementia, or PD. In some embodiments, the neurological disease comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, the neurodegenerative disease comprises, consists essentially of, or consists of prion disease. In some embodiments, the neurodegenerative disease comprises, consists essentially of, or consists of a non-human prion disease such as scrapie, chronic wasting disease, or BSE.

Predictive Medicine

The present disclosure also pertains to the field of predictive medicine in which diagnostic assays, prognostic assays, and monitoring of clinical trials are used for prognostic (predictive) purposes to thereby treat an individual prophylactically.

Accordingly, one aspect of the present disclosure relates to diagnostic assays for determining the expression and/or activity level of targets of the disclosure, including targets listed in Table 2 and/or Table 4 and/or Table 6 and/or Table 7 and/or the Examples or fragments thereof, in the context of a biological sample (e.g., blood, serum, cells, or tissue) to thereby determine whether an individual is afflicted with a disease or disorder (e.g., a neurological disease or disorder), or is at risk of developing a disorder, associated with aberrant or unwanted target expression or activity. In some embodiments, methods for preventing or reducing the likelihood of a neurological disease or disorder are provided. Neurological diseases or disorders include, but are not limited to AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, MS, AIDS-related dementia complex, or a combination of two or more of the listed items. By way of example, neurological diseases or disorders can include (but are not limited to) AD, dementia, age-related dementia, PD, cerebral edema, ALS, PANDAS, meningitis, hemorrhagic stroke, ASD, brain tumor, and epilepsy. In some embodiments, the neurological disease comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, the neurological disease or disorder is AD, dementia, or PD. In some embodiments, the neurodegenerative disease comprises, consists essentially of, or consists of prion disease. In some embodiments, the neurodegenerative disease comprises, consists essentially of, or consists of a non-human prion disease such as scrapie, chronic wasting disease, or BSE. The present disclosure also provides for prognostic (or predictive) assays for determining whether an individual is at risk of developing a disorder associated with target polypeptide, nucleic acid expression or activity. For example, mutations in one or more targets gene can be assayed in a biological sample.

Such assays can be used for prognostic or predictive purpose to thereby prophylactically treat an individual prior to the onset of a disorder characterized by or associated with target polypeptide, nucleic acid expression or activity.

In some embodiments there are methods provided of monitoring the influence of agents (e.g., drugs, compounds, and small nucleic acid-based molecules) on the expression or activity of targets of the disclosure, including targets listed in Table 2 and/or Table 4 and/or Table 6 and/or Table 7 and/or the Examples, or fragments thereof, in clinical trials. These and other agents are described in further detail in the following sections.

1. Diagnostic Assays

The present disclosure provides, in part, methods, systems, and code for accurately classifying whether a biological sample is associated with a neurological disease or disorder. Neurological diseases or disorders include, but are not limited to AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, MS, AIDS-related dementia complex, or a combination of two or more of the listed items. By way of example, neurological diseases or disorders can include (but are not limited to) AD, dementia, age-related dementia, PD, cerebral edema, ALS, PANDAS, meningitis, hemorrhagic stroke, ASD, brain tumor, and epilepsy. In some embodiments, the neurological disease comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, the neurodegenerative disease comprises, consists essentially of, or consists of prion disease. In some embodiments, the neurodegenerative disease comprises, consists essentially of, or consists of a non-human prion disease such as scrapie, chronic wasting disease, or BSE. In some embodiments, the neurological disease or disorder is AD, dementia, or PD. In some embodiments, the present disclosure is useful for classifying a sample (e.g., from a subject) as a neurological disease or disorder sample using a statistical algorithm and/or empirical data (e.g., the presence or level of one or targets described herein). In some embodiments, the method of classifying whether a sample is associated with a neurological disease or disorder comprises identifying the subject from whom the sample was obtained as having or being at risk for the neurological disease. The method can further comprise administering a therapy for the neurological disease, for example a therapy comprising, consisting of, or consisting essentially of an agent that modulates the expression of one or more targets of the disclosure, as described herein. In some embodiments, the method of classifying whether a sample is associated with a neurological disease or disorder comprises identifying the subject from whom the sample was obtained as having or being at risk for the neurological disease. The method can further comprise a therapeutic method for the identified disease as described herein.

An exemplary method for detecting the level of expression or activity of one or more targets of the disclosure, including one or more targets listed in Table 2 and/or Table 4 and/or Table 6 and/or Table 7 and/or the Examples or fragments thereof, and thus useful for classifying whether a sample is associated with a neurological disease or disorder (e.g., AD, dementia, PD), involves obtaining a biological sample from a test subject and contacting the biological sample with a compound or an agent capable of detecting the target (e.g., polypeptide or nucleic acid that encodes the target or fragments thereof) such that the level of expression or activity of the target is detected in the biological sample. In some embodiments, the presence or level of at least one, two, three, four, five, six, seven, eight, nine, ten, fifty, hundred, or more targets of the disclosure are determined in the individual's sample. In certain instances, the statistical algorithm is a single learning statistical classifier system. Exemplary statistical analyses are presented in the Examples and can be used in some embodiments. In other embodiments, a single learning statistical classifier system can be used to classify a sample as a neurological disease or disorder sample, or a non-neurological disease or disorder sample based upon a prediction or probability value and the presence or level of one or more targets described herein. The use of a single learning statistical classifier system typically classifies the sample as a neurological disease or disorder sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or a range defined by any two of the preceding values.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, in some embodiments in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning {e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In some embodiments, the method of the present disclosure further comprises sending the neurological disease or disorder classification results to a clinician, e.g., an oncologist or hematologist.

In some embodiment, the method of the present disclosure further provides a diagnosis in the form of a probability that the individual has a neurological disease or disorder. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater, or a range defined by any two of the preceding values, probability of having a neurological disease or disorder. In some embodiments, the method of the present disclosure further provides a prognosis of a neurological disease or disorder in the individual. For example, the prognosis can be surgery, development of a clinical subtype of the neurological disease or disorder, development of one or more symptoms, development of a neurological disease or disorder, or recovery from the disease. In some instances, the method of classifying a sample as a neurological disease or disorder sample is further based on the symptoms (e.g., clinical factors) of the individual from which the sample is obtained. In some embodiments, the diagnosis of an individual as having a neurological disease or disorder is followed by administering to the individual a therapeutically effective amount of a drug useful for treating one or more symptoms associated with the neurological disease or disorder.

In some embodiments, an agent for detecting target mRNA, genomic DNA, or fragments thereof is a labeled nucleic acid probe capable of hybridizing to target mRNA, genomic DNA, or fragments thereof. The nucleic acid probe can be, for example, full-length target nucleic acid, or a portion thereof, such as an oligonucleotide of at least 15, 30, 50, 100, 250 or 500, or a range defined by any two of the preceding values, nucleotides in length and sufficient to specifically hybridize under stringent conditions well known to a skilled artisan to target mRNA or genomic DNA. Other suitable probes for use in the diagnostic assays of the disclosure are described herein. In some embodiments, the nucleic acid probe is designed to detect transcript variants (e.g., different splice forms) of a gene.

An agent for detecting one or more targets listed in Table 2 and/or Table 4 and/or Table 6 and/or Table 7 and/or the Examples or a fragment thereof is an antibody capable of binding to the target, and in some embodiments is an antibody with a detectable label. Antibodies can be polyclonal, or in some embodiments is monoclonal. An intact antibody, or a fragment thereof (e.g., Fab or F(ab')2) can be used. The term "labeled", with regard to the probe or antibody, is intended to encompass direct labeling of the probe or antibody by coupling (e.g., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the disclosure can be used to detect target mR A, polypeptide, genomic DNA, or fragments thereof, in a biological sample in vitro as well as in vivo. For example, in vitro techniques for detection of target mRNA or a fragment thereof include Northern hybridizations and in situ hybridizations. In vitro techniques for detection of target polypeptide include enzyme linked immunosorbent assays (ELISAs), Western blots, immunoprecipitations and immunofluorescence. In vitro techniques for detection of target genomic DNA or a fragment thereof include Southern hybridizations. Furthermore, in vivo techniques for detection of one or more targets polypeptide or a fragment thereof include introducing into a subject a labeled anti-target antibody. For example, the antibody can be labeled with a radioactive marker whose presence and location in a subject can be detected by standard imaging techniques.

In some embodiments, the biological sample contains polypeptide molecules from the test subject. In some embodiments, the biological sample can contain mRNA molecules from the test subject or genomic DNA molecules from the test subject. In some embodiments, a biological sample is a hematological tissue (e.g., a sample comprising blood, CSF, ISF, etc.) sample isolated by conventional means from a subject.

In some embodiment, the methods further involve obtaining a control biological sample from a control subject, contacting the control sample with a compound or agent capable of detecting polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof of one or more targets listed in Table 2 and/or Table 4 and/or Table 6 and/or Table 7 and/or the Examples such that the presence of target polypeptide, mRNA, genomic DNA, or fragments thereof, is detected in the biological sample, and comparing the presence of target polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof in the control sample with the presence of target polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof in the test sample.

The disclosure also encompasses kits for detecting the presence of a polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof, of one or more targets listed in Table 2 and/or Table 4 and/or Table 6 and/or Table 7 and/or the Examples in a biological sample. For example, the kit can comprise a labeled compound or agent capable of detecting one or more targets polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof, in a biological sample; means for determining the amount of the target polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof in the sample; and means for comparing the amount of the target polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof, in the sample with a standard. The compound or agent can be packaged in a suitable container. The kit can further comprise instructions for using the kit to detect the target polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof.

In some embodiments, therapies tailored to treat stratified patient populations based on the described diagnostic assays are further administered.

In some embodiments, the disclosure provides a method of determining whether a subject is afflicted with a neurological disease, the method comprising:
  a) obtaining a biological sample from the subject;
  b) determining the copy number, level of expression, or level of activity of one or more targets listed in Table 2 and/or Table 4 and/or Table 6 and/or Table 7, in the subject sample; and
  c) comparing the copy number, level of expression, or level of activity of said one or more targets detected in steps b) to the copy number, level of expression, or level of activity of the one or more targets in a control; wherein a significant increase and/or decrease in the copy number, level of expression, or level of activity of the one or more targets in the subject sample relative to the control copy number, level of expression, or level of activity of the one or more targets indicates that the subject is afflicted with a neurological disease.

In some embodiments, the disclosure provides a method of determining whether a subject is afflicted with a neurological disease resulting from or characterized by an aberrant decrease in meningeal lymphatic drainage, the method comprising;
  a) obtaining a biological sample from the subject;
  b) determining the copy number, level of expression, or level of activity of one or more targets listed in Table 2 and/or Table 4 and/or Table 6 and/or Table 7, in the subject sample; and
  c) comparing the copy number, level of expression, or level of activity of said one or more targets detected in steps b) to the copy number, level of expression, or level of activity of the one or more targets in a control; wherein a significant increase and/or decrease in the copy number, level of expression, or level of activity of the one or more targets in the subject sample relative to the control copy number, level of expression, or level of activity of the one or more targets indicates that the subject afflicted with a neurological disease resulting from or characterized by an aberrant decrease in meningeal lymphatic drainage.

2. Prognostic Assays

The diagnostic methods described herein can furthermore be utilized to identify subjects having or at risk of developing a neurological disease or neurological disorder associated with aberrant expression or activity of one or more targets of the disclosure, including one or more targets listed in Table 2 and/or Table 4 and/or Table 6 and/or Table 7 and/or the Examples, or a fragment thereof. As used herein, the term "aberrant" has its ordinary meaning as understood in the art in view of the specification, and includes target expression or activity levels which deviates from the normal expression or activity in a control.

The assays described herein, such as the preceding diagnostic assays or the following assays, can be utilized to identify a subject having or at risk of developing a disorder associated with a misregulation of target activity or expression, such as in a neurological disease or disorder. Neurological diseases or disorders include, but are not limited to AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, MS, AIDS-related dementia complex, or a combination of two or more of the listed items. By way of example, neurological diseases or disorders can include (but are not limited to) AD, dementia, age-related dementia, PD, cerebral edema, ALS, PANDAS, meningitis, hemorrhagic stroke, ASD, brain tumor, and epilepsy. In some embodiments, the neurological disease or disorder is AD, dementia, or PD. In some embodiments, the neurological disease or disorder comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, the neurodegenerative disease comprises, consists essentially of, or consists of prion disease. In some embodiments, the neurodegenerative disease comprises, consists essentially of, or consists of a non-human prion disease such as scrapie, chronic wasting disease, or BSE. In some embodiments, the prognostic assays can be used to identify a subject having or at risk for developing a disorder associated with a misregulation of target activity or expression. Thus, the present disclosure provides a method for identifying and/or classifying a disease associated with aberrant expression or activity of one or more targets of the disclosure, including one or more targets listed in Table 2 and/or Table 4 and/or Table 6 and/or Table 7 and/or the Examples, or a fragment thereof. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant target expression or activity. For example, such methods can be used to determine whether a subject can be effectively treated with an agent for a neurological disease (e.g., AD, dementia, PD). Thus, the present disclosure provides methods for determining whether a subject can be effectively treated with an agent for a disease associated with aberrant target expression or activity in which a test sample is obtained and target polypeptide or nucleic acid expression or activity is detected (e.g., wherein a significant increase or decrease in target polypeptide or nucleic acid expression or activity relative to a control is diagnostic for a subject that can be administered the agent to treat a disorder associated with aberrant target expression or activity). In some embodiments, significant increase or decrease in target expression or activity comprises at least 2 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher or lower, or a range defined by any two of the preceding values, respectively, than the expression activity or level of the marker in a control sample.

The methods of the disclosure can also be used to detect genetic alterations in one or more targets of the disclosure, including one or more targets listed in Table 2 and/or Table 4 and/or Table 6 and/or Table 7 and/or the Examples or a fragment thereof, thereby determining if a subject with the altered target is at risk for neurological disease (e.g., AD, dementia, PD) characterized by aberrant target activity or expression levels. In some embodiments, the methods include detecting, in a sample of cells from the subject, the presence or absence of a genetic alteration characterized by at least one alteration affecting the integrity of a gene encoding one or more targets polypeptide, or the mis-expression of the target (e.g., mutations and/or splice variants). For example, such genetic alterations can be detected by ascertaining the existence of at least one of 1) a deletion of one or more nucleotides from one or more targets gene, 2) an addition of one or more nucleotides to one or more targets gene, 3) a substitution of one or more nucleotides of one or more targets gene, 4) a chromosomal rearrangement of one or more targets gene, 5) an alteration in the level of a messenger RNA transcript of one or more targets gene, 6) aberrant modification of one or more targets gene, such as of the methylation pattern of the genomic DNA, 7) the presence of a non-wild type splicing pattern of a messenger RNA transcript of one or more targets gene, 8) a non-wild type level of one or more targets polypeptide, 9) allelic loss of one or more targets gene, and 10) inappropriate post-translational modification of one or more targets polypeptide. As described herein, there are a large number of assays known in the art which can be used for detecting alterations in one or more targets gene. In some embodiments, the biological sample is a tissue or serum sample isolated by conventional means from a subject.

In some embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, In some embodiments, in a ligation chain reaction (LCR) (see, e.g., Landegran et al. (1 88) Science 241: 1077-1080; and Naka-zawa et al. (1994) Proc. Natl. Acad. Sci. USA 91:360-364), the latter of which can be particularly useful for detecting point mutations in one or more targets gene (see Abravaya et al. (1995) Nucleic Acids Res. 23:675-682). This method can include the steps of collecting a sample of cells from a subject, isolating nucleic acid {e.g., genomic DNA, mRNA, cDNA, small RNA, mature miRNA, pre-miRNA, pri-miRNA, miRNA*, anti-miRNA, or a miRNA binding site, or a variant thereof) from the cells of the sample, contacting the nucleic acid sample with one or more primers which specifically hybridize to one or more targets gene of the disclosure, including the target genes listed in Table 2 and/or Table 4 and/or Table 6 and/or Table 7 and/or the Examples, or fragments thereof, under conditions such that hybridization and amplification of the target gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87: 1874-1878), transcriptional amplification system (Kwoh, D. Y. et al. (1989) Proc. Natl. Acad. Sci. USA 86: 1173-1177), Q-Beta Replicase (Lizardi, P. M. et al. (1 88) Bio-Technology 6:1 197), or any other nucleic acid amplification method, followed by the detection of the amplified molecules using techniques well known to those of skill in the art. These detection schemes are especially useful for the detection of nucleic acid molecules if such molecules are present in very low numbers.

In an embodiment, mutations in one or more targets gene of the disclosure, including one or more targets listed in Table 2 and/or Table 4 and/or Table 6 and/or Table 7 and/or the Examples, or a fragment thereof, from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In an embodiment, genetic mutations in one or more targets gene of the disclosure, including a gene listed in Table 2 and/or Table 4 and/or Table 6 and/or Table 7 and/or the Examples, or a fragment thereof, can be identified by hybridizing a sample and control nucleic acids, e.g., DNA, RNA, mRNA, small RNA, cDNA, mature miRNA, pre-miRNA, pri-miRNA, miRNA*, anti-miRNA, or a miRNA binding site, or a variant thereof, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in one or more targets can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In some embodiments, any of a variety of sequencing reactions known in the art can be used to directly sequence one or more targets gene of the disclosure, including a gene listed in Table 2 and/or Table 4 and/or Table 6 and/or Table 7 and/or the Examples, or a fragment thereof, and detect mutations by comparing the sequence of the sample target gene with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36: 127-162; and Griffin et al. (1993) Appl. Biochem. Biotechnol. 38:147-159).

Other methods for detecting mutations in one or more targets gene of the disclosure, including a gene listed in Table 2 and/or Table 4 and/or Table 6 and/or Table 7 and/or the Examples, or fragments thereof, include methods in which protection from cleavage agents is used to detect mismatched bases in RNA RNA or RNA DNA heteroduplexes (Myers et al. (1985) Science 230: 1242). In general, the art technique of "mismatch cleavage" starts by providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA DNA duplexes can be treated with RNase and DNA/DNA hybrids treated with SI nuclease to enzymatically digest the mismatched regions. In other embodiments, either DNA DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217: 286-295. In some embodiments, the control DNA or RNA can be labeled for detection.

In an embodiment, the mismatch cleavage reaction employs one or more proteins that recognize mismatched base pairs in double-stranded DNA (so called "DNA mismatch repair" enzymes) in defined systems for detecting and mapping point mutations in target genes of the disclosure, including genes listed in Table 2 and/or Table 4 and/or Table 6 and/or Table 7 and/or the Examples, or fragments thereof, obtained from samples of cells. For example, the mutY enzyme of $E.$ $coli$ cleaves A at G/A mismatches and the thymidine DNA glycosylase from HeLa cells cleaves T at G/T mismatches (Hsu et al. (1994) Carcinogenesis 15:1657-1662). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in target genes of the disclosure, including genes listed in Table 2 and/or Table 4 and/or Table 6 and/or Table 7 and/or the Examples, or fragments thereof. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) utat. Res. 285:125-144 and Hayashi (1992) Genet. Anal. Tech. Appl. 9:73-79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In some embodiments, the subject method utilizes heteroduplex analysis to separate double stranded heteroduplex molecules on the basis of changes in electrophoretic mobility (Keen et al. (1991) Trends Genet. 7:5).

In some embodiments the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265: 12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1 89) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA. In some embodiments, the hybridization reactions can occur using biochips, microarrays, etc., or other array technology that are well known in the art.

In some embodiments, allele specific amplification technology which depends on selective PCR amplification may be used in conjunction with the instant disclosure. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6: 1). It is anticipated that in some embodiments amplification may also be performed using Taq ligase for amplification (Barany (1991) Proc. Natl. Acad. Sci USA 88: 189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving one or more targets of the disclosure, including one or more targets listed in Table 2 and/or Table 4 and/or Table 6 and/or Table 7 and/or the Examples, or fragments thereof.

In some embodiments, the disclosure provides a method of determining whether a subject is at risk for developing a neurological disease, the method comprising: a) obtaining a biological sample from the subject; b) determining the copy number, level of expression, or level of activity of one or more targets listed in Table 2 and/or Table 4 and/or Table 6 and/or Table 7, in the subject sample; and c) comparing the copy number, level of expression, or level of activity of said one or more targets detected in steps b) to the copy number, level of expression, or level of activity of the one or more targets in a control; wherein a significant increase and/or decrease in the copy number, level of expression, or level of activity of the one or more targets in the subject sample relative to the control copy number, level of expression, or level of activity of the one or more targets indicates that the subject is at risk for developing a neurological disease.

In some embodiments, the disclosure provides a method of determining whether a subject is at risk for developing a neurological disease resulting from or characterized by an aberrant decrease in meningeal lymphatic drainage, the method comprising; a) obtaining a biological sample from the subject; b) determining the copy number, level of expression, or level of activity of one or more targets listed in Table 2 and/or Table 4 and/or Table 6 and/or Table 7, in the subject sample; and c) comparing the copy number, level of expression, or level of activity of said one or more targets detected in steps b) to the copy number, level of expression, or level of activity of the one or more targets in a control; wherein a significant increase and/or decrease in the copy number, level of expression, or level of activity of the one or more targets in the subject sample relative to the control copy number, level of expression, or level of activity of the one or more targets indicates that the subject is at risk for developing a neurological disease resulting from or characterized by an aberrant decrease in meningeal lymphatic drainage.

3. Monitoring of Effects During Treatment

Monitoring the influence of agents (e.g., drugs) on the expression or activity of one or more targets of the disclosure, including one or more targets listed in Table 2 and/or Table 4 and/or Table 6 and/or Table 7 and/or the Examples, or a fragment thereof (e.g., the modulation of a neurological disease or disorder) can be employed during treatment, including, but not limited to, clinical trials. Neurological diseases or disorders include, but are not limited to AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, MS, AIDS-related dementia complex, or a combination of two or more of the listed items. By way of example, neurological diseases or disorders can include (but are not limited to) AD, dementia, age-related dementia, PD, cerebral edema, ALS, PANDAS, meningitis, hemorrhagic stroke, ASD, brain tumor, and epilepsy. In some embodiments, the neurological disease or disorder comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, the neurodegenerative disease comprises, consists essentially of, or consists of prion disease. In some embodiments, the neurodegenerative disease comprises, consists essentially of, or consists of a non-human prion disease such as scrapie, chronic wasting disease, or BSE. In some embodiments, the neurological disease or disorder is AD, dementia, or PD. For example, the effectiveness of an agent determined by a screening assay as described herein to increase expression and/or activity of one or more targets of the disclosure, including one or more targets listed in Table 2 and/or Table 4 and/or Table 6 and/or Table 7 and/or the Examples or a fragment thereof, can be monitored during the treatment of subjects exhibiting decreased expression and/or activity of one or more targets of the disclosure, including one or more targets listed in Table 2 and/or Table 4 and/or Table 6 and/or Table 7 and/or the Examples, or a fragment thereof, relative to a control reference. In some embodiments, the effectiveness of an agent determined by a screening assay to decrease expression and/or activity of one or more targets of the disclosure, including one or more targets listed in Table 2 and/or Table 4 and/or Table 6 and/or Table 7 and/or the Examples, or a fragment thereof, can be monitored during the treatment of subjects exhibiting decreased expression and/or activity of the target of the disclosure, including one or more targets listed in Table 2 and/or Table 4 and/or Table 6 and/or Table 7 and/or the Examples or a fragment thereof relative to a control reference. In treatment settings (e.g., clinical trials), the expression and/or activity of the target can be used as a "read out" or marker of the phenotype of a particular cell.

In some embodiments, the present disclosure provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression and/or activity of one or more targets of the disclosure, including one or more targets listed in Table 2 and/or Table 4 and/or Table 6 and/or Table 7 and/or the Examples or fragments thereof in the preadministration sample; (iii) obtaining one or more post-administration samples from the subject; (iv) detecting the level of expression or activity of the target in the post-administration samples; (v) comparing the level of expression or activity of the target or fragments thereof in the pre-administration sample with the that of the target in the post administration sample or samples; and (vi) altering the administration of the agent to the subject accordingly. For example, increased administration of the agent may be desirable to increase the expression or activity of one or more targets to higher levels than detected (e.g., to increase the effectiveness of the agent.) In some embodiments, decreased administration of the agent may be desirable to decrease expression or activity of the target to lower levels than detected (e.g., to decrease the effectiveness of the agent). According to such an embodiment, target expression or activity may be used as an indicator of the effectiveness of an agent, even in the absence of an observable phenotypic response.

In some embodiments, the disclosure provides a method for identifying a compound which treats a neurological disease, the method comprising: a) contacting a cell with a test compound; and b) determining the effect of the test compound on the copy number, level of expression, or level of activity of the one or more targets listed in Table 2 and/or Table 4 and/or Table 6 and/or Table 7 in the cell to thereby identify a compound which treats a neurological disease.

In some embodiments, the disclosure provides a method of determining the efficacy of a test compound for treating a neurological disease in a subject, the method comprising: a) determining the copy number, level of expression, or level of activity of one or more targets listed in Table 2 and/or Table 4 and/or Table 6 and/or Table 7, in a first sample obtained from the subject and exposed to the test compound; b) determining the copy number, level of expression, or level of activity of the one or more targets in a second sample obtained from the subject, wherein the second sample is not exposed to the test compound, and c) comparing the copy number, level of expression, or level of activity of the one or more targets in the first and second samples, wherein a significantly modulated copy number, level of expression, or level of activity of the target, relative to the second sample, is an indication that the test compound is efficacious for treating the neurological disease in the subject.

In some embodiments, the disclosure provides a method for monitoring the progression of a neurological disease in a subject, the method comprising: a) detecting in a subject sample at a first point in time the copy number, level of expression, or level of activity of one or more targets listed in Table 2 and/or Table 4 and/or Table 6 and/or Table 7; b) repeating step a) at a subsequent point in time; and c) comparing the copy number, level of expression, or level of activity of said one or more targets detected in steps a) and b) to monitor the progression of the neurological disease.

In some embodiments, the disclosure provides a method of determining the efficacy of a test compound for treating a neurological disease in a subject, the method comprising: a) determining the copy number, level of expression, or level of activity of one or more targets listed in Table 2 and/or Table 4 and/or Table 6 and/or Table 7, in a first sample obtained from the subject and exposed to the test compound; b) determining the copy number, level of expression, or level of activity of the one or more targets in a second sample obtained from the subject, wherein the second sample is not exposed to the test compound, and c) comparing the copy number, level of expression, or level of activity of the one or more targets in the first and second samples, wherein a significantly modulated copy number, level of expression, or level of activity of the target, relative to the second sample, is an indication that the test compound is efficacious for treating the neurological disease in the subject.

Methods of Treatment

The present disclosure provides for both prophylactic and therapeutic methods of treating a subject at risk of (or susceptible to) a neurological disease or disorder characterized by insufficient or excessive production of targets of the disclosure, including targets listed in Table 2 and/or Table 4 and/or Table 6 and/or Table 7 and/or the Examples or fragments thereof, which have aberrant expression or activity compared to a control. Neurological diseases or disorders include, but are not limited to AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, MS, AIDS-related dementia complex, or a combination of two or more of the listed items. By way of example, neurological diseases or disorders can include (but are not limited to) AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of the listed items. By way of example, neurological diseases or disorders can include (but are not limited to) AD, dementia, age-related dementia, PD, cerebral edemaALS, PANDAS, meningitis, hemorrhagic stroke, ASD, brain tumor, and epilepsy. In some embodiments, the neurological disease or disorder comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, the neurological disease or disorder is AD, dementia, or PD. In some embodiments, the neurodegenerative disease comprises, consists essentially of, or consists of prion disease. In some embodiments, the neurodegenerative disease comprises, consists essentially of, or consists of a non-human prion disease such as scrapie, chronic wasting disease, or BSE. Moreover, agents of the disclosure described herein can be used to detect and isolate the targets or fragments thereof, regulate the bioavailability of the targets or fragments thereof, and modulate target expression levels or activity.

1. Prophylactic Methods

In one aspect, the disclosure provides a method for preventing or reducing the likelihood in a subject, a disease or condition associated with an aberrant expression or activity of one or more targets of the disclosure, including one or more targets listed in Table 2 and/or Table 4 and/or Table 6 and/or Table 7 and/or the Examples or a fragment thereof, by administering to the subject an agent which modulates (e.g., increases or decreases) target expression or at least one activity of the target. In some embodiments, methods for preventing or reducing the likelihood of a neurological disease or disorder are provided. Neurological diseases or disorders include, but are not limited to AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, MS, AIDS-related dementia complex, or a combination of two or more of the listed items. By way of example, neurological diseases or disorders can include (but are not limited to) AD, dementia, age-related dementia, PD, cerebral edema, ALS, PANDAS, meningitis, hemorrhagic stroke, ASD, brain tumor, and epilepsy. In some embodiments, the neurological disease or disorder comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, the neurological disease or disorder is AD, dementia, or PD. In some embodiments, the neurodegenerative disease comprises, consists essentially of, or consists of prion disease. In some embodiments, the neurodegenerative disease comprises, consists essentially of, or consists of a non-human prion disease such as scrapie, chronic wasting disease, or BSE. Subjects at risk for a disease or disorder which is caused or contributed to by aberrant target expression or activity can be identified by, for example, any or a combination of diagnostic or prognostic assays as described herein. Administration of a prophylactic agent can occur prior to the manifestation of symptoms characteristic of the target expression or activity aberrancy, such that a disease or disorder is prevented or, In some embodiments, delayed in its progression.

2. Therapeutic Methods

In some embodiments there are provided methods of modulating (e.g., increasing or decreasing) the expression or activity or interaction with natural binding partner(s) of one or more targets of the disclosure, including one or more targets listed in Table 2 and/or Table 4 and/or Table 6 and/or Table 7 and/or the Examples or fragments thereof, for therapeutic purposes. The targets of the disclosure have been demonstrated to correlate with a neurological disease or disorder (e.g., AD, PD, dementia). Accordingly, the activity and/or expression of the target, as well as the interaction between one or more targets or a fragment thereof and its natural binding partners) or a fragment(s) thereof can be modulated in order to treat a neurological disease or disorder. In some embodiments, methods for preventing or reducing the likelihood of a neurological disease or disorder are provided. Neurological diseases or disorders include, but are not limited to AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/ SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, MS, AIDS-related dementia complex, or a combination of two or more of the listed items. By way of example, neurological diseases or disorders can include (but are not limited to) AD, dementia, age-related dementia, PD, cerebral edema, ALS, PANDAS, meningitis, hemorrhagic stroke, ASD, brain tumor, and epilepsy. In some embodiments, the neurological disease or disorder comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/ SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, the neurodegenerative disease comprises, consists essentially of, or consists of prion disease. In some embodiments, the neurodegenerative disease comprises, consists essentially of, or consists of a non-human prion disease such as scrapie, chronic wasting disease, or BSE. In some embodiments, the neurological disease or disorder is AD, dementia, or PD.

Modulatory methods of the disclosure involve contacting a cell with one or more targets of the disclosure, including one or more targets of the disclosure, including one or more targets listed in Table 2 and/or Table 4 and/or Table 6 and/or Table 7 and/or the Examples or a fragment thereof or agent that modulates one or more of the activities of target activity associated with the cell. In some embodiments, the targets are or encode secreted molecules such that contacting a cell with one or more targets of the disclosure or agent that modulates one or more of the activities of target activity is unnecessary and contact with a bodily fluid (e.g., blood, serum, lung pleural fluid, etc.) is sufficient. An agent that modulates target activity can be an agent as described herein, such as a nucleic acid or a polypeptide, a naturally-occurring binding partner of the target, an antibody against the target, a combination of antibodies against the target and antibodies against other neurological disease or disorder related targets, one or more targets agonist or antagonist, a peptidomimetic of one or more targets agonist or antagonist, one or more targets peptidomimetic, other small molecule, or small RNA directed against or a mimic of one or more targets nucleic acid gene expression product.

An agent that modulates the expression of one or more targets of the disclosure, including one or more targets of the disclosure, including one or more targets listed in Table 2 and/or Table 4 and/or Table 6 and/or Table 7 and/or the Examples or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more targets polypeptide. For example, an oligonucleotide complementary to the area around one or more targets polypeptide translation initiation site can be synthesized. One or more antisense oligonucleotides can be added to cell media, typically at 200 μg/ml, or administered to a patient to prevent the synthesis of one or more targets polypeptide. The antisense oligonucleotide is taken up by cells and hybridizes to one or more targets mRNA to prevent translation. In some embodiments, an oligonucleotide which binds double-stranded DNA to form a triplex construct to prevent DNA unwinding and transcription can be used. As a result of either, synthesis of target polypeptide is blocked. When target expression is modulated, in some embodiments, such modulation occurs by a means other than by knocking out the target gene.

Agents which modulate expression, by virtue of the fact that they control the amount of target in a cell, can also modulate the total amount of target activity in a cell.

In some embodiments, the agent increases or stimulates one or more activities of one or more targets of the disclosure, including one or more targets listed in Table 2 and/or Table 4 and/or Table 6 and/or Table 7 and/or the Examples or a fragment thereof. Examples of such stimulatory agents include active target polypeptide or a fragment thereof and a nucleic acid molecule encoding the target or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In some embodiment, the agent decreases or inhibits one or more target activities. In some embodiments, the agent inhibits or enhances the interaction of the target with its natural binding partner(s). Examples of such inhibitory agents include antisense nucleic acid molecules, anti-target antibodies, target inhibitors, and compounds identified in the screening assays described herein.

These modulatory methods can be performed in vitro (e.g., by contacting the cell with the agent) or, in some embodiments, by contacting an agent with cells in vivo (e.g., by administering the agent to a subject). As such, the present disclosure provides methods of treating an individual afflicted with a condition or disorder that would benefit from up- or down-modulation of one or more targets of the disclosure listed in Table 2 and/or Table 4 and/or Table 6 and/or Table 7 and/or the Examples or a fragment thereof, e.g., a disorder characterized by unwanted, insufficient, or aberrant expression or activity of the target or fragments thereof. In some embodiments, the method involves administering an agent (e.g., an agent identified by a screening assay described herein), or combination of agents that modulates (e.g., upregulates or downregulates) target expression or activity. In some embodiment, the method involves administering one or more targets polypeptide or nucleic acid molecule as therapy to compensate for reduced, aberrant, or unwanted target expression or activity.

Stimulation of target activity is desirable in situations in which the target is abnormally downregulated and/or in which increased target activity is likely to have a beneficial effect. Likewise, inhibition of target activity is desirable in situations in which target is abnormally upregulated and/or in which decreased target activity is likely to have a beneficial effect.

In some embodiments, the agent decreases the copy number, level of expression, or level of activity of one or more targets in Table 2 and/or Table 4 and/or Table 6 and/or Table 7 and/or in the Examples. In some embodiments, the agent increases the copy number, level of expression, or level of activity of one or more targets in Table 2 and/or Table 4 and/or Table 6 and/or Table 7 and/or in the Examples. In some embodiments, the agent decreases the copy number, level of expression, or level of activity of one or more targets upregulated or down-regulated in Table 2 and/or Table 4 and/or Table 6 and/or Table 7 and/or in the Examples. In some embodiments, the agent increases the copy number, level of expression, or level of activity of one or more targets upregulated or downregulated in Table 2 and/or Table 4 and/or Table 6 and/or Table 7 and/or in the Examples. In some embodiments, the agent decreases the copy number, level of expression, or level of activity of one or more targets upregulated in Table 2 and/or Table 4 and/or Table 6 and/or Table 7 and/or in the Examples. In some embodiments, the agent increases the copy number, level of expression, or level of activity of one or more targets downregulated in Table 2 and/or Table 4 and/or Table 6 and/or Table 7 and/or in the Examples.

In some embodiments, the disclosure provides a method for treating a subject afflicted with a neurological disease, the method comprising administering to said subject an agent that: i) decreases the copy number, level of expression, or level of activity of one or more targets upregulated in Table 2 and/or Table 4 and/or Table 6 and/or Table 7, and/or ii) increases the copy number, level of expression, or level of activity of one or more targets downregulated in Table 2 and/or Table 4 and/or Table 6 and/or Table 7, such that the neurological disease is treated.

In some embodiments, the disclosure provides a method for treating a subject afflicted with a neurological disease, the method comprising administering to said subject an agent that decreases the copy number, level of expression, or level of activity of one or more targets in Table 2 and/or Table 4 and/or Table 6 and/or Table 7, such that the neurological disease is treated.

In some embodiments, the disclosure provides a method for treating a subject afflicted with a neurological disease, the method comprising administering to said subject an agent that increases the copy number, level of expression, or level of activity of one or more targets in Table 2 and/or Table 4 and/or Table 6 and/or Table 7, such that the neurological disease is treated.

In some embodiments, the disclosure provides a method of increasing flow of fluid in the central nervous system of a subject, the method comprising: determining the subject to be in need of increased fluid flow in the central nervous system; and administering to a meningeal space of the subject in need an effective amount of an agent that: i) decreases the copy number, level of expression, or level of activity of one or more targets upregulated in Table 2 and/or Table 4 and/or Table 6 and/or Table 7, and/or ii) increases the copy number, level of expression, or level of activity of one or more targets downregulated in Table 2 and/or Table 4 and/or Table 6 and/or Table 7, thereby increasing fluid flow in the central nervous system of the subject.

In some embodiments, the disclosure provides a method of increasing flow of fluid in the central nervous system of a subject, the method comprising: determining the subject to be in need of increased fluid flow in the central nervous system; and administering to a meningeal space of the subject in need an effective amount of an agent that decreases the copy number, level of expression, or level of activity of one or more targets in Table 2 and/or Table 4 and/or Table 6 and/or Table 7, thereby increasing fluid flow in the central nervous system of the subject.

In some embodiments, the disclosure provides a method of increasing flow of fluid in the central nervous system of a subject, the method comprising: determining the subject to be in need of increased fluid flow in the central nervous system; and administering to a meningeal space of the subject in need an effective amount of an agent that increases the copy number, level of expression, or level of activity of one or more targets in Table 2 and/or Table 4 and/or Table 6 and/or Table 7, thereby increasing fluid flow in the central nervous system of the subject.

In some embodiments, the disclosure provides a method of reducing the accumulation of, or reducing a quantity of, accumulated amyloid-beta plaques in a subject having a neurodegenerative disease or a risk factor therefor, the method comprising: determining the subject to have the neurodegenerative disease or the risk factor; and administering to a meningeal space of the subject in need an effective amount of an agent that: i) decreases the copy number, level of expression, or level of activity of one or more targets upregulated in Table 2 and/or Table 4 and/or Table 6 and/or Table 7, and/or ii) increases the copy number, level of expression, or level of activity of one or more targets downregulated in Table 2 and/or Table 4 and/or Table 6 and/or Table 7, thereby reducing the quantity of accumulated amyloid-beta plaques in the subject.

In some embodiments, the disclosure provides a method of reducing the accumulation of, or reducing a quantity of, accumulated amyloid-beta plaques in a subject having a neurodegenerative disease or a risk factor therefor, the method comprising: determining the subject to have the neurodegenerative disease or the risk factor; and administering to a meningeal space of the subject in need an effective amount of an agent that decreases the copy number, level of expression, or level of activity of one or more targets in Table 2 and/or Table 4 and/or Table 6 and/or Table 7, thereby reducing the quantity of accumulated amyloid-beta plaques in the subject.

In some embodiments, the disclosure provides a method of reducing the accumulation of, or reducing a quantity of, accumulated amyloid-beta plaques in a subject having a neurodegenerative disease or a risk factor therefor, the method comprising: determining the subject to have the neurodegenerative disease or the risk factor; and administering to a meningeal space of the subject in need an effective amount of an agent that increases the copy number, level of expression, or level of activity of one or more targets in Table 2 and/or Table 4 and/or Table 6 and/or Table 7, thereby reducing the quantity of accumulated amyloid-beta plaques in the subject.

In some embodiments, the disclosure provides a method of increasing clearance of molecules from a central nervous system (CNS) of a subject, comprising administering to a meningeal space of the subject in need an effective amount of an agent that: i) decreases the copy number, level of expression, or level of activity of one or more targets upregulated in Table 2 and/or Table 4 and/or Table 6 and/or Table 7, and/or ii) increases the copy number, level of expression, or level of activity of one or more targets downregulated in Table 2 and/or Table 4 and/or Table 6 and/or Table 7, thereby increasing clearance of molecules from the CNS of the subject.

In some embodiments, the disclosure provides a method of increasing clearance of molecules from a central nervous system (CNS) of a subject, comprising administering to a meningeal space of the subject in need an effective amount of an agent that decreases the copy number, level of expression, or level of activity of one or more targets in Table 2 and/or Table 4 and/or Table 6 and/or Table 7, thereby increasing clearance of molecules from the CNS of the subject.

In some embodiments, the disclosure provides a method of increasing clearance of molecules from a central nervous system (CNS) of a subject, comprising administering to a meningeal space of the subject in need an effective amount of an agent that increases the copy number, level of expression, or level of activity of one or more targets in Table 2 and/or Table 4 and/or Table 6 and/or Table 7, thereby increasing clearance of molecules from the CNS of the subject.

In some embodiments, the disclosure provides a method for treating a subject afflicted with a neurological disease, the method comprising administering to the hippocampus of the subject in need an effective amount of an agent that: i) decreases the copy number, level of expression, or level of activity of one or more targets upregulated in Table 2 and/or Table 4 and/or Table 6 and/or Table 7, and/or ii) increases the copy number, level of expression, or level of activity of one or more targets downregulated in Table 2 and/or Table 4 and/or Table 6 and/or Table 7, such that the neurological disease is treated.

In some embodiments, the disclosure provides a method for treating a subject afflicted with a neurological disease, the method comprising administering to the hippocampus of the subject in need an effective amount of an agent that decreases the copy number, level of expression, or level of activity of one or more targets in Table 2 and/or Table 4 and/or Table 6 and/or Table 7, such that the neurological disease is treated.

In some embodiments, the disclosure provides a method for treating a subject afflicted with a neurological disease, the method comprising administering to the hippocampus of the subject in need an effective amount of an agent that increases the copy number, level of expression, or level of activity of one or more targets in Table 2 and/or Table 4 and/or Table 6 and/or Table 7, such that the neurological disease is treated.

Pharmaceutical Compositions

In some embodiments, the present disclosure provides pharmaceutically acceptable compositions which comprise a therapeutically-effective amount of an agent that modulates (e.g., increases or decreases) the copy number, level of expression, or level of activity of one or more targets listed in Table 2 and/or Table 4 and/or Table 6 and/or Table 7, formulated together with one or more pharmaceutically acceptable carriers (additives) and/or diluents. As described in detail below, the pharmaceutical compositions of the present disclosure may be specially formulated for administration in solid or liquid form, including those adapted for the following: (1) intrathecal administration; (2) nasal administration; (3) transcranial administration; (4) contact with cerebral spinal fluid (CSF) of the subject; (5) pumping into CSF of the subject; (6) implantation into the skull or brain; (7) contacting a thinned skull or skull portion of the subject with the agent; (8) oral administration, for example, drenches (aqueous or non-aqueous solutions or suspensions), tablets, boluses, powders, granules, pastes; (9) parenteral administration, for example, by subcutaneous, intramuscular or intravenous injection as, for example, a sterile solution or suspension; (10) topical application, for example, as a cream, ointment or spray applied to the skin; (11) intravaginally or intrarectally, for example, as a pessary, cream or foam; or (12) aerosol, for example, as an aqueous aerosol, liposomal preparation or solid particles containing the compound.

The phrase "therapeutically-effective amount" as used herein has its ordinary meaning as understood in the art in view of the specification, and includes an amount of an agent that modulates (e.g., inhibits) target levels, or expression and/or activity of the receptor/ligand complex, or composition comprising an agent that modulates (e.g., inhibits) target levels, or expression and/or activity of the receptor/ligand complex, which is effective for producing some desired therapeutic effect, e.g., a neurological disease treatment, at a reasonable benefit risk ratio.

The phrase "pharmaceutically acceptable" is employed herein has its ordinary meaning as understood in the art in view of the specification, and includes to refer to those agents, materials, compositions, and or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein has its ordinary meaning as understood in the art in view of the specification, and includes a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) Target levels, or expression and/or activity of the receptor/ligand complex encompassed by the disclosure. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", J. Pharm. Sci. 66: 1-19).

In other cases, the agents useful in the methods of the present disclosure may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates Target levels, or expression and/or activity of the receptor/ligand complex. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al, supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present disclosure include those suitable for transcranial administration, administration by contact with cerebral spinal fluid (CSF) of the subject, administration by pumping into CSF of the subject, administration by implantation into the skull or brain, administration by contacting a thinned skull or skull portion of the subject with the agent; oral administration, nasal administration, topical administration (including buccal and sublingual), rectal administration, vaginal administration, aerosol administration and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1% to about 99% of active ingredient, and in some embodiments from about 5% to about 70%, and in some embodiments from about 10% to about 30%.

Methods of preparing these formulations or compositions include the step of bringing into association an agent that modulates (e.g., increases or decreases) Target levels, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or in some embodiments, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases or decreases) Target levels include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases or decreases) Target levels, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases or decreases) Target levels, can be In some embodiments administered by aerosol. This is accomplished by preparing an aqueous aerosol, liposomal preparation or solid particles containing the compound. A nonaqueous (e.g., fluorocarbon propellant) suspension could be used. Sonic nebulizers are employed in some embodiments because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form.

In some embodiments, delayed absorption of a parenterally-administered drug form is accomplished by dissolving or suspending the drug in an oil vehicle.

Injectable depot forms are made by forming microencapsule matrices of an agent that modulates e.g., increases or decreases) Target levels, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions, which are compatible with body tissue.

When the respiration uncoupling agents of the present disclosure are administered as pharmaceuticals, to humans and animals, they can be given per se or as a pharmaceutical composition containing, for example, 0.1 to 99.5% (in some embodiments, 0.5 to 90%) of active ingredient in combination with a pharmaceutically acceptable carrier.

Actual dosage levels of the active ingredients in the pharmaceutical compositions of this disclosure may be determined by the methods of the present disclosure so as to obtain an amount of the active ingredient, which is effective to achieve the desired therapeutic response for a particular subject, composition, and mode of administration, without being toxic to the subject.

The nucleic acid molecules of the disclosure can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1 94) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. In some embodiments, where the complete gene delivery vector can be produced intact from recombinant cells, e.g., retroviral vectors, the pharmaceutical preparation can include one or more cells which produce the gene delivery system.

Administration of Agents

The neurological disease diagnostic, prognostic, prevention, and/or treatment modulating agents of the disclosure are administered to subjects in a biologically compatible form suitable for pharmaceutical administration in vivo, to treat, prevent, or reduce the likelihood of a neurological disease or disorder are provided. Neurological diseases or disorders include, but are not limited to AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, MS, AIDS-related dementia complex, or a combination of two or more of the listed items. By way of example, neurological diseases or disorders include, but are not limited to AD (such as familial AD and/or sporadic AD), dementia, age-related dementia, PD, cerebral edema, ALS, PANDAS, meningitis, hemorrhagic stroke, ASD, brain tumor (such as glioblastoma), epilepsy, Down's syndrome, HCHWA-D, Familial Danish/British dementia, DLB, LB variant of AD, MSA, FENIB, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of the listed items. By way of example, neurological diseases or disorders can include (but are not limited to) AD, dementia, age-related dementia, PD, cerebral edema, ALS, PANDAS, meningitis, hemorrhagic stroke, ASD, brain tumor, and epilepsy. In some embodiments, the neurological disease or disorder comprises, consists essentially of, or consists of a proteinopathy, for example AD (such as familial AD and/or sporadic AD), Down's syndrome, HCHWA-D, Familial Danish/British dementia, PD, DLB, LB variant of AD, MSA, FENIB, ALS, FTD, HD, Kennedy disease/SBMA, DRPLA; SCA type I, SCA2, SCA3 (Machado-Joseph disease), SCA6, SCA7, SCA17, CJD (such as familial CJD), Kuru, GSS, FFI, CBD, PSP, CAA, or a combination of two or more of any of the listed items. In some embodiments, the neurological disease or disorder is AD, dementia, or PD. In some embodiments, the neurodegenerative disease comprises, consists essentially of, or consists of prion disease. In some embodiments, the neurodegenerative disease comprises, consists essentially of, or consists of a non-human prion disease such as scrapie, chronic wasting disease, or BSE. By "biologically compatible form suitable for administration in vivo" is meant a form of the protein to be administered in which any toxic effects are outweighed by the therapeutic effects of the protein. The term "subject" is intended to include living organisms in which a neurological disease or disorder can be identified, e.g., mammals. Examples of subjects include humans, dogs, cats, mice, rats, and transgenic species thereof.

Administration of an agent as described herein can be in any pharmacological form including a therapeutically active amount of an agent alone or in combination with a pharmaceutically acceptable carrier.

Administration of a therapeutically active amount of the therapeutic composition of the present disclosure is defined as an amount effective, at dosages and for periods of time necessary, to achieve the desired result. For example, a therapeutically active amount of a blocking antibody may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation. The agents of the disclosure described herein can be administered in a convenient manner such as by transcranial administration, administration by contact with cerebral spinal fluid (CSF) of the subject, administration by pumping into CSF of the subject, administration by implantation into the skull or brain, administration by contacting a thinned skull or skull portion of the subject with the agent, injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) J. Neuroimmunol. 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will in some embodiments be sterile and must be fluid to the extent that easy syringeability exists. It will in some embodiments be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the disclosure (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, and, in some embodiments methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" has its ordinary meaning as understood in the art in view of the specification, and includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, has its ordinary meaning as understood in the art in view of the specification, and includes physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by, and directly dependent on, (a) the unique characteristics of the active compound and the particular therapeutic effect to be achieved, and (b) the limitations inherent in the art of compounding such an active compound for the treatment of sensitivity in individuals. In some embodiments, an agent of the disclosure is an antibody. As defined herein, a therapeutically effective amount of antibody (e.g., an effective dosage) ranges from about 0.001 to 30 mg kg body weight, in some embodiments about 0.01 to 25 mg kg body weight, in some embodiments about 0.1 to 20 mg kg body weight, and in some embodiments about 1 to 10 mg/kg, 2 to 9 mg/kg, 3 to 8 mg kg, 4 to 7 mg/kg, or 5 to 6 mg kg, or a range defined by any two of the preceding values, body weight. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of an antibody can include a single treatment or, in some embodiments, can include a series of treatments. In some embodiments, a subject is treated with antibody in the range of between about 0.1 to 20 mg kg body weight, one time per week for between about 1 to 10 weeks, in some embodiments between 2 to 8 weeks, in some embodiments between about 3 to 7 weeks, and in some embodiments for about 4, 5, or 6 weeks, or a range defined by any two of the preceding values. It will also be appreciated that the effective dosage of antibody used for treatment may increase or decrease over the course of a particular treatment. Changes in dosage may result from the results of diagnostic assays. In addition, an antibody of the disclosure can also be administered in combination therapy with, e.g., chemotherapeutic agents, hormones, antiangiogens, radiolabeled, compounds, or with surgery, cryotherapy, and/or radiotherapy. An antibody of the disclosure can also be administered in conjunction with other forms of conventional therapy, either consecutively with, pre- or post-conventional therapy. For example, the antibody can be administered with a therapeutically effective dose of chemotherapeutic agent. In some embodiment, the antibody can be administered in conjunction with chemotherapy to enhance the activity and efficacy of the chemotherapeutic agent. The Physicians' Desk Reference (PDR) discloses dosages of chemotherapeutic agents that have been used in the treatment of various neurological disease and disorders. The dosing regimen and dosages of these aforementioned chemotherapeutic drugs that are therapeutically effective will depend on the particular neurological disease or disorder, being treated, the extent of the disease and other factors familiar to the physician of skill in the art and can be determined by the physician.

In addition, the agents of the disclosure described herein can be administered using nanoparticle-based composition and delivery methods well known to the skilled artisan. For example, nanoparticle-based delivery for improved nucleic acid (e.g., small RNAs) therapeutics are well known in the art (Expert Opinion on Biological Therapy 7: 1811-1822).

EXAMPLES

Materials and Methods
Mouse Strains and Housing

Male or female wild-type mice (C57BL/6J background) were either bred in-house, purchased from the Jackson Laboratory (Bar Harbor, Maine, USA) or provided by the National Institutes of Health/National Institute on Aging (Bethesda, MD, USA). All mice were maintained in the animal facility for habituation for at least 1 week prior to the start of the manipulation/experimentation. C57BL/6J wild-type mice were tested at 2-3, 12-14 and 20-24 months of age. Male hemizygous B6.Cg-Tg(PDGFB-APPSwInd)20Lms/2Mmjax (J20, JAX stock #006293) and B6.Cg-Tg(APPSw-FlLon,PSEN1*M146L*L286V)6799Vas/Mmjax (5xFAD, JAX stock #008730) were purchased from the Jackson Laboratory and bred in-house on a C57BL/6J background. J20 hemizygous mice present diffuse Aβ deposition in the dentate gyrus and neocortex at 5-7 months, with all transgenic mice exhibiting plaques by the age of 8-10 months[44]. 5xFAD hemizygous mice overexpress the transgene constructs under neural-specific elements of the mouse thymocyte differentiation antigen 1 promoter and present accelerated accumulation of $A\beta_{42}$ and deposition of amyloid and gliosis in the brain starting at 2 months of age, with dramatic amyloid plaque load without major behavioral deficits at 5 months[45]. In-house bred male transgene carriers and non-carrier (WT) littermates were used at different ages that are indicated throughout the manuscript. $Prox1^{LacZ}$ mice (designated $Prox1^{+/-}$ mice in this manuscript) on a NMRI background (kindly provided by Dr. Guillermo Oliver, Northwestern University, Chicago, IL) were also bred in-house and used in this study as a constitutive model for dysfunctional lymphatic vessels[46]. Mice of all strains were housed in an environment with controlled temperature and humidity, on 12 hours light/dark cycles (lights on at 7:00), and fed with regular rodent's chow and sterilized tap water ad libitum. All experiments were approved by the Institutional Animal Care and Use Committee of the University of Virginia.

Intra-Cisterna Magna Injections

Mice were anaesthetized by intraperitoneal (i.p.) injection of a mixed solution of ketamine (100 mg/Kg) and xylazine (10 mg/Kg) in saline. The skin of the neck was shaved and cleaned with iodine and 70% ethanol, ophthalmic solution placed on the eyes to prevent drying and the mouse's head was secured in a stereotaxic frame. After making a skin incision, the muscle layers were retracted and the cisterna magna exposed. Using a Hamilton syringe (coupled to a 33-gauge needle), the volume of the desired tracer solution was injected into the CSF-filled cisterna magna compartment. For brain CSF influx and lymphatic drainage experiments, 2 or 5 μL of Alexa Fluor® 594 or 647 conjugated OVA (Thermo Fisher Scientific), at 0.5 mg/mL in artificial CSF (#597316, Harvard Apparatus U.K.), were injected at a rate of 2.5 μL/min. After injecting, the syringe was left in place for additional 2 min to prevent back-flow of CSF. The neck skin was then sutured, the mice were subcutaneously injected with ketoprofen (2 mg/Kg) and allowed to recover on a heating pad until fully awake.

Meningeal Lymphatic Vessel Ablation

Selective ablation of the meningeal lymphatic vessels was achieved by i.c.m. injection and transcranial photoconversion of Visudyne® (verteporfin for injection, Valeant Ophtalmics). Visudyne was reconstituted following manufacturer instructions and 5 μL was injected i.c.m. following the previously described procedure. After 15 min, an incision was performed in the skin to expose the skull bone and Visudyne was photoconverted by pointing a 689-nm wavelength non-thermal red light (Coherent Opal Photoactivator, Lumenis) on 5 different spots above the intact skull (1 on the injection site, 1 on the superior sagittal sinus, 1 at the junction of all sinuses and 2 on the transverse sinuses). Each spot was irradiated with a light dose of 50 $J/cm^2$ at an intensity of 600 $mW/cm^2$ for a total of 83 s. Controls were injected with the same volume of Visudyne (without the photoconversion step) or sterile saline plus photoconversion (vehicle/photoconversion). The scalp skin was then sutured, the mice were subcutaneously injected with ketoprofen (2 mg/Kg) and allowed to recover on a heating pad until fully awake.

Lymphatic Vessel Ligation

Surgical ligation of the lymphatics afferent to the dCLNs was performed as described before[47]. Briefly, mice were anaesthetized by i.p. injection with ketamine and xylazine in saline, the skin of the neck was shaved and cleaned with iodine and 70% ethanol and ophthalmic solution placed on the eyes to prevent drying. A midline incision was made 5 mm superior to the clavicle. The sternocleidomastoid muscles were retracted and the dCLNs were exposed on each side. Ligation of the afferent lymphatic vessels on each side was performed with 10-0 synthetic, non-absorbable suture. Control mice were submitted to a sham surgery consisting of the skin incision and retraction of the sternocleidomastoid muscle only. The skin was then sutured, the mice were subcutaneously injected with ketoprofen (2 mg/Kg) and allowed to recover on a heating pad until fully awake.

Brain Parenchymal Injections

Mice were anaesthetized by i.p. injection of ketamine and xylazine in saline and the head was secured in a stereotaxic frame. An incision was made in the skin to expose the skull and a hole was drilled at +1.5 mm in the anterior-posterior axis and −1.5 mm in the medial-lateral axis relative to bregma. Then, using a Hamilton syringe (coupled to a 33-gauge needle) placed at +2.5 mm in the dorsal-ventral axis (relative to bregma), 1 μL of either Alexa Fluor® 647 conjugated OVA (at 0.5 mg/mL), HiLyte™ Fluor 647 conjugated $A\beta_{42}$ (at 0.05 μg/mL, AnaSpec, Inc.) or BODIPY™ FL conjugated low density lipoprotein (LDL) from human plasma (at 0.1 mg/mL, Thermo Fisher Scientific) in artificial CSF were injected at a rate of 0.2 μL/min into the brain parenchyma. Concentrations of the injected fluorescent $A\beta_{42}$ and LDL molecular tracers were chosen in order to be comparable to levels detected in brain ISF of AD transgenic mice[47] and in plasma of C57BL/6 mice[48], respectively. After injecting, the syringe was left in place for additional 5 min to prevent back-flow. The scalp skin was then sutured, the mice were subcutaneously injected with ketoprofen (2 mg/Kg) and allowed to recover on a heating pad until further use.

AAV Delivery

For experiments assessing the effect of viral-mediated expression of mVEGF-C(NM_009506.2) on meningeal lymphatics, 2 μL of artificial CSF containing $10^{13}$ genome copies per mL of AAV1-CMV-mVEGF-C, or control AAV1-CMV-EGFP (AAV1, adeno-associated virus serotype 1; CMV, cytomegalovirus promoter; EGFP, enhanced green fluorescent protein; purchased from Vector BioLabs, Philadelphia), were injected directly into the cisterna magna CSF at a rate of 2 μL/min, following the previously described i.c.m. injection procedure.

Transcranial Recombinant VEGF-C Delivery

A hydrogel of 1.4% hyaluronic acid and 3% methylcellulose alone (vehicle) or with 200 ng/mL of encapsulated human VEGF-C (PeproTech) or VEGF-C156S (R&D Systems) was prepared as described elsewhere[49]. Briefly, lyophilized, sterile methylcellulose (4000 cP, Sigma-Aldrich) and sterile hyaluronic acid (1500-1800 kDa, Sigma-Aldrich) were sequentially dissolved in sterile 0.1 M phosphate buffered saline (PBS) at 4° C. overnight. Lyophilized VEGF-C or VEGF-C156S were resuspended as particulate at 2000 ng/mL in 0.5% sterile methylcellulose in PBS. The particulate solution, or vehicle 0.5% methylcellulose, was mixed into the hydrogel pre-solution at 1:10, and loaded into a syringe for gelation at 37° C. The methylcellulose provided more stability, by promoting thermal gelation, and increased the hydrophobic properties of the gel[49], sustaining the release of VEGF-C or VEGF-C156S up to 7-10 days in vitro (verified using an ELISA for human VEGF-C, R&D Systems). The hydrogels were prepared on the day of the experiment and kept warm inside the individual syringes until applied onto the mouse's skull. The mouse was anaesthetized by i.p. injection of ketamine and xylazine in saline and the head was secured in a stereotaxic frame. An incision was made in the scalp skin and the skull was thinned at the junction of all sinuses and above the transverse sinus. The shear-thinning properties of the polymers allowed the extrusion of 100 μL of each hydrogel solution from the syringe into the thinned skull surface. The scalp skin was then sutured on top of the solidified hydrogel, the mice were subcutaneously injected with ketoprofen (2 mg/Kg) and allowed to recover on a heating pad until fully awake. Taking the into account the release kinetics of 7-10 days, hydrogels were re-applied, following the same methodology, 2 weeks after the first treatment.

MRI Acquisitions and Analysis

All MRI acquisitions were performed at the University of Virginia Molecular Imaging Core facilities in a 7T Clinscan system (Bruker, Ettlingen, Germany) equipped with a 30 mm diameter cylindrical RF Coil. For analysis of mouse intracranial vascular structure, mice were placed in the 7T Clinscan system under light anaesthesia with isoflurane (1-1.25% in oxygen). Structural imaging data of intracranial arteries (magnetic resonance angiography or MRA) was acquired with a high-resolution 3D isotropic Spiral Cine Phase Contrast (SCPC) technique: repetition time (TR)=15 ms, echo time (TE)=0.63 ms, field of view (FOV)=25×25 mm, slice thickness=0.01 mm, number of sagittal slices=160, number of averages per phase-encode step (NEX)=1 and flip angle (FA)=20°. Total imaging time was of about 15 min per mouse. Structural imaging data of intracranial veins (magnetic resonance venography or MRV) was acquired with a high-resolution 3D isotropic SCPC technique with a saturation band positioned caudal to the slices, in order to saturate the arterial signal: TR=17 ms, TE=4.54 ms, FOV=17×26 mm, slice thickness=0.3 mm, number of sagittal slices=160, NEX=2 and FA=90°. Total imaging time was of about 13 min per mouse. Vascular volume and diameters were quantified using semi-automatic segmentation tools provided in the OsiriX software. For analysis of mouse brain ventricular volume, mice were placed in the 7T Clinscan system under light anaesthesia with isoflurane and structural imaging data were acquired with a high-resolution 3D isotropic T2-weighted SPACE technique with the following parameters: TR=3000 ms, TE=139 ms, FOV=26×20.5 mm, slice thickness=0.13 mm, number of slices=160 and NEX=3, requiring a total acquisition time of about 16 min per mouse. Ventricular volumes were quantified using semi-automatic segmentation tools provided in the OsiriX software.

Measurement of blood-brain barrier integrity was based on previously published methodology with minor modifications (Li, W. et al. *A quantitative MRI method for imaging blood-brain barrier leakage in experimental traumatic brain injury. PLoS One* 9, e114173, (2014)). Initially, a pre-contrast image was acquired after placing the mice in the 7T Clinscan system under light anaesthesia with isoflurane. Gadobenate dimeglumine (gadolinium or Gd, MultiHance, Bracco Diagnostics, Princeton, New Jersey) at 0.3 mmol/kg was then injected intravenously (i.v.), through a catheter inserted in the tail vein. To assess the rate of influx of a CSF tracer into the brain, mice were anaesthetized by i.p. injection of ketamine and xylazine in saline and an i.c.m. injection of 5 μL of Gd at a concentration of 25 mM in saline was performed. The Gd concentration of 25 mM was chosen based on previous published methodology (Iliff, J. J. et al. *Brain-wide pathway for waste clearance captured by contrast-enhanced MRI. J Clin Invest* 123, 1299-1309, (2013)) and on MRI acquisitions performed after i.c.m. injection of 1, 10 or 25 mM Gd (see FIGS. 7A-V). The mice were placed in the MRI apparatus and maintained under light anaesthesia with isoflurane. For MRI acquisition, maximum gradient strength of the system was 500 mT/m and the peak slew rate achievable was 6667 mT/m/ms. After i.v. injection of Gd or 10 min after injecting gadolinium into the CSF, a series of post-contrast T1-weighted images were taken through the head with the following parameters: TR=500 ms, TE=11 ms, FOV=20×20 mm with a 192×192 matrix (104 μm×104 μm resolution), slice thickness=0.7 mm, number of slices=22 and NEX=2. For i.v. Gd injection 5 post-contrast images were acquired requiring about 16 min per mouse (each sequence taken every 194 s). For brain influx of Gd injected into the CSF, the total acquisition time was of about 52 min per mouse (194 s×16 sequences per mouse), meaning that T1 images were acquired for approximately 1 hour post-injection.

MR-compatible physiological monitoring and gating system for mice (SA Instruments, Inc., Stony Brook, NY) was used for T1 and T2 acquisitions.

Measurement of gadolinium influx rate and modeling of tracer advection-diffusion within the brain were achieved using Lymph4D, a software developed in-house and available for revision purposes on the following link on the world wide web: viva-lab.ece.virginia.edu/lymph4d. To allow for a direct comparison between the different conditions, the MRI stacks $S_i(x, y, z, t)$ of the imaged mice (4 vehicle and 4 Visudyne) were aligned to a Visudyne stack $V_1(x, y, z, t)$, chosen as reference. Before proceeding with the automated registration in the (x, y) plane, the stacks were manually aligned along the z (sagittal) direction, to ensure the correspondence between (x, y) (transversal plane) slices, and cropped both in the z and t (time) direction, to ensure that each set of coordinates (x, y, z, t) contained meaningful data. To optimize the slice alignment in the (x, y) plane, scale pyramids (Adelson, E. H., Anderson, C. H., Bergen, J. R., Burt, P. J. & Ogden, J. M. Pyramid methods in image processing. RCA engineer 29, 33-41, (1984).) (3 levels deep) were computed for both the image to be registered and the reference. Starting from the coarser scale, the optimal non-reflective transformation matrix (restricted to translation, rotation, and scaling) was evaluated by using an iterative process based on the steep gradient descent method with a mean square error (MSE) cost function. After reaching algorithm convergence at the largest scale, or the maximum number of allowed iterations, the alignment was refined using progressively finer scales. A linear interpolation mapping was then used to reconstruct the image registered using the optimized transformation matrix. The following alignment strategy was used. Given a stack $S_i$ to be aligned to $V_1$, for every slice $z_j(t)=S_i(x, y, z_j, t)$ at a given location in the sagittal direction ($z=z_j$), the optimal transformation matrix was evaluated at every available time (t) and the quality (MSE) of the resulting alignment measured. The transformation resulting in the lowest MSE (highest quality) was used to re-align all the $z_i(t)$ slices for each available time (t), ensuring consistent alignment along the temporal direction. This was key to the analysis of the transport model described next. After the alignment, rate of contrast agent influx in outlined regions of the brain (namely hippocampus and cortex) was obtained by measuring the gain in signal intensity after subtraction of the baseline values (sequence 1) to the images in sequence 2 and subsequent sequences. Also, after the alignment, contrast measurement, providing the difference between the maximum and the minimum values observed along the temporal direction during the experiment duration (variability in tracer signal intensity over time), was evaluated for a given (x, y, z) location in the $S_i$ stack using:

$$\Delta L_i(x, y, z) = \max_t S_i(x, y, z, t) - \min_t S_i(x, y, z, t)$$

To evaluate the component of the transport mechanism within the brain a model combining the microscopic diffusive and the macroscopic advective (bulk motion) processes, with the presence of sources/sinks, was implemented. The model used is described by the following differential equation:

$$\frac{\partial \phi(x, t)}{\partial t} = \nabla \cdot [D(x, t)\nabla \phi(x, t)] - \nabla \cdot [\phi(x, t)u(x, t)] + \sigma(x, t)$$

where:

$\phi(x, t)$ is the concentration $\left[\frac{\text{amount}}{L^3}\right]$ $D(x, t)$ is the diffusion coefficient $\left[\frac{L^2}{T}\right]$ $u(x, t)$ is the velocity field $\left[\frac{L}{T}\right]$ $\sigma(x, t)$ are the sources/sinks $\left[\frac{\text{amount}}{L^3 T}\right]$ $(x, t)$ are location $[L]$ and time $[T]$ The model was discretized using the forward-time central-space (FTCS) finite difference method (Ferziger, J. H. & Perić, M. *Finite Difference Methods. In: Computational Methods for Fluid Dynamics.* 3rd edition, 39-69, Springer, Berlin, Heidelberg, (2002).) after the following assumptions. The concentration (x, t) was considered proportional to the measured MRI signal intensity. The diffusion coefficient D(x, t) was considered isotropic and constant over the duration of the experiment. Velocity field (x, t) and sources/sinks (x, t) were considered constant over the duration of the experiment. Furthermore, due the difference in spatial sampling between the sagittal and transversal directions (0.7 mm vs. 104 µm), each transversal slice $z_i(t)$ was considered independently with the source/sink term summarizing the results of potential interactions with the neighboring slices along the sagittal direction. The final discretized model was used in an inverse problem framework to evaluate the parameters (D(x), u(x), and σ(x)) generating the concentration spatiotemporal evolution φ(x, t) that best matched the MRI data. For every location x, the matching problem was posed as a constrained least-square optimization using data extracted from a spatiotemporal neighborhood of x. The results of the optimization were presented as a 2D maps, one for each of the model parameters: isotropic diffusion coefficient (used in this study), velocity components and derived magnitude and direction, and sources and sinks. 2D maps of isotropic diffusion coefficient were further used to assess the area fraction of high, medium and low coefficient values, by means of the tools available in FIJI image processing software (NIH), and calculate the difference between Visudyne and vehicle in each of the stacks.

Photoacoustic Imaging

Adult mice were maintained under anesthesia with 1.5% isoflurane and at a constant body temperature with the aid of a heating pad. A surgical incision was made in the scalp and the fascia was removed to expose the skull. One day prior to the imaging, the skull over the region of interest was thinned to the desired thickness (~100 µm). Mice were then imaged by multi-parametric photoacoustic microscopy, which is capable of simultaneously image oxygen saturation of hemoglobin (sO2) and blood flow speed as described previously[50]. Using the oxy-hemoglobin and deoxy-hemoglobin values, recorded using two nanosecond-pulsed lasers (532 and 559 nm), it is possible to compute the final sO2. Correlation analysis of adjacent A-line signals allows the quantification of blood flow speed within individual vessels. By segmenting major vessels within the region of interest, average values of the blood flow speed and sO2 were extracted for quantitative analysis.

Open Field Test

Open field was performed following a published protocol[51] with minor modifications. Mice were carried to the behavior room to habituate at least 30 min before starting the test. Mice were then placed into the open field arena (made of opaque white plastic material, 35 cm×35 cm) by a blinded experimenter and allowed to explore it for 15 min. Total distance (cm) and % time spent in the center (22 cm×22 cm) were quantified using video tracking software (TopScan, CleverSys, Inc.).

Novel Location Recognition Test

Novel location recognition test was performed following a published protocol[52] with modifications. The experimental apparatus used in this study was the same square box made of opaque white plastic (35 cm×35 cm) used in the Open field test. The mice were first habituated to the apparatus for 15 min. Two different plastic objects (one red and the other blue and with different shapes) were then positioned in a defined spatial orientation, namely on each corner of the arena and 5 cm away from each adjacent arena wall. Mice were then placed in the arena (by a blinded experimenter), facing the wall farther away from the objects and allowed to explore the arena and objects for 10 min. Twenty-four hours later, the mice were placed in the same box with the same two objects, but one of them had switched location and was placed in a new quadrant, obliquely to the familiar object (novel location test). The time spent exploring the objects in the familiar and novel locations was also measured for 10 min. Exploration of an object was assumed when the mouse approached an object and touched it with its vibrissae, snout or forepaws and was measured using a video tracking software (TopScan, CleverSys, Inc.). The object location preference (% of time with object) was calculated as the exploration time of the objects in the familiar or in the novel location/total exploration time.

Contextual Fear Conditioning Test

This behavioral test was performed following a published protocol[53] with modifications. In this associative learning task, mice are presented with a neutral conditioned cue stimulus that is paired with an aversive unconditioned stimulus in a particular context. The mice learn that the chamber context and the cue stimulus predict the aversive stimulus and elicit a specific behavioral response, namely freezing. Mice were brought into the testing room to acclimate for at least 30 minutes before testing. For the test, we used two Habitest® chambers (Coulbourn Instruments, Allentown, PA, USA) with stainless grid floors attached to a shock generator for foot shock delivery and dimly illuminated with a white fluorescent light bulb. The chambers were cleaned and made odor-free before starting the experiment and between each session (or each mouse). The fear conditioning test was conducted over 2 days. On day 1, mice were placed in the conditioning chamber and allowed to habituate for 3 minutes. Then, mice received three pairs of cue-aversive stimuli, consisting of tone (18 s, 5 kHz, 75 dB)-shock (2 s, 0.5 mA) pairings, separated by an interval of 40 s (total of 3 minutes). Mice were returned to their home cage 30 sec after the last shock presentation. On day 2, mice were tested and scored for conditioned fear to the training context for 3 minutes (context test), but with no presentation of the cue stimulus. Two hours later, mice were presented to a novel context, where the light intensity was slightly increased, the grid and walls of the chamber were covered by plastic inserts with different texture and colours and the inside of the chamber was scented with a paper towel dabbed with vanilla extract placed under the floor grid. In this last session, mice were placed in the conditioning chamber and allowed to habituate for 3 minutes, after which they received a continuous cue stimulus (tone) for an additional 3 minutes (cued test). Mice behaviour was recorded by a digital video camera mounted above the conditioning chamber and freezing was manually scored by a blinded experimenter using the Etholog V2.2 software. Parameters analysed included the percentage of time freezing during the 3 minutes of the context test and the last 3 minutes of the cued test.

MWM Test

The Morris water maze test was performed as described before[53], but with modifications. Mice were transported to the behavior room to habituate at least 30 min before starting the test. The MWM test consisted of 4 days of acquisition, 1 day of probe trial and 2 days of reversal. In the acquisition, mice performed four trials per day, for 4 consecutive days, to find a hidden 10-cm diameter platform located 1 cm below the water surface in a pool 1 m in diameter. Tap water was made opaque with nontoxic tempera white paint and the water temperature was kept at 23±1° C. A dim light source was placed within the testing room and only distal visual cues were available above each quadrant of the swimming pool to aid in the spatial navigation and location of the submerged platform. The latency to platform, e.g., the time required by the mouse to find and climb onto the platform, was recorded for up to 60 s. Each mouse was allowed to remain on the platform for 20 s and was then moved from the maze to its home cage. If the mouse did not find the platform within 60 s, it was manually placed on the platform and returned to its home cage after 20 s. The inter-trial interval for each mouse was of at least 5 min. On day 5, the platform was removed from the pool, and each mouse was tested in a probe trial for 60 s. On days 1 and 2 of the reversal, without changing the position of the visual cues, the platform was placed in the quadrant opposite to the original acquisition quadrant and the mouse was retrained for four trials per day. All MWM testing was performed between 1 p.m. and 6 p.m., during the lights-on phase, by a blinded experimenter. During the acquisition, probe and reversal, data were recorded using the EthoVision automated tracking system (Noldus Information Technology). The mean latency (in s) of the four trials was calculated for each day of test. The % of time in the platform quadrant was calculated for the probe trial. Additionally, using a modified version of previous published methods[54,55], the full tracked path taken by each mouse in every trial of the acquisition and reversal days was used to classify the type of navigation strategy as either egocentric or allocentric by a blinded experimenter. The mean % of allocentric navigation of four trials was calculated for each day.

CSF and Tissue Collection and Processing

Mice were given a lethal dose of anesthetics by intraperitoneal (i.p.) injection of Euthasol (10% v/v in saline). When needed, CSF was collected from the cisterna magna using a 0.5 mm diameter borosilicate glass pipette with internal filament and immediately stored at −80° C. Mice were then transcardially perfused with ice cold PBS with heparin (10 U/mL). Deep cervical lymph nodes were dissected and drop fixed in 4% paraformaldehyde (PFA) for 12 hours at 4° C. After stripping the skin and muscle from the bone the head was collected and drop fixed in 4% PFA. After removal of the mandibles and the skull rostral to maxillae, the top of the skull (skullcap) was removed with surgical curved scissors by cutting clockwise, beginning and ending inferior to the right post-tympanic hook and kept in PBS 0.02% azide at 4° C. until further use. The brains were kept in 4% PFA for additional 24 hours (48 hours in total). Fixed brain and dCLNs were then washed with PBS, cryoprotected with 30% sucrose and frozen in Tissue-Plus® O.C.T. compound (Thermo Fisher Scientific). Fixed and frozen brains were sliced (100 μm thick sections) with a cryostat (Leica) and kept in PBS 0.02% azide at 4° C. Frozen lymph nodes were sliced (30 μm thick sections) in a cryostat, collected into gelatin-coated Superfrost™ Plus slides (Thermo Fisher Scientific) and stored at −20° C. In some embodiments, after euthanizing and perfusing the mouse, the skullcap was removed from the mouse's head and drop fixed in 4% PFA for 12 hours, and the brains were immediately collected into O.C.T. compound, snap frozen in dry ice and stored at −80° C. Fresh frozen brains were then sliced (30 μm thick sections) in the cryostat and sections were directly collected into Superfrost™ Plus slides and kept at −20° C. until further use. Fixed meninges (dura mater and arachnoid) were carefully dissected from the skullcaps with Dumont #5 forceps (Fine Science Tools) and kept in PBS 0.02% azide at 4° C. until further use.

Aβ Measurement in CSF

To measure the concentration of Aβ$_{1-37/42}$ peptides in the CSF of J20 mice an in-house direct ELISA assay was used. Briefly, Nunc MaxiSorp® flat-bottom 96-well plates (ThermoFisher Scientific) were coated with 2 μL of CSF diluted in 98 μL of a $KH_2PO_4/K_2HPO_4$ buffer (pH 8.0) solution (1:50 dilution factor), for 2 h at 37° C. After washing with PBS 0.05% Tween® 20 (Sigma-Aldrich), a blocking step with PBS 1% skim milk was performed for 1 h at room temperature (RT). Then, consecutive incubations for 1 h at RT were performed: first with rabbit anti-$A\beta_{1-37/42}$ (Cell Signaling, clone D54D2, 1:500), second with biotinylated goat anti-rabbit (Vector Laboratories, BA-1000, 1:500) and third with streptavidin-horseradish peroxidase (1:2500, Sigma-Aldrich). Each incubation step was separated by thorough washes with PBS 0.05% Tween® 20 and PBS. Finally, a citrate-phosphate buffer (pH 4.3) solution containing 0.1% of 2,2'-azino-bis(3-ethylbenzothiazoline-6-sulfonic acid) diammonium salt (ABTS, Sigma-Aldrich) was added to each well and absorbance was read at 405 nm. The standard curve used to extrapolate the concentration of $A\beta_{1-37/42}$ in the CSF was obtained using known concentrations of human $A\beta_{42}$ (AnaSpec, Inc.) that ranged from 0.1 to 100 ng/mL (considering the linearity of the assay). Data processing was done with Excel and statistical analysis performed using Prism 7.0a (GraphPad Software, Inc.).

Human Samples

Autopsy specimens of human brain and dura from non-AD (n=8) or AD (n=9) patients were obtained from the Department of Pathology at the University of Virginia. All samples were from consenting patients that gave no restriction to the use of their body for research and teaching (through an UVA's Institutional Review Board for Health Sciences Research). Diagnosis criteria and pathological score were performed following the National Institute on Aging/Alzheimer's Association guidelines[56], based on the ABC (Amyloid, Braak, CERAD) score, for seven of the AD cases; old guidelines were used to diagnose and score two of the AD cases (Table 1). All obtained samples were fixed in a 20% formalin solution and kept in paraffin blocks until further sectioning. Prior to immunohistochemical staining, slides containing 10 μm thick sections were heated to 70° C. for 30 min and de-paraffinized by washing sections with xylene, xylene 1:1 100% ethanol (v/v), and 100, 95, 70 and 50% ethanol in water. Finally tissue sections were rehydrated by rinsing with cold tap water.

Immunohistochemistry, Imaging and Quantifications

Mouse fresh frozen brain sections were fixed with 4% PFA for 30 min, rinsed in $dH_2O$ and submitted to a heat-induced antigen retrieval step with 10 mM citrate buffer for 20 min. After de-paraffinization, sections of human brain or dura were submitted to the same antigen retrieval step for 20 min. The steps described next were generally applied for mouse fresh frozen or fixed free-floating brain sections, lymph node sections on slide, meningeal whole-mounts and human fixed tissue. For immunofluorescence staining, tissue was rinsed in PBS and washed with PBS 0.5% Triton-X-100 for 10 min, followed by incubation in PBS 0.5% Triton-X-100 containing 0.5% of normal serum (either goat or chicken) and 0.5% bovine serum albumin (BSA) for 1 hour at RT. This blocking step was followed by incubation with appropriate dilutions of primary antibodies: anti-LYVE-1 eFluor 660 or anti-LYVE-1 Alexa Fluor® 488 (eBioscience, clone ALY7, 1:200), anti-CD31 (Millipore Sigma, MAB1398Z, clone 2H8, 1:200), anti-IBA1 (Abcam, ab5076, 1:300), anti-GFAP (Millipore Sigma, ab5541, 1:300), anti-AQP4 (Millipore Sigma, A5971, 1:200), anti-Ki67 (Abcam, ab15580, 1:100), anti-$hA\beta_{1-16}$ (BioLegend, clone 6E10, 1:200), anti-$A\beta_{1-37/42}$ (Cell Signaling, clone D54D2, 1:300) and anti-GFP (Abcam, ab6556, 1:300) in PBS 0.5% Triton-X-100 containing 0.5% of normal serum and 0.5% BSA overnight at 4° C. Meningeal whole-mounts or tissue sections were then washed 3 times for 5 min at RT in PBS 0.5% Triton-X-100 followed by incubation with the appropriate chicken, goat or donkey Alexa Fluor® 488, 546, 594, or 647 anti-rat, -goat, -rabbit, -mouse or -Armenian hamster IgG antibodies (Thermo Fisher Scientific, 1:500) for 1 or 2 hours at RT in PBS 0.5% Triton-X-100. After an incubation for 10 min with 1:2000 DAPI in PBS, the tissue was washed 3 times for 5 min with PBS at RT and mounted with Aqua-Mount (Lerner) and glass coverslips. Preparations were stored at 4° C. for no more than 1 week until images were acquired either using a widefield microscope (Leica) or a confocal microscope (FV1200 Laser Scanning Confocal Microscope, Olympus). Quantitative analysis using the acquired images was performed on FIJI software. For the assessment of brain fluorescent tracer influx or efflux or AQP4 coverage, 10 representative brain sections were imaged using the widefield microscope and the mean area fraction was calculated using Microsoft Excel. For lymph nodes, the area fraction of drained fluorescent tracer or lymphatic vessels was assessed in alternate sections (representing a total of 10-15 sections per sample) using the confocal microscope and the mean was calculated for each sample. Area of coverage by $CD31^+$ blood vessels and $AQP4^+$ astrocyte endfeet in the brain cortex was achieved by calculating the mean value of 10 representative fields (5 images in each cerebral hemisphere) per sample acquired using the confocal microscope. For lymphatic vessel diameter, images of the same region of the superior sagittal sinus or of the transverse sinus were acquired in the confocal microscope and the mean of 100 individual lymphatic vessel diameter measurements (50 measurements in each lymphatic vessel lining the sinus using FIJI) was calculated for each sample by a blinded experimenter (due to different criteria used by distinct experimenters, this quantification method is often associated with a variability of ±15% in absolute diameter values). For assessment of meningeal lymphatic vessel coverage and complexity, images of meningeal whole-mounts were acquired in the confocal microscope and FIJI was used for quantifications. When applicable, the same images were used to assess the % of field coverage by $LYVE-1^-CD31^+$ vessels. To quantify the number of proliferating $Ki67^+$ cells in the hippocampal dentate gyrus, images of the entire dentate gyrus of 3 representative brain sections per sample were obtained using the confocal microscope. Fiji was used to assess the number of $Ki67^+$ per $mm^2$ of DAPI cells that composed the granular zone, which were then used to calculate the average density of cells per sample. For assessment of amyloid burden in the dorsal hippocampus, tile scans of the entire dorsal hippocampus from 10 coronal brain sections (~180 μm apart from each other) were obtained using the confocal microscope. FIJI was used to quantify amyloid plaque size, number and total coverage.

Flow Cytometry

Mice were injected i.p. with Euthasol solution and were then transcardially perfused with ice cold PBS with heparin. Individual meninges were immediately dissected from the mouse's skull cap and digested 15 min at 37° C. with 1.4 U/ml of Collagenase VIII (Sigma Aldrich) and 35 U/ml of DNAse I (Sigma Aldrich) in complete media consisting of DMEM (Gibco) with 2% FBS (Atlas Biologicals), 1% L-Glutamine (Gibco), 1% penicillin/streptomycin (Gibco), 1% Sodium pyruvate (Gibco), 1% non-essential amino-acid (Gibco) and 1.5% Hepes (Gibco). The cell pellets were washed, resuspended in ice-cold fluorescence-activated cell sorting (FACS) buffer (pH 7.4; 0.1 M PBS; 1 mM EDTA and 1% BSA) and stained for extracellular markers with the following antibodies: rat anti-CD90.2 FITC (553013; BD Bioscience), rat anti-CD11b FITC (557396; BD Bioscience), rat monoclonal anti-CD19 PE (12-0193-82; eBioscience), rat anti-CD45 PerCP-Cy5.5 (550994; BD Bioscience), rat anti-Ly6C PerCP-Cy5.5 (560525; BD Bioscience), mouse anti-NK1.1 PE-Cy7 (552878; BD Bioscience), rat anti-Ly6G PE-Cy7 (560601; BD Bioscience), rat anti-CD4 APC (553051; BD Bioscience), rat anti-CD45 AF700 (560510; BD Bioscience), hamster anti-TCRb BV711 (563135; BD Bioscience), rat anti-CD8 Pacific blue (558106; BD Bioscience) and rat anti-Siglec-F BV421 (562681; BD Bioscience). Cell viability was determined by using the Zombie Aqua™ Fixable Viability Kit following the manufacturer's instructions (BioLegend). After an incubation period of 30 min at 4° C., cells were washed and fixed in 1% PFA in PBS. Fluorescence data was collected with a Gallios™ Flow Cytometer (Beckman Coulter, Inc.) then analyzed using FlowJo software (Tree Star, Inc.). Briefly, singlets were gated using the height, area and the pulse width of the forward and side scatter and then viable cells were selected as AQUA⁻. Cells were then gated for the appropriate cell type markers. An aliquot of unstained cells of each sample was counted using Cellometer Auto2000 (Nexcelor) to provide accurate counts for each population. Data processing was done with Excel and statistical analysis performed using Prism 7.0a (GraphPad Software, Inc.).

Sorting of meningeal LECs

To obtain a suspension of meningeal lymphatic endothelial cells (LECs) from the meninges of young-adult (2-3 months) and old (20-24 months) mice by FACS, mice were euthanized by i.p. injection of Euthasol and transcardially perfused with ice cold PBS with heparin. Skullcaps were quickly collected and meninges (dura mater and arachnoid) were dissected using Dumont #5 forceps in complete media composed of DMEM (Gibco) with 2% FBS (Atlas Biologicals), 1% L-glutamine (Gibco), 1% penicillin/streptomycin (Gibco), 1% sodium pyruvate (Gibco), 1% non-essential amino-acids (Gibco) and 1.5% Hepes buffer (Gibco). Individual meninges were then incubated with 1 mL of complete media with 1.4 U/mL of Collagenase VIII (Sigma-Aldrich) and 35 U/mL of DNAse I (Sigma-Aldrich) for 15 min at 37° C. Individual samples consisted of cell suspensions pooled from 10 meninges that were obtained after filtration through a 70 μm nylon mesh cell strainer. Cell suspensions were then pelleted, resuspended in ice-cold FACS buffer containing DAPI (1:1000, Thermo Fisher Scientific), anti-CD45-BB515 (1:200, clone 30-F11, BD Biosciences), anti-CD31-Alexa Fluor® 647 (1:200, clone 390, BD Biosciences) and anti-Podoplanin-PE (1:200, clone 8.1.1, eBioscience) and incubated for 15 min at 4° C. Cells were then washed and resuspended in ice-cold FACS buffer. Briefly, singlets were gated using the pulse width of the side scatter and forward scatter. Cells negative for DAPI were selected for being viable cells. The LECs were then gated as CD45⁻CD31⁺ Podoplanin⁺ (see FIGS. 10A-R for representative dot plots) and sorted into a 96-well plate containing 100 μL of lysis buffer (Arcturus PicoPure RNA Isolation Kit, Thermo Fisher Scientific) using the Influx™ Cell Sorter (BD Biosciences) that is available at the University of Virginia Flow Cytometry Core Facility.

RNA Extraction and Sequencing

For total RNA extraction from whole hippocampus, the tissue was macrodissected from the brain in ice-cold PBS, immersed in the appropriate volume of extraction buffer from the RNA isolation kit, immediately snap frozen in dry ice and stored at −80° C. until further use. After defrosting in ice, samples were mechanically dissociated in extraction buffer and RNA was isolated using the kit components according to the manufacturer's instructions (RNeasy mini kit, cat. no. 74106, Qiagen). The Illumina TruSeq Stranded Total RNA Library Prep Kit was used for cDNA library preparation from total RNA samples. Sample quality control was performed on an Agilent 4200 TapeStation Instrument, using the Agilent D1000 kit, and on the Qubit Fluorometer (Thermo Fisher Scientific). For RNA sequencing (RNA-seq), libraries were loaded on to a NextSeq 500 (Illumina) using an Illumina NextSeq High Output (150 cycle) cartridge (#FC-404-2002).

Total RNA was extracted from LECs (previously sorted by FACS) using the Arcturus PicoPure RNA Isolation Kit (Thermo Fisher Scientific), following the manufacturer's instructions. All RNA sample processing (including linear RNA amplification and cDNA library generation) and RNA-seq was performed by HudsonAlpha Genomic Services Laboratory (Huntsville, AL).

The raw sequencing reads (FASTQ files) were first chastity filtered, which removes any clusters that have a higher than expected intensity of the called base compared to other bases. The quality of the reads was then evaluated using FastQC[57], and after passing quality control (QC), the expression of the transcripts was quantified against the UCSC mm10 genome[58] using Salmon[59]. These transcript abundances were then imported into R and summarized with tximport[60], and then DESeq2[61] was used to normalize the raw counts, perform exploratory analysis (e.g., principal component analysis), and to perform differential expression (DE) analysis. Before DE analysis of the meningeal LECs from adult vs old mice dataset, surrogate variable analysis[62] (SVA) was used to identify and adjust for latent sources of unwanted variation as implemented in the SVA package[63]. The P-values from the DE analysis were corrected for multiple hypothesis testing with the Benjamini-Hochberg false discovery rate procedure (adj. P-value). Functional enrichment of DE genes, using gene sets from Gene Ontology (GO) and Kyoto Encyclopedia of Genes and Genomes (KEGG), was determined with Fisher's exact test as implemented in the clusterProfiler[64] Bioconductor package. Heatmaps of the DE genes and enriched gene sets were generated with the R package pheatmap[65]. Normalized counts of selected transcripts were used to calculate the fold change relative to respective controls.

Statistical Analysis and Reproducibility

Sample sizes were chosen on the basis of standard power calculations (with $\alpha=0.05$ and power of 0.8) performed for similar experiments that were previously published. In general, statistical methods were not used to re-calculate or predetermine sample sizes. The Kolmogorov-Smirnov test was used to assess normal distribution of the data. Variance was similar within comparable experimental groups. Animals from different cages, but within the same experimental group, were selected to assure randomization. Experimenters were blinded to the identity of experimental groups from the time of euthanasia until the end of data collection and analysis for at least one of the independent experiments. Statistical tests for each figure were justified to be appropriate. One-way ANOVA, with Bonferroni's post-hoc test or Holm-Sidak's post-hoc test, was used to compare 3 independent groups. Two-group comparisons were made using two-tailed unpaired Mann-Whitney test. For comparisons of multiple factors (for example, age vs treatment), two-way ANOVA with Bonferroni's post-hoc test was used. Repeated measures two-way ANOVA with Bonferroni's post-hoc test was used for day vs treatment comparisons with repeated observations. Statistical analysis (data was always presented as mean±s.e.m.) was performed using Prism 7.0a (GraphPad Software, Inc.).

Summary of Examples

Aging is a major risk factor for many neurological pathologies and the mechanisms underlying brain aging remain elusive. Unlike other tissues, the central nervous system (CNS) parenchyma is devoid of lymphatic vasculature and removal of waste products is performed mainly through a paravascular route. (Re)discovery and characterization of meningeal lymphatic vessels prompted for an assessment of their role in CNS waste clearance. Here we show that meningeal lymphatics are draining macromolecules from the CNS (CSF and ISF) into the cervical lymph nodes. Impairment of meningeal lymphatic function slows paravascular influx of CSF macromolecules and efflux of ISF macromolecules, and induces cognitive impairment. Treatment of aged mice with vascular endothelial growth factor C enhances meningeal lymphatic drainage of CSF macromolecules, improving brain perfusion and learning and memory performance. Disruption of meningeal lymphatic vessels in transgenic mouse models of Alzheimer's disease (AD) promotes amyloid deposition in the meninges, which closely resembles human meningeal pathology, and aggravates parenchymal amyloid accumulation. Our findings show that meningeal lymphatic dysfunction is an aggravating factor in AD pathology and in age-associated cognitive decline. Thus, augmentation of meningeal lymphatic function is (such as, for example, by modulating one or more of the targets identified in the RNA-seq studies disclosed herein) a promising therapeutic target for preventing or delaying age-associated neurological diseases.

Figure 5A:
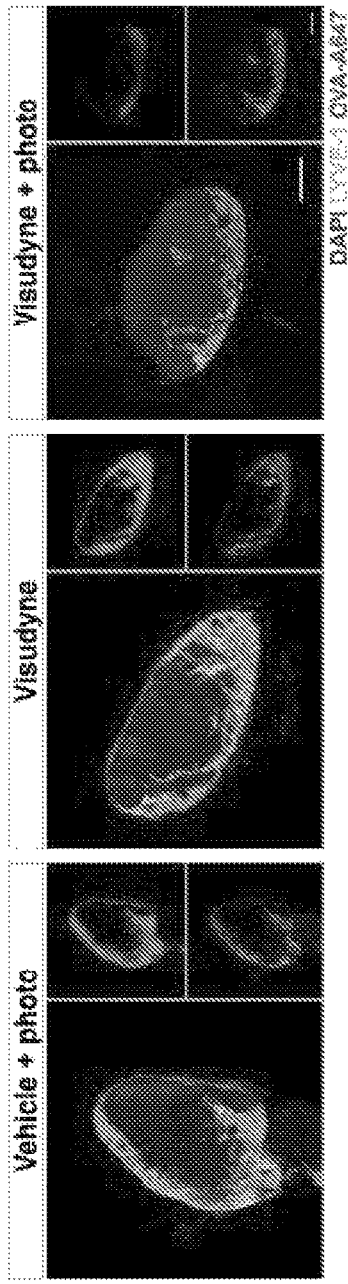
Figure 5B:
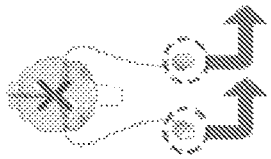
Figure 5B:
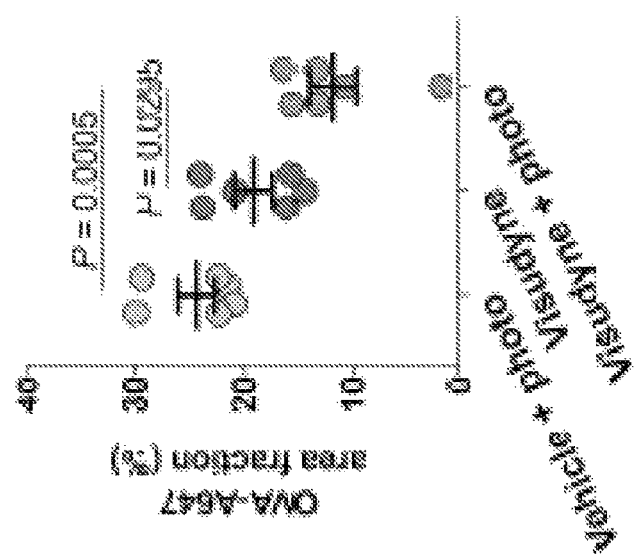
Figure 5C:
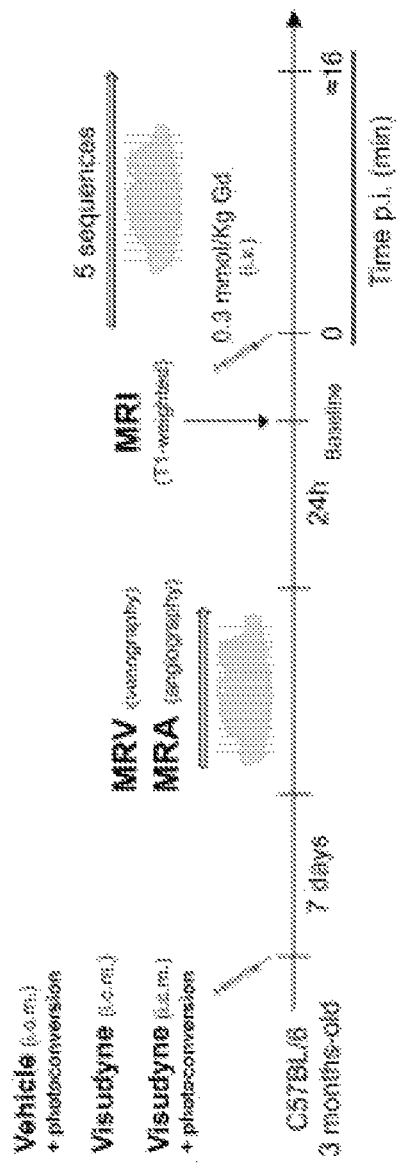
Figure 5D:
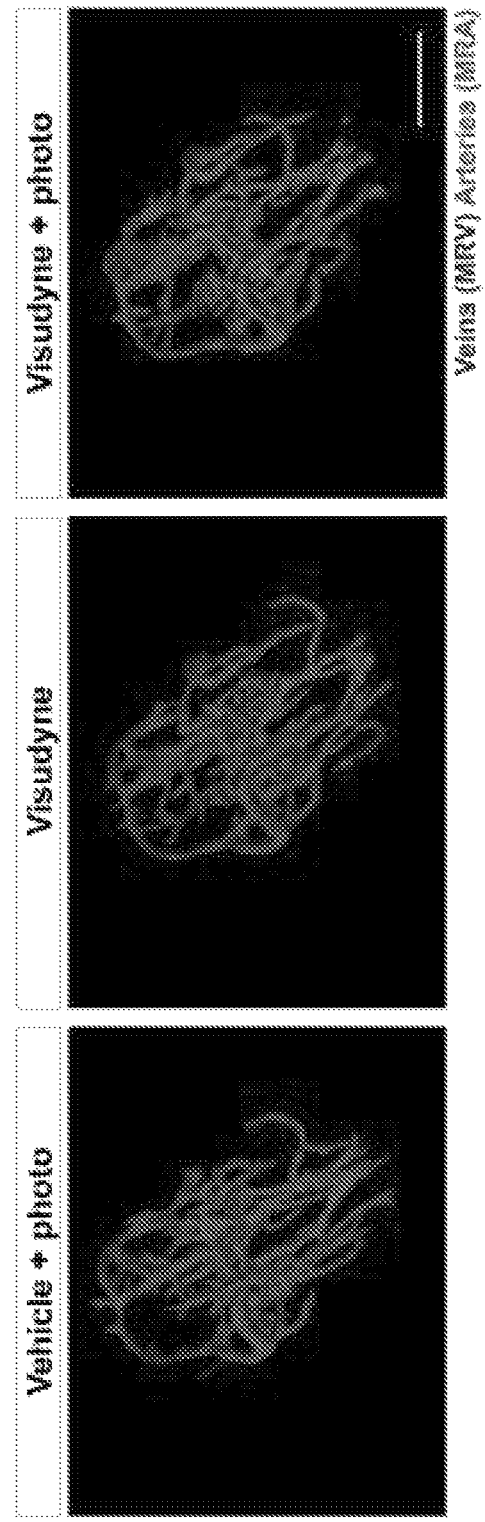
Figures 5E, 5F, 5G, 5H:
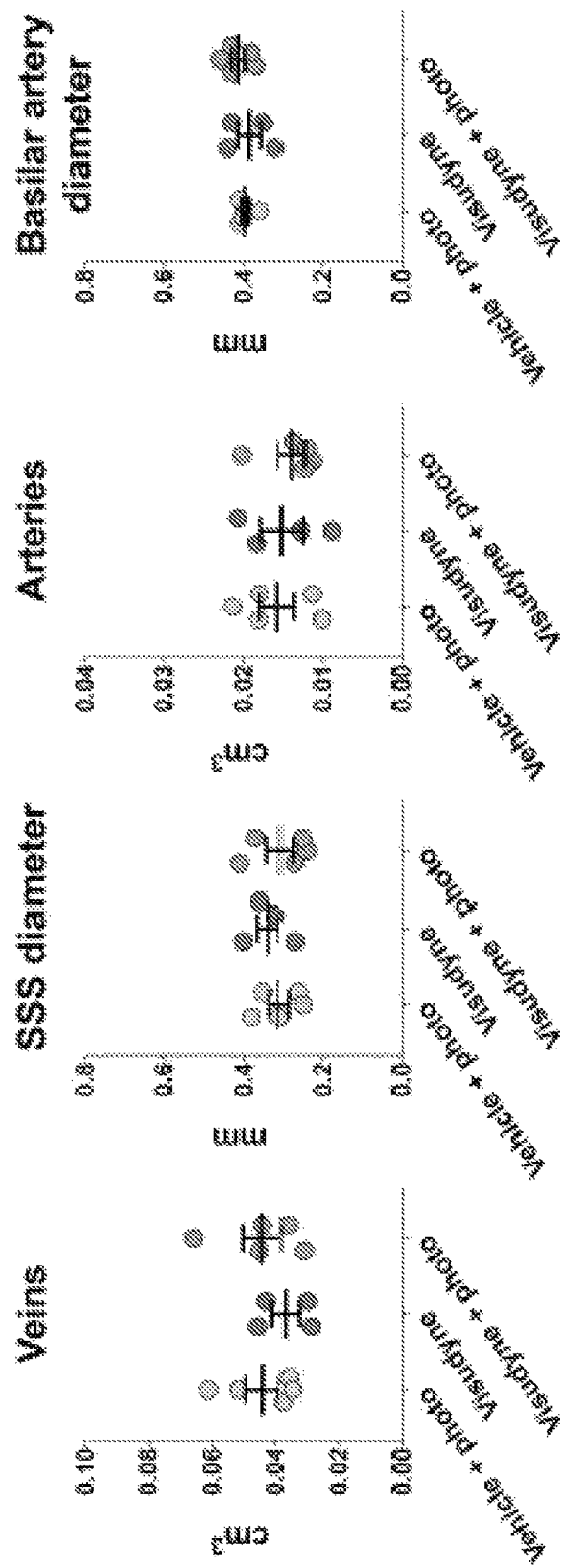
Figure 5M:
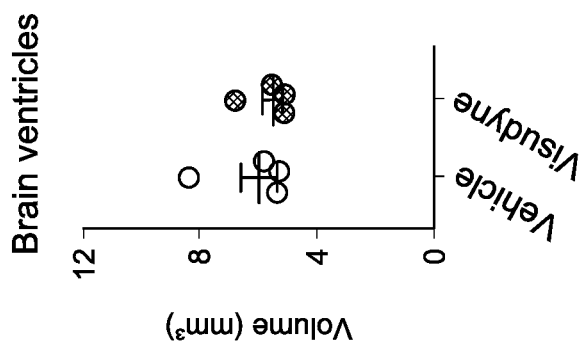
Figure 5K:
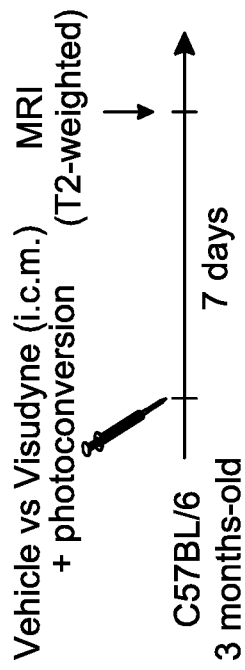
Figure 5L:
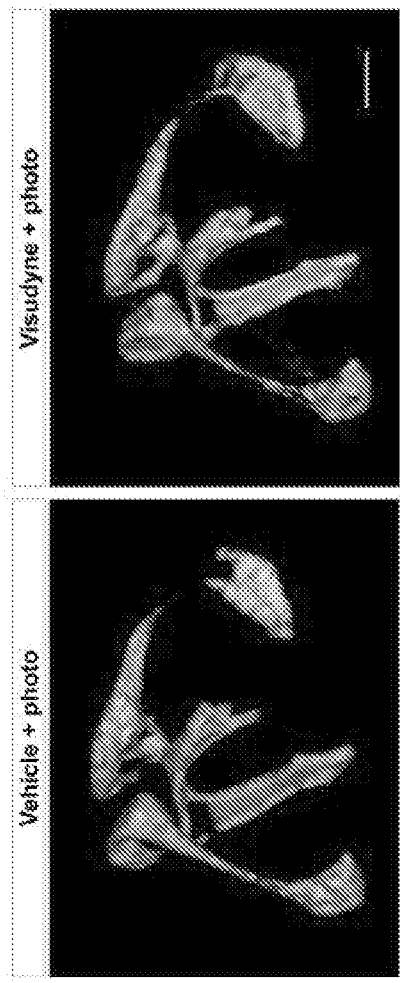

Example 1—Impairment of Meningeal Lymphatic Vessels Causes Impaired Brain Perfusion by CSF Macromolecules Given the close communication and ongoing exchange of molecular contents between the CSF and ISF[5,12], we postulated that brain influx of CSF macromolecules through the paravascular pathway is impacted by the meningeal lymphatics. To test this hypothesis, we ablated meningeal lymphatic vessels by injecting a photodynamic drug, Visudyne (verteporfin for injection), into the CSF, which upon photoconversion has been shown to preferentially damage the lymphatic endothelial cells (LECs)[23,24]. Injection of vehicle followed by photoconversion and of Visudyne without the photoconversion step were used as two controls (FIG. 1A). The use of this method resulted in effective ablation of meningeal lymphatics lasting for at least 7 days (FIGS. 1B, 1C), without any detectable off-target effect in meningeal blood vasculature coverage (FIG. 1D). To confirm functional impairment upon meningeal lymphatic ablation, we injected 5 μL of fluorescent ovalbumin-Alexa 647 (OVA-A647; ~45 kDa) into the cisterna magna (i.c.m.) and measured the drainage of this tracer from the CSF into the deep cervical lymph nodes (dCLNs) (FIG. 5A). A significant reduction in OVA-A647 drainage was observed in the Visudyne/photoconversion group compared to controls (FIG. 5B). Importantly, the structure of major intracranial veins and arteries was not altered (FIGS. 5C-H). Likewise, the integrity of the blood-brain barrier, assessed by T1-weighted magnetic resonance imaging (MRI) after intravenous injection of gadolinium (Gd) as contrast agent (FIGS. 5I and 5J), or the ventricular volume measured by T2-weighted SPACE MRI (FIGS. 5K-M) also remained unaltered after ablation of meningeal lymphatics.

Brain perfusion by the CSF tracer was found to be significantly lower in the Visudyne/photoconversion group than in their control counterparts (FIGS. 1E-F and FIGS. 6A and 6B). Similar findings on brain perfusion by CSF were observed when meningeal lymphatic drainage was disrupted by surgical ligation of the vessels afferent to the dCLNs (FIGS. 7A-D). Prospero homeobox protein 1 (Prox1) heterozygous mice, a genetic model of lymphatic vessel malfunction[25], also presented impaired perfusion through the brain parenchyma and impaired CSF drainage (FIGS. 7E-I). Altogether, three different models of impaired meningeal lymphatic function (pharmacological, surgical, and genetic) showed a significant impact on brain perfusion by CSF macromolecules.

Figure 1E:
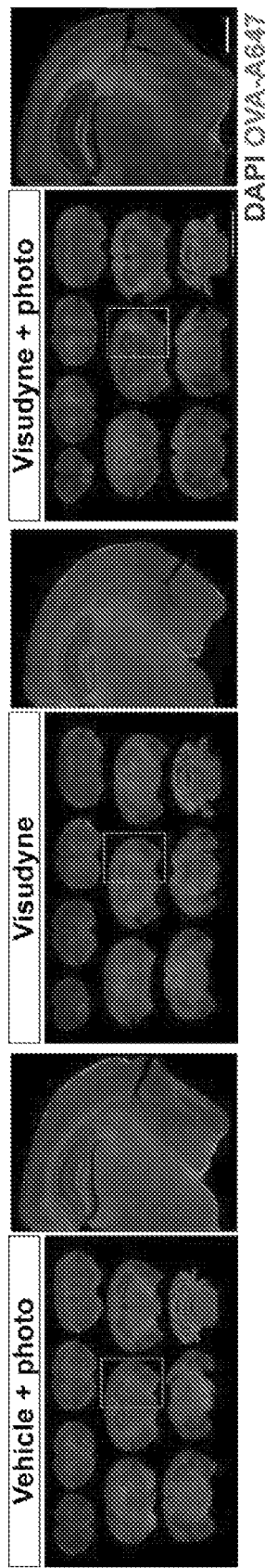
Figure 1G:
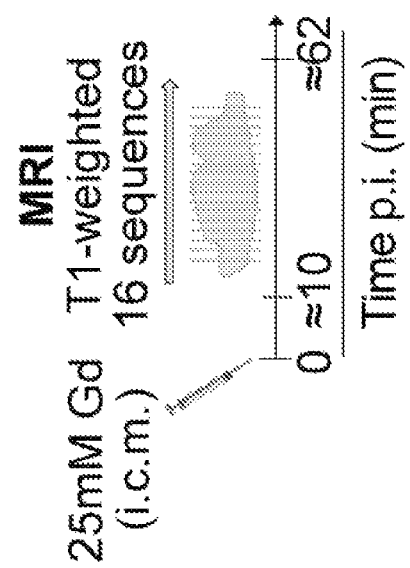
Figure 1F:
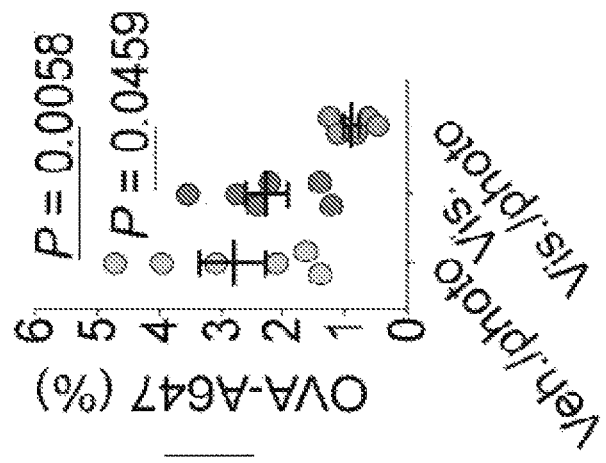
Figure 1H:
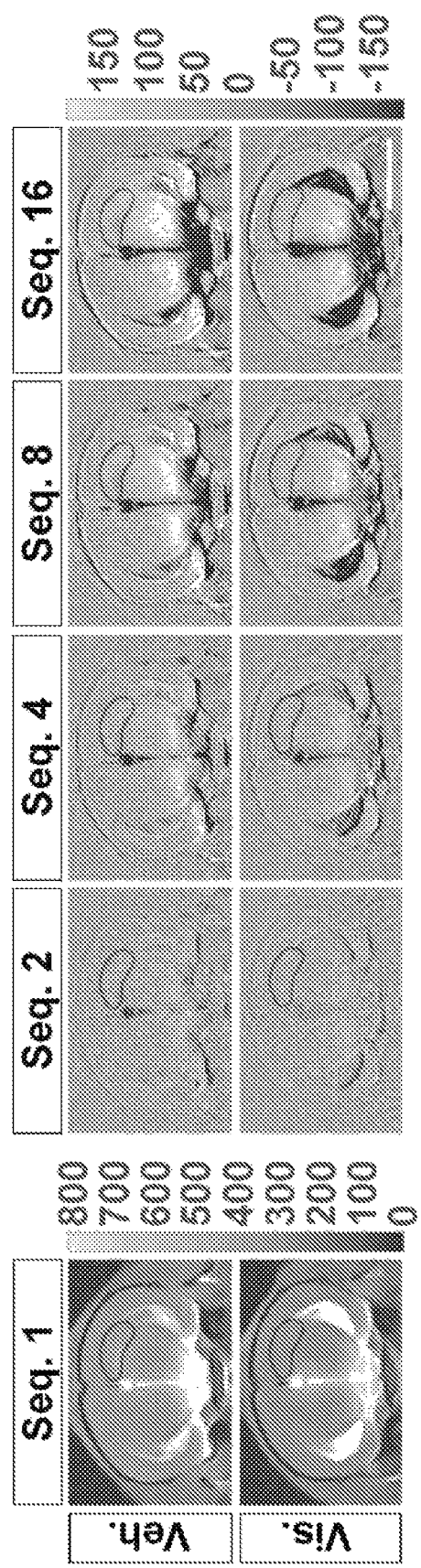
Figure 1I:
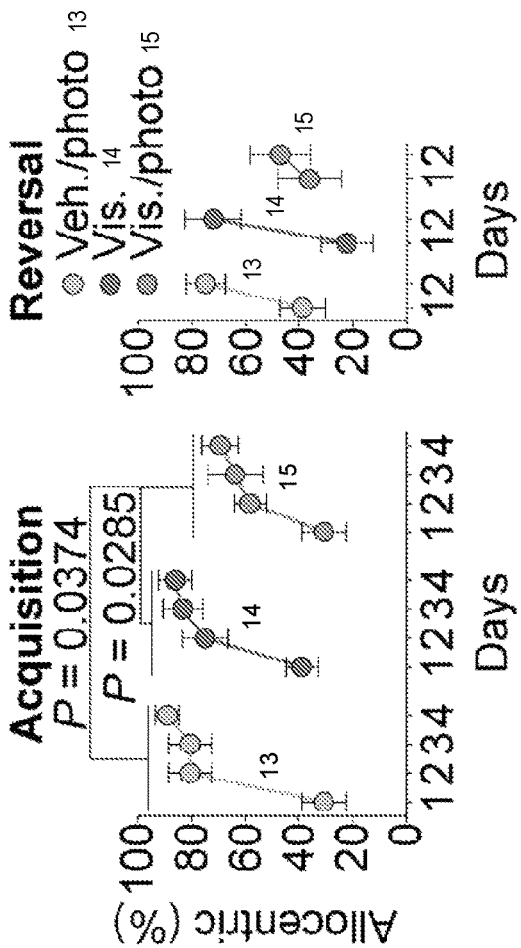
Figure 7J:
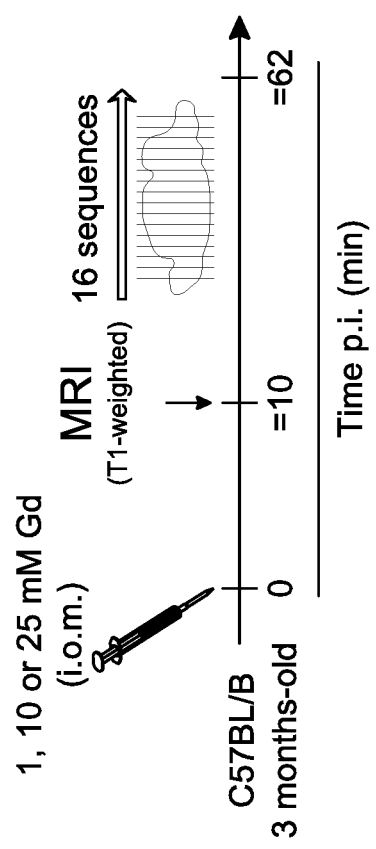
FIGS. 7A-V show impaired brain perfusion by CSF macromolecules is observed in lymphatic ligated and in Prox1$^{+/-}$ mice and does not correlate with AQP4 levels. Adult mice were submitted to surgical ligation of the lymphatic vessels afferent to the dCLNs. One week after the procedure, 5 μL of OVA-A647 was injected into the CSF (i.c.m.) and mice were transcardially perfused 2 h later. Representative brain sections stained with DAPI (blue) showing OVA-A647 (red) influx into the brain parenchyma of ligated and sham-operated mice (scale bar, 5 mm; inset scale bar, 2 mm) (FIG. 7A). Quantification of OVA-A647 area fraction (%) in brain sections showed a significant decrease in the ligation group (FIG. 7B). Representative sections of dCLNs stained with DAPI (blue) and for LYVE-1 (green), showing OVA-A647 (red) coverage in the ligation and sham-operated groups (scale bar, 200 μm) (FIG. 7C). Quantification of OVA-A647 area fraction (%) in the dCLNs showed a significant decrease in the ligation group (FIG. 7D). Data in FIGS. 7B and 7D are presented as mean s.e.m., n=8 per group; two-tailed Mann-Whitney test was used in FIGS. 7B and 7D; data in FIGS. 7A-D was pooled from 2 independent experiments and is representative of 3 independent experiments. Wild-type (WT) and Prox1$^{+/-}$ mice (2-3 months-old) were injected with 5 μL of OVA-A647 into the CSF (i.c.m.) and transcardially perfused 2 h later (FIG. 7E). Representative brain sections stained with DAPI (blue) showing OVA-A647 (red) influx into the brain parenchyma of Prox1$^{+/-}$ and WT mice (scale bar, 5 mm) (FIG. 7F). Quantification of OVA-A647 area fraction (%) in brain sections showed a significant decrease in Prox1$^{+/-}$ mice (FIG. 7G). Representative sections of dCLNs stained with DAPI (blue) and for LYVE-1 (green), showing OVA-A647 (red) coverage in the dCLNs of Prox1$^{+/-}$ and WT mice (scale bar, 500 μm) (FIG. 7H). Quantification of OVA-A647 area fraction (%) in the dCLNs showed a significant decrease in Prox1$^{+/-}$ mice (FIG. 7I). Data in FIGS. 7G and 7I are presented as mean s.e.m., n=15 in WT, n=12 in Prox1$^{+/-}$; two-tailed Mann-Whitney test was used in FIGS. 7G and 7I; data in FIGS. 7E-I were pooled from 2 independent experiments. Rate of brain paravascular influx of the contrast agent gadolinium (Gd), injected i.c.m. at 1, 10 or 25 mM (in saline), was assessed in adult mice (3 months-old) by T1-weighted magnetic resonance imaging (MRI) (FIG. 7J). Representative MRI images obtained using Lymph4D software showing brain signal intensity for different concentrations of injected Gd (scale bar, 3 mm) (FIG. 7K). Experiments in FIGS. 7J-K were performed once. Adult mice were subjected to meningeal lymphatic ablation by Visudyne photoconversion. One week later, T1-weighted MRI acquisition was performed after i.c.m. injection of 5 μL of Gd (25 mM in saline) (FIG. 7L). Using the Lymph4D software, it was possible to measure the rate of contrast agent influx into the delineated brain cortical region of mice from both groups (scale bar, 3 mm). Images in sequence 2 and subsequent were obtained by subtraction of sequence 1. Quantification of the signal intensity gain (relative to sequence 1) in the brain cortex revealed a significant decrease in the Visudyne/photoconversion group, when compared to vehicle/photoconversion (FIG. 7M). Coronal sections of the brain of vehicle- or Visudyne-treated mice (n=4 per group) were aligned and stacked into 2D colormaps (concatenated from 16 MRI sequences) showing (FIG. 7N) contrast of Gd signal intensity and (FIG. 7O) isotropic diffusion coefficient (scale bars, 3 mm). Area fraction quantification of high, medium and low values of isotropic diffusion coefficient in the four 2D stacks, in Visudyne relative to vehicle (FIG. 7P). Data in FIGS. 7M and 7P are presented as mean±s.e.m., n=4 per group; repeated measures two-way ANOVA with Bonferroni's post-hoc test was used in FIG. 7M and one-way ANOVA with Bonferroni's post-hoc test was used in FIG. 7P.
FIGS. 7L-P are representative of 2 independent experiments.
FIG. 7Q shows representative confocal images of DAPI (blue) and aquaporin 4 (AQP4, green) staining and OVA-A647 (red) levels in brain sections from vehicle- and Visudyne-treated mice (scale bar, 500 μm).
FIG. 7R shows quantification of area fraction (%) of AQP4 in the brains of mice treated with vehicle or Visudyne showing no differences between groups. Images showing representative staining for AQP4$^+$ astrocytic endfeet (red) and CD31$^+$ blood vessels (green) in the brain cortex of mice from vehicle and Visudyne groups (scale bar, 50 μm) (FIG. 7S). No changes were observed in the area of AQP4$^+$ astrocytic endfeet (FIG. 7T) and of CD31$^+$ blood vessels (FIG. 7U) or in the ratio between area of AQP4$^+$ and of CD31$^+$ (FIG. 7V). Data in FIG. 7R and FIGS. 7T-V are presented as mean±s.e.m., n=7 per group; two-tailed Mann-Whitney test was used in FIG. 7R and FIGS. 7T-V; data in FIGS. 7Q-V were pooled from 2 independent experiments and is representative of 3 independent experiments.
Figure 7K:
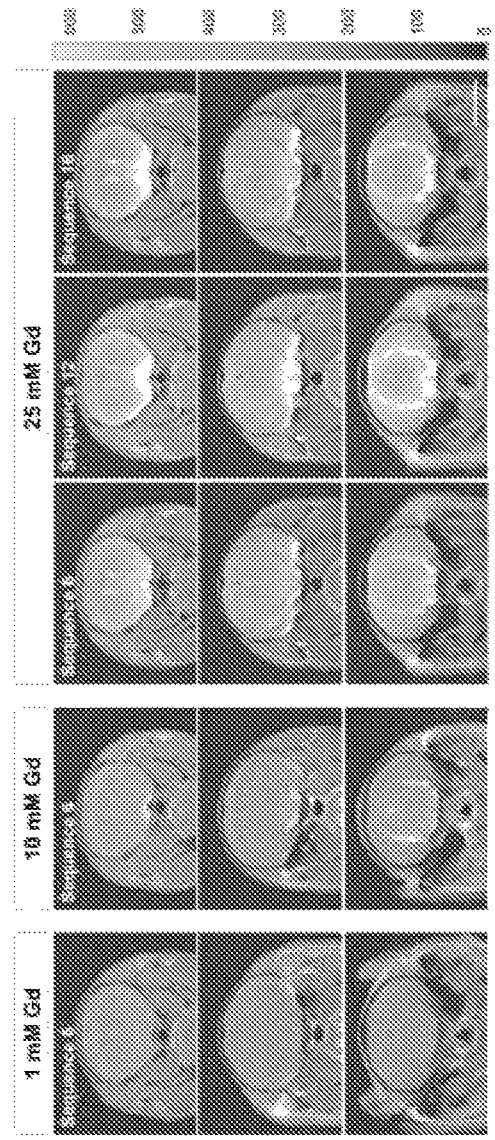
Figure 7L:
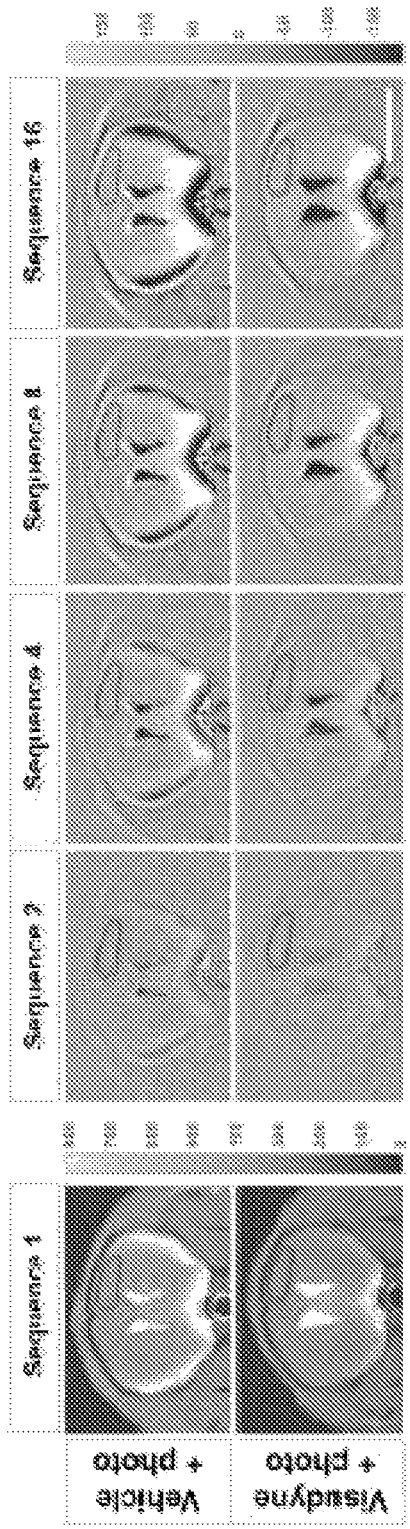
Figure 7M:
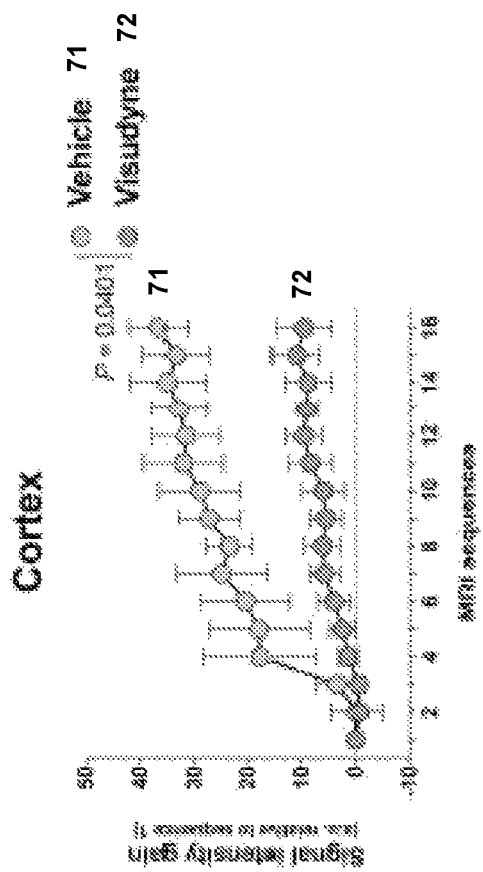

To evaluate the effect of meningeal lymphatic ablation on the rate of brain perfusion by CSF, we injected Gd (i.c.m.) and performed brain T1-weighted MRI. Three different concentrations of Gd-1, 10 and 25 mM-were tested (FIGS. 7J, 7K) and, due to better signal-to-noise ratio, the 25 mM concentration was used in subsequent experiments (FIG. 1G). A software developed in-house, Lymph4D (see Supplementary Methods section for more details), was used to process and analyze the images acquired by MRI. After 16 sequences of MRI acquisition (~52 min), the observed signal gain in two brain regions (hippocampus and cortex) was significantly lower in the Visudyne group when compared to vehicle-treated (FIGS. 1H-I and FIGS. 7L-M). Interestingly, along with the lower influx of Gd into the parenchyma, we observed higher contrast in signal intensity (over ~52 min) in the ventricles of Visudyne-treated mice, suggesting Gd accumulation in the CSF (FIG. 7N). Moreover, using the advection-diffusion model in Lymph4D, we found that mice presented lower coefficient values of isotropic diffusion of Gd in the brain after meningeal lymphatic ablation (FIGS. 7O-P), suggesting a lower rate of molecular diffusion in the brain parenchyma when meningeal lymphatic drainage is reduced.

Within the brain parenchyma, it was shown that astrocytes play an important role in the modulation of paravascular CSF macromolecule influx and efflux (glymphatic[12]) through aquaporin 4 (AQP4)[12,13]. Deletion of Aqp4 in AD transgenic mice also resulted in increased amyloid plaque burden and exacerbated cognitive impairment[19]. Moreover, decreased perivascular AQP4 localization was observed in brain tissue from AD patients[27]. We could not detect changes either in overall brain coverage by AQP4 (FIGS. 7Q-R) or in perivascular localization of AQP4+ astrocytic endfeet between vehicle-treated and Visudyne-treated mice (FIGS. 7S-V), suggesting that upon meningeal lymphatic dysfunction, impairment of brain perfusion by CSF is independent of AQP4.

Example 2: Study of Efflux of ISF Macromolecules

It was explored whether the efflux of ISF macromolecules from the brain parenchyma would also be affected by meningeal lymphatics. We used three different tracers, the smaller peptides $A\beta_{42}$-HyLite647 (~4 kDa) and OVA-A647, and the large protein complex, low density lipoprotein-BODIPY FL (LDL-BODIPY FL, ~500 kDa). One hour after stereotaxic injection, the levels of the remaining tracers were assessed in the parenchyma of mice from lymphatic ablated or control groups (FIGS. 8A-H). Independently of the nature of the fluorescent tracer, higher levels of remnants were detected in the brains of mice from the Visudyne/photoconversion groups when compared to both control groups (FIGS. 8A-H). These findings, demonstrate that efflux of parenchymal/ISF macromolecules and their drainage into dCLNs are impaired as a consequence of meningeal lymphatic dysfunction, therefore functionally connecting meningeal lymphatics with CSF influx/ISF efflux mechanisms.

Example 3: Investigation of Impaired Meningeal Lymphatics on Brain Function

Figure 1J:
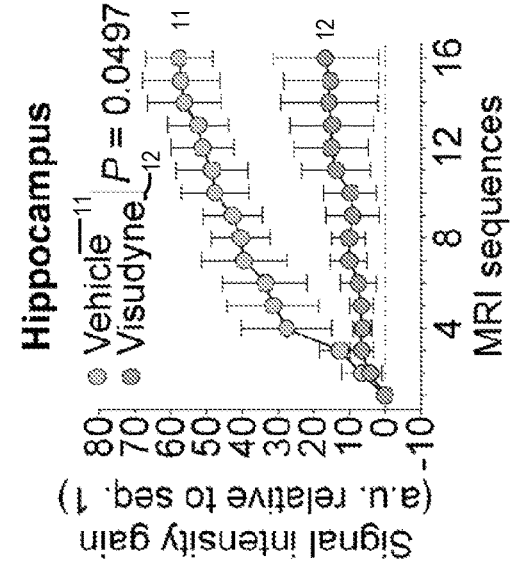
Figure 1N:
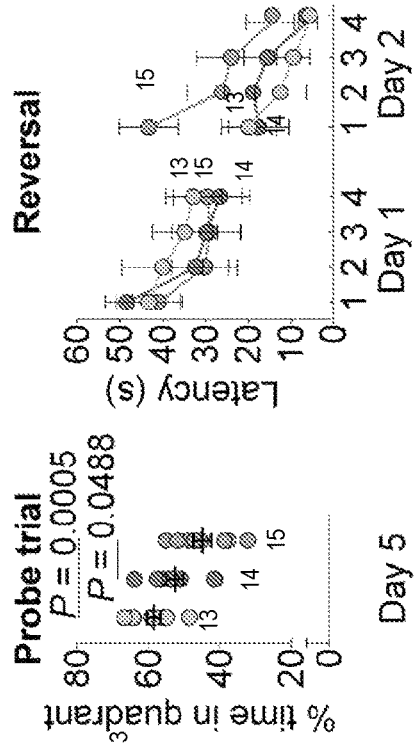
Figure 1O:
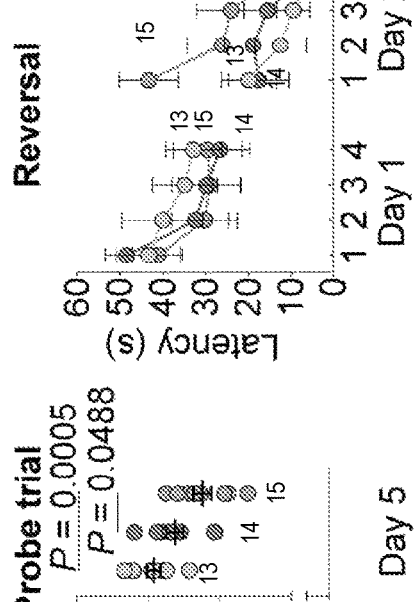
Figures 1K, 1L, 1M:
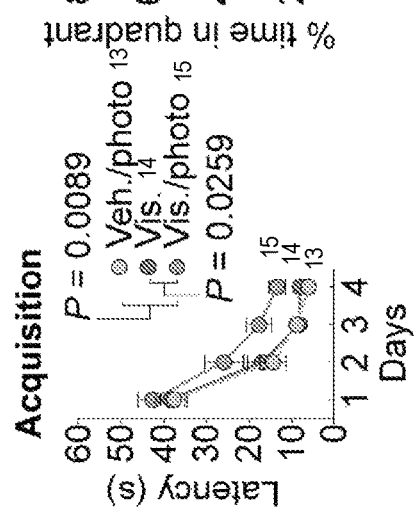

To understand the implications of impaired meningeal lymphatics for brain function, we performed meningeal lymphatic ablation twice, allowing a two-week interval between procedures to ensure prolonged lymphatic ablation, and then assessed mice behavior in the open field (OF), novel location recognition (NLR), contextual fear conditioning (CFC), and Morris water maze (MWM) tests (FIG. 1J). No differences between the groups were detected in total distance and time spent in the center of the arena in the open field test (FIGS. 9A-B) or in time spent with the object placed in a novel location in the NLR test (FIGS. 9C-D). A significant difference between control groups and Visudyne/photoconversion group was observed in the cued test of the CFC (FIGS. 9E-F), which points to an impairment in fear memory and in hippocampal-amygdala neuronal circuitry[28] in mice with impaired meningeal lymphatic function. Mice with ablated meningeal lymphatics also showed significant deficits in spatial learning in the MWM (FIG. 1K-O). Similar impairments in spatial learning and memory were observed in mice that had undergone lymphatic ligation (FIGS. 9G-J), further demonstrating that the observed effect is a result of dysfunctional meningeal lymphatic drainage and not an artifact of the ablation method using Visudyne.

Example 4: Investigation of Role of Meningeal Lymphatic Vessels in AD Pathology

Our findings above regarding the effects of meningeal lymphatic ablation on brain function prompted us to explore the impact of meningeal lymphatic function on the pathophysiology of AD, a neurodegenerative disease is characterized by the progressive accumulation of toxic amyloid deposits in the brain and marked cognitive decline with aging. Based on previous findings concerning the role of paravascular CSF/ISF recirculation in the context of AD[12,14,19,27] and our present results on the interdependence between meningeal lymphatic function and brain perfusion by CSF, we postulated that modulating meningeal lymphatic function would impact the behavior and brain pathology in AD transgenic mice. The potential effect of mVEGF-C treatment (through viral vector delivery) was first tested on J20 transgenic mice at 6-7 months of age (FIGS. 12A-N), when mice already present marked cognitive deficits and start to show amyloid deposition in the brain parenchyma[39,40]. We were not able to improve J20 mice hyperactive phenotype in the open field or cognitive performance in the MWM (FIGS. 12A-F). Moreover, viral expression of mVEGF-C did not significantly affect meningeal lymphatic vessel diameter, the level of Aβ in the CSF, or amyloid deposition in the hippocampus (FIGS. 12G-N). In order to explain the lack of effect of the mVEGF-C treatment in J20 mice, we measured meningeal lymphatic drainage in J20 mice and in wild-type (WT) littermate controls. The same measurement was performed in a more aggressive AD transgenic mouse model—the 5xFAD—that already presents amyloid plaques at 3 months of age[41] (FIG. 12O).

Independently of the model, the level of CSF tracer drained into the dCLNs was comparable between AD transgenic mice and age-matched WT littermates (FIGS. 12P-S). Similarly, meningeal lymphatic vessel morphology and coverage did not differ between WT and 5xFAD mice at 3-4 months of age (FIGS. 12T-U). Collectively, these data point to no apparent meningeal lymphatic dysfunction in AD transgenic mice at younger ages, which might explain the inefficacy of mVEGF-C treatment.

Figure 3B:
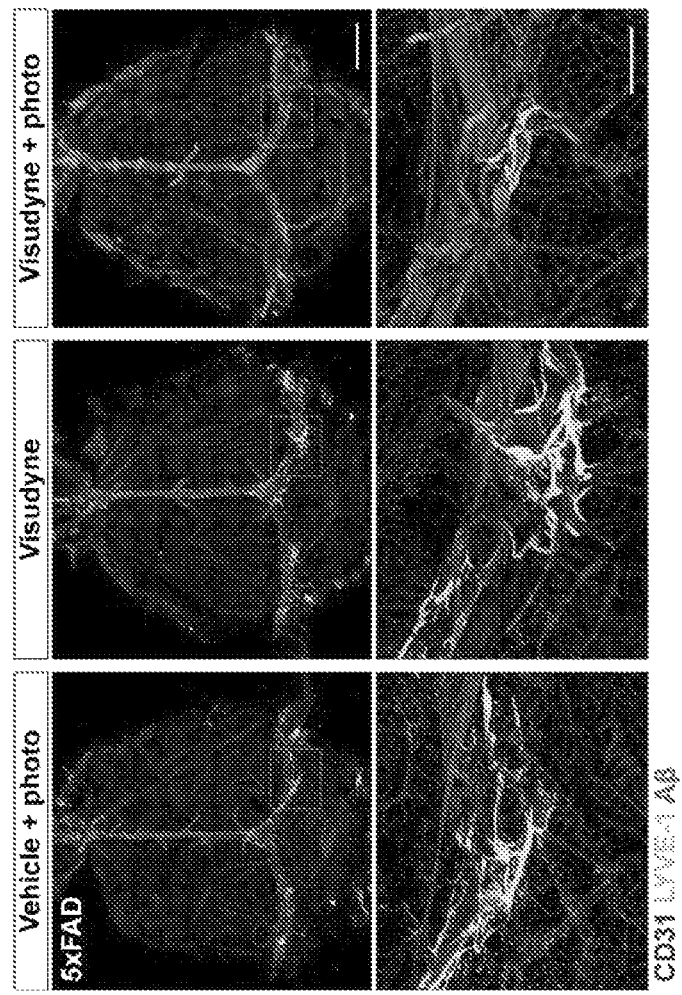
Figure 3A:
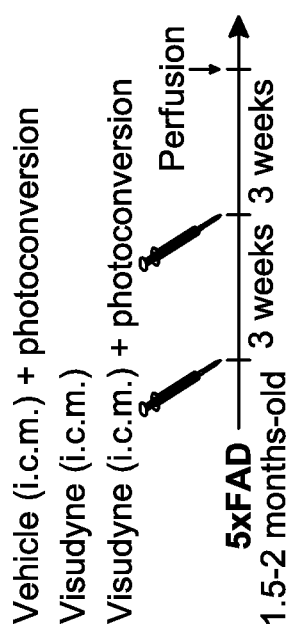
Figure 3C:
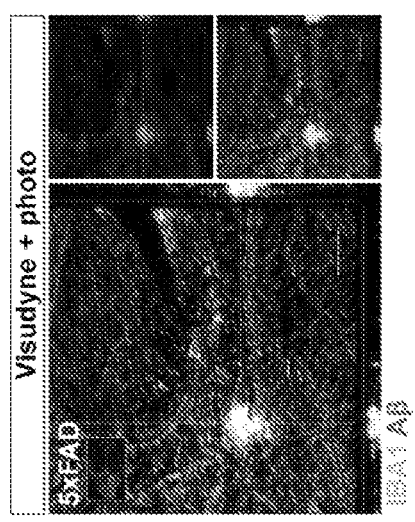

Although age is the major risk factor for late-onset AD[15,16], most transgenic mouse models that mimic early-onset AD develop amyloid pathology at young age and, therefore, may be lacking the aspect of age-related lymphatic dysfunction. To this end, we induced prolonged meningeal lymphatic ablation in 5xFAD mice by repeated (every 3 weeks) injection and photoconversion of Visudyne for a total of 1.5 months, starting at ~2 months of age (FIG. 3A). Taking into account the marked brain amyloid deposition presented by these mice at ~3 months of age, surprisingly, no obvious Aβ deposition was detected in the meninges of 5xFAD mice from the two control groups (FIG. 3B). Yet, the 5xFAD mice with ablated meningeal lymphatics demonstrated marked deposition of amyloid in the meninges (FIG. 3B), as well as macrophage recruitment to large Aβ aggregates (FIG. 3C). Photoacoustic imaging 1 week after lymphatic ablation demonstrated no differences in blood flow and oxygenation between 5xFAD mice from the different groups (FIGS. 13A-C). Assessment of lymphoid and myeloid cell populations in the meninges (FIG. 13D) demonstrated a significant increase in the number of macrophages upon lymphatic ablation, when compared to both control groups (FIG. 13E), which might be correlated with increased amyloid deposition and inflammation in the meninges. Interestingly, along with meningeal amyloid pathology, we observed an aggravation of brain amyloid burden in the hippocampi of 5xFAD mice with dysfunctional meningeal lymphatics (FIGS. 3D-G). A similar outcome was observed in J20 transgenic mice after a total of 3 months of meningeal lymphatic ablation (FIG. 13F); Aβ aggregates had formed in the meninges (FIG. 13G) and the Aβ plaque load in the hippocampi was significantly increased (FIGS. 13H-K).

Our discovery of meningeal amyloid pathology in mice after meningeal lymphatic vessel ablation led us to assess meningeal amyloid pathology in AD patients (FIG. 3H). Staining for Aβ in the brains of 9 AD patients and 8 non-AD controls (Table 1) revealed, as expected, marked parenchymal deposition of amyloid in the AD, but not in the non-AD brains (FIGS. 13L-M). Interestingly, when compared to tissue from non-AD cases, all samples from AD patients demonstrated striking vascular amyloid pathology in the cortical leptomeninges (FIGS. 13L-M) and Aβ deposition in the dura mater adjacent to the superior sagittal sinus (FIGS. 3I-J) or further away from the sinus (FIGS. 3K-L). Macrophages in the dura of AD cases were also found in close proximity to Aβ deposits (FIG. 3L). These findings show that prominent meningeal amyloid deposition observed in AD patients was only seen in AD mouse models when lymphatic vessels were ablated. Meningeal lymphatic function, therefore, is a precipitating factor in AD pathology.

TABLE 1

DEMOGRAPHIC DATA OF AD AND NON-AD CASES

| | Age (years) | Gender | Diagnosis criteria | Pathological score |
|---|---|---|---|---|
| AD | 62 | F | Intermediate probability* | A2, B3, C2-3; CAA |
| | 64 | M | Possible | CERAD C; BB I/II; CAA |
| | 72 | M | High probability* | A3, B3, C3; CAA |
| | 76 | F | High probability* | A3. B3, C3; CAA |
| | 79 | M | High probability* | A3, B3, C3; CAA |
| | 83 | F | High probability* | A3, B3, C3; CAA |
| | 83 | M | Intermediate probability* | A2, B2, C2 |
| | 88 | F | High probability* | A3, B3, C3; CAA |
| | 95 | F | Definitive | CERAD C; BB V/VI; CAA |
| Mean ± SE | 78 ± 3.6 | | | |

| | Age (years) | Gender | Cause of death |
|---|---|---|---|
| Non-AD | 63 | F | Multi-organ failure after motor vehicle accident |
| | 63 | M | Acute myocardial infarct |
| | 64 | M | Bilater ulmonary emboli |
| | 65 | F | Decompensated ischemic cardiomyopathy |
| | 70 | M | Bronchopneumonia |
| | 73 | F | Septicemia |
| | 80 | F | Bronchopneumonia |
| | 91 | F | Cardiovascular atherosclerotic disease |
| Mean ± SE | 71.1 ± 3.5 | | |

*new criteria for diagnosis following the guidelines of NIA-AA based on ABC (Amyloid, Braak, CERAD) score
AD—Alzheimer's disease,
CERAD—Consorium to Establish a Registry for Alzheimer's disease;
BB—Braek and Braak stage;
CAA—cerebral amyloid angiopathy

Example 5: RNA-seq Ablation Study

Given our present discovery that mice with ablated meningeal lymphatics also showed significant deficits in spatial learning in the MWM, we performed RNA sequencing (RNA-seq) studies to elucidate the molecular mechanisms of how dysfunctional meningeal lymphatic drainage causes impairments in spatial learning and memory. Using RNA sequencing (RNA-seq) we assessed the effect of Visudyne/photoconversion treatment on hippocampal gene expression before and after performing MWM. Principal component analysis showed that four weeks of meningeal lymphatic ablation did not induce significant changes in the hippocampal transcriptome (FIGS. 9K-L). However, significant differences in hippocampal gene expression were unfolded in response to MWM performance after prolonged meningeal lymphatic ablation (FIGS. 9M-N). Contrary to what was observed without MWM performance (FIGS. 9K-L), individual samples from each group clustered together after the mice performed the test (FIGS. 9M-N). Interestingly, although the fold change of significantly altered genes after lymphatic ablation and MWM was moderate (−1.79<log 2(fold change)<1.69), functional enrichment analysis (FIGS. 9O-P) revealed changes in gene sets associated with neurodegenerative diseases, such as Huntington's, Parkinson's and Alzheimer's (FIG. 9O). Significant transcriptional alterations were also associated with excitatory synaptic remodeling and plasticity, hippocampal neuronal transmission[29], learning and memory and aging-related cognitive decline[30] (FIGS. 9Q-R). Furthermore, different gene sets involved in the regulation of metabolite generation and processing, glycolysis and mitochondrial respiration and oxidative stress were also significantly altered in the hippocampus upon lymphatic ablation and performance of the behavior test (FIGS. 9P, 9S-9V). Differentially expressed genes are listed in Table 2 and enriched GO and KEGG terms are listed in Table 3. These findings demonstrate that impaired meningeal lymphatic drainage causes decreased CSF influx/ISF efflux, alters the pattern of CSF/ISF diffusion within the parenchyma, modulates the metabolic status and neuronal function in the brain hippocampus, and ultimately impacts learning behavior. Further, these findings identify molecular targets in the hippocampus modulating these impairments that can be employed in therapeutic and diagnostic methods.

TABLE 3

ENRICHED GO AND KEGG TERMS IN HIPPOCAMPAL TRANSCRIPTOME AFTER IMPAIRING MENINGEAL LYMPHATIC FUNCTION

| Pathway | GO/KEGG Pathway ID |
|---|---|
| Huntington's disease | mmu05016 |
| Parkinson's disease | mmu05012 |
| Postsynaptic density | GO:0014069 |
| Excitatory synapse | GO:0060076 |
| Alzheimer's disease | mmu05010 |
| Modulation of synaptic transmission | GO:0050804 |
| Longevity regulating pathway | mmu04211 |
| Regulation of synaptic plasticity | GO:0048167 |
| Rho GTPase binding | GO:0017048 |
| Cognition | GO:0050890 |
| Dendritic spine development | GO:0060996 |
| Learning or memory | GO:0007611 |
| Neurotrophin signaling pathway | mmu04722 |
| Calmodulin-dependent protein kinase activity | GO:0004683 |
| Insulin signaling pathway | mmu04910 |
| Oxytocin signaling pathway | mmu04921 |
| Glutamate receptor binding | GO:0035254 |
| Glutamatergic synapse | mmu04724 |
| GnRH signaling pathway | mmu04912 |
| Long-term potentiation | mmu04720 |
| Oxidative phosphorylation | mmu00190 |
| Mitochondrial respiratory chain | GO:0005746 |
| NADH dehydrogenase complex | GO:0030964 |
| Non-alcoholic fatty liver disease - NAFLD | mmu04932 |
| Generation of precursor metabolites and energy | GO:0006091 |
| Purine nucleoside monophosphate metabolic process | GO:0009126 |
| Energy derivation by oxidation of organic compounds | GO:0015980 |

TABLE 3-continued

ENRICHED GO AND KEGG TERMS IN HIPPOCAMPAL
TRANSCRIPTOME AFTER IMPAIRING
MENINGEAL LYMPHATIC FUNCTION

| Pathway | GO/KEGG Pathway ID |
| --- | --- |
| Regulation of autophagy | GO:0010506 |
| Proteasomal protein catabolic process | GO:0010498 |
| Response to oxidative stress | GO:0006979 |
| Carbon metabolism | mmu01200 |
| Glutamate receptor signaling pathway | GO:0007215 |
| Carbohydrate metabolic process | GO:0005975 |
| Cellular response to oxidative stress | GO:0034599 |
| Cellular response to nitrogen compound | GO:1901699 |
| Pyridine-containing compound metabolic process | GO:0072524 |
| Glycolytic process | GO:0006096 |
| Cellular response to reactive oxygen species | GO:0034614 |
| Monovalent inorganic cation transport | GO:0015672 |
| Response to toxic substance | GO:0009636 |

Figure 2B:
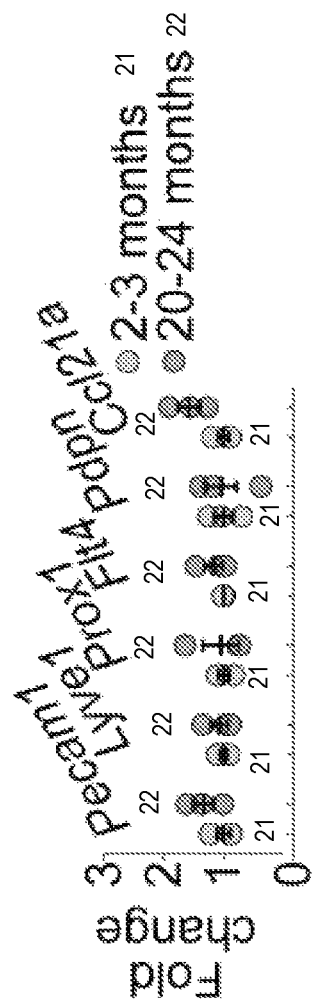
Figure 2A:
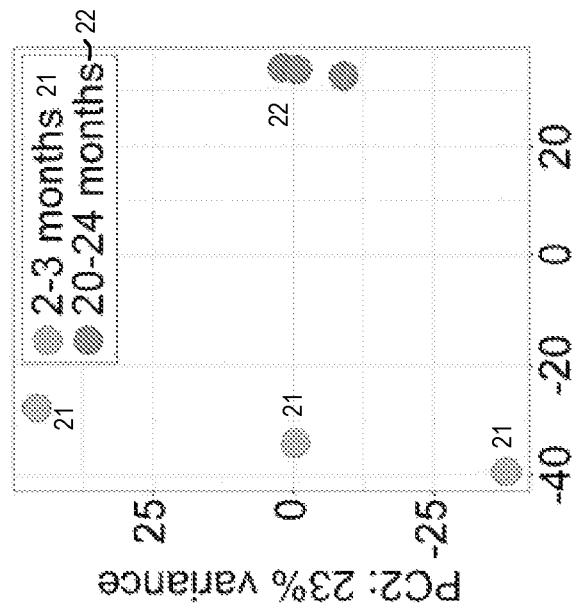
FIGS. 2A-T show improving meningeal lymphatic function in aged mice increases brain perfusion and alleviates cognitive deficits. Principal component (PC) analysis plot for RNA-seq of lymphatic endothelial cells (LECs) from meninges of young-adult and aged mice. 230 genes up- and 377 genes down-regulated in meningeal LECs at 20-24 months (FIG. 2A). Expression of Pecam1, Lyve1, Prox1, Flt4, Pdpn and Ccl21a (FIG. 2B). Gene sets obtained by functional enrichment of differentially expressed genes in meningeal LECs at 20-24 months (FIG. 2C). Heatmap showing relative expression level of genes involved in Transmembrane receptor protein tyrosine kinase signaling pathway (color scale bar values represent standardized r log-transformed values across samples) (FIG. 2D). Data in FIGS. 2A-D consists of n=3 per group (individual RNA samples result from LECs pooled from 10 meninges over 2 independent experiments); data in FIG. 2B are presented as mean±s.e.m. with two-way ANOVA with Bonferroni's post-hoc test.
Figures 2C, 2D:
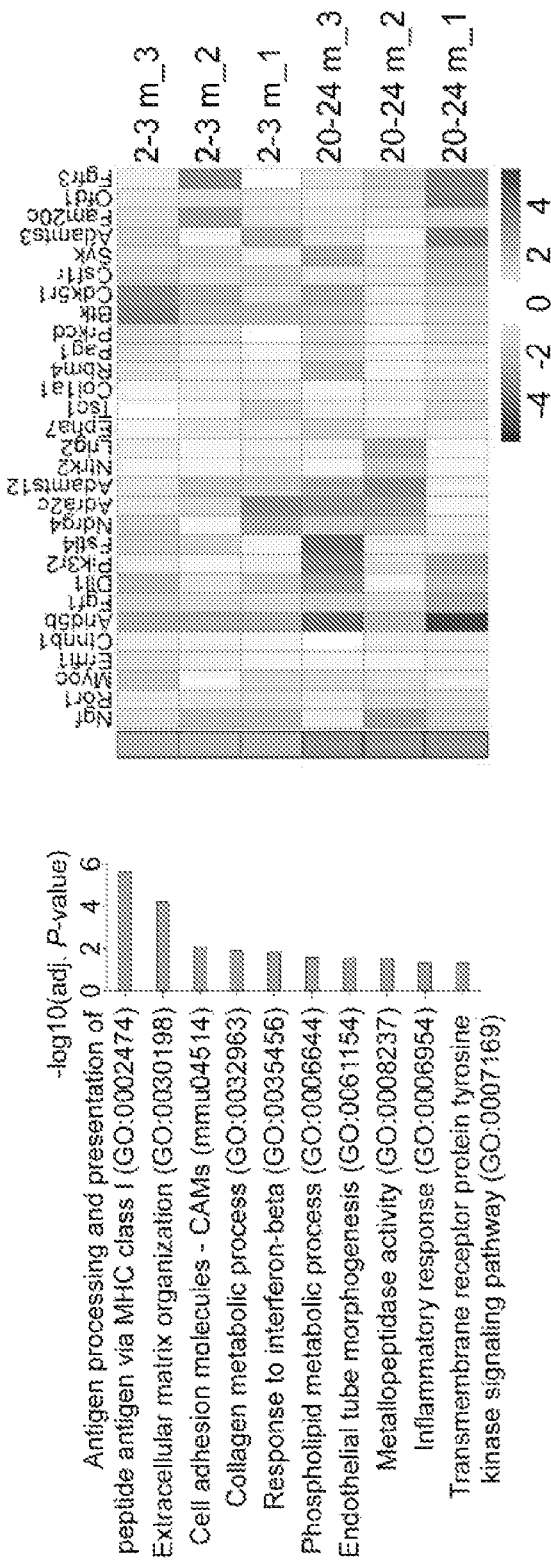

Example 6: RNA-sea Analysis of the Lymphatic Endothelial Cell Transcriptome of Meninges of Young-adult and Aged Mice Aging is the principal risk factor for many neurological disorders, including AD[15,16], and has a detrimental effect on brain CSF/ISF paravascular recirculation[13]. The reported findings that aging is also associated with peripheral lymphatic dysfunction[20-22] led us to hypothesize that deterioration of meningeal lymphatic vessels underlies some aspects of age-associated cognitive decline. Indeed, old mice demonstrate reduced brain perfusion by CSF macromolecules as compared to young counterparts (FIGS. 10A-B). Impaired brain perfusion by CSF in old mice was accompanied by a decrease in meningeal lymphatic vessel diameter and coverage, as well as decreased drainage of CSF macromolecules into dCLNs in both females and males (FIGS. 10C-F). To further address the effect of aging on meningeal lymphatics, we performed RNA-seq analysis of LECs sorted from the meninges of young-adult and old mice (FIG. 10G and FIG. 2A). Differential expression of 607 genes was detected in the meningeal LECs of old when compared to young-adult mice (FIG. 2A). Differentially expressed genes are listed in Table 4 and enriched GO and KEGG terms are listed in Table 5. Of note, the expression of genes encoding for classical markers of LECs, including Flt4 that encodes the vascular endothelial growth factor C (VEGF-C) receptor tyrosine kinase VEGFR3, was not significantly altered at 20-24 months (FIG. 2B). Enrichment analysis revealed, however, changes in gene sets involved in immune and inflammatory responses, phospholipid metabolism, extracellular matrix organization, cellular adhesion and endothelial tube morphogenesis, all suggestive of functional alterations in meningeal LECs with age (FIG. 2C). The altered expression of genes involved in transmembrane receptor protein tyrosine kinase signaling pathway in old mice, namely the down-regulation of Cdk5r1[31], Adamts3[32] and Fgfr3[33], pointed to possible changes in signaling by lymphangiogenic growth factors in old meningeal LECs (FIG. 2D). These findings demonstrate that aging impacts the meningeal lymphatic transcriptome and identify molecular targets and targets in the meningeal LECs responsible for age-related deterioration of meningeal lymphatic vessels that can be employed in therapeutic and diagnostic methods disclosed herein.

TABLE 5

ENRICHED GO AND KEGG TERMS IN LYMPHATIC
ENDOTHELIAL CELL TRANSCRIPTOME OF
MENINGES OF YOUNG-ADULT AND AGED MICE

| Pathway | GO/KEGG Pathway ID |
| --- | --- |
| Antigen processing and presentation of peptide antigen via MHC class I | GO:0002474 |
| Extracellular matrix organization | GO:0030198 |
| Cell adhesion molecules - CAMs | mmu04514 |
| Collagen metabolic process | GO:0032963 |
| Response to interferon-beta | GO:0035456 |
| Phospholipid metabolic process | GO:0006644 |
| Endothelial tube morphogenesis | GO:0061154 |
| Metallopeptidase activity | GO:0008237 |
| Inflammatory response | GO:0006954 |
| Transmembrane receptor protein tyrosine kinase signaling pathway | GO:0007169 |

Example 7: Proof of Principle for Treatment of Aged Mice by Modulation of Meningeal Lymphatic Targets Having identified molecular mechanisms mediating meningeal lymphatic dysfunction in Examples 5 and 6, we sought to determine if the therapeutic targeting and modulation of a factor implicated in meningeal lymphatic dysfunction (e.g., upregulation of an target identified as being unexpressed in Tables 2 and 4 by an overexpression viral vector) could improve the function of meningeal lymphatic vessels. To that end, we first began by hypothesizing that VEGF-C treatment may improve the function of meningeal lymphatic vessels in old mice, and tested this hypothesis by examining the effect of an adeno-associated virus serotype 1 (AAV1)-mediated overexpression of mouse VEGF-C (mVEGF-C) on meningeal lymphatics. We have previously shown that treatment with recombinant VEGF-C increases the diameter of meningeal lymphatic vessels[4]. Furthermore, delivery of VEGF-C by adenoviral gene therapy was previously found to efficiently boost peripheral lymphatic sprouting and function[34,35]. A similar adeno-associated virus serotype 1 (AAV1) vector was used here to express mVEGF-C or enhanced green fluorescent protein (EGFP) as control. At 2 and 4 weeks post i.c.m. injection, AAV1-infected cells expressing EGFP were limited to the pia around the brain, meninges (dura and arachnoid), and pineal gland (FIGS. 10H-J). Treatment of young mice with AAV1-CMV-mVEGF-C resulted in a significant increase in meningeal lymphatic vessel diameter, without affecting blood vessel coverage (FIGS. 10K-M).

Treatment of old mice (at 20-24 months) with AAV1-CMV-mVEGF-C also resulted in increased lymphatic vessel diameter (as compared to AAV1-CMV-EGFP) without detectable off-target effects on the meningeal blood vasculature coverage and on meningeal/brain vascular hemodynamics (FIGS. 2E-H and FIGS. 10N-P). One month after AAV1-CMV-mVEGF-C treatment, old mice showed a significant increase in CSF tracer drainage into the dCLNs, which was not due to increased lymphatic vessel coverage in the nodes (FIGS. 2I, 2J). Importantly, the rate of tracer influx into the brain parenchyma was significantly increased as a result of enhanced meningeal lymphatic function (FIGS. 2K-L and FIG. 10Q).

Transcranial delivery (through a thinned skull surface) of hydrogel-encapsulated VEGF-C peptide also resulted in increased diameter of meningeal lymphatics in young and old mice (FIGS. 11A-C). This VEGF-C treatment led to a significant increase in the function of meningeal lymphatics in old mice, whereas young-adult mice did not respond to the treatment (FIGS. 11D-E), probably due to the ceiling effect of their existing drainage capacity. The increased drainage after VEGF-C treatment in old mice also correlated with enhanced brain perfusion by CSF macromolecules (FIGS. 11F-G).

To avoid potential VEGF-C off-target effects on the blood vasculature through VEGFR2[34,36], we employed transcranial delivery of VEGF-C156S (FIG. 11H), a mutant protein that binds specifically to VEGFR3 and spares its effects on VEGFR2[34,36]. Treatment with VEGF-C156S resulted in a significant increase in meningeal lymphatic diameter (FIGS. 11I-J), drainage of tracer from the CSF (FIGS. 11K-L), and paravascular influx of tracer into the brains of old mice (FIGS. 11M-N).

To determine the functional role of enhanced meningeal lymphatics in the learning behavior of mice at different ages we again used viral delivery of mVEGF-C (FIGS. 11O-U). This method was selected to avoid submitting aged mice to consecutive surgeries, involving general anesthesia and skull thinning. Treatment of young-adult mice with AAV1-CMV-mVEGF-C for 1 month did not improve spatial learning and memory (FIGS. 11P, 11S), suggestive of a ceiling effect in MWM performance at this age. However, AAV1-CMV-mVEGF-C treatment resulted in significant improvement in the latency to platform and in the percentage of allocentric navigation strategies, in the MWM reversal in 12-14 months-old mice (FIGS. 11Q, 11T) and in the MWM acquisition and reversal in 20-22 months-old mice (FIGS. 11R, 11U), when compared to AAV1-CMV-EGFP-treated age-matched mice.

Figure 2P:
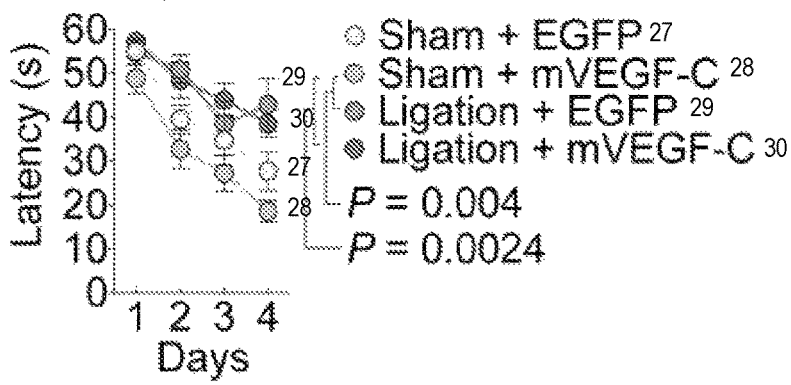
Figure 2Q:
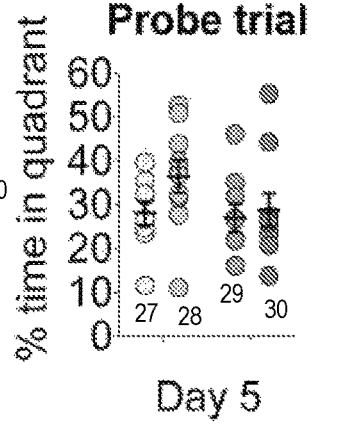
Figure 2R:
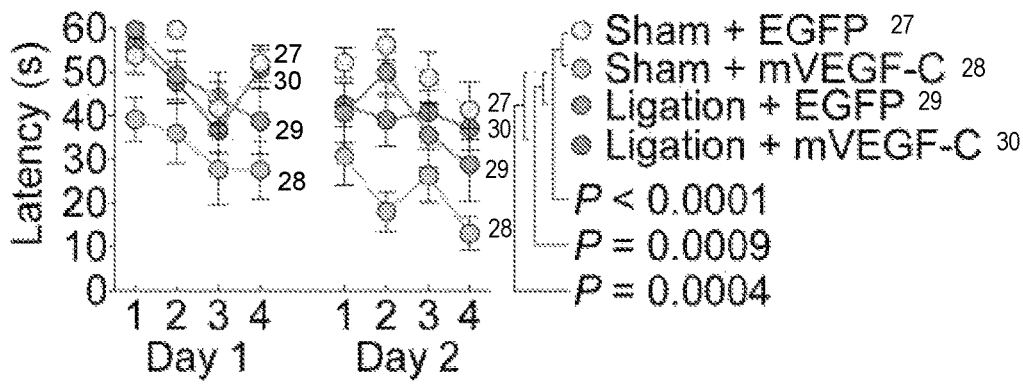
Figure 2S:
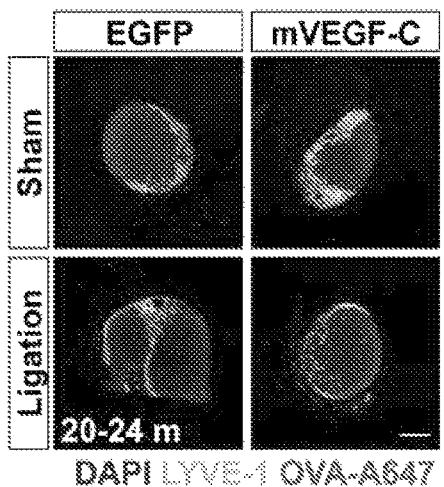
Figure 2T:
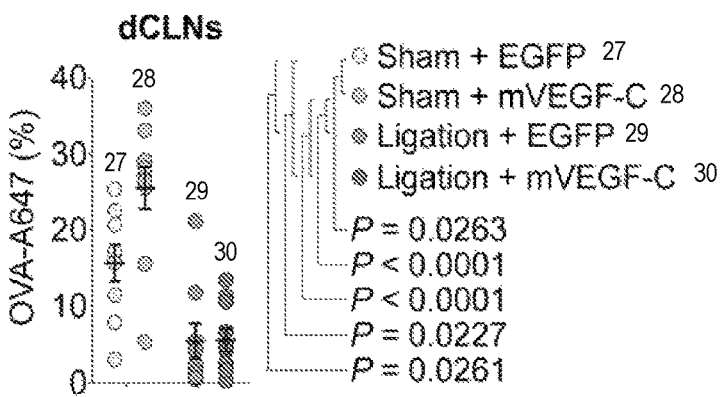

To demonstrate that the beneficial effect of mVEGF-C treatment on cognitive behavior was through improved meningeal lymphatic drainage, we injected old mice with the EGFP or mVEGF-C viruses and concomitantly ligated the lymphatics afferent to the dCLNs. Assessment of learning and memory was performed 1 month after the procedures (FIG. 2M). The beneficial effect of mVEGF-C treatment in mice from the sham group, which performed significantly better in the NLR (FIGS. 2N, 2O) and in the MWM (FIGS. 2P-R) tests, was abrogated in mice submitted to ligation of the CSF-draining lymphatics. Accordingly, the drainage of CSF macromolecules into dCLNs was significantly higher in the sham-operated mice treated with mVEGF-C when compared to all other groups (FIGS. 2S, 2T).

These results, thus, compellingly demonstrate that learning behavior in aged mice can be improved specifically through regulation of meningeal lymphatic function by targeted intervention. Modulation of meningeal lymphatic function in aging individuals using the methods and compositions provided herein represent a novel preventive therapeutic strategy, not only to delay AD initiation and progression but also for use against other brain proteinopathies that are exacerbated by aging. While this example demonstrates an improvement in cognitive behavior by viral-mediated expression of factor regulating meningeal lymphatic function, the skilled artesian would appreciate these results provide proof of principle for other types of therapeutic modulation provided herein, such as, for example, shRNA-mediated downregulation of an aberrantly overexpressed protein in LECs causative of meningeal lymphatic dysregulation.

Altogether, the present findings highlight the importance of meningeal lymphatic drainage in brain physiology. Aged mice demonstrated significant disruption of meningeal lymphatic function, which underlies some of the aspects of age-associated cognitive decline. Augmentation of meningeal lymphatic drainage in aged mice can ultimately facilitate the clearance of CSF macromolecules from the brain, resulting in improved cognitive function. On the other hand, induced dysfunction of meningeal lymphatics resulted in accelerated amyloid pathology in mouse models of AD. Transgenic AD mouse models recapitulated many features of brain amyloid pathology observed in the human AD brain.

Example 8: Connectivity Map Analysis of the Meningeal LEC Transcriptome of Old Mice To discover candidate therapeutics to revert the observed gene expression differences observed in old meningeal LECs and thereby treat neurodegenerative diseases, Connectivity Map (CMap) analysis of the meningeal LEC transcriptome of old mice was performed. FIG. 4A shows a PCA plot of transcripts from RNA-seq of lymphatic endothelial cells (LECs) sorted from the meninges of young-adult (2-3 months-old) and old (20-24 months-old) mice. A functional enrichment of differentially expressed genes revealed changes in gene sets important for the properties of LECs and the function of the lymphatic vessels (FIG. 4B). Running a list of significantly altered genes (134 upregulated and 150 downregulated) on the CMap software (LINCS L1000 small molecule assay, Broad Institute Cambridge MA) revealed target genes that modulate some of the altered functional pathways in meningeal LECs from old mice (FIG. 4C). Running the same genes in the L1000CDS$^2$ tool, which also uses the LINCS L1000 small molecule expression profile dataset (developed by the Ma'ayan Lab, Icahn School of Medicine at Mount Sinai) disclosed candidate compounds/drugs, many of them FDA-approved and commercially available, that are predicted to revert the observed gene expression differences observed in old meningeal LECs (FIG. 4D).

Example 9: Meningeal Lymphatic Dysfunction in 5×FAD Mice Lead to Unique Changes in the Microglial Transcriptome Effects of meningeal ablation on gene expression were studied in 5×FAD mice. Single cell RNA-seq of brain myeloid cells from 4 months old wild type (WT) and 5×FAD mice were injected with Visudyne alone (Vis., functional meningeal lymphatics) or injected with Visudyne and subjected to transcranial photoconversion (Vis.+photo., ablated meningeal lymphatics). Meningeal lymphatic ablation step was performed twice within a span of 3 weeks and brain myeloid cells were isolated 3 weeks after the last step. Data were obtained from sorted live Ly6G$^{neg}$CD45$^+$CD11b$^+$ brain myeloid cells pooled from 3 mice per group (FIGS. 14A-B). Unsupervised clustering of brain myeloid single cells using t-distributed Stochastic Neighbor Embedding (t-SNE) plotted by group (FIG. 14A) or by distinct cell cluster (FIG. 14B). Frequency of cells from each cluster within the total 354, 487 and 308 cells from WT Vis., 5×FAD Vis. and 5×FAD Vis.+photo. groups, respectively (FIG. 14C). Genes involved in the acquisition of the disease-associated microglia phenotype, depicting the homeostatic, TREM2-independent and TREM2-dependent signatures within each cell were depicted in a heatmap (FIG. 14D). Cells are grouped by cluster and genes are grouped by signature (FIG. 14D). Upset plots were generated for all cells (FIG. 14E) or cluster 1 cells (FIG. 14F) showing the overlap in differentially expressed genes for comparisons between 5xFAD Vis. or 5xFAD Vis.+photo. and WT Vis. A heatmap with 24 genes whose expression is significantly different between 5xFAD Vis.+photo. and WT Vis., but not significantly different between 5xFAD Vis. and WT Vis., in cluster 1 is depicted in FIG. 14G. Expression values are averaged across cells within each group. Normalized enrichment score for GSEA pathways were obtained by Fisher's exact test with Benjamini-Hochberg corrections for the 24 differentially expressed genes in cluster 1 is shown in FIG. 14H. Enrichment analysis was performed in R using the clusterProfiler package. Depicted in FIG. 14I is a heatmap showing the mean-centered average log normalized expression of each gene contributing to the core-enrichment of the "Lysosome" GSEA pathway. Expression values are averaged across cells within each group. All scales show mean-centered, log-normalized expression values.

The genes whose brain myeloid cell expression is significantly different between 5xFAD Vis.+photo. and WT Vis., but not significantly different between 5xFAD Vis. and WT Vis., in cluster 1 (as shown in FIG. 14G) are depicted in Table 6, below. A "+" refers to relative upregulation of gene expression for the noted conditions. A "-" refers to relative downregulation of gene expression for the noted conditions. It will be understood that wherever a murine gene is listed, use of the *Homo sapiens* ortholog of that gene is expressly contemplated. For the items in Table 6, an Entrez accession number for the corresponding *Homo sapiens* gene is provided, when applicable.

TABLE 6

| Gene | Entrez | Rel. Expr. WT Vis. | Rel. Expr. 5xFAD Vis. | Rel. Expr. 5xFAD Vis. + photo |
|---|---|---|---|---|
| Serinc3 | 10955 | + | + | − |
| Hexb | 3074 | + | + | − |
| Lgmn | 5641 | + | + | − |
| Rtp4 | 64108 | − | − | + |
| Lpl | 4023 | − | + | + |
| HS-Q7 | 10229 | − | − | + |
| Axl | 558 | − | − | + |
| Ctdnep1 | 23399 | − | + | + |
| Fabp5 | 16592 | − | + | + |
| Nampt | 10135 | − | + | + |
| Tfdp1 | 7027 | − | − | + |
| Hspb11 | 51668 | − | − | + |
| Tyrobp | 22177 | − | + | + |
| Tpt1 | 7178 | − | − | + |
| Fth1 | 2495 | − | + | + |
| Eef1a1 | 1915 | − | − | + |
| Lgals3bp | 3959 | − | + | + |
| Ifitm3 | 10410 | − | + | + |
| Atp5h | 71679 | − | + | + |
| Fau | 2197 | − | + | + |
| Ftl1 | 2512 | − | + | + |
| H2-K1 | 14972 (*Mus musculus*) | − | + | + |
| Tmsb4x | 7114 | − | − | + |
| Uba52 | 7311 | − | − | + |

Table 7 lists the genes identified in FIG. 14I as contributing to the core enrichment of the GSEA lysosome pathway. It is noted that each gene in FIG. 14I (and Table 7) is identified as being relatively downregulated for 5xFAD visudyne with photo ablation.

TABLE 7

| Lgmn | Ctsz | LMbrd1 |
| Hexb | Milr1 | Pla2g15 |
| Hexa | Aga | Scarb2 |
| Rnaset2b | Rnf19b | Ctsa |

TABLE 7-continued

| Cd63 | Cat | Hsp90ab1 |
| Grn | Plbd2 | Lamp2 |
| Lamp1 | Laptm4a | Unc93b1 |
| Fuca1 | Tmbim1 | Hspa8 |
| Hck | Atraid | Asah1 |
| Gusb | Shkbp1 | Ctsc |
| Ctsl | Atp13a2 | Itm2c |
| Cd68 | Ggh | Fuca2 |
| Ctsb | Rptor | |
| Ctsd | Ctsf | |

Thus, the data show that meningeal lymphatic dysfunction in 5xFAD mice leads to unique changes in the microglial transcriptome.

Example 10: Abnormal Accumulation of Meningeal T Cells Aggravates Brain Amyloid Pathology, Affects Microglial Response and Worsens Cognitive Performance in 5xFAD Mice Abnormal accumulation of meningeal T cells was induced in WT and 5xFAD mice. tSNE plots obtained after CyTOF assessment of meningeal immune cell populations from WT and 5xFAD mice on $CCR7^{+/+}$ or CCR7 backgrounds (littermates at 4-5 months of age) are depicted in FIG. 15A. Frequencies of total $CD45^+$ live leukocytes and of specific leukocyte population clusters within total CD45 live are depicted in FIGS. 15IB-G. No significant changes were observed in the frequency of meningeal leukocytes between the groups (FIG. 15B). Deficiency in CCR7 resulted in a significant increase in the frequency of CD4 (FIG. 15C) and of CD8 (FIG. 15D) T cells and a significant decrease in macrophage $2(CD11b^+F4/80^+CD64^+)$ population in both WT and 5xFAD mice (FIG. 15F). No changes were observed in B cells (FIG. 15E) and infiltrating monocytes $(CD11b^+F4/80^{neg}CD64^{neg/low}Ly6C^{high})$ (FIG. 15G). Results in FIGS. 15B-G are presented as mean±s.e.m.; n=5 per group; Two-way ANOVA with Sidak's multiple comparison test. tSNE plots obtained by re-clustering the meningeal $CD4^+$ and $CD8^+$ T cell populations using Flowsome and a 10 cluster-restricting condition are depicted in FIG. 15H. After removal of remnant contaminating macrophages and dendritic cells a total of four distinct clusters of $CD4^+$ T cells (4, 6, 7 and 10) and six distinct clusters of $CD8^+$ T cells (1, 2, 3, 5, 8 and 9) were identified (FIGS. 15J-L), There was a significant decrease in $CD4^+CD44^+PD-1^{neg}$ (FIG. 15I) and $CD8^+CD44^+$ $Tbet^{high}$ (FIG. 15K) and a significant increase in $CD4^+CD44^+FOXp3^+$ (FIG. 15J) and $CD8^+CD44^+Tbet^{low}$ (FIG. 15L) cell frequency. Results in FIG. 15I-L are presented as mean±s.e.m.; n=5 per group; Unpaired Student's T test. Representative images of brain sections of male $CCR7^{+/+}$ or $CCR7^{-/-}$ 5xFAD mice stained for Aβ (red) and with DAPI (blue); scale bar, 2 mm (FIG. 15M). Also quantified were number of plaques per $mm^2$ (FIG. 15N), plaque average size (in $\mu m^2$) (FIG. 15O), and coverage (% area of section) (FIG. 15P). Representative images of brain cortex stained for Aβ (green) and IBA1 (red) and with DAPI (blue); scale bar, 100 μm were obtained (FIG. 15Q). Quantification of IBA1+ cells clustered around plaques (FIG. 15R). Results in FIG. 15N-P and FIG. 15R are presented as mean±s.e.m.; in n-p, n=14 in 5xFAD::$CCR7^{+/+}$ and n=15 in 5xFAD::$CCR7^{-/-}$ groups pooled from 2 independent experiments; in r, n=6 per group representative of 2 independent experiments; Unpaired Student's T test. FIGS. 15S-U depict performance in the MWM acquisition (FIG. 15S), probe trial (FIG. 15T) and reversal (FIG. 15U) revealed statistically significant differences between WT::CCR7$^{+/+}$ and 5×FAD:: CCR7$^{-/-}$ at days 3 and 4 of the acquisition, in the probe trial and in the 2nd day of reversal (day 6 of the test). Statistically significant differences were also observed between WT:: CCR7$^{+/+}$ and WT::CCR7$^{-/-}$ mice in the probe trial. Results in FIG. 15S-U are presented as mean±s.e.m.; n=9 in WT:: CCR7$^{+/+}$ and in 5×FAD::CCR7$^{-/-}$, n=7 in WT::CCR7$^{-/-}$, n=8 in 5×FAD::CCR7$^{+/+}$ groups; Repeated measures Two-way ANOVA with Sidak's multiple comparison test in FIGS. 15S and 6U; Two-way ANOVA with Sidak's multiple comparison test in FIG. 15T.

Thus, abnormal meningeal T cell response in CCR7$^{-/-}$ mice is associated with worse brain Aβ pathology, altered microglial response and worse cognitive performance Ablation of meningeal lymphatic vessels aggravates Aβ deposition in the meninges and brain of 5×FAD transgenic mice. It is contemplated that accumulation of T cells in the meningeal lymphatics can aggravate brain pathology, affect microglial response, and worsen cognitive performance in AD.

REFERENCES

1. Hasek, M., Chutna, J., Sladecek, M. & Lodin, Z. Immunological tolerance and tumor allografts in the brain. *Nature* 268, 68-69, (1977).
2. Louveau, A., Harris, T. H. & Kipnis, J. Revisiting the Mechanisms of CNS Immune Privilege. *Trends Immunol* 36, 569-577, (2015).
3. Kipnis, J. Multifaceted interactions between adaptive immunity and the central nervous system. *Science* 353, 766-771, (2016).
4. Louveau, A. et al. Structural and functional features of central nervous system lymphatic vessels. *Nature* 523, 337-341, (2015).
5. Aspelund, A. et al. A dural lymphatic vascular system that drains brain interstitial fluid and macromolecules. *J Exp Med* 212, 991-999, (2015).
6. Absinta, M. et al. Human and nonhuman primate meninges harbor lymphatic vessels that can be visualized non-invasively by MRI. *Elife* 6, (2017).
7. Deane, R. et al. apoE isoform-specific disruption of amyloid beta peptide clearance from mouse brain. *J Clin Invest* 118, 4002-4013, (2008).
8. Zhao, Z. et al. Central role for PICALM in amyloid-beta blood-brain barrier transcytosis and clearance. *Nat Neurosci* 18, 978-987, (2015).
9. Deane, R. et al. RAGE mediates amyloid-beta peptide transport across the blood-brain barrier and accumulation in brain. *Nat Med* 9, 907-913, (2003).
10. Mildner, A. et al. Distinct and non-redundant roles of microglia and myeloid subsets in mouse models of Alzheimer's disease. *J Neurosci* 31, 11159-11171, (2011).
11. Keren-Shaul, H. et al. A Unique Microglia Type Associated with Restricting Development of Alzheimer's Disease. *Cell* 169, 1276-1290 e1217, (2017).
12. Iliff, J. J. et al. A paravascular pathway facilitates CSF flow through the brain parenchyma and the clearance of interstitial solutes, including amyloid beta. *Sci Transl Med* 4, 147ra111, (2012).
13. Kress, B. T. et al. Impairment of paravascular clearance pathways in the aging brain. *Ann Neurol* 76, 845-861, (2014).
14. Peng, W. et al. Suppression of glymphatic fluid transport in a mouse model of Alzheimer's disease. *Neurobiol Dis* 93, 215-225, (2016).
15. Brookmeyer, R., Abdalla, N., Kawas, C. H. & Corrada, M. M. Forecasting the prevalence of preclinical and clinical Alzheimer's disease in the United States. *Alzheimers Dement* 14, 121-129, (2018).
16. Erkkinen, M. G., Kim, M. O. & Geschwind, M. D. Clinical Neurology and Epidemiology of the Major Neurodegenerative Diseases. *Cold Spring Harb Perspect Biol* 10, (2018).
17. Benilova, I., Karran, E. & De Strooper, B. The toxic Abeta oligomer and Alzheimer's disease: an emperor in need of clothes. *Nat Neurosci* 15, 349-357, (2012).
18. Joachim, C. L., Duffy, L. K., Morris, J. H. & Selkoe, D. J. Protein chemical and immunocytochemical studies of meningovascular beta-amyloid protein in Alzheimer's disease and normal aging. *Brain Res* 474, 100-111, (1988).
19. Xu, Z. et al. Deletion of aquaporin-4 in APP/PS1 mice exacerbates brain Abeta accumulation and memory deficits. *Mol Neurodegener* 10, 58, (2015).
20. Chevalier, S., Ferland, G. & Tuchweber, B. Lymphatic absorption of retinol in young, mature, and old rats: influence of dietary restriction. *FASEB J* 10, 1085-1090, (1996).
21. Hos, D., Bachmann, B., Bock, F., Onderka, J. & Cursiefen, C. Age-related changes in murine limbal lymphatic vessels and corneal lymphangiogenesis. *Exp Eye Res* 87, 427-432, (2008).
22. Nagai, T., Bridenbaugh, E. A. & Gashev, A. A. Aging-associated alterations in contractility of rat mesenteric lymphatic vessels. *Microcirculation* 18, 463-473, (2011).
23. Tammela, T. et al. Photodynamic ablation of lymphatic vessels and intralymphatic cancer cells prevents metastasis. *Sci Transl Med* 3, 69ra11, (2011).
24. Kilarski, W. W. et al. Optimization and regeneration kinetics of lymphatic-specific photodynamic therapy in the mouse dermis. *Angiogenesis* 17, 347-357, (2014).
25. Escobedo, N. et al. Restoration of lymphatic function rescues obesity in Prox1-haploinsufficient mice. *JCI Insight* 1, (2016).
26. Ringstad, G., Vatnehol, S. A. S. & Eide, P. K. Glymphatic MRI in idiopathic normal pressure hydrocephalus. *Brain*, (2017).
27. Zeppenfeld, D. M. et al. Association of Perivascular Localization of Aquaporin-4 With Cognition and Alzheimer Disease in Aging Brains. *JAMA Neurol* 74, 91-99, (2017).
28. Rudy, J. W., Huff, N. C. & Matus-Amat, P. Understanding contextual fear conditioning: insights from a two-process model. *Neurosci Biobehav Rev* 28, 675-685, (2004).
29. Owen, S. F. et al. Oxytocin enhances hippocampal spike transmission by modulating fast-spiking interneurons. *Nature* 500, 458-462, (2013).
30. Zhang, G. et al. Hypothalamic programming of systemic ageing involving IKK-beta, NF-kappaB and GnRH. *Nature* 497, 211-216, (2013).
31. Liebl, J. et al. Cdk5 controls lymphatic vessel development and function by phosphorylation of Foxc2. *Nat Commun* 6, 7274, (2015).
32. Jeltsch, M. et al. CCBE1 enhances lymphangiogenesis via A disintegrin and metalloprotease with thrombospondin motifs-3-mediated vascular endothelial growth factor-C activation. *Circulation* 129, 1962-1971, (2014).
33. Shin, J. W. et al. Prox1 promotes lineage-specific expression of fibroblast growth factor (FGF) receptor-3 in lymphatic endothelium: a role for FGF signaling in lymphangiogenesis. *Mol Biol Cell* 17, 576-584, (2006).

34. Saaristo, A. et al. Lymphangiogenic gene therapy with minimal blood vascular side effects. *J Exp Med* 196, 719-730, (2002).
35. Karkkainen, M. J. et al. A model for gene therapy of human hereditary lymphedema. *Proc Natl Acad Sci USA* 98, 12677-12682, (2001).
36. Joukov, V. et al. A recombinant mutant vascular endothelial growth factor-C that has lost vascular endothelial growth factor receptor-2 binding, activation, and vascular permeability activities. *J Biol Chem* 273, 6599-6602, (1998).
37. Han, J. et al. Vascular endothelial growth factor receptor 3 controls neural stem cell activation in mice and humans. *Cell Rep* 10, 1158-1172, (2015).
38. Meshi, D. et al. Hippocampal neurogenesis is not required for behavioral effects of environmental enrichment. *Nat Neurosci* 9, 729-731, (2006).
39. Harris, J. A. et al. Many neuronal and behavioral impairments in transgenic mouse models of Alzheimer's disease are independent of caspase cleavage of the amyloid precursor protein. *J Neurosci* 30, 372-381, (2010).
40. Palop, J. J. et al. Aberrant excitatory neuronal activity and compensatory remodeling of inhibitory hippocampal circuits in mouse models of Alzheimer's disease. *Neuron* 55, 697-711, (2007).
41. Oakley, H. et al. Intraneuronal beta-amyloid aggregates, neurodegeneration, and neuron loss in transgenic mice with five familial Alzheimer's disease mutations: potential factors in amyloid plaque formation. *J Neurosci* 26, 10129-10140, (2006).
42. Sagare, A. P. et al. Pericyte loss influences Alzheimer-like neurodegeneration in mice. *Nat Commun* 4, 2932, (2013).
43. Sevigny, J. et al. Addendum: The antibody aducanumab reduces Abeta plaques in Alzheimer's disease. *Nature* 546, 564, (2017).

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

Although the foregoing has been described in some detail by way of illustrations and examples for purposes of clarity and understanding, it will be understood by those of skill in the art that modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the embodiments of the disclosure(s). For each method described herein, relevant compositions for use in the method are expressly contemplated, uses of compositions in the method, and, as applicable, methods of making a medicament for use in the method are also expressly contemplated. For example, for methods of increasing flow that comprise a flow modulator, flow modulators for use in the corresponding method are also contemplated, as are uses of a flow modulator in increasing flow according to the method, as are methods of making a medicament comprising the flow modulator for use in increasing flow.

It is contemplated that various combinations or subcombinations of the specific features and aspects of the embodiments disclosed above may be made and still fall within one or more of the disclosures. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosure. Thus, it is intended that the scope of the present disclosure should not be limited by the particular disclosed embodiments described above. Moreover, while the disclosure is susceptible to various modifications, and alternative forms, specific examples thereof have been shown in the drawings and are herein described in detail. It should be understood, however, that the disclosure is not to be limited to the particular forms or methods disclosed, but to the contrary, the disclosure is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a composition" include "instructing the administration of a composition." In addition, where features or aspects of the disclosure are described in terms of Markush groups, those skilled in the art will recognize that the disclosure is also thereby described in terms of any individual member or subgroup of members of the Markush group. Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a composition having at least one of A, B, or C" would include but not be limited to compositions that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like.

The indefinite article "a" or "an" does not exclude a plurality. The term "about" as used herein to, for example, define the values and ranges of molecular weights means that the indicated values and/or range limits can vary within ±20%, e.g., within ±10%. The use of "about" before a number includes the number itself. For example, "about 5" provides express support for "5".

TABLE 2

| Ensembl | Entrez | Symbol | log2FoldChange | padj | Name |
|---|---|---|---|---|---|
| ENSMUSG00000097505 | | | 1.68721446 | 7.77E−11 | |
| ENSMUSG00000040856 | 13386 | Dlk1 | 1.199724568 | 2.72E−06 | delta-like 1 homolog (*Drosophila*) |
| ENSMUSG00000002699 | 16822 | Lcp2 | 1.110117429 | 3.72E−08 | lymphocyte cytosolic protein 2 |
| ENSMUSG00000005763 | 12503 | Cd247 | 1.020106646 | 0.000247057 | CD247 antigen |
| ENSMUSG00000043015 | 227094 | Nemp2 | 1.018814294 | 0.000291652 | nuclear envelope integral membrane protein 2 |
| ENSMUSG00000038760 | 22045 | Trhr | 1.001846613 | 8.22E−07 | thyrotropin releasing hormone receptor |
| ENSMUSG00000096262 | | | 0.96622226 | 1.43E−05 | |
| ENSMUSG00000062168 | 237178 | Ppef1 | 0.95663948 | 0.000120062 | protein phosphatase with EF hand calcium-binding domain 1 |
| ENSMUSG00000091243 | 73569 | Vgll3 | 0.895521935 | 0.000839965 | vestigial like family member 3 |
| ENSMUSG00000097347 | | | 0.874879747 | 0.00055368 | |
| ENSMUSG00000097272 | | | 0.874421526 | 5.31E−07 | |
| ENSMUSG00000026228 | 15559 | Htr2b | 0.84970882 | 0.001999733 | 5-hydroxytryptamine (serotonin) receptor 2B |
| ENSMUSG00000019817 | 22634 | Plagl1 | 0.837739519 | 5.35E−08 | pleiomorphic adenoma gene-like 1 |
| ENSMUSG00000083013 | | | 0.830625744 | 0.003274596 | |
| ENSMUSG00000056025 | 12722 | Clca3a1 | 0.823943159 | 0.00289335 | chloride channel accessory 3A1 |
| ENSMUSG00000098097 | | | 0.815344327 | 3.31E−06 | |
| ENSMUSG00000079426 | 68089 | Arpc4 | 0.811879362 | 0.001389066 | actin related protein 2/3 complex, subunit 4 |
| ENSMUSG00000025905 | 18387 | Oprk1 | 0.806597562 | 0.000451714 | opioid receptor, kappa 1 |
| ENSMUSG00000041380 | 15560 | Htr2c | 0.791830589 | 7.05E−07 | 5-hydroxytryptamine (serotonin) receptor 2C |
| ENSMUSG00000030551 | 11819 | Nr2f2 | 0.776745812 | 0.000163755 | nuclear receptor subfamily 2, group F, member 2 |
| ENSMUSG00000070780 | 245945 | Rbm47 | 0.752306861 | 0.005332296 | RNA binding motif protein 47 |
| ENSMUSG00000002944 | 12491 | Cd36 | 0.748353433 | 0.006744831 | CD36 antigen |
| ENSMUSG00000069132 | 18232 | Nxph2 | 0.739166981 | 0.000713891 | neurexophilin 2 |
| ENSMUSG00000038112 | 244810 | AW551984 | 0.726317164 | 3.21E−06 | expressed sequence AW551984 |
| ENSMUSG00000050926 | 245403 | Dcaf12l2 | 0.724473623 | 0.00033091 | DDB1 and CUL4 associated factor 12-like 2 |
| ENSMUSG00000041570 | 67886 | Camsap2 | 0.721377326 | 0.000471706 | calmodulin regulated spectrin-associated protein family, member 2 |
| ENSMUSG00000042943 | | | 0.720735414 | 0.007277655 | |
| ENSMUSG00000051777 | 208426 | Iqcj | 0.712918031 | 0.004661875 | IQ motif containing J |
| ENSMUSG00000083396 | | | 0.7121342 | 0.009752335 | |
| ENSMUSG00000031380 | 14205 | Vegfd | 0.71111146 | 0.00865258 | vascular endothelial growth factor D |
| ENSMUSG00000005268 | 19116 | Prlr | 0.709629589 | 0.012137013 | prolactin receptor |
| ENSMUSG00000019929 | 13179 | Dcn | 0.700780853 | 0.000517444 | decorin |
| ENSMUSG00000084859 | 73489 | 1700080N15Rik | 0.700646663 | 0.006275636 | RIKEN cDNA 1700080N15 gene |
| ENSMUSG00000086843 | 338535 | E030013I19Rik | 0.700458964 | 1.30E−05 | RIKEN cDNA E030013I19 gene |
| ENSMUSG00000044471 | 232685 | Lncpint | 0.700124507 | 0.008278978 | long non-protein coding RNA, Trp53 induced transcript |
| ENSMUSG00000086022 | 209550 | Rad51ap2 | 0.694515547 | 0.000423168 | RAD51 associated protein 2 |
| ENSMUSG00000065701 | 19872 | Rny1 | 0.690600037 | 0.004878006 | RNA, Y1 small cytoplasmic, Ro-associated |
| ENSMUSG00000000567 | 20682 | Sox9 | 0.686823743 | 3.97E−08 | SRY (sex determining region Y)-box 9 |
| ENSMUSG00000089651 | | | 0.684852115 | 0.005516804 | |
| ENSMUSG00000083821 | | | 0.684071174 | 0.012468526 | |
| ENSMUSG00000010064 | 76257 | Slc38a3 | 0.672808987 | 0.017099976 | solute carrier family 38, member 3 |
| ENSMUSG00000087947 | | | 0.672499687 | 0.015647371 | |
| ENSMUSG00000078880 | 100043381 | Gm14308 | 0.671330541 | 0.000279932 | predicted gene 14308 |
| ENSMUSG00000015843 | 20183 | Rxrg | 0.670549456 | 0.016873714 | retinoid X receptor gamma |
| ENSMUSG00000090877 | 15511 | Hspa1b | 0.669250449 | 0.0037729 | heat shock protein 1B |
| ENSMUSG00000019768 | 13982 | Esr1 | 0.664783495 | 0.001747233 | estrogen receptor 1 (alpha) |
| ENSMUSG00000035694 | 353265 | Caps2 | 0.661645077 | 0.000412819 | calcyphosphine 2 |
| ENSMUSG00000056145 | 229694 | AI504432 | 0.661262584 | 2.72E−06 | expressed sequence AI504432 |
| ENSMUSG00000031558 | 20563 | Slit2 | 0.659521683 | 3.72E−08 | slit homolog 2 (*Drosophila*) |
| ENSMUSG00000037573 | 22057 | Tob1 | 0.654584 | 5.39E−06 | transducer of ErbB-2.1 |
| ENSMUSG00000050558 | 246313 | Prokr2 | 0.653178642 | 3.63E−05 | prokineticin receptor 2 |
| ENSMUSG00000029334 | 19092 | Prkg2 | 0.651056307 | 0.007055857 | protein kinase, cGMP-dependent, type II |
| ENSMUSG00000090066 | 102634333 | LOC102634333 | 0.648199198 | 0.006528024 | uncharacterized LOC102634333 |
| ENSMUSG00000080440 | | | 0.648057404 | 0.02194544 | |
| ENSMUSG00000095550 | 100862359 | Gm21671 | 0.644780992 | 0.007089549 | predicted gene, 21671 |
| ENSMUSG00000031355 | 11856 | Arhgap6 | 0.643913591 | 0.00826777 | Rho GTPase activating protein 6 |
| ENSMUSG00000025058 | 71398 | 5430427O19Rik | 0.643635951 | 0.015293069 | RIKEN cDNA 5430427O19 gene |
| ENSMUSG00000069743 | 75424 | Zfp820 | 0.639137651 | 0.007561881 | zinc finger protein 820 |
| ENSMUSG00000026107 | 109019 | Nabp1 | 0.638642566 | 6.36E−06 | nucleic acid binding protein 1 |
| ENSMUSG00000075270 | 241489 | Pde11a | 0.630854687 | 1.37E−06 | phosphodiesterase 11A |
| ENSMUSG00000091455 | 628870 | Otogl | 0.630128639 | 0.000760116 | otogelin-like |
| ENSMUSG00000019880 | 72780 | Rspo3 | 0.629342854 | 1.86E−06 | R-spondin 3 |
| ENSMUSG00000047935 | 434280 | Gm5607 | 0.625794471 | 0.024817752 | predicted gene 5607 |
| ENSMUSG00000096768 | 170942 | Erdr1 | 0.620783031 | 0.024448559 | erythroid differentiation regulator 1 |

TABLE 2-continued

| Ensembl | Entrez | Symbol | log2FoldChange | padj | Name |
|---|---|---|---|---|---|
| ENSMUSG00000098188 | 268301 | Sowahc | 0.618887968 | 0.002174172 | sosondowah ankyrin repeat domain family member C |
| ENSMUSG00000085526 | | | 0.616681569 | 0.012256826 | |
| ENSMUSG00000098061 | | | 0.607314987 | 0.00471505 | |
| ENSMUSG00000097311 | | | 0.606208837 | 0.004517231 | |
| ENSMUSG00000073656 | | | 0.605702402 | 0.008137864 | |
| ENSMUSG00000099025 | | | 0.602079481 | 0.031167682 | |
| ENSMUSG00000071665 | 436240 | Foxr2 | 0.599276079 | 0.02563755 | forkhead box R2 |
| ENSMUSG00000064945 | 19874 | Rny3 | 0.595384027 | 0.0330309 | RNA, Y3 small cytoplasmic (associated with Ro protein) |
| ENSMUSG00000055567 | 329178 | Unc80 | 0.594358294 | 0.0012163 | unc-80, NALCN activator |
| ENSMUSG00000097924 | | | 0.594161234 | 0.000186491 | |
| ENSMUSG00000047678 | 319200 | Gpr82 | 0.594006797 | 0.028890287 | G protein-coupled receptor 82 |
| ENSMUSG00000091476 | 545391 | Gm16432 | 0.591818984 | 0.012681585 | predicted gene 16432 |
| ENSMUSG00000038257 | 110304 | Glra3 | 0.590571061 | 0.006708852 | glycine receptor, alpha 3 subunit |
| ENSMUSG00000023073 | 20494 | Slc10a2 | 0.590182319 | 0.020962258 | solute carrier family 10, member 2 |
| ENSMUSG00000044145 | 329509 | 1810024B03Rik | 0.586805268 | 0.008173345 | RIKEN cDNA 1810024B03 gene |
| ENSMUSG00000094825 | 100041012 | Gm3095 | 0.586682974 | 0.005193975 | predicted gene 3095 |
| ENSMUSG00000028172 | 21338 | Tacr3 | 0.585283032 | 0.004181826 | tachykinin receptor 3 |
| ENSMUSG00000039257 | 58188 | Vstm2b | 0.580672469 | 0.026648841 | V-set and transmembrane domain containing 2B |
| ENSMUSG00000084917 | | | 0.580348036 | 0.01804631 | |
| ENSMUSG00000094832 | | | 0.580049998 | 0.017297968 | |
| ENSMUSG00000057836 | 22445 | Xlr3a | 0.579720384 | 0.039089041 | X-linked lymphocyte-regulated 3A |
| ENSMUSG00000039115 | 104099 | Itga9 | 0.578591373 | 0.005951911 | integrin alpha 9 |
| ENSMUSG00000078906 | | | 0.577695448 | 0.024829386 | |
| ENSMUSG00000042498 | 102871 | D330045A20Rik | 0.576955778 | 0.026579452 | RIKEN cDNA D330045A20 gene |
| ENSMUSG00000032346 | 67968 | Ooep | 0.576675873 | 0.02836652 | oocyte expressed protein |
| ENSMUSG00000080365 | | | 0.574491605 | 0.041221106 | |
| ENSMUSG00000032246 | 75600 | Calml4 | 0.573770116 | 0.038342642 | calmodulin-like 4 |
| ENSMUSG00000068122 | 11609 | Agtr2 | 0.573570136 | 0.041842461 | angiotensin II receptor, type 2 |
| ENSMUSG00000085109 | | | 0.571929805 | 0.039345584 | |
| ENSMUSG00000021187 | 74413 | Tc2n | 0.568307958 | 0.044424767 | tandem C2 domains, nuclear |
| ENSMUSG00000026601 | 77352 | Axdnd1 | 0.567999004 | 0.024578427 | axonemal dynein light chain domain containing 1 |
| ENSMUSG00000023737 | | | 0.566902945 | 0.005467068 | |
| ENSMUSG00000039480 | 319638 | Nt5dc1 | 0.565588748 | 0.003122633 | 5'-nucleotidase domain containing 1 |
| ENSMUSG00000097417 | | | 0.564726586 | 0.004088241 | |
| ENSMUSG00000051323 | 279653 | Pcdh19 | 0.564321603 | 6.31E−06 | protocadherin 19 |
| ENSMUSG00000097234 | | | 0.563911854 | 0.010607724 | |
| ENSMUSG00000096947 | | | 0.563636589 | 0.004223079 | |
| ENSMUSG00000048915 | 13640 | Efna5 | 0.563066393 | 0.002197588 | ephrin A5 |
| ENSMUSG00000099001 | | | 0.56264897 | 0.020056896 | |
| ENSMUSG00000097148 | | | 0.562505742 | 0.011189913 | |
| ENSMUSG00000034361 | 234577 | Cpne2 | 0.561210783 | 0.004484016 | copine II |
| ENSMUSG00000062319 | | | 0.560912392 | 0.026648841 | |
| ENSMUSG00000020185 | 52679 | E2f7 | 0.560750818 | 0.011466877 | E2F transcription factor 7 |
| ENSMUSG00000078184 | | | 0.559897082 | 0.02412924 | |
| ENSMUSG00000045871 | 239250 | Slitrk6 | 0.557514738 | 0.022323986 | SLIT and NTRK-like family, member 6 |
| ENSMUSG00000031309 | 110651 | Rps6ka3 | 0.556129963 | 1.46E−07 | ribosomal protein S6 kinase polypeptide 3 |
| ENSMUSG00000027896 | 229699 | Slc16a4 | 0.555574845 | 0.000268286 | solute carrier family 16 (monocarboxylic acid transporters), member 4 |
| ENSMUSG00000066652 | 320202 | Lefty2 | 0.55539262 | 0.029288325 | left-right determination factor 2 |
| ENSMUSG00000093843 | | | 0.555302564 | 0.043784958 | |
| ENSMUSG00000031285 | 13193 | Dcx | 0.553851128 | 8.22E−07 | doublecortin |
| ENSMUSG00000027750 | 50706 | Postn | 0.553208309 | 0.045365211 | periostin, osteoblast specific factor |
| ENSMUSG00000052415 | 99681 | Tchh | 0.553132444 | 0.010544674 | trichohyalin |
| ENSMUSG00000097265 | | | 0.552895269 | 0.001370223 | |
| ENSMUSG00000049148 | 239318 | Plcxd3 | 0.551735034 | 0.000412819 | phosphatidylinositol-specific phospholipase C, X domain containing 3 |
| ENSMUSG00000097300 | | | 0.550710585 | 0.009052194 | |
| ENSMUSG00000097338 | | | 0.549493455 | 0.009763137 | |
| ENSMUSG00000049799 | 100061 | Lrrc19 | 0.546705465 | 0.03156779 | leucine rich repeat containing 19 |
| ENSMUSG00000041633 | 207474 | Kctd12b | 0.545766636 | 0.000533095 | potassium channel tetramerisation domain containing 12b |
| ENSMUSG00000061039 | 258783 | Olfr920 | 0.545232904 | 0.026071951 | olfactory receptor 920 |
| ENSMUSG00000032899 | 243659 | Styk1 | 0.544383899 | 0.009889169 | serine/threonine/tyrosine kinase 1 |
| ENSMUSG00000028868 | 242687 | Wasf2 | 0.543604188 | 0.001276768 | WAS protein family, member 2 |
| ENSMUSG00000051455 | 268491 | Meioc | 0.543451707 | 0.00519215 | meiosis specific with coiled-coil domain |
| ENSMUSG00000050022 | 231842 | Amz1 | 0.539378249 | 0.011109797 | archaelysin family metallopeptidase 1 |
| ENSMUSG00000015882 | 209707 | Lcorl | 0.538184995 | 5.35E−08 | ligand dependent nuclear receptor corepressor-like |

TABLE 2-continued

| Ensembl | Entrez | Symbol | log2FoldChange | padj | Name |
|---|---|---|---|---|---|
| ENSMUSG00000039531 | 72580 | Zufsp | 0.53699343 | 0.002238309 | zinc finger with UFM1-specific peptidase domain |
| ENSMUSG00000033542 | 54324 | Arhgef5 | 0.536297325 | 0.01495083 | Rho guanine nucleotide exchange factor (GEF) 5 |
| ENSMUSG00000026361 | 214498 | Cdc73 | 0.535998111 | 3.57E−05 | cell division cycle 73, Paf1/RNA polymerase II complex component |
| ENSMUSG00000037490 | 353169 | Slc2a12 | 0.534718538 | 0.022874753 | solute carrier family 2 (facilitated glucose transporter), member 12 |
| ENSMUSG00000030237 | 28250 | Slco1a4 | 0.534493618 | 0.000523977 | solute carrier organic anion transporter family, member 1a4 |
| ENSMUSG00000034810 | 20272 | Scn7a | 0.533525685 | 0.005002265 | sodium channel, voltage-gated, type VII, alpha |
| ENSMUSG00000044702 | 233826 | Palb2 | 0.532616466 | 0.036087882 | partner and localizer of BRCA2 |
| ENSMUSG00000056888 | 73690 | Glipr1 | 0.531723026 | 0.029288325 | GLI pathogenesis-related 1 (glioma) |
| ENSMUSG00000032925 | 223272 | Itgbl1 | 0.531370042 | 0.000183125 | integrin, beta-like 1 |
| ENSMUSG00000087885 | | | 0.530830094 | 0.019506351 | |
| ENSMUSG00000020311 | 66753 | Erlec1 | 0.530200343 | 3.72E−08 | endoplasmic reticulum lectin 1 |
| ENSMUSG00000042453 | 19699 | Reln | 0.529929446 | 0.00359003 | reelin |
| ENSMUSG00000089790 | | | 0.528280721 | 0.007905396 | |
| ENSMUSG00000085543 | | | 0.528217312 | 0.031409398 | |
| ENSMUSG00000085440 | 319940 | Sorbs2os | 0.527686011 | 0.008435647 | sorbin and SH3 domain containing 2, opposite strand |
| ENSMUSG00000079011 | | | 0.52744814 | 0.034548655 | |
| ENSMUSG00000073594 | | | 0.526337169 | 0.004877014 | |
| ENSMUSG00000027009 | 16401 | Itga4 | 0.526193002 | 1.53E−06 | integrin alpha 4 |
| ENSMUSG00000021806 | 18074 | Nid2 | 0.525833241 | 0.026472481 | nidogen 2 |
| ENSMUSG00000093490 | | | 0.525470991 | 0.025890844 | |
| ENSMUSG00000097267 | 74303 | 1700109K24Rik | 0.525452749 | 0.020314314 | RIKEN cDNA 1700109K24 gene |
| ENSMUSG00000024691 | 107373 | Fam111a | 0.525305131 | 0.002102796 | family with sequence similarity 111, member A |
| ENSMUSG00000036502 | 245386 | Tmem255a | 0.525258513 | 1.61E−05 | transmembrane protein 255A |
| ENSMUSG00000067929 | | | 0.52339337 | 0.032136093 | |
| ENSMUSG00000097455 | | | 0.52333229 | 0.021273945 | |
| ENSMUSG00000042514 | 225266 | Klhl14 | 0.523080806 | 0.045505582 | kelch-like 14 |
| ENSMUSG00000084911 | | | 0.522510842 | 0.001250258 | |
| ENSMUSG00000098841 | | | 0.520797205 | 0.032410655 | |
| ENSMUSG00000072693 | | | 0.518059434 | 0.010238271 | |
| ENSMUSG00000053205 | 56291 | Styx | 0.517383802 | 0.027323589 | serine/threonine/tyrosine interaction protein |
| ENSMUSG00000097884 | | | 0.516698801 | 0.046860057 | |
| ENSMUSG00000052676 | 215693 | Zmat1 | 0.516377052 | 0.000223378 | zinc finger, matrin type 1 |
| ENSMUSG00000086986 | | | 0.516091782 | 0.035995265 | |
| ENSMUSG00000025937 | 212442 | Lactb2 | 0.515287241 | 0.009093064 | lactamase, beta 2 |
| ENSMUSG00000060445 | 320558 | Sycp2 | 0.515252611 | 0.027543196 | synaptonemal complex protein 2 |
| ENSMUSG00000064336 | | | 0.51505068 | 0.049177438 | |
| ENSMUSG00000028370 | 18491 | Pappa | 0.514522945 | 0.006361553 | pregnancy-associated plasma protein A |
| ENSMUSG00000097203 | 100042484 | 4732419C18Rik | 0.514165603 | 0.032840549 | RIKEN cDNA 4732419C18 gene |
| ENSMUSG00000003657 | 12308 | Calb2 | 0.513755733 | 0.001768632 | calbindin 2 |
| ENSMUSG00000020950 | 15228 | Foxg1 | 0.511271076 | 0.000315513 | forkhead box G1 |
| ENSMUSG00000072774 | 626391 | Zfp951 | 0.510582837 | 0.00613556 | zinc finger protein 951 |
| ENSMUSG00000043498 | | | 0.509817584 | 0.001670181 | |
| ENSMUSG00000019888 | 67569 | Mgat4c | 0.509753117 | 0.000228196 | MGAT4 family, member C |
| ENSMUSG00000093528 | 75170 | Nrg3os | 0.509521344 | 0.017528498 | neuregulin 3, opposite strand |
| ENSMUSG00000075316 | 20274 | Scn9a | 0.507606113 | 0.00985516 | sodium channel, voltage-gated, type IX, alpha |
| ENSMUSG00000074637 | 20674 | Sox2 | 0.507097871 | 0.002053567 | SRY (sex determining region Y)-box 2 |
| ENSMUSG00000084262 | | | 0.506113913 | 0.038438174 | |
| ENSMUSG00000037362 | 18133 | Nov | 0.506023432 | 0.002899047 | nephroblastoma overexpressed gene |
| ENSMUSG00000034218 | 11920 | Atm | 0.505158444 | 9.29E−08 | ataxia telangiectasia mutated |
| ENSMUSG00000074643 | 266692 | Cpne1 | 0.504642946 | 0.037663101 | copine I |
| ENSMUSG00000035274 | 21983 | Tpbg | 0.503905786 | 0.003338321 | trophoblast glycoprotein |
| ENSMUSG00000089998 | 100125931 | Phtf1os | 0.503831496 | 0.002884513 | putative homeodomain transcription factor 1, opposite strand |
| ENSMUSG00000097546 | | | 0.503689616 | 0.040504699 | |
| ENSMUSG00000034324 | 208213 | Tmem132c | 0.503308536 | 0.042049422 | transmembrane protein 132C |
| ENSMUSG00000086450 | | | 0.501926208 | 0.023209714 | |
| ENSMUSG00000091509 | | | 0.501827906 | 0.000382537 | |
| ENSMUSG00000074505 | 270120 | Fat3 | 0.501248331 | 0.013696197 | FAT atypical cadherin 3 |
| ENSMUSG00000097352 | 606736 | C920009B18Rik | 0.498126636 | 0.038529318 | RIKEN cDNA C920009B18 gene |
| ENSMUSG00000059588 | 54598 | Calcrl | 0.498074864 | 0.001345392 | calcitonin receptor-like |
| ENSMUSG00000016493 | 17221 | Cd46 | 0.497530349 | 0.009477244 | CD46 antigen, complement regulatory protein |
| ENSMUSG00000037169 | 18109 | Mycn | 0.496875115 | 0.006693208 | v-myc avian myelocytomatosis viral related oncogene, neuroblastoma derived |
| ENSMUSG00000016150 | 23963 | Tenm1 | 0.496134171 | 0.000104072 | teneurin transmembrane protein 1 |
| ENSMUSG00000085181 | 100504717 | Gm12709 | 0.496115006 | 0.012005397 | predicted gene 12709 |

TABLE 2-continued

| Ensembl | Entrez | Symbol | log2FoldChange | padj | Name |
|---|---|---|---|---|---|
| ENSMUSG00000084984 | 69295 | Far1os | 0.494597967 | 0.026020807 | fatty acyl CoA reductase 1, opposite strand |
| ENSMUSG00000071456 | 100043040 | 1110002L01Rik | 0.493877466 | 0.007135331 | RIKEN cDNA 1110002L01 gene |
| ENSMUSG00000085913 | | | 0.493830464 | 0.026214939 | |
| ENSMUSG00000095295 | 666329 | Gm3317 | 0.492910445 | 0.035883734 | predicted gene 3317 |
| ENSMUSG00000027015 | 73649 | Cybrd1 | 0.491950077 | 0.002781949 | cytochrome b reductase 1 |
| ENSMUSG00000053510 | 230598 | Nrd1 | 0.491886098 | 0.00017155 | nardilysin, N-arginine dibasic convertase, NRD convertase 1 |
| ENSMUSG00000087431 | | | 0.491728239 | 0.003129849 | |
| ENSMUSG00000090353 | | | 0.491368617 | 0.023922204 | |
| ENSMUSG00000079658 | 67923 | Tceb1 | 0.490025915 | 0.018597016 | transcription elongation factor B (SIII), polypeptide 1 |
| ENSMUSG00000039697 | 211329 | Ncoa7 | 0.489484962 | 0.000324396 | nuclear receptor coactivator 7 |
| ENSMUSG00000040850 | 103554 | Psme4 | 0.48830771 | 3.72E−08 | proteasome (prosome, macropain) activator subunit 4 |
| ENSMUSG00000095746 | | | 0.48807648 | 0.00055368 | |
| ENSMUSG00000089940 | | | 0.487414868 | 0.025364617 | |
| ENSMUSG00000062542 | 60510 | Syt9 | 0.487413164 | 0.007550519 | synaptotagmin IX |
| ENSMUSG00000051497 | 16517 | Kcnj16 | 0.486840676 | 0.000161791 | potassium inwardly-rectifying channel, subfamily J, member 16 |
| ENSMUSG00000021714 | 60411 | Cenpk | 0.486773722 | 0.038187701 | centromere protein K |
| ENSMUSG00000075266 | 66311 | Cenpw | 0.486254211 | 0.045653534 | centromere protein W |
| ENSMUSG00000022206 | 18162 | Npr3 | 0.485723012 | 0.002374377 | natriuretic peptide receptor 3 |
| ENSMUSG00000078117 | | | 0.485340954 | 0.005290988 | |
| ENSMUSG00000097385 | | | 0.484502638 | 0.03628183 | |
| ENSMUSG00000048047 | 56805 | Zbtb33 | 0.483286471 | 0.000558417 | zinc finger and BTB domain containing 33 |
| ENSMUSG00000062949 | 320940 | Atp11c | 0.48325947 | 0.00066384 | ATPase, class VI, type 11C |
| ENSMUSG00000006262 | 68473 | Mob1b | 0.483218568 | 0.001411939 | MOB kinase activator 1B |
| ENSMUSG00000082361 | 12223 | Btc | 0.482747094 | 0.049663261 | betacellulin, epidermal growth factor family member |
| ENSMUSG00000074733 | 414758 | Zfp950 | 0.482465043 | 0.000772175 | zinc finger protein 950 |
| ENSMUSG00000025665 | 67071 | Rps6ka6 | 0.482397858 | 0.000523977 | ribosomal protein S6 kinase polypeptide 6 |
| ENSMUSG00000050549 | 70617 | 5730508B09Rik | 0.481486862 | 0.047890046 | RIKEN cDNA 5730508B09 gene |
| ENSMUSG00000079410 | 100040671 | Gm2897 | 0.481384489 | 0.030463248 | predicted gene 2897 |
| ENSMUSG00000026994 | 14425 | Galnt3 | 0.481301663 | 0.011462086 | UDP-N-acetyl-alpha-D-galactosamine:polypeptide N-acetylgalactosaminyltransferase 3 |
| ENSMUSG00000045519 | 434377 | Zfp560 | 0.480667041 | 0.008392979 | zinc finger protein 560 |
| ENSMUSG00000035258 | 320712 | Abi3bp | 0.48051453 | 0.040637733 | ABI gene family, member 3 (NESH) binding protein |
| ENSMUSG00000029108 | 54216 | Pcdh7 | 0.480114553 | 0.011630092 | protocadherin 7 |
| ENSMUSG00000024517 | 225642 | Grp | 0.478337109 | 0.014460399 | gastrin releasing peptide |
| ENSMUSG00000064262 | 243374 | Gimap8 | 0.477865776 | 0.029858386 | GTPase, IMAP family member 8 |
| ENSMUSG00000063760 | 268291 | Rnf217 | 0.477650213 | 0.001527259 | ring finger protein 217 |
| ENSMUSG00000029823 | 192196 | Luc712 | 0.47751002 | 9.24E−05 | LUC7-like 2 (*S. cerevisiae*) |
| ENSMUSG00000097859 | | | 0.477151657 | 0.028481058 | |
| ENSMUSG00000074807 | | | 0.477024102 | 0.013589272 | |
| ENSMUSG00000022686 | 108105 | B3gnt5 | 0.476900957 | 0.036032893 | UDP-GlcNAc:betaGal beta-1,3-N-acetylglucosaminyltransferase 5 |
| ENSMUSG00000009376 | 17295 | Met | 0.476772959 | 0.008353927 | met proto-oncogene |
| ENSMUSG00000015653 | 74051 | Steap2 | 0.476721818 | 0.031942742 | six transmembrane epithelial antigen of prostate 2 |
| ENSMUSG00000038369 | 56406 | Ncoa6 | 0.476584379 | 0.000154452 | nuclear receptor coactivator 6 |
| ENSMUSG00000044770 | 268297 | Scml4 | 0.476275268 | 0.013210052 | sex comb on midleg-like 4 (*Drosophila*) |
| ENSMUSG00000022342 | 67498 | Kcnv1 | 0.475809806 | 0.001434658 | potassium channel, subfamily V, member 1 |
| ENSMUSG00000091002 | 70571 | Tcerg1l | 0.475078841 | 0.007355486 | transcription elongation regulator 1-like |
| ENSMUSG00000089774 | 53881 | Slc5a3 | 0.474851416 | 3.21E−05 | solute carrier family 5 (inositol transporters), member 3 |
| ENSMUSG00000034551 | 245596 | Hdx | 0.473827523 | 0.001788941 | highly divergent homeobox |
| ENSMUSG00000019230 | 16876 | Lhx9 | 0.472988428 | 0.003295585 | LIM homeobox protein 9 |
| ENSMUSG00000044365 | 319478 | Cxxc4 | 0.472643901 | 0.000250755 | CXXC finger 4 |
| ENSMUSG00000047230 | 12738 | Cldn2 | 0.471604867 | 0.039087346 | claudin 2 |
| ENSMUSG00000051329 | 59015 | Nup160 | 0.470739009 | 0.002788076 | nucleoporin 160 |
| ENSMUSG00000064357 | 17705 | ATP6 | 0.470339701 | 9.80E−05 | ATP synthase F0 subunit 6 |
| ENSMUSG00000098202 | | | 0.470193876 | 0.028011998 | |
| ENSMUSG00000025592 | 93837 | Dach2 | 0.470081883 | 0.018478822 | dachshund 2 (*Drosophila*) |
| ENSMUSG00000097876 | | | 0.468292086 | 0.014007017 | |
| ENSMUSG00000093383 | | | 0.468287156 | 0.040922821 | |
| ENSMUSG00000036466 | 214058 | Megf11 | 0.468248376 | 5.63E−06 | multiple EGF-like-domains 11 |
| ENSMUSG00000088036 | | | 0.468214061 | 0.044873606 | |
| ENSMUSG00000092341 | 72289 | Malat1 | 0.467798529 | 0.001445922 | metastasis associated lung adenocarcinoma transcript 1 (non-coding RNA) |

TABLE 2-continued

| Ensembl | Entrez | Symbol | log2FoldChange | padj | Name |
|---|---|---|---|---|---|
| ENSMUSG00000029212 | 14400 | Gabrb1 | 0.467450726 | 6.31E−06 | gamma-aminobutyric acid (GABA) A receptor, subunit beta 1 |
| ENSMUSG00000068859 | 381373 | Sp9 | 0.467149428 | 0.0330309 | trans-acting transcription factor 9 |
| ENSMUSG00000042942 | 381157 | Greb1l | 0.466809875 | 0.001441714 | growth regulation by estrogen in breast cancer-like |
| ENSMUSG00000090608 | | | 0.466778559 | 0.047069415 | |
| ENSMUSG00000021549 | 218397 | Rasa1 | 0.466365272 | 0.000104562 | RAS p21 protein activator 1 |
| ENSMUSG00000039313 | 209743 | AF529169 | 0.466245916 | 0.016059298 | cDNA sequence AF529169 |
| ENSMUSG00000040037 | 320840 | Negr1 | 0.46569292 | 0.000412819 | neuronal growth regulator 1 |
| ENSMUSG00000020680 | 70439 | Taf15 | 0.465486089 | 0.002259207 | TATA-box binding protein associated factor 15 |
| ENSMUSG00000048616 | 18121 | Nog | 0.4648968 | 0.033717539 | noggin |
| ENSMUSG00000063626 | 210801 | Unc5d | 0.462846052 | 0.000773339 | unc-5 netrin receptor D |
| ENSMUSG00000073274 | | | 0.462811444 | 0.007068264 | |
| ENSMUSG00000075324 | 60344 | Fign | 0.462428849 | 0.042816513 | fidgetin |
| ENSMUSG00000097737 | | | 0.461664177 | 0.044017617 | |
| ENSMUSG00000051235 | 209334 | Gen1 | 0.461537736 | 0.016879613 | GEN1, Holliday junction 5' flap endonuclease |
| ENSMUSG00000096629 | 100041012 | Gm3095 | 0.461338511 | 0.031409398 | predicted gene 3095 |
| ENSMUSG00000085917 | | | 0.460674704 | 0.030656145 | |
| ENSMUSG00000000365 | 30054 | Rnf17 | 0.460267859 | 0.018239947 | ring finger protein 17 |
| ENSMUSG00000086629 | 69964 | 2810403D21Rik | 0.460256471 | 0.020855555 | RIKEN cDNA 2810403D21 gene |
| ENSMUSG00000036377 | 320827 | C530008M17Rik | 0.459606235 | 1.09E−07 | RIKEN cDNA C530008M17 gene |
| ENSMUSG00000019936 | 13516 | Epyc | 0.459497614 | 0.011041008 | epiphycan |
| ENSMUSG00000050808 | 269328 | Muc15 | 0.458360381 | 0.04287943 | mucin 15 |
| ENSMUSG00000098284 | | | 0.45777125 | 0.014297364 | |
| ENSMUSG00000058006 | 100019 | Mdn1 | 0.456996536 | 4.54E−05 | midasin AAA ATPase 1 |
| ENSMUSG00000020027 | 216233 | Socs2 | 0.456812104 | 6.31E−06 | suppressor of cytokine signaling 2 |
| ENSMUSG00000097375 | | | 0.456677425 | 0.001687001 | |
| ENSMUSG00000032403 | 69478 | 2300009A05Rik | 0.455538111 | 0.037244366 | RIKEN cDNA 2300009A05 gene |
| ENSMUSG00000000560 | 14395 | Gabra2 | 0.455363454 | 0.016610567 | gamma-aminobutyric acid (GABA) A receptor, subunit alpha 2 |
| ENSMUSG00000033949 | 28105 | Trim36 | 0.455098111 | 0.001236347 | tripartite motif-containing 36 |
| ENSMUSG00000028034 | 51886 | Fubp1 | 0.454957929 | 0.000386363 | far upstream element (FUSE) binding protein 1 |
| ENSMUSG00000050148 | 54609 | Ubqln2 | 0.454510923 | 1.31E−05 | ubiquilin 2 |
| ENSMUSG00000097263 | | | 0.45435349 | 0.005959608 | |
| ENSMUSG00000061171 | 320106 | Slc38a11 | 0.453576 | 0.036476 | solute carrier family 38, member 11 |
| ENSMUSG00000026565 | 18986 | Pou2f1 | 0.452883411 | 0.00544402 | POU domain, class 2, transcription factor 1 |
| ENSMUSG00000045284 | 245404 | Dcaf12l1 | 0.452804978 | 0.001999733 | DDB1 and CUL4 associated factor 12-like 1 |
| ENSMUSG00000095193 | 1000441 | Gm20939 | 0.452112322 | 0.005496172 | predicted gene, 20939 |
| ENSMUSG00000032293 | 64602 | Ireb2 | 0.451859395 | 0.000641268 | iron responsive element binding protein 2 |
| ENSMUSG00000041649 | 245671 | Klf8 | 0.451785983 | 0.006738514 | Kruppel-like factor 8 |
| ENSMUSG00000064363 | 17719 | ND4 | 0.451733411 | 0.000374422 | NADH dehydrogenase subunit 4 |
| ENSMUSG00000043991 | 19290 | Pura | 0.451178646 | 0.002428227 | purine rich element binding protein A |
| ENSMUSG00000073293 | 102954 | Nudt10 | 0.451165018 | 0.003073692 | nudix (nucleoside diphosphate linked moiety X)-type motif 10 |
| ENSMUSG00000078902 | | | 0.451030452 | 0.009960377 | |
| ENSMUSG00000022329 | 56274 | Stk3 | 0.450679717 | 0.00584403 | serine/threonine kinase 3 |
| ENSMUSG00000033774 | 226304 | Npbwr1 | 0.45028203 | 0.041942814 | neuropeptides B/W receptor 1 |
| ENSMUSG00000021590 | 75571 | Spata9 | 0.450256278 | 0.033528287 | spermatogenesis associated 9 |
| ENSMUSG00000068617 | 66793 | Efcab1 | 0.449639982 | 0.011630092 | EF hand calcium binding domain 1 |
| ENSMUSG00000056004 | 231014 | 9330182L06Rik | 0.449336801 | 0.000665254 | RIKEN cDNA 9330182L06 gene |
| ENSMUSG00000026393 | 59125 | Nek7 | 0.449057521 | 0.016213124 | NIMA (never in mitosis gene a)-related expressed kinase 7 |
| ENSMUSG00000017548 | 52615 | Suz12 | 0.448551962 | 0.002483237 | suppressor of zeste 12 homolog (*Drosophila*) |
| ENSMUSG00000092448 | | | 0.446972465 | 0.029716511 | |
| ENSMUSG00000035948 | 380660 | Acss3 | 0.44690546 | 0.019103418 | acyl-CoA synthetase short-chain family member 3 |
| ENSMUSG00000044150 | 382252 | A830080D01Rik | 0.446434639 | 0.001709724 | RIKEN cDNA A830080D01 gene |
| ENSMUSG00000031095 | 72584 | Cul4b | 0.446030436 | 0.003471635 | cullin 4B |
| ENSMUSG00000031290 | 210297 | Lrch2 | 0.445987498 | 0.001656773 | leucine-rich repeats and calponin homology (CH) domain containing 2 |
| ENSMUSG00000068154 | 53626 | Insm1 | 0.445781717 | 0.02900422 | insulinoma-associated 1 |
| ENSMUSG00000034610 | 230594 | Zcchc11 | 0.443793903 | 0.000760116 | zinc finger, CCHC domain containing 11 |
| ENSMUSG00000089788 | | | 0.443483698 | 0.002899047 | |
| ENSMUSG00000045328 | 229841 | Cenpe | 0.443410529 | 0.023616654 | centromere protein E |
| ENSMUSG00000064368 | 17722 | ND6 | 0.443156764 | 0.001254458 | NADH dehydrogenase subunit 6 |
| ENSMUSG00000026492 | 15278 | Tfb2m | 0.442881793 | 0.000713891 | transcription factor B2, mitochondrial |
| ENSMUSG00000024268 | 108013 | Celf4 | 0.442334784 | 0.000291652 | CUGBP, Elav-like family member 4 |
| ENSMUSG00000046167 | 235379 | Gldn | 0.442195772 | 0.036713429 | gliomedin |
| ENSMUSG00000030077 | 12661 | Chl1 | 0.441899986 | 0.000608724 | cell adhesion molecule L1-like |
| ENSMUSG00000087606 | | | 0.441890779 | 0.026238123 | |

TABLE 2-continued

| Ensembl | Entrez | Symbol | log2FoldChange | padj | Name |
|---|---|---|---|---|---|
| ENSMUSG00000034701 | 18012 | Neurod1 | 0.441247335 | 0.003507256 | neurogenic differentiation 1 |
| ENSMUSG00000031200 | 17763 | Mtcp1 | 0.44077279 | 0.005831225 | mature T cell proliferation 1 |
| ENSMUSG00000042523 | 105000 | Dnal1 | 0.440733018 | 0.0043121 | dynein, axonemal, light chain 1 |
| ENSMUSG00000047161 | 71367 | Chst9 | 0.439464458 | 0.027847707 | carbohydrate (N-acetylgalactosamine 4-0) sulfotransferase 9 |
| ENSMUSG00000090698 | 381823 | Apold1 | 0.438442342 | 0.002485879 | apolipoprotein L domain containing |
| ENSMUSG00000022865 | 13052 | Cxadr | 0.438433983 | 0.002137938 | coxsackie virus and adenovirus receptor |
| ENSMUSG00000041685 | 218503 | Fcho2 | 0.437732257 | 0.002081857 | FCH domain only 2 |
| ENSMUSG00000045441 | 243385 | Gprin3 | 0.43748571 | 0.00033091 | GPRIN family member 3 |
| ENSMUSG00000018589 | 237213 | Glra2 | 0.436565672 | 0.013642625 | glycine receptor, alpha 2 subunit |
| ENSMUSG00000098066 | | | 0.436555924 | 0.048744199 | |
| ENSMUSG00000039704 | 320506 | Lmbrd2 | 0.436096581 | 0.000186491 | LMBR1 domain containing 2 |
| ENSMUSG00000020309 | 68044 | Chac2 | 0.435968323 | 0.001428319 | ChaC, cation transport regulator 2 |
| ENSMUSG00000055639 | 13134 | Dach1 | 0.435760984 | 0.012578958 | dachshund 1 (*Drosophila*) |
| ENSMUSG00000085328 | | | 0.43555647 | 0.010384153 | |
| ENSMUSG00000063273 | 74838 | Naa15 | 0.43515332 | 0.00037302 | N(alpha)-acetyltransferase 15, NatA auxiliary subunit |
| ENSMUSG00000004980 | 53379 | Hnrnpa2b1 | 0.434688219 | 0.006822305 | heterogeneous nuclear ribonucleoprotein A2/B1 |
| ENSMUSG00000037808 | 72826 | Fam76b | 0.434549646 | 0.000124156 | family with sequence similarity 76, member B |
| ENSMUSG00000028212 | 12448 | Ccne2 | 0.433632766 | 0.002137066 | cyclin E2 |
| ENSMUSG00000019564 | 13496 | Arid3a | 0.432840259 | 0.025138051 | AT rich interactive domain 3A (BRIGHT-like) |
| ENSMUSG00000069114 | 229055 | Zbtb10 | 0.432628225 | 0.004274052 | zinc finger and BTB domain containing 10 |
| ENSMUSG00000033031 | 224171 | C330027C09Rik | 0.432540663 | 0.001998408 | RIKEN cDNA C330027C09 gene |
| ENSMUSG00000095253 | 240064 | Zfp799 | 0.431297355 | 0.013938543 | zinc finger protein 799 |
| ENSMUSG00000090386 | 77994 | Mir99ahg | 0.430951745 | 0.014083479 | Mir99a and Mirlet7c-1 host gene (non-protein coding) |
| ENSMUSG00000028771 | 19248 | Ptpn12 | 0.430755509 | 0.002498541 | protein tyrosine phosphatase, non-receptor type 12 |
| ENSMUSG00000054976 | 241134 | Nyap2 | 0.430750119 | 0.005496172 | neuronal tyrosine-phophorylated phosphoinositide 3-kinase adaptor 2 |
| ENSMUSG00000084771 | 331547 | A230072E10Rik | 0.430142992 | 0.035678264 | RIKEN cDNA A230072E10 gene |
| ENSMUSG00000025077 | 55947 | Dclre1a | 0.42884201 | 0.031965353 | DNA cross-link repair 1A |
| ENSMUSG00000097337 | | | 0.428489063 | 0.037667395 | |
| ENSMUSG00000056870 | 70676 | Gulp1 | 0.428437839 | 0.02855274 | GULP, engulfment adaptor PTB domain containing 1 |
| ENSMUSG00000045991 | 225631 | Onecut2 | 0.428427627 | 0.002630166 | one cut domain, family member 2 |
| ENSMUSG00000003282 | 56711 | Plag1 | 0.428035955 | 0.011462458 | pleiomorphic adenoma gene 1 |
| ENSMUSG00000091511 | 625131 | Vmn2r87 | 0.427887831 | 0.032348689 | vomeronasal 2, receptor 87 |
| ENSMUSG00000055761 | 269513 | Nkain3 | 0.427315933 | 0.009752335 | Na+/K+ transporting ATPase interacting 3 |
| ENSMUSG00000023845 | 240028 | Lnpep | 0.427191255 | 0.000773339 | leucyl/cystinyl aminopeptidase |
| ENSMUSG00000057706 | 108797 | Mex3b | 0.426719369 | 0.027063785 | mex3 RNA binding family member B |
| ENSMUSG00000024766 | 381236 | Lipo3 | 0.426683033 | 0.016578272 | lipase, member O3 |
| ENSMUSG00000031626 | 234214 | Sorbs2 | 0.426620533 | 0.0002207 | sorbin and SH3 domain containing 2 |
| ENSMUSG00000086429 | 14910 | Gt(ROSA)26Sor | 0.426413189 | 0.003577611 | gene trap ROSA 26, Philippe Soriano |
| ENSMUSG00000074951 | 258439 | Olfr1309 | 0.426221316 | 0.029357419 | olfactory receptor 1309 |
| ENSMUSG00000026579 | 14067 | F5 | 0.426034615 | 0.043780099 | coagulation factor V |
| ENSMUSG00000036019 | 278279 | Tmtc2 | 0.425579817 | 0.002483237 | transmembrane and tetratricopeptide repeat containing 2 |
| ENSMUSG00000085234 | 102640951 | Gm15614 | 0.425573694 | 0.044227199 | predicted gene 15614 |
| ENSMUSG00000016756 | 12763 | Cmah | 0.424998175 | 0.015573718 | cytidine monophospho-N-acetylneuraminic acid hydroxylase |
| ENSMUSG00000036815 | 269109 | Dpp 10 | 0.424714128 | 0.012054644 | dipeptidylpeptidase 10 |
| ENSMUSG00000047216 | 227485 | Cdh19 | 0.423800199 | 0.001994942 | cadherin 19, type 2 |
| ENSMUSG00000051341 | 22710 | Zfp52 | 0.423365887 | 0.007038176 | zinc finger protein 52 |
| ENSMUSG00000020305 | 65257 | Asb3 | 0.422559088 | 0.001431759 | ankyrin repeat and SOCS box-containing 3 |
| ENSMUSG00000063632 | 20666 | Sox11 | 0.421513803 | 0.000233312 | SRY (sex determining region Y)-box 11 |
| ENSMUSG00000028019 | 54635 | Pdgfc | 0.421076901 | 0.030224424 | platelet-derived growth factor, C polypeptide |
| ENSMUSG00000031902 | 18021 | Nfatc3 | 0.420633195 | 0.001026104 | nuclear factor of activated T cells, cytoplasmic, calcineurin dependent 3 |
| ENSMUSG00000022309 | 11600 | Angpt1 | 0.420235591 | 0.02910784 | angiopoietin 1 |
| ENSMUSG00000059005 | 229279 | Hnrnpa3 | 0.419391817 | 0.000665254 | heterogeneous nuclear ribonucleoprotein A3 |
| ENSMUSG00000031278 | 50790 | Acsl4 | 0.419194953 | 0.001115808 | acyl-CoA synthetase long-chain family member 4 |
| ENSMUSG00000033308 | 99586 | Dpyd | 0.419166811 | 6.58E−05 | dihydropyrimidine dehydrogenase |
| ENSMUSG00000042595 | 245622 | Fam199x | 0.418156085 | 0.001946993 | family with sequence similarity 199, X-linked |
| ENSMUSG00000051951 | 497097 | Xkr4 | 0.417805571 | 0.000618195 | X-linked Kx blood group related 4 |
| ENSMUSG00000029017 | 73078 | Pmpcb | 0.417777004 | 5.70E−05 | peptidase (mitochondrial processing) beta |
| ENSMUSG00000068428 | 239789 | Gmnc | 0.417119146 | 0.028840169 | geminin coiled-coil domain containing |
| ENSMUSG00000021693 | 16563 | Kif2a | 0.415197513 | 0.000108197 | kinesin family member 2A |

TABLE 2-continued

| Ensembl | Entrez | Symbol | log2FoldChange | padj | Name |
|---|---|---|---|---|---|
| ENSMUSG00000073131 | 67048 | Vma21 | 0.414652729 | 0.007370161 | VMA21 vacuolar H+-ATPase homolog (S. cerevisiae) |
| ENSMUSG00000040322 | 229731 | Slc25a24 | 0.414199361 | 0.019924053 | solute carrier family 25 (mitochondrial carrier, phosphate carrier), member 24 |
| ENSMUSG00000047213 | 229096 | Ythdf3 | 0.413941548 | 0.002899047 | YTH domain family 3 |
| ENSMUSG00000073147 | 269630 | 5031425E22Rik | 0.41371887 | 0.011985063 | RIKEN cDNA 5031425E22 gene |
| ENSMUSG00000052155 | 11480 | Acvr2a | 0.413538933 | 0.000547886 | activin receptor IIA |
| ENSMUSG00000064369 | | | 0.413535427 | 0.048997766 | |
| ENSMUSG00000027132 | 72425 | Katnbl1 | 0.413528327 | 0.001694389 | katanin p80 subunit B like 1 |
| ENSMUSG00000035277 | 11878 | Arx | 0.413494471 | 0.012725383 | aristaless related homeobox |
| ENSMUSG00000067851 | 211673 | Arfgef1 | 0.41305857 | 0.000503803 | ADP-ribosylation factor guanine nucleotide-exchange factor 1(brefeldin A-inhibited) |
| ENSMUSG00000021700 | 67295 | Rab3c | 0.412885548 | 0.000910301 | RAB3C, member RAS oncogene family |
| ENSMUSG00000097619 | 75768 | 4833422M21Rik | 0.412812022 | 0.035359295 | RIKEN cDNA 4833422M21 gene |
| ENSMUSG00000035283 | 11554 | Adrb1 | 0.412688904 | 0.012230064 | adrenergic receptor, beta 1 |
| ENSMUSG00000042581 | 210417 | Thsd7b | 0.412596839 | 0.003550826 | thrombospondin, type I, domain containing 7B |
| ENSMUSG00000021959 | 50523 | Lats2 | 0.412590045 | 0.035643348 | large tumor suppressor 2 |
| ENSMUSG00000071267 | 73233 | Zfp942 | 0.412315636 | 0.00289335 | zinc finger protein 942 |
| ENSMUSG00000019841 | 19714 | Rev3l | 0.411768338 | 0.000773339 | REV3 like, DNA directed polymerase zeta catalytic subunit |
| ENSMUSG00000057924 | | | 0.411676587 | 0.027260292 | |
| ENSMUSG00000087651 | 69784 | 1500009L16Rik | 0.411569487 | 0.002701235 | RIKEN cDNA 1500009L16 gene |
| ENSMUSG00000041741 | 54611 | Pde3a | 0.411502478 | 0.010607724 | phosphodiesterase 3A, cGMP inhibited |
| ENSMUSG00000056260 | 321000 | Lrif1 | 0.410651669 | 0.003915191 | ligand dependent nuclear receptor interacting factor 1 |
| ENSMUSG00000064360 | 17718 | ND3 | 0.410520006 | 0.000312629 | NADH dehydrogenase subunit 3 |
| ENSMUSG00000033964 | 226470 | Zbtb41 | 0.410204447 | 0.004619104 | zinc finger and BTB domain containing 41 |
| ENSMUSG00000026500 | 66359 | Cox20 | 0.409544679 | 0.009746584 | COX20 Cox2 chaperone |
| ENSMUSG00000045031 | 207175 | Cetn4 | 0.409355161 | 0.010706841 | centrin 4 |
| ENSMUSG00000064356 | 17706 | ATP8 | 0.409260953 | 0.002259207 | ATP synthase F0 subunit 8 |
| ENSMUSG00000037814 | | | 0.408976953 | 0.014885882 | |
| ENSMUSG00000020745 | 18472 | Pafah1b1 | 0.408572359 | 0.008435647 | platelet-activating factor acetylhydrolase, isoform 1b, subunit 1 |
| ENSMUSG00000054693 | 11487 | Adam10 | 0.408474234 | 0.001694389 | a disintegrin and metallopeptidase domain 10 |
| ENSMUSG00000064345 | 17717 | ND2 | 0.408282022 | 0.001401869 | NADH dehydrogenase subunit 2 |
| ENSMUSG00000018800 | 217265 | Abca5 | 0.407537843 | 0.003780714 | ATP-binding cassette, sub-family A (ABC1), member 5 |
| ENSMUSG00000026319 | 227446 | 2310035C23Rik | 0.407511447 | 0.007281733 | RIKEN cDNA 2310035C23 gene |
| ENSMUSG00000027806 | 72033 | Tsc22d2 | 0.407086266 | 0.001441714 | TSC22 domain family, member 2 |
| ENSMUSG00000042460 | 94192 | C1galt1 | 0.406517393 | 0.005002265 | core 1 synthase, glycoprotein-N-acetylgalactosamine 3-beta-galactosyltransferase, 1 |
| ENSMUSG00000039801 | 73692 | 2410089E03Rik | 0.40641055 | 0.011255603 | RIKEN cDNA 2410089E03 gene |
| ENSMUSG00000014907 | 234344 | Naf1 | 0.406265954 | 0.01170562 | nuclear assembly factor 1 ribonucleoprotein |
| ENSMUSG00000064367 | 17721 | ND5 | 0.405983901 | 0.001768632 | NADH dehydrogenase subunit 5 |
| ENSMUSG00000046699 | 245446 | Slitrk4 | 0.405545764 | 0.000310253 | SLIT and NTRK-like family, member 4 |
| ENSMUSG00000039782 | 231207 | Cpeb2 | 0.405534353 | 0.000167537 | cytoplasmic polyadenylation element binding protein 2 |
| ENSMUSG00000050587 | 241568 | Lrrc4c | 0.40544767 | 0.000374222 | leucine rich repeat containing 4C |
| ENSMUSG00000032413 | 114713 | Rasa2 | 0.405388318 | 0.044406522 | RAS p21 protein activator 2 |
| ENSMUSG00000071362 | | | 0.405251988 | 0.045065078 | |
| ENSMUSG00000097469 | | | 0.405104679 | 0.019796215 | |
| ENSMUSG00000035847 | 15931 | Ids | 0.404760063 | 0.001467472 | iduronate 2-sulfatase |
| ENSMUSG00000064341 | 17716 | ND1 | 0.403341494 | 0.000773339 | NADH dehydrogenase subunit 1 |
| ENSMUSG00000028572 | 77963 | Hook1 | 0.403322322 | 0.004154959 | hook microtubule tethering protein 1 |
| ENSMUSG00000006373 | 53328 | Pgrmc1 | 0.402801352 | 0.003128875 | progesterone receptor membrane component 1 |
| ENSMUSG00000020530 | 217039 | Ggnbp2 | 0.402469411 | 0.002205344 | gametogenetin binding protein 2 |
| ENSMUSG00000071855 | 240261 | Ccdc112 | 0.40201877 | 0.009783693 | coiled-coil domain containing 112 |
| ENSMUSG00000067336 | 12168 | Bmpr2 | 0.401881216 | 0.002699758 | bone morphogenetic protein receptor, type II (serine/threonine kinase) |
| ENSMUSG00000063406 | 73130 | Tmed5 | 0.401505835 | 0.0012163 | transmembrane emp24 protein transport domain containing 5 |
| ENSMUSG00000026153 | 68187 | Fam135a | 0.401395569 | 0.002947909 | family with sequence similarity 135, member A |
| ENSMUSG00000020140 | 14160 | Lgr5 | 0.401286146 | 0.001370223 | leucine rich repeat containing G protein coupled receptor 5 |
| ENSMUSG00000025893 | 69149 | Kbtbd3 | 0.401081891 | 0.02613129 | kelch repeat and BTB (POZ) domain containing 3 |
| ENSMUSG00000022668 | 66067 | Gtpbp8 | 0.400878269 | 0.005002265 | GTP-binding protein 8 (putative) |
| ENSMUSG00000028125 | 11304 | Abca4 | 0.40051429 | 0.033850143 | ATP-binding cassette, sub-family A (ABC1), member 4 |
| ENSMUSG00000020275 | 19696 | Rel | 0.400421582 | 0.009538378 | reticuloendotheliosis oncogene |

TABLE 2-continued

| Ensembl | Entrez | Symbol | log2FoldChange | padj | Name |
|---|---|---|---|---|---|
| ENSMUSG00000029203 | 53323 | Ube2k | 0.400335519 | 0.017334618 | ubiquitin-conjugating enzyme E2K |
| ENSMUSG00000025019 | 212391 | Lcor | 0.399912636 | 0.000772175 | ligand dependent nuclear receptor corepressor |
| ENSMUSG00000025860 | 11798 | Xiap | 0.399811406 | 0.001999733 | X-linked inhibitor of apoptosis |
| ENSMUSG00000031647 | 71306 | Mfap3l | 0.399686014 | 0.002995299 | microfibrillar-associated protein 3-like |
| ENSMUSG00000027550 | 71710 | Lrrcc1 | 0.398556329 | 0.002126936 | leucine rich repeat and coiled-coil domain containing 1 |
| ENSMUSG00000032648 | 19309 | Pygm | 0.397836948 | 0.034186434 | muscle glycogen phosphorylase |
| ENSMUSG00000097911 | | | 0.397828069 | 0.048406436 | |
| ENSMUSG00000034480 | 54004 | Diaph2 | 0.397616533 | 0.005802278 | diaphanous related formin 2 |
| ENSMUSG00000054871 | 72309 | Tmem 158 | 0.397502458 | 0.040628364 | transmembrane protein 158 |
| ENSMUSG00000021244 | 56531 | Ylpm1 | 0.397307469 | 9.80E−05 | YLP motif containing 1 |
| ENSMUSG00000097073 | 320692 | 9430037G07Rik | 0.397067656 | 0.023445746 | RIKEN cDNA 9430037G07 gene |
| ENSMUSG00000043259 | 71721 | Fam13c | 0.396376642 | 0.007687952 | family with sequence similarity 13, member C |
| ENSMUSG00000098557 | 239217 | Kctd12 | 0.395595836 | 0.006634909 | potassium channel tetramerisation domain containing 12 |
| ENSMUSG00000026904 | 94229 | Slc4a10 | 0.395227169 | 0.000608724 | solute carrier family 4, sodium bicarbonate cotransporter-like, member 10 |
| ENSMUSG00000056763 | 211660 | Cspp1 | 0.394572599 | 1.64E−05 | centrosome and spindle pole associated protein 1 |
| ENSMUSG00000053877 | 100043597 | Srcap | 0.393768783 | 0.037183844 | Snf2-related CREBBP activator protein |
| ENSMUSG00000029265 | 13486 | Dr1 | 0.393490888 | 0.005025262 | down-regulator of transcription 1 |
| ENSMUSG00000067377 | 56496 | Tspan6 | 0.393027336 | 0.004437582 | tetraspanin 6 |
| ENSMUSG00000032377 | 235527 | Plscr4 | 0.392562919 | 0.013513918 | phospholipid scramblase 4 |
| ENSMUSG00000097796 | 100504601 | Gm16702 | 0.392493032 | 0.026533867 | predicted gene, 16702 |
| ENSMUSG00000021816 | 19056 | Ppp3cb | 0.392308377 | 0.002899047 | protein phosphatase 3, catalytic subunit, beta isoform |
| ENSMUSG00000060735 | 239336 | Rxfp3 | 0.392180266 | 0.022502596 | relaxin family peptide receptor 3 |
| ENSMUSG00000026014 | 77300 | Raph1 | 0.391584907 | 0.00437341 | Ras association (RalGDS/AF-6) and pleckstrin homology domains 1 |
| ENSMUSG00000089756 | 667962 | Zfp966 | 0.391334759 | 0.004947973 | zinc finger protein 966 |
| ENSMUSG00000093436 | | | 0.391298589 | 0.043553862 | |
| ENSMUSG00000047412 | 235132 | Zbtb44 | 0.39124058 | 0.001276768 | zinc finger and BTB domain containing 44 |
| ENSMUSG00000063446 | 272031 | Plppr1 | 0.391042093 | 0.003104002 | phospholipid phosphatase related 1 |
| ENSMUSG00000078898 | 100043914 | Zfp968 | 0.39093535 | 0.001441714 | zinc finger protein 968 |
| ENSMUSG00000031229 | 22589 | Atrx | 0.39064903 | 0.001794256 | alpha thalassemia/mental retardation syndrome X-linked |
| ENSMUSG00000039607 | 207181 | Rbms3 | 0.390470336 | 0.002468217 | RNA binding motif, single stranded interacting protein |
| ENSMUSG00000026395 | 19264 | Ptprc | 0.390449459 | 0.029624426 | protein tyrosine phosphatase, receptor type, C |
| ENSMUSG00000085334 | | | 0.390305843 | 0.015909519 | |
| ENSMUSG00000082724 | | | 0.390028498 | 0.034386122 | |
| ENSMUSG00000064352 | | | 0.390010974 | 0.028304822 | |
| ENSMUSG00000021696 | 74559 | Elovl7 | 0.389941282 | 0.049474183 | ELOVL family member 7, elongation of long chain fatty acids (yeast) |
| ENSMUSG00000040423 | 381305 | Rc3h1 | 0.38990587 | 0.000215182 | RING CCCH (C3H) domains 1 |
| ENSMUSG00000033793 | 108664 | Atp6v1h | 0.389764354 | 0.01523467 | ATPase, H+ transporting, lysosomal V1 subunit H |
| ENSMUSG00000025815 | 209692 | Dhtkd1 | 0.389530367 | 0.016643684 | dehydrogenase E1 and transketolase domain containing 1 |
| ENSMUSG00000017057 | 16164 | Il13ra1 | 0.388658501 | 0.01254821 | interleukin 13 receptor, alpha 1 |
| ENSMUSG00000014813 | 20855 | Stc1 | 0.388476626 | 0.009398557 | stanniocalcin 1 |
| ENSMUSG00000024073 | 12211 | Birc6 | 0.388364847 | 2.76E−05 | baculoviral IAP repeat-containing 6 |
| ENSMUSG00000071753 | 331424 | C230004F18Rik | 0.388336601 | 0.01277139 | RIKEN cDNA C230004F18 gene |
| ENSMUSG00000019256 | 11622 | Ahr | 0.388333054 | 0.002391979 | aryl-hydrocarbon receptor |
| ENSMUSG00000048347 | 93889 | Pcdhb18 | 0.387820961 | 0.003980677 | protocadherin beta 18 |
| ENSMUSG00000037434 | 22782 | Slc30a1 | 0.38736032 | 0.001401869 | solute carrier family 30 (zinc transporter), member 1 |
| ENSMUSG00000040118 | 12293 | Cacna2d1 | 0.387356822 | 0.005712909 | calcium channel, voltage-dependent, alpha2/delta subunit 1 |
| ENSMUSG00000027520 | 73884 | Zdbf2 | 0.387293613 | 0.01556022 | zinc finger, DBF-type containing 2 |
| ENSMUSG00000026156 | 280645 | B3gat2 | 0.386765911 | 0.001179584 | beta-1,3-glucuronyltransferase 2 (glucuronosyltransferase S) |
| ENSMUSG00000049511 | 15551 | Htr1b | 0.38646666 | 0.036036001 | 5-hydroxytryptamine (serotonin) receptor 1B |
| ENSMUSG00000027168 | 18508 | Pax6 | 0.386305035 | 0.012725383 | paired box 6 |
| ENSMUSG00000097367 | | | 0.385903105 | 0.032388462 | |
| ENSMUSG00000073664 | 269198 | Nbeal1 | 0.385341399 | 0.00194812 | neurobeachin like 1 |
| ENSMUSG00000031112 | 70415 | Stk26 | 0.385262937 | 0.011462086 | serine/threonine kinase 26 |
| ENSMUSG00000031246 | 56726 | Sh3bgrl | 0.385106113 | 0.012488008 | SH3-binding domain glutamic acid-rich protein like |
| ENSMUSG00000055963 | 208820 | Triqk | 0.384888244 | 0.015909519 | triple QxxK/R motif containing |
| ENSMUSG00000039375 | 244484 | Wdr17 | 0.384872069 | 8.36E−05 | WD repeat domain 17 |
| ENSMUSG00000056673 | 20592 | Kdm5d | 0.3843982 | 0.002899047 | lysine (K)-specific demethylase 5D |

TABLE 2-continued

| Ensembl | Entrez | Symbol | log2FoldChange | padj | Name |
|---|---|---|---|---|---|
| ENSMUSG00000031659 | 11513 | Adcy7 | 0.38431988 | 0.033530806 | adenylate cyclase 7 |
| ENSMUSG00000033319 | 240263 | Fem1c | 0.384036539 | 0.001531229 | fem-1 homolog c (*C.elegans*) |
| ENSMUSG00000022892 | 11820 | App | 0.383702589 | 0.048569817 | amyloid beta (A4) precursor protein |
| ENSMUSG00000056758 | 15364 | Hmga2 | 0.383569479 | 0.039834855 | high mobility group AT-hook 2 |
| ENSMUSG00000030729 | 70974 | Pgm2l1 | 0.383558772 | 0.002908433 | phosphoglucomutase 2-like 1 |
| ENSMUSG00000020122 | 13649 | Egfr | 0.383350343 | 0.000486312 | epidermal growth factor receptor |
| ENSMUSG00000029267 | 17765 | Mtf2 | 0.383131536 | 0.000136769 | metal response element binding transcription factor 2 |
| ENSMUSG00000042473 | 245638 | Tbc1d8b | 0.382639977 | 0.017334618 | TBC1 domain family, member 8B |
| ENSMUSG00000049100 | 18526 | Pcdh10 | 0.382610072 | 0.00289335 | protocadherin 10 |
| ENSMUSG00000043629 | 67080 | 1700019D03Rik | 0.382569785 | 0.002080874 | RIKEN cDNA 1700019D03 gene |
| ENSMUSG00000035236 | 320271 | Scai | 0.382382698 | 0.002275482 | suppressor of cancer cell invasion |
| ENSMUSG00000031367 | 108012 | Ap1s2 | 0.382335072 | 0.009191292 | adaptor-related protein complex 1, sigma 2 subunit |
| ENSMUSG00000042446 | 67785 | Zmym4 | 0.38160862 | 0.009122426 | zinc finger, MYM-type 4 |
| ENSMUSG00000078870 | | | 0.381188517 | 0.000186491 | |
| ENSMUSG00000051285 | 319263 | Pcmtd1 | 0.381181069 | 0.001913946 | protein-L-isoaspartate (D-aspartate) O-methyltransferase domain containing 1 |
| ENSMUSG00000025001 | 15201 | Hells | 0.381106818 | 0.017498886 | helicase, lymphoid specific |
| ENSMUSG00000046532 | 11835 | Ar | 0.380595358 | 0.000641268 | androgen receptor |
| ENSMUSG00000022698 | 72117 | Naa50 | 0.380279602 | 0.005169983 | N(alpha)-acetyltransferase 50, NatE catalytic subunit |
| ENSMUSG00000031870 | 18667 | Pgr | 0.38022898 | 0.012004419 | progesterone receptor |
| ENSMUSG00000098927 | | | 0.380143959 | 0.030468562 | |
| ENSMUSG00000058897 | 77018 | Col25a1 | 0.3799763 | 0.010339821 | collagen, type XXV, alpha 1 |
| ENSMUSG00000031343 | 14396 | Gabra3 | 0.379974728 | 0.004754638 | gamma-aminobutyric acid (GABA) A receptor, subunit alpha 3 |
| ENSMUSG00000000838 | 14265 | Fmr1 | 0.379771464 | 0.002922923 | fragile X mental retardation syndrome 1 |
| ENSMUSG00000021127 | 12192 | Zfp36l1 | 0.379667077 | 0.043310304 | zinc finger protein 36, C3H type-like 1 |
| ENSMUSG00000009628 | 104271 | Tex15 | 0.37965156 | 0.028959511 | testis expressed gene 15 |
| ENSMUSG00000059921 | 22253 | Unc5c | 0.379090986 | 4.55E−05 | unc-5 netrin receptor C |
| ENSMUSG00000004360 | 212448 | 9330159F19Rik | 0.379079133 | 0.002356321 | RIKEN cDNA 9330159F19 gene |
| ENSMUSG00000036371 | 66870 | Serbp1 | 0.378949379 | 0.011144735 | serpine1 mRNA binding protein 1 |
| ENSMUSG00000033849 | 26878 | B3galt2 | 0.378725929 | 0.000382537 | UDP-Gal:betaGlcNAc beta 1,3-galactosyltransferase, polypeptide 2 |
| ENSMUSG00000036916 | 208968 | Zfp280c | 0.378587254 | 0.003780714 | zinc finger protein 280C |
| ENSMUSG00000072763 | | | 0.378570967 | 0.00437341 | |
| ENSMUSG00000067780 | 94227 | Pi15 | 0.378345825 | 0.017191724 | peptidase inhibitor 15 |
| ENSMUSG00000028646 | 54170 | Rragc | 0.377811013 | 0.010787801 | Ras-related GTP binding C |
| ENSMUSG00000031242 | 67028 | 2610002M06Rik | 0.37757001 | 0.00519215 | RIKEN cDNA 2610002M06 gene |
| ENSMUSG00000027006 | 66861 | Dnajc10 | 0.377273812 | 0.0042042 | DnaJ heat shock protein family (Hsp40) member C10 |
| ENSMUSG00000073062 | 668166 | Zxdb | 0.376754582 | 0.015865452 | zinc finger, X-linked, duplicated B |
| ENSMUSG00000078624 | 259104 | Olfr613 | 0.376695862 | 0.048312414 | olfactory receptor 613 |
| ENSMUSG00000022311 | 239420 | Csmd3 | 0.376548619 | 0.000547117 | CUB and Sushi multiple domains 3 |
| ENSMUSG00000020120 | 56193 | Plek | 0.376150635 | 0.006032204 | pleckstrin |
| ENSMUSG00000020594 | 80913 | Pum2 | 0.375340011 | 0.00240031 | pumilio RNA-binding family member 2 |
| ENSMUSG00000020014 | 380654 | Cfap54 | 0.375328265 | 0.039525489 | cilia and flagella associated protein 54 |
| ENSMUSG00000035293 | 217558 | G2e3 | 0.375113677 | 0.005445438 | G2/M-phase specific E3 ubiquitin ligase |
| ENSMUSG00000020130 | 66687 | Tbc1d15 | 0.3750215 | 0.00428232 | TBC1 domain family, member 15 |
| ENSMUSG00000090110 | 17763 | Mtcp1 | 0.374754408 | 0.034106521 | mature T cell proliferation 1 |
| ENSMUSG00000022119 | 74213 | Rbm26 | 0.37471698 | 0.000387043 | RNA binding motif protein 26 |
| ENSMUSG00000026761 | 26428 | Orc4 | 0.374659035 | 0.002498541 | origin recognition complex, subunit 4 |
| ENSMUSG00000064370 | 17711 | CYTB | 0.374573946 | 0.003076373 | cytochrome b |
| ENSMUSG00000037270 | 229227 | 4932438A13Rik | 0.374521674 | 0.004274052 | RIKEN cDNA 4932438A13 gene |
| ENSMUSG00000030779 | 19647 | Rbbp6 | 0.37406757 | 0.000244505 | retinoblastoma binding protein 6 |
| ENSMUSG00000048108 | 319776 | Tmem72 | 0.373726234 | 0.027009464 | transmembrane protein 72 |
| ENSMUSG00000069755 | | | 0.373277173 | 0.017297968 | |
| ENSMUSG00000020037 | 71137 | Rfx4 | 0.373227632 | 0.016005104 | regulatory factor X, 4 (influences HLA class II expression) |
| ENSMUSG00000027981 | 67225 | Rnpc3 | 0.373126818 | 0.002571517 | RNA-binding region (RNP1, RRM) containing 3 |
| ENSMUSG00000025666 | 192216 | Tmem47 | 0.372501029 | 0.019322459 | transmembrane protein 47 |
| ENSMUSG00000044288 | 12801 | Cnr1 | 0.372470147 | 0.001181038 | cannabinoid receptor 1 (brain) |
| ENSMUSG00000056342 | 17847 | Usp34 | 0.372230225 | 0.006822305 | ubiquitin specific peptidase 34 |
| ENSMUSG00000021377 | 110052 | Dek | 0.372101928 | 0.008955901 | DEK oncogene (DNA binding) |
| ENSMUSG00000024172 | 240119 | St6gal2 | 0.37192624 | 0.018894423 | beta galactoside alpha 2,6 sialyltransferase 2 |
| ENSMUSG00000055737 | 14600 | Ghr | 0.371237452 | 0.006515271 | growth hormone receptor |
| ENSMUSG00000015568 | 16956 | Lpl | 0.370897609 | 0.012384943 | lipoprotein lipase |
| ENSMUSG00000050069 | 23893 | Grem2 | 0.370702049 | 0.022571151 | gremlin 2, DAN family BMP antagonist |
| ENSMUSG00000044461 | 219134 | Shisa2 | 0.370064634 | 0.030907801 | shisa family member 2 |
| ENSMUSG00000052783 | 14772 | Grk4 | 0.369704855 | 0.042416852 | G protein-coupled receptor kinase 4 |
| ENSMUSG00000056579 | 544752 | Tug1 | 0.369544561 | 0.007699151 | taurine upregulated gene 1 |
| ENSMUSG00000034098 | 213262 | Fstl5 | 0.369501762 | 0.009986585 | follistatin-like 5 |
| ENSMUSG00000030760 | 66190 | Acer3 | 0.36926167 | 0.040439707 | alkaline ceramidase 3 |
| ENSMUSG00000037674 | 319758 | Rfx7 | 0.369087276 | 0.000228196 | regulatory factor X, 7 |

TABLE 2-continued

| Ensembl | Entrez | Symbol | log2FoldChange | padj | Name |
|---|---|---|---|---|---|
| ENSMUSG00000051515 | 58238 | Fam181b | 0.369059706 | 0.013823958 | family with sequence similarity 181, member B |
| ENSMUSG00000017291 | 216965 | Taok1 | 0.368973629 | 0.004779417 | TAO kinase 1 |
| ENSMUSG00000032384 | 214897 | Csnk1g1 | 0.368887534 | 0.001624593 | casein kinase 1, gamma 1 |
| ENSMUSG00000028134 | 56195 | Ptbp2 | 0.368721932 | 0.004139301 | polypyrimidine tract binding protein 2 |
| ENSMUSG00000090061 | 319807 | Nwd2 | 0.36834537 | 0.023616654 | NACHT and WD repeat domain containing 2 |
| ENSMUSG00000021548 | 66671 | Ccnh | 0.368304699 | 0.001824594 | cyclin H |
| ENSMUSG00000075470 | 380959 | Alg10b | 0.368268958 | 0.006039119 | asparagine-linked glycosylation 10B (alpha-1,2-glucosyltransferase) |
| ENSMUSG00000034349 | 70099 | Smc4 | 0.36799407 | 0.003234256 | structural maintenance of chromosomes 4 |
| ENSMUSG00000027160 | 68201 | Ccdc34 | 0.367666871 | 0.004315106 | coiled-coil domain containing 34 |
| ENSMUSG00000074994 | 99003 | Qser1 | 0.367350635 | 0.000291652 | glutamine and serine rich 1 |
| ENSMUSG00000055228 | 71508 | Zfp935 | 0.367252084 | 0.018183863 | zinc finger protein 935 |
| ENSMUSG00000039910 | 17684 | Cited2 | 0.367141159 | 0.009349993 | Cbp/p300-interacting transactivator, with Glu/Asp-rich carboxy-terminal domain, 2 |
| ENSMUSG00000071424 | 14804 | Grid2 | 0.366999805 | 0.01277139 | glutamate receptor, ionotropic, delta 2 |
| ENSMUSG00000045780 | 258189 | Olfr624 | 0.36679386 | 0.042565195 | olfactory receptor 624 |
| ENSMUSG00000029833 | 21848 | Trim24 | 0.366745088 | 0.00289335 | tripartite motif-containing 24 |
| ENSMUSG00000044501 | 224598 | Zfp758 | 0.366522494 | 0.017200534 | zinc finger protein 758 |
| ENSMUSG00000062184 | 50786 | Hs6st2 | 0.366441043 | 0.035883779 | heparan sulfate 6-O-sulfotransferase 2 |
| ENSMUSG00000096014 | 20664 | Sox1 | 0.366358402 | 0.021606747 | SRY (sex determining region Y)-box 1 |
| ENSMUSG00000032525 | 18087 | Nktr | 0.366238288 | 5.12E−05 | natural killer tumor recognition sequence |
| ENSMUSG00000073678 | 241062 | Pgap1 | 0.365875245 | 0.009303766 | post-GPI attachment to proteins 1 |
| ENSMUSG00000003929 | 224694 | Zfp81 | 0.365793854 | 0.005496172 | zinc finger protein 81 |
| ENSMUSG00000021730 | 15165 | Hcn1 | 0.365746076 | 0.001763689 | hyperpolarization-activated, cyclic nucleotide-gated K+ 1 |
| ENSMUSG00000027349 | 68215 | Fam98b | 0.36545434 | 0.005859215 | family with sequence similarity 98, member B |
| ENSMUSG00000080709 | | | 0.365090151 | 0.049067771 | |
| ENSMUSG00000036202 | 51869 | Rif1 | 0.365073912 | 0.008955901 | replication timing regulatory factor 1 |
| ENSMUSG00000097769 | 100503380 | Snhg4 | 0.36504966 | 0.013316028 | small nucleolar RNA host gene 4 |
| ENSMUSG00000074345 | 244882 | Tnfaip8l3 | 0.364984664 | 0.002296608 | tumor necrosis factor, alpha-induced protein 8-like 3 |
| ENSMUSG00000051451 | 233490 | Crebzf | 0.364765871 | 0.013315984 | CREB/ATF bZIP transcription factor |
| ENSMUSG00000067942 | 224585 | Zfp160 | 0.36462944 | 0.003471635 | zinc finger protein 160 |
| ENSMUSG00000039046 | 98910 | Usp6nl | 0.364336614 | 0.024781175 | USP6 N-terminal like |
| ENSMUSG00000002617 | 22700 | Zfp40 | 0.364256516 | 0.003544118 | zinc finger protein 40 |
| ENSMUSG00000036197 | 223827 | Gxylt1 | 0.364188492 | 0.002564879 | glucoside xylosyltransferase 1 |
| ENSMUSG00000030209 | 14812 | Grin2b | 0.364119944 | 0.003036844 | glutamate receptor, ionotropic, NMDA2B (epsilon 2) |
| ENSMUSG00000058748 | 233987 | Zfp958 | 0.363331874 | 0.039135095 | zinc finger protein 958 |
| ENSMUSG00000087620 | 100043213 | 5330434G04Rik | 0.363109372 | 0.005831496 | RIKEN cDNA 5330434G04 gene |
| ENSMUSG00000025094 | 214084 | Slc18a2 | 0.363019737 | 0.026161559 | solute carrier family 18 (vesicular monoamine), member 2 |
| ENSMUSG00000034021 | 100710 | Pds5b | 0.362994583 | 0.00458175 | PDS5 cohesin associated factor B |
| ENSMUSG00000034780 | 26877 | B3galt1 | 0.362891049 | 0.004494339 | UDP-Gal:betaGlcNAc beta 1,3-galactosyltransferase, polypeptide 1 |
| ENSMUSG00000016984 | 68145 | Etaa1 | 0.362850771 | 0.008718986 | Ewing tumor-associated antigen 1 |
| ENSMUSG00000031938 | 70984 | 4931406C07Rik | 0.362704353 | 0.023342687 | RIKEN cDNA 4931406C07 gene |
| ENSMUSG00000060314 | 407812 | Zfp941 | 0.362587762 | 0.000652509 | zinc finger protein 941 |
| ENSMUSG00000046230 | 271564 | Vps13a | 0.362347328 | 0.004702628 | vacuolar protein sorting 13A |
| ENSMUSG00000071862 | 107065 | Lrrtm2 | 0.36232506 | 0.007948733 | leucine rich repeat transmembrane neuronal 2 |
| ENSMUSG00000097461 | | | 0.362030176 | 0.039025991 | |
| ENSMUSG00000034163 | 216345 | Zfc3h1 | 0.361954837 | 0.01403019 | zinc finger, C3H1-type containing |
| ENSMUSG00000028229 | 66302 | Rmdn1 | 0.36172956 | 0.002590947 | regulator of microtubule dynamics 1 |
| ENSMUSG00000028222 | 12307 | Calb1 | 0.361592724 | 0.016129379 | calbindin 1 |
| ENSMUSG00000032417 | 69519 | Rwdd2a | 0.361405251 | 0.002391979 | RWD domain containing 2A |
| ENSMUSG00000058624 | 14544 | Gda | 0.361356649 | 0.000893237 | guanine deaminase |
| ENSMUSG00000044465 | 74349 | Fam160a2 | 0.360997026 | 0.00011403 | family with sequence similarity 160, member A2 |
| ENSMUSG00000063887 | 192167 | Nlgn1 | 0.360866288 | 0.007447036 | neuroligin 1 |
| ENSMUSG00000044350 | 210808 | Lacc1 | 0.360639443 | 0.03033682 | laccase (multicopper oxidoreductase) domain containing 1 |
| ENSMUSG00000030075 | 18488 | Cntn3 | 0.360615926 | 0.01338217 | contactin 3 |
| ENSMUSG00000030265 | 16653 | Kras | 0.360431445 | 0.000738982 | Kirsten rat sarcoma viral oncogene homolog |
| ENSMUSG00000070733 | 72313 | Fryl | 0.35959363 | 0.01759523 | FRY like transcription coactivator |
| ENSMUSG00000025979 | 19070 | Mob4 | 0.359204078 | 0.018647984 | MOB family member 4, phocein |
| ENSMUSG00000025321 | 320910 | Itgb8 | 0.358670566 | 0.017048863 | integrin beta 8 |
| ENSMUSG00000043668 | 244579 | Tox3 | 0.358090534 | 0.043469419 | TOX high mobility group box family member 3 |
| ENSMUSG00000027829 | 56706 | Ccnl1 | 0.357951592 | 0.007776971 | cyclin L1 |
| ENSMUSG00000052364 | 102941 | B630019K06Rik | 0.357886868 | 0.008378227 | novel protein similar to F-box and leucine-rich repeat protein 17 (Fbxl17) |
| ENSMUSG00000062561 | | | 0.357799014 | 0.03193194 | |

TABLE 2-continued

| Ensembl | Entrez | Symbol | log2FoldChange | padj | Name |
|---|---|---|---|---|---|
| ENSMUSG00000029878 | 386753 | Dbpht2 | 0.357357106 | 0.040794538 | DNA binding protein with his-thr domain |
| ENSMUSG00000097340 | | | 0.357185215 | 0.011318474 | |
| ENSMUSG00000063253 | 56367 | Scoc | 0.357071202 | 0.012004419 | short coiled-coil protein |
| ENSMUSG00000051671 | 67892 | Coa6 | 0.3559681 | 0.039488098 | cytochrome c oxidase assembly factor 6 |
| ENSMUSG00000005371 | 225055 | Fbxo11 | 0.355796763 | 0.002911871 | F-box protein 11 |
| ENSMUSG00000022052 | 71978 | Ppp2r2a | 0.355652143 | 2.53E−06 | protein phosphatase 2, regulatory subunit B, alpha |
| ENSMUSG00000093752 | 13480 | Dpm1 | 0.355455608 | 0.000260636 | dolichol-phosphate (beta-D) mannosyltransferase 1 |
| ENSMUSG00000022247 | 67832 | Brix1 | 0.35537098 | 0.034486323 | BRX1, biogenesis of ribosomes |
| ENSMUSG00000055373 | 14348 | Fut9 | 0.355217926 | 0.019153869 | fucosyltransferase 9 |
| ENSMUSG00000034732 | 93728 | Pabpc5 | 0.354897946 | 0.038423662 | poly(A) binding protein, cytoplasmic 5 |
| ENSMUSG00000074785 | 54712 | Plxnc1 | 0.354738533 | 0.000640548 | plexin C1 |
| ENSMUSG00000032328 | 69981 | Tmem30a | 0.354521039 | 0.01088127 | transmembrane protein 30A |
| ENSMUSG00000035597 | 328110 | Prpf39 | 0.354166887 | 0.001525992 | pre-mRNA processing factor 39 |
| ENSMUSG00000047227 | 217648 | Gm527 | 0.354157553 | 0.046147529 | predicted gene 527 |
| ENSMUSG00000038816 | 54366 | Ctnnal1 | 0.354050634 | 0.02223065 | catenin (cadherin associated protein), alpha-like 1 |
| ENSMUSG00000037610 | 72413 | Kcnmb2 | 0.35403465 | 0.041279551 | potassium large conductance calcium-activated channel, subfamily M, beta member 2 |
| ENSMUSG00000042851 | 78751 | Zc3h6 | 0.353778489 | 0.01012773 | zinc finger CCCH type containing 6 |
| ENSMUSG00000055480 | 238690 | Zfp458 | 0.353503474 | 0.006916914 | zinc finger protein 458 |
| ENSMUSG00000035840 | 80289 | Lysmd3 | 0.353413084 | 0.012384943 | LysM, putative peptidoglycan-binding, domain containing 3 |
| ENSMUSG00000043881 | 211255 | Kbtbd7 | 0.353396253 | 0.010352088 | kelch repeat and BTB (POZ) domain containing 7 |
| ENSMUSG00000038024 | 329877 | Dennd4c | 0.353050281 | 0.024699207 | DENN/MADD domain containing 4C |
| ENSMUSG00000031592 | 18536 | Pcm1 | 0.353017811 | 0.016463732 | pericentriolar material 1 |
| ENSMUSG00000052372 | 331461 | Il1rapl1 | 0.352810717 | 0.0048687 | interleukin 1 receptor accessory protein-like 1 |
| ENSMUSG00000032423 | 56403 | Syncrip | 0.352657668 | 0.006391429 | synaptotagmin binding, cytoplasmic RNA interacting protein |
| ENSMUSG00000038147 | 12523 | Cd84 | 0.352609922 | 0.020167127 | CD84 antigen |
| ENSMUSG00000030031 | 243574 | Kbtbd8 | 0.352595716 | 0.022899126 | kelch repeat and BTB (POZ) domain containing 8 |
| ENSMUSG00000041688 | 27494 | Amot | 0.352268072 | 0.001610457 | angiomotin |
| ENSMUSG00000020362 | 104625 | Cnot6 | 0.352120871 | 0.003988806 | CCR4-NOT transcription complex, subunit 6 |
| ENSMUSG00000030386 | 67370 | Zfp606 | 0.351748777 | 0.016444908 | zinc finger protein 606 |
| ENSMUSG00000036282 | 70646 | Naa30 | 0.35164749 | 0.009338173 | N(alpha)-acetyltransferase 30, NatC catalytic subunit |
| ENSMUSG00000036095 | 217480 | Dgkb | 0.351215939 | 0.006434883 | diacylglycerol kinase, beta |
| ENSMUSG00000040918 | 116914 | Slc19a2 | 0.351015207 | 0.022502596 | solute carrier family 19 (thiamine transporter), member 2 |
| ENSMUSG00000075700 | 69227 | Selt | 0.350969733 | 0.008152517 | selenoprotein T |
| ENSMUSG00000078887 | 626832 | Gm6710 | 0.350967422 | 0.029270978 | predicted gene 6710 |
| ENSMUSG00000075318 | 110876 | Scn2a | 0.350845006 | 0.000773339 | sodium channel, voltage-gated, type II, alpha |
| ENSMUSG00000064351 | 17708 | COX1 | 0.350773717 | 0.006443265 | cytochrome c oxidase subunit I |
| ENSMUSG00000085241 | 399101 | Snhg3 | 0.350182581 | 0.048672076 | small nucleolar RNA host gene 3 |
| ENSMUSG00000030759 | 67420 | Far1 | 0.349728914 | 0.000167537 | fatty acyl CoA reductase 1 |
| ENSMUSG00000026753 | 67857 | Ppp6c | 0.349656767 | 0.00289335 | protein phosphatase 6, catalytic subunit |
| ENSMUSG00000078307 | 330941 | AI593442 | 0.34944689 | 0.035833724 | expressed sequence AI593442 |
| ENSMUSG00000015222 | 17756 | Map2 | 0.349196723 | 0.004738391 | microtubule-associated protein 2 |
| ENSMUSG00000050321 | 246317 | Neto1 | 0.34919392 | 0.000315513 | neuropilin (NRP) and tolloid (TLL)-like 1 |
| ENSMUSG00000051098 | 72852 | Mblac2 | 0.348913181 | 0.009115655 | metallo-beta-lactamase domain containing 2 |
| ENSMUSG00000033306 | 210126 | Lpp | 0.348873239 | 0.012953688 | LIM domain containing preferred translocation partner in lipoma |
| ENSMUSG00000036990 | 73945 | Otud4 | 0.348649597 | 0.002890609 | OTU domain containing 4 |
| ENSMUSG00000001300 | 13642 | Efnb2 | 0.348258447 | 0.022746493 | ephrin B2 |
| ENSMUSG00000049252 | 94217 | Lrp1b | 0.34805745 | 0.016696572 | low density lipoprotein-related protein 1B (deleted in tumors) |
| ENSMUSG00000052479 | 234624 | A330008L17Rik | 0.347944722 | 0.028890287 | RIKEN cDNA A330008L17 gene |
| ENSMUSG00000036676 | 237500 | Tmtc3 | 0.347654776 | 0.004836381 | transmembrane and tetratricopeptide repeat containing 3 |
| ENSMUSG00000008333 | 20639 | Snrpb2 | 0.347507723 | 0.005438399 | U2 small nuclear ribonucleoprotein B |
| ENSMUSG00000091754 | 100041151 | Gm3636 | 0.347484421 | 0.031366726 | predicted gene 3636 |
| ENSMUSG00000003746 | 17155 | Man1a | 0.347303869 | 0.025322192 | mannosidase 1, alpha |
| ENSMUSG00000027479 | 13589 | Mapre1 | 0.347118137 | 0.00889147 | microtubule-associated protein, RP/EB family, member 1 |
| ENSMUSG00000069662 | 17118 | Marcks | 0.347051724 | 0.018647984 | myristoylated alanine rich protein kinase C substrate |
| ENSMUSG00000024383 | 26405 | Map3k2 | 0.347009436 | 0.003036844 | mitogen-activated protein kinase kinase kinase 2 |
| ENSMUSG00000009207 | 69605 | Lnpk1 | 0.34674816 | 0.007839005 | ER junction formation factor 1 |
| ENSMUSG00000061778 | 76763 | Mospd2 | 0.346589206 | 0.003274596 | motile sperm domain containing 2 |

TABLE 2-continued

| Ensembl | Entrez | Symbol | log2FoldChange | padj | Name |
|---|---|---|---|---|---|
| ENSMUSG00000047139 | 12484 | Cd24a | 0.34636138 | 0.02855274 | CD24a antigen |
| ENSMUSG00000022533 | 224088 | Atp13a3 | 0.346195402 | 0.00437341 | ATPase type 13A3 |
| ENSMUSG00000051037 | 218311 | Zfp455 | 0.346109893 | 0.016376632 | zinc finger protein 455 |
| ENSMUSG00000027176 | 228410 | Cstf3 | 0.346035967 | 0.005490488 | cleavage stimulation factor, 3' pre-RNA, subunit 3 |
| ENSMUSG00000049969 | 71801 | Plekhf2 | 0.345856447 | 0.016245091 | pleckstrin homology domain containing, family F (with FYVE domain) member 2 |
| ENSMUSG00000036699 | 72693 | Zcchc12 | 0.345689591 | 0.012839798 | zinc finger, CCHC domain containing 12 |
| ENSMUSG00000048281 | 239133 | Dleu7 | 0.345305546 | 0.035467359 | deleted in lymphocytic leukemia, 7 |
| ENSMUSG00000041483 | 226442 | Zfp281 | 0.345267912 | 0.018786628 | zinc finger protein 281 |
| ENSMUSG00000024614 | 67988 | Tmx3 | 0.344659551 | 0.006970524 | thioredoxin-related transmembrane protein 3 |
| ENSMUSG00000025997 | 22779 | Ikzf2 | 0.344435357 | 0.001982089 | IKAROS family zinc finger 2 |
| ENSMUSG00000021707 | 13361 | Dhfr | 0.344374151 | 0.047565032 | dihydrofolate reductase |
| ENSMUSG00000032076 | 54725 | Cadm1 | 0.344327349 | 0.000339608 | cell adhesion molecule 1 |
| ENSMUSG00000097709 | 73270 | 1700024F13Rik | 0.344204743 | 0.037516279 | RIKEN cDNA 1700024F13 gene |
| ENSMUSG00000022016 | 219181 | Akap11 | 0.344045473 | 0.004757367 | A kinase (PRKA) anchor protein 11 |
| ENSMUSG00000026234 | 17975 | Ncl | 0.343762612 | 0.004950678 | nucleolin |
| ENSMUSG00000034329 | 237911 | Brip1 | 0.343492627 | 0.031060625 | BRCA1 interacting protein C-terminal helicase 1 |
| ENSMUSG00000027677 | 67120 | Ttc14 | 0.343298392 | 0.003321575 | tetratricopeptide repeat domain 14 |
| ENSMUSG00000035566 | 219228 | Pcdh17 | 0.343152578 | 0.006515271 | protocadherin 17 |
| ENSMUSG00000039096 | 237926 | Rsad1 | 0.342882086 | 0.009303766 | radical S-adenosyl methionine domain containing 1 |
| ENSMUSG00000047414 | 399558 | Flrt2 | 0.342836697 | 0.016245091 | fibronectin leucine rich transmembrane protein 2 |
| ENSMUSG00000020650 | 12033 | Bcap29 | 0.342701703 | 0.00545052 | B cell receptor associated protein 29 |
| ENSMUSG00000035530 | 20918 | Eif1 | 0.342369899 | 0.005001218 | eukaryotic translation initiation factor 1 |
| ENSMUSG00000029270 | 67266 | Fam69a | 0.342314791 | 0.0059963 | family with sequence similarity 69, member A |
| ENSMUSG00000034317 | 66949 | Trim59 | 0.342254754 | 0.041938586 | tripartite motif-containing 59 |
| ENSMUSG00000028518 | 108079 | Prkaa2 | 0.342252202 | 0.010238271 | protein kinase, AMP-activated, alpha 2 catalytic subunit |
| ENSMUSG00000032184 | 70082 | Lysmd2 | 0.342192623 | 0.019501117 | LysM, putative peptidoglycan-binding, domain containing 2 |
| ENSMUSG00000045962 | 232341 | Wnk1 | 0.342145453 | 0.001402636 | WNK lysine deficient protein kinase 1 |
| ENSMUSG00000040855 | 194590 | Reps2 | 0.341717018 | 0.006920453 | RALBP1 associated Eps domain containing protein 2 |
| ENSMUSG00000035509 | 213311 | Fbxl21 | 0.341480989 | 0.028243863 | F-box and leucine-rich repeat protein 21 |
| ENSMUSG00000045817 | 12193 | Zfp36l2 | 0.341237843 | 0.042241705 | zinc finger protein 36, C3H type-like 2 |
| ENSMUSG00000032217 | 93836 | Rnf111 | 0.341137358 | 0.014987601 | ring finger 111 |
| ENSMUSG00000061601 | 26875 | Pclo | 0.340793558 | 0.003104002 | piccolo (presynaptic cytomatrix protein) |
| ENSMUSG00000060924 | 94109 | Csmd1 | 0.34055445 | 0.006916914 | CUB and Sushi multiple domains 1 |
| ENSMUSG00000064339 | | | 0.340511798 | 0.011144735 | |
| ENSMUSG00000051242 | 93880 | Pcdhb9 | 0.340472268 | 0.033143243 | protocadherin beta 9 |
| ENSMUSG00000010592 | 13164 | Dazl | 0.340153349 | 0.049589475 | deleted in azoospermia-like |
| ENSMUSG00000069135 | 75296 | Fgfr1op | 0.340124382 | 0.002908389 | Fgfr1 oncogene partner |
| ENSMUSG00000021643 | 20365 | Serf1 | 0.339749297 | 0.019955804 | small EDRK-rich factor 1 |
| ENSMUSG00000026065 | 110895 | Slc9a4 | 0.339702822 | 0.028313696 | solute carrier family 9 (sodium/hydrogen exchanger), member 4 |
| ENSMUSG00000038535 | 235469 | Zfp280d | 0.339622741 | 0.00574018 | zinc finger protein 280D |
| ENSMUSG00000092035 | 170676 | Peg10 | 0.33954033 | 0.0170158 | paternally expressed 10 |
| ENSMUSG00000062866 | 215789 | Phactr2 | 0.338963657 | 0.035442904 | phosphatase and actin regulator 2 |
| ENSMUSG00000026103 | 14660 | Gls | 0.33837621 | 0.003780714 | glutaminase |
| ENSMUSG00000048379 | 67296 | Socs4 | 0.338295619 | 0.00403525 | suppressor of cytokine signaling 4 |
| ENSMUSG00000022820 | 68194 | Ndufb4 | 0.338072654 | 0.019099734 | NADH dehydrogenase (ubiquinone) 1 beta subcomplex 4 |
| ENSMUSG00000036093 | 75423 | Arl5a | 0.338057705 | 0.007089549 | ADP-ribosylation factor-like 5A |
| ENSMUSG00000035649 | 319885 | Zcchc7 | 0.338000815 | 0.029432921 | zinc finger, CCHC domain containing 7 |
| ENSMUSG00000053347 | 74670 | Zfp943 | 0.337965503 | 0.015447668 | zinc finger prtoein 943 |
| ENSMUSG00000031197 | 22327 | Vbp1 | 0.337687588 | 0.013513918 | von Hippel-Lindau binding protein 1 |
| ENSMUSG00000014905 | 27362 | Dnajb9 | 0.337597802 | 0.021635982 | DnaJ heat shock protein family (Hsp40) member B9 |
| ENSMUSG00000068966 | 241311 | Zbtb34 | 0.337531978 | 0.033117638 | zinc finger and BTB domain containing 34 |
| ENSMUSG00000021733 | 218756 | Slc4a7 | 0.337315404 | 0.006295462 | solute carrier family 4, sodium bicarbonate cotransporter, member 7 |
| ENSMUSG00000020385 | 12750 | Clk4 | 0.337231044 | 0.003153519 | CDC like kinase 4 |
| ENSMUSG00000038702 | 319901 | Dsel | 0.337110443 | 0.020381783 | dermatan sulfate epimerase-like |
| ENSMUSG00000032336 | 20320 | Nptn | 0.33704447 | 0.024411777 | neuroplastin |
| ENSMUSG00000094483 | 19291 | Purb | 0.336823953 | 0.021334464 | purine rich element binding protein B |
| ENSMUSG00000028497 | 66775 | Hacd4 | 0.336590746 | 0.029406848 | 3-hydroxyacyl-CoA dehydratase 4 |
| ENSMUSG00000015342 | 22439 | Xk | 0.3363117 | 0.026800447 | X-linked Kx blood group |
| ENSMUSG00000037475 | 331291 | Thoc2 | 0.335832998 | 0.010347103 | THO complex 2 |
| ENSMUSG00000009418 | 215690 | Nav1 | 0.335744678 | 0.001576542 | neuron navigator 1 |
| ENSMUSG00000046785 | 77781 | Epm2aip1 | 0.335646969 | 0.006066796 | EPM2A (laforin) interacting protein 1 |
| ENSMUSG00000026768 | 241226 | Itga8 | 0.335408014 | 0.029716511 | integrin alpha 8 |

TABLE 2-continued

| Ensembl | Entrez | Symbol | log2FoldChange | padj | Name |
|---|---|---|---|---|---|
| ENSMUSG00000064061 | 224170 | Dzip3 | 0.334482904 | 0.003210676 | DAZ interacting protein 3, zinc finger |
| ENSMUSG00000014592 | 100072 | Camta1 | 0.334475115 | 0.002080874 | calmodulin binding transcription activator 1 |
| ENSMUSG00000046449 | 245555 | C77370 | 0.334329047 | 0.009250917 | expressed sequence C77370 |
| ENSMUSG00000046351 | 218100 | Zfp322a | 0.333883448 | 0.006569439 | zinc finger protein 322A |
| ENSMUSG00000049624 | 235504 | Slc17a5 | 0.333668807 | 0.005641342 | solute carrier family 17 (anion/sugar transporter), member 5 |
| ENSMUSG00000024759 | 109168 | Atl3 | 0.333495067 | 0.005290988 | atlastin GTPase 3 |
| ENSMUSG00000079065 | 100042165 | BC005561 | 0.33342163 | 0.013871936 | cDNA sequence BC005561 |
| ENSMUSG00000031337 | 17772 | Mtm1 | 0.333367532 | 0.009962344 | X-linked myotubular myopathy gene 1 |
| ENSMUSG00000027823 | 229363 | Gmps | 0.33332613 | 0.010238271 | guanine monophosphate synthetase |
| ENSMUSG00000036894 | 74012 | Rap2b | 0.333265355 | 0.015854098 | RAP2B, member of RAS oncogene family |
| ENSMUSG00000025558 | 105445 | Dock9 | 0.333219905 | 0.010015218 | dedicator of cytokinesis 9 |
| ENSMUSG00000028341 | 18124 | Nr4a3 | 0.332833744 | 0.010084472 | nuclear receptor subfamily 4, group A, member 3 |
| ENSMUSG00000040896 | 56543 | Kcnd3 | 0.332561294 | 0.000925589 | potassium voltage-gated channel, Shal-related family, member 3 |
| ENSMUSG00000075376 | 319817 | Rc3h2 | 0.332353927 | 0.00498096 | ring finger and CCCH-type zinc finger domains 2 |
| ENSMUSG00000036641 | 227933 | Ccdc148 | 0.332180888 | 0.001070978 | coiled-coil domain containing 148 |
| ENSMUSG00000024072 | 67864 | Yipf4 | 0.332152827 | 0.023789087 | Yip1 domain family, member 4 |
| ENSMUSG00000045210 | 70675 | Vcpip1 | 0.332152688 | 0.006528024 | valosin containing protein (p97)/p47 complex interacting protein 1 |
| ENSMUSG00000073987 | 14590 | Ggh | 0.33199136 | 0.02836652 | gamma-glutamyl hydrolase |
| ENSMUSG00000022679 | 93734 | Mpv17l | 0.331557348 | 0.014385882 | Mpv17 transgene, kidney disease mutant-like |
| ENSMUSG00000020300 | 67579 | Cpeb4 | 0.331471448 | 0.009884379 | cytoplasmic polyadenylation element binding protein 4 |
| ENSMUSG00000050229 | 67556 | Pigm | 0.331295146 | 0.005290988 | phosphatidylinositol glycan anchor biosynthesis, class M |
| ENSMUSG00000039270 | 230316 | Megf9 | 0.330607466 | 0.009746584 | multiple EGF-like-domains 9 |
| ENSMUSG00000020361 | 15525 | Hspa4 | 0.330597291 | 0.009783693 | heat shock protein 4 |
| ENSMUSG00000024378 | 170459 | Stard4 | 0.330042721 | 0.022262271 | StAR-related lipid transfer (START) domain containing 4 |
| ENSMUSG00000074863 | | | 0.329806754 | 0.006693208 | |
| ENSMUSG00000041912 | 72634 | Tdrkh | 0.329399453 | 0.005121961 | tudor and KH domain containing protein |
| ENSMUSG00000013663 | 19211 | Pten | 0.329321627 | 0.007957811 | phosphatase and tensin homolog |
| ENSMUSG00000023068 | 52014 | Nus1 | 0.329278355 | 0.006685782 | NUS1 dehydrodolichyl diphosphate synthase subunit |
| ENSMUSG00000068457 | 22290 | Uty | 0.329071775 | 0.00969777 | ubiquitously transcribed tetratricopeptide repeat gene, Y chromosome |
| ENSMUSG00000022674 | 70620 | Ube2v2 | 0.328949174 | 0.023538008 | ubiquitin-conjugating enzyme E2 variant 2 |
| ENSMUSG00000062604 | 20817 | Srpk2 | 0.328829417 | 0.010998106 | serine/arginine-rich protein specific kinase 2 |
| ENSMUSG00000073639 | 19330 | Rab18 | 0.328767306 | 0.013821259 | RAB18, member RAS oncogene family |
| ENSMUSG00000048978 | 22360 | Nrsn1 | 0.328698324 | 0.009129658 | neurensin 1 |
| ENSMUSG00000079083 | 77532 | Jrkl | 0.328563486 | 0.019622786 | Jrk-like |
| ENSMUSG00000066415 | 77853 | Msl2 | 0.328346192 | 0.009601656 | male-specific lethal 2 homolog (*Drosophila*) |
| ENSMUSG00000066829 | 235050 | Zfp810 | 0.328341506 | 0.011345897 | zinc finger protein 810 |
| ENSMUSG00000045875 | 11549 | Adra1a | 0.328169591 | 0.021527806 | adrenergic receptor, alpha 1a |
| ENSMUSG00000012429 | 66308 | Mplkip | 0.328059574 | 0.030998737 | M-phase specific PLK1 intereacting protein |
| ENSMUSG00000028312 | 14211 | Smc2 | 0.328023634 | 0.013823958 | structural maintenance of chromosomes 2 |
| ENSMUSG00000021519 | 66410 | Mterf3 | 0.327993592 | 0.003845974 | mitochondrial transcription termination factor 3 |
| ENSMUSG00000024228 | 67993 | Nudt12 | 0.327985463 | 0.045505582 | nudix (nucleoside diphosphate linked moiety X)-type motif 12 |
| ENSMUSG00000036902 | 74513 | Neto2 | 0.327834418 | 0.038664268 | neuropilin (NRP) and tolloid (TLL)-like 2 |
| ENSMUSG00000036469 | 72925 | 1-Mar | 0.327834269 | 0.000412819 | membrane-associated ring finger (C3HC4) 1 |
| ENSMUSG00000025531 | 12662 | Chm | 0.327620242 | 0.008685332 | choroidermia (RAB escort protein 1) |
| ENSMUSG00000026878 | 68365 | Rab14 | 0.327482413 | 0.001768632 | RAB14, member RAS oncogene family |
| ENSMUSG00000041014 | 18183 | Nrg3 | 0.327450171 | 0.000114355 | neuregulin 3 |
| ENSMUSG00000068748 | 19283 | Ptprz1 | 0.327102816 | 0.00545052 | protein tyrosine phosphatase, receptor type Z, polypeptide 1 |
| ENSMUSG00000050088 | 67912 | 1600012H06Rik | 0.326857186 | 0.006074222 | RIKEN cDNA 1600012H06 gene |
| ENSMUSG00000095139 | 18992 | Pou3f2 | 0.326484418 | 0.02223065 | POU domain, class 3, transcription factor 2 |
| ENSMUSG00000043313 | 93890 | Pcdhb19 | 0.326109022 | 0.032965829 | protocadherin beta 19 |
| ENSMUSG00000022672 | 19090 | Prkdc | 0.325917719 | 0.000186491 | protein kinase, DNA activated, catalytic polypeptide |
| ENSMUSG00000021318 | 14634 | Gli3 | 0.325743933 | 0.011462086 | GLI-Kruppel family member GLI3 |
| ENSMUSG00000049336 | 23964 | Tenm2 | 0.325658739 | 0.037555358 | teneurin transmembrane protein 2 |
| ENSMUSG00000053774 | 224111 | Ubxn7 | 0.325381949 | 0.004049099 | UBX domain protein 7 |
| ENSMUSG00000035762 | 72745 | Tmem161b | 0.325109689 | 0.011144735 | transmembrane protein 161B |
| ENSMUSG00000044308 | 68795 | Ubr3 | 0.324596175 | 0.000508895 | ubiquitin protein ligase E3 component n-recognin 3 |

TABLE 2-continued

| Ensembl | Entrez | Symbol | log2FoldChange | padj | Name |
|---|---|---|---|---|---|
| ENSMUSG00000064337 | | | 0.32441133 | 0.005890487 | |
| ENSMUSG00000028522 | 71148 | Mier1 | 0.3243185 | 0.000215182 | MEIR1 treanscription regulator |
| ENSMUSG00000001441 | 19155 | Npepps | 0.323888147 | 0.00560995 | aminopeptidase puromycin sensitive |
| ENSMUSG00000020561 | 28071 | Twistnb | 0.323862364 | 0.01627831 | twist basic helix-loop-helix transcription factor 1 neighbor |
| ENSMUSG00000043424 | 100042807 | Eif3j2 | 0.323666404 | 0.035521529 | eukaryotic translation initiation factor 3, subunit J2 |
| ENSMUSG00000024287 | 225160 | Thoc1 | 0.323001489 | 0.007370161 | THO complex 1 |
| ENSMUSG00000041440 | 235533 | Gk5 | 0.322562689 | 0.040977061 | glycerol kinase 5 (putative) |
| ENSMUSG00000021732 | 14165 | Fgf10 | 0.322497653 | 0.023121738 | fibroblast growth factor 10 |
| ENSMUSG00000040229 | 23890 | Gpr34 | 0.322285251 | 0.044174795 | G protein-coupled receptor 34 |
| ENSMUSG00000046994 | 212679 | Mars2 | 0.322267013 | 0.005946305 | methionine-tRNA synthetase 2 (mitochondrial) |
| ENSMUSG00000074415 | 73144 | 3110039I08Rik | 0.322250585 | 0.001961898 | RIKEN cDNA 3110039I08 gene |
| ENSMUSG00000058704 | 76890 | Memo1 | 0.322208595 | 0.006855182 | mediator of cell motility 1 |
| ENSMUSG00000026158 | 70155 | Ogfrl1 | 0.322165992 | 0.023209714 | opioid growth factor receptor-like 1 |
| ENSMUSG00000022797 | 22042 | Tfrc | 0.322071995 | 0.025061285 | transferrin receptor |
| ENSMUSG00000024498 | 56070 | Tcerg1 | 0.322025512 | 0.006546749 | transcription elongation regulator 1 (CA150) |
| ENSMUSG00000010608 | 67039 | Rbm25 | 0.32193496 | 0.00261075 | RNA binding motif protein 25 |
| ENSMUSG00000060771 | 211484 | Tsga10 | 0.321696523 | 0.002102796 | testis specific 10 |
| ENSMUSG00000027207 | 69976 | Galk2 | 0.321678558 | 0.023285008 | galactokinase 2 |
| ENSMUSG00000066324 | 242291 | Impad1 | 0.320941807 | 0.013017268 | inositol monophosphatase domain containing 1 |
| ENSMUSG00000005871 | 11789 | Apc | 0.320719283 | 0.001467472 | adenomatosis polyposis coli |
| ENSMUSG00000017485 | 21974 | Top2b | 0.3207117 | 0.012036816 | topoisomerase (DNA) II beta |
| ENSMUSG00000029832 | 18025 | Nfe2l3 | 0.320508898 | 0.027260292 | nuclear factor, erythroid derived 2, like 3 |
| ENSMUSG00000058446 | 387524 | Znrf2 | 0.320442769 | 0.007609083 | zinc and ring finger 2 |
| ENSMUSG00000029798 | 67138 | Herc6 | 0.319775296 | 0.023564678 | hect domain and RLD 6 |
| ENSMUSG00000025921 | 98711 | Rdh10 | 0.319642705 | 0.011706934 | retinol dehydrogenase 10 (all-trans) |
| ENSMUSG00000049164 | 72672 | Zfp518a | 0.319614701 | 0.027543196 | zinc finger protein 518A |
| ENSMUSG00000025262 | 207375 | Fam120c | 0.319190661 | 0.000893237 | family with sequence similarity 120, member C |
| ENSMUSG00000069729 | 239985 | Arid1b | 0.31902197 | 0.001405029 | AT rich interactive domain 1B (SWI-like) |
| ENSMUSG00000012422 | 66074 | Tmem167 | 0.318936596 | 0.013557723 | transmembrane protein 167 |
| ENSMUSG00000032449 | 192287 | Slc25a36 | 0.318644218 | 0.000456337 | solute carrier family 25, member 36 |
| ENSMUSG00000004364 | 26554 | Cul3 | 0.318472043 | 0.004198828 | cullin 3 |
| ENSMUSG00000036790 | 245450 | Slitrk2 | 0.318407063 | 0.008027523 | SLIT and NTRK-like family, member 2 |
| ENSMUSG00000037266 | 27981 | Rsrp1 | 0.318399165 | 0.006166166 | arginine/serine rich protein 1 |
| ENSMUSG00000046567 | 68281 | 4930430F08Rik | 0.318199958 | 0.031060625 | RIKEN cDNA 4930430F08 gene |
| ENSMUSG00000031438 | 66889 | Rnf128 | 0.317836036 | 0.029222521 | ring finger protein 128 |
| ENSMUSG00000049755 | 319475 | Zfp672 | 0.317364007 | 0.002783667 | zinc finger protein 672 |
| ENSMUSG00000057715 | 320492 | A830018L16Rik | 0.317174971 | 0.002911871 | RIKEN cDNA A830018L16 gene |
| ENSMUSG00000048109 | 229700 | Rbm15 | 0.316688286 | 0.013459926 | RNA binding motif protein 15 |
| ENSMUSG00000022634 | 67057 | Yaf2 | 0.316585784 | 0.015013285 | YY1 associated factor 2 |
| ENSMUSG00000021557 | 67269 | Agtpbp1 | 0.316569905 | 0.012384943 | ATP/GTP binding protein 1 |
| ENSMUSG00000060002 | 212862 | Chpt1 | 0.315877099 | 0.017150711 | choline phosphotransferase 1 |
| ENSMUSG00000024241 | 20662 | Sos1 | 0.31570519 | 0.00437341 | son of sevenless homolog 1 (Drosophila) |
| ENSMUSG00000019831 | 83767 | Wasf1 | 0.315509097 | 0.004568734 | WAS protein family, member 1 |
| ENSMUSG00000021969 | 75965 | Zdhhc20 | 0.315346466 | 0.007714497 | zinc finger, DHHC domain containing 20 |
| ENSMUSG00000031198 | 67391 | Fundc2 | 0.315274863 | 0.01523467 | FUN14 domain containing 2 |
| ENSMUSG00000020189 | 237542 | Osbpl8 | 0.315098889 | 0.010883507 | oxysterol binding protein-like 8 |
| ENSMUSG00000029669 | 269831 | Tspan12 | 0.31462945 | 0.018695515 | tetraspanin 12 |
| ENSMUSG00000031202 | 67790 | Rab39b | 0.31445934 | 0.015531205 | RAB39B, member RAS oncogene family |
| ENSMUSG00000031010 | 22284 | Usp9x | 0.31438384 | 0.013036571 | ubiquitin specific peptidase 9, X chromosome |
| ENSMUSG00000040128 | 108767 | Pnrc1 | 0.314314591 | 0.017091709 | proline-rich nuclear receptor coactivator 1 |
| ENSMUSG00000038879 | 223473 | Nipal2 | 0.314171029 | 0.035442904 | NIPA-like domain containing 2 |
| ENSMUSG00000028556 | 67299 | Dock7 | 0.313689124 | 0.006668084 | dedicator of cytokinesis 7 |
| ENSMUSG00000019984 | 70208 | Med23 | 0.313430135 | 0.007040197 | mediator complex subunit 23 |
| ENSMUSG00000074873 | | | 0.313337379 | 0.048312414 | |
| ENSMUSG00000032985 | | | 0.313163982 | 0.04928913 | |
| ENSMUSG00000017550 | 237877 | Atad5 | 0.312959105 | 0.017282572 | ATPase family, AAA domain containing 5 |
| ENSMUSG00000087143 | | | 0.31282637 | 0.018598528 | |
| ENSMUSG00000018425 | 67487 | Dhx40 | 0.312814898 | 0.022327936 | DEAH (Asp-Glu-Ala-His) box polypeptide 40 |
| ENSMUSG00000052534 | 18514 | Pbx1 | 0.312813235 | 0.001441714 | pre B cell leukemia homeobox 1 |
| ENSMUSG00000021072 | 72736 | Tmx1 | 0.312806843 | 0.024672575 | thioredoxin-related transmembrane protein 1 |
| ENSMUSG00000040452 | 215654 | Cdh12 | 0.312737399 | 0.008880825 | cadherin 12 |
| ENSMUSG00000048280 | 408068 | Zfp738 | 0.312268364 | 0.000713891 | zinc finger protein 738 |
| ENSMUSG00000028546 | 15572 | Elavl4 | 0.312162534 | 0.010691053 | ELAV (embryonic lethal, abnormal vision, Drosophila)-like 4 (Hu antigen D) |
| ENSMUSG00000031327 | 12212 | Chic1 | 0.312118598 | 0.014617077 | cysteine-rich hydrophobic domain 1 |
| ENSMUSG00000038602 | 215085 | Slc35f1 | 0.311830149 | 0.023285008 | solute carrier family 35, member F1 |
| ENSMUSG00000017778 | 12867 | Cox7c | 0.311721589 | 0.005466565 | cytochrome c oxidase subunit VIIc |
| ENSMUSG00000024479 | 105853 | Mal2 | 0.311627549 | 0.022354231 | mal, T cell differentiation protein 2 |

TABLE 2-continued

| Ensembl | Entrez | Symbol | log2FoldChange | padj | Name |
|---|---|---|---|---|---|
| ENSMUSG00000021180 | 73086 | Rps6ka5 | 0.311429312 | 0.013480009 | ribosomal protein S6 kinase, polypeptide 5 |
| ENSMUSG00000045996 | 17749 | Polr2k | 0.311428929 | 0.008514338 | polymerase (RNA) II (DNA directed) polypeptide K |
| ENSMUSG00000063663 | 382236 | Brwd3 | 0.311208348 | 0.00461886 | bromodomain and WD repeat domain containing 3 |
| ENSMUSG00000078878 | 668030 | Gm14432 | 0.311201048 | 0.024307603 | predicted gene 14432 |
| ENSMUSG00000043391 | 72190 | 2510009E07Rik | 0.311191264 | 0.018472842 | RIKEN cDNA 2510009E07 gene |
| ENSMUSG00000000787 | 13205 | Ddx3x | 0.311185949 | 0.013106178 | DEAD/H (Asp-Glu-Ala-Asp/His) box polypeptide 3, X-linked |
| ENSMUSG00000039988 | 433667 | Ankrd13c | 0.310668173 | 0.024712971 | ankyrin repeat domain 13c |
| ENSMUSG00000022788 | 224014 | Fgd4 | 0.310535352 | 0.001169454 | FYVE, RhoGEF and PH domain containing 4 |
| ENSMUSG00000030960 | 72096 | Mettl10 | 0.310325329 | 0.029470151 | methyltransferase like 10 |
| ENSMUSG00000024384 | 73473 | Iws1 | 0.310142048 | 0.00289335 | IWS1 homolog (*S. cerevisiae*) |
| ENSMUSG00000030560 | 13032 | Ctsc | 0.31004533 | 0.037306701 | cathepsin C |
| ENSMUSG00000025766 | 73852 | D3Ertd751e | 0.309980702 | 0.027543196 | DNA segment, Chr 3, ERATO Doi 751, expressed |
| ENSMUSG00000024712 | 54391 | Rfk | 0.309762729 | 0.04188267 | riboflavin kinase |
| ENSMUSG00000066613 | 69504 | Zfp932 | 0.309681252 | 0.004198828 | zinc finger protein 932 |
| ENSMUSG00000060935 | 103266 | Tmem263 | 0.309546821 | 0.02299377 | transmembrane protein 263 |
| ENSMUSG00000057614 | 14677 | Gnai1 | 0.309535822 | 0.01458373 | guanine nucleotide binding protein (G protein), alpha inhibiting 1 |
| ENSMUSG00000090000 | 66191 | Ier3ip 1 | 0.309430949 | 0.010238271 | immediate early response 3 interacting protein 1 |
| ENSMUSG00000021555 | 78689 | Naa35 | 0.309189607 | 0.043556047 | N(alpha)-acetyltransferase 35, NatC auxiliary subunit |
| ENSMUSG00000078879 | 545490 | Zfp973 | 0.309078116 | 0.02510451 | zinc finger protein 973 |
| ENSMUSG00000031174 | 19893 | Rpgr | 0.308870381 | 0.011702159 | retinitis pigmentosa GTPase regulator |
| ENSMUSG00000020290 | 103573 | Xpo1 | 0.308802523 | 0.018090945 | exportin 1 |
| ENSMUSG00000026721 | 29809 | Rabgap1l | 0.308771759 | 0.019405549 | RAB GTPase activating protein 1-like |
| ENSMUSG00000033419 | 20616 | Snap91 | 0.30871865 | 0.00387367 | synaptosomal-associated protein 91 |
| ENSMUSG00000053070 | 234912 | 9230110C19Rik | 0.308619378 | 0.019153869 | RIKEN cDNA 9230110C19 gene |
| ENSMUSG00000022307 | 170719 | Oxr1 | 0.308306767 | 0.007766073 | oxidation resistance 1 |
| ENSMUSG00000045083 | 242384 | Lingo2 | 0.308128045 | 0.010849269 | leucine rich repeat and Ig domain containing 2 |
| ENSMUSG00000037608 | 72567 | Bclaf1 | 0.308066907 | 0.019862373 | BCL2-associated transcription factor 1 |
| ENSMUSG00000045103 | 13405 | Dmd | 0.307912588 | 0.002483237 | dystrophin, muscular dystrophy |
| ENSMUSG00000068151 | | | 0.307860032 | 0.024126111 | |
| ENSMUSG00000027087 | 16410 | Itgav | 0.307760993 | 0.024027306 | integrin alpha V |
| ENSMUSG00000062209 | 13869 | Erbb4 | 0.307715332 | 0.003274596 | erb-b2 receptor tyrosine kinase 4 |
| ENSMUSG00000025742 | 110639 | Prps2 | 0.307188324 | 0.033143167 | phosphoribosyl pyrophosphate synthetase 2 |
| ENSMUSG00000040520 | 242362 | Manea | 0.307133404 | 0.018478822 | mannosidase, endo-alpha |
| ENSMUSG00000074519 | 626848 | Zfp971 | 0.307008549 | 0.020988384 | zinc finger protein 971 |
| ENSMUSG00000025529 | 245595 | Zfp711 | 0.306797939 | 0.022370858 | zinc finger protein 711 |
| ENSMUSG00000031284 | 18481 | Pak3 | 0.306718508 | 0.003927483 | p21 protein (Cdc42/Rac)-activated kinase 3 |
| ENSMUSG00000059173 | 18573 | Pde1a | 0.306715967 | 0.001670181 | phosphodiesterase 1A, calmodulin-dependent |
| ENSMUSG00000041245 | 279561 | Wnk3 | 0.306708061 | 0.012398837 | WNK lysine deficient protein kinase 3 |
| ENSMUSG00000040710 | 20452 | St8sia4 | 0.306481278 | 0.043223052 | ST8 alpha-N-acetyl-neuraminide alpha-2,8-sialyltransferase 4 |
| ENSMUSG00000034158 | 320184 | Lrrc58 | 0.306157941 | 0.013403755 | leucine rich repeat containing 58 |
| ENSMUSG00000028809 | 51796 | Srrm1 | 0.306001667 | 0.001070978 | serine/arginine repetitive matrix 1 |
| ENSMUSG00000029840 | 14489 | Mtpn | 0.305931419 | 0.026458143 | myotrophin |
| ENSMUSG00000026434 | 98415 | Nucks1 | 0.305762597 | 0.017878795 | nuclear casein kinase and cyclin-dependent kinase substrate 1 |
| ENSMUSG00000069237 | 97863 | Fam8a1 | 0.305683655 | 0.015780391 | family with sequence similarity 8, member A1 |
| ENSMUSG00000021592 | 77041 | Arsk | 0.305477468 | 0.033939371 | arylsulfatase K |
| ENSMUSG00000029684 | 73178 | Wasl | 0.305475715 | 0.019107568 | Wiskott-Aldrich syndrome-like (human) |
| ENSMUSG00000063531 | 20349 | Sema3e | 0.305441475 | 0.020049146 | sema domain, immunoglobulin domain (Ig), short basic domain, secreted, (semaphorin) 3E |
| ENSMUSG00000040473 | 207686 | Cfap69 | 0.305436523 | 0.042021355 | cilia and flagella associated protein 69 |
| ENSMUSG00000024293 | 77805 | Esco1 | 0.30499281 | 0.020389259 | establishment of sister chromatid cohesion N-acetyltransferase 1 |
| ENSMUSG00000007989 | 14365 | Fzd3 | 0.304310376 | 0.004568734 | frizzled class receptor 3 |
| ENSMUSG00000057329 | 12043 | Bcl2 | 0.304264642 | 0.023802758 | B cell leukemia/lymphoma 2 |
| ENSMUSG00000037722 | 54342 | Gnpnat1 | 0.304241771 | 0.007417862 | glucosamine-phosphate N-acetyltransferase 1 |
| ENSMUSG00000030465 | 234353 | Psd3 | 0.304153535 | 0.0033123 | pleckstrin and Sec7 domain containing 3 |
| ENSMUSG00000046873 | 270669 | Mbtps2 | 0.303615715 | 0.003321575 | membrane-bound transcription factor peptidase, site 2 |
| ENSMUSG00000005534 | 16337 | Insr | 0.303566964 | 0.000713189 | insulin receptor |
| ENSMUSG00000037652 | 241915 | Phc3 | 0.303175476 | 0.00194812 | polyhomeotic-like 3 (*Drosophila*) |
| ENSMUSG00000026834 | 269275 | Acvr1c | 0.302983491 | 0.035541705 | activin A receptor, type IC |
| ENSMUSG00000022837 | 320299 | Iqcb1 | 0.302895189 | 4.60E−05 | IQ calmodulin-binding motif containing 1 |

TABLE 2-continued

| Ensembl | Entrez | Symbol | log2FoldChange | padj | Name |
|---|---|---|---|---|---|
| ENSMUSG00000026678 | 19737 | Rgs5 | 0.302871917 | 0.00560995 | regulator of G-protein signaling 5 |
| ENSMUSG00000034269 | 72895 | Setd5 | 0.302673127 | 8.33E−07 | SET domain containing 5 |
| ENSMUSG00000049583 | 108071 | Grm5 | 0.302472796 | 0.009351392 | glutamate receptor, metabotropic 5 |
| ENSMUSG00000028719 | 66588 | Cmpk1 | 0.302325775 | 0.015764011 | cytidine monophosphate (UMP-CMP) kinase 1 |
| ENSMUSG00000026771 | 76857 | Spopl | 0.302293308 | 0.00987597 | speckle-type POZ protein-like |
| ENSMUSG00000003721 | 72999 | Insig2 | 0.302089295 | 0.002391979 | insulin induced gene 2 |
| ENSMUSG00000039717 | 76897 | Ralyl | 0.30172509 | 0.035883734 | RALY RNA binding protein-like |
| ENSMUSG00000021929 | 16648 | Kpna3 | 0.301718393 | 0.016368248 | karyopherin (importin) alpha 3 |
| ENSMUSG00000035161 | 18130 | Ints6 | 0.301649759 | 0.002380912 | integrator complex subunit 6 |
| ENSMUSG00000049184 | 75029 | Purg | 0.301529127 | 0.015730811 | purine-rich element binding protein G |
| ENSMUSG00000051920 | 239405 | Rspo2 | 0.301186062 | 0.048997766 | R-spondin 2 |
| ENSMUSG00000039579 | 242443 | Grin3a | 0.301100576 | 0.003001153 | glutamate receptor ionotropic, NMDA3A |
| ENSMUSG00000020255 | 28109 | D10Wsu102e | 0.300729555 | 0.029583518 | DNA segment, Chr 10, Wayne State University 102, expressed |
| ENSMUSG00000041935 | 106064 | AW549877 | 0.300723256 | 0.019700695 | expressed sequence AW549877 |
| ENSMUSG00000027272 | 22222 | Ubr1 | 0.300560013 | 0.005859696 | ubiquitin protein ligase E3 component n-recognin 1 |
| ENSMUSG00000042197 | 98403 | Zfp451 | 0.300478257 | 0.009523378 | zinc finger protein 451 |
| ENSMUSG00000040760 | 72993 | Appl1 | 0.300466632 | 0.002590947 | adaptor protein, phosphotyrosine interaction, PH domain and leucine zipper containing 1 |
| ENSMUSG00000057406 | 107823 | Whsc1 | 0.300199794 | 0.040749845 | Wolf-Hirschhorn syndrome candidate 1 (human) |
| ENSMUSG00000074829 | 630836 | 2010315B03Rik | 0.300156405 | 0.016109381 | RIKEN cDNA 2010315B03 gene |
| ENSMUSG00000042063 | 56220 | Zfp386 | 0.29951455 | 0.014778334 | zinc finger protein 386 (Kruppel-like) |
| ENSMUSG00000048040 | 76976 | Arxes2 | 0.299433681 | 0.013992158 | adipocyte-related X-chromosome expressed sequence 2 |
| ENSMUSG00000040370 | 67636 | Lyrm5 | 0.299385056 | 0.029864835 | LYR motif containing 5 |
| ENSMUSG00000031119 | 14735 | Gpc4 | 0.299263408 | 0.007811377 | glypican 4 |
| ENSMUSG00000062931 | 237411 | Zfp938 | 0.299254476 | 0.032723617 | zinc finger protein 938 |
| ENSMUSG00000021510 | 212281 | Zfp729a | 0.298854075 | 0.028457339 | zinc finger protein 729a |
| ENSMUSG00000030022 | 101401 | Adamts9 | 0.298692103 | 0.01812301 | a disintegrin-like and metallopeptidase (reprolysin type) with thrombospondin type 1 motif, 9 |
| ENSMUSG00000026775 | 27377 | Yme1l1 | 0.29866056 | 0.014360023 | YME1-like 1 (S. cerevisiae) |
| ENSMUSG00000043190 | 218341 | Rfesd | 0.29837378 | 0.029269343 | Rieske (Fe-S) domain containing |
| ENSMUSG00000020149 | 19324 | Rab1a | 0.298322486 | 0.00978101 | RAB1A, member RAS oncogene family |
| ENSMUSG00000028132 | 99887 | Tmem56 | 0.298250213 | 0.018993844 | transmembrane protein 56 |
| ENSMUSG00000068882 | 20823 | Ssb | 0.298177314 | 0.031025244 | Sjogren syndrome antigen B |
| ENSMUSG00000056537 | 19820 | Rlim | 0.298098514 | 0.005647889 | ring finger protein, LIM domain interacting |
| ENSMUSG00000050538 | 68127 | B230217C12Rik | 0.297991517 | 0.004293051 | RIKEN cDNA B230217C12 gene |
| ENSMUSG00000020359 | 72947 | Phykpl | 0.297908781 | 0.011552938 | 5-phosphohydroxy-L-lysine phospholyase |
| ENSMUSG00000004317 | 12728 | Clcn5 | 0.297833959 | 0.036713429 | chloride channel, voltage-sensitive 5 |
| ENSMUSG00000025612 | 12013 | Bach1 | 0.297673972 | 0.04346628 | BTB and CNC homology 1, basic leucine zipper transcription factor 1 |
| ENSMUSG00000021109 | 15251 | Hif1a | 0.297578312 | 0.007192726 | hypoxia inducible factor 1, alpha subunit |
| ENSMUSG00000014956 | 19046 | Ppp1cb | 0.297510463 | 0.036233487 | protein phosphatase 1, catalytic subunit, beta isoform |
| ENSMUSG00000021111 | 18789 | Papola | 0.297437017 | 0.001694389 | poly (A) polymerase alpha |
| ENSMUSG00000029290 | 54367 | Zfp326 | 0.297364467 | 0.020167127 | zinc finger protein 326 |
| ENSMUSG00000025911 | 76187 | Adhfe1 | 0.297073021 | 0.015854098 | alcohol dehydrogenase, iron containing, 1 |
| ENSMUSG00000024491 | 225432 | Rbm27 | 0.29698267 | 0.01170562 | RNA binding motif protein 27 |
| ENSMUSG00000040747 | 12508 | Cd53 | 0.296892173 | 0.034288043 | CD53 antigen |
| ENSMUSG00000069601 | 11735 | Ank3 | 0.296873215 | 0.012009915 | ankyrin 3, epithelial |
| ENSMUSG00000033543 | 235459 | Gtf2a2 | 0.296773045 | 0.028421178 | general transcription factor II A, 2 |
| ENSMUSG00000024290 | 19877 | Rock1 | 0.296657757 | 0.009900233 | Rho-associated coiled-coil containing protein kinase 1 |
| ENSMUSG00000021596 | 78771 | Mctp1 | 0.296336096 | 0.007038176 | multiple C2 domains, transmembrane 1 |
| ENSMUSG00000035133 | 11855 | Arhgap5 | 0.2959974 | 0.03971197 | Rho GTPase activating protein 5 |
| ENSMUSG00000022762 | 17968 | Ncam2 | 0.295842 | 0.007957811 | neural cell adhesion molecule 2 |
| ENSMUSG00000050029 | 72065 | Rap2c | 0.295840635 | 0.018595618 | RAP2C, member of RAS oncogene family |
| ENSMUSG00000044067 | 73010 | Gpr22 | 0.295560322 | 0.028127966 | G protein-coupled receptor 22 |
| ENSMUSG00000037720 | 67878 | Tmem33 | 0.29551633 | 0.016770762 | transmembrane protein 33 |
| ENSMUSG00000036769 | 72404 | Wdr44 | 0.295424606 | 0.019664441 | WD repeat domain 44 |
| ENSMUSG00000020738 | 170930 | Sumo2 | 0.29530926 | 0.048814561 | small ubiquitin-like modifier 2 |
| ENSMUSG00000040865 | 227195 | Ino80d | 0.295253348 | 0.011086721 | INO80 complex subunit D |
| ENSMUSG00000072582 | 217057 | Ptrh2 | 0.295027175 | 0.029269343 | peptidyl-tRNA hydrolase 2 |
| ENSMUSG00000043929 | 236904 | Klhl15 | 0.295003347 | 0.005968002 | kelch-like 15 |
| ENSMUSG00000042505 | 71238 | Sdhaf3 | 0.294955683 | 0.029846252 | succinate dehydrogenase complex assembly factor 3 |
| ENSMUSG00000074212 | 70604 | Dnajb14 | 0.294918314 | 0.004702628 | DnaJ heat shock protein family (Hsp40) member B14 |
| ENSMUSG00000028226 | 17389 | Mmp16 | 0.294917105 | 0.012060747 | matrix metallopeptidase 16 |
| ENSMUSG00000026384 | 19258 | Ptpn4 | 0.294788977 | 0.047074587 | protein tyrosine phosphatase, non-receptor type 4 |
| ENSMUSG00000040321 | 228491 | Zfp770 | 0.294679193 | 0.029288325 | zinc finger protein 770 |
| ENSMUSG00000042605 | 20239 | Atxn2 | 0.294676836 | 0.04031328 | ataxin 2 |

TABLE 2-continued

| Ensembl | Entrez | Symbol | log2FoldChange | padj | Name |
|---|---|---|---|---|---|
| ENSMUSG00000025404 | 71750 | R3hdm2 | 0.294022489 | 0.032464424 | R3H domain containing 2 |
| ENSMUSG00000017831 | 271457 | Rab5a | 0.293729374 | 0.027651551 | RAB5A, member RAS oncogene family |
| ENSMUSG00000016308 | 22209 | Ube2a | 0.293657837 | 0.042321638 | ubiquitin-conjugating enzyme E2A |
| ENSMUSG00000034297 | 327987 | Med13 | 0.29362194 | 0.009601656 | mediator complex subunit 13 |
| ENSMUSG00000047879 | 59025 | Usp14 | 0.293514764 | 0.009303766 | ubiquitin specific peptidase 14 |
| ENSMUSG00000000247 | 16870 | Lhx2 | 0.293483696 | 0.031443847 | LIM homeobox protein 2 |
| ENSMUSG00000036792 | 109241 | Mbd5 | 0.293464492 | 0.000623009 | methyl-CpG binding domain protein 5 |
| ENSMUSG00000062627 | 320713 | Mysm1 | 0.293365597 | 0.002126936 | myb-like, SWIRM and MPN domains 1 |
| ENSMUSG00000044043 | 93885 | Pcdhb14 | 0.29312764 | 0.021451395 | protocadherin beta 14 |
| ENSMUSG00000025551 | 14169 | Fgf14 | 0.292858165 | 0.005386645 | fibroblast growth factor 14 |
| ENSMUSG00000028630 | 69181 | Dyrk2 | 0.292800792 | 0.013052318 | dual-specificity tyrosine-(Y)-phosphorylation regulated kinase 2 |
| ENSMUSG00000024726 | 67383 | Carnmt1 | 0.292763648 | 0.028689222 | carnosine N-methyltransferase 1 |
| ENSMUSG00000090641 | 78251 | Zfp712 | 0.292690236 | 0.047890046 | zinc finger protein 712 |
| ENSMUSG00000061244 | 105504 | Exoc5 | 0.292547399 | 0.01709371 | exocyst complex component 5 |
| ENSMUSG00000056124 | 56386 | B4galt6 | 0.292440558 | 0.007368041 | UDP-Gal:betaGlcNAc beta 1,4-galactosyltransferase, polypeptide 6 |
| ENSMUSG00000022261 | 15529 | Sdc2 | 0.292172754 | 0.023522014 | syndecan 2 |
| ENSMUSG00000020063 | 93759 | Sirt1 | 0.291654992 | 0.022746493 | sirtuin 1 |
| ENSMUSG00000003226 | 19386 | Ranbp2 | 0.291557428 | 0.023839741 | RAN binding protein 2 |
| ENSMUSG00000019818 | 53599 | Cd164 | 0.291515493 | 0.033504003 | CD164 antigen |
| ENSMUSG00000084849 | | | 0.291392718 | 0.03685414 | |
| ENSMUSG00000072437 | 332397 | Nanos1 | 0.291249889 | 0.035710273 | nanos homolog 1 (*Drosophila*) |
| ENSMUSG00000069171 | 13865 | Nr2f1 | 0.291229758 | 0.03364494 | nuclear receptor subfamily 2, group F, member 1 |
| ENSMUSG00000029403 | 53886 | Cdkl2 | 0.291192326 | 0.00289335 | cyclin-dependent kinase-like 2 (CDC2-related kinase) |
| ENSMUSG00000038630 | 100041581 | Zkscan16 | 0.291190228 | 0.005995981 | zinc finger with KRAB and SCAN domains 16 |
| ENSMUSG00000030660 | 18704 | Pik3c2a | 0.2909895 | 0.024578427 | phosphatidylinositol 3-kinase, C2 domain containing, alpha polypeptide |
| ENSMUSG00000036810 | 382030 | Cnep1r1 | 0.290977199 | 0.031293476 | CTD nuclear envelope phosphatase 1 regulatory subunit 1 |
| ENSMUSG00000037234 | 320191 | Hook3 | 0.290787536 | 1.65E−05 | hook microtubule tethering protein 3 |
| ENSMUSG00000044167 | 56458 | Foxo1 | 0.290709469 | 0.014675859 | forkhead box 01 |
| ENSMUSG00000022893 | 11504 | Adamts1 | 0.29050246 | 0.035737588 | a disintegrin-like and metallopeptidase (reprolysin type) with thrombospondin type 1 motif, 1 |
| ENSMUSG00000072872 | 56353 | Rybp | 0.290491095 | 0.018905339 | RING1 and YY1 binding protein |
| ENSMUSG00000021597 | 105377 | Slf1 | 0.290463953 | 0.005442158 | SMC5-SMC6 complex localization factor 1 |
| ENSMUSG00000020644 | 15902 | Id2 | 0.290460226 | 0.026579452 | inhibitor of DNA binding 2 |
| ENSMUSG00000096433 | 240038 | Zfp994 | 0.290343867 | 0.039345584 | zinc finger protein 994 |
| ENSMUSG00000062078 | 19317 | Qk | 0.290227805 | 0.033675591 | quaking |
| ENSMUSG00000073563 | 70425 | Csnk1g3 | 0.29021273 | 0.016104543 | casein kinase 1, gamma 3 |
| ENSMUSG00000040339 | 329739 | Fam102b | 0.290072483 | 0.008353927 | family with sequence similarity 102, member B |
| ENSMUSG00000019894 | 103098 | Slc6a15 | 0.290058456 | 0.025890921 | solute carrier family 6 (neurotransmitter transporter), member 15 |
| ENSMUSG00000025602 | 80902 | Zfp202 | 0.289952783 | 0.047890046 | zinc finger protein 202 |
| ENSMUSG00000028252 | 51813 | Ccnc | 0.289802384 | 0.029076392 | cyclin C |
| ENSMUSG00000030647 | 68197 | Ndufc2 | 0.289714734 | 0.036674205 | NADH dehydrogenase (ubiquinone) 1, subcomplex unknown, 2 |
| ENSMUSG00000034724 | 231464 | Cnot6l | 0.289699274 | 0.031051608 | CCR4-NOT transcription complex, subunit 6-like |
| ENSMUSG00000038128 | 12326 | Camk4 | 0.28964015 | 0.016376632 | calcium/calmodulin-dependent protein kinase IV |
| ENSMUSG00000043671 | 233115 | Dpy19l3 | 0.28930463 | 0.032716483 | dpy-19-like 3 (*C. elegans*) |
| ENSMUSG00000030557 | 17258 | Mef2a | 0.288670051 | 0.01495083 | myocyte enhancer factor 2A |
| ENSMUSG00000020074 | 67500 | Ccar1 | 0.288435983 | 0.006443265 | cell division cycle and apoptosis regulator 1 |
| ENSMUSG00000040693 | 227394 | Slco4c1 | 0.288400188 | 0.031060625 | solute carrier organic anion transporter family, member 4C1 |
| ENSMUSG00000058093 | 100416706 | Zfp729b | 0.288352587 | 0.02613129 | zinc finger protein 729b |
| ENSMUSG00000044519 | 382867 | Zfp488 | 0.288173437 | 0.036213287 | zinc finger protein 488 |
| ENSMUSG00000071072 | 56351 | Ptges3 | 0.288011189 | 0.022912258 | prostaglandin E synthase 3 |
| ENSMUSG00000065947 | 17720 | ND4L | 0.28783127 | 0.011156839 | NADH dehydrogenase subunit 4L |
| ENSMUSG00000001855 | 227720 | Nup214 | 0.287608145 | 0.013490102 | nucleoporin 214 |
| ENSMUSG00000055026 | 14407 | Gabrg3 | 0.287486446 | 0.003076373 | gamma-aminobutyric acid (GABA) A receptor, subunit gamma 3 |
| ENSMUSG00000024079 | 19106 | Eif2ak2 | 0.287390744 | 0.027721019 | eukaryotic translation initiation factor 2-alpha kinase 2 |
| ENSMUSG00000049536 | 237052 | Tceal1 | 0.287320922 | 0.016052276 | transcription elongation factor A (SII)-like 1 |
| ENSMUSG00000018199 | 20822 | Trove2 | 0.287234361 | 0.017946736 | TROVE domain family, member 2 |
| ENSMUSG00000027618 | 18041 | Nfs1 | 0.287171056 | 0.034642156 | nitrogen fixation gene 1 (*S. cerevisiae*) |
| ENSMUSG00000031093 | 75974 | Dock11 | 0.286939979 | 0.045353479 | dedicator of cytokinesis 11 |
| ENSMUSG00000057766 | 225187 | Ankrd29 | 0.286929926 | 0.024699207 | ankyrin repeat domain 29 |

TABLE 2-continued

| Ensembl | Entrez | Symbol | log2FoldChange | padj | Name |
|---|---|---|---|---|---|
| ENSMUSG00000017376 | 18099 | Nlk | 0.286832461 | 0.039014193 | nemo like kinase |
| ENSMUSG00000051444 | 241950 | Bbs12 | 0.28677076 | 0.035357639 | Bardet-Biedl syndrome 12 (human) |
| ENSMUSG00000032418 | 17436 | Me1 | 0.286504463 | 0.006146316 | malic enzyme 1, NADP(+)-dependent, cytosolic |
| ENSMUSG00000020132 | 216344 | Rab21 | 0.286477541 | 0.007473461 | RAB21, member RAS oncogene family |
| ENSMUSG00000062203 | 14852 | Gspt1 | 0.286224521 | 0.027651551 | G1 to S phase transition 1 |
| ENSMUSG00000025950 | 15926 | Idh1 | 0.286217501 | 0.011519919 | isocitrate dehydrogenase 1 (NADP+), soluble |
| ENSMUSG00000036053 | 71409 | Fmnl2 | 0.286146043 | 0.026161559 | formin-like 2 |
| ENSMUSG00000040738 | 72656 | Ints8 | 0.286029861 | 0.017200534 | integrator complex subunit 8 |
| ENSMUSG00000041135 | 192656 | Ripk2 | 0.285880218 | 0.045170572 | receptor (TNFRSF)-interacting serine-threonine kinase 2 |
| ENSMUSG00000021103 | 17420 | Mnat1 | 0.28569197 | 0.027325301 | menage a trois 1 |
| ENSMUSG00000044934 | 238673 | Zfp367 | 0.28567128 | 0.018215632 | zinc finger protein 367 |
| ENSMUSG00000073643 | 69368 | Wdfy1 | 0.285417384 | 0.006152944 | WD repeat and FYVE domain containing 1 |
| ENSMUSG00000073295 | 58242 | Nudt11 | 0.285380858 | 0.022215108 | nudix (nucleoside diphosphate linked moiety X)-type motif 11 |
| ENSMUSG00000061024 | 59014 | Rrs1 | 0.285300983 | 0.035643348 | ribosome biogenesis regulator 1 |
| ENSMUSG00000078861 | 353208 | Zfp931 | 0.285296656 | 0.038124631 | zinc finger protein 931 |
| ENSMUSG00000041040 | 72750 | Fam117b | 0.285067873 | 0.009931345 | family with sequence similarity 117, member B |
| ENSMUSG00000040651 | 218850 | Fam208a | 0.285046014 | 0.025322192 | family with sequence similarity 208, member A |
| ENSMUSG00000022757 | 21787 | Tfg | 0.284791394 | 0.046806985 | Trk-fused gene |
| ENSMUSG00000067194 | 66235 | Eif1ax | 0.284711159 | 0.022252373 | eukaryotic translation initiation factor 1A, X-linked |
| ENSMUSG00000059208 | 76936 | Hnrnpm | 0.284632489 | 0.009001685 | heterogeneous nuclear ribonucleoprotein M |
| ENSMUSG00000047344 | 236285 | Lancl3 | 0.284425973 | 0.02357533 | LanC lantibiotic synthetase component C-like 3 (bacterial) |
| ENSMUSG00000061665 | 12488 | Cd2ap | 0.284384163 | 0.017512637 | CD2-associated protein |
| ENSMUSG00000026784 | 56075 | Pdss1 | 0.284321298 | 0.03551309 | prenyl (solanesyl) diphosphate synthase, subunit 1 |
| ENSMUSG00000028576 | 67694 | Ift74 | 0.284318659 | 0.009783693 | intraflagellar transport 74 |
| ENSMUSG00000026782 | 329165 | Abi2 | 0.284252236 | 0.0487454 | abl-interactor 2 |
| ENSMUSG00000034912 | 320772 | Mdga2 | 0.284101853 | 0.021628342 | MAM domain containing glycosylphosphatidylinositol anchor 2 |
| ENSMUSG00000022205 | 20024 | Sub1 | 0.283949932 | 0.020690944 | SUB1 homolog (S. cerevisiae) |
| ENSMUSG00000026667 | 16589 | Uhmk1 | 0.283924807 | 0.007645477 | U2AF homology motif (UHM) kinase 1 |
| ENSMUSG00000071014 | 230075 | Ndufb6 | 0.283920018 | 0.033554414 | NADH dehydrogenase (ubiquinone) 1 beta subcomplex, 6 |
| ENSMUSG00000087370 | 621976 | Tmem170b | 0.283835866 | 0.01547191 | transmembrane protein 170B |
| ENSMUSG00000070866 | 241514 | Zfp804a | 0.283625587 | 0.006131244 | zinc finger protein 804A |
| ENSMUSG00000036499 | 216238 | Eea1 | 0.283288751 | 0.014692027 | early endosome antigen 1 |
| ENSMUSG00000024480 | 11777 | Ap3s1 | 0.283098286 | 0.039345584 | adaptor-related protein complex 3, sigma 1 subunit |
| ENSMUSG00000014226 | 12301 | Cacybp | 0.282998412 | 0.030873091 | calcyclin binding protein |
| ENSMUSG00000043542 | 67306 | Zc2hc1a | 0.282882954 | 0.029477001 | zinc finger, C2HC-type containing 1A |
| ENSMUSG00000026623 | 226856 | Lpgat1 | 0.282760741 | 0.008378227 | lysophosphatidylglycerol acyltransferase 1 |
| ENSMUSG00000031508 | 102334 | Ankrd10 | 0.282391258 | 0.015500869 | ankyrin repeat domain 10 |
| ENSMUSG00000020687 | 217232 | Cdc27 | 0.282265349 | 0.023463949 | cell division cycle 27 |
| ENSMUSG00000016534 | 16784 | Lamp2 | 0.282231199 | 0.02273 | lysosomal-associated membrane protein 2 |
| ENSMUSG00000027893 | 229709 | Ahcyl1 | 0.282225732 | 0.013557723 | S-adenosylhomocysteine hydrolase-like 1 |
| ENSMUSG00000021010 | 27386 | Npas3 | 0.282096729 | 0.012371516 | neuronal PAS domain protein 3 |
| ENSMUSG00000024259 | 67453 | Slc25a46 | 0.281954875 | 0.020792344 | solute carrier family 25, member 46 |
| ENSMUSG00000020134 | 67245 | Peli1 | 0.28194937 | 0.010268575 | pellino 1 |
| ENSMUSG00000035517 | 100121 | Tdrd7 | 0.281926117 | 0.032840881 | tudor domain containing 7 |
| ENSMUSG00000066880 | 170938 | Zfp617 | 0.281801249 | 0.032410655 | zinc finger protein 617 |
| ENSMUSG00000054770 | 51960 | Kctd18 | 0.281775485 | 0.014193146 | potassium channel tetramerisation domain containing 18 |
| ENSMUSG00000028557 | 29864 | Rnf11 | 0.281649823 | 0.041347609 | ring finger protein 11 |
| ENSMUSG00000027104 | 11909 | Atf2 | 0.281569348 | 0.018530599 | activating transcription factor 2 |
| ENSMUSG00000054942 | 215708 | Miga1 | 0.281535778 | 0.011381006 | mitoguardin 1 |
| ENSMUSG00000050965 | 18750 | Prkca | 0.281498784 | 0.045596678 | protein kinase C, alpha |
| ENSMUSG00000042133 | 228005 | Ppig | 0.281393711 | 0.013985727 | peptidyl-prolyl isomerase G (cyclophilin G) |
| ENSMUSG00000001773 | 53320 | Folh1 | 0.281376835 | 0.037187025 | folate hydrolase 1 |
| ENSMUSG00000021013 | 76260 | Ttc8 | 0.281198387 | 0.022895459 | tetratricopeptide repeat domain 8 |
| ENSMUSG00000026893 | 227960 | Gca | 0.281111208 | 0.044230875 | grancalcin |
| ENSMUSG00000032407 | 67958 | U2surp | 0.281097807 | 0.048997766 | U2 snRNP-associated SURP domain containing |
| ENSMUSG00000025059 | 14933 | Gk | 0.281053827 | 0.010727545 | glycerol kinase |
| ENSMUSG00000028189 | 74245 | Ctbs | 0.280890786 | 0.02234913 | chitobiase, di-N-acetyl- |
| ENSMUSG00000022292 | 382985 | Rrm2b | 0.280765388 | 0.032175372 | ribonucleotide reductase M2 B (TP53 inducible) |

TABLE 2-continued

| Ensembl | Entrez | Symbol | log2FoldChange | padj | Name |
|---|---|---|---|---|---|
| ENSMUSG00000019920 | 110829 | Lims1 | 0.280630991 | 0.012524331 | LIM and senescent cell antigen-like domains 1 |
| ENSMUSG00000007836 | 77134 | Hnrnpa0 | 0.28043287 | 0.048842992 | heterogeneous nuclear ribonucleoprotein A0 |
| ENSMUSG00000037416 | 240283 | Dmxl1 | 0.280311301 | 0.010683913 | Dmx-like 1 |
| ENSMUSG00000033054 | 244879 | Npat | 0.279964803 | 0.01283701 | nuclear protein in the AT region |
| ENSMUSG00000003452 | 12121 | Bicd1 | 0.279574034 | 0.000556123 | bicaudal D homolog 1 (*Drosophila*) |
| ENSMUSG00000078899 | 627914 | Gm14430 | 0.279472186 | 0.011086721 | predicted gene 14430 |
| ENSMUSG00000038916 | 67412 | Soga3 | 0.278968907 | 0.004382499 | SOGA family member 3 |
| ENSMUSG00000097452 | | | 0.278886933 | 0.026558756 | |
| ENSMUSG00000055430 | 58243 | Nap1l5 | 0.278806093 | 0.014800621 | nucleosome assembly protein 1-like 5 |
| ENSMUSG00000066232 | 233726 | Ipo7 | 0.278696654 | 0.028243863 | importin 7 |
| ENSMUSG00000020863 | 67684 | Luc7l3 | 0.278604127 | 0.01857334 | LUC7-like 3 (*S. cerevisiae*) |
| ENSMUSG00000097498 | | | 0.278406433 | 0.040368494 | |
| ENSMUSG00000022338 | 223527 | Eny2 | 0.278268775 | 0.031366726 | enhancer of yellow 2 homolog (*Drosophila*) |
| ENSMUSG00000039968 | 242860 | Rsbn1l | 0.277949502 | 0.026938218 | round spermatid basic protein 1-like |
| ENSMUSG00000034488 | 13612 | Edil3 | 0.277817391 | 0.016953303 | EGF-like repeats and discoidin I-like domains 3 |
| ENSMUSG00000046675 | 320351 | Tmem251 | 0.277775442 | 0.016697053 | transmembrane protein 251 |
| ENSMUSG00000022636 | 11658 | Alcam | 0.277558651 | 0.015941294 | activated leukocyte cell adhesion molecule |
| ENSMUSG00000040297 | 226551 | Suco | 0.277447442 | 0.019700695 | SUN domain containing ossification factor |
| ENSMUSG00000024511 | 80718 | Rab27b | 0.277124347 | 0.022790168 | RAB27B, member RAS oncogene family |
| ENSMUSG00000042198 | 66433 | Chchd7 | 0.277075682 | 0.037187025 | coiled-coil-helix-coiled-coil-helix domain containing 7 |
| ENSMUSG00000090498 | | | 0.27707176 | 0.039087346 | |
| ENSMUSG00000052387 | 226025 | Trpm3 | 0.277053046 | 0.035883734 | transient receptor potential cation channel, subfamily M, member 3 |
| ENSMUSG00000042208 | 71675 | 0610010F05Rik | 0.277025081 | 0.023522014 | RIKEN cDNA 0610010F05 gene |
| ENSMUSG00000039967 | 30046 | Zfp292 | 0.276763334 | 0.012214359 | zinc finger protein 292 |
| ENSMUSG00000021051 | 26932 | Ppp2r5e | 0.276703575 | 0.003780714 | protein phosphatase 2, regulatory subunit B', epsilon |
| ENSMUSG00000031370 | 22184 | Zrsr2 | 0.276498131 | 0.029357419 | zinc finger (CCCH type), RNA binding motif and serine/arginine rich 2 |
| ENSMUSG00000038628 | 67005 | Polr3k | 0.276232901 | 0.028264626 | polymerase (RNA) III (DNA directed) polypeptide K |
| ENSMUSG00000091537 | 66167 | Tma7 | 0.27607541 | 0.024609965 | translational machinery associated 7 |
| ENSMUSG00000024095 | 72692 | Hnrnpll | 0.27601522 | 0.00170807 | heterogeneous nuclear ribonucleoprotein L-like |
| ENSMUSG00000032253 | 83946 | Phip | 0.276006663 | 0.025950367 | pleckstrin homology domain interacting protein |
| ENSMUSG00000039361 | 233489 | Picalm | 0.275796512 | 0.026071951 | phosphatidylinositol binding clathrin assembly protein |
| ENSMUSG00000057858 | 76539 | Fam204a | 0.275670844 | 0.043223052 | family with sequence similarity 204, member A |
| ENSMUSG00000034723 | 52837 | Tmx4 | 0.275560822 | 0.012719029 | thioredoxin-related transmembrane protein 4 |
| ENSMUSG00000022523 | 14167 | Fgf12 | 0.275092053 | 0.040222459 | fibroblast growth factor 12 |
| ENSMUSG00000036766 | 227325 | Dner | 0.275073249 | 0.032546234 | delta/notch-like EGF repeat containing |
| ENSMUSG00000030019 | 101358 | Fbxl14 | 0.274991951 | 0.03560175 | F-box and leucine-rich repeat protein 14 |
| ENSMUSG00000037152 | 66377 | Ndufc1 | 0.274914323 | 0.046525045 | NADH dehydrogenase (ubiquinone) 1, subcomplex unknown, 1 |
| ENSMUSG00000028248 | 66625 | Pnisr | 0.274801615 | 0.028457339 | PNN interacting serine/arginine-rich |
| ENSMUSG00000097451 | | | 0.274518323 | 0.001949789 | |
| ENSMUSG00000063694 | 13063 | Cycs | 0.274459587 | 0.041714469 | cytochrome c, somatic |
| ENSMUSG00000023025 | 207214 | Larp4 | 0.274264116 | 0.024270912 | La ribonucleoprotein domain family, member 4 |
| ENSMUSG00000026349 | 72949 | Ccnt2 | 0.274119225 | 0.001179316 | cyclin T2 |
| ENSMUSG00000024750 | 22682 | Zfand5 | 0.273820075 | 0.048744199 | zinc finger, AN1-type domain 5 |
| ENSMUSG00000039100 | 223455 | 6-Mar | 0.273660457 | 0.019098741 | membrane-associated ring finger (C3HC4) 6 |
| ENSMUSG00000043463 | 319642 | Rab9b | 0.273582707 | 0.04287943 | RAB9B, member RAS oncogene family |
| ENSMUSG00000086370 | 78878 | Ftx | 0.27332442 | 0.04096928 | Ftx transcript, Xist regulator (non-protein coding) |
| ENSMUSG00000038679 | 83925 | Trps1 | 0.273288888 | 0.030017839 | trichorhinophalangeal syndrome I (human) |
| ENSMUSG00000064138 | 68675 | Fam172a | 0.273251652 | 0.049745533 | family with sequence similarity 172, member A |
| ENSMUSG00000019132 | 79555 | BC005537 | 0.273163336 | 0.008913482 | cDNA sequence BC005537 |
| ENSMUSG00000071708 | 20603 | Sms | 0.273022705 | 0.016109381 | spermine synthase |
| ENSMUSG00000032262 | 83603 | Elovl4 | 0.272946195 | 0.022899126 | elongation of very long chain fatty acids (FEN1/Elo2, SUR4/Elo3, yeast)-like 4 |
| ENSMUSG00000048279 | 50720 | Sacs | 0.272817751 | 0.032175372 | sacsin |

TABLE 2-continued

| Ensembl | Entrez | Symbol | log2FoldChange | padj | Name |
|---|---|---|---|---|---|
| ENSMUSG00000028577 | 18786 | Plaa | 0.272553121 | 0.015410183 | phospholipase A2, activating protein |
| ENSMUSG00000020929 | 20624 | Eftud2 | 0.272155693 | 0.029716511 | elongation factor Tu GTP binding domain containing 2 |
| ENSMUSG00000026064 | 19243 | Ptp4a1 | 0.272047245 | 0.026895831 | protein tyrosine phosphatase 4a1 |
| ENSMUSG00000018846 | 211347 | Pank3 | 0.272041501 | 0.022746493 | pantothenate kinase 3 |
| ENSMUSG00000072501 | 239510 | Phf20l1 | 0.271779806 | 0.014675859 | PHD finger protein 20-like 1 |
| ENSMUSG00000038733 | 226757 | Wdr26 | 0.271740026 | 0.000979658 | WD repeat domain 26 |
| ENSMUSG00000025261 | 59026 | Huwe1 | 0.271716985 | 0.016059298 | HECT, UBA and WWE domain containing 1 |
| ENSMUSG00000042331 | 432572 | Specc1 | 0.271561394 | 0.013652997 | sperm antigen with calponin homology and coiled-coil domains 1 |
| ENSMUSG00000058558 | 100503670 | Rpl5 | 0.271515885 | 0.048312414 | ribosomal protein L5 |
| ENSMUSG00000049658 | 544971 | Bdp1 | 0.271476643 | 0.006546749 | B double prime 1, subunit of RNA polymerase III transcription initiation factor IIIB |
| ENSMUSG00000040387 | 212390 | Klhl32 | 0.271359544 | 0.013418393 | kelch-like 32 |
| ENSMUSG00000000276 | 56077 | Dgke | 0.271245181 | 0.024369844 | diacylglycerol kinase, epsilon |
| ENSMUSG00000044712 | 625098 | Slc38a6 | 0.271084086 | 0.004786928 | solute carrier family 38, member 6 |
| ENSMUSG00000007812 | 72611 | Zfp655 | 0.270798136 | 0.021964618 | zinc finger protein 655 |
| ENSMUSG00000031007 | 70495 | Atp6ap2 | 0.270499438 | 0.02559961 | ATPase, H+ transporting, lysosomal accessory protein 2 |
| ENSMUSG00000041328 | 74737 | Pcf11 | 0.270339627 | 0.019701573 | PCF11 cleavage and polyadenylation factor subunit |
| ENSMUSG00000006678 | 18968 | Pola1 | 0.270232589 | 0.049081064 | polymerase (DNA directed), alpha 1 |
| ENSMUSG00000028180 | 53861 | Zranb2 | 0.269822997 | 0.015293069 | zinc finger, RAN-binding domain containing 2 |
| ENSMUSG00000027770 | 72162 | Dhx36 | 0.269814423 | 0.036714481 | DEAH (Asp-Glu-Ala-His) box polypeptide 36 |
| ENSMUSG00000022339 | 55960 | Ebag9 | 0.269691891 | 0.01357521 | estrogen receptor-binding fragment-associated gene 9 |
| ENSMUSG00000011831 | 14020 | Evi5 | 0.269508324 | 0.002404843 | ecotropic viral integration site 5 |
| ENSMUSG00000039128 | 98828 | Cdc123 | 0.269297168 | 0.02855274 | cell division cycle 123 |
| ENSMUSG00000017677 | 78889 | Wsb1 | 0.26919065 | 0.041114891 | WD repeat and SOCS box-containing 1 |
| ENSMUSG00000027957 | 229782 | Slc35a3 | 0.26871088 | 0.023699881 | solute carrier family 35 (UDP-N-acetylglucosamine (UDP-GlcNAc) transporter), member 3 |
| ENSMUSG00000051306 | 76800 | Usp42 | 0.268681704 | 0.046508388 | ubiquitin specific peptidase 42 |
| ENSMUSG00000014767 | 21374 | Tbp | 0.268664511 | 0.014701725 | TATA box binding protein |
| ENSMUSG00000053754 | 67772 | Chd8 | 0.268580117 | 0.046079316 | chromodomain helicase DNA binding protein 8 |
| ENSMUSG00000071748 | | | 0.26857515 | 0.037187025 | |
| ENSMUSG00000018068 | 70422 | Ints2 | 0.26847829 | 0.013084261 | integrator complex subunit 2 |
| ENSMUSG00000021270 | 15519 | Hsp90aa1 | 0.267695154 | 0.025364617 | heat shock protein 90, alpha (cytosolic), class A member 1 |
| ENSMUSG00000072704 | 381820 | Smim10l1 | 0.267615809 | 0.047913743 | small integral membrane protein 10 like 1 |
| ENSMUSG00000032002 | 76863 | Dcun1d5 | 0.267552124 | 0.01971677 | DCN1, defective in cullin neddylation 1, domain containing 5 (S. cerevisiae) |
| ENSMUSG00000038174 | 213056 | Fam126b | 0.267254868 | 0.036714481 | family with sequence similarity 126, member B |
| ENSMUSG00000056216 | 12611 | Cebpg | 0.26712613 | 0.025454387 | CCAAT/enhancer binding protein (C/EBP), gamma |
| ENSMUSG00000074527 | 100504263 | 2210418O10Rik | 0.267029333 | 0.002590106 | predicted gene 2210418O10Rik |
| ENSMUSG00000024298 | 208292 | Zfp871 | 0.267026478 | 0.006004909 | zinc finger protein 871 |
| ENSMUSG00000029253 | 12617 | Cenpc1 | 0.266923113 | 0.013870995 | centromere protein C1 |
| ENSMUSG00000000355 | 68995 | Mcts1 | 0.266818572 | 0.03825231 | malignant T cell amplified sequence 1 |
| ENSMUSG00000027184 | 53872 | Caprin1 | 0.266766631 | 0.017200534 | cell cycle associated protein 1 |
| ENSMUSG00000046138 | 240613 | 9930021J03Rik | 0.266415193 | 0.011569878 | RIKEN cDNA 9930021J03 gene |
| ENSMUSG00000025066 | 67788 | Sfr1 | 0.266069555 | 0.041372365 | SWI5 dependent recombination repair 1 |
| ENSMUSG00000054737 | 319535 | Zfp182 | 0.266048513 | 0.043128863 | zinc finger protein 182 |
| ENSMUSG00000036087 | 75991 | Slain2 | 0.265855784 | 0.049513327 | SLAIN motif family, member 2 |
| ENSMUSG00000027365 | 58800 | Trpm7 | 0.265832986 | 0.010090704 | transient receptor potential cation channel, subfamily M, member 7 |
| ENSMUSG00000031644 | 18004 | Nek1 | 0.265607862 | 0.008859633 | NIMA (never in mitosis gene a)-related expressed kinase 1 |
| ENSMUSG00000048388 | 241520 | Fam171b | 0.265451748 | 0.014692027 | family with sequence similarity 171, member B |
| ENSMUSG00000055884 | 104806 | Fancm | 0.265248867 | 0.031060625 | Fanconi anemia, complementation group M |
| ENSMUSG00000006586 | 12395 | Runx1t1 | 0.265062976 | 0.005730959 | runt-related transcription factor 1; translocated to, 1 (cyclin D-related) |
| ENSMUSG00000030869 | 70316 | Ndufab1 | 0.265002143 | 0.041347609 | NADH dehydrogenase (ubiquinone) 1, alpha/beta subcomplex, 1 |
| ENSMUSG00000055660 | 76781 | Mettl4 | 0.264996488 | 0.048569817 | methyltransferase like 4 |
| ENSMUSG00000039630 | 51810 | Hnrnpu | 0.264954373 | 0.019915829 | heterogeneous nuclear ribonucleoprotein U |
| ENSMUSG00000040147 | 109731 | Maob | 0.264716529 | 0.04287943 | monoamine oxidase B |
| ENSMUSG00000057894 | 67230 | Zfp329 | 0.264541446 | 0.014827389 | zinc finger protein 329 |

TABLE 2-continued

| Ensembl | Entrez | Symbol | log2FoldChange | padj | Name |
|---|---|---|---|---|---|
| ENSMUSG00000003923 | 21780 | Tfam | 0.264428932 | 0.005379092 | transcription factor A, mitochondrial |
| ENSMUSG00000052144 | 232314 | Ppp4r2 | 0.264321714 | 0.044599594 | protein phosphatase 4, regulatory subunit 2 |
| ENSMUSG00000002428 | 20585 | Hltf | 0.264314095 | 0.016697053 | helicase-like transcription factor |
| ENSMUSG00000015522 | 11863 | Arnt | 0.264194917 | 0.021629316 | aryl hydrocarbon receptor nuclear translocator |
| ENSMUSG00000029328 | 50926 | Hnrnpdl | 0.264074688 | 0.030873091 | heterogeneous nuclear ribonucleoprotein D-like |
| ENSMUSG00000031137 | 14168 | Fgf13 | 0.26407163 | 0.039410304 | fibroblast growth factor 13 |
| ENSMUSG00000039652 | 208922 | Cpeb3 | 0.263885663 | 0.012725383 | cytoplasmic polyadenylation element binding protein 3 |
| ENSMUSG00000032745 | 73274 | Gpbp1 | 0.263792805 | 0.02333511 | GC-rich promoter binding protein 1 |
| ENSMUSG00000059742 | 170738 | Kcnh7 | 0.263788241 | 0.022939006 | potassium voltage-gated channel, subfamily H (eag-related), member 7 |
| ENSMUSG00000021930 | 66674 | Spryd7 | 0.263438114 | 0.045482841 | SPRY domain containing 7 |
| ENSMUSG00000053641 | 102442 | Dennd4a | 0.263337213 | 0.027847707 | DENN/MADD domain containing 4A |
| ENSMUSG00000004151 | 14009 | Etv1 | 0.263215302 | 0.014789257 | ets variant 1 |
| ENSMUSG00000014355 | 17222 | Anapc1 | 0.263012636 | 0.003780714 | anaphase promoting complex subunit 1 |
| ENSMUSG00000025544 | 68059 | Tm9sf2 | 0.262934588 | 0.038996555 | transmembrane 9 superfamily member 2 |
| ENSMUSG00000071337 | 21841 | Tia1 | 0.26281787 | 0.015611569 | cytotoxic granule-associated RNA binding protein 1 |
| ENSMUSG00000027804 | 67738 | Ppid | 0.262768276 | 0.012177821 | peptidylprolyl isomerase D (cyclophilin D) |
| ENSMUSG00000043535 | 269254 | Setx | 0.262376578 | 0.033747098 | senataxin |
| ENSMUSG00000022360 | 70472 | Atad2 | 0.262121641 | 0.033939371 | ATPase family, AAA domain containing 2 |
| ENSMUSG00000025907 | 12421 | Rb1cc1 | 0.26168864 | 0.022502596 | RB1-inducible coiled-coil 1 |
| ENSMUSG00000024059 | 78785 | Clip4 | 0.261643179 | 0.00825964 | CAP-GLY domain containing linker protein family, member 4 |
| ENSMUSG00000024597 | 20496 | Slc12a2 | 0.261293983 | 0.041478328 | solute carrier family 12, member 2 |
| ENSMUSG00000028343 | 76299 | Erp44 | 0.26119918 | 0.029962408 | endoplasmic reticulum protein 44 |
| ENSMUSG00000019302 | 11975 | Atp6v0a1 | 0.261111395 | 0.002365415 | ATPase, H+ transporting, lysosomal V0 subunit A1 |
| ENSMUSG00000060227 | 319996 | Casc4 | 0.261075286 | 0.035537227 | cancer susceptibility candidate 4 |
| ENSMUSG00000039318 | 98732 | Rab3gap2 | 0.26087584 | 0.001555125 | RAB3 GTPase activating protein subunit 2 |
| ENSMUSG00000021054 | 81535 | Sgpp1 | 0.260845563 | 0.038963537 | sphingosine-1-phosphate phosphatase 1 |
| ENSMUSG00000020900 | 77579 | Myh10 | 0.26072141 | 0.004082709 | myosin, heavy polypeptide 10, non-muscle |
| ENSMUSG00000030691 | 207278 | Fchsd2 | 0.260377361 | 0.003415124 | FCH and double SH3 domains 2 |
| ENSMUSG00000022507 | 69053 | 1810013L24Rik | 0.26003619 | 0.016008835 | RIKEN cDNA 1810013L24 gene |
| ENSMUSG00000028033 | 226922 | Kcnq5 | 0.259885217 | 0.014857527 | potassium voltage-gated channel, subfamily Q, member 5 |
| ENSMUSG00000035367 | 74386 | Rmi1 | 0.259817065 | 0.033939371 | RecQ mediated genome instability 1 |
| ENSMUSG00000026781 | 74159 | Acbd5 | 0.259681886 | 0.03788271 | acyl-Coenzyme A binding domain containing 5 |
| ENSMUSG00000026021 | 22218 | Sumo1 | 0.259580733 | 0.040479409 | small ubiquitin-like modifier 1 |
| ENSMUSG00000041658 | 245670 | Rragb | 0.259464165 | 0.032278232 | Ras-related GTP binding B |
| ENSMUSG00000020273 | 216578 | Papolg | 0.259202603 | 0.026540021 | poly(A) polymerase gamma |
| ENSMUSG00000055733 | 54561 | Nap1l3 | 0.259183995 | 0.034979811 | nucleosome assembly protein 1-like 3 |
| ENSMUSG00000020849 | 22627 | Ywhae | 0.259178701 | 0.022477283 | tyrosine 3-monooxygenase/tryptophan 5-monooxygenase activation protein, epsilon polypeptide |
| ENSMUSG00000024283 | 225131 | Wac | 0.25911895 | 0.011920626 | WW domain containing adaptor with coiled-coil |
| ENSMUSG00000074781 | 93765 | Ube2n | 0.258985171 | 0.027743402 | ubiquitin-conjugating enzyme E2N |
| ENSMUSG00000042444 | 235461 | Fam63b | 0.258857456 | 0.029224357 | family with sequence similarity 63, member B |
| ENSMUSG00000043419 | 80515 | Chd3os | 0.2587624 | 0.018593209 | chromodomain helicase DNA binding protein 3, opposite strand |
| ENSMUSG00000021831 | 50527 | Ero1l | 0.258587588 | 0.025407964 | ERO1-like (S. cerevisiae) |
| ENSMUSG00000026824 | 16519 | Kcnj3 | 0.258481775 | 0.048370046 | potassium inwardly-rectifying channel, subfamily J, member 3 |
| ENSMUSG00000044098 | 229675 | Rsbn1 | 0.258256084 | 0.028462508 | rosbin, round spermatid basic protein 1 |
| ENSMUSG00000052684 | 16476 | Jun | 0.257998778 | 0.005496172 | jun proto-oncogene |
| ENSMUSG00000020078 | 30930 | Vps26a | 0.257954923 | 0.029406848 | VPS26 retromer complex component A |
| ENSMUSG00000025862 | 20843 | Stag2 | 0.257878675 | 0.024369844 | stromal antigen 2 |
| ENSMUSG00000059146 | 18213 | Ntrk3 | 0.257593948 | 0.028570977 | neurotrophic tyrosine kinase, receptor, type 3 |
| ENSMUSG00000024976 | 56392 | Shoc2 | 0.257210882 | 0.028304822 | soc-2 (suppressor of clear) homolog (C. elegans) |
| ENSMUSG00000021534 | 69315 | 1700001L19Rik | 0.25717972 | 0.046767248 | RIKEN cDNA 1700001L19 gene |
| ENSMUSG00000067928 | 240034 | Zfp760 | 0.257135646 | 0.038423662 | zinc finger protein 760 |
| ENSMUSG00000008575 | 18028 | Nfib | 0.256771529 | 0.04648534 | nuclear factor I/B |
| ENSMUSG00000053702 | 74103 | Nebl | 0.256607003 | 0.033747098 | nebulette |
| ENSMUSG00000061080 | 268890 | Lsamp | 0.256583353 | 0.007550519 | limbic system-associated membrane protein |
| ENSMUSG00000051166 | 319670 | Eml5 | 0.2565348 | 0.014449618 | echinoderm microtubule associated protein like 5 |
| ENSMUSG00000021877 | 11843 | Arf4 | 0.256470819 | 0.039147968 | ADP-ribosylation factor 4 |
| ENSMUSG00000044763 | 52575 | Trmt10c | 0.256303162 | 0.034445271 | tRNA methyltransferase 10C |
| ENSMUSG00000041459 | 230908 | Tardbp | 0.256031886 | 0.024688022 | TAR DNA binding protein |

TABLE 2-continued

| Ensembl | Entrez | Symbol | log2FoldChange | padj | Name |
|---|---|---|---|---|---|
| ENSMUSG00000055531 | 432508 | Cpsf6 | 0.255955012 | 0.006955797 | cleavage and polyadenylation specific factor 6 |
| ENSMUSG00000040123 | 219105 | Zmym5 | 0.255840355 | 0.020101173 | zinc finger, MYM-type 5 |
| ENSMUSG00000033400 | 77559 | Agl | 0.255805013 | 0.006059865 | amylo-1,6-glucosidase, 4-alpha-glucanotransferase |
| ENSMUSG00000043496 | 66873 | Tril | 0.255679476 | 0.041114891 | TLR4 interactor with leucine-rich repeats |
| ENSMUSG00000021537 | 12626 | Cetn3 | 0.255639315 | 0.026818319 | centrin 3 |
| ENSMUSG00000072969 | 494468 | Armcx5 | 0.255575371 | 0.037872455 | armadillo repeat containing, X-linked 5 |
| ENSMUSG00000026096 | 72085 | Osgepl1 | 0.255286433 | 0.045826365 | O-sialoglycoprotein endopeptidase-like 1 |
| ENSMUSG00000025939 | 66799 | Ube2w | 0.2552439 | 0.017866449 | ubiquitin-conjugating enzyme E2W (putative) |
| ENSMUSG00000068205 | 72899 | Macrod2 | 0.255076989 | 0.002590106 | MACRO domain containing 2 |
| ENSMUSG00000025104 | 29877 | Hdgfrp3 | 0.254898287 | 0.03102444 | hepatoma-derived growth factor, related protein 3 |
| ENSMUSG00000062691 | 68554 | Cebpzos | 0.254865342 | 0.033117638 | CCAAT/enhancer binding protein (C/EBP), zeta, opposite strand |
| ENSMUSG00000027175 | 320554 | Tcp11l1 | 0.254820788 | 0.016334183 | t-complex 11 like 1 |
| ENSMUSG00000006740 | 16573 | Kif5b | 0.254773834 | 0.046702542 | kinesin family member 5B |
| ENSMUSG00000091264 | 108934 | Smim13 | 0.254759834 | 0.018238801 | small integral membrane protein 13 |
| ENSMUSG00000027708 | 114893 | Dcun1d1 | 0.254570888 | 0.040368494 | DCN1, defective in cullin neddylation 1, domain containing 1 (*S. cerevisiae*) |
| ENSMUSG00000078903 | 665001 | Gm14391 | 0.254385123 | 0.032665653 | predicted gene 14391 |
| ENSMUSG00000062257 | 330908 | Opcml | 0.254329399 | 0.020792344 | opioid binding protein/cell adhesion molecule-like |
| ENSMUSG00000029167 | 19017 | Ppargc1a | 0.254290977 | 0.003076373 | peroxisome proliferative activated receptor, gamma, coactivator 1 alpha |
| ENSMUSG00000041769 | 52432 | Ppp2r2d | 0.254246393 | 0.019153869 | protein phosphatase 2, regulatory subunit B, delta |
| ENSMUSG00000028221 | 72519 | Tmem55a | 0.254213737 | 0.040628364 | transmembrane protein 55A |
| ENSMUSG00000001998 | 108011 | Ap4e1 | 0.254176841 | 0.048796738 | adaptor-related protein complex AP-4, epsilon 1 |
| ENSMUSG00000019802 | 140740 | Sec63 | 0.254141433 | 0.020130225 | SEC63-like (*S. cerevisiae*) |
| ENSMUSG00000072964 | 70237 | Bhlhb9 | 0.25412958 | 0.031480569 | basic helix-loop-helix domain containing, class B9 |
| ENSMUSG00000007613 | 21812 | Tgfbr1 | 0.254119042 | 0.039931632 | transforming growth factor, beta receptor I |
| ENSMUSG00000029366 | 13178 | Dck | 0.254101295 | 0.043194165 | deoxycytidine kinase |
| ENSMUSG00000035992 | 216742 | Fnip1 | 0.254073524 | 0.038963537 | folliculin interacting protein 1 |
| ENSMUSG00000024483 | 210105 | Zfp719 | 0.253811033 | 0.011733585 | zinc finger protein 719 |
| ENSMUSG00000031751 | 23802 | Amfr | 0.253773842 | 0.011300029 | autocrine motility factor receptor |
| ENSMUSG00000005610 | 13690 | Eif4g2 | 0.253661488 | 0.032716483 | eukaryotic translation initiation factor 4, gamma 2 |
| ENSMUSG00000036879 | 102093 | Phkb | 0.253646345 | 0.043223052 | phosphorylase kinase beta |
| ENSMUSG00000021840 | 218975 | Mapk1ip1 | 0.253490661 | 0.0295498 | mitogen-activated protein kinase 1 interacting protein 1-like |
| ENSMUSG00000024294 | 225164 | Mib1 | 0.253455757 | 0.043223052 | mindbomb E3 ubiquitin protein ligase 1 |
| ENSMUSG00000067242 | 56839 | Lgi1 | 0.253416265 | 0.038218085 | leucine-rich repeat LGI family, member 1 |
| ENSMUSG00000024483 | 108857 | Ankhd1 | 0.253264611 | 0.017863115 | ankyrin repeat and KH domain containing 1 |
| ENSMUSG00000025764 | 269424 | Jade1 | 0.253133842 | 0.024688022 | jade family PHD finger 1 |
| ENSMUSG00000025658 | 245684 | Cnksr2 | 0.253060278 | 0.035995265 | connector enhancer of kinase suppressor of Ras 2 |
| ENSMUSG00000030275 | 75320 | Etnk1 | 0.253019313 | 0.021587282 | ethanolamine kinase 1 |
| ENSMUSG00000050730 | 71544 | Arhgap42 | 0.252799023 | 0.035995265 | Rho GTPase activating protein 42 |
| ENSMUSG00000050812 | 230249 | AI314180 | 0.252794533 | 0.002238309 | expressed sequence AI314180 |
| ENSMUSG00000001774 | 66917 | Chordc1 | 0.252736368 | 0.04708058 | cysteine and histidine-rich domain (CHORD)-containing, zinc-binding protein 1 |
| ENSMUSG00000030105 | 67166 | Arl8b | 0.252613196 | 0.024578427 | ADP-ribosylation factor-like 8B |
| ENSMUSG00000024231 | 71745 | Cul2 | 0.252547805 | 0.035932332 | cullin 2 |
| ENSMUSG00000023087 | 12457 | Noct | 0.252383566 | 0.005959608 | nocturnin |
| ENSMUSG00000024304 | 12558 | Cdh2 | 0.252206122 | 0.001815611 | cadherin 2 |
| ENSMUSG00000025323 | 20688 | Sp4 | 0.252115151 | 0.043003032 | trans-acting transcription factor 4 |
| ENSMUSG00000022789 | 74006 | Dnm1l | 0.25200039 | 0.011284766 | dynamin 1-like |
| ENSMUSG00000026610 | 26381 | Esrrg | 0.25195783 | 0.046125916 | estrogen-related receptor gamma |
| ENSMUSG00000019810 | 66848 | Fuca2 | 0.251810395 | 0.02613129 | fucosidase, alpha-L-2, plasma |
| ENSMUSG00000042228 | 17096 | Lyn | 0.251579036 | 0.043784958 | LYN proto-oncogene, Src family tyrosine kinase |
| ENSMUSG00000034981 | 231440 | Parm1 | 0.251549033 | 0.009597852 | prostate androgen-regulated mucin-like protein 1 |
| ENSMUSG00000055670 | 195018 | Zzef1 | 0.251378302 | 0.043208207 | zinc finger, ZZ-type with EF hand domain 1 |
| ENSMUSG00000021669 | 68018 | Col4a3bp | 0.251356606 | 0.026558756 | collagen, type IV, alpha 3 (Goodpasture antigen) binding protein |
| ENSMUSG00000071796 | 547150 | 6820431F20Rik | 0.251319052 | 0.029438723 | cadherin 11 pseudogene |
| ENSMUSG00000051950 | 381694 | B3glct | 0.251091443 | 0.033494396 | beta-3-glucosyltransferase |
| ENSMUSG00000027822 | 11416 | Slc33a1 | 0.251025485 | 0.026015723 | solute carrier family 33 (acetyl-CoA transporter), member 1 |

TABLE 2-continued

| Ensembl | Entrez | Symbol | log2FoldChange | padj | Name |
|---|---|---|---|---|---|
| ENSMUSG00000046442 | 320472 | Ppm1e | 0.250724814 | 0.021276359 | protein phosphatase 1E (PP2C domain containing) |
| ENSMUSG00000047714 | 66849 | Ppp1r2 | 0.250479454 | 0.018417239 | protein phosphatase 1, regulatory (inhibitor) subunit 2 |
| ENSMUSG00000029836 | 12417 | Cbx3 | 0.250435715 | 0.045505582 | chromobox 3 |
| ENSMUSG00000024477 | 225467 | Pggt1b | 0.250365215 | 0.048127675 | protein geranylgeranyltransferase type I, beta subunit |
| ENSMUSG00000024924 | 22359 | Vldlr | 0.249795716 | 0.004154959 | very low density lipoprotein receptor |
| ENSMUSG00000052572 | 23859 | Dlg2 | 0.249779119 | 0.005072478 | discs, large homolog 2 (*Drosophila*) |
| ENSMUSG00000031176 | 67117 | Dynlt3 | 0.249651398 | 0.046253609 | dynein light chain Tctex-type 3 |
| ENSMUSG00000050697 | 105787 | Prkaa1 | 0.249020227 | 0.049620653 | protein kinase, AMP-activated, alpha 1 catalytic subunit |
| ENSMUSG00000040785 | 22129 | Ttc3 | 0.248823175 | 0.01458373 | tetratricopeptide repeat domain 3 |
| ENSMUSG00000026031 | 12633 | Cflar | 0.24874643 | 0.01769277 | CASP8 and FADD-like apoptosis regulator |
| ENSMUSG00000034168 | 238330 | Irf2bpl | 0.248696426 | 0.049620653 | interferon regulatory factor 2 binding protein-like |
| ENSMUSG00000036745 | 70892 | Ttll7 | 0.248656435 | 0.034186434 | tubulin tyrosine ligase-like family, member 7 |
| ENSMUSG00000025898 | 244672 | Cwf19l2 | 0.248399416 | 0.046371538 | CWF19-like 2, cell cycle control (*S. pombe*) |
| ENSMUSG00000041343 | 73845 | Ankrd42 | 0.248070239 | 0.041680615 | ankyrin repeat domain 42 |
| ENSMUSG00000026511 | 27058 | Srp9 | 0.247965905 | 0.035678264 | signal recognition particle 9 |
| ENSMUSG00000031133 | 73341 | Arhgef6 | 0.247763959 | 0.011065529 | Rac/Cdc42 guanine nucleotide exchange factor (GEF) 6 |
| ENSMUSG00000026490 | 226751 | Cdc42bpa | 0.247654888 | 0.028232579 | CDC42 binding protein kinase alpha |
| ENSMUSG00000037643 | 18759 | Prkci | 0.247640326 | 0.005618554 | protein kinase C, iota |
| ENSMUSG00000033943 | 29808 | Mga | 0.247433825 | 0.006981623 | MAX gene associated |
| ENSMUSG00000025986 | 227059 | Slc39a10 | 0.247306782 | 0.026558756 | solute carrier family 39 (zinc transporter), member 10 |
| ENSMUSG00000002107 | 14007 | Celf2 | 0.247000846 | 0.046004314 | CUGBP, Elav-like family member 2 |
| ENSMUSG00000036943 | 235442 | Rab8b | 0.246817326 | 0.031829589 | RAB8B, member RAS oncogene family |
| ENSMUSG00000037369 | 22289 | Kdm6a | 0.246672677 | 0.025164033 | lysine (K)-specific demethylase 6A |
| ENSMUSG00000020962 | 83602 | Gtf2a1 | 0.246654648 | 0.034600134 | general transcription factor II A, 1 |
| ENSMUSG00000042167 | 100715 | Papd4 | 0.246524128 | 0.0345667 | PAP associated domain containing 4 |
| ENSMUSG00000074746 | 107368 | Pdzd8 | 0.246446808 | 0.049316845 | PDZ domain containing 8 |
| ENSMUSG00000024261 | 20983 | Syt4 | 0.246413912 | 0.034218613 | synaptotagmin IV |
| ENSMUSG00000021945 | 76007 | Zmym2 | 0.246290768 | 0.042148216 | zinc finger, MYM-type 2 |
| ENSMUSG00000028391 | 71354 | Wdr31 | 0.246285944 | 0.026458143 | WD repeat domain 31 |
| ENSMUSG00000026095 | 70396 | Asnsd1 | 0.245992769 | 0.023371841 | asparagine synthetase domain containing 1 |
| ENSMUSG00000071567 |  |  | 0.245911556 | 0.014460399 |  |
| ENSMUSG00000056258 | 110862 | Kcnq3 | 0.245799294 | 0.04928913 | potassium voltage-gated channel, subfamily Q, member 3 |
| ENSMUSG00000037315 | 382207 | Jade3 | 0.245364689 | 0.017297968 | jade family PHD finger 3 |
| ENSMUSG00000026718 | 20844 | Stam | 0.245356824 | 0.023699881 | signal transducing adaptor molecule (SH3 domain and ITAM motif) 1 |
| ENSMUSG00000079508 | 68316 | Apoo | 0.245330001 | 0.047913743 | apolipoprotein O |
| ENSMUSG00000022321 | 320873 | Cdh10 | 0.245258653 | 0.010268575 | cadherin 10 |
| ENSMUSG00000035325 | 69162 | Sec31a | 0.24512347 | 0.045482841 | Sec31 homolog A (*S. cerevisiae*) |
| ENSMUSG00000020390 | 22210 | Ube2b | 0.245065744 | 0.014455417 | ubiquitin-conjugating enzyme E2B |
| ENSMUSG00000033578 | 67564 | Tmem35a | 0.244936195 | 0.010774326 | transmembrane protein 35A |
| ENSMUSG00000046111 | 319675 | Cep295 | 0.244870391 | 0.010482667 | centrosomal protein 295 |
| ENSMUSG00000020590 | 217463 | Snx13 | 0.244836089 | 0.039037088 | sorting nexin 13 |
| ENSMUSG00000026787 | 14417 | Gad2 | 0.244766694 | 0.04708058 | glutamic acid decarboxylase 2 |
| ENSMUSG00000024143 | 104215 | Rhoq | 0.243886257 | 0.038687074 | ras homolog family member Q |
| ENSMUSG00000036391 | 77371 | Sec24a | 0.243738634 | 0.028534161 | Sec24 related gene family, member A (*S. cerevisiae*) |
| ENSMUSG00000029234 | 21982 | Tmem165 | 0.243448709 | 0.017703765 | transmembrane protein 165 |
| ENSMUSG00000069844 | 52892 | Sco1 | 0.243286729 | 0.022167882 | SCO1 cytochrome c oxidase assembly protein |
| ENSMUSG00000051695 | 23983 | Pcbp1 | 0.242940488 | 0.014721741 | poly(rC) binding protein 1 |
| ENSMUSG00000085438 | 66602 | 1700020I14Rik | 0.242754581 | 0.043350799 | RIKEN cDNA 1700020I14 gene |
| ENSMUSG00000031673 | 12552 | Cdh11 | 0.242688498 | 0.03788271 | cadherin 11 |
| ENSMUSG00000030304 | 67456 | Ergic2 | 0.24207077 | 0.02810182 | ERGIC and golgi 2 |
| ENSMUSG00000046603 | 382117 | Tcaim | 0.241927768 | 0.043223052 | T cell activation inhibitor, mitochondrial |
| ENSMUSG00000039478 | 78506 | Micu3 | 0.241886319 | 0.038394424 | mitochondrial calcium uptake family, member 3 |
| ENSMUSG00000027589 | 245867 | Pcmtd2 | 0.241724196 | 0.032771674 | protein-L-isoaspartate (D-aspartate) O-methyltransferase domain containing 2 |
| ENSMUSG00000049421 | 26466 | Zfp260 | 0.241445708 | 0.023140793 | zinc finger protein 260 |
| ENSMUSG00000022641 | 70508 | Bbx | 0.241262257 | 0.014092799 | bobby sox homolog (*Drosophila*) |
| ENSMUSG00000028842 | 214150 | Ago3 | 0.24102002 | 0.04097831 | argonaute RISC catalytic subunit 3 |
| ENSMUSG00000040359 | 67490 | Ufl1 | 0.24096504 | 0.04346628 | UFM1 specific ligase 1 |
| ENSMUSG00000047193 | 110350 | Dync2h1 | 0.240910924 | 0.018482527 | dynein cytoplasmic 2 heavy chain 1 |
| ENSMUSG00000024472 | 70640 | Dcp2 | 0.240875483 | 0.013956118 | decapping mRNA 2 |
| ENSMUSG00000021171 | 52635 | Esyt2 | 0.240638353 | 0.022746493 | extended synaptotagmin-like protein 2 |
| ENSMUSG00000029787 | 78937 | Avl9 | 0.24046708 | 0.042643683 | AVL9 homolog (*S. cerevisiae*) |

TABLE 2-continued

| Ensembl | Entrez | Symbol | log2FoldChange | padj | Name |
|---|---|---|---|---|---|
| ENSMUSG00000004319 | 12725 | Clcn3 | 0.240419455 | 0.042579831 | chloride channel, voltage-sensitive 3 |
| ENSMUSG00000030671 | 18576 | Pde3b | 0.240233744 | 0.020579532 | phosphodiesterase 3B, cGMP-inhibited |
| ENSMUSG00000049804 | 100503043 | Armcx4 | 0.240051369 | 0.003274596 | armadillo repeat containing, X-linked 4 |
| ENSMUSG00000041670 | 116837 | Rims1 | 0.239625925 | 0.02303347 | regulating synaptic membrane exocytosis 1 |
| ENSMUSG00000063108 | 22688 | Zfp26 | 0.239598332 | 0.031409398 | zinc finger protein 26 |
| ENSMUSG00000035967 | 236790 | Ints6l | 0.239365073 | 0.022323986 | integrator complex subunit 6 like |
| ENSMUSG00000021665 | 15212 | Hexb | 0.239303668 | 0.045128357 | hexosaminidase B |
| ENSMUSG00000021360 | 14538 | Gcnt2 | 0.239241442 | 0.01760059 | glucosaminyl (N-acetyl) transferase 2, I-branching enzyme |
| ENSMUSG00000022024 | 67955 | Sugt1 | 0.2391553 | 0.039862558 | SGT1, suppressor of G2 allele of SKP1 (*S. cerevisiae*) |
| ENSMUSG00000028484 | 101739 | Psip1 | 0.239098307 | 0.042342823 | PC4 and SFRS1 interacting protein 1 |
| ENSMUSG00000075703 | 28042 | Ept1 | 0.238912972 | 0.018585287 | ethanolaminephosphotransferase 1 (CDP-ethanolamine-specific) |
| ENSMUSG00000043154 | 235542 | Ppp2r3a | 0.23883486 | 0.037555073 | protein phosphatase 2, regulatory subunit B", alpha |
| ENSMUSG00000027534 | 74718 | Snx16 | 0.238490461 | 0.033419319 | sorting nexin 16 |
| ENSMUSG00000028995 | 84652 | Fam126a | 0.238481019 | 0.019953964 | family with sequence similarity 126, member A |
| ENSMUSG00000020620 | 27404 | Abca8b | 0.238389537 | 0.022323986 | ATP-binding cassette, sub-family A (ABC1), member 8b |
| ENSMUSG00000054752 | 319636 | Fsd1l | 0.23824852 | 0.016284626 | fibronectin type III and SPRY domain containing 1-like |
| ENSMUSG00000055447 | 16423 | Cd47 | 0.238071376 | 0.021696902 | CD47 antigen (Rh-related antigen, integrin-associated signal transducer) |
| ENSMUSG00000027427 | 70408 | Polr3f | 0.238065116 | 0.03810266 | polymerase (RNA) III (DNA directed) polypeptide F |
| ENSMUSG00000038301 | 71982 | Snx10 | 0.238020378 | 0.026006131 | sorting nexin 10 |
| ENSMUSG00000046178 | 18231 | Nxph1 | 0.237915559 | 0.039318498 | neurexophilin 1 |
| ENSMUSG00000039585 | 270163 | Myo9a | 0.237866582 | 0.04201503 | myosin IXa |
| ENSMUSG00000036402 | 14701 | Gng12 | 0.237810369 | 0.047465487 | guanine nucleotide binding protein (G protein), gamma 12 |
| ENSMUSG00000019889 | 19272 | Ptprk | 0.237724131 | 0.03715243 | protein tyrosine phosphatase, receptor type, K |
| ENSMUSG00000045763 | 70350 | Basp1 | 0.237417012 | 0.019109666 | brain abundant, membrane attached signal protein 1 |
| ENSMUSG00000048720 | 209478 | Tbc1d12 | 0.236714657 | 0.041847227 | TBC1D12: TBC1 domain family, member 12 |
| ENSMUSG00000021087 | 104001 | Rtn1 | 0.236571833 | 0.031409398 | reticulon 1 |
| ENSMUSG00000040225 | 226562 | Prrc2c | 0.236055618 | 0.006758078 | proline-rich coiled-coil 2C |
| ENSMUSG00000055239 | 74287 | Kcmf1 | 0.235888603 | 0.043003032 | potassium channel modulatory factor 1 |
| ENSMUSG00000060510 | 77519 | Zfp266 | 0.235597145 | 0.040407787 | zinc finger protein 266 |
| ENSMUSG00000056851 | 18521 | Pcbp2 | 0.235536857 | 0.008681315 | poly(rC) binding protein 2 |
| ENSMUSG00000096188 | 97487 | Cmtm4 | 0.234630877 | 0.028689222 | CKLF-like MARVEL transmembrane domain containing 4 |
| ENSMUSG00000059811 | 56298 | Atl2 | 0.234498408 | 0.021635982 | atlastin GTPase 2 |
| ENSMUSG00000029405 | 23881 | G3bp2 | 0.234223568 | 0.034583934 | GTPase activating protein (SH3 domain) binding protein 2 |
| ENSMUSG00000026083 | 226982 | Eif5b | 0.233127842 | 0.034961135 | eukaryotic translation initiation factor 5B |
| ENSMUSG00000052299 | 78913 | Ltn1 | 0.23299939 | 0.023987976 | listerin E3 ubiquitin protein ligase 1 |
| ENSMUSG00000033237 | 77044 | Arid2 | 0.232859357 | 0.020056896 | AT rich interactive domain 2 (ARID, RFX-like) |
| ENSMUSG00000021745 | 19270 | Ptprg | 0.232794671 | 0.014800621 | protein tyrosine phosphatase, receptor type, G |
| ENSMUSG00000004591 | 109333 | Pkn2 | 0.232548165 | 0.019252649 | protein kinase N2 |
| ENSMUSG00000027201 | 17876 | Myef2 | 0.232390557 | 0.019796215 | myelin basic protein expression factor 2, repressor |
| ENSMUSG00000032740 | 108686 | Ccdc88a | 0.231791954 | 0.045072844 | coiled coil domain containing 88A |
| ENSMUSG00000028293 | 24060 | Slc35a1 | 0.231689579 | 0.030550087 | solute carrier family 35 (CMP-sialic acid transporter), member 1 |
| ENSMUSG00000024487 | 67180 | Yipf5 | 0.231595588 | 0.031722327 | Yip1 domain family, member 5 |
| ENSMUSG00000040250 | 71177 | Asun | 0.23140679 | 0.019701573 | asunder, spermatogenesis regulator |
| ENSMUSG00000016382 | 102866 | Pls3 | 0.231322041 | 0.031395961 | plastin 3 (T-isoform) |
| ENSMUSG00000015597 | 57908 | Zfp318 | 0.231297293 | 0.01155039 | zinc finger protein 318 |
| ENSMUSG00000038729 | 11641 | Akap2 | 0.231032639 | 0.023573194 | A kinase (PRKA) anchor protein 2 |
| ENSMUSG00000040818 | 211922 | Dennd6a | 0.230848638 | 0.023802758 | DENN/MADD domain containing 6A |
| ENSMUSG00000030283 | 20449 | St8sia1 | 0.230814882 | 0.040222459 | ST8 alpha-N-acetyl-neuraminide alpha-2,8-sialyltransferase 1 |
| ENSMUSG00000033352 | 26398 | Map2k4 | 0.230732176 | 0.024638958 | mitogen-activated protein kinase kinase 4 |
| ENSMUSG00000036478 | 12226 | Btg1 | 0.230491967 | 0.046846311 | B cell translocation gene 1, anti-proliferative |
| ENSMUSG00000072847 | | | 0.230182676 | 0.041629703 | |
| ENSMUSG00000056158 | 72605 | Car10 | 0.229696839 | 0.039949042 | carbonic anhydrase 10 |
| ENSMUSG00000049232 | 68140 | Tigd2 | 0.229450369 | 0.023377296 | tigger transposable element derived 2 |
| ENSMUSG00000038121 | 108654 | Fam210a | 0.229418073 | 0.020897538 | family with sequence similarity 210, member A |
| ENSMUSG00000032826 | 109676 | Ank2 | 0.229012118 | 0.017047503 | ankyrin 2, brain |

TABLE 2-continued

| Ensembl | Entrez | Symbol | log2FoldChange | padj | Name |
|---|---|---|---|---|---|
| ENSMUSG00000048787 | 233805 | Dcun1d3 | 0.228848972 | 0.042816513 | DCN1, defective in cullin neddylation 1, domain containing 3 (S. cerevisiae) |
| ENSMUSG00000037259 | 241688 | Dzank1 | 0.228204039 | 0.043045679 | double zinc ribbon and ankyrin repeat domains 1 |
| ENSMUSG00000056832 | 264134 | Ttc26 | 0.228007458 | 0.020792344 | tetratricopeptide repeat domain 26 |
| ENSMUSG00000049321 | 22678 | Zfp2 | 0.22764209 | 0.038664268 | zinc finger protein 2 |
| ENSMUSG00000015961 | 11566 | Adss | 0.226751458 | 0.049518592 | adenylosuccinate synthetase, non muscle |
| ENSMUSG00000035437 | 227800 | Rabgap1 | 0.226514385 | 0.006634909 | RAB GTPase activating protein 1 |
| ENSMUSG00000015243 | 11303 | Abca1 | 0.226450014 | 0.016221993 | ATP-binding cassette, sub-family A (ABC1), member 1 |
| ENSMUSG00000022661 | 17470 | Cd200 | 0.225742345 | 0.030387239 | CD200 antigen |
| ENSMUSG00000042712 | 22381 | Wbp5 | 0.225596188 | 0.049474183 | WW domain binding protein 5 |
| ENSMUSG00000097164 | 67723 | Cep83os | 0.225535122 | 0.04188267 | centrosomal protein 83, opposite strand |
| ENSMUSG00000029422 | 208606 | Rsrc2 | 0.225415872 | 0.035542085 | arginine/serine-rich coiled-coil 2 |
| ENSMUSG00000000804 | 237898 | Usp32 | 0.225208622 | 0.035277781 | ubiquitin specific peptidase 32 |
| ENSMUSG00000050912 | 71929 | Tmem123 | 0.225011918 | 0.038813575 | transmembrane protein 123 |
| ENSMUSG00000063145 | 72569 | Bbs5 | 0.224938684 | 0.041921608 | Bardet-Biedl syndrome 5 (human) |
| ENSMUSG00000022829 | 207227 | Stxbp5l | 0.224595826 | 0.046823764 | syntaxin binding protein 5-like |
| ENSMUSG00000035572 | 242418 | Dcaf10 | 0.224014001 | 0.026006131 | DDB1 and CUL4 associated factor 10 |
| ENSMUSG00000027601 | 67472 | Mtfr1 | 0.223650577 | 0.041605282 | mitochondrial fission regulator 1 |
| ENSMUSG00000024943 | 226026 | Smc5 | 0.223582451 | 0.03810266 | structural maintenance of chromosomes 5 |
| ENSMUSG00000050334 | 320203 | C130071C03Rik | 0.223573986 | 0.024580372 | RIKEN cDNA C130071C03 gene |
| ENSMUSG00000028399 | 19266 | Ptprd | 0.223113281 | 0.01321842 | protein tyrosine phosphatase, receptor type, D |
| ENSMUSG00000079157 | 270028 | Fam155a | 0.222102287 | 0.027332246 | family with sequence similarity 155, member A |
| ENSMUSG00000049800 | 58172 | Sertad2 | 0.221939855 | 0.036713429 | SERTA domain containing 2 |
| ENSMUSG00000079184 | 75339 | Mphosph8 | 0.221591847 | 0.04437153 | M-phase phosphoprotein 8 |
| ENSMUSG00000040265 | 103967 | Dnm3 | 0.221432169 | 0.022767786 | dynamin 3 |
| ENSMUSG00000042520 | 74383 | Ubap2l | 0.221368973 | 0.016610567 | ubiquitin-associated protein 2-like |
| ENSMUSG00000024068 | 50850 | Spast | 0.221017476 | 0.048976124 | spastin |
| ENSMUSG00000034621 | 237943 | Gpatch8 | 0.220793652 | 0.028462508 | G patch domain containing 8 |
| ENSMUSG00000032582 | 19654 | Rbm6 | 0.220784886 | 0.004528565 | RNA binding motif protein 6 |
| ENSMUSG00000050064 | 242109 | Zfp697 | 0.220285637 | 0.036713429 | zinc finger protein 697 |
| ENSMUSG00000056267 | 68121 | Cep70 | 0.219880057 | 0.037187025 | centrosomal protein 70 |
| ENSMUSG00000032186 | 50876 | Tmod2 | 0.219569946 | 0.012314063 | tropomodulin 2 |
| ENSMUSG00000054414 | 66500 | Slc30a7 | 0.219535068 | 0.033129059 | solute carrier family 30 (zinc transporter), member 7 |
| ENSMUSG00000020541 | 71943 | Tom1l1 | 0.218960786 | 0.033729709 | target of myb1-like 1 (chicken) |
| ENSMUSG00000038774 | 77987 | Ascc3 | 0.218595797 | 0.023342687 | activating signal cointegrator 1 complex subunit 3 |
| ENSMUSG00000020128 | 245944 | Vps54 | 0.217833134 | 0.025407964 | VPS54 GARP complex subunit |
| ENSMUSG00000047888 | 213988 | Tnrc6b | 0.217700709 | 0.01155039 | trinucleotide repeat containing 6b |
| ENSMUSG00000042508 | 23857 | Dmtf1 | 0.217413777 | 0.015096311 | cyclin D binding myb-like transcription factor 1 |
| ENSMUSG00000040612 | 100039795 | Ildr2 | 0.217380561 | 0.031409398 | immunoglobulin-like domain containing receptor 2 |
| ENSMUSG00000027796 | 55994 | Smad9 | 0.216355728 | 0.048459616 | SMAD family member 9 |
| ENSMUSG00000057716 | 434008 | Tmem178b | 0.216200573 | 0.007996324 | transmembrane protein 178B |
| ENSMUSG00000027433 | 24128 | Xrn2 | 0.215610012 | 0.013981585 | 5'-3' exoribonuclease 2 |
| ENSMUSG00000022961 | 20658 | Son | 0.215511877 | 0.02071922 | Son DNA binding protein |
| ENSMUSG00000070544 | 21969 | Top1 | 0.21540305 | 0.02022099 | topoisomerase (DNA) I |
| ENSMUSG00000039037 | 26938 | St6galnac5 | 0.215098072 | 0.014440908 | ST6 (alpha-N-acetyl-neuraminyl-2,3-beta-galactosyl-1,3)-N-acetylgalactosaminide alpha-2,6-sialyltransferase 5 |
| ENSMUSG00000021188 | 109181 | Trip11 | 0.214975615 | 0.047213986 | thyroid hormone receptor interactor 11 |
| ENSMUSG00000060371 | 140904 | Caln1 | 0.214576168 | 0.008435647 | calneuron 1 |
| ENSMUSG00000039126 | 353211 | Prune2 | 0.214254493 | 0.008027523 | prune homolog 2 |
| ENSMUSG00000071533 | 76302 | Pcnp | 0.213665207 | 0.039345584 | PEST proteolytic signal containing nuclear protein |
| ENSMUSG00000022781 | 224105 | Pak2 | 0.213641046 | 0.035736425 | p21 protein (Cdc42/Rac)-activated kinase 2 |
| ENSMUSG00000026576 | 11931 | Atp1b1 | 0.213610727 | 0.011083033 | ATPase, Na+/K+ transporting, beta 1 polypeptide |
| ENSMUSG00000033417 | 78832 | Cacul1 | 0.213523412 | 0.048997766 | CDK2 associated, cullin domain 1 |
| ENSMUSG00000008489 | 15569 | Elavl2 | 0.213304059 | 0.020056896 | ELAV (embryonic lethal, abnormal vision, Drosophila)-like 2 (Hu antigen B) |
| ENSMUSG00000001986 | 53623 | Gria3 | 0.213131533 | 0.020897538 | glutamate receptor, ionotropic, AMPA3 (alpha 3) |
| ENSMUSG00000062519 | 272347 | Zfp398 | 0.212698046 | 0.021696902 | zinc finger protein 398 |
| ENSMUSG00000042105 | 101490 | Inpp5f | 0.212484715 | 0.035537227 | inositol polyphosphate-5-phosphatase F |
| ENSMUSG00000024542 | 70799 | Cep192 | 0.212412542 | 0.045128357 | centrosomal protein 192 |
| ENSMUSG00000034154 | 68142 | Ino80 | 0.212367965 | 0.029470151 | INO80 complex subunit |
| ENSMUSG00000033499 | 217980 | Larp4b | 0.212353266 | 0.026938218 | La ribonucleoprotein domain family, member 4B |

TABLE 2-continued

| Ensembl | Entrez | Symbol | log2FoldChange | padj | Name |
|---|---|---|---|---|---|
| ENSMUSG00000048027 | 68799 | Rgmb | 0.212134772 | 0.018226427 | repulsive guidance molecule family member B |
| ENSMUSG00000027663 | 22401 | Zmat3 | 0.212047788 | 0.035883734 | zinc finger matrin type 3 |
| ENSMUSG00000028273 | 56376 | Pdlim5 | 0.212005741 | 0.03063369 | PDZ and LIM domain 5 |
| ENSMUSG00000074656 | 67204 | Eif2s2 | 0.211960589 | 0.049513327 | eukaryotic translation initiation factor 2, subunit 2 (beta) |
| ENSMUSG00000028245 | 18201 | Nsmaf | 0.21116987 | 0.012278298 | neutral sphingomyelinase (N-SMase) activation associated factor |
| ENSMUSG00000036006 | 193385 | Fam65b | 0.210705468 | 0.010568122 | family with sequence similarity 65, member B |
| ENSMUSG00000029629 | 75725 | Phf14 | 0.210419073 | 0.048894448 | PHD finger protein 14 |
| ENSMUSG00000063142 | 16531 | Kcnma1 | 0.210307206 | 0.012536473 | potassium large conductance calcium-activated channel, subfamily M, alpha member 1 |
| ENSMUSG00000020516 | 72508 | Rps6kb1 | 0.20998703 | 0.026020807 | ribosomal protein S6 kinase, polypeptide 1 |
| ENSMUSG00000036099 | 215008 | Vezt | 0.209555467 | 0.003638852 | vezatin, adherens junctions transmembrane protein |
| ENSMUSG00000040044 | 50793 | Orc3 | 0.209337896 | 0.048044254 | origin recognition complex, subunit 3 |
| ENSMUSG00000000197 | 338370 | Nalcn | 0.208351291 | 0.043203402 | sodium leak channel, non-selective |
| ENSMUSG00000008763 | 17156 | Man1a2 | 0.208320344 | 0.035537227 | mannosidase, alpha, class 1A, member 2 |
| ENSMUSG00000061887 | 72475 | Ssbp3 | 0.208086148 | 0.015854098 | single-stranded DNA binding protein 3 |
| ENSMUSG00000042305 | 57439 | Tmem183a | 0.208052758 | 0.031897722 | transmembrane protein 183A |
| ENSMUSG00000049038 | 74238 | Mterf2 | 0.207964401 | 0.048312414 | mitochondrial transcription termination factor 2 |
| ENSMUSG00000023092 | 14199 | Fhl1 | 0.207942328 | 0.033238428 | four and a half LIM domains 1 |
| ENSMUSG00000014353 | 72477 | Tmem87b | 0.207740378 | 0.040736943 | transmembrane protein 87B |
| ENSMUSG00000038546 | 56705 | Ranbp9 | 0.207471924 | 0.038112875 | RAN binding protein 9 |
| ENSMUSG00000044807 | 30944 | Zfp354c | 0.207179403 | 0.047593635 | zinc finger protein 354C |
| ENSMUSG00000029992 | 14583 | Gfpt1 | 0.207145919 | 0.017334618 | glutamine fructose-6-phosphate transaminase 1 |
| ENSMUSG00000022973 | 104015 | Synj1 | 0.206904254 | 0.015244082 | synaptojanin 1 |
| ENSMUSG00000025245 | 93730 | Lztfl1 | 0.206675736 | 0.029269343 | leucine zipper transcription factor-like 1 |
| ENSMUSG00000026425 | 14270 | Srgap2 | 0.206009175 | 0.004704938 | SLIT-ROBO Rho GTPase activating protein 2 |
| ENSMUSG00000031922 | 74360 | Cep57 | 0.205750008 | 0.03327754 | centrosomal protein 57 |
| ENSMUSG00000035954 | 238130 | Dock4 | 0.20573986 | 0.03715243 | dedicator of cytokinesis 4 |
| ENSMUSG00000074749 | 228730 | Kiz | 0.205584594 | 0.041526111 | kizuna centrosomal protein |
| ENSMUSG00000025092 | 73442 | Hspa12a | 0.205330067 | 0.013905744 | heat shock protein 12A |
| ENSMUSG00000020070 | 70432 | Rufy2 | 0.205258052 | 0.014172146 | RUN and FYVE domain-containing 2 |
| ENSMUSG00000018501 | 20185 | Ncor1 | 0.204732915 | 0.028689222 | nuclear receptor co-repressor 1 |
| ENSMUSG00000090100 | 140810 | Ttbk2 | 0.204587478 | 0.048688376 | tau tubulin kinase 2 |
| ENSMUSG00000047126 | 67300 | Cltc | 0.204299841 | 0.049841511 | clathrin, heavy polypeptide (Hc) |
| ENSMUSG00000033282 | 244585 | Rpgrip1l | 0.2041518 | 0.026780897 | Rpgrip1-like |
| ENSMUSG00000033436 | 67416 | Armcx2 | 0.204144786 | 0.028313696 | armadillo repeat containing, X-linked 2 |
| ENSMUSG00000021690 | 57748 | Jmy | 0.204108774 | 0.039879385 | junction-mediating and regulatory protein |
| ENSMUSG00000020454 | 74203 | Eif4enif1 | 0.203423506 | 0.017109066 | eukaryotic translation initiation factor 4E nuclear import factor 1 |
| ENSMUSG00000021474 | 14057 | Sfxn1 | 0.203336349 | 0.026966187 | sideroflexin 1 |
| ENSMUSG00000034111 | 382620 | Tmed8 | 0.203091949 | 0.044474565 | transmembrane emp24 domain containing 8 |
| ENSMUSG00000037533 | 192786 | Rapgef6 | 0.20289038 | 0.026899327 | Rap guanine nucleotide exchange factor (GEF) 6 |
| ENSMUSG00000027620 | 170791 | Rbm39 | 0.202584465 | 0.019700695 | RNA binding motif protein 39 |
| ENSMUSG00000021007 | 104871 | Spata7 | 0.202364487 | 0.028689222 | spermatogenesis associated 7 |
| ENSMUSG00000071659 | 68693 | Hnrnpul2 | 0.201873332 | 0.00874997 | heterogeneous nuclear ribonucleoprotein U-like 2 |
| ENSMUSG00000003992 | 66970 | Ssbp2 | 0.201507353 | 0.029222521 | single-stranded DNA binding protein 2 |
| ENSMUSG00000023883 | 72057 | Phf10 | 0.2012423 | 0.046012024 | PHD finger protein 10 |
| ENSMUSG00000009575 | 12419 | Cbx5 | 0.200969005 | 0.032840549 | chromobox 5 |
| ENSMUSG00000069769 | 76626 | Msi2 | 0.200795909 | 0.039283859 | musashi RNA-binding protein 2 |
| ENSMUSG00000024109 | 18189 | Nrxn1 | 0.200056394 | 0.016961463 | neurexin I |
| ENSMUSG00000022141 | 71175 | Nipbl | 0.199938208 | 0.03788271 | Nipped-B homolog (*Drosophila*) |
| ENSMUSG00000041303 | 98488 | Gtf3c3 | 0.199377062 | 0.042747738 | general transcription factor IIIC, polypeptide 3 |
| ENSMUSG00000038187 | 68815 | Btbd10 | 0.199334818 | 0.042539146 | BTB (POZ) domain containing 10 |
| ENSMUSG00000031529 | 21951 | Tnks | 0.198462089 | 0.035190472 | tankyrase, TRF1-interacting ankyrin-related ADP-ribose polymerase |
| ENSMUSG00000040537 | 11496 | Adam22 | 0.198275407 | 0.040444896 | a disintegrin and metallopeptidase domain 22 |
| ENSMUSG00000026587 | 11899 | Astn1 | 0.198045384 | 0.027978558 | astrotactin 1 |
| ENSMUSG00000027012 | 13427 | Dync1i2 | 0.197949549 | 0.018993844 | dynein cytoplasmic 1 intermediate chain 2 |
| ENSMUSG00000024500 | 72930 | Ppp2r2b | 0.197795507 | 0.03327754 | protein phosphatase 2, regulatory subunit B, beta |
| ENSMUSG00000017421 | 22680 | Zfp207 | 0.197769038 | 0.043045679 | zinc finger protein 207 |
| ENSMUSG00000041923 | 319211 | Nol4 | 0.197697174 | 0.036209718 | nucleolar protein 4 |
| ENSMUSG00000031256 | 108062 | Cstf2 | 0.197277527 | 0.028143464 | cleavage stimulation factor, 3' pre-RNA subunit 2 |

TABLE 2-continued

| Ensembl | Entrez | Symbol | log2FoldChange | padj | Name |
|---|---|---|---|---|---|
| ENSMUSG00000034243 | 224139 | Golgb1 | 0.196566309 | 0.033370145 | golgi autoantigen, golgin subfamily b, macrogolgin 1 |
| ENSMUSG00000015968 | 12289 | Cacna1d | 0.195669015 | 0.038174076 | calcium channel, voltage-dependent, L type, alpha 1D subunit |
| ENSMUSG00000035623 | 233532 | Rsf1 | 0.195052102 | 0.023375279 | remodeling and spacing factor 1 |
| ENSMUSG00000044647 | 77771 | Csrnp3 | 0.194881214 | 0.034451439 | cysteine-serine-rich nuclear protein 3 |
| ENSMUSG00000068036 | 17356 | Afdn | 0.194796004 | 0.004136676 | afadin, adherens junction formation factor |
| ENSMUSG00000026113 | 269180 | Inpp4a | 0.194386911 | 0.025893233 | inositol polyphosphate-4-phosphatase, type I |
| ENSMUSG00000042447 | 252875 | Mios | 0.194277072 | 0.041478328 | missing oocyte, meiosis regulator, homolog (*Drosophila*) |
| ENSMUSG00000042249 | 320129 | Grk3 | 0.194110031 | 0.035938921 | G protein-coupled receptor kinase 3 |
| ENSMUSG00000020859 | 70834 | Spag9 | 0.193267233 | 0.043223052 | sperm associated antigen 9 |
| ENSMUSG00000042302 | 216565 | Ehbp1 | 0.192933231 | 0.037667395 | EH domain binding protein 1 |
| ENSMUSG00000030264 | 14911 | Thumpd3 | 0.192341342 | 0.045447791 | THUMP domain containing 3 |
| ENSMUSG00000066760 | 26436 | Psg16 | 0.192238427 | 0.030498329 | pregnancy specific glycoprotein 16 |
| ENSMUSG00000053025 | 64176 | Sv2b | 0.192183513 | 0.046469129 | synaptic vesicle glycoprotein 2 b |
| ENSMUSG00000053477 | 21413 | Tcf4 | 0.191263436 | 0.035542085 | transcription factor 4 |
| ENSMUSG00000025949 | 18711 | Pikfyve | 0.190942512 | 0.038996555 | phosphoinositide kinase, FYVE finger containing |
| ENSMUSG00000028514 | 329908 | Usp24 | 0.190918234 | 0.014644358 | ubiquitin specific peptidase 24 |
| ENSMUSG00000057181 | 70591 | 5730455P16Rik | 0.190707943 | 0.013111259 | RIKEN cDNA 5730455P16 gene |
| ENSMUSG00000056050 | | | 0.190432627 | 0.041140952 | |
| ENSMUSG00000020170 | 327826 | Frs2 | 0.190061497 | 0.033756594 | fibroblast growth factor receptor substrate 2 |
| ENSMUSG00000034593 | 17918 | Myo5a | 0.18970683 | 0.031060625 | myosin VA |
| ENSMUSG00000027506 | 21985 | Tpd52 | 0.189325395 | 0.046539706 | tumor protein D52 |
| ENSMUSG00000025423 | 17344 | Pias2 | 0.189177883 | 0.031817567 | protein inhibitor of activated STAT 2 |
| ENSMUSG00000006818 | 20656 | Sod2 | 0.188856211 | 0.048290317 | superoxide dismutase 2, mitochondrial |
| ENSMUSG00000040389 | 99512 | Wdr47 | 0.187129138 | 0.038687074 | WD repeat domain 47 |
| ENSMUSG00000036667 | 77574 | Tcaf1 | 0.18677506 | 0.017406464 | TRPM8 channel-associated factor 1 |
| ENSMUSG00000068373 | 241589 | D430041D05Rik | 0.186248243 | 0.017109066 | RIKEN cDNA D430041D05 gene |
| ENSMUSG00000031878 | 234664 | Nae1 | 0.186232738 | 0.047268143 | NEDD8 activating enzyme E1 subunit 1 |
| ENSMUSG00000025060 | 20874 | Slk | 0.185955846 | 0.038017312 | STE20-like kinase |
| ENSMUSG00000036698 | 239528 | Ago2 | 0.182500471 | 0.047890046 | argonaute RISC catalytic subunit 2 |
| ENSMUSG00000024581 | 108123 | Napg | 0.181986394 | 0.039480072 | N-ethylmaleimide sensitive fusion protein attachment protein gamma |
| ENSMUSG00000002265 | 18616 | Peg3 | 0.181748888 | 0.011462086 | paternally expressed 3 |
| ENSMUSG00000019790 | 78808 | Stxbp5 | 0.18159848 | 0.030539402 | syntaxin binding protein 5 (tomosyn) |
| ENSMUSG00000035151 | 244548 | Elmod2 | 0.181443093 | 0.026020381 | ELMO/CED-12 domain containing 2 |
| ENSMUSG00000005893 | 22026 | Nr2c2 | 0.18119774 | 0.031518194 | nuclear receptor subfamily 2, group C, member 2 |
| ENSMUSG00000053580 | 77097 | Tanc2 | 0.179562478 | 0.029269343 | tetratricopeptide repeat, ankyrin repeat and coiled-coil containing 2 |
| ENSMUSG00000001173 | 320634 | Ocrl | 0.17898632 | 0.017200534 | oculocerebrorenal syndrome of Lowe |
| ENSMUSG00000037071 | 20249 | Scd1 | 0.17892271 | 0.049177438 | stearoyl-Coenzyme A desaturase 1 |
| ENSMUSG00000073725 | 68421 | Lmbrd1 | 0.178054939 | 0.035584241 | LMBR1 domain containing 1 |
| ENSMUSG00000022635 | 67197 | Zcrb1 | 0.177374602 | 0.030770903 | zinc finger CCHC-type and RNA binding motif 1 |
| ENSMUSG00000020368 | 12330 | Canx | 0.177076056 | 0.045205969 | calnexin |
| ENSMUSG00000038664 | 235439 | Herc1 | 0.177034586 | 0.017095122 | HECT and RLD domain containing E3 ubiquitin protein ligase family member 1 |
| ENSMUSG00000052727 | 17755 | Map 1b | 0.175613276 | 0.033729709 | microtubule-associated protein 1B |
| ENSMUSG00000070520 | 66647 | Ndnl2 | 0.175540305 | 0.041942669 | necdin-like 2 |
| ENSMUSG00000027652 | 228850 | Ralgapb | 0.173660631 | 0.011131959 | Ral GTPase activating protein, beta subunit (non-catalytic) |
| ENSMUSG00000058690 | 72972 | Ccser2 | 0.172423489 | 0.030550087 | coiled-coil serine rich 2 |
| ENSMUSG00000024045 | 56399 | Akap8 | 0.1706881 | 0.047959508 | A kinase (PRKA) anchor protein 8 |
| ENSMUSG00000033214 | 75409 | Slitrk5 | 0.16984834 | 0.037187025 | SLIT and NTRK-like family, member 5 |
| ENSMUSG00000029227 | 66899 | Fip1l1 | 0.168854483 | 0.028481058 | FIP1 like 1 (*S. cerevisiae*) |
| ENSMUSG00000052707 | 233833 | Tnrc6a | 0.167931926 | 0.048569817 | trinucleotide repeat containing 6a |
| ENSMUSG00000041268 | 235380 | Dmxl2 | 0.166442852 | 0.049841511 | Dmx-like 2 |
| ENSMUSG00000020721 | 78455 | Helz | 0.164635905 | 0.037791214 | helicase with zinc finger domain |
| ENSMUSG00000075478 | 76965 | Slitrk 1 | 0.156154492 | 0.030579905 | SLIT and NTRK-like family, member 1 |
| ENSMUSG00000037487 | 70790 | Ubr5 | 0.155027023 | 0.035495479 | ubiquitin protein ligase E3 component n-recognin 5 |
| ENSMUSG00000056755 | 108073 | Grm7 | 0.154925095 | 0.044895847 | glutamate receptor, metabotropic 7 |
| ENSMUSG00000020181 | 260315 | Nav3 | 0.149307136 | 0.024128717 | neuron navigator 3 |
| ENSMUSG00000054263 | 16880 | Lifr | 0.145811607 | 0.031362416 | leukemia inhibitory factor receptor |
| ENSMUSG00000018326 | 54401 | Ywhab | 0.140769822 | 0.043780099 | tyrosine 3-monooxygenase/tryptophan 5-monooxygenase activation protein, beta polypeptide |
| ENSMUSG00000022536 | 74022 | Glyr1 | −0.138679754 | 0.043784958 | glyoxylate reductase 1 homolog (Arabidopsis) |
| ENSMUSG00000042506 | 216825 | Usp22 | −0.145447512 | 0.046702542 | ubiquitin specific peptidase 22 |
| ENSMUSG00000058594 | 50755 | Fbxo18 | −0.150809272 | 0.038687074 | F-box protein 18 |

TABLE 2-continued

| Ensembl | Entrez | Symbol | log2FoldChange | padj | Name |
|---|---|---|---|---|---|
| ENSMUSG00000027220 | 80976 | Syt13 | −0.15437275 | 0.038745523 | synaptotagmin XIII |
| ENSMUSG00000035569 | 77087 | Ankrd11 | −0.154374168 | 0.029804508 | ankyrin repeat domain 11 |
| ENSMUSG00000028478 | 12757 | Clta | −0.157325437 | 0.043223052 | clathrin, light polypeptide (Lca) |
| ENSMUSG00000021476 | 56541 | Habp4 | −0.158566968 | 0.047740412 | hyaluronic acid binding protein 4 |
| ENSMUSG00000025871 | 97820 | 4833439L19Rik | −0.161880625 | 0.022746493 | RIKEN cDNA 4833439L19 gene |
| ENSMUSG00000010277 | 72503 | 2610507B11Rik | −0.163240505 | 0.038308662 | RIKEN cDNA 2610507B11 gene |
| ENSMUSG00000015176 | 70769 | Nolc1 | −0.165994795 | 0.04928913 | nucleolar and coiled-body phosphoprotein 1 |
| ENSMUSG00000047388 | 234776 | Atmin | −0.166658253 | 0.040368494 | ATM interactor |
| ENSMUSG00000021559 | 69635 | Dapk1 | −0.167752445 | 0.03551309 | death associated protein kinase 1 |
| ENSMUSG00000026473 | 14645 | Glul | −0.168883489 | 0.048396812 | glutamate-ammonia ligase (glutamine synthetase) |
| ENSMUSG00000027475 | 16569 | Kif3b | −0.168979198 | 0.030432753 | kinesin family member 3B |
| ENSMUSG00000025217 | 12234 | Btrc | −0.170148737 | 0.035190472 | beta-transducin repeat containing protein |
| ENSMUSG00000026032 | 66495 | Ndufb3 | −0.171593291 | 0.022606731 | NADH dehydrogenase (ubiquinone) 1 beta subcomplex 3 |
| ENSMUSG00000001380 | 15115 | Hars | −0.17310952 | 0.039965226 | histidyl-tRNA synthetase |
| ENSMUSG00000029120 | 269643 | Ppp2r2c | −0.173575781 | 0.036258437 | protein phosphatase 2, regulatory subunit B, gamma |
| ENSMUSG00000039067 | 17463 | Psmd7 | −0.175424201 | 0.040511844 | proteasome (prosome, macropain) 26S subunit, non-ATPase, 7 |
| ENSMUSG00000024983 | 53611 | Vti1a | −0.176367744 | 0.0125064 | vesicle transport through interaction with t-SNAREs 1A |
| ENSMUSG00000031532 | 67887 | Saraf | −0.17655837 | 0.045023342 | store-operated calcium entry-associated regulatory factor |
| ENSMUSG00000061576 | 13483 | Dpp6 | −0.176858764 | 0.026540021 | dipeptidylpeptidase 6 |
| ENSMUSG00000020946 | 56494 | Gosr2 | −0.179072063 | 0.026071951 | golgi SNAP receptor complex member 2 |
| ENSMUSG00000003660 | 320632 | Snrnp200 | −0.180114257 | 0.02636368 | small nuclear ribonucleoprotein 200 (U5) |
| ENSMUSG00000089682 | 12050 | Bcl2l2 | −0.180180564 | 0.026540021 | BCL2-like 2 |
| ENSMUSG00000067150 | 72354 | Xpo5 | −0.182116252 | 0.048744199 | exportin 5 |
| ENSMUSG00000021991 | 12294 | Cacna2d3 | −0.18356419 | 0.041680615 | calcium channel, voltage-dependent, alpha2/delta subunit 3 |
| ENSMUSG00000031320 | 20102 | Rps4x | −0.184579839 | 0.046964086 | ribosomal protein S4, X-linked |
| ENSMUSG00000045994 | 76898 | B3gat1 | −0.18462435 | 0.049286013 | beta-1,3-glucuronyltransferase 1 (glucuronosyltransferase P) |
| ENSMUSG00000068749 | 26442 | Psma5 | −0.186619396 | 0.038963537 | proteasome (prosome, macropain) subunit, alpha type 5 |
| ENSMUSG00000033047 | 223691 | Eif3l | −0.187111746 | 0.020172596 | eukaryotic translation initiation factor 3, subunit L |
| ENSMUSG00000059796 | 13681 | Eif4a1 | −0.187414425 | 0.038664268 | eukaryotic translation initiation factor 4A1 |
| ENSMUSG00000033389 | 216831 | Arhgap44 | −0.187523841 | 0.016494733 | Rho GTPase activating protein 44 |
| ENSMUSG00000028452 | 269523 | Vcp | −0.187902893 | 0.030382365 | valosin containing protein |
| ENSMUSG00000037742 | 13627 | Eef1a1 | −0.188668132 | 0.004772212 | eukaryotic translation elongation factor 1 alpha 1 |
| ENSMUSG00000054309 | 54451 | Cpsf3 | −0.189370559 | 0.042772306 | cleavage and polyadenylation specificity factor 3 |
| ENSMUSG00000033545 | 170737 | Znrf1 | −0.190227146 | 0.026006131 | zinc and ring finger 1 |
| ENSMUSG00000019124 | 69938 | Scrn1 | −0.192415207 | 0.013155585 | secernin 1 |
| ENSMUSG00000025413 | 72354 | Ttc4 | −0.192495357 | 0.045563064 | tetratricopeptide repeat domain 4 |
| ENSMUSG00000022946 | 70028 | Dopey2 | −0.193730574 | 0.0330309 | dopey family member 2 |
| ENSMUSG00000024302 | 13527 | Dtna | −0.193962497 | 0.043223052 | dystrobrevin alpha |
| ENSMUSG00000027634 | 29812 | Ndrg3 | −0.194040936 | 0.029184119 | N-myc downstream regulated gene 3 |
| ENSMUSG00000041594 | 11603 | Agrn | −0.194948906 | 0.028841303 | agrin |
| ENSMUSG00000000532 | 11479 | Acvr1b | −0.195542299 | 0.027890383 | activin A receptor, type 1B |
| ENSMUSG00000027878 | 18129 | Notch2 | −0.196270494 | 0.038665663 | notch 2 |
| ENSMUSG00000025189 | 83674 | Cnnm1 | −0.196312748 | 0.025337605 | cyclin M1 |
| ENSMUSG00000026000 | 14768 | Lancl1 | −0.197025048 | 0.002356321 | LanC (bacterial lantibiotic synthetase component C)-like 1 |
| ENSMUSG00000029763 | 20336 | Exoc4 | −0.197556886 | 0.013814483 | exocyst complex component 4 |
| ENSMUSG00000022771 | 66053 | Ppil2 | −0.197730481 | 0.031406769 | peptidylprolyl isomerase (cyclophilin)-like 2 |
| ENSMUSG00000057649 | 105246 | Brd9 | −0.19949826 | 0.032410655 | bromodomain containing 9 |
| ENSMUSG00000070304 | 72821 | Scn2b | −0.200289311 | 0.018129063 | sodium channel, voltage-gated, type II, beta |
| ENSMUSG00000028936 | 19934 | Rpl22 | −0.200528059 | 0.035810911 | ribosomal protein L22 |
| ENSMUSG00000036932 | 26926 | Aifm1 | −0.200925166 | 0.048251151 | apoptosis-inducing factor, mitochondrion-associated 1 |
| ENSMUSG00000024104 | 28006 | Fam21 | −0.201298401 | 0.026779212 | family with sequence similarity 21 |
| ENSMUSG00000031971 | 73420 | Ccsap | −0.20242383 | 0.01406418 | centriole, cilia and spindle associated protein |
| ENSMUSG00000021772 | 69721 | Nkiras1 | −0.202438175 | 0.011733585 | NFKB inhibitor interacting Ras-like protein 1 |
| ENSMUSG00000041263 | 72296 | Rusc1 | −0.202457035 | 0.043322327 | RUN and SH3 domain containing 1 |
| ENSMUSG00000073755 | 230757 | 5730409E04Rik | −0.203587014 | 0.006198195 | RIKEN cDNA 5730409E04Rik gene |
| ENSMUSG00000058997 | 219189 | Vwa8 | −0.203770279 | 0.033554414 | von Willebrand factor A domain containing 8 |
| ENSMUSG00000038467 | 75608 | Chmp4b | −0.203855894 | 0.015941664 | charged multivesicular body protein 4B |
| ENSMUSG00000029364 | 59043 | Wsb2 | −0.204250543 | 0.043223052 | WD repeat and SOCS box-containing 2 |
| ENSMUSG00000006717 | 66834 | Acot13 | −0.204438511 | 0.017297968 | acyl-CoA thioesterase 13 |

TABLE 2-continued

| Ensembl | Entrez | Symbol | log2FoldChange | padj | Name |
|---|---|---|---|---|---|
| ENSMUSG00000021895 | 71704 | Arhgef3 | −0.204439028 | 0.027361188 | Rho guanine nucleotide exchange factor (GEF) 3 |
| ENSMUSG00000022957 | 16443 | Itsn1 | −0.204455407 | 0.044255811 | intersectin 1 (SH3 domain protein 1A) |
| ENSMUSG00000030127 | 26894 | Cops7a | −0.205081451 | 0.046094906 | COP9 signalosome subunit 7A |
| ENSMUSG00000046058 | 386655 | Eid2 | −0.205183032 | 0.046981184 | EP300 interacting inhibitor of differentiation 2 |
| ENSMUSG00000031668 | 13666 | Eif2ak3 | −0.205376279 | 0.021275924 | eukaryotic translation initiation factor 2 alpha kinase 3 |
| ENSMUSG00000020850 | 192159 | Prpf8 | −0.205930338 | 0.04590473 | pre-mRNA processing factor 8 |
| ENSMUSG00000029463 | 68948 | Fam216a | −0.205981552 | 0.035521529 | family with sequence similarity 216, member A |
| ENSMUSG00000031729 | 71955 | Ist1 | −0.206031606 | 0.043360813 | increased sodium tolerance 1 homolog (yeast) |
| ENSMUSG00000038485 | 192157 | Socs7 | −0.206043117 | 0.005602219 | suppressor of cytokine signaling 7 |
| ENSMUSG00000037353 | 68614 | Letmd1 | −0.206523345 | 0.024079012 | LETM1 domain containing 1 |
| ENSMUSG00000029434 | 77573 | Vps33a | −0.206537444 | 0.00969777 | VPS33A CORVET/HOPS core subunit |
| ENSMUSG00000051359 | 52589 | Ncald | −0.207174018 | 0.021486914 | neurocalcin delta |
| ENSMUSG00000015536 | 17434 | Mocs2 | −0.207295797 | 0.026378656 | molybdenum cofactor synthesis 2 |
| ENSMUSG00000030286 | 66087 | Emc3 | −0.208480884 | 0.040749845 | ER membrane protein complex subunit 3 |
| ENSMUSG00000037902 | 19261 | Sirpa | −0.209055274 | 0.029400927 | signal-regulatory protein alpha |
| ENSMUSG00000026709 | 226539 | Dars2 | −0.209152384 | 0.032175372 | aspartyl-tRNA synthetase 2 (mitochondrial) |
| ENSMUSG00000032118 | 235180 | Fez1 | −0.209175253 | 0.004676242 | fasciculation and elongation protein zeta 1 (zygin I) |
| ENSMUSG00000029518 | 77407 | Rab35 | −0.209475621 | 0.032306534 | RAB35, member RAS oncogene family |
| ENSMUSG00000005510 | 68349 | Ndufs3 | −0.209553222 | 0.026161559 | NADH dehydrogenase (ubiquinone) Fe-S protein 3 |
| ENSMUSG00000053414 | 26559 | Hunk | −0.209670911 | 0.04984278 | hormonally upregulated Neu-associated kinase |
| ENSMUSG00000030930 | 77590 | Chst15 | −0.210028893 | 0.045287645 | carbohydrate (N-acetylgalactosamine 4-sulfate 6-O) sulfotransferase 15 |
| ENSMUSG00000062070 | 18655 | Pgk1 | −0.210482945 | 0.01662651 | phosphoglycerate kinase 1 |
| ENSMUSG00000019731 | 270066 | Slc35e1 | −0.210510112 | 0.018223783 | solute carrier family 35, member E1 |
| ENSMUSG00000030337 | 22317 | Vamp1 | −0.210790563 | 0.046363687 | vesicle-associated membrane protein 1 |
| ENSMUSG00000022619 | 60597 | Mapk8ip2 | −0.211149308 | 0.027381181 | mitogen-activated protein kinase 8 interacting protein 2 |
| ENSMUSG00000050379 | 56526 | 6-Sep | −0.211279355 | 0.005496172 | septin 6 |
| ENSMUSG00000004096 | 66070 | Cwc15 | −0.211687754 | 0.031409398 | CWC 15 spliceosome-associated protein |
| ENSMUSG00000071866 | 268373 | Ppia | −0.211954889 | 0.025407964 | peptidylprolyl isomerase A |
| ENSMUSG00000039828 | 545085 | Wdr70 | −0.213159742 | 0.047008504 | WD repeat domain 70 |
| ENSMUSG00000050608 | 433771 | Minos1 | −0.213326337 | 0.044706566 | mitochondrial inner membrane organizing system 1 |
| ENSMUSG00000003518 | 72349 | Dusp3 | −0.213492361 | 0.009783693 | dual specificity phosphatase 3 (vaccinia virus phosphatase VH1-related) |
| ENSMUSG00000000374 | 216131 | Trappc10 | −0.214486941 | 0.023209714 | trafficking protein particle complex 10 |
| ENSMUSG00000071657 | 14705 | Bscl2 | −0.214756417 | 0.041620932 | Berardinelli-Seip congenital lipodystrophy 2 (seipin) |
| ENSMUSG00000027998 | 53317 | Plrg1 | −0.215987999 | 0.021145965 | pleiotropic regulator 1 |
| ENSMUSG00000027624 | 13821 | Epb4.1l1 | −0.216351461 | 0.042975023 | erythrocyte membrane protein band 4.1 like 1 |
| ENSMUSG00000038615 | 18023 | Nfe2l1 | −0.216394005 | 0.042591379 | nuclear factor, erythroid derived 2,-like 1 |
| ENSMUSG00000004069 | 83945 | Dnaja3 | −0.216406962 | 0.00947679 | DnaJ heat shock protein family (Hsp40) member A3 |
| ENSMUSG00000024454 | 15183 | Hdac3 | −0.216764627 | 0.046609841 | histone deacetylase 3 |
| ENSMUSG00000044788 | 328035 | Fads6 | −0.216884703 | 0.040749845 | fatty acid desaturase domain family, member 6 |
| ENSMUSG00000001416 | 12462 | Cct3 | −0.216962467 | 0.013131686 | chaperonin containing Tcp1, subunit 3 (gamma) |
| ENSMUSG00000026991 | 227937 | Pkp4 | −0.218036216 | 0.020167127 | plakophilin 4 |
| ENSMUSG00000024527 | 69597 | Afg3l2 | −0.218857206 | 0.013676415 | AFG3-like AAA ATPase 2 |
| ENSMUSG00000035629 | 100502698 | Rubcn | −0.219179624 | 0.032903723 | RUN domain and cysteine-rich domain containing, Beclin 1-interacting protein |
| ENSMUSG00000026933 | 227634 | Camsap1 | −0.21920183 | 0.032644375 | calmodulin regulated spectrin-associated protein 1 |
| ENSMUSG00000007097 | 98660 | Atp1a2 | −0.220480783 | 0.021167204 | ATPase, Na+/K+ transporting, alpha 2 polypeptide |
| ENSMUSG00000003469 | 105653 | Phyhip | −0.220635892 | 0.02498669 | phytanoyl-CoA hydroxylase interacting protein |
| ENSMUSG00000052712 | 80748 | BC004004 | −0.220798343 | 0.005077667 | cDNA sequence BC004004 |
| ENSMUSG00000031153 | 54645 | Gripap1 | −0.221028039 | 0.032160015 | GRIP1 associated protein 1 |
| ENSMUSG00000043733 | 19247 | Ptpn11 | −0.221075103 | 0.001404888 | protein tyrosine phosphatase, non-receptor type 11 |
| ENSMUSG00000001036 | 13855 | Epn2 | −0.221324473 | 0.034724663 | epsin 2 |
| ENSMUSG00000028745 | 12345 | Capzb | −0.221865136 | 0.022755217 | capping protein (actin filament) muscle Z-line, beta |

TABLE 2-continued

| Ensembl | Entrez | Symbol | log2FoldChange | padj | Name |
|---|---|---|---|---|---|
| ENSMUSG00000029319 | 71883 | Coq2 | −0.222617582 | 0.040863165 | coenzyme Q2 4-hydroxybenzoate polyprenyltransferase |
| ENSMUSG00000022389 | 21685 | Tef | −0.222625528 | 0.01203162 | thyrotroph embryonic factor |
| ENSMUSG00000035877 | 320799 | Zhx3 | −0.223590906 | 0.017297968 | zinc fingers and homeoboxes 3 |
| ENSMUSG00000030058 | 54161 | Copg1 | −0.223914952 | 0.034746341 | coatomer protein complex, subunit gamma 1 |
| ENSMUSG00000032020 | 72828 | Ubash3b | −0.224460452 | 0.043858934 | ubiquitin associated and SH3 domain containing, B |
| ENSMUSG00000035776 | 171486 | Cd99l2 | −0.224482905 | 0.020897538 | CD99 antigen-like 2 |
| ENSMUSG00000021094 | 66375 | Dhrs7 | −0.224631635 | 0.044942054 | dehydrogenase/reductase (SDR family) member 7 |
| ENSMUSG00000025221 | 80906 | Kcnip2 | −0.225293577 | 0.017378516 | Kv channel-interacting protein 2 |
| ENSMUSG00000034354 | 74302 | Mtmr3 | −0.225672393 | 0.011874647 | myotubularin related protein 3 |
| ENSMUSG00000032305 | 78323 | Fam219b | −0.22741976 | 0.035580328 | family with sequence similarity 219, member B |
| ENSMUSG00000031453 | 19414 | Rasa3 | −0.227503009 | 0.026868762 | RAS p21 protein activator 3 |
| ENSMUSG00000066640 | 231863 | Fbxl18 | −0.227725146 | 0.049177438 | F-box and leucine-rich repeat protein 18 |
| ENSMUSG00000006932 | 12387 | Ctnnb1 | −0.228529697 | 0.022323986 | catenin (cadherin associated protein), beta 1 |
| ENSMUSG00000005936 | 66989 | Kctd20 | −0.228777278 | 0.017048863 | potassium channel tetramerisation domain containing 20 |
| ENSMUSG00000024248 | 20463 | Cox7a2l | −0.229228525 | 0.007699151 | cytochrome c oxidase subunit VIIa polypeptide 2-like |
| ENSMUSG00000029471 | 207565 | Camkk2 | −0.230282848 | 0.005120064 | calcium/calmodulin-dependent protein kinase kinase 2, beta |
| ENSMUSG00000033278 | 19274 | Ptprm | −0.230962417 | 0.046066757 | protein tyrosine phosphatase, receptor type, M |
| ENSMUSG00000018547 | 108083 | Pip4k2b | −0.231445173 | 0.043360813 | phosphatidylinositol-5-phosphate 4-kinase, type II, beta |
| ENSMUSG00000025025 | 17859 | Mxi1 | −0.231620868 | 0.011118862 | MAX interactor 1, dimerization protein |
| ENSMUSG00000064145 | 23807 | Arih2 | −0.232017715 | 0.021420593 | ariadne RBR E3 ubiquitin protein ligase 2 |
| ENSMUSG00000024978 | 14732 | Gpam | −0.232689688 | 0.00387336 | glycerol-3-phosphate acyltransferase, mitochondrial |
| ENSMUSG00000006127 | 19062 | Inpp5k | −0.234148561 | 0.021628342 | inositol polyphosphate 5-phosphatase K |
| ENSMUSG00000011179 | 18263 | Odc1 | −0.234441839 | 0.016961463 | ornithine decarboxylase, structural 1 |
| ENSMUSG00000016552 | 239554 | Foxred2 | −0.235857463 | 0.045128357 | FAD-dependent oxidoreductase domain containing 2 |
| ENSMUSG00000034432 | 108679 | Cops8 | −0.23590515 | 0.002911063 | COP9 signalosome subunit 8 |
| ENSMUSG00000071650 | 14376 | Ganab | −0.236235899 | 0.009551105 | alpha glucosidase 2 alpha neutral subunit |
| ENSMUSG00000014349 | 268470 | Ube2z | −0.236320525 | 0.044840327 | ubiquitin-conjugating enzyme E2Z |
| ENSMUSG00000026927 | 68112 | Sdccag3 | −0.236652 | 0.028232579 | serologically defined colon cancer antigen 3 |
| ENSMUSG00000001786 | 69754 | Fbxo7 | −0.23673792 | 0.034153296 | F-box protein 7 |
| ENSMUSG00000020628 | 217449 | Trappc12 | −0.23703382 | 0.019951725 | trafficking protein particle complex 12 |
| ENSMUSG00000055675 | 74901 | Kbtbd11 | −0.237156874 | 0.00601558 | kelch repeat and BTB (POZ) domain containing 11 |
| ENSMUSG00000037257 | 66939 | Aagab | −0.237354851 | 0.016109381 | alpha- and gamma-adaptin binding protein |
| ENSMUSG00000005886 | 17978 | Ncoa2 | −0.237953584 | 0.047256007 | nuclear receptor coactivator 2 |
| ENSMUSG00000041852 | 21411 | Tcf20 | −0.238041359 | 0.024578427 | transcription factor 20 |
| ENSMUSG00000031819 | 18117 | Emc8 | −0.23834092 | 0.010364417 | ER membrane protein complex subunit 8 |
| ENSMUSG00000053838 | 209586 | Nudcd3 | −0.238370675 | 0.027571434 | NudC domain containing 3 |
| ENSMUSG00000016940 | 70382 | Kctd2 | −0.238910209 | 0.036040264 | potassium channel tetramerisation domain containing 2 |
| ENSMUSG00000046862 | 242736 | Pramef8 | −0.238996248 | 0.048997766 | PRAME family member 8 |
| ENSMUSG00000020898 | 68964 | Ctc1 | −0.239516961 | 0.047069415 | CTS telomere maintenance complex component 1 |
| ENSMUSG00000024640 | 107272 | Psat1 | −0.239620074 | 0.007738756 | phosphoserine aminotransferase 1 |
| ENSMUSG00000031700 | 108682 | Gpt2 | −0.239821424 | 0.013571754 | glutamic pyruvate transaminase (alanine aminotransferase) 2 |
| ENSMUSG00000029063 | 192185 | Nadk | −0.240453253 | 0.031599635 | NAD kinase |
| ENSMUSG00000071369 | 26408 | Map3k5 | −0.2407662 | 0.01807201 | mitogen-activated protein kinase kinase kinase 5 |
| ENSMUSG00000004460 | 67838 | Dnajb11 | −0.240797203 | 0.02009524 | DnaJ heat shock protein family (Hsp40) member B11 |
| ENSMUSG00000039671 | 228880 | Zmynd8 | −0.240809592 | 0.033483715 | zinc finger, MYND-type containing 8 |
| ENSMUSG00000038486 | 64051 | Sv2a | −0.241259894 | 0.039626368 | synaptic vesicle glycoprotein 2 a |
| ENSMUSG00000037536 | 78938 | Fbxo34 | −0.241274331 | 0.039484285 | F-box protein 34 |
| ENSMUSG00000029076 | 20318 | Sdf4 | −0.241313897 | 0.016463732 | stromal cell derived factor 4 |
| ENSMUSG00000030350 | 381813 | Prmt8 | −0.241685333 | 0.007880612 | protein arginine N-methyltransferase 8 |
| ENSMUSG00000002052 | 20926 | Supt6 | −0.24190341 | 0.032964116 | suppressor of Ty 6 |
| ENSMUSG00000028567 | 66073 | Txndc12 | −0.242281823 | 0.02357533 | thioredoxin domain containing 12 (endoplasmic reticulum) |
| ENSMUSG00000031376 | 320707 | Atp2b3 | −0.242705225 | 0.044619432 | ATPase, Ca++ transporting, plasma membrane 3 |

TABLE 2-continued

| Ensembl | Entrez | Symbol | log2FoldChange | padj | Name |
|---|---|---|---|---|---|
| ENSMUSG00000037287 | 272589 | Tbcel | −0.242897538 | 0.047589623 | tubulin folding cofactor E-like |
| ENSMUSG00000038170 | 83679 | Pde4dip | −0.242980235 | 0.008856376 | phosphodiesterase 4D interacting protein (myomegalin) |
| ENSMUSG00000059213 | 13199 | Ddn | −0.24357295 | 0.007417862 | dendrin |
| ENSMUSG00000028957 | 18628 | Per3 | −0.243682008 | 0.014122378 | period circadian clock 3 |
| ENSMUSG00000023800 | 24001 | Tiam2 | −0.24409618 | 0.027987337 | T cell lymphoma invasion and metastasis 2 |
| ENSMUSG00000026424 | 171469 | Gpr371l | −0.244139325 | 0.017297968 | G protein-coupled receptor 37-like 1 |
| ENSMUSG00000017639 | 268451 | Rab11fip4 | −0.244486555 | 0.022252373 | RAB11 family interacting protein 4 (class II) |
| ENSMUSG00000020523 | 67726 | Fam114a2 | −0.245127009 | 0.016087195 | family with sequence similarity 114, member A2 |
| ENSMUSG00000025151 | 94275 | Maged1 | −0.246201433 | 0.038687074 | melanoma antigen, family D, 1 |
| ENSMUSG00000034839 | 67557 | Larp6 | −0.246599411 | 0.01495083 | La ribonucleoprotein domain family, member 6 |
| ENSMUSG00000031985 | 14712 | Gnpat | −0.246918807 | 0.021507544 | glyceronephosphate O-acyltransferase |
| ENSMUSG00000022426 | 74158 | Josd1 | −0.247653373 | 0.00947519 | Josephin domain containing 1 |
| ENSMUSG00000008683 | 267019 | Rps15a | −0.247739274 | 0.014546441 | ribosomal protein S15A |
| ENSMUSG00000017734 | 52840 | Dbndd2 | −0.248002377 | 0.008913482 | dysbindin (dystrobrevin binding protein 1) domain containing 2 |
| ENSMUSG00000021820 | 12325 | Camk2g | −0.248201996 | 0.017109066 | calcium/calmodulin-dependent protein kinase II gamma |
| ENSMUSG00000032612 | 22258 | Usp4 | −0.248208545 | 0.015293069 | ubiquitin specific peptidase 4 (proto-oncogene) |
| ENSMUSG00000020571 | 71853 | Pdia6 | −0.248577455 | 0.028840169 | protein disulfide isomerase associated 6 |
| ENSMUSG00000052833 | 56459 | Sae1 | −0.248752943 | 0.00519215 | SUMO1 activating enzyme subunit 1 |
| ENSMUSG00000050947 | 229715 | Amigo1 | −0.248856766 | 0.007370161 | adhesion molecule with Ig like domain 1 |
| ENSMUSG00000041720 | 224020 | Pi4ka | −0.249088519 | 0.027987337 | phosphatidylinositol 4-kinase, catalytic, alpha polypeptide |
| ENSMUSG00000034190 | 105513 | Chmp7 | −0.249438567 | 0.044474565 | charged multivesicular body protein 7 |
| ENSMUSG00000035086 | 56208 | Becn1 | −0.249793913 | 0.002356321 | beclin 1, autophagy related |
| ENSMUSG00000015711 | 229589 | Prune1 | −0.250548105 | 0.032272577 | prune exopolyphosphatase |
| ENSMUSG00000027406 | 170718 | Idh3b | −0.250742874 | 0.006275636 | isocitrate dehydrogenase 3 (NAD+) beta |
| ENSMUSG00000006736 | 67125 | Tspan31 | −0.252335231 | 0.043784958 | tetraspanin 31 |
| ENSMUSG00000025422 | 216439 | Agap2 | −0.252447936 | 0.047193717 | ArfGAP with GTPase domain, ankyrin repeat and PH domain 2 |
| ENSMUSG00000024065 | 57440 | Ehd3 | −0.252540632 | 0.006413641 | EH-domain containing 3 |
| ENSMUSG00000031840 | 19339 | Rab3a | −0.252598202 | 0.026540021 | RAB3A, member RAS oncogene family |
| ENSMUSG00000025133 | 101861 | Ints4 | −0.253140724 | 0.013947569 | integrator complex subunit 4 |
| ENSMUSG00000009733 | 21422 | Tfcp2 | −0.253204299 | 0.03102444 | transcription factor CP2 |
| ENSMUSG00000072825 | 217882 | Cep170b | −0.253390509 | 0.035181459 | centrosomal protein 170B |
| ENSMUSG00000032383 | 19035 | Ppib | −0.253587729 | 0.017512637 | peptidylprolyl isomerase B |
| ENSMUSG00000045114 | 69017 | Prrt2 | −0.253742671 | 0.041981997 | proline-rich transmembrane protein 2 |
| ENSMUSG00000055932 | 26383 | Fto | −0.253860756 | 0.024740354 | fat mass and obesity associated |
| ENSMUSG00000022454 | 54003 | Nell2 | −0.254157578 | 0.016245091 | NEL-like 2 |
| ENSMUSG00000008604 | 94232 | Ubqln4 | −0.254501884 | 0.013003374 | ubiquilin 4 |
| ENSMUSG00000033732 | 101943 | Sf3b3 | −0.255126853 | 0.014950845 | splicing factor 3b, subunit 3 |
| ENSMUSG00000028081 | 20091 | Rps3a1 | −0.255341373 | 0.001801515 | ribosomal protein S3A1 |
| ENSMUSG00000005683 | 12974 | Cs | −0.255420438 | 0.018198169 | citrate synthase |
| ENSMUSG00000039461 | 102791 | Tcta | −0.255658755 | 0.021656475 | T cell leukemia translocation altered gene |
| ENSMUSG00000090213 | 407243 | Tmem189 | −0.255659118 | 0.045276898 | transmembrane protein 189 |
| ENSMUSG00000020431 | 432530 | Adcy1 | −0.255682914 | 0.038004045 | adenylate cyclase 1 |
| ENSMUSG00000028430 | 230082 | Nol6 | −0.255696151 | 0.024027306 | nucleolar protein family 6 (RNA-associated) |
| ENSMUSG00000026851 | 227707 | BC005624 | −0.255886165 | 0.030738659 | cDNA sequence BC005624 |
| ENSMUSG00000020923 | 21429 | Ubtf | −0.257168101 | 0.008685332 | upstream binding transcription factor, RNA polymerase I |
| ENSMUSG00000048458 | 109050 | Fam212b | −0.257197282 | 0.006022688 | family with sequence similarity 212, member B |
| ENSMUSG00000021578 | 67433 | Ccdc127 | −0.257454584 | 0.01809243 | coiled-coil domain containing 127 |
| ENSMUSG00000005103 | 22388 | Wdr1 | −0.257867003 | 0.017044825 | WD repeat domain 1 |
| ENSMUSG00000053436 | 26416 | Mapk14 | −0.25806173 | 0.003295585 | mitogen-activated protein kinase 14 |
| ENSMUSG00000021130 | 108760 | Galnt16 | −0.258191833 | 0.03165462 | UDP-N-acetyl-alpha-D-galactosamine:polypeptide N-acetylgalactosaminyltransferase 16 |
| ENSMUSG00000042763 | 215090 | Maneal | −0.258424057 | 0.005178912 | mannosidase, endo-alpha-like |
| ENSMUSG00000015087 | 227624 | Rabl6 | −0.258851216 | 0.001577619 | RAB, member RAS oncogene family-like 6 |
| ENSMUSG00000022031 | 74195 | Elp3 | −0.25910213 | 0.034351299 | elongator acetyltransferase complex subunit 3 |
| ENSMUSG00000022185 | 56215 | Acin1 | −0.259511769 | 0.009783693 | apoptotic chromatin condensation inducer 1 |
| ENSMUSG00000033444 | 74392 | Speccl1 | −0.259665912 | 0.020318811 | sperm antigen with calponin homology and coiled-coil domains 1-like |

TABLE 2-continued

| Ensembl | Entrez | Symbol | log2FoldChange | padj | Name |
|---|---|---|---|---|---|
| ENSMUSG00000032470 | 17532 | Mras | −0.259683372 | 0.006705787 | muscle and microspikes RAS |
| ENSMUSG00000038437 | 246198 | Mllt6 | −0.259841394 | 0.025454387 | myeloid/lymphoid or mixed-lineage leukemia; translocated to, 6 |
| ENSMUSG00000046364 | 26451 | Rpl27a | −0.260120642 | 0.00437341 | ribosomal protein L27A |
| ENSMUSG00000020032 | 77976 | Nuak1 | −0.261764777 | 0.049477202 | NUAK family, SNF1-like kinase, 1 |
| ENSMUSG00000033615 | 12889 | Cplx1 | −0.262056726 | 0.029357419 | complexin 1 |
| ENSMUSG00000031154 | 54644 | Otud5 | −0.262347914 | 0.002170917 | OTU domain containing 5 |
| ENSMUSG00000032802 | 76650 | Srxn1 | −0.262762027 | 0.014432784 | sulfiredoxin 1 homolog (*S. cerevisiae*) |
| ENSMUSG00000025369 | 68094 | Smarcc2 | −0.262810899 | 0.00889147 | SWI/SNF related, matrix associated, actin dependent regulator of chromatin, subfamily c, member 2 |
| ENSMUSG00000022779 | 21976 | Top3b | −0.263630867 | 0.038750304 | topoisomerase (DNA) III beta |
| ENSMUSG00000024414 | 94064 | Mrpl27 | −0.263790624 | 0.019823985 | mitochondrial ribosomal protein L27 |
| ENSMUSG00000029649 | 66537 | Pomp | −0.264199131 | 0.029804508 | proteasome maturation protein |
| ENSMUSG00000029053 | 18762 | Prkcz | −0.264571882 | 0.007162559 | protein kinase C, zeta |
| ENSMUSG00000017802 | 67998 | Fam134c | −0.264798924 | 0.011630092 | family with sequence similarity 134, member C |
| ENSMUSG00000056602 | 320365 | Fry | −0.265290085 | 0.038578288 | FRY microtubule binding protein |
| ENSMUSG00000013275 | 98396 | Slc41a1 | −0.265689786 | 0.006126242 | solute carrier family 41, member 1 |
| ENSMUSG00000020484 | 22433 | Xbp1 | −0.266190848 | 0.007536879 | X-box binding protein 1 |
| ENSMUSG00000049807 | 58996 | Arhgap23 | −0.266684834 | 0.015230798 | Rho GTPase activating protein 23 |
| ENSMUSG00000004071 | 66626 | Cdip1 | −0.267090184 | 0.007828246 | cell death inducing Trp53 target 1 |
| ENSMUSG00000071646 | 23942 | Mta2 | −0.267433356 | 0.01769178 | metastasis-associated gene family, member 2 |
| ENSMUSG00000041765 | 68889 | Ubac2 | −0.267499891 | 0.038867887 | ubiquitin associated domain containing 2 |
| ENSMUSG00000078429 | 52468 | Ctdsp2 | −0.267725772 | 0.012332469 | CTD (carboxy-terminal domain, RNA polymerase II, polypeptide A) small phosphatase 2 |
| ENSMUSG00000058975 | 16502 | Kcnc1 | −0.267797701 | 0.032980662 | potassium voltage gated channel, Shaw-related subfamily, member 1 |
| ENSMUSG00000040236 | 66682 | Trappc5 | −0.267849002 | 0.040736943 | trafficking protein particle complex 5 |
| ENSMUSG00000036062 | 230085 | Phf24 | −0.267991346 | 0.018319296 | PHD finger protein 24 |
| ENSMUSG00000022965 | 15980 | Ifngr2 | −0.268210743 | 0.005443427 | interferon gamma receptor 2 |
| ENSMUSG00000004789 | 78920 | Dlst | −0.26850413 | 0.007433333 | dihydrolipoamide S-succinyltransferase (E2 component of 2-oxo-glutarate complex) |
| ENSMUSG00000038332 | 140742 | Sesn1 | −0.268658257 | 0.005450124 | sestrin 1 |
| ENSMUSG00000034853 | 329910 | Acot11 | −0.26913719 | 0.045343381 | acyl-CoA thioesterase 11 |
| ENSMUSG00000018999 | 58246 | Slc35b4 | −0.269321213 | 0.021964618 | solute carrier family 35, member B4 |
| ENSMUSG00000025130 | 18453 | P4hb | −0.270072214 | 0.007905396 | prolyl 4-hydroxylase, beta polypeptide |
| ENSMUSG00000015094 | 18146 | Npdc1 | −0.270741054 | 0.037032533 | neural proliferation, differentiation and control 1 |
| ENSMUSG00000028140 | 78523 | Mrpl9 | −0.270884974 | 0.013208788 | mitochondrial ribosomal protein L9 |
| ENSMUSG00000021254 | 70373 | Gpatch2l | −0.271654793 | 0.011201756 | G patch domain containing 2 like |
| ENSMUSG00000004031 | 240843 | Brinp2 | −0.272252125 | 0.048997766 | bone morphogenic protein/retinoic acid inducible neural-specific 2 |
| ENSMUSG00000031835 | 56453 | Mbtps1 | −0.272856187 | 0.016433439 | membrane-bound transcription factor peptidase, site 1 |
| ENSMUSG00000025332 | 20591 | Kdm5c | −0.272983696 | 0.009303766 | lysine (K)-specific demethylase 5C |
| ENSMUSG00000027378 | 53885 | Nphp1 | −0.273558446 | 0.026986427 | nephronophthisis 1 (juvenile) homolog (human) |
| ENSMUSG00000018411 | 17762 | Mapt | −0.27386097 | 0.011423699 | microtubule-associated protein tau |
| ENSMUSG00000024528 | 67222 | Srfbp 1 | −0.274710411 | 0.025909535 | serum response factor binding protein 1 |
| ENSMUSG00000032773 | 12669 | Chrm1 | −0.274961337 | 0.033511304 | cholinergic receptor, muscarinic 1, CNS |
| ENSMUSG00000017715 | 74451 | Pgs1 | −0.275048146 | 0.010460161 | phosphatidylglycerophosphate synthase 1 |
| ENSMUSG00000022390 | 20286 | Zc3h7b | −0.275530007 | 0.027496156 | zinc finger CCCH type containing 7B |
| ENSMUSG00000049299 | 245828 | Trappc1 | −0.275783491 | 0.029288325 | trafficking protein particle complex 1 |
| ENSMUSG00000023094 | 76467 | Msrb2 | −0.276158319 | 0.009037806 | methionine sulfoxide reductase B2 |
| ENSMUSG00000044117 | 67254 | 2900011O08Rik | −0.276543261 | 0.032181211 | RIKEN cDNA 2900011O08 gene |
| ENSMUSG00000027894 | 229706 | Slc6a17 | −0.276804722 | 0.041478328 | solute carrier family 6 (neurotransmitter transporter), member 17 |
| ENSMUSG00000032507 | 72179 | Fbxl2 | −0.277336239 | 0.026983762 | F-box and leucine-rich repeat protein 2 |
| ENSMUSG00000027533 | 16592 | Fabp5 | −0.277484476 | 0.00667933 | fatty acid binding protein 5, epidermal |
| ENSMUSG00000039976 | 207592 | Tbc1d16 | −0.277686025 | 0.027651551 | TBC1 domain family, member 16 |
| ENSMUSG00000033208 | 20203 | S100b | −0.277950133 | 0.00574018 | S100 protein, beta polypeptide, neural |
| ENSMUSG00000027651 | 70470 | Rprd1b | −0.278602782 | 0.016805775 | regulation of nuclear pre-mRNA domain containing 1B |
| ENSMUSG00000036046 | 223739 | 5031439G07Rik | −0.27921004 | 0.009037806 | RIKEN cDNA 5031439G07 gene |
| ENSMUSG00000069631 | 72149 | Strada | −0.279246788 | 0.024688022 | STE20-related kinase adaptor alpha |
| ENSMUSG00000064037 | 74254 | Gpn1 | −0.279368202 | 0.043310304 | GPN-loop GTPase 1 |
| ENSMUSG00000031913 | 116733 | Vps4a | −0.279799411 | 0.00584403 | vacuolar protein sorting 4A |
| ENSMUSG00000024855 | 107975 | Pacs1 | −0.280109529 | 0.039147363 | phosphofurin acidic cluster sorting protein 1 |
| ENSMUSG00000025823 | 12304 | Pdia4 | −0.280717999 | 0.034815271 | protein disulfide isomerase associated 4 |
| ENSMUSG00000029819 | 109648 | Npy | −0.280748722 | 0.02613129 | neuropeptide Y |

TABLE 2-continued

| Ensembl | Entrez | Symbol | log2FoldChange | padj | Name |
|---|---|---|---|---|---|
| ENSMUSG00000040055 | 14623 | Gjb6 | −0.280803906 | 0.043553862 | gap junction protein, beta 6 |
| ENSMUSG00000001150 | 54387 | Mcm3ap | −0.281020192 | 0.0195895 | minichromosome maintenance complex component 3 associated protein |
| ENSMUSG00000063600 | 75740 | Egfem1 | −0.281061275 | 0.029164509 | EGF-like and EMI domain containing 1 |
| ENSMUSG00000029621 | 56443 | Arpc1a | −0.281500235 | 0.000874286 | actin related protein 2/3 complex, subunit 1A |
| ENSMUSG00000004267 | 13807 | Eno2 | −0.281697033 | 0.00971298 | enolase 2, gamma neuronal |
| ENSMUSG00000030701 | 27276 | Plekhb1 | −0.281878856 | 0.002485879 | pleckstrin homology domain containing, family B (evectins) member 1 |
| ENSMUSG00000014606 | 67863 | Slc25a11 | −0.28198418 | 0.006765342 | solute carrier family 25 (mitochondrial carrier oxoglutarate carrier), member 11 |
| ENSMUSG00000026127 | 27993 | Imp4 | −0.282363405 | 0.005812859 | IMP4, U3 small nucleolar ribonucleoprotein |
| ENSMUSG00000056596 | 69539 | Trnp1 | −0.282765038 | 0.032546234 | TMF1-regulated nuclear protein 1 |
| ENSMUSG00000069833 | 66395 | Ahnak | −0.282987866 | 0.03948349 | AHNAK nucleoprotein (desmoyokin) |
| ENSMUSG00000028495 | 20104 | Rps6 | −0.283031078 | 0.001913946 | ribosomal protein S6 |
| ENSMUSG00000020848 | 13447 | Doc2b | −0.283322791 | 0.033162403 | double C2, beta |
| ENSMUSG00000056201 | 12631 | Cfl1 | −0.283685888 | 0.024530589 | cofilin 1, non-muscle |
| ENSMUSG00000024966 | 20867 | Stip1 | −0.283859275 | 0.041135049 | stress-induced phosphoprotein 1 |
| ENSMUSG00000034341 | 22378 | Wbp2 | −0.28403338 | 0.018695515 | WW domain binding protein 2 |
| ENSMUSG00000025825 | 66383 | Iscu | −0.284189936 | 0.020792344 | iron-sulfur cluster assembly enzyme |
| ENSMUSG00000037010 | 30878 | Apln | −0.284725138 | 0.04909936 | apelin |
| ENSMUSG00000071662 | 67710 | Polr2g | −0.284825765 | 0.008516764 | polymerase (RNA) II (DNA directed) polypeptide G |
| ENSMUSG00000023805 | 20975 | Synj2 | −0.284862594 | 0.024592739 | synaptojanin 2 |
| ENSMUSG00000035953 | 219024 | Tmem55b | −0.285119741 | 0.045505582 | transmembrane protein 55b |
| ENSMUSG00000022312 | 68135 | Eif3h | −0.285683451 | 0.004568734 | eukaryotic translation initiation factor 3, subunit H |
| ENSMUSG00000028351 | 56710 | Brinp1 | −0.285938262 | 0.002185654 | bone morphogenic protein/retinoic acid inducible neural specific 1 |
| ENSMUSG00000043683 | 14154 | Fem1a | −0.286239306 | 0.015573718 | feminization 1 homolog a (C. elegans) |
| ENSMUSG00000002741 | 56418 | Ykt6 | −0.286637494 | 0.011630092 | YKT6 v-SNARE homolog (S. cerevisiae) |
| ENSMUSG00000046240 | 72927 | Hepacam | −0.286647043 | 0.019066758 | hepatocyte cell adhesion molecule |
| ENSMUSG00000079557 | 224703 | 2-Mar | −0.286664706 | 0.013454563 | membrane-associated ring finger (C3HC4) 2 |
| ENSMUSG00000046722 | 57912 | Cdc42se1 | −0.286975526 | 0.022262271 | CDC42 small effector 1 |
| ENSMUSG00000028608 | 74098 | 0610037L13Rik | −0.287107976 | 0.037506875 | RIKEN cDNA 0610037L 13 gene |
| ENSMUSG00000023030 | 18174 | Slc11a2 | −0.28760126 | 0.019386777 | solute carrier family 11 (proton-coupled divalent metal ion transporters), member 2 |
| ENSMUSG00000031149 | 54637 | Praf2 | −0.287777044 | 0.01418109 | PRA1 domain family 2 |
| ENSMUSG00000078794 | 629378 | Dact3 | −0.287893444 | 0.043630648 | dishevelled-binding antagonist of beta-catenin 3 |
| ENSMUSG00000004633 | 69993 | Chn2 | −0.288212803 | 0.012060747 | chimerin 2 |
| ENSMUSG00000004032 | 14866 | Gstm5 | −0.288222247 | 0.002227954 | glutathione S-transferase, mu 5 |
| ENSMUSG00000006998 | 21762 | Psmd2 | −0.288423538 | 0.009122426 | proteasome (prosome, macropain) 26S subunit, non-ATPase, 2 |
| ENSMUSG00000020430 | 64934 | Pes1 | −0.288497628 | 0.027675598 | pescadillo ribosomal biogenesis factor 1 |
| ENSMUSG00000026848 | 30934 | Tor1b | −0.288517427 | 0.01753848 | torsin family 1, member B |
| ENSMUSG00000020737 | 15374 | Hn1 | −0.288870436 | 0.017530941 | hematological and neurological expressed sequence 1 |
| ENSMUSG00000022538 | 224092 | Lsg1 | −0.289339168 | 0.047268143 | large 60S subunit nuclear export GTPase 1 |
| ENSMUSG00000011158 | 72308 | Brf1 | −0.290032122 | 0.032840549 | BRF1, RNA polymerase III transcription initiation factor 90 kDa subunit |
| ENSMUSG00000084786 | 66177 | Ubl5 | −0.290066604 | 0.011128691 | ubiquitin-like 5 |
| ENSMUSG00000029020 | 170731 | Mfn2 | −0.290472301 | 0.008949062 | mitofusin 2 |
| ENSMUSG00000027978 | 19142 | Prss12 | −0.291032962 | 0.034430047 | protease, serine 12 neurotrypsin (motopsin) |
| ENSMUSG00000057738 | 20740 | Sptan1 | −0.291436269 | 0.001554193 | spectrin alpha, non-erythrocytic 1 |
| ENSMUSG00000050511 | 18386 | Oprd1 | −0.291575146 | 0.020629005 | opioid receptor, delta 1 |
| ENSMUSG00000025157 | 74168 | Zdhhc16 | −0.291753876 | 0.013823958 | zinc finger, DHHC domain containing 16 |
| ENSMUSG00000061751 | 545156 | Kalrn | −0.292244781 | 0.000676208 | kalirin, RhoGEF kinase |
| ENSMUSG00000005949 | 83429 | Ctns | −0.292522523 | 0.045210685 | cystinosis, nephropathic |
| ENSMUSG00000027540 | 19246 | Ptpn1 | −0.293148509 | 0.009454367 | protein tyrosine phosphatase, non-receptor type 1 |
| ENSMUSG00000000827 | 66314 | Tpd52l2 | −0.293191954 | 0.011118862 | tumor protein D52-like 2 |
| ENSMUSG00000021536 | 210044 | Adcy2 | −0.293334748 | 0.002298661 | adenylate cyclase 2 |
| ENSMUSG00000022437 | 68653 | Samm50 | −0.293338761 | 0.010339821 | SAMM50 sorting and assembly machinery component |
| ENSMUSG00000093909 | | | −0.294060473 | 0.043223052 | |
| ENSMUSG00000041815 | 73826 | Poldip3 | −0.29406907 | 0.014122378 | polymerase (DNA-directed), delta interacting protein 3 |
| ENSMUSG00000053475 | 21930 | Tnfaip6 | −0.294376129 | 0.023140793 | tumor necrosis factor alpha induced protein 6 |
| ENSMUSG00000051041 | 244198 | Olfml1 | −0.294524772 | 0.031355072 | olfactomedin-like 1 |
| ENSMUSG00000002546 | 99412 | Golga2 | −0.294818142 | 0.031240021 | golgi autoantigen, golgin subfamily a, 2 |
| ENSMUSG00000022472 | 28075 | Desi1 | −0.295082625 | 0.002485879 | desumoylating isopeptidase 1 |
| ENSMUSG00000004070 | 15369 | Hmox2 | −0.29513803 | 0.000840189 | heme oxygenase 2 |

TABLE 2-continued

| Ensembl | Entrez | Symbol | log2FoldChange | padj | Name |
|---|---|---|---|---|---|
| ENSMUSG00000041329 | 11932 | Atp1b2 | −0.295240137 | 0.010268575 | ATPase, Na+/K+ transporting, beta 2 polypeptide |
| ENSMUSG00000022962 | 14450 | Gart | −0.295876674 | 0.030363562 | phosphoribosylglycinamide formyltransferase |
| ENSMUSG00000059981 | 381921 | Taok2 | −0.296159324 | 0.026361512 | TAO kinase 2 |
| ENSMUSG00000029330 | 74596 | Cds1 | −0.296221867 | 0.024712971 | CDP-diacylglycerol synthase 1 |
| ENSMUSG00000031969 | 66948 | Acad8 | −0.296478278 | 0.016410003 | acyl-Coenzyme A dehydrogenase family, member 8 |
| ENSMUSG00000032537 | 270190 | Ephb1 | −0.296519061 | 0.029299273 | Eph receptor B1 |
| ENSMUSG00000009394 | 20965 | Syn2 | −0.297262991 | 0.046363687 | synapsin II |
| ENSMUSG00000060098 | 214572 | Prmt7 | −0.297486145 | 0.030363562 | protein arginine N-methyltransferase 7 |
| ENSMUSG00000024347 | 74002 | Psd2 | −0.29755659 | 0.034057706 | pleckstrin and Sec7 domain containing 2 |
| ENSMUSG00000031409 | 66104 | Tceal6 | −0.297771278 | 0.009241937 | transcription elongation factor A (SII)-like 6 |
| ENSMUSG00000034613 | 319468 | Ppm1h | −0.297906703 | 0.004754638 | protein phosphatase 1H (PP2C domain containing) |
| ENSMUSG00000043602 | 193043 | Zfp3 | −0.298252721 | 0.021056594 | zinc finger protein 3 |
| ENSMUSG00000037703 | 241638 | Lzts3 | −0.29825409 | 0.001608434 | leucine zipper, putative tumor suppressor family member 3 |
| ENSMUSG00000017999 | 228889 | Ddx27 | −0.298699142 | 0.035792905 | DEAD (Asp-Glu-Ala-Asp) box polypeptide 27 |
| ENSMUSG00000052353 | 80982 | Cemip | −0.29895152 | 0.010367112 | cell migration inducing protein, hyaluronan binding |
| ENSMUSG00000036975 | 66343 | Tmem177 | −0.298973662 | 0.037182588 | transmembrane protein 177 |
| ENSMUSG00000073888 | 20301 | Ccl27a | −0.299147815 | 0.032181211 | chemokine (C-C motif) ligand 27A |
| ENSMUSG00000046721 | 100040970 | Rpl14-ps1 | −0.299176498 | 0.011255603 | ribosomal protein L14, pseudogene 1 |
| ENSMUSG00000015396 | 12522 | Cd83 | −0.299743276 | 0.025364617 | CD83 antigen |
| ENSMUSG00000042671 | 67792 | Rgs8 | −0.299778785 | 0.004198828 | regulator of G-protein signaling 8 |
| ENSMUSG00000040797 | 243621 | Iqsec3 | −0.300157197 | 0.038151975 | IQ motif and Sec7 domain 3 |
| ENSMUSG00000045538 | 71986 | Ddx28 | −0.301080639 | 0.04928913 | DEAD (Asp-Glu-Ala-Asp) box polypeptide 28 |
| ENSMUSG00000021361 | 66154 | Tmem14c | −0.30109939 | 0.030092121 | transmembrane protein 14C |
| ENSMUSG00000029458 | 72399 | Brap | −0.30155661 | 0.000387043 | BRCA1 associated protein |
| ENSMUSG00000002326 | 105446 | Gmpr2 | −0.301754667 | 0.01535456 | guanosine monophosphate reductase 2 |
| ENSMUSG00000029310 | 74167 | Nudt9 | −0.301846024 | 0.012661937 | nudix (nucleoside diphosphate linked moiety X)-type motif 9 |
| ENSMUSG00000029223 | 22223 | Uchl1 | −0.302021404 | 0.042928119 | ubiquitin carboxy-terminal hydrolase L1 |
| ENSMUSG00000035934 | 208076 | Pknox2 | −0.302083903 | 0.043208207 | Pbx/knotted 1 homeobox 2 |
| ENSMUSG00000039826 | 227682 | Trub2 | −0.302171734 | 0.012750094 | TruB pseudouridine (psi) synthase family member 2 |
| ENSMUSG00000029392 | 75695 | Rilpl1 | −0.302995099 | 0.0043121 | Rab interacting lysosomal protein-like 1 |
| ENSMUSG00000028882 | 100336 | Ppp1r8 | −0.303221359 | 0.0125064 | protein phosphatase 1, regulatory (inhibitor) subunit 8 |
| ENSMUSG00000040722 | 56807 | Scamp5 | −0.303973938 | 0.004141489 | secretory carrier membrane protein 5 |
| ENSMUSG00000021018 | 245841 | Polr2h | −0.304056216 | 0.026755536 | polymerase (RNA) II (DNA directed) polypeptide H |
| ENSMUSG00000025228 | 54130 | Actr1a | −0.304728942 | 0.006473466 | ARP1 actin-related protein 1A, centractin alpha |
| ENSMUSG00000016664 | 23970 | Pacsin2 | −0.304823613 | 0.023391328 | protein kinase C and casein kinase substrate in neurons 2 |
| ENSMUSG00000031858 | 74549 | Mau2 | −0.304855921 | 0.002371494 | MAU2 sister chromatid cohesion factor |
| ENSMUSG00000025393 | 11947 | Atp5b | −0.304914484 | 0.001345392 | ATP synthase, H+ transporting mitochondrial F1 complex, beta subunit |
| ENSMUSG00000037151 | 216011 | Lrrc20 | −0.304966334 | 0.026648841 | leucine rich repeat containing 20 |
| ENSMUSG00000015656 | 15481 | Hspa8 | −0.305025001 | 0.007306839 | heat shock protein 8 |
| ENSMUSG00000020706 | 56095 | Ftsj3 | −0.305147509 | 0.002099181 | FtsJ RNA methyltransferase homolog 3 (E. coli) |
| ENSMUSG00000060288 | 66101 | Ppih | −0.305260779 | 0.030816813 | peptidyl prolyl isomerase H |
| ENSMUSG00000028797 | 76799 | Tmem234 | −0.306515434 | 0.0330309 | transmembrane protein 234 |
| ENSMUSG00000022234 | 12465 | Cct5 | −0.30683986 | 0.003102924 | chaperonin containing Tcp1, subunit 5 (epsilon) |
| ENSMUSG00000020515 | 69125 | Cnot8 | −0.307317077 | 0.002080874 | CCR4-NOT transcription complex, subunit 8 |
| ENSMUSG00000029578 | 74781 | Wipi2 | −0.307354558 | 0.007514582 | WD repeat domain, phosphoinositide interacting 2 |
| ENSMUSG00000024841 | 69860 | Eif1ad | −0.307407284 | 0.023564678 | eukaryotic translation initiation factor 1A domain containing |
| ENSMUSG00000022553 | 68877 | Maf1 | −0.307651341 | 0.029269343 | MAF1 homolog, negative regulator of RNA polymerase III |
| ENSMUSG00000028439 | 71901 | Fam219a | −0.307992489 | 0.016873714 | family with sequence similarity 219, member A |
| ENSMUSG00000040687 | 228355 | Madd | −0.30835274 | 0.021104421 | MAP-kinase activating death domain |
| ENSMUSG00000021508 | 57266 | Cxcl14 | −0.308856612 | 0.002884513 | chemokine (C-X-C motif) ligand 14 |
| ENSMUSG00000032786 | 11655 | Alas1 | −0.309094505 | 0.011109797 | aminolevulinic acid synthase 1 |
| ENSMUSG00000078746 | 545611 | Fam205a2 | −0.309161522 | 0.031366726 | family with sequence similarity 205, member A2 |
| ENSMUSG00000015806 | 110391 | Qdpr | −0.309274634 | 0.025024021 | quinoid dihydropteridine reductase |

TABLE 2-continued

| Ensembl | Entrez | Symbol | log2FoldChange | padj | Name |
|---|---|---|---|---|---|
| ENSMUSG00000033526 | 327655 | Ppip5k1 | −0.310575386 | 0.012177561 | diphosphoinositol pentakisphosphate kinase 1 |
| ENSMUSG00000066687 | 235320 | Zbtb16 | −0.310638389 | 0.005001017 | zinc finger and BTB domain containing 16 |
| ENSMUSG00000046598 | 71911 | Bdh1 | −0.310774887 | 0.04984278 | 3-hydroxybutyrate dehydrogenase, type 1 |
| ENSMUSG00000022354 | 66218 | Ndufb9 | −0.311888733 | 0.000885305 | NADH dehydrogenase (ubiquinone) 1 beta subcomplex, 9 |
| ENSMUSG00000032135 | 84004 | Mcam | −0.3119953 | 0.028890287 | melanoma cell adhesion molecule |
| ENSMUSG00000025047 | 18572 | Pdcd11 | −0.31211358 | 0.036610034 | programmed cell death 11 |
| ENSMUSG00000005981 | 68015 | Trap1 | −0.31223935 | 0.009783693 | TNF receptor-associated protein 1 |
| ENSMUSG00000058076 | 66052 | Sdhc | −0.312447752 | 0.007370161 | succinate dehydrogenase complex, subunit C, integral membrane protein |
| ENSMUSG00000034566 | 71679 | Atp5h | −0.312626898 | 0.003036844 | ATP synthase, H+ transporting, mitochondrial F0 complex, subunit D |
| ENSMUSG00000031755 | 67378 | Bbs2 | −0.312695135 | 0.01809243 | Bardet-Biedl syndrome 2 (human) |
| ENSMUSG00000021203 | 68149 | Otub2 | −0.312765785 | 0.011874647 | OTU domain, ubiquitin aldehyde binding 2 |
| ENSMUSG00000069227 | 26913 | Gprin1 | −0.312925086 | 0.004250411 | G protein-regulated inducer of neurite outgrowth 1 |
| ENSMUSG00000013033 | 330814 | Adgrl1 | −0.312933427 | 0.032136093 | adhesion G protein-coupled receptor L1 |
| ENSMUSG00000050002 | 75731 | Idnk | −0.31303167 | 0.027675598 | idnK gluconokinase homolog (E. coli) |
| ENSMUSG00000004446 | 12122 | Bid | −0.313097514 | 0.043463041 | BH3 interacting domain death agonist |
| ENSMUSG00000018765 | 23879 | Fxr2 | −0.313531899 | 0.028840169 | fragile X mental retardation, autosomal homolog 2 |
| ENSMUSG00000032038 | 20443 | St3gal4 | −0.313548464 | 0.024578427 | ST3 beta-galactoside alpha-2,3-sialyltransferase 4 |
| ENSMUSG00000046861 | 76608 | Hectd3 | −0.313889603 | 0.003980677 | HECT domain containing 3 |
| ENSMUSG00000021242 | 67963 | Npc2 | −0.314442792 | 0.02907184 | Niemann-Pick type C2 |
| ENSMUSG00000025223 | 16825 | Ldb1 | −0.314469452 | 0.046774546 | LIM domain binding 1 |
| ENSMUSG00000007338 | 18120 | Mrpl49 | −0.314825030 | 0.004747987 | mitochondrial ribosomal protein L49 |
| ENSMUSG00000021484 | 66890 | Lman2 | −0.314961879 | 0.007306839 | lectin, mannose-binding 2 |
| ENSMUSG00000039294 | 217370 | BC017643 | −0.314967346 | 0.029858114 | cDNA sequence BC017643 |
| ENSMUSG00000046329 | 66972 | Slc25a23 | −0.315186358 | 0.018953988 | solute carrier family 25 (mitochondrial carrier; phosphate carrier), member 23 |
| ENSMUSG00000045349 | 230863 | Sh2d5 | −0.315421577 | 0.031409398 | SH2 domain containing 5 |
| ENSMUSG00000015790 | 20930 | Surf1 | −0.315490625 | 0.019700695 | surfeit gene 1 |
| ENSMUSG00000064105 | 94219 | Cnnm2 | −0.315626275 | 0.002310026 | cyclin M2 |
| ENSMUSG00000022131 | 58245 | Gpr180 | −0.316336384 | 0.026986427 | G protein-coupled receptor 180 |
| ENSMUSG00000025417 | 117150 | Pip4k2c | −0.316490134 | 0.013808316 | phosphatidylinositol-5-phosphate 4-kinase, type II, gamma |
| ENSMUSG00000024661 | 14319 | Fth1 | −0.316630105 | 0.005302389 | ferritin heavy polypeptide 1 |
| ENSMUSG00000032788 | 216134 | Pdxk | −0.316723253 | 0.023185223 | pyridoxal (pyridoxine, vitamin B6) kinase |
| ENSMUSG00000019295 | 68366 | Tmem129 | −0.31679614 | 0.007467518 | transmembrane protein 129 |
| ENSMUSG00000051343 | 52055 | Rab11fip5 | −0.317037593 | 0.040504699 | RAB11 family interacting protein 5 (class I) |
| ENSMUSG00000030844 | 67865 | Rgs10 | −0.317292957 | 0.004926149 | regulator of G-protein signalling 10 |
| ENSMUSG00000031781 | 109006 | Ciapin1 | −0.317684725 | 0.011130995 | cytokine induced apoptosis inhibitor 1 |
| ENSMUSG00000021481 | 26919 | Zfp346 | −0.317887075 | 0.012923927 | zinc finger protein 346 |
| ENSMUSG00000044197 | 80290 | Gpr146 | −0.317928877 | 0.015208833 | G protein-coupled receptor 146 |
| ENSMUSG00000020876 | 74479 | Snx11 | −0.318100757 | 0.019513994 | sorting nexin 11 |
| ENSMUSG00000025178 | 84095 | Pi4k2a | −0.318479974 | 0.02613129 | phosphatidylinositol 4-kinase type 2 alpha |
| ENSMUSG00000005575 | 22192 | Ube2m | −0.318551242 | 0.011570096 | ubiquitin-conjugating enzyme E2M |
| ENSMUSG00000028830 | 100317 | AU040320 | −0.318741976 | 0.024777333 | expressed sequence AU040320 |
| ENSMUSG00000017631 | 109934 | Abr | −0.318819674 | 0.000325542 | active BCR-related gene |
| ENSMUSG00000068099 | 76505 | 1500009C09Rik | −0.318986864 | 0.032175372 | RIKEN cDNA 1500009C09 gene |
| ENSMUSG00000034156 | 207777 | Bzrap1 | −0.319130243 | 0.026540021 | benzodiazepine receptor associated protein 1 |
| ENSMUSG00000042747 | 66059 | Krtcap2 | −0.319925111 | 0.039408609 | keratinocyte associated protein 2 |
| ENSMUSG00000027933 | 229543 | Ints3 | −0.320064507 | 0.048312414 | integrator complex subunit 3 |
| ENSMUSG00000004040 | 20848 | Stat3 | −0.320070639 | 0.006275636 | signal transducer and activator of transcription 3 |
| ENSMUSG00000071793 | 381598 | 2610005L07Rik | −0.320182271 | 0.04188267 | cadherin 11 pseudogene |
| ENSMUSG00000024767 | 107260 | Otub1 | −0.320288603 | 0.020422743 | OTU domain, ubiquitin aldehyde binding 1 |
| ENSMUSG00000002006 | 245469 | Pdzd4 | −0.320525321 | 0.017334618 | PDZ domain containing 4 |
| ENSMUSG00000025873 | 76577 | Faf2 | −0.32070168 | 0.04219464 | Fas associated factor family member 2 |
| ENSMUSG00000049751 | 66483 | Rpl36al | −0.320993822 | 0.013036571 | ribosomal protein L36A-like |
| ENSMUSG00000017764 | 71971 | Zswim1 | −0.321211671 | 0.028243863 | zinc finger SWIM-type containing 1 |
| ENSMUSG00000017493 | 16010 | Igfbp4 | −0.321586659 | 0.01155039 | insulin-like growth factor binding protein 4 |
| ENSMUSG00000028821 | 68592 | Syf2 | −0.322145515 | 0.001311399 | SYF2 homolog, RNA splicing factor (S. cerevisiae) |
| ENSMUSG00000031556 | 69742 | Tm2d2 | −0.322260181 | 0.023285008 | TM2 domain containing 2 |
| ENSMUSG00000038025 | 18676 | Phf2 | −0.322474604 | 0.007609083 | PHD finger protein 2 |
| ENSMUSG00000021062 | 104886 | Rab15 | −0.322548442 | 0.033129059 | RAB15, member RAS oncogene family |
| ENSMUSG00000023036 | 93707 | Pcdhgc4 | −0.322795189 | 0.001292972 | protocadherin gamma subfamily C, 4 |

TABLE 2-continued

| Ensembl | Entrez | Symbol | log2FoldChange | padj | Name |
|---|---|---|---|---|---|
| ENSMUSG00000024926 | 81601 | Kat5 | −0.323240552 | 0.038996555 | K(lysine) acetyltransferase 5 |
| ENSMUSG00000036306 | 211134 | Lzts1 | −0.32340781 | 0.037667395 | leucine zipper, putative tumor suppressor 1 |
| ENSMUSG00000052369 | 380967 | Tmem106c | −0.32370107 | 0.027987164 | transmembrane protein 106C |
| ENSMUSG00000026749 | 59126 | Nek6 | −0.324091647 | 0.014563503 | NIMA (never in mitosis gene a)-related expressed kinase 6 |
| ENSMUSG00000028656 | 12331 | Cap1 | −0.324351729 | 0.00033091 | CAP, adenylate cyclase-associated protein 1 (yeast) |
| ENSMUSG00000021279 | 217866 | Cdc42bpb | −0.324563435 | 0.021167204 | CDC42 binding protein kinase beta |
| ENSMUSG00000041733 | 52064 | Coq5 | −0.325001444 | 0.047591187 | coenzyme Q5 methyltransferase |
| ENSMUSG00000005338 | 94332 | Cadm3 | −0.326068749 | 0.033508222 | cell adhesion molecule 3 |
| ENSMUSG00000031060 | 236732 | Rbm10 | −0.326186701 | 0.016699692 | RNA binding motif protein 10 |
| ENSMUSG00000052214 | 403187 | Opa3 | −0.326242735 | 0.016842671 | optic atrophy 3 |
| ENSMUSG00000031775 | 67801 | Pllp | −0.326268383 | 0.019655417 | plasma membrane proteolipid |
| ENSMUSG00000048351 | 69893 | Coa7 | −0.326542848 | 0.046351286 | cytochrome c oxidase assembly factor 7 |
| ENSMUSG00000032402 | 17127 | Smad3 | −0.32657309 | 0.004392249 | SMAD family member 3 |
| ENSMUSG00000054199 | 76022 | Gon4l | −0.326594234 | 0.043413713 | gon-4-like (*C.elegans*) |
| ENSMUSG00000022956 | 28080 | Atp5o | −0.326799296 | 0.018759052 | ATP synthase, H+ transporting, mitochondrial F1 complex, O subunit |
| ENSMUSG00000056692 | 224647 | D17Wsu92e | −0.326987786 | 0.001138433 | DNA segment, Chr 17, Wayne State University 92, expressed |
| ENSMUSG00000030806 | 56216 | Stx1b | −0.327037903 | 0.022746493 | syntaxin 1B |
| ENSMUSG00000038296 | 233733 | Galnt18 | −0.327435806 | 0.047334732 | UDP-N-acetyl-alpha-D-galactosamine:polypeptide N-acetylgalactosaminyltransferase 18 |
| ENSMUSG00000038976 | 217124 | Ppp1r9b | −0.327473158 | 0.00215507 | protein phosphatase 1, regulatory subunit 9B |
| ENSMUSG00000003814 | 12317 | Calr | −0.327901039 | 0.003300445 | calreticulin |
| ENSMUSG00000047824 | 68911 | Pygo2 | −0.327967487 | 0.029296777 | pygopus 2 |
| ENSMUSG00000027498 | 67337 | Cstf1 | −0.328157787 | 0.034462369 | cleavage stimulation factor, 3' pre-RNA, subunit 1 |
| ENSMUSG00000021038 | 104799 | Vipas39 | −0.328974454 | 0.007162559 | VPS33B interacting protein, apical-basolateral polarity regulator, spe-39 homolog |
| ENSMUSG00000022856 | 66664 | Tmem41a | −0.329263063 | 0.043659178 | transmembrane protein 41a |
| ENSMUSG00000031144 | 20977 | Syp | −0.330371582 | 0.021017426 | synaptophysin |
| ENSMUSG00000013089 | 104156 | Etv5 | −0.330703307 | 0.026458143 | ets variant 5 |
| ENSMUSG00000031834 | 18709 | Pik3r2 | −0.33076012 | 0.041221106 | phosphatidylinositol 3-kinase, regulatory subunit, polypeptide 2 (p85 beta) |
| ENSMUSG00000025425 | 225742 | St8sia5 | −0.330844284 | 0.011630092 | ST8 alpha-N-acetyl-neuraminide alpha-2,8-sialyltransferase 5 |
| ENSMUSG00000013160 | 11972 | Atp6v0d1 | −0.33092492 | 0.001896146 | ATPase, H+ transporting, lysosomal V0 subunit D1 |
| ENSMUSG00000029121 | 12933 | Crmp1 | −0.331074977 | 0.037133347 | collapsin response mediator protein 1 |
| ENSMUSG00000042616 | 230751 | Oscp1 | −0.331184379 | 0.006391429 | organic solute carrier partner 1 |
| ENSMUSG00000054920 | 71778 | Klhl5 | −0.331697153 | 0.001788941 | kelch-like 5 |
| ENSMUSG00000019494 | 26893 | Cops6 | −0.332395424 | 0.003641705 | COP9 signalosome subunit 6 |
| ENSMUSG00000031821 | 272551 | Gins2 | −0.332812437 | 0.025038712 | GINS complex subunit 2 (Psf2 homolog) |
| ENSMUSG00000027339 | 215653 | Rassf2 | −0.333453648 | 0.001763689 | Ras association (RalGDS/AF-6) domain family member 2 |
| ENSMUSG00000033720 | 94282 | Sfxn5 | −0.333637842 | 0.003180866 | sideroflexin 5 |
| ENSMUSG00000000325 | 80987 | Nckipsd | −0.333644815 | 0.027651551 | NCK interacting protein with SH3 domain |
| ENSMUSG00000037887 | 18218 | Dusp8 | −0.333686234 | 0.002405195 | dual specificity phosphatase 8 |
| ENSMUSG00000004530 | 23790 | Coro1c | −0.333921922 | 0.017200534 | coronin, actin binding protein 1C |
| ENSMUSG00000031161 | 15185 | Hdac6 | −0.334113461 | 0.013059409 | histone deacetylase 6 |
| ENSMUSG00000053931 | 71994 | Cnn3 | −0.334481759 | 0.008913342 | calponin 3, acidic |
| ENSMUSG00000030591 | 57296 | Psmd8 | −0.334502829 | 0.009601656 | proteasome (prosome, macropain) 26S subunit, non-ATPase, 8 |
| ENSMUSG00000060212 | 270109 | Pcnx2 | −0.334526015 | 0.020167127 | pecanex homolog 2 |
| ENSMUSG00000030842 | 66508 | Lamtor1 | −0.33464918 | 0.041942669 | late endosomal/lysosomal adaptor, MAPK and MTOR activator 1 |
| ENSMUSG00000026496 | 11545 | Parp1 | −0.334739023 | 0.004484016 | poly (ADP-ribose) polymerase family, member 1 |
| ENSMUSG00000025375 | 11302 | Aatk | −0.33503892 | 0.009652543 | apoptosis-associated tyrosine kinase |
| ENSMUSG00000029623 | 231887 | Pdap1 | −0.335329256 | 0.018482527 | PDGFA associated protein 1 |
| ENSMUSG00000038740 | 72543 | Mvb12b | −0.335896152 | 0.021334198 | multivesicular body subunit 12B |
| ENSMUSG00000016528 | 17164 | Mapkapk2 | −0.335950693 | 0.042321638 | MAP kinase-activated protein kinase 2 |
| ENSMUSG00000039477 | 231861 | Tnrc18 | −0.336023917 | 0.036437189 | trinucleotide repeat containing 18 |
| ENSMUSG00000020321 | 17449 | Mdh1 | −0.336267324 | 0.001150495 | malate dehydrogenase 1, NAD (soluble) |
| ENSMUSG00000001105 | 55978 | Ift20 | −0.336319182 | 0.005764002 | intraflagellar transport 20 |
| ENSMUSG00000038059 | 106900 | Smim3 | −0.336378757 | 0.041411412 | small integral membrane protein 3 |
| ENSMUSG00000031543 | 11733 | Ank1 | −0.336404253 | 0.048251151 | ankyrin 1, erythroid |
| ENSMUSG00000090071 | 12570 | Cdk5r2 | −0.336534247 | 0.015573718 | cyclin-dependent kinase 5, regulatory subunit 2 (p39) |
| ENSMUSG00000068221 | | | −0.336629374 | 0.011640555 | |
| ENSMUSG00000001802 | 435965 | Lrp3 | −0.337304159 | 0.030269998 | low density lipoprotein receptor-related protein 3 |
| ENSMUSG00000042810 | 77827 | Krba1 | −0.337349554 | 0.043194165 | KRAB-A domain containing 1 |

TABLE 2-continued

| Ensembl | Entrez | Symbol | log2FoldChange | padj | Name |
|---|---|---|---|---|---|
| ENSMUSG00000029861 | 76156 | Fam131b | −0.337798395 | 0.000558417 | family with sequence similarity 131, member B |
| ENSMUSG00000040746 | 70510 | Rnf167 | −0.33780061 | 0.00033091 | ring finger protein 167 |
| ENSMUSG00000026176 | 227292 | Ctdsp1 | −0.338392903 | 0.032607196 | CTD (carboxy-terminal domain, RNA polymerase II, polypeptide A) small phosphatase 1 |
| ENSMUSG00000035885 | 12868 | Cox8a | −0.338951846 | 0.023628099 | cytochrome c oxidase subunit VIIIa |
| ENSMUSG00000021951 | 68043 | Eef1akmt1 | −0.339204302 | 0.010883507 | eukaryotic translation elongation factor 1 alpha lysine methyltransferase 1 |
| ENSMUSG00000000738 | 234847 | Spg7 | −0.339361071 | 0.034290693 | spastic paraplegia 7 homolog (human) |
| ENSMUSG00000033940 | 101314 | Brk1 | −0.339611385 | 0.004494339 | BRICK1, SCAR/WAVE actin-nucleating complex subunit |
| ENSMUSG00000033174 | 23945 | Mgll | −0.339662807 | 0.004619104 | monoglyceride lipase |
| ENSMUSG00000009075 | 192650 | Cabp7 | −0.339781125 | 0.006172045 | calcium binding protein 7 |
| ENSMUSG00000076439 | 17441 | Mog | −0.339990853 | 0.006766543 | myelin oligodendrocyte glycoprotein |
| ENSMUSG00000040385 | 19045 | Ppp1ca | −0.340049091 | 0.002298661 | protein phosphatase 1, catalytic subunit, alpha isoform |
| ENSMUSG00000002496 | 22084 | Tsc2 | −0.340197745 | 0.02082677 | tuberous sclerosis 2 |
| ENSMUSG00000032633 | 216805 | Flcn | −0.340457212 | 0.043194165 | folliculin |
| ENSMUSG00000020823 | 74136 | Sec14l1 | −0.340549677 | 0.000163755 | SEC14-like lipid binding 1 |
| ENSMUSG00000036315 | 66136 | Znrd1 | −0.340572849 | 0.045144585 | zinc ribbon domain containing, 1 |
| ENSMUSG00000023967 | 68565 | Mrps18a | −0.340877981 | 0.028840169 | mitochondrial ribosomal protein S18A |
| ENSMUSG00000027247 | 228359 | Arhgap1 | −0.341938369 | 0.011819155 | Rho GTPase activating protein 1 |
| ENSMUSG00000040363 | 71458 | Bcor | −0.342106268 | 0.008378227 | BCL6 interacting corepressor |
| ENSMUSG00000026790 | 18286 | Odf2 | −0.342603591 | 0.030907801 | outer dense fiber of sperm tails 2 |
| ENSMUSG00000022519 | 106393 | Srl | −0.34270412 | 0.000412819 | sarcalumenin |
| ENSMUSG00000027296 | 228550 | Itpka | −0.342799337 | 0.002922923 | inositol 1,4,5-trisphosphate 3-kinase A |
| ENSMUSG00000018909 | 109689 | Arrb1 | −0.343166401 | 0.001500998 | arrestin, beta 1 |
| ENSMUSG00000029638 | 170772 | Glcci1 | −0.343194444 | 0.003305609 | glucocorticoid induced transcript 1 |
| ENSMUSG00000025580 | 192170 | Eif4a3 | −0.343268463 | 0.006769786 | eukaryotic translation initiation factor 4A3 |
| ENSMUSG00000038302 | 215951 | Lace1 | −0.34338981 | 0.005961326 | lactation elevated 1 |
| ENSMUSG00000035960 | 11792 | Apex1 | −0.343710815 | 0.015761024 | apurinic/apyrimidinic endonuclease 1 |
| ENSMUSG00000039130 | 232679 | Zc3hc1 | −0.34371563 | 0.035495479 | zinc finger, C3HC type 1 |
| ENSMUSG00000062352 | 16413 | Itgb1bp1 | −0.344222281 | 0.001479578 | integrin beta 1 binding protein 1 |
| ENSMUSG00000043670 | 208666 | Diras1 | −0.344424381 | 0.049620653 | DIRAS family, GTP-binding RAS-like 1 |
| ENSMUSG00000042066 | 68857 | Tmcc2 | −0.344503121 | 0.013403755 | transmembrane and coiled-coil domains 2 |
| ENSMUSG00000000959 | 69089 | Oxa1l | −0.344901144 | 0.031029908 | oxidase assembly 1-like |
| ENSMUSG00000039367 | 218811 | Sec24c | −0.345234498 | 0.003544118 | Sec24 related gene family, member C (S. cerevisiae) |
| ENSMUSG00000013846 | 20442 | St3gal1 | −0.345274641 | 0.003544118 | ST3 beta-galactoside alpha-2,3-sialyltransferase 1 |
| ENSMUSG00000027546 | 11981 | Atp9a | −0.345695537 | 0.029477001 | ATPase, class II, type 9A |
| ENSMUSG00000052738 | 56451 | Suclg1 | −0.345797635 | 0.005070228 | succinate-CoA ligase, GDP-forming, alpha subunit |
| ENSMUSG00000032178 | 16201 | Ilf3 | −0.34588327 | 0.01170562 | interleukin enhancer binding factor 3 |
| ENSMUSG00000040620 | 216877 | Dhx33 | −0.345935027 | 0.000171186 | DEAH (Asp-Glu-Ala-His) box polypeptide 33 |
| ENSMUSG00000006289 | 66246 | Osgep | −0.346381816 | 0.01971677 | O-sialoglycoprotein endopeptidase |
| ENSMUSG00000029614 | 19988 | Rpl6 | −0.346457056 | 0.005831225 | ribosomal protein L6 |
| ENSMUSG00000031865 | 13191 | Dctn1 | −0.346528391 | 0.004878006 | dynactin 1 |
| ENSMUSG00000047603 | 56525 | Zfp235 | −0.3468553 | 0.003343172 | zinc finger protein 235 |
| ENSMUSG00000028654 | 16918 | Mycl | −0.346977097 | 0.016221993 | v-myc avian myelocytomatosis viral oncogene lung carcinoma derived |
| ENSMUSG00000070738 | 227333 | Dgkd | −0.347770155 | 0.002071738 | diacylglycerol kinase, delta |
| ENSMUSG00000025374 | 69917 | Nabp2 | −0.34779577 | 0.037368195 | nucleic acid binding protein 2 |
| ENSMUSG00000024163 | 30957 | Mapk8ip3 | −0.347806718 | 0.040407787 | mitogen-activated protein kinase 8 interacting protein 3 |
| ENSMUSG00000001445 | 107732 | Mrpl10 | −0.34790495 | 0.011560182 | mitochondrial ribosomal protein L10 |
| ENSMUSG00000031934 | 55991 | Panx1 | −0.348386304 | 0.021334464 | pannexin 1 |
| ENSMUSG00000044734 | 66222 | Serpinb1a | −0.348630337 | 0.043223052 | serine (or cysteine) peptidase inhibitor, clade B, member 1a |
| ENSMUSG00000029778 | 11517 | Adcyap1r1 | −0.349205917 | 0.002590947 | adenylate cyclase activating polypeptide 1 receptor 1 |
| ENSMUSG00000025743 | 20970 | Sdc3 | −0.349474211 | 0.026364678 | syndecan 3 |
| ENSMUSG00000014748 | 21766 | Tex261 | −0.349881472 | 0.005869273 | testis expressed gene 261 |
| ENSMUSG00000017478 | 76014 | Zc3h18 | −0.349921146 | 0.007541271 | zinc finger CCCH-type containing 18 |
| ENSMUSG00000061650 | 192191 | Med9 | −0.351219464 | 0.006409516 | mediator complex subunit 9 |
| ENSMUSG00000020183 | 70574 | Cpm | −0.351234239 | 0.00204174 | carboxypeptidase M |
| ENSMUSG00000038991 | 105245 | Txndc5 | −0.351352468 | 0.003641705 | thioredoxin domain containing 5 |
| ENSMUSG00000022951 | 54720 | Rcan1 | −0.351591824 | 0.00289335 | regulator of calcineurin 1 |
| ENSMUSG00000037754 | 228852 | Ppp1r16b | −0.351677267 | 1.20E−05 | protein phosphatase 1, regulatory (inhibitor) subunit 16B |
| ENSMUSG00000005882 | 56046 | Uqcc1 | −0.351855132 | 0.003780714 | ubiquinol-cytochrome c reductase complex assembly factor 1 |
| ENSMUSG00000028811 | 107271 | Yars | −0.35200232 | 0.02303347 | tyrosyl-tRNA synthetase |
| ENSMUSG00000031545 | 102247 | Gpat4 | −0.352080176 | 0.03828137 | glycerol-3-phosphate acyltransferase 4 |
| ENSMUSG00000006418 | 81018 | Rnf114 | −0.352120661 | 0.010930348 | ring finger protein 114 |
| ENSMUSG00000027560 | 76829 | Dok5 | −0.352249346 | 0.04182136 | docking protein 5 |

TABLE 2-continued

| Ensembl | Entrez | Symbol | log2FoldChange | padj | Name |
|---|---|---|---|---|---|
| ENSMUSG00000001100 | 67811 | Poldip2 | −0.352497516 | 0.011338004 | polymerase (DNA-directed), delta interacting protein 2 |
| ENSMUSG00000044080 | 20193 | S100a1 | −0.352613728 | 0.01827654 | S100 calcium binding protein A1 |
| ENSMUSG00000018470 | 16499 | Kcnab3 | −0.352974293 | 0.026255197 | potassium voltage-gated channel, shaker-related subfamily, beta member 3 |
| ENSMUSG00000059991 | 53324 | Nptx2 | −0.353268472 | 0.020049146 | neuronal pentraxin 2 |
| ENSMUSG00000003559 | 57344 | As3mt | −0.353300242 | 0.034548655 | arsenic (+3 oxidation state) methyltransferase |
| ENSMUSG00000021385 | 75678 | Ippk | −0.353463921 | 0.00066384 | inositol 1,3,4,5,6-pentakisphosphate 2-kinase |
| ENSMUSG00000070802 | 434128 | Pnmal2 | −0.353602299 | 0.008368703 | PNMA-like 2 |
| ENSMUSG00000053841 | 109658 | Txlna | −0.354190141 | 0.004187848 | taxilin alpha |
| ENSMUSG00000022552 | 106025 | Sharpin | −0.354792213 | 0.022323986 | SHANK-associated RH domain interacting protein |
| ENSMUSG00000032171 | 23988 | Pin1 | −0.355155691 | 0.027272704 | protein (peptidyl-prolyl cis/trans isomerase) NIMA-interacting 1 |
| ENSMUSG00000066306 | 101706 | Numa1 | −0.355385678 | 0.040871044 | nuclear mitotic apparatus protein 1 |
| ENSMUSG00000058239 | 22282 | Usf2 | −0.355426913 | 0.003076373 | upstream transcription factor 2 |
| ENSMUSG00000025209 | 226153 | Peo1 | −0.355434077 | 0.042495965 | progressive external ophthalmoplegia 1 (human) |
| ENSMUSG00000038429 | 22225 | Usp5 | −0.355590846 | 0.023209714 | ubiquitin specific peptidase 5 (isopeptidase T) |
| ENSMUSG00000041645 | 27225 | Ddx24 | −0.355776694 | 0.005812978 | DEAD (Asp-Glu-Ala-Asp) box polypeptide 24 |
| ENSMUSG00000034799 | 382018 | Unc13a | −0.356286903 | 0.002710684 | unc-13 homolog A (C. elegans) |
| ENSMUSG00000018572 | 78246 | Phf23 | −0.356355895 | 0.012278298 | PHD finger protein 23 |
| ENSMUSG00000017299 | 76233 | Dnttip1 | −0.356449355 | 0.048701722 | deoxynucleotidyltransferase, terminal, interacting protein 1 |
| ENSMUSG00000053929 | 54151 | Cyhr1 | −0.356466592 | 0.01403019 | cysteine and histidine rich 1 |
| ENSMUSG00000059355 | 414077 | Wdr83os | −0.356564522 | 0.043223052 | WD repeat domain 83 opposite strand |
| ENSMUSG00000050751 | 209966 | Pgbd5 | −0.356768767 | 0.002227954 | piggyBac transposable element derived 5 |
| ENSMUSG00000037787 | 68020 | Apopt1 | −0.357198885 | 0.01044046 | apoptogenic, mitochondrial 1 |
| ENSMUSG00000032834 | 110816 | Pwp2 | −0.357841774 | 0.016494288 | PWP2 periodic tryptophan protein homolog (yeast) |
| ENSMUSG00000032840 | 76792 | 2410131K14Rik | −0.35785024 | 0.020056896 | RIKEN cDNA 2410131K14 gene |
| ENSMUSG00000004393 | 52513 | Ddx56 | −0.358060723 | 0.023630664 | DEAD (Asp-Glu-Ala-Asp) box polypeptide 56 |
| ENSMUSG00000060012 | 16554 | Kif13b | −0.358332862 | 0.001999733 | kinesin family member 13B |
| ENSMUSG00000069814 | 432582 | Ccdc92b | −0.358485521 | 0.025417454 | coiled-coil domain containing 92B |
| ENSMUSG00000035891 | 223753 | Cerk | −0.359109622 | 0.011702159 | ceramide kinase |
| ENSMUSG00000009863 | 67680 | Sdhb | −0.359462208 | 0.001417258 | succinate dehydrogenase complex, subunit B, iron sulfur (Ip) |
| ENSMUSG00000015714 | 76893 | Cers2 | −0.359629611 | 0.000535573 | ceramide synthase 2 |
| ENSMUSG00000038576 | 96935 | Susd4 | −0.359691559 | 0.00055368 | sushi domain containing 4 |
| ENSMUSG00000059456 | 19229 | Ptk2b | −0.36026566 | 0.003076373 | PTK2 protein tyrosine kinase 2 beta |
| ENSMUSG00000031820 | 68251 | Babam1 | −0.360456411 | 0.006522269 | BRISC and BRCA1 A complex member 1 |
| ENSMUSG00000022477 | 11429 | Aco2 | −0.360929722 | 0.010084472 | aconitase 2, mitochondrial |
| ENSMUSG00000021866 | 11744 | Anxa11 | −0.361037484 | 0.024578427 | annexin A11 |
| ENSMUSG00000036980 | 21343 | Taf6 | −0.361047041 | 0.044316417 | TATA-box binding protein associated factor 6 |
| ENSMUSG00000023988 | 53414 | Bysl | −0.361181447 | 0.01495083 | bystin-like |
| ENSMUSG00000022066 | 100862375 | Gm21685 | −0.361264895 | 0.002743257 | predicted gene, 21685 |
| ENSMUSG00000018659 | 103711 | Pnpo | −0.361284549 | 0.038764319 | pyridoxine 5'-phosphate oxidase |
| ENSMUSG00000028793 | 75234 | Rnf19b | −0.361307283 | 0.000517792 | ring finger protein 19B |
| ENSMUSG00000023952 | 56055 | Gtpbp2 | −0.36147211 | 0.035303081 | GTP binding protein 2 |
| ENSMUSG00000035064 | 13631 | Eef2k | −0.361772503 | 0.00529321 | eukaryotic elongation factor-2 kinase |
| ENSMUSG00000078812 | 276770 | Eif5a | −0.36242618 | 0.013403755 | eukaryotic translation initiation factor 5A |
| ENSMUSG00000000740 | 270106 | Rpl13 | −0.362469654 | 0.003780714 | ribosomal protein L13 |
| ENSMUSG00000062202 | 224671 | Btbd9 | −0.362609625 | 0.001441714 | BTB (POZ) domain containing 9 |
| ENSMUSG00000025153 | 14104 | Fasn | −0.362986389 | 0.042021355 | fatty acid synthase |
| ENSMUSG00000028542 | 14664 | Slc6a9 | −0.363006506 | 0.049081064 | solute carrier family 6 (neurotransmitter transporter, glycine), member 9 |
| ENSMUSG00000030872 | 74105 | Gga2 | −0.363173767 | 0.012650359 | golgi associated, gamma adaptin ear containing, ARF binding protein 2 |
| ENSMUSG00000051786 | 328580 | Tubgcp6 | −0.363249821 | 0.038308662 | tubulin, gamma complex associated protein 6 |
| ENSMUSG00000026811 | 50935 | St6galnac6 | −0.363359232 | 0.02333511 | ST6 (alpha-N-acetyl-neuraminyl-2,3-beta-galactosyl-1,3)-N-acetylgalactosaminide alpha-2,6-sialyltransferase 6 |
| ENSMUSG00000024827 | 104174 | Gldc | −0.363942613 | 0.003655288 | glycine decarboxylase |
| ENSMUSG00000017801 | 21428 | Mlx | −0.363950961 | 0.002238309 | MAX-like protein X |
| ENSMUSG00000001419 | 17261 | Mef2d | −0.364061728 | 0.001141891 | myocyte enhancer factor 2D |
| ENSMUSG00000024212 | 64144 | Mllt1 | −0.364254419 | 0.037368195 | myeloid/lymphoid or mixed-lineage leukemia; translocated to, 1 |
| ENSMUSG00000019505 | 22187 | Ubb | −0.364317227 | 0.029591155 | ubiquitin B |
| ENSMUSG00000035781 | 109284 | R3hdm4 | −0.364614062 | 0.005053643 | R3H domain containing 4 |

TABLE 2-continued

| Ensembl | Entrez | Symbol | log2FoldChange | padj | Name |
|---|---|---|---|---|---|
| ENSMUSG00000030603 | 23996 | Psmc4 | −0.364938392 | 0.002590106 | proteasome (prosome, macropain) 26S subunit, ATPase, 4 |
| ENSMUSG00000049670 | 226123 | Morn4 | −0.365262386 | 0.022734363 | MORN repeat containing 4 |
| ENSMUSG00000047547 | 74325 | Cltb | −0.365411716 | 0.002922923 | clathrin, light polypeptide (Lcb) |
| ENSMUSG00000042532 | 71146 | Golga7b | −0.365529945 | 0.020236323 | golgi autoantigen, golgin subfamily a, 7B |
| ENSMUSG00000029822 | 71720 | Osbpl3 | −0.365561514 | 0.002630166 | oxysterol binding protein-like 3 |
| ENSMUSG00000030084 | 18844 | Plxna1 | −0.36578001 | 0.026540021 | plexin A1 |
| ENSMUSG00000032356 | 19417 | Rasgrf1 | −0.365828466 | 0.000151843 | RAS protein-specific guanine nucleotide-releasing factor 1 |
| ENSMUSG00000009739 | 19009 | Pou6f1 | −0.365843559 | 0.001414046 | POU domain, class 6, transcription factor 1 |
| ENSMUSG00000028688 | 68276 | Toe1 | −0.366072921 | 0.031599635 | target of EGR1, member 1 (nuclear) |
| ENSMUSG00000030168 | 68465 | Adipor2 | −0.366159978 | 0.011125067 | adiponectin receptor 2 |
| ENSMUSG00000030268 | 12035 | Bcat1 | −0.366829107 | 0.004702628 | branched chain aminotransferase 1, cytosolic |
| ENSMUSG00000024012 | 56462 | Mtch1 | −0.36691109 | 0.031060625 | mitochondrial carrier 1 |
| ENSMUSG00000065990 | 66077 | Aurkaip1 | −0.367010829 | 0.040096548 | aurora kinase A interacting protein 1 |
| ENSMUSG00000031078 | 13043 | Cttn | −0.367195997 | 0.00437341 | cortactin |
| ENSMUSG00000018509 | 73139 | Cenpv | −0.367233965 | 0.035995265 | centromere protein V |
| ENSMUSG00000014547 | 268752 | Wdfy2 | −0.367597482 | 0.018472842 | WD repeat and FYVE domain containing 2 |
| ENSMUSG00000001794 | 12336 | Capns1 | −0.367699237 | 0.027795296 | calpain, small subunit 1 |
| ENSMUSG00000021809 | 67725 | Nudt13 | −0.367794651 | 0.036714481 | nudix (nucleoside diphosphate linked moiety X)-type motif 13 |
| ENSMUSG00000062580 | 21854 | Timm17a | −0.367880589 | 0.002238309 | translocase of inner mitochondrial membrane 17a |
| ENSMUSG00000020109 | 56709 | Dnajb12 | −0.368140534 | 0.026823288 | DnaJ heat shock protein family (Hsp40) member B12 |
| ENSMUSG00000002342 | 234371 | Tmem161a | −0.368193191 | 0.034163386 | transmembrane protein 161A |
| ENSMUSG00000030839 | 27414 | Sergef | −0.368258055 | 0.044619432 | secretion regulating guanine nucleotide exchange factor |
| ENSMUSG00000014602 | 16560 | Kif1a | −0.36839249 | 0.021670961 | kinesin family member 1A |
| ENSMUSG00000015776 | 20933 | Med22 | −0.368414812 | 0.033384297 | mediator complex subunit 22 |
| ENSMUSG00000045482 | 100683 | Trrap | −0.368510356 | 0.009161283 | transformation/transcription domain-associated protein |
| ENSMUSG00000024743 | 54525 | Syt7 | −0.368567714 | 0.001187307 | synaptotagmin VII |
| ENSMUSG00000024429 | 14670 | Gnl1 | −0.369295242 | 0.016245091 | guanine nucleotide binding protein-like 1 |
| ENSMUSG00000021743 | 54713 | Fezf2 | −0.369982391 | 0.046806985 | Fez family zinc finger 2 |
| ENSMUSG00000066036 | 69116 | Ubr4 | −0.370144047 | 0.040368494 | ubiquitin protein ligase E3 component n-recognin 4 |
| ENSMUSG00000035824 | 57813 | Tk2 | −0.370186147 | 0.044599594 | thymidine kinase 2, mitochondrial |
| ENSMUSG00000042628 | 217695 | Zfyve1 | −0.370189848 | 0.005673907 | zinc finger, FYVE domain containing 1 |
| ENSMUSG00000068267 | 12616 | Cenpb | −0.370232361 | 0.014394062 | centromere protein B |
| ENSMUSG00000033429 | 73724 | Mcee | −0.370931488 | 0.046359106 | methylmalonyl CoA epimerase |
| ENSMUSG00000005417 | 26936 | Mprip | −0.370989075 | 0.00307985 | myosin phosphatase Rho interacting protein |
| ENSMUSG00000030161 | 57436 | Gabarapl1 | −0.371023156 | 0.00394116 | gamma-aminobutyric acid (GABA) A receptor-associated protein-like 1 |
| ENSMUSG00000031059 | 104130 | Ndufb11 | −0.371028533 | 0.006064415 | NADH dehydrogenase (ubiquinone) 1 beta subcomplex, 11 |
| ENSMUSG00000040010 | 20539 | Slc7a5 | −0.3711742 | 0.046525045 | solute carrier family 7 (cationic amino acid transporter, y+ system), member 5 |
| ENSMUSG00000034353 | 51801 | Ramp1 | −0.371594016 | 0.033140464 | receptor (calcitonin) activity modifying protein 1 |
| ENSMUSG00000056116 | 15039 | H2-T22 | −0.371799229 | 0.038141122 | histocompatibility 2, T region locus 22 |
| ENSMUSG00000022994 | 11512 | Adcy6 | −0.372041638 | 0.047193031 | adenylate cyclase 6 |
| ENSMUSG00000061461 | 66278 | Smim20 | −0.372162793 | 0.017095122 | small integral membrane protein 20 |
| ENSMUSG00000057322 | 67671 | Rpl38 | −0.372218325 | 0.001231811 | ribosomal protein L38 |
| ENSMUSG00000040640 | 238988 | Erc2 | −0.372501306 | 0.026648841 | ELKS/RAB6-interacting/CAST family member 2 |
| ENSMUSG00000044600 | 66818 | Smim7 | −0.372983779 | 0.000228196 | small integral membrane protein 7 |
| ENSMUSG00000027581 | 20262 | Stmn3 | −0.373113998 | 0.01627831 | stathmin-like 3 |
| ENSMUSG00000031948 | 85305 | Kars | −0.373136614 | 0.003780714 | lysyl-tRNA synthetase |
| ENSMUSG00000045039 | 269878 | Megf8 | −0.373270455 | 0.027455238 | multiple EGF-like-domains 8 |
| ENSMUSG00000024853 | 319322 | Sf3b2 | −0.373394174 | 0.003210676 | splicing factor 3b, subunit 2 |
| ENSMUSG00000040945 | 108911 | Rcc2 | −0.373476159 | 0.031472627 | regulator of chromosome condensation 2 |
| ENSMUSG00000078816 | 18752 | Prkcg | −0.373509691 | 0.010320509 | protein kinase C, gamma |
| ENSMUSG00000074129 | 22121 | Rpl13a | −0.373881124 | 0.006059865 | ribosomal protein L13A |
| ENSMUSG00000034274 | 107829 | Thoc5 | −0.373886962 | 0.019110285 | THO complex 5 |
| ENSMUSG00000013593 | 226646 | Ndufs2 | −0.374182226 | 0.000772175 | NADH dehydrogenase (ubiquinone) Fe-S protein 2 |
| ENSMUSG00000001942 | 22619 | Siae | −0.374319328 | 0.031339561 | sialic acid acetylesterase |
| ENSMUSG00000020821 | 16562 | Kif1c | −0.374359918 | 0.000665254 | kinesin family member 1C |
| ENSMUSG00000052296 | 243819 | Ppp6r1 | −0.374551501 | 0.018993844 | protein phosphatase 6, regulatory subunit 1 |
| ENSMUSG00000091475 | 72834 | 2810468N07Rik | −0.375184287 | 0.005302389 | RIKEN cDNA 2810468N07 gene |
| ENSMUSG00000054793 | 260299 | Cadm4 | −0.375253225 | 0.017946736 | cell adhesion molecule 4 |

TABLE 2-continued

| Ensembl | Entrez | Symbol | log2FoldChange | padj | Name |
|---|---|---|---|---|---|
| ENSMUSG00000045598 | 233887 | Zfp553 | −0.375286009 | 0.026966187 | zinc finger protein 553 |
| ENSMUSG00000015149 | 64383 | Sirt2 | −0.375318115 | 0.01523467 | sirtuin 2 |
| ENSMUSG00000040957 | 63955 | Cables1 | −0.375321637 | 0.049126103 | CDK5 and Abl enzyme substrate 1 |
| ENSMUSG00000030036 | 57377 | Mogs | −0.375326101 | 0.033747098 | mannosyl-oligosaccharide glucosidase |
| ENSMUSG00000024130 | 27410 | Abca3 | −0.375418759 | 0.0125064 | ATP-binding cassette, sub-family A (ABC1), member 3 |
| ENSMUSG00000027350 | 12653 | Chgb | −0.375510883 | 0.002046634 | chromogranin B |
| ENSMUSG00000039678 | 70296 | Tbc1d13 | −0.375727269 | 0.012398837 | TBC1 domain family, member 13 |
| ENSMUSG00000024530 | 225655 | Slmo1 | −0.376091812 | 0.003927483 | slowmo homolog 1 (Drosophila) |
| ENSMUSG00000025730 | 224624 | Rab40c | −0.376130279 | 0.038187701 | Rab40C, member RAS oncogene family |
| ENSMUSG00000026207 | 11790 | Speg | −0.37629451 | 0.012548827 | SPEG complex locus |
| ENSMUSG00000028467 | 230101 | Gba2 | −0.376385089 | 0.041942814 | glucosidase beta 2 |
| ENSMUSG00000042429 | 11539 | Adora1 | −0.376538271 | 0.002590947 | adenosine A1 receptor |
| ENSMUSG00000040506 | 228361 | Ambra1 | −0.376564955 | 0.00037302 | autophagy/beclin 1 regulator 1 |
| ENSMUSG00000038055 | 58239 | Dexi | −0.376895013 | 0.006768948 | dexamethasone-induced transcript |
| ENSMUSG00000032127 | 71732 | Vps11 | −0.376903575 | 0.023802758 | VPS11, CORVET/HOPS core subunit |
| ENSMUSG00000000399 | 66108 | Ndufa9 | −0.376913162 | 0.029275142 | NADH dehydrogenase (ubiquinone) 1 alpha subcomplex, 9 |
| ENSMUSG00000024883 | 225870 | Rin1 | −0.377009205 | 0.004088241 | Ras and Rab interactor 1 |
| ENSMUSG00000034135 | 70661 | Sik3 | −0.377112182 | 0.001181038 | SIK family kinase 3 |
| ENSMUSG00000032177 | 18577 | Pde4a | −0.377224885 | 0.027732257 | phosphodiesterase 4A, cAMP specific |
| ENSMUSG00000048385 | 170729 | Scrt1 | −0.377295047 | 0.040749845 | scratch family zinc finger 1 |
| ENSMUSG00000030519 | 11784 | Apba2 | −0.377517837 | 0.015573718 | amyloid beta (A4) precursor protein-binding, family A, member 2 |
| ENSMUSG00000095463 | 67464 | Entpd4 | −0.378223909 | 0.003845974 | ectonucleoside triphosphate diphosphohydrolase 4 |
| ENSMUSG00000025868 | 67044 | Higd2a | −0.378267673 | 0.027873124 | HIG1 domain family, member 2A |
| ENSMUSG00000026959 | 14810 | Grin1 | −0.378280892 | 0.007336304 | glutamate receptor, ionotropic, NMDA1 (zeta 1) |
| ENSMUSG00000079056 | 56461 | Kcnip3 | −0.378441768 | 0.009753505 | Kv channel interacting protein 3, calsenilin |
| ENSMUSG00000021420 | 69955 | Fars2 | −0.378503246 | 0.017528498 | phenylalanine-tRNA synthetase 2 (mitochondrial) |
| ENSMUSG00000063511 | 20637 | Snrnp70 | −0.379568522 | 0.042254694 | small nuclear ribonucleoprotein 70 (U1) |
| ENSMUSG00000021224 | 18222 | Numb | −0.380081266 | 0.001340294 | numb homolog (Drosophila) |
| ENSMUSG00000057531 | 94245 | Dtnbp1 | −0.380081999 | 0.002321386 | dystrobrevin binding protein 1 |
| ENSMUSG00000020396 | 380684 | Nefh | −0.380502376 | 0.000953123 | neurofilament, heavy polypeptide |
| ENSMUSG00000021901 | 104416 | Bap1 | −0.381469536 | 0.01278908 | Brca1 associated protein 1 |
| ENSMUSG00000040048 | 68342 | Ndufb10 | −0.381480167 | 0.016143316 | NADH dehydrogenase (ubiquinone) 1 beta subcomplex, 10 |
| ENSMUSG00000024772 | 13660 | Ehd1 | −0.381495379 | 0.01029641 | EH-domain containing 1 |
| ENSMUSG00000035757 | 223776 | Selo | −0.381636085 | 0.034549421 | selenoprotein O |
| ENSMUSG00000029103 | 16976 | Lrpap1 | −0.38165004 | 0.005516804 | low density lipoprotein receptor-related protein associated protein 1 |
| ENSMUSG00000028099 | 74414 | Polr3c | −0.381664354 | 0.01857334 | polymerase (RNA) III (DNA directed) polypeptide C |
| ENSMUSG00000031065 | 18555 | Cdk16 | −0.381768196 | 0.013808316 | cyclin-dependent kinase 16 |
| ENSMUSG00000032399 | 67891 | Rpl4 | −0.382047016 | 0.001181038 | ribosomal protein L4 |
| ENSMUSG00000071847 | 494504 | Apcdd1 | −0.38233106 | 0.026779212 | adenomatosis polyposis coli down-regulated 1 |
| ENSMUSG00000031487 | 66653 | Brf2 | −0.382332677 | 0.033554414 | BRF2, RNA polymerase III transcription initiation factor 50kDa subunit |
| ENSMUSG00000061787 | 20068 | Rps17 | −0.382462655 | 0.013955084 | ribosomal protein S17 |
| ENSMUSG00000044030 | 272359 | Irf2bp1 | −0.382544558 | 0.038250702 | interferon regulatory factor 2 binding protein 1 |
| ENSMUSG00000032513 | 74498 | Gorasp1 | −0.383091733 | 0.011214407 | golgi reassembly stacking protein 1 |
| ENSMUSG00000035910 | 195208 | Dcdc2a | −0.383335562 | 0.019823985 | doublecortin domain containing 2a |
| ENSMUSG00000003234 | 27406 | Abcf3 | −0.38345514 | 0.003481044 | ATP-binding cassette, sub-family F (GCN20), member 3 |
| ENSMUSG00000007594 | 330790 | Hapln4 | −0.384242144 | 0.037182588 | hyaluronan and proteoglycan link protein 4 |
| ENSMUSG00000053664 | | | −0.384493758 | 0.038688163 | |
| ENSMUSG00000021044 | 72113 | Adck1 | −0.384526674 | 0.004984742 | aarF domain containing kinase 1 |
| ENSMUSG00000028803 | 74552 | Nipal3 | −0.384559706 | 0.003845974 | NIPA-like domain containing 3 |
| ENSMUSG00000017760 | 19025 | Ctsa | −0.384832818 | 0.004154959 | cathepsin A |
| ENSMUSG00000022791 | 51789 | Tnk2 | −0.385061747 | 0.048568047 | tyrosine kinase, non-receptor, 2 |
| ENSMUSG00000024873 | 12794 | Cnih2 | −0.385439566 | 0.003073692 | cornichon family AMPA receptor auxiliary protein 2 |
| ENSMUSG00000024740 | 13194 | Ddb1 | −0.385455605 | 0.002934641 | damage specific DNA binding protein 1 |
| ENSMUSG00000022490 | 58200 | Ppp1r1a | −0.385524345 | 0.006413641 | protein phosphatase 1, regulatory (inhibitor) subunit 1A |
| ENSMUSG00000031672 | 14719 | Got2 | −0.385756251 | 0.0159529 | glutamatic-oxaloacetic transaminase 2, mitochondrial |
| ENSMUSG00000066839 | 26940 | Ecsit | −0.38601203 | 0.040352116 | ECSIT signalling integrator |
| ENSMUSG00000055003 | 211187 | Lrtm2 | −0.386077825 | 0.005386525 | leucine-rich repeats and transmembrane domains 2 |
| ENSMUSG00000060671 | 54667 | Atp8b2 | −0.386403788 | 0.02971216 | ATPase, class I, type 8B, member 2 |

TABLE 2-continued

| Ensembl | Entrez | Symbol | log2FoldChange | padj | Name |
|---|---|---|---|---|---|
| ENSMUSG00000024785 | 59028 | Rcl1 | −0.386522287 | 0.032712905 | RNA terminal phosphate cyclase-like 1 |
| ENSMUSG00000067713 | 19082 | Prkag1 | −0.386789563 | 0.004702628 | protein kinase, AMP-activated, gamma 1 non-catalytic subunit |
| ENSMUSG00000026975 | 67228 | Dph7 | −0.387078067 | 0.01364348 | diphthamine biosynethesis 7 |
| ENSMUSG00000032733 | 235406 | Snx33 | −0.387789436 | 0.030873091 | sorting nexin 33 |
| ENSMUSG00000031375 | 12111 | Bgn | −0.388166704 | 0.041980709 | biglycan |
| ENSMUSG00000020752 | 170472 | Recql5 | −0.388192936 | 0.032266398 | RecQ protein-like 5 |
| ENSMUSG00000028677 | 66743 | Rnf220 | −0.388364195 | 0.027858372 | ring finger protein 220 |
| ENSMUSG00000029535 | 69076 | Triap1 | −0.388565523 | 0.028312782 | TP53 regulated inhibitor of apoptosis 1 |
| ENSMUSG00000026701 | 11758 | Prdx6 | −0.388978406 | 0.017748324 | peroxiredoxin 6 |
| ENSMUSG00000026452 | 20980 | Syt2 | −0.389308318 | 0.030766481 | synaptotagmin II |
| ENSMUSG00000025532 | 12909 | Crcp | −0.389320276 | 0.019973467 | calcitonin gene-related peptide-receptor component protein |
| ENSMUSG00000011114 | 21376 | Tbrg1 | −0.389759105 | 0.002911871 | transforming growth factor beta regulated gene 1 |
| ENSMUSG00000037805 | 19896 | Rpl10a | −0.389793995 | 0.031536917 | ribosomal protein L10A |
| ENSMUSG00000031168 | 13595 | Ebp | −0.389934028 | 0.017334618 | phenylalkylamine Ca2+ antagonist (emopamil) binding protein |
| ENSMUSG00000050854 | 230678 | Tmem125 | −0.389984293 | 0.039087346 | transmembrane protein 125 |
| ENSMUSG00000042992 | 67774 | Borcs5 | −0.389989404 | 0.005750028 | BLOC-1 related complex subunit 5 |
| ENSMUSG00000048232 | 269529 | Fbxo10 | −0.390351043 | 0.001584318 | F-box protein 10 |
| ENSMUSG00000033161 | 11928 | Atp1a1 | −0.390410086 | 0.002356321 | ATPase, Na+/K+ transporting, alpha 1 polypeptide |
| ENSMUSG00000032615 | 103850 | Nt5m | −0.390501646 | 0.02159926 | 5',3'-nucleotidase, mitochondrial |
| ENSMUSG00000021179 | 217827 | Nrde2 | −0.39066288 | 0.01944585 | nrde-2 necessary for RNA interference, domain containing |
| ENSMUSG00000032528 | 22354 | Vipr1 | −0.390747824 | 0.033789662 | vasoactive intestinal peptide receptor 1 |
| ENSMUSG00000042978 | 104175 | Sbk1 | −0.390918977 | 0.010474876 | SH3-binding kinase 1 |
| ENSMUSG00000044709 | 69731 | Gemin7 | −0.39121056 | 0.017297968 | gem (nuclear organelle) associated protein 7 |
| ENSMUSG00000032777 | 233863 | Gtf3c1 | −0.391561691 | 0.015028462 | general transcription factor III C 1 |
| ENSMUSG00000037351 | 226977 | Actr1b | −0.391998155 | 0.003657207 | ARP1 actin-related protein 1B, centractin beta |
| ENSMUSG00000070343 | | | −0.392524798 | 0.008173345 | |
| ENSMUSG00000041697 | 12861 | Cox6a1 | −0.392736366 | 0.013826795 | cytochrome c oxidase subunit VIa polypeptide 1 |
| ENSMUSG00000014873 | 20931 | Surf2 | −0.39340598 | 0.044345359 | surfeit gene 2 |
| ENSMUSG00000066152 | 20530 | Slc31a2 | −0.39343632 | 0.019664441 | solute carrier family 31, member 2 |
| ENSMUSG00000021868 | 105675 | Ppif | −0.393797365 | 0.003364058 | peptidylprolyl isomerase F (cyclophilin F) |
| ENSMUSG00000039725 | 381406 | Trp53rka | −0.394048261 | 0.016546471 | transformation related protein 53 regulating kinase A |
| ENSMUSG00000029625 | 54188 | Cpsf4 | −0.394242397 | 0.049620653 | cleavage and polyadenylation specific factor 4 |
| ENSMUSG00000025793 | 15239 | Hgs | −0.394530735 | 0.003927483 | HGF-regulated tyrosine kinase substrate |
| ENSMUSG00000048142 | 269642 | Nat8l | −0.394541808 | 0.001441714 | N-acetyltransferase 8-like |
| ENSMUSG00000061232 | 14972 | H2-K1 | −0.394690147 | 0.029470151 | histocompatibility 2, K1, K region |
| ENSMUSG00000030298 | 110379 | Sec13 | −0.394837839 | 0.000605244 | SEC13 homolog, nuclear pore and COPII coat complex component |
| ENSMUSG00000034902 | 18717 | Pip5k1c | −0.394877565 | 0.023809696 | phosphatidylinositol-4-phosphate 5-kinase, type 1 gamma |
| ENSMUSG00000036026 | 224807 | Tmem63b | −0.395200749 | 0.01746526 | transmembrane protein 63b |
| ENSMUSG00000029413 | 67111 | Naaa | −0.395233576 | 0.006981623 | N-acylethanolamine acid amidase |
| ENSMUSG00000021978 | 54616 | Extl3 | −0.395268224 | 0.006693208 | exostoses (multiple)-like 3 |
| ENSMUSG00000023806 | 100037282 | Rsph3b | −0.395314174 | 0.021628342 | radial spoke 3B homolog (Chlamydomonas) |
| ENSMUSG00000034757 | 72053 | Tmub2 | −0.395862684 | 0.033143243 | transmembrane and ubiquitin-like domain containing 2 |
| ENSMUSG00000031791 | 74166 | Tmem38a | −0.396125986 | 0.002846283 | transmembrane protein 38A |
| ENSMUSG00000083364 | | | −0.396156823 | 0.03810266 | |
| ENSMUSG00000021266 | 22375 | Wars | −0.396160418 | 0.001763689 | tryptophanyl-tRNA synthetase |
| ENSMUSG00000039474 | 22393 | Wfs1 | −0.396205613 | 0.015455313 | Wolfram syndrome 1 homolog (human) |
| ENSMUSG00000018322 | 67145 | Tomm34 | −0.396268338 | 0.003129849 | translocase of outer mitochondrial membrane 34 |
| ENSMUSG00000025510 | 12476 | Cd151 | −0.39628844 | 0.032348689 | CD151 antigen |
| ENSMUSG00000027951 | 56417 | Adar | −0.396669165 | 0.02432179 | adenosine deaminase, RNA-specific |
| ENSMUSG00000049327 | 67956 | Kmt5a | −0.397074454 | 0.005831225 | lysine methyltransferase 5A |
| ENSMUSG00000043964 | 269999 | Orai3 | −0.397270082 | 0.036013699 | ORAI calcium release-activated calcium modulator 3 |
| ENSMUSG00000028411 | 66408 | Aptx | −0.397397784 | 0.016664474 | aprataxin |
| ENSMUSG00000038555 | 225362 | Reep2 | −0.397521553 | 0.028481058 | receptor accessory protein 2 |
| ENSMUSG00000022982 | 20655 | Sod1 | −0.39805011 | 0.000837803 | superoxide dismutase 1, soluble |
| ENSMUSG00000022678 | 67203 | Nde1 | −0.398052509 | 0.001441714 | nudE neurodevelopment protein 1 |
| ENSMUSG00000031774 | 102122 | Fam192a | −0.398067884 | 0.024053525 | family with sequence similarity 192, member A |
| ENSMUSG00000047013 | 330369 | Fbxo41 | −0.398233372 | 0.003301436 | F-box protein 41 |
| ENSMUSG00000031565 | 14182 | Fgfr1 | −0.398494183 | 0.024688022 | fibroblast growth factor receptor 1 |

TABLE 2-continued

| Ensembl | Entrez | Symbol | log2FoldChange | padj | Name |
|---|---|---|---|---|---|
| ENSMUSG00000007050 | 27756 | Lsm2 | −0.398919066 | 0.039934633 | LSM2 homolog, U6 small nuclear RNA and mRNA degradation associated |
| ENSMUSG00000030854 | 19259 | Ptpn5 | −0.399380033 | 0.024672575 | protein tyrosine phosphatase, non-receptor type 5 |
| ENSMUSG00000037740 | 99045 | Mrps26 | −0.399531679 | 0.009551186 | mitochondrial ribosomal protein S26 |
| ENSMUSG00000044345 | 277010 | Marveld1 | −0.40027337 | 0.026015941 | MARVEL (membrane-associating) domain containing 1 |
| ENSMUSG00000032939 | 71805 | Nup93 | −0.400348195 | 0.038753213 | nucleoporin 93 |
| ENSMUSG00000038665 | 320127 | Dgki | −0.400566519 | 0.002044759 | diacylglycerol kinase, iota |
| ENSMUSG00000036752 | 227613 | Tubb4b | −0.400972572 | 0.009626355 | tubulin, beta 4B class IVB |
| ENSMUSG00000024063 | 77889 | Lbh | −0.401376203 | 0.000315513 | limb-bud and heart |
| ENSMUSG00000035547 | 12337 | Capn5 | −0.401590721 | 0.017054735 | calpain 5 |
| ENSMUSG00000068739 | 20226 | Sars | −0.401641771 | 0.008353927 | seryl-aminoacyl-tRNA synthetase |
| ENSMUSG00000036751 | 110323 | Cox6b1 | −0.401760848 | 0.045128357 | cytochrome c oxidase, subunit VIb polypeptide 1 |
| ENSMUSG00000002064 | 20316 | Sdf2 | −0.401923419 | 0.020167127 | stromal cell derived factor 2 |
| ENSMUSG00000053310 | 64011 | Nrgn | −0.402322473 | 0.002700578 | neurogranin |
| ENSMUSG00000005469 | 18747 | Prkaca | −0.402358873 | 0.023391328 | protein kinase, cAMP dependent, catalytic, alpha |
| ENSMUSG00000044341 | | | −0.40259556 | 0.00254744 | |
| ENSMUSG00000036606 | 140570 | Plxnb2 | −0.40275252 | 0.047308678 | plexin B2 |
| ENSMUSG00000029580 | 11461 | Actb | −0.402875511 | 0.003544118 | actin, beta |
| ENSMUSG00000058756 | 21833 | Thra | −0.402905031 | 0.015764011 | thyroid hormone receptor alpha |
| ENSMUSG00000031753 | 102339 | Cog4 | −0.403127673 | 0.000558417 | component of oligomeric golgi complex 4 |
| ENSMUSG00000095334 | | | −0.403383778 | 0.010947205 | |
| ENSMUSG00000030890 | 16202 | Ilk | −0.403468799 | 0.018927105 | integrin linked kinase |
| ENSMUSG00000015120 | 22196 | Ube2i | −0.403529422 | 0.001036644 | ubiquitin-conjugating enzyme E2I |
| ENSMUSG00000061360 | 68479 | Phf5a | −0.403710225 | 0.032175372 | PHD finger protein 5A |
| ENSMUSG00000002625 | 54194 | Akap8l | −0.403844452 | 0.004702628 | A kinase (PRKA) anchor protein 8-like |
| ENSMUSG00000032959 | 23980 | Pebp1 | −0.404281954 | 0.002781949 | phosphatidylethanolamine binding protein 1 |
| ENSMUSG00000037979 | 215707 | Ccdc92 | −0.40523914 | 0.034956851 | coiled-coil domain containing 92 |
| ENSMUSG00000022503 | 26425 | Nubp1 | −0.405425319 | 0.01458373 | nucleotide binding protein 1 |
| ENSMUSG00000062661 | 14299 | Ncs1 | −0.405492745 | 0.002554176 | neuronal calcium sensor 1 |
| ENSMUSG00000009927 | 75617 | Rps25 | −0.405839282 | 0.045014345 | ribosomal protein S25 |
| ENSMUSG00000048796 | 72023 | Cyb561d1 | −0.406221678 | 0.011404212 | cytochrome b-561 domain containing 1 |
| ENSMUSG00000033068 | 12497 | Entpd6 | −0.406864018 | 0.021334198 | ectonucleoside triphosphate diphosphohydrolase 6 |
| ENSMUSG00000027489 | 56846 | Necab3 | −0.406868659 | 0.02193081 | N-terminal EF-hand calcium binding protein 3 |
| ENSMUSG00000033902 | 26390 | Mapkbp1 | −0.407080207 | 0.016697053 | mitogen-activated protein kinase binding protein 1 |
| ENSMUSG00000042380 | 80284 | Smim12 | −0.40761196 | 0.043156611 | small integral membrane protein 12 |
| ENSMUSG00000029592 | 100756 | Usp30 | −0.407775764 | 0.004049099 | ubiquitin specific peptidase 30 |
| ENSMUSG00000093989 | 52898 | Rnasek | −0.407907628 | 0.007766073 | ribonuclease, RNase K |
| ENSMUSG00000079499 | 76220 | 6530402F18Rik | −0.408145013 | 0.018136418 | RIKEN cDNA 6530402F18 gene |
| ENSMUSG00000026278 | 51800 | Bok | −0.408255254 | 0.005802278 | BCL2-related ovarian killer |
| ENSMUSG00000041115 | 245666 | Iqsec2 | −0.408330801 | 0.005169983 | IQ motif and Sec7 domain 2 |
| ENSMUSG00000028795 | 66264 | Ccdc28b | −0.408514735 | 0.047740412 | coiled coil domain containing 28B |
| ENSMUSG00000020451 | 16886 | Limk2 | −0.408585815 | 0.000659059 | LIM motif-containing protein kinase 2 |
| ENSMUSG00000001783 | 28088 | Rtcb | −0.408749327 | 0.001404895 | RNA 2′,3′-cyclic phosphate and 5′-OH ligase |
| ENSMUSG00000029559 | 72357 | 2210016L21Rik | −0.409056882 | 0.022755217 | RIKEN cDNA 2210016L21 gene |
| ENSMUSG00000015994 | 14272 | Fnta | −0.409061277 | 0.00100225 | farnesyltransferase, CAAX box, alpha |
| ENSMUSG00000062785 | 16504 | Kcnc3 | −0.409260341 | 0.016426155 | potassium voltage gated channel, Shaw-related subfamily, member 3 |
| ENSMUSG00000020935 | 68087 | Dcakd | −0.409276431 | 0.039408609 | dephospho-CoA kinase domain containing |
| ENSMUSG00000026819 | 227731 | Slc25a25 | −0.409503342 | 0.028689222 | solute carrier family 25 (mitochondrial carrier, phosphate carrier), member 25 |
| ENSMUSG00000000326 | 12846 | Comt | −0.409984285 | 0.003102924 | catechol-O-methyltransferase |
| ENSMUSG00000032115 | 12282 | Hyou1 | −0.41004395 | 0.009747667 | hypoxia up-regulated 1 |
| ENSMUSG00000005621 | 233410 | Zfp592 | −0.410152832 | 0.002590947 | zinc finger protein 592 |
| ENSMUSG00000005674 | 641376 | Tomm40l | −0.41073973 | 0.014070185 | translocase of outer mitochondrial membrane 40 homolog-like (yeast) |
| ENSMUSG00000054889 | 109620 | Dsp | −0.410828483 | 0.047069415 | desmoplakin |
| ENSMUSG00000020684 | 276952 | Rasl10b | −0.410895545 | 0.010820876 | RAS-like, family 10, member B |
| ENSMUSG00000022843 | 12724 | Clcn2 | −0.41120088 | 0.041221106 | chloride channel, voltage-sensitive 2 |
| ENSMUSG00000031546 | 109145 | Gins4 | −0.411283822 | 0.007447036 | GINS complex subunit 4 (Sld5 homolog) |
| ENSMUSG00000032741 | 252972 | Tpcn1 | −0.411431535 | 0.017946736 | two pore channel 1 |
| ENSMUSG00000004961 | 53420 | Syt5 | −0.411728202 | 0.012111277 | synaptotagmin V |
| ENSMUSG00000007564 | 51792 | Ppp2r1a | −0.41192792 | 0.002590106 | protein phosphatase 2, regulatory subunit A, alpha |
| ENSMUSG00000067288 | 54127 | Rps28 | −0.411941274 | 0.019047157 | ribosomal protein S28 |
| ENSMUSG00000042078 | 68666 | Svop | −0.412285422 | 0.032965829 | SV2 related protein |
| ENSMUSG00000026816 | 70239 | Gtf3c5 | −0.412479865 | 0.035537227 | general transcription factor IIIC, polypeptide 5 |
| ENSMUSG00000042203 | 381085 | Tbc1d22b | −0.412539292 | 0.006413641 | TBC1 domain family, member 22B |

TABLE 2-continued

| Ensembl | Entrez | Symbol | log2FoldChange | padj | Name |
|---|---|---|---|---|---|
| ENSMUSG00000026603 | 226830 | Smyd2 | −0.412780253 | 0.00893054 | SET and MYND domain containing 2 |
| ENSMUSG00000006390 | 54325 | Elovl1 | −0.413409515 | 0.032175372 | elongation of very long chain fatty acids (FEN1/Elo2, SUR4/Elo3, yeast)-like 1 |
| ENSMUSG00000066900 | 71954 | Suds3 | −0.413484764 | 0.000893237 | suppressor of defective silencing 3 homolog (S. cerevisiae) |
| ENSMUSG00000013997 | 27045 | Nit1 | −0.413504909 | 0.00391181 | nitrilase 1 |
| ENSMUSG00000028700 | 68273 | Pomgnt1 | −0.413557344 | 0.003340584 | protein O-linked mannose beta 1,2-N-acetylglucosaminyltransferase |
| ENSMUSG00000029009 | 17769 | Mthfr | −0.413630276 | 0.01495083 | 5, 10-methylenetetrahydrofolate reductase |
| ENSMUSG00000097915 | 380977 | A330009N23Rik | −0.413947943 | 0.048794894 | RIKEN cDNA A330009N23 gene |
| ENSMUSG00000031824 | 234797 | 6430548M08Rik | −0.414340869 | 0.016770762 | RIKEN cDNA 6430548M08 gene |
| ENSMUSG00000006575 | 51799 | Rundc3a | −0.414401509 | 0.019550142 | RUN domain containing 3A |
| ENSMUSG00000044550 | 594844 | Tceal3 | −0.414435823 | 0.005467068 | transcription elongation factor A (SII)-like 3 |
| ENSMUSG00000031782 | 67914 | Coq9 | −0.414644921 | 0.013036571 | coenzyme Q9 |
| ENSMUSG00000042734 | 69480 | Ttc9 | −0.414909913 | 0.025385578 | tetratricopeptide repeat domain 9 |
| ENSMUSG00000039849 | 228866 | Pcif1 | −0.415083074 | 0.017334618 | PDX1 C-terminal inhibiting factor 1 |
| ENSMUSG00000036098 | 225908 | Myrf | −0.415182303 | 0.026436683 | myelin regulatory factor |
| ENSMUSG00000070394 | 69186 | Tmem256 | −0.415286744 | 0.013616429 | transmembrane protein 256 |
| ENSMUSG00000006728 | 12567 | Cdk4 | −0.415479016 | 0.000228196 | cyclin-dependent kinase 4 |
| ENSMUSG00000016933 | 18803 | Plcg1 | −0.415784453 | 0.009746584 | phospholipase C, gamma 1 |
| ENSMUSG00000020780 | 217337 | Srp68 | −0.415965955 | 0.009351392 | signal recognition particle 68 |
| ENSMUSG00000055745 | 223732 | Ldoc1l | −0.416124926 | 0.01321842 | leucine zipper, down-regulated in cancer 1-like |
| ENSMUSG00000019338 | 78266 | Zfp687 | −0.416130658 | 0.032840549 | zinc finger protein 687 |
| ENSMUSG00000033065 | 18642 | Pfkm | −0.416467027 | 0.005004721 | phosphofructokinase, muscle |
| ENSMUSG00000038271 | 320678 | Iffo1 | −0.416553139 | 0.028792888 | intermediate filament family orphan 1 |
| ENSMUSG00000040463 | 18432 | Mybbp1a | −0.416787453 | 0.016129379 | MYB binding protein (P160) 1a |
| ENSMUSG00000001062 | 72325 | Vps9d1 | −0.416855378 | 0.024820087 | VPS9 domain containing 1 |
| ENSMUSG00000027610 | 14854 | Gss | −0.416875454 | 0.028737384 | glutathione synthetase |
| ENSMUSG00000032875 | 207212 | Arhgef17 | −0.417048199 | 0.010452276 | Rho guanine nucleotide exchange factor (GEF) 17 |
| ENSMUSG00000018648 | 56405 | Dusp14 | −0.417199152 | 0.002485879 | dual specificity phosphatase 14 |
| ENSMUSG00000031385 | 140571 | Plxnb3 | −0.417229252 | 0.012111277 | plexin B3 |
| ENSMUSG00000037428 | 381677 | Vgf | −0.41722998 | 0.016392072 | VGF nerve growth factor inducible |
| ENSMUSG00000022212 | 12891 | Cpne6 | −0.417667094 | 0.018238801 | copine VI |
| ENSMUSG00000017188 | 52469 | Coa3 | −0.418210542 | 0.01748766 | cytochrome C oxidase assembly factor 3 |
| ENSMUSG00000024735 | 28000 | Prpf19 | −0.418316666 | 0.024057421 | pre-mRNA processing factor 19 |
| ENSMUSG00000062867 | 23918 | Impdh2 | −0.418944054 | 0.007421345 | inosine 5′-phosphate dehydrogenase 2 |
| ENSMUSG00000071719 | 620592 | Tmem28 | −0.418960331 | 0.005169983 | transmembrane protein 28 |
| ENSMUSG00000071757 | 387609 | Zhx2 | −0.419929859 | 0.00128312 | zinc fingers and homeoboxes 2 |
| ENSMUSG00000057036 | | | −0.419997601 | 0.035303081 | |
| ENSMUSG00000004207 | 19156 | Psap | −0.420243104 | 0.008008766 | prosaposin |
| ENSMUSG00000050856 | 11958 | Atp5k | −0.420763136 | 0.013155585 | ATP synthase, H+ transporting, mitochondrial F1F0 complex, subunit E |
| ENSMUSG00000022442 | 319953 | Ttll1 | −0.420913883 | 0.022801138 | tubulin tyrosine ligase-like 1 |
| ENSMUSG00000050164 | 207911 | Mchr1 | −0.421206197 | 0.024672575 | melanin-concentrating hormone receptor 1 |
| ENSMUSG00000024208 | 67267 | Uqcc2 | −0.421279314 | 0.015425157 | ubiquinol-cytochrome c reductase complex assembly factor 2 |
| ENSMUSG00000030330 | 28019 | Ing4 | −0.421466339 | 0.004361963 | inhibitor of growth family, member 4 |
| ENSMUSG00000028953 | 27407 | Abcf2 | −0.421480813 | 0.000855162 | ATP-binding cassette, sub-family F (GCN20), member 2 |
| ENSMUSG00000033684 | 104009 | Qsox1 | −0.421703756 | 0.020101173 | quiescin Q6 sulfhydryl oxidase 1 |
| ENSMUSG00000018858 | 68572 | Mrpl58 | −0.42187407 | 0.034979811 | mitochondrial ribosomal protein L58 |
| ENSMUSG00000002550 | 22245 | Uck1 | −0.422085573 | 0.045668966 | uridine-cytidine kinase 1 |
| ENSMUSG00000009681 | 110279 | Bcr | −0.422098833 | 0.001231811 | breakpoint cluster region |
| ENSMUSG00000074736 | 433485 | Syndig1 | −0.422343884 | 0.000222519 | synapse differentiation inducing 1 |
| ENSMUSG00000022841 | 11773 | Ap2m1 | −0.422473628 | 0.011144735 | adaptor-related protein complex 2, mu 1 subunit |
| ENSMUSG00000026411 | 66241 | Tmem9 | −0.4224835 | 0.047465487 | transmembrane protein 9 |
| ENSMUSG00000071654 | 107197 | Uqcc3 | −0.422660405 | 0.037182588 | ubiquinol-cytochrome c reductase complex assembly factor 3 |
| ENSMUSG00000020792 | 53413 | Exoc7 | −0.422729168 | 0.043310304 | exocyst complex component 7 |
| ENSMUSG00000049396 | 276919 | Gemin4 | −0.423059556 | 0.028481058 | gem (nuclear organelle) associated protein 4 |
| ENSMUSG00000040276 | 23969 | Pacsin1 | −0.423298031 | 0.016961463 | protein kinase C and casein kinase substrate in neurons 1 |
| ENSMUSG00000020196 | 104248 | Cabin1 | −0.423332663 | 0.017849495 | calcineurin binding protein 1 |
| ENSMUSG00000054452 | 14797 | Aes | −0.423618058 | 0.015884241 | amino-terminal enhancer of split |
| ENSMUSG00000019210 | 11973 | Atp6v1e1 | −0.423744368 | 0.000594965 | ATPase, H+ transporting, lysosomal V1 subunit E1 |
| ENSMUSG00000003534 | 12305 | Ddr1 | −0.423867501 | 0.024978071 | discoidin domain receptor family, member 1 |

TABLE 2-continued

| Ensembl | Entrez | Symbol | log2FoldChange | padj | Name |
|---|---|---|---|---|---|
| ENSMUSG00000001103 | 18292 | Sebox | −0.424334111 | 0.024829386 | SEBOX homeobox |
| ENSMUSG00000027883 | 76123 | Gpsm2 | −0.424391656 | 0.002213398 | G-protein signalling modulator 2 (AGS3-like, C. elegans) |
| ENSMUSG00000068206 | 18693 | Pick1 | −0.424593487 | 0.01458373 | protein interacting with C kinase 1 |
| ENSMUSG00000020284 | 67884 | 1810043G02Rik | −0.424621884 | 0.00921572 | RIKEN cDNA 1810043G02 gene |
| ENSMUSG00000034254 | 55979 | Agpat1 | −0.42490165 | 0.005081029 | 1-acylglycerol-3-phosphate O-acyltransferase 1 (lysophosphatidic acid acyltransferase, alpha) |
| ENSMUSG00000031157 | 54633 | Pqbp1 | −0.424976257 | 0.002380912 | polyglutamine binding protein 1 |
| ENSMUSG00000036372 | 69038 | Tmem258 | −0.424986258 | 0.030455219 | transmembrane protein 258 |
| ENSMUSG00000025155 | 68730 | Dus1l | −0.425156599 | 0.009046513 | dihydrouridine synthase 1-like (S. cerevisiae) |
| ENSMUSG00000030079 | 56505 | Ruvbl1 | −0.425210142 | 0.004248922 | RuvB-like protein 1 |
| ENSMUSG00000092558 | 56771 | Med20 | −0.425453601 | 0.005587517 | mediator complex subunit 20 |
| ENSMUSG00000031783 | 20021 | Polr2c | −0.425601452 | 0.011630092 | polymerase (RNA) II (DNA directed) polypeptide C |
| ENSMUSG00000024187 | 106581 | Fam234a | −0.425654097 | 0.028659139 | family with sequence similarity 234, member A |
| ENSMUSG00000001741 | 16170 | Il16 | −0.42586669 | 0.016485376 | interleukin 16 |
| ENSMUSG00000053769 | 217779 | Lysmd1 | −0.425910238 | 0.005764002 | LysM, putative peptidoglycan-binding, domain containing 1 |
| ENSMUSG00000038026 | 16524 | Kcnj9 | −0.426293197 | 0.030461682 | potassium inwardly-rectifying channel, subfamily J, member 9 |
| ENSMUSG00000026090 | 72097 | 2010300C02Rik | −0.426511332 | 0.000605244 | RIKEN cDNA 2010300C02 gene |
| ENSMUSG00000045318 | 11553 | Adra2c | −0.426636113 | 0.018816655 | adrenergic receptor, alpha 2c |
| ENSMUSG00000020708 | 19184 | Psmc5 | −0.426810173 | 0.004154959 | protease (prosome, macropain) 26S subunit, ATPase 5 |
| ENSMUSG00000017404 | 19921 | Rpl19 | −0.427422881 | 0.01292974 | ribosomal protein L19 |
| ENSMUSG00000023473 | 107934 | Celsr3 | −0.427689161 | 0.024712971 | cadherin, EGF LAG seven-pass G-type receptor 3 |
| ENSMUSG00000025381 | 56530 | Cnpy2 | −0.427898297 | 0.003900916 | canopy FGF signaling regulator 2 |
| ENSMUSG00000024132 | 13177 | Eci1 | −0.427999691 | 0.012390159 | enoyl-Coenzyme A delta isomerase 1 |
| ENSMUSG00000024620 | 18596 | Pdgfrb | −0.428196212 | 0.014193146 | platelet derived growth factor receptor, beta polypeptide |
| ENSMUSG00000075467 | 52838 | Dnlz | −0.428376249 | 0.045447791 | DNL-type zinc finger |
| ENSMUSG00000017264 | 50912 | Exosc10 | −0.428663107 | 0.012181426 | exosome component 10 |
| ENSMUSG00000056167 | 78893 | Cnot10 | −0.429808702 | 0.008023518 | CCR4-NOT transcription complex, subunit 10 |
| ENSMUSG00000020832 | 57837 | Eral1 | −0.43005253 | 0.0074626 | Era (G-protein)-like 1 (E. coli) |
| ENSMUSG00000037946 | 30938 | Fgd3 | −0.430264235 | 0.028481058 | FYVE, RhoGEF and PH domain containing 3 |
| ENSMUSG00000024844 | 23825 | Banf1 | −0.4303595 | 0.02425828 | barrier to autointegration factor 1 |
| ENSMUSG00000025575 | 76025 | Cant1 | −0.4308807 | 0.00366546 | calcium activated nucleotidase 1 |
| ENSMUSG00000033712 | 219158 | Ccar2 | −0.430886489 | 0.002158721 | cell cycle activator and apoptosis regulator 2 |
| ENSMUSG00000031812 | 67443 | Map1lc3b | −0.431188853 | 0.000332881 | microtubule-associated protein 1 light chain 3 beta |
| ENSMUSG00000006299 | 227290 | Aamp | −0.431284619 | 0.040922829 | angio-associated migratory protein |
| ENSMUSG00000056749 | 18030 | Nfil3 | −0.431413905 | 0.01292974 | nuclear factor, interleukin 3, regulated |
| ENSMUSG00000063856 | 14775 | Gpx1 | −0.431514049 | 0.007068264 | glutathione peroxidase 1 |
| ENSMUSG00000023011 | 72393 | Faim2 | −0.43188823 | 0.022405858 | Fas apoptotic inhibitory molecule 2 |
| ENSMUSG00000005161 | 21672 | Prdx2 | −0.431985993 | 0.003780714 | peroxiredoxin 2 |
| ENSMUSG00000003037 | 17274 | Rab8a | −0.432082844 | 0.00499607 | RAB8A, member RAS oncogene family |
| ENSMUSG00000028729 | 69072 | Ebna1bp2 | −0.432115045 | 0.003122633 | EBNA1 binding protein 2 |
| ENSMUSG00000036002 | 230088 | Fam214b | −0.432353261 | 0.034902014 | family with sequence similarity 214, member B |
| ENSMUSG00000053046 | 75770 | Brsk2 | −0.432705841 | 0.009521511 | BR serine/threonine kinase 2 |
| ENSMUSG00000022947 | 109857 | Cbr3 | −0.432868299 | 0.031240021 | carbonyl reductase 3 |
| ENSMUSG00000025410 | 69654 | Dctn2 | −0.432916036 | 0.008027523 | dynactin 2 |
| ENSMUSG00000038150 | 66612 | Ormdl3 | −0.432958801 | 0.009747667 | ORM1-like 3 (S. cerevisiae) |
| ENSMUSG00000020393 | 84035 | Kremen1 | −0.43299793 | 0.002922923 | kringle containing transmembrane protein 1 |
| ENSMUSG00000006676 | 71472 | Usp19 | −0.433153367 | 0.007421345 | ubiquitin specific peptidase 19 |
| ENSMUSG00000028927 | 18600 | Padi2 | −0.433362519 | 0.005193975 | peptidyl arginine deiminase, type II |
| ENSMUSG00000014601 | 229707 | Strip1 | −0.433373888 | 0.005496172 | striatin interacting protein 1 |
| ENSMUSG00000053297 | 243373 | AI854703 | −0.433452888 | 0.013557723 | expressed sequence AI854703 |
| ENSMUSG00000057841 | 19951 | Rpl32 | −0.433725685 | 0.009784493 | ribosomal protein L32 |
| ENSMUSG00000041958 | 276846 | Pigs | −0.43403495 | 0.016109381 | phosphatidylinositol glycan anchor biosynthesis, class S |
| ENSMUSG00000059278 | 78304 | Naa38 | −0.434205417 | 0.04637251 | N(alpha)-acetyltransferase 38, NatC auxiliary subunit |
| ENSMUSG00000013236 | 19280 | Ptprs | −0.434265845 | 0.039879385 | protein tyrosine phosphatase, receptor type, S |
| ENSMUSG00000028029 | 13722 | Aimp1 | −0.434392872 | 0.002238309 | aminoacyl tRNA synthetase complex-interacting multifunctional protein 1 |

TABLE 2-continued

| Ensembl | Entrez | Symbol | log2FoldChange | padj | Name |
|---|---|---|---|---|---|
| ENSMUSG00000023809 | 20112 | Rps6ka2 | −0.434660381 | 0.002106191 | ribosomal protein S6 kinase, polypeptide 2 |
| ENSMUSG00000025237 | 67287 | Parp6 | −0.43503443 | 0.007929783 | poly (ADP-ribose) polymerase family, member 6 |
| ENSMUSG00000001240 | 54409 | Ramp2 | −0.435035316 | 0.031536917 | receptor (calcitonin) activity modifying protein 2 |
| ENSMUSG00000030986 | 101437 | Dhx32 | −0.435290062 | 0.005922988 | DEAH (Asp-Glu-Ala-His) box polypeptide 32 |
| ENSMUSG00000077450 | 19326 | Rab11b | −0.435393216 | 0.024829386 | RAB11B, member RAS oncogene family |
| ENSMUSG00000046691 | 214987 | Chtf8 | −0.435634668 | 0.009303766 | CTF8, chromosome transmission fidelity factor 8 |
| ENSMUSG00000049303 | 171180 | Syt12 | −0.435697324 | 0.010534996 | synaptotagmin XII |
| ENSMUSG00000032500 | 245038 | Dclk3 | −0.436025169 | 0.004361963 | doublecortin-like kinase 3 |
| ENSMUSG00000026442 | 269116 | Nfasc | −0.436274005 | 0.00396437 | neurofascin |
| ENSMUSG00000040462 | 216440 | Os9 | −0.436485062 | 0.010115734 | amplified in osteosarcoma |
| ENSMUSG00000078684 | | | −0.436524177 | 0.004073422 | |
| ENSMUSG00000022075 | 246710 | Rhobtb2 | −0.436738006 | 0.013826795 | Rho-related BTB domain containing 2 |
| ENSMUSG00000023452 | 320951 | Pisd | −0.436944217 | 0.004971504 | phosphatidylserine decarboxylase |
| ENSMUSG00000003585 | 67815 | Sec14l2 | −0.437016365 | 0.000312629 | SEC14-like lipid binding 2 |
| ENSMUSG00000063882 | 66576 | Uqcrh | −0.437644056 | 0.001786293 | ubiquinol-cytochrome c reductase hinge protein |
| ENSMUSG00000033510 | 170711 | Otud7a | −0.437703925 | 0.005802278 | OTU domain containing 7A |
| ENSMUSG00000036620 | 103534 | Mgat4b | −0.438767934 | 0.004945764 | mannoside acetylglucosaminyltransferase 4, isoenzyme B |
| ENSMUSG00000037049 | 20597 | Smpd1 | −0.43883657 | 0.015735034 | sphingomyelin phosphodiesterase 1, acid lysosomal |
| ENSMUSG00000020918 | 14534 | Kat2a | −0.438899338 | 0.008874366 | K(lysine) acetyltransferase 2A |
| ENSMUSG00000016252 | 67126 | Atp5e | −0.438935842 | 0.014234161 | ATP synthase, H+ transporting, mitochondrial F1 complex, epsilon subunit |
| ENSMUSG00000029056 | 269614 | Pank4 | −0.438995419 | 0.002053194 | pantothenate kinase 4 |
| ENSMUSG00000032936 | 235604 | Camkv | −0.439054128 | 0.045542912 | CaM kinase-like vesicle-associated |
| ENSMUSG00000018865 | 29859 | Sult4a1 | −0.439824532 | 0.00451666 | sulfotransferase family 4A, member 1 |
| ENSMUSG00000019173 | 19345 | Rab5c | −0.439910432 | 0.002168825 | RAB5C, member RAS oncogene family |
| ENSMUSG00000063646 | 76071 | Jakmip1 | −0.440557659 | 0.048406436 | janus kinase and microtubule interacting protein 1 |
| ENSMUSG00000021259 | 13116 | Cyp46a1 | −0.440729845 | 0.024984318 | cytochrome P450, family 46, subfamily a, polypeptide 1 |
| ENSMUSG00000028847 | 27096 | Trappc3 | −0.440740933 | 0.000250755 | trafficking protein particle complex 3 |
| ENSMUSG00000007038 | 18010 | Neu1 | −0.440781545 | 0.01663545 | neuraminidase 1 |
| ENSMUSG00000074886 | 26385 | Grk6 | −0.441513211 | 0.002947909 | G protein-coupled receptor kinase 6 |
| ENSMUSG00000045216 | 50785 | Hs6st1 | −0.441731025 | 0.008949062 | heparan sulfate 6-O-sulfotransferase 1 |
| ENSMUSG00000022658 | 56370 | Tagln3 | −0.442006583 | 0.001768632 | transgelin 3 |
| ENSMUSG00000017670 | 140579 | Elmo2 | −0.442160175 | 1.92E−05 | engulfment and cell motility 2 |
| ENSMUSG00000006301 | 69660 | Tmbim1 | −0.442450938 | 2.32E−05 | transmembrane BAX inhibitor motif containing 1 |
| ENSMUSG00000037523 | 228607 | Mavs | −0.443222268 | 0.045343776 | mitochondrial antiviral signaling protein |
| ENSMUSG00000024381 | 30948 | Bin1 | −0.443259628 | 0.007008349 | bridging integrator 1 |
| ENSMUSG00000033335 | 13430 | Dnm2 | −0.443507008 | 0.002834999 | dynamin 2 |
| ENSMUSG00000029608 | 19894 | Rph3a | −0.443577897 | 0.003032627 | rabphilin 3A |
| ENSMUSG00000029577 | 117146 | Ube3b | −0.443845896 | 0.010869481 | ubiquitin protein ligase E3B |
| ENSMUSG00000015474 | 54397 | Ppt2 | −0.444074009 | 0.034386122 | palmitoyl-protein thioesterase 2 |
| ENSMUSG00000032485 | 235623 | Scap | −0.444120876 | 0.014692027 | SREBF chaperone |
| ENSMUSG00000027255 | 77038 | Arfgap2 | −0.444378166 | 0.016697053 | ADP-ribosylation factor GTPase activating protein 2 |
| ENSMUSG00000038564 | 67661 | Ift172 | −0.44460788 | 0.045505582 | intraflagellar transport 172 |
| ENSMUSG00000046182 | 269994 | Gsg1l | −0.444751468 | 0.00584403 | GSG1-like |
| ENSMUSG00000039194 | 19771 | Rlbp1 | −0.444842823 | 0.000800597 | retinaldehyde binding protein 1 |
| ENSMUSG00000048755 | 223722 | Mcat | −0.444940098 | 0.018597016 | malonyl CoA:ACP acyltransferase (mitochondrial) |
| ENSMUSG00000071655 | 225896 | Ubxn1 | −0.445188802 | 0.021216764 | UBX domain protein 1 |
| ENSMUSG00000025190 | 14718 | Got1 | −0.445300516 | 0.00142299 | glutamic-oxaloacetic transaminase 1, soluble |
| ENSMUSG00000025739 | 64337 | Gng13 | −0.445360899 | 0.017297968 | guanine nucleotide binding protein (G protein), gamma 13 |
| ENSMUSG00000029528 | 19303 | Pxn | −0.44542184 | 0.027554901 | paxillin |
| ENSMUSG00000083282 | 56464 | Ctsf | −0.44549357 | 0.00584403 | cathepsin F |
| ENSMUSG00000025484 | 54399 | Bet1l | −0.445806352 | 0.025550525 | Bet1 golgi vesicular membrane trafficking protein like |
| ENSMUSG00000079197 | 19188 | Psme2 | −0.445931413 | 0.009191831 | proteasome (prosome, macropain) activator subunit 2 (PA28 beta) |
| ENSMUSG00000071645 | 70044 | Tut1 | −0.446046886 | 0.034956851 | terminal uridylyl transferase 1, U6 snRNA-specific |
| ENSMUSG00000029472 | 59008 | Anapc5 | −0.446060513 | 0.000573052 | anaphase-promoting complex subunit 5 |
| ENSMUSG00000006435 | 18011 | Neurl1a | −0.446323224 | 0.007447036 | neuralized E3 ubiquitin protein ligase 1A |

TABLE 2-continued

| Ensembl | Entrez | Symbol | log2FoldChange | padj | Name |
|---|---|---|---|---|---|
| ENSMUSG00000097636 | 381232 | Mirt1 | −0.446501225 | 0.049928 | myocardial infarction associated transcript 1 |
| ENSMUSG00000031029 | 66085 | Eif3f | −0.447036686 | 0.000386363 | eukaryotic translation initiation factor 3, subunit F |
| ENSMUSG00000041740 | 50849 | Rnf10 | −0.447072876 | 0.000317383 | ring finger protein 10 |
| ENSMUSG00000059552 | 22059 | Trp53 | −0.447192511 | 0.044710335 | transformation related protein 53 |
| ENSMUSG00000038489 | 66491 | Polr2l | −0.447527394 | 0.026558756 | polymerase (RNA) II (DNA directed) polypeptide L |
| ENSMUSG00000023018 | 83797 | Smarcd1 | −0.447719756 | 0.005496172 | SWI/SNF related, matrix associated, actin dependent regulator of chromatin, subfamily d, member 1 |
| ENSMUSG00000053898 | 51798 | Ech1 | −0.448033515 | 0.01812301 | enoyl coenzyme A hydratase 1, peroxisomal |
| ENSMUSG00000029627 | 67235 | Zkscan14 | −0.44839787 | 0.015806709 | zinc finger with KRAB and SCAN domains 14 |
| ENSMUSG00000037012 | 15275 | Hk1 | −0.448449502 | 0.007190034 | hexokinase 1 |
| ENSMUSG00000010376 | 18002 | Nedd8 | −0.448467487 | 0.01168441 | neural precursor cell expressed, developmentally down-regulated gene 8 |
| ENSMUSG00000015461 | 12915 | Atf6b | −0.448527509 | 0.005431104 | activating transcription factor 6 beta |
| ENSMUSG00000022391 | 19387 | Rangap1 | −0.448632709 | 0.017531305 | RAN GTPase activating protein 1 |
| ENSMUSG00000024947 | 17283 | Men1 | −0.448771184 | 0.015244082 | multiple endocrine neoplasia 1 |
| ENSMUSG00000008393 | 52502 | Carhsp1 | −0.448791442 | 2.50E−05 | calcium regulated heat stable protein 1 |
| ENSMUSG00000008734 | 64297 | Gprc5b | −0.449101668 | 6.37E−05 | G protein-coupled receptor, family C, group 5, member B |
| ENSMUSG00000035198 | 103733 | Tubg1 | −0.449582432 | 0.036826627 | tubulin, gamma 1 |
| ENSMUSG00000017664 | 228875 | Slc35c2 | −0.449584586 | 0.03852293 | solute carrier family 35, member C2 |
| ENSMUSG00000048758 | 19944 | Rpl29 | −0.449591521 | 0.020921641 | ribosomal protein L29 |
| ENSMUSG00000028470 | 68917 | Hint2 | −0.449715071 | 0.038341633 | histidine triad nucleotide binding protein 2 |
| ENSMUSG00000027270 | 76161 | Lamp5 | −0.449790443 | 0.014257842 | lysosomal-associated membrane protein family, member 5 |
| ENSMUSG00000028785 | 15444 | Hpca | −0.449813738 | 0.00437341 | hippocalcin |
| ENSMUSG00000029387 | 209357 | Gtf2h3 | −0.449848132 | 0.012390159 | general transcription factor IIH, polypeptide 3 |
| ENSMUSG00000023971 | 224823 | Rrp36 | −0.44997584 | 0.032402893 | ribosomal RNA processing 36 homolog (S. cerevisiae) |
| ENSMUSG00000020230 | 15468 | Prmt2 | −0.450951734 | 0.011221844 | protein arginine N-methyltransferase 2 |
| ENSMUSG00000025967 | 55949 | Eef1b2 | −0.450994598 | 0.001833082 | eukaryotic translation elongation factor 1 beta 2 |
| ENSMUSG00000031960 | 234734 | Aars | −0.451165372 | 0.00366546 | alanyl-tRNA synthetase |
| ENSMUSG00000039715 | 71820 | Wdr34 | −0.451270476 | 0.026002247 | WD repeat domain 34 |
| ENSMUSG00000035007 | 217201 | Rundc1 | −0.451276222 | 0.002590106 | RUN domain containing 1 |
| ENSMUSG00000024194 | 67675 | Cuta | −0.451403367 | 0.015531205 | cutA divalent cation tolerance homolog |
| ENSMUSG00000029454 | 17165 | Mapkapk5 | −0.451798023 | 0.000369563 | MAP kinase-activated protein kinase 5 |
| ENSMUSG00000044216 | 16520 | Kcnj4 | −0.451839239 | 0.024057421 | potassium inwardly-rectifying channel, subfamily J, member 4 |
| ENSMUSG00000037989 | 75607 | Wnk2 | −0.452006492 | 0.04654012 | WNK lysine deficient protein kinase 2 |
| ENSMUSG00000036611 | 67484 | Eepd1 | −0.452386261 | 0.000447331 | endonuclease/exonuclease/phosphatase family domain containing 1 |
| ENSMUSG00000078193 | | | −0.452536922 | 0.01278908 | |
| ENSMUSG00000005069 | 19305 | Pex5 | −0.452559188 | 0.001150495 | peroxisomal biogenesis factor 5 |
| ENSMUSG00000037126 | 73728 | Psd | −0.453027105 | 0.011955188 | pleckstrin and Sec7 domain containing |
| ENSMUSG00000028057 | 19769 | Rit1 | −0.453175129 | 0.005053643 | Ras-like without CAAX 1 |
| ENSMUSG00000034781 | 14672 | Gna11 | −0.453898766 | 0.014563503 | guanine nucleotide binding protein, alpha 11 |
| ENSMUSG00000039747 | 269717 | Orai2 | −0.45393103 | 0.000839965 | ORAI calcium release-activated calcium modulator 2 |
| ENSMUSG00000030630 | 14085 | Fah | −0.453936543 | 0.027332246 | fumarylacetoacetate hydrolase |
| ENSMUSG00000045777 | 320802 | Ifitm10 | −0.453946249 | 0.017200534 | interferon induced transmembrane protein 10 |
| ENSMUSG00000031104 | 19337 | Rab33a | −0.454285895 | 0.042094277 | RAB33A, member RAS oncogene family |
| ENSMUSG00000033423 | 140546 | Eri3 | −0.454484339 | 0.003544118 | exoribonuclease 3 |
| ENSMUSG00000038351 | 97761 | Sgsm2 | −0.454624313 | 0.029164509 | small G protein signaling modulator 2 |
| ENSMUSG00000029071 | 13542 | Dvl1 | −0.45470957 | 0.003853041 | dishevelled segment polarity protein 1 |
| ENSMUSG00000018761 | 24070 | Mpdu1 | −0.454802136 | 0.02855274 | mannose-P-dolichol utilization defect 1 |
| ENSMUSG00000044730 | | | −0.454880926 | 0.001900142 | |
| ENSMUSG00000005716 | 19293 | Pvalb | −0.454956582 | 0.00445791 | parvalbumin |
| ENSMUSG00000031400 | 14381 | G6pdx | −0.455534757 | 0.002817651 | glucose-6-phosphate dehydrogenase X-linked |
| ENSMUSG00000035805 | 170790 | Mlc1 | −0.455906445 | 0.001910419 | megalencephalic leukoencephalopathy with subcortical cysts 1 homolog (human) |
| ENSMUSG00000037339 | 74504 | Fam53a | −0.456115627 | 0.01257086 | family with sequence similarity 53, member A |
| ENSMUSG00000034105 | 74347 | Tldc1 | −0.456291972 | 0.011721626 | TBC/LysM associated domain containing 1 |

TABLE 2-continued

| Ensembl | Entrez | Symbol | log2FoldChange | padj | Name |
|---|---|---|---|---|---|
| ENSMUSG00000021285 | 21981 | Ppp1r13b | −0.456326834 | 0.000163755 | protein phosphatase 1, regulatory (inhibitor) subunit 13B |
| ENSMUSG00000000308 | 12716 | Ckmt1 | −0.456794742 | 0.012719029 | creatine kinase, mitochondrial 1, ubiquitous |
| ENSMUSG00000020658 | 668212 | Efr3b | −0.456907856 | 0.035584241 | EFR3 homolog B |
| ENSMUSG00000014426 | 26407 | Map3k4 | −0.456957155 | 0.000315513 | mitogen-activated protein kinase kinase kinase 4 |
| ENSMUSG00000032977 | 108707 | Fam207a | −0.457093101 | 0.039769443 | family with sequence similarity 207, member A |
| ENSMUSG00000045838 | 214239 | A430105119Rik | −0.457292694 | 0.015941294 | RIKEN cDNA A430105119 gene |
| ENSMUSG00000041609 | 75665 | Ccdc64 | −0.457482717 | 0.035578226 | coiled-coil domain containing 64 |
| ENSMUSG00000035390 | 381979 | Brsk1 | −0.457597146 | 0.015400867 | BR serine/threonine kinase 1 |
| ENSMUSG00000073436 | 193838 | Eme2 | −0.4576449 | 0.014193146 | essential meiotic structure-specific endonuclease subunit 2 |
| ENSMUSG00000027327 | 67326 | 1700037H04Rik | −0.457772964 | 0.027811472 | RIKEN cDNA 1700037H04 gene |
| ENSMUSG00000032330 | 12866 | Cox7a2 | −0.457918918 | 0.002700783 | cytochrome c oxidase subunit VIIa 2 |
| ENSMUSG00000029036 | 108888 | Atad3a | −0.458147068 | 0.041077784 | ATPase family, AAA domain containing 3A |
| ENSMUSG00000022516 | 66911 | Nudt16l1 | −0.458237304 | 0.008372348 | nudix (nucleoside diphosphate linked moiety X)-type motif 16-like 1 |
| ENSMUSG00000032735 | 319713 | Ablim3 | −0.458319798 | 0.000839965 | actin binding LIM protein family, member 3 |
| ENSMUSG00000034614 | 216505 | Pik3ip1 | −0.458665562 | 0.001788941 | phosphoinositide-3-kinase interacting protein 1 |
| ENSMUSG00000025402 | 17937 | Nab2 | −0.458816163 | 0.033530806 | Ngfi-A binding protein 2 |
| ENSMUSG00000045174 | 211383 | Amer3 | −0.459103928 | 0.003115724 | APC membrane recruitment 3 |
| ENSMUSG00000026527 | 24012 | Rgs7 | −0.45919365 | 0.000689438 | regulator of G protein signaling 7 |
| ENSMUSG00000056204 | 66522 | Pgpep1 | −0.459477115 | 0.004631864 | pyroglutamyl-peptidase I |
| ENSMUSG00000034145 | 217733 | Tmem63c | −0.459750097 | 0.012390159 | transmembrane protein 63c |
| ENSMUSG00000000902 | 20587 | Smarcb1 | −0.460344092 | 0.009601656 | SWI/SNF related, matrix associated, actin dependent regulator of chromatin, subfamily b, member 1 |
| ENSMUSG00000025499 | 15461 | Hras | −0.460812597 | 0.007038176 | Harvey rat sarcoma virus oncogene |
| ENSMUSG00000024875 | 68090 | Yif1a | −0.461346517 | 0.038187701 | Yip1 interacting factor homolog A (S. cerevisiae) |
| ENSMUSG00000005580 | 11515 | Adcy9 | −0.461662272 | 0.00033091 | adenylate cyclase 9 |
| ENSMUSG00000003235 | 224045 | Eif2b5 | −0.461796863 | 0.010287216 | eukaryotic translation initiation factor 2B, subunit 5 epsilon |
| ENSMUSG00000091515 | | | −0.462664795 | 0.035654262 | |
| ENSMUSG00000002031 | 76568 | Ift46 | −0.463005605 | 0.004198828 | intraflagellar transport 46 |
| ENSMUSG00000034958 | 16467 | Atcay | −0.463301356 | 0.002306956 | ataxia, cerebellar, Cayman type |
| ENSMUSG00000028048 | 14466 | Gba | −0.463445489 | 0.00987106 | glucosidase, beta, acid |
| ENSMUSG00000092607 | 69269 | Scnm1 | −0.46386084 | 0.000677785 | sodium channel modifier 1 |
| ENSMUSG00000024038 | 78330 | Ndufv3 | −0.464208703 | 0.033593366 | NADH dehydrogenase (ubiquinone) flavoprotein 3 |
| ENSMUSG00000026489 | 67426 | Coq8a | −0.464445318 | 0.039087346 | coenzyme Q8A |
| ENSMUSG00000004846 | 26433 | Plod3 | −0.46451114 | 0.047890046 | procollagen-lysine, 2-oxoglutarate 5-dioxygenase 3 |
| ENSMUSG00000031770 | 64209 | Herpud1 | −0.464556751 | 0.003780714 | homocysteine-inducible, endoplasmic reticulum stress-inducible, ubiquitin-like domain member 1 |
| ENSMUSG00000024644 | 66054 | Cndp2 | −0.464644629 | 0.003036844 | CNDP dipeptidase 2 (metallopeptidase M20 family) |
| ENSMUSG00000029406 | 19679 | Pitpnm2 | −0.464741318 | 0.003076373 | phosphatidylinositol transfer protein, membrane-associated 2 |
| ENSMUSG00000022199 | 59049 | Slc22a17 | −0.464742716 | 0.018238801 | solute carrier family 22 (organic cation transporter), member 17 |
| ENSMUSG00000000325 | 11877 | Arvcf | −0.46482706 | 0.048896666 | armadillo repeat gene deleted in velo-cardio-facial syndrome |
| ENSMUSG00000041571 | 20364 | Sepw1 | −0.464865873 | 0.010121634 | selenoprotein W, muscle 1 |
| ENSMUSG00000021143 | 217893 | Pacs2 | −0.464890307 | 0.00029359 | phosphofurin acidic cluster sorting protein 2 |
| ENSMUSG00000031505 | 69225 | Naxd | −0.465232682 | 0.035744797 | NAD(P)HX dehydratase |
| ENSMUSG00000037509 | 226970 | Arhgef4 | −0.465246042 | 0.006708852 | Rho guanine nucleotide exchange factor (GEF) 4 |
| ENSMUSG00000050621 | 100043813 | Rps27rt | −0.46557073 | 0.000455457 | ribosomal protein S27, retrogene |
| ENSMUSG00000050121 | 226115 | Opalin | −0.46581104 | 0.001079007 | oligodendrocytic myelin paranodal and inner loop protein |
| ENSMUSG00000059534 | 66152 | Uqcr10 | −0.466152672 | 0.029477001 | ubiquinol-cytochrome c reductase, complex III subunit X |
| ENSMUSG00000016179 | 215303 | Camk1g | −0.466297067 | 0.003122633 | calcium/calmodulin-dependent protein kinase I gamma |
| ENSMUSG00000023328 | 11423 | Ache | −0.466358105 | 0.025770684 | acetylcholinesterase |
| ENSMUSG00000021720 | 71816 | Rnf180 | −0.466704446 | 0.024307603 | ring finger protein 180 |
| ENSMUSG00000002580 | 103742 | Mien1 | −0.467066747 | 0.001434658 | migration and invasion enhancer 1 |
| ENSMUSG00000008958 | 21427 | Vps72 | −0.467274867 | 0.02071922 | vacuolar protein sorting 72 |
| ENSMUSG00000052949 | 217340 | Rnf157 | −0.467365605 | 0.005796824 | ring finger protein 157 |

TABLE 2-continued

| Ensembl | Entrez | Symbol | log2FoldChange | padj | Name |
|---|---|---|---|---|---|
| ENSMUSG00000034171 | 14073 | Faah | −0.467498863 | 0.004206198 | fatty acid amide hydrolase |
| ENSMUSG00000003934 | 13643 | Efnb3 | −0.467861209 | 0.00289335 | ephrin B3 |
| ENSMUSG00000027603 | 207182 | Ggt7 | −0.467920646 | 0.006708852 | gamma-glutamyltransferase 7 |
| ENSMUSG00000030707 | 12721 | Coro1a | −0.467989273 | 0.002418557 | coronin, actin binding protein 1A |
| ENSMUSG00000021819 | 268721 | Zswim8 | −0.468391558 | 0.027598975 | zinc finger SWIM-type containing 8 |
| ENSMUSG00000020444 | 14923 | Guk1 | −0.468888881 | 0.003102924 | guanylate kinase 1 |
| ENSMUSG00000002763 | 224824 | Pex6 | −0.468964418 | 0.033939371 | peroxisomal biogenesis factor 6 |
| ENSMUSG00000005481 | 68278 | Ddx39 | −0.469248313 | 0.013991274 | DEAD (Asp-Glu-Ala-Asp) box polypeptide 39 |
| ENSMUSG00000008690 | 52683 | Ncaph2 | −0.469435852 | 0.002747619 | non-SMC condensin II complex, subunit H2 |
| ENSMUSG00000040659 | 27984 | Efhd2 | −0.469695569 | 0.004568369 | EF hand domain containing 2 |
| ENSMUSG00000029095 | 231148 | Ablim2 | −0.469869794 | 0.03031987 | actin-binding LIM protein 2 |
| ENSMUSG00000024953 | 54683 | Prdx5 | −0.470294395 | 0.002590106 | peroxiredoxin 5 |
| ENSMUSG00000036398 | 76497 | Ppp1r11 | −0.470537662 | 0.009334101 | protein phosphatase 1, regulatory (inhibitor) subunit 11 |
| ENSMUSG00000071652 | 109077 | Ints5 | −0.471128881 | 0.018953988 | integrator complex subunit 5 |
| ENSMUSG00000061981 | 14252 | Flot2 | −0.471314275 | 0.00548322 | flotillin 2 |
| ENSMUSG00000017344 | 22370 | Vtn | −0.471414155 | 0.004588363 | vitronectin |
| ENSMUSG00000025318 | 57340 | Jph3 | −0.47166891 | 0.002228254 | junctophilin 3 |
| ENSMUSG00000008140 | 69683 | Emc10 | −0.471760657 | 0.016376632 | ER membrane protein complex subunit 10 |
| ENSMUSG00000028373 | 56079 | Astn2 | −0.471806874 | 0.003473018 | astrotactin 2 |
| ENSMUSG00000074247 | 66494 | Dda1 | −0.471935939 | 0.022370858 | DET1 and DDB1 associated 1 |
| ENSMUSG00000017400 | 217154 | Stac2 | −0.472005431 | 0.027987337 | SH3 and cysteine rich domain 2 |
| ENSMUSG00000038244 | 320878 | Mical2 | −0.472050735 | 0.001624593 | microtubule associated monooxygenase, calponin and LIM domain containing 2 |
| ENSMUSG00000030401 | 20167 | Rtn2 | −0.472277583 | 0.007905396 | reticulon 2 (Z-band associated protein) |
| ENSMUSG00000020741 | 74148 | Cluh | −0.472418309 | 0.026983762 | clustered mitochondria (cluA/CLU1) homolog |
| ENSMUSG00000018286 | 19175 | Psmb6 | −0.472463164 | 0.003577611 | proteasome (prosome, macropain) subunit, beta type 6 |
| ENSMUSG00000018830 | 17880 | Myh11 | −0.472733268 | 0.04287943 | myosin, heavy polypeptide 11, smooth muscle |
| ENSMUSG00000081485 | | | −0.472773851 | 0.028554581 | |
| ENSMUSG00000033326 | 230674 | Kdm4a | −0.472986222 | 0.001441714 | lysine (K)-specific demethylase 4A |
| ENSMUSG00000008318 | 320100 | Relt | −0.47305838 | 0.04491813 | RELT tumor necrosis factor receptor |
| ENSMUSG00000028741 | 69902 | Mrto4 | −0.473090367 | 0.001276768 | mRNA turnover 4, ribosome maturation factor |
| ENSMUSG00000020455 | 94091 | Trim11 | −0.473418873 | 0.020101173 | tripartite motif-containing 11 |
| ENSMUSG00000060036 | 27367 | Rpl3 | −0.473990549 | 0.000368076 | ribosomal protein L3 |
| ENSMUSG00000030376 | 110891 | Slc8a2 | −0.474330952 | 0.002549057 | solute carrier family 8 (sodium/calcium exchanger), member 2 |
| ENSMUSG00000022415 | 20972 | Syngr1 | −0.4743447 | 0.011109797 | synaptogyrin 1 |
| ENSMUSG00000038252 | 68298 | Ncapd2 | −0.474406672 | 0.031409398 | non-SMC condensin I complex, subunit D2 |
| ENSMUSG00000003527 | 27886 | Dgcr14 | −0.474431971 | 0.023018223 | DiGeorge syndrome critical region gene 14 |
| ENSMUSG00000024660 | 16319 | Incenp | −0.474648437 | 0.028232579 | inner centromere protein |
| ENSMUSG00000029674 | 16885 | Limk1 | −0.474747717 | 0.034549618 | LIM-domain containing, protein kinase |
| ENSMUSG00000001415 | 229512 | Smg5 | −0.47476601 | 0.018472842 | Smg-5 homolog, nonsense mediated mRNA decay factor (C. elegans) |
| ENSMUSG00000061718 | 19049 | Ppp1r1b | −0.474875621 | 0.041477233 | protein phosphatase 1, regulatory (inhibitor) subunit 1B |
| ENSMUSG00000020198 | 11776 | Ap3d1 | −0.474895844 | 0.005856448 | adaptor-related protein complex 3, delta 1 subunit |
| ENSMUSG00000032182 | 74766 | Yipf2 | −0.474911616 | 0.020108743 | Yip1 domain family, member 2 |
| ENSMUSG00000042502 | 70233 | Cd2bp2 | −0.475038397 | 6.36E−06 | CD2 antigen (cytoplasmic tail) binding protein 2 |
| ENSMUSG00000021222 | 73828 | Dcaf4 | −0.475040136 | 0.023930739 | DDB1 and CUL4 associated factor 4 |
| ENSMUSG00000018334 | 16706 | Ksr1 | −0.475255843 | 0.000418558 | kinase suppressor of ras 1 |
| ENSMUSG00000011306 | 70616 | Sugp1 | −0.475516217 | 0.026713815 | SURP and G patch domain containing 1 |
| ENSMUSG00000057897 | 12323 | Camk2b | −0.475550606 | 0.000845793 | calcium/calmodulin-dependent protein kinase II, beta |
| ENSMUSG00000029436 | 23948 | Mmp17 | −0.475680165 | 0.00889147 | matrix metallopeptidase 17 |
| ENSMUSG00000029610 | 231872 | Aimp2 | −0.475723628 | 0.02357533 | aminoacyl tRNA synthetase complex-interacting multifunctional protein 2 |
| ENSMUSG00000027076 | 30059 | Timm10 | −0.47608563 | 0.011001423 | translocase of inner mitochondrial membrane 10 |
| ENSMUSG00000017314 | 50997 | Mpp2 | −0.476185941 | 0.010364417 | membrane protein, palmitoylated 2 (MAGUK p55 subfamily member 2) |
| ENSMUSG00000022517 | 17237 | Mgrn1 | −0.476499826 | 0.003098105 | mahogunin, ring finger 1 |
| ENSMUSG00000052934 | 76454 | Fbxo31 | −0.476770085 | 0.025178945 | F-box protein 31 |
| ENSMUSG00000018293 | 18643 | Pfn1 | −0.477010554 | 0.006198195 | profilin 1 |
| ENSMUSG00000020889 | 217166 | Nr1d1 | −0.477047641 | 0.022245909 | nuclear receptor subfamily 1, group D, member 1 |

TABLE 2-continued

| Ensembl | Entrez | Symbol | log2FoldChange | padj | Name |
|---|---|---|---|---|---|
| ENSMUSG00000059409 | 21770 | Ppp2r5d | −0.477099122 | 0.001670236 | protein phosphatase 2, regulatory subunit B', delta |
| ENSMUSG00000029447 | | | −0.477661377 | 0.000605244 | |
| ENSMUSG00000004187 | 16581 | Kifc2 | −0.477924097 | 0.004389278 | kinesin family member C2 |
| ENSMUSG00000024826 | 19708 | Dpf2 | −0.478294111 | 0.005587517 | D4, zinc and double PHD fingers family 2 |
| ENSMUSG00000045374 | 192652 | Wdr81 | −0.478302914 | 0.042540153 | WD repeat domain 81 |
| ENSMUSG00000000149 | 14673 | Gna12 | −0.478563507 | 0.002227954 | guanine nucleotide binding protein, alpha 12 |
| ENSMUSG00000030881 | 76932 | Arfip2 | −0.478575287 | 0.006472733 | ADP-ribosylation factor interacting protein 2 |
| ENSMUSG00000062075 | 16907 | Lmnb2 | −0.478645445 | 0.039525489 | lamin B2 |
| ENSMUSG00000024219 | 224650 | Anks1 | −0.478715829 | 0.032315156 | ankyrin repeat and SAM domain containing 1 |
| ENSMUSG00000037060 | 109042 | Prkcdbp | −0.478824413 | 0.009551105 | protein kinase C, delta binding protein |
| ENSMUSG00000047415 | 238377 | Gpr68 | −0.480136624 | 0.00437341 | G protein-coupled receptor 68 |
| ENSMUSG00000027566 | 26444 | Psma7 | −0.480209886 | 0.000689438 | proteasome (prosome, macropain) subunit, alpha type 7 |
| ENSMUSG00000042389 | 381802 | Tsen2 | −0.48053746 | 0.002391979 | tRNA splicing endonuclease subunit 2 |
| ENSMUSG00000034949 | 103406 | Zfr2 | −0.480559156 | 0.024027306 | zinc finger RNA binding protein 2 |
| ENSMUSG00000093954 | | | −0.48077011 | 0.026006131 | |
| ENSMUSG00000015013 | 59005 | Trappc2l | −0.480891592 | 0.007699151 | trafficking protein particle complex 2-like |
| ENSMUSG00000012114 | 94112 | Med15 | −0.481085309 | 0.001744984 | mediator complex subunit 15 |
| ENSMUSG00000040997 | 105501 | Abhd4 | −0.481098391 | 0.007699151 | abhydrolase domain containing 4 |
| ENSMUSG00000049960 | 66242 | Mrps16 | −0.481163062 | 0.009188631 | mitochondrial ribosomal protein S16 |
| ENSMUSG00000057177 | 606496 | Gsk3a | −0.482069808 | 0.000574921 | glycogen synthase kinase 3 alpha |
| ENSMUSG00000022756 | 224022 | Slc7a4 | −0.482091136 | 0.047206329 | solute carrier family 7 (cationic amino acid transporter, y+ system), member 4 |
| ENSMUSG00000035047 | 215194 | Kri1 | −0.48211844 | 0.017297968 | KRI1 homolog |
| ENSMUSG00000025132 | 192662 | Arhgdia | −0.482313828 | 0.003180866 | Rho GDP dissociation inhibitor (GDI) alpha |
| ENSMUSG00000043079 | 104027 | Synpo | −0.482380377 | 0.002836558 | synaptopodin |
| ENSMUSG00000034463 | 219151 | Scara3 | −0.48243992 | 0.000122145 | scavenger receptor class A, member 3 |
| ENSMUSG00000025931 | 74229 | Paqr8 | −0.48310298 | 0.009477937 | progestin and adipoQ receptor family member VIII |
| ENSMUSG00000020486 | 18952 | 4-Sep | −0.483118579 | 0.002496844 | septin 4 |
| ENSMUSG00000026849 | 30931 | Tor1a | −0.483257496 | 0.002310026 | torsin family 1, member A (torsin A) |
| ENSMUSG00000028458 | 21754 | Tesk1 | −0.483258472 | 0.025770684 | testis specific protein kinase 1 |
| ENSMUSG00000021606 | 407785 | Ndufs6 | −0.483722311 | 0.014253904 | NADH dehydrogenase (ubiquinone) Fe-S protein 6 |
| ENSMUSG00000024181 | 68611 | Mrpl28 | −0.483786803 | 0.022405858 | mitochondrial ribosomal protein L28 |
| ENSMUSG00000032554 | 22041 | Trf | −0.484105254 | 0.000254355 | transferrin |
| ENSMUSG00000055401 | 50762 | Fbxo6 | −0.484545776 | 0.049663261 | F-box protein 6 |
| ENSMUSG00000036678 | 223921 | Aaas | −0.4845888 | 0.018472842 | achalasia, adrenocortical insufficiency, alacrimia |
| ENSMUSG00000039686 | 227693 | Zer1 | −0.485376118 | 0.022343397 | zyg-11 related, cell cycle regulator |
| ENSMUSG00000033316 | 231605 | Galnt9 | −0.485450781 | 0.022135171 | UDP-N-acetyl-alpha-D-galactosamine:polypeptide N-acetylgalactosaminyltransferase 9 |
| ENSMUSG00000026309 | 67444 | Ilkap | −0.485515147 | 0.011833224 | integrin-linked kinase-associated serine/threonine phosphatase 2C |
| ENSMUSG00000024665 | 56473 | Fads2 | −0.4855765 | 0.017200534 | fatty acid desaturase 2 |
| ENSMUSG00000060152 | 117109 | Pop5 | −0.485682963 | 0.022614745 | processing of precursor 5, ribonuclease P/MRP family (S. cerevisiae) |
| ENSMUSG00000040447 | 216892 | Spns2 | −0.486836006 | 0.005047972 | spinster homolog 2 |
| ENSMUSG00000031388 | 56292 | Naa10 | −0.486963884 | 0.003956691 | N(alpha)-acetyltransferase 10, NatA catalytic subunit |
| ENSMUSG00000039844 | 107746 | Rapgef1 | −0.487151687 | 0.005007905 | Rap guanine nucleotide exchange factor (GEF) 1 |
| ENSMUSG00000021486 | 66494 | Prelid1 | −0.487165872 | 0.012633169 | PRELI domain containing 1 |
| ENSMUSG00000027575 | 228998 | Arfgap 1 | −0.487430131 | 0.016118522 | ADP-ribosylation factor GTPase activating protein 1 |
| ENSMUSG00000059714 | 14251 | Flot1 | −0.48748728 | 0.015854098 | flotillin 1 |
| ENSMUSG00000050248 | 68525 | Evc2 | −0.487611029 | 0.013696197 | Ellis van Creveld syndrome 2 |
| ENSMUSG00000026810 | 13481 | Dpm2 | −0.487763663 | 0.029846252 | dolichol-phosphate (beta-D) mannosyltransferase 2 |
| ENSMUSG00000009293 | 22213 | Ube2g2 | −0.487944836 | 0.001716117 | ubiquitin-conjugating enzyme E2G 2 |
| ENSMUSG00000025020 | 20562 | Slit1 | −0.488487047 | 0.016873714 | slit homolog 1 (Drosophila) |
| ENSMUSG00000047797 | 14618 | Gjb1 | −0.488676424 | 0.022149064 | gap junction protein, beta 1 |
| ENSMUSG00000026853 | 12908 | Crat | −0.488784594 | 0.002701235 | carnitine acetyltransferase |
| ENSMUSG00000020709 | 216991 | Adap2 | −0.488820709 | 0.03085575 | ArfGAP with dual PH domains 2 |
| ENSMUSG00000026965 | 99152 | Anapc2 | −0.489114821 | 0.016772605 | anaphase promoting complex subunit 2 |
| ENSMUSG00000019179 | 17448 | Mdh2 | −0.489489195 | 0.001401869 | malate dehydrogenase 2, NAD (mitochondrial) |

TABLE 2-continued

| Ensembl | Entrez | Symbol | log2FoldChange | padj | Name |
|---|---|---|---|---|---|
| ENSMUSG00000038861 | 107650 | Pi4kb | −0.489491053 | 0.000120062 | phosphatidylinositol 4-kinase, catalytic, beta polypeptide |
| ENSMUSG00000039148 | 20227 | Sart1 | −0.489730296 | 0.008002963 | squamous cell carcinoma antigen recognized by T cells 1 |
| ENSMUSG00000003444 | 67224 | Med29 | −0.489965167 | 0.047890046 | mediator complex subunit 29 |
| ENSMUSG00000092329 | 108148 | Galnt2 | −0.49000466 | 0.004322265 | UDP-N-acetyl-alpha-D-galactosamine:polypeptide N-acetylgalactosaminyltransferase 2 |
| ENSMUSG00000059316 | 26569 | Slc27a4 | −0.491229383 | 0.029361926 | solute carrier family 27 (fatty acid transporter), member 4 |
| ENSMUSG00000060803 | 14870 | Gstp1 | −0.491264831 | 0.006720299 | glutathione S-transferase, pi 1 |
| ENSMUSG00000027316 | 14588 | Gfra4 | −0.49140322 | 0.003378931 | glial cell line derived neurotrophic factor family receptor alpha 4 |
| ENSMUSG00000001909 | 212528 | Trmt1 | −0.491417241 | 0.004770599 | tRNA methyltransferase 1 |
| ENSMUSG00000003429 | 27207 | Rps11 | −0.491537873 | 0.001244476 | ribosomal protein S11 |
| ENSMUSG00000030102 | 16438 | Itpr1 | −0.491603595 | 0.013871936 | inositol 1,4,5-trisphosphate receptor 1 |
| ENSMUSG00000025503 | 21351 | 1 | −0.491660142 | 0.004398936 | transaldolase 1 |
| ENSMUSG00000057666 | 14433 | Gapdh | −0.492046079 | 0.020319335 | glyceraldehyde-3-phosphate dehydrogenase |
| ENSMUSG00000035226 | 241770 | Rims4 | −0.492046243 | 0.019386777 | regulating synaptic membrane exocytosis 4 |
| ENSMUSG00000083380 | | | −0.492147088 | 0.00255369 | |
| ENSMUSG00000040532 | 68758 | Abhd11 | −0.492189147 | 0.033939371 | abhydrolase domain containing 11 |
| ENSMUSG00000051557 | 433813 | Pusl1 | −0.492595947 | 0.020056896 | pseudouridylate synthase-like 1 |
| ENSMUSG00000032040 | 69305 | Dcps | −0.493100147 | 0.00200527 | decapping enzyme, scavenger |
| ENSMUSG00000027188 | 210622 | Pamr1 | −0.493100944 | 0.001755721 | peptidase domain containing associated with muscle regeneration 1 |
| ENSMUSG00000051390 | 81630 | Zbtb22 | −0.493115794 | 0.031060625 | zinc finger and BTB domain containing 22 |
| ENSMUSG00000040907 | 232975 | Atp1a3 | −0.493202142 | 0.017152334 | ATPase, Na+/K+ transporting, alpha 3 polypeptide |
| ENSMUSG00000029500 | 72542 | Pgam5 | −0.493371617 | 0.011559924 | phosphoglycerate mutase family member 5 |
| ENSMUSG00000063445 | 67824 | Nmral1 | −0.493477188 | 0.015573718 | NmrA-like family domain containing 1 |
| ENSMUSG00000059824 | 13170 | Dbp | −0.493971142 | 0.049891677 | D site albumin promoter binding protein |
| ENSMUSG00000030103 | 20893 | Bhlhe40 | −0.494033101 | 5.70E−05 | basic helix-loop-helix family, member e40 |
| ENSMUSG00000032855 | 18763 | Pkd1 | −0.494128697 | 0.011256294 | polycystic kidney disease 1 homolog |
| ENSMUSG00000025854 | 80752 | Fam20c | −0.494390396 | 0.024463739 | family with sequence similarity 20, member C |
| ENSMUSG00000002233 | 11853 | Rhoc | −0.495158368 | 0.037182588 | ras homolog family member C |
| ENSMUSG00000036270 | 234699 | Edc4 | −0.495419925 | 0.005642365 | enhancer of mRNA decapping 4 |
| ENSMUSG00000028069 | 66614 | Gpatch4 | −0.495979844 | 0.031599635 | G patch domain containing 4 |
| ENSMUSG00000003360 | 74351 | Ddx23 | −0.496428319 | 0.009521511 | DEAD (Asp-Glu-Ala-Asp) box polypeptide 23 |
| ENSMUSG00000087679 | | | −0.496757422 | 0.003338321 | |
| ENSMUSG00000002948 | 26400 | Map2k7 | −0.497122976 | 0.003655288 | mitogen-activated protein kinase kinase 7 |
| ENSMUSG00000044005 | 216456 | Gls2 | −0.49713867 | 0.008949062 | glutaminase 2 (liver, mitochondrial) |
| ENSMUSG00000039661 | 66959 | Dusp26 | −0.497532005 | 0.045700724 | dual specificity phosphatase 26 (putative) |
| ENSMUSG00000028893 | 230784 | Sesn2 | −0.497559765 | 0.027461267 | sestrin 2 |
| ENSMUSG00000006095 | 66411 | Tbcb | −0.497931271 | 0.034364454 | tubulin folding cofactor B |
| ENSMUSG00000095567 | 57741 | Noc2l | −0.497954869 | 0.009188631 | NOC2 like nucleolar associated transcriptional repressor |
| ENSMUSG00000025512 | 68038 | Chid1 | −0.498281977 | 0.00155821 | chitinase domain containing 1 |
| ENSMUSG00000021990 | 219140 | Spata13 | −0.498486334 | 0.003108046 | spermatogenesis associated 13 |
| ENSMUSG00000022438 | 170736 | Parvb | −0.498610822 | 0.028264626 | parvin, beta |
| ENSMUSG00000028779 | 67898 | Pef1 | −0.499090931 | 0.006446155 | penta-EF hand domain containing 1 |
| ENSMUSG00000018677 | 68066 | Slc25a39 | −0.499241033 | 0.020283803 | solute carrier family 25, member 39 |
| ENSMUSG00000040415 | 80904 | Dtx3 | −0.499305441 | 0.002590106 | deltex 3, E3 ubiquitin ligase |
| ENSMUSG00000025377 | 78777 | Tepsin | −0.499307115 | 0.04437153 | TEPSIN, adaptor related protein complex 4 accessory protein |
| ENSMUSG00000028838 | 56219 | Extl1 | −0.499715994 | 0.016005104 | exostoses (multiple)-like 1 |
| ENSMUSG00000045665 | 106073 | Mfsd5 | −0.499777514 | 0.022891291 | major facilitator superfamily domain containing 5 |
| ENSMUSG00000061589 | 208266 | Dot1l | −0.499786441 | 0.017044825 | DOT1-like, histone H3 methyltransferase (S. cerevisiae) |
| ENSMUSG00000087881 | | | −0.499840726 | 0.045505582 | |
| ENSMUSG00000068264 | 69596 | Ap5s1 | −0.499908121 | 0.044386421 | adaptor-related protein 5 complex, sigma 1 subunit |
| ENSMUSG00000020496 | 108660 | Rnf187 | −0.499957146 | 0.001404895 | ring finger protein 187 |
| ENSMUSG00000021288 | 16593 | Klc1 | −0.500115641 | 0.003338321 | kinesin light chain 1 |
| ENSMUSG00000039427 | 208211 | Alg1 | −0.500334557 | 0.028072393 | asparagine-linked glycosylation 1 (beta-1,4-mannosyltransferase) |
| ENSMUSG00000041598 | 56699 | Cdc42ep4 | −0.500630647 | 0.004198828 | CDC42 effector protein (Rho GTPase binding) 4 |
| ENSMUSG00000041351 | 110351 | Rap1gap | −0.500667389 | 0.003471742 | Rap1 GTPase-activating protein |
| ENSMUSG00000024851 | 18739 | Pitpnm1 | −0.500997741 | 0.016059298 | phosphatidylinositol transfer protein, membrane-associated 1 |
| ENSMUSG00000015599 | 106763 | Ttbk1 | −0.501203577 | 0.01495083 | tau tubulin kinase 1 |

TABLE 2-continued

| Ensembl | Entrez | Symbol | log2FoldChange | padj | Name |
|---|---|---|---|---|---|
| ENSMUSG00000028964 | 57320 | Park7 | −0.501421564 | 0.009277221 | Parkinson disease (autosomal recessive, early onset) 7 |
| ENSMUSG00000041801 | 27280 | Phlda3 | −0.501487264 | 0.027154117 | pleckstrin homology like domain, family A, member 3 |
| ENSMUSG00000068290 | 77006 | Ddrgk1 | −0.501570086 | 0.008078592 | DDRGK domain containing 1 |
| ENSMUSG00000026202 | 22145 | Tuba4a | −0.501686396 | 0.002422149 | tubulin, alpha 4A |
| ENSMUSG00000058135 | 14862 | Gstm1 | −0.501816988 | 0.011810283 | glutathione S-transferase, mu 1 |
| ENSMUSG00000054708 | 70615 | Ankrd24 | −0.50198397 | 0.025811986 | ankyrin repeat domain 24 |
| ENSMUSG00000027411 | 80743 | Vps16 | −0.502173376 | 0.001070978 | VSP16 CORVET/HOPS core subunit |
| ENSMUSG00000042216 | 52850 | Sgsm1 | −0.502644167 | 0.01203162 | small G protein signaling modulator 1 |
| ENSMUSG00000031485 | 114863 | Prosc | −0.502902499 | 0.016349652 | proline synthetase co-transcribed |
| ENSMUSG00000018042 | 109754 | Cyb5r3 | −0.502968499 | 0.01523467 | cytochrome b5 reductase 3 |
| ENSMUSG00000032281 | 94180 | Acsbg1 | −0.503228779 | 0.001370223 | acyl-CoA synthetase bubblegum family member 1 |
| ENSMUSG00000001995 | 244668 | Sipa1l2 | −0.503228801 | 0.000665254 | signal-induced proliferation-associated 1 like 2 |
| ENSMUSG00000024392 | 224727 | Bag6 | −0.503379101 | 0.00376467 | BCL2-associated athanogene 6 |
| ENSMUSG00000001962 | 108160 | Fam50a | −0.504058008 | 0.013513918 | family with sequence similarity 50, member A |
| ENSMUSG00000026223 | 64294 | Itm2c | −0.504600271 | 0.008949062 | integral membrane protein 2C |
| ENSMUSG00000063146 | 269713 | Clip2 | −0.50471253 | 0.013154889 | CAP-GLY domain containing linker protein 2 |
| ENSMUSG00000040699 | 67803 | Limd2 | −0.50522157 | 0.00355822 | LIM domain containing 2 |
| ENSMUSG00000020435 | 74309 | Osbp2 | −0.505276433 | 0.001578322 | oxysterol binding protein 2 |
| ENSMUSG00000055762 | 66656 | Eef1d | −0.505487187 | 0.017095122 | eukaryotic translation elongation factor 1 delta (guanine nucleotide exchange protein) |
| ENSMUSG00000006333 | 76846 | Rps9 | −0.505664594 | 0.014879228 | ribosomal protein S9 |
| ENSMUSG00000027404 | 20638 | Snrpb | −0.505817422 | 0.000354254 | small nuclear ribonucleoprotein B |
| ENSMUSG00000039959 | 215114 | Hip1 | −0.505956871 | 0.001231811 | huntingtin interacting protein 1 |
| ENSMUSG00000022099 | 13829 | Dmtn | −0.506072651 | 0.001150495 | dematin actin binding protein |
| ENSMUSG00000016637 | 67042 | Ift27 | −0.506243015 | 0.030906143 | intraflagellar transport 27 |
| ENSMUSG00000036686 | 212139 | Cc2d1a | −0.506404686 | 0.035551788 | coiled-coil and C2 domain containing 1A |
| ENSMUSG00000052752 | 224619 | Traf7 | −0.50702428 | 0.014498847 | TNF receptor-associated factor 7 |
| ENSMUSG00000032763 | 216136 | Ilvbl | −0.507258095 | 0.018472842 | ilvB (bacterial acetolactate synthase)-like |
| ENSMUSG00000046432 | 12070 | Bex3 | −0.507412791 | 0.000638691 | brain expressed X-linked 3 |
| ENSMUSG00000094936 | 19653 | Rbm4 | −0.507495612 | 0.006131244 | RNA binding motif protein 4 |
| ENSMUSG00000029033 | 140500 | Acap3 | −0.507527964 | 0.008949062 | ArfGAP with coiled-coil, ankyrin repeat and PH domains 3 |
| ENSMUSG00000002984 | 53333 | Tomm40 | −0.508105971 | 0.03434691 | translocase of outer mitochondrial membrane 40 homolog (yeast) |
| ENSMUSG00000022515 | 72615 | Anks3 | −0.508290633 | 0.006126577 | ankyrin repeat and sterile alpha motif domain containing 3 |
| ENSMUSG00000033595 | 213469 | Lgi3 | −0.508523326 | 0.000713891 | leucine-rich repeat LGI family, member 3 |
| ENSMUSG00000023272 | 76737 | Creld2 | −0.508659923 | 0.016376632 | cysteine-rich with EGF-like domains 2 |
| ENSMUSG00000097718 | | | −0.508824924 | 0.046266554 | |
| ENSMUSG00000059248 | 53860 | 9-Sep | −0.509211346 | 0.006076319 | septin 9 |
| ENSMUSG00000020061 | 109272 | Mybpc1 | −0.509218228 | 0.034186434 | myosin binding protein C, slow-type |
| ENSMUSG00000005986 | 68423 | Ankrd13d | −0.509236306 | 0.020989507 | ankyrin repeat domain 13 family, member D |
| ENSMUSG00000073684 | 67513 | Faap20 | −0.509334133 | 0.038170025 | Fanconi anemia core complex associated protein 20 |
| ENSMUSG00000020936 | 18107 | Nmt1 | −0.509365232 | 5.68E−05 | N-myristoyltransferase 1 |
| ENSMUSG00000024053 | 246707 | Emilin2 | −0.509594079 | 0.043170567 | elastin microfibril interfacer 2 |
| ENSMUSG00000042312 | 20196 | S100a13 | −0.509766654 | 0.004770599 | S100 calcium binding protein A13 |
| ENSMUSG00000030956 | 77938 | Fam53b | −0.510480171 | 0.001703968 | family with sequence similarity 53, member B |
| ENSMUSG00000022193 | 19173 | Psmb5 | −0.510551155 | 0.015573718 | proteasome (prosome, macropain) subunit, beta type 5 |
| ENSMUSG00000029001 | 230903 | Fbxo44 | −0.510745862 | 0.005193975 | F-box protein 44 |
| ENSMUSG00000020190 | 17347 | Mknk2 | −0.510941956 | 0.03828137 | MAP kinase-interacting serine/threonine kinase 2 |
| ENSMUSG00000028840 | 68040 | Zfp593 | −0.51119213 | 0.045482841 | zinc finger protein 593 |
| ENSMUSG00000017221 | 22123 | Psmd3 | −0.51136001 | 0.004865671 | proteasome (prosome, macropain) 26S subunit, non-ATPase, 3 |
| ENSMUSG00000038793 | 13590 | Lefty1 | −0.511473919 | 0.012352326 | left right determination factor 1 |
| ENSMUSG00000022089 | 57784 | Bin3 | −0.511617048 | 0.009153418 | bridging integrator 3 |
| ENSMUSG00000001482 | 23854 | Def8 | −0.512049732 | 0.003274596 | differentially expressed in FDCP 8 |
| ENSMUSG00000032078 | 22687 | Zpr1 | −0.512118442 | 0.008623613 | ZPR1 zinc finger |
| ENSMUSG00000023456 | 21991 | Tpi1 | −0.512177224 | 0.005228196 | triosephosphate isomerase 1 |
| ENSMUSG00000028062 | 83409 | Lamtor2 | −0.512494256 | 0.026648841 | late endosomal/lysosomal adaptor, MAPK and MTOR activator 2 |
| ENSMUSG00000032231 | 12306 | Anxa2 | −0.512959127 | 0.027698853 | annexin A2 |
| ENSMUSG00000036561 | 71474 | Ppp6r2 | −0.513279755 | 0.008949062 | protein phosphatase 6, regulatory subunit 2 |
| ENSMUSG00000049191 | 331474 | Rgag4 | −0.513698865 | 0.023394386 | retrotransposon gag domain containing 4 |
| ENSMUSG00000028070 | 246703 | Apoa1bp | −0.514291234 | 0.001434658 | apolipoprotein A-I binding protein |
| ENSMUSG00000030761 | 17921 | Myo7a | −0.514745292 | 0.030579905 | myosin VIIA |

TABLE 2-continued

| Ensembl | Entrez | Symbol | log2FoldChange | padj | Name |
|---|---|---|---|---|---|
| ENSMUSG00000033021 | 69080 | Gmppa | −0.514772279 | 0.03102444 | GDP-mannose pyrophosphorylase A |
| ENSMUSG00000022623 | 58234 | Shank3 | −0.514989396 | 0.010950287 | SH3/ankyrin domain gene 3 |
| ENSMUSG00000004849 | 11769 | Ap1s1 | −0.515307823 | 0.008137864 | adaptor protein complex AP-1, sigma 1 |
| ENSMUSG00000038539 | 107503 | Atf5 | −0.516068648 | 0.016953044 | activating transcription factor 5 |
| ENSMUSG00000006782 | 12799 | Cnp | −0.516097848 | 9.60E−06 | 2',3'-cyclic nucleotide 3' phosphodiesterase |
| ENSMUSG00000001334 | 384061 | Fndc5 | −0.516120287 | 0.000228196 | fibronectin type III domain containing 5 |
| ENSMUSG00000041453 | 19933 | Rpl21 | −0.516411582 | 0.000952982 | ribosomal protein L21 |
| ENSMUSG00000039501 | 98999 | Znfx1 | −0.516424651 | 0.004351526 | zinc finger, NFX1-type containing 1 |
| ENSMUSG00000070319 | 53356 | Eif3g | −0.516432478 | 0.007414004 | eukaryotic translation initiation factor 3, subunit G |
| ENSMUSG00000023004 | 22143 | Tuba1b | −0.516712623 | 0.005000229 | tubulin, alpha 1B |
| ENSMUSG00000066043 | 100169 | Phactr4 | −0.516825502 | 0.029269343 | phosphatase and actin regulator 4 |
| ENSMUSG00000038517 | 73174 | Tbkbp1 | −0.517541847 | 0.029743912 | TBK1 binding protein 1 |
| ENSMUSG00000014856 | 66320 | Tmem208 | −0.517551246 | 0.016169267 | transmembrane protein 208 |
| ENSMUSG00000040824 | 107686 | Snrpd2 | −0.517599709 | 0.040697606 | small nuclear ribonucleoprotein D2 |
| ENSMUSG00000052423 | 57370 | B4galt3 | −0.517941234 | 0.001884303 | UDP-Gal:betaGlcNAc beta 1,4-galactosyltransferase, polypeptide 3 |
| ENSMUSG00000020536 | 16897 | Lgl1 | −0.518084382 | 0.032160015 | lethal giant larvae homolog 1 (Drosophila) |
| ENSMUSG00000024142 | 56716 | Mlst8 | −0.518329649 | 0.004702628 | MTOR associated protein, LST8 homolog (S. cerevisiae) |
| ENSMUSG00000037280 | 207839 | Galnt6 | −0.518410075 | 0.00893054 | UDP-N-acetyl-alpha-D-galactosamine:polypeptide N-acetylgalactosaminyltransferase 6 |
| ENSMUSG00000050908 | 383103 | Tvp23a | −0.518440264 | 0.010774326 | trans-golgi network vesicle protein 23A |
| ENSMUSG00000067274 | 11837 | Rplp0 | −0.518497949 | 0.002902043 | ribosomal protein, large, P0 |
| ENSMUSG00000003402 | 19089 | Prkcsh | −0.518648209 | 0.016059298 | protein kinase C substrate 80K-H |
| ENSMUSG00000041607 | 17196 | Mbp | −0.518979348 | 0.000374222 | myelin basic protein |
| ENSMUSG00000025875 | 74257 | Tspan17 | −0.519126323 | 0.02677357 | tetraspanin 17 |
| ENSMUSG00000024560 | 74322 | Cxxc1 | −0.519296236 | 0.013444742 | CXXC finger 1 (PHD domain) |
| ENSMUSG00000095677 | 100040531 | Dynlt1f | −0.519322631 | 0.035181459 | dynein light chain Tctex-type 1F |
| ENSMUSG00000054013 | 104885 | Tmem179 | −0.519493936 | 0.016376632 | transmembrane protein 179 |
| ENSMUSG00000006024 | 108124 | Napa | −0.519525939 | 0.000104562 | N-ethylmaleimide sensitive fusion protein attachment protein alpha |
| ENSMUSG00000096847 | 210573 | Tmem151b | −0.519872831 | 0.002485879 | transmembrane protein 151B |
| ENSMUSG00000025156 | 209318 | Gps1 | −0.520012289 | 0.002391979 | G protein pathway suppressor 1 |
| ENSMUSG00000021048 | 108156 | Mthfd1 | −0.520260881 | 0.036126392 | methylenetetrahydrofolate dehydrogenase (NADP+ dependent), methenyltetrahydrofolate cyclohydrolase, formyltetrahydrofolate synthase |
| ENSMUSG00000022570 | 22122 | Tsta3 | −0.520550471 | 0.034351299 | tissue specific transplantation antigen P35B |
| ENSMUSG00000022489 | 18574 | Pde1b | −0.520865127 | 0.000173264 | phosphodiesterase 1B, Ca2+-calmodulin dependent |
| ENSMUSG00000052087 | 51791 | Rgs14 | −0.521015955 | 0.015244082 | regulator of G-protein signaling 14 |
| ENSMUSG00000078606 | 100042856 | Gm4070 | −0.521080764 | 0.008027523 | predicted gene 4070 |
| ENSMUSG00000022394 | 214669 | L3mbtl2 | −0.521234087 | 0.010384153 | l(3)mbt-like 2 (Drosophila) |
| ENSMUSG00000027223 | 19099 | Mapk8ip1 | −0.521514507 | 0.001610457 | mitogen-activated protein kinase 8 interacting protein 1 |
| ENSMUSG00000044502 | 69556 | Bod1 | −0.521955197 | 8.36E−05 | biorientation of chromosomes in cell division 1 |
| ENSMUSG00000038034 | 140559 | Igsf8 | −0.522087422 | 0.018993844 | immunoglobulin superfamily, member 8 |
| ENSMUSG00000022548 | 11815 | Apod | −0.522310536 | 5.91E−05 | apolipoprotein D |
| ENSMUSG00000050860 | 237928 | Phospho1 | −0.522426986 | 0.03909353 | phosphatase, orphan 1 |
| ENSMUSG00000034312 | 232227 | Iqsec1 | −0.522634136 | 0.00560995 | IQ motif and Sec7 domain 1 |
| ENSMUSG00000039382 | 54636 | Wdr45 | −0.522669523 | 0.008685332 | WD repeat domain 45 |
| ENSMUSG00000019467 | 52666 | Arhgef25 | −0.52286276 | 0.001394193 | Rho guanine nucleotide exchange factor (GEF) 25 |
| ENSMUSG00000026966 | 68475 | Ssna1 | −0.522868393 | 0.007068264 | SS nuclear autoantigen 1 |
| ENSMUSG00000024858 | 110355 | Grk2 | −0.522894898 | 4.75E−06 | G protein-coupled receptor kinase 2 |
| ENSMUSG00000036427 | 14751 | Gpi1 | −0.523181247 | 0.009960377 | glucose phosphate isomerase 1 |
| ENSMUSG00000026879 | 227753 | Gsn | −0.523468526 | 0.017044825 | gelsolin |
| ENSMUSG00000039834 | 329559 | Zfp335 | −0.523521712 | 0.032074092 | zinc finger protein 335 |
| ENSMUSG00000026854 | 74270 | Usp20 | −0.523641711 | 0.007281574 | ubiquitin specific peptidase 20 |
| ENSMUSG00000020485 | 20922 | Supt4a | −0.523865864 | 0.000713891 | suppressor of Ty 4A |
| ENSMUSG00000035735 | 269060 | Dagla | −0.523894427 | 0.002590106 | diacylglycerol lipase, alpha |
| ENSMUSG00000033124 | 245860 | Atg9a | −0.524037683 | 0.005923142 | autophagy related 9A |
| ENSMUSG00000037235 | 17122 | Mxd4 | −0.524123771 | 0.000893237 | Max dimerization protein 4 |
| ENSMUSG00000002395 | 67023 | Use1 | −0.524250753 | 0.016842671 | unconventional SNARE in the ER 1 homolog (S. cerevisiae) |
| ENSMUSG00000046756 | 50529 | Mrps7 | −0.524289684 | 0.000570513 | mitchondrial ribosomal protein S7 |
| ENSMUSG00000075705 | 27361 | Msrb1 | −0.524433552 | 0.007528062 | methionine sulfoxide reductase B1 |
| ENSMUSG00000074064 | 56690 | Mlycd | −0.524508339 | 0.025454387 | malonyl-CoA decarboxylase |
| ENSMUSG00000026519 | 208795 | Tmem63a | −0.524734265 | 0.015573718 | transmembrane protein 63a |
| ENSMUSG00000035964 | 67937 | Tmem59l | −0.524765367 | 0.005719432 | transmembrane protein 59-like |
| ENSMUSG00000030685 | 233877 | Kctd13 | −0.526059033 | 0.003180866 | potassium channel tetramerisation domain containing 13 |
| ENSMUSG00000002658 | 98053 | Gtf2f1 | −0.526069114 | 0.020450087 | general transcription factor IIF, polypeptide 1 |

TABLE 2-continued

| Ensembl | Entrez | Symbol | log2FoldChange | padj | Name |
|---|---|---|---|---|---|
| ENSMUSG00000036862 | 233651 | Dchs1 | −0.526294297 | 0.030382365 | dachsous 1 (Drosophila) |
| ENSMUSG00000026858 | 108958 | Miga2 | −0.526381252 | 0.009610675 | mitoguardin 2 |
| ENSMUSG00000046822 | 106947 | Slc39a3 | −0.526569541 | 0.00985516 | solute carrier family 39 (zinc transporter), member 3 |
| ENSMUSG00000040260 | 76441 | Daam2 | −0.526685914 | 0.000845793 | dishevelled associated activator of morphogenesis 2 |
| ENSMUSG00000034714 | 117160 | Ttyh2 | −0.527221675 | 0.0002645 | tweety family member 2 |
| ENSMUSG00000014294 | 17991 | Ndufa2 | −0.527344316 | 0.016938234 | NADH dehydrogenase (ubiquinone) 1 alpha subcomplex, 2 |
| ENSMUSG00000031955 | 12927 | Bcar1 | −0.527426618 | 0.030791098 | breast cancer anti-estrogen resistance 1 |
| ENSMUSG00000081534 | 67739 | Slc48a1 | −0.527499092 | 0.000638691 | solute carrier family 48 (heme transporter), member 1 |
| ENSMUSG00000069682 | | | −0.527520982 | 0.024672575 | |
| ENSMUSG00000020477 | 64660 | Mrps24 | −0.527561932 | 0.002238309 | mitochondrial ribosomal protein S24 |
| ENSMUSG00000003528 | 13358 | Slc25a1 | −0.527579947 | 0.012719029 | solute carrier family 25 (mitochondrial carrier, citrate transporter), member 1 |
| ENSMUSG00000060716 | 211945 | Plekhh1 | −0.528384901 | 0.006708852 | pleckstrin homology domain containing, family H (with MyTH4 domain) member 1 |
| ENSMUSG00000071711 | 246221 | Mpst | −0.52843881 | 0.033003475 | mercaptopyruvate sulfurtransferase |
| ENSMUSG00000057103 | 66116 | Nat8f1 | −0.528620364 | 0.01971677 | N-acetyltransferase 8 (GCN5-related) family member 1 |
| ENSMUSG00000022554 | 59053 | Hgh1 | −0.529289129 | 0.031240021 | HGH1 homolog |
| ENSMUSG00000032297 | 76183 | Celf6 | −0.529310664 | 8.41E−05 | CUGBP, Elav-like family member 6 |
| ENSMUSG00000034570 | 170835 | Inpp5j | −0.529695731 | 0.023857207 | inositol polyphosphate 5-phosphatase J |
| ENSMUSG00000029034 | 71957 | Cpsf3l | −0.529967707 | 0.008027523 | cleavage and polyadenylation specific factor 3-like |
| ENSMUSG00000052584 | 72661 | Serp2 | −0.530433118 | 0.0043121 | stress-associated endoplasmic reticulum protein family member 2 |
| ENSMUSG00000037254 | 16425 | Itih2 | −0.530657558 | 0.040061936 | inter-alpha trypsin inhibitor, heavy chain 2 |
| ENSMUSG00000052229 | 574402 | Gpr17 | −0.530679627 | 6.31E−06 | G protein-coupled receptor 17 |
| ENSMUSG00000036613 | 380752 | Tssc1 | −0.530690542 | 0.003076373 | tumor suppressing subtransferable candidate 1 |
| ENSMUSG00000062591 | 22153 | Tubb4a | −0.530891086 | 0.009290425 | tubulin, beta 4A class IVA |
| ENSMUSG00000034807 | 234407 | Colgalt1 | −0.531270045 | 0.044539813 | collagen beta(1-O) galactosyltransferase 1 |
| ENSMUSG00000026895 | 68375 | Ndufa8 | −0.531304187 | 0.012785675 | NADH dehydrogenase (ubiquinone) 1 alpha subcomplex, 8 |
| ENSMUSG00000028969 | 12568 | Cdk5 | −0.531610528 | 0.00093571 | cyclin-dependent kinase 5 |
| ENSMUSG00000020163 | 66594 | Uqcr11 | −0.531672652 | 0.042167571 | ubiquinol-cytochrome c reductase, complex III subunit XI |
| ENSMUSG00000091735 | 436090 | Gpr62 | −0.531936345 | 0.001441714 | G protein-coupled receptor 62 |
| ENSMUSG00000030787 | 114332 | Lyve1 | −0.532376292 | 0.045050576 | lymphatic vessel endothelial hyaluronan receptor 1 |
| ENSMUSG00000047423 | 107242 | AI837181 | −0.532524944 | 0.048886372 | expressed sequence AI837181 |
| ENSMUSG00000071644 | 67160 | Eef1g | −0.532671044 | 0.000652509 | eukaryotic translation elongation factor 1 gamma |
| ENSMUSG00000015981 | 57740 | Stk32c | −0.532680707 | 0.007180621 | serine/threonine kinase 32C |
| ENSMUSG00000022474 | 29858 | Pmm1 | −0.532735016 | 0.018154713 | phosphomannomutase 1 |
| ENSMUSG00000004268 | 14791 | Emg1 | −0.533257635 | 0.001181038 | EMG1 N1-specific pseudouridine methyltransferase |
| ENSMUSG00000020882 | 12295 | Cacnb1 | −0.533262676 | 0.002106191 | calcium channel, voltage-dependent, beta 1 subunit |
| ENSMUSG00000060166 | 27801 | Zdhhc8 | −0.533401373 | 0.005223418 | zinc finger, DHHC domain containing 8 |
| ENSMUSG00000049124 | | | −0.533460844 | 0.01309563 | |
| ENSMUSG00000033706 | 232187 | Smyd5 | −0.533812038 | 0.025770684 | SET and MYND domain containing 5 |
| ENSMUSG00000047284 | 216860 | Neurl4 | −0.534228921 | 0.005721909 | neuralized E3 ubiquitin protein ligase 4 |
| ENSMUSG00000031837 | 117148 | Necab2 | −0.534530285 | 0.020913199 | N-terminal EF-hand calcium binding protein 2 |
| ENSMUSG00000039234 | 69608 | Sec24d | −0.534676465 | 0.027523167 | Sec24 related gene family, member D (S. cerevisiae) |
| ENSMUSG00000078235 | 625638 | Fam43b | −0.535254857 | 0.02251744 | family with sequence similarity 43, member B |
| ENSMUSG00000028757 | 13200 | Ddost | −0.535748794 | 0.000456337 | dolichyl-di-phosphooligosaccharide-protein glycotransferase |
| ENSMUSG00000006205 | 56213 | Htra1 | −0.535849169 | 0.001347174 | HtrA serine peptidase 1 |
| ENSMUSG00000000489 | 18591 | Pdgfb | −0.536340348 | 0.01946358 | platelet derived growth factor, B polypeptide |
| ENSMUSG00000003573 | 26558 | Homer3 | −0.536821594 | 0.026895831 | homer scaffolding protein 3 |
| ENSMUSG00000056211 | 226412 | R3hdm1 | −0.536840164 | 0.016298666 | R3H domain containing 1 |
| ENSMUSG00000023909 | 76498 | Paqr4 | −0.536914077 | 0.001070978 | progestin and adipoQ receptor family member IV |
| ENSMUSG00000034891 | 104069 | Sncb | −0.537360229 | 0.019955804 | synuclein, beta |
| ENSMUSG00000011589 | 240121 | Fsd1 | −0.537404415 | 0.030463248 | fibronectin type 3 and SPRY domain-containing protein |

TABLE 2-continued

| Ensembl | Entrez | Symbol | log2FoldChange | padj | Name |
|---|---|---|---|---|---|
| ENSMUSG00000021240 | 19300 | Abcd4 | −0.53773979 | 0.031599635 | ATP-binding cassette, sub-family D (ALD), member 4 |
| ENSMUSG00000004677 | 17925 | Myo9b | −0.53778101 | 0.003471742 | myosin IXb |
| ENSMUSG00000078570 | 68920 | 1110065P20Rik | −0.537984517 | 0.041221106 | RIKEN cDNA 1110065P20 gene |
| ENSMUSG00000073982 | 56212 | Rhog | −0.53824404 | 0.042173014 | ras homolog family member G |
| ENSMUSG00000073702 | 114641 | Rpl31 | −0.538718878 | 0.006981623 | ribosomal protein L31 |
| ENSMUSG00000075031 | 319178 | Hist1h2bb | −0.538800742 | 0.046147529 | histone cluster 1, H2bb |
| ENSMUSG00000051375 | 75599 | Pcdh1 | −0.538874075 | 0.010218518 | protocadherin 1 |
| ENSMUSG00000026958 | 83768 | Dpp7 | −0.539154182 | 0.001877068 | dipeptidylpeptidase 7 |
| ENSMUSG00000026421 | 13007 | Csrp1 | −0.539275241 | 5.03E−06 | cysteine and glycine-rich protein 1 |
| ENSMUSG00000024622 | 106894 | Hmgxb3 | −0.539414972 | 0.000659059 | HMG box domain containing 3 |
| ENSMUSG00000060591 | 80876 | Ifitm2 | −0.539724835 | 0.035477901 | interferon induced transmembrane protein 2 |
| ENSMUSG00000022594 | 23936 | Lynx1 | −0.539748698 | 0.003780714 | Ly6/neurotoxin 1 |
| ENSMUSG00000004667 | 66420 | Polr2e | −0.539758901 | 0.041746015 | polymerase (RNA) II (DNA directed) polypeptide E |
| ENSMUSG00000024213 | 56409 | Nudt3 | −0.539845533 | 0.004324306 | nudix (nucleotide diphosphate linked moiety X)-type motif 3 |
| ENSMUSG00000031823 | 102193 | Zdhhc7 | −0.539895998 | 0.028735433 | zinc finger, DHHC domain containing 7 |
| ENSMUSG00000049892 | 19416 | Rasd1 | −0.540166437 | 0.003473018 | RAS, dexamethasone-induced 1 |
| ENSMUSG00000042642 | 319945 | Flad1 | −0.540223389 | 0.009986585 | flavin adenine dinucleotide synthetase 1 |
| ENSMUSG00000078532 | 67149 | Nkain1 | −0.540265782 | 0.024234281 | Na+/K+ transporting ATPase interacting 1 |
| ENSMUSG00000002010 | 15929 | Idh3g | −0.540288264 | 0.002213576 | isocitrate dehydrogenase 3 (NAD+), gamma |
| ENSMUSG00000029616 | 67397 | Erp29 | −0.540309145 | 0.012723172 | endoplasmic reticulum protein 29 |
| ENSMUSG00000027890 | 14865 | Gstm4 | −0.54049154 | 0.021606747 | glutathione S-transferase, mu 4 |
| ENSMUSG00000032014 | 102644 | Oaf | −0.540799156 | 0.019180029 | out at first homolog |
| ENSMUSG00000030357 | 14228 | Fkbp4 | −0.540811731 | 0.003608794 | FK506 binding protein 4 |
| ENSMUSG00000023904 | 353502 | Hcfc1r1 | −0.54096107 | 0.000874286 | host cell factor C1 regulator 1 (XPO1-dependent) |
| ENSMUSG00000031778 | 20312 | Cx3cl1 | −0.540971604 | 0.001063084 | chemokine (C-X3-C motif) ligand 1 |
| ENSMUSG00000040811 | 72205 | Eml2 | −0.541014258 | 0.032471348 | echinoderm microtubule associated protein like 2 |
| ENSMUSG00000062006 | 68436 | Rpl34 | −0.541209369 | 0.001873548 | ribosomal protein L34 |
| ENSMUSG00000020828 | 18806 | Pld2 | −0.541218712 | 0.020167127 | phospholipase D2 |
| ENSMUSG00000042106 | 68176 | Fam212a | −0.541368324 | 0.047104258 | family with sequence similarity 212, member A |
| ENSMUSG00000033128 | 106039 | Gga1 | −0.541515623 | 0.046178509 | golgi associated, gamma adaptin ear containing, ARF binding protein 1 |
| ENSMUSG00000021702 | 21828 | Thbs4 | −0.541817847 | 0.004747987 | thrombospondin 4 |
| ENSMUSG00000018340 | 11749 | Anxa6 | −0.542143879 | 0.00200527 | annexin A6 |
| ENSMUSG00000050761 | 14724 | Gp1bb | −0.54215648 | 0.030387239 | glycoprotein 1b, beta polypeptide |
| ENSMUSG00000024944 | 56327 | Arl2 | −0.542229227 | 0.03292934 | ADP-ribosylation factor-like 2 |
| ENSMUSG00000024959 | 12015 | Bad | −0.542507258 | 0.037187025 | BCL2-associated agonist of cell death |
| ENSMUSG00000001123 | 16859 | Lgals9 | −0.543011066 | 0.015293069 | lectin, galactose binding, soluble 9 |
| ENSMUSG00000006356 | 68337 | Crip2 | −0.543290998 | 0.048986438 | cysteine rich protein 2 |
| ENSMUSG00000012296 | 74094 | Tjap1 | −0.543799635 | 0.049647531 | tight junction associated protein 1 |
| ENSMUSG00000005566 | 21849 | Trim28 | −0.54429898 | 0.000315513 | tripartite motif-containing 28 |
| ENSMUSG00000003575 | 382056 | Crtc1 | −0.544502042 | 0.01044046 | CREB regulated transcription coactivator 1 |
| ENSMUSG00000037003 | 209039 | Tns2 | −0.544740049 | 0.047890046 | tensin 2 |
| ENSMUSG00000033272 | 67843 | Slc35a4 | −0.544785434 | 0.005084403 | solute carrier family 35, member A4 |
| ENSMUSG00000030801 | 67773 | Kat8 | −0.544811745 | 0.001612703 | K(lysine) acetyltransferase 8 |
| ENSMUSG00000029602 | 19415 | Rasal1 | −0.544875311 | 0.046981184 | RAS protein activator like 1 (GAP1 like) |
| ENSMUSG00000002147 | 20852 | Stat6 | −0.545024854 | 0.005431104 | signal transducer and activator of transcription 6 |
| ENSMUSG00000021448 | 20418 | Shc3 | −0.545253189 | 0.018124822 | src homology 2 domain-containing transforming protein C3 |
| ENSMUSG00000030611 | 67994 | Mrps11 | −0.545568696 | 0.036032893 | mitochondrial ribosomal protein S11 |
| ENSMUSG00000032174 | 15898 | Icam5 | −0.545706249 | 0.021527806 | intercellular adhesion molecule 5, telencephalin |
| ENSMUSG00000024019 | 74157 | Cmtr1 | −0.545839495 | 0.003295585 | cap methyltransferase 1 |
| ENSMUSG00000028541 | 53418 | B4galt2 | −0.546586931 | 0.029592492 | UDP-Gal:betaGlcNAc beta 1,4-galactosyltransferase, polypeptide 2 |
| ENSMUSG00000010086 | 22671 | Rnf112 | −0.546611342 | 0.003779219 | ring finger protein 112 |
| ENSMUSG00000019837 | 67371 | Gtf3c6 | −0.546689528 | 0.032796349 | general transcription factor IIIC, polypeptide 6, alpha |
| ENSMUSG00000015542 | 66176 | Nat9 | −0.546729335 | 0.027360589 | N-acetyltransferase 9 (GCN5-related, putative) |
| ENSMUSG00000024942 | 12333 | Capn1 | −0.546763839 | 0.022939006 | calpain 1 |
| ENSMUSG00000020893 | 18626 | Per1 | −0.546998938 | 0.032723617 | period circadian clock 1 |
| ENSMUSG00000063430 | 320916 | Wscd2 | −0.5471067 | 0.006569439 | WSC domain containing 2 |
| ENSMUSG00000000915 | 29816 | Hip1r | −0.547368091 | 0.004721169 | huntingtin interacting protein 1 related |
| ENSMUSG00000022098 | 12153 | Bmp1 | −0.547415848 | 0.011221844 | bone morphogenetic protein 1 |
| ENSMUSG00000043866 | 24075 | Taf10 | −0.547518393 | 0.008435647 | TATA-box binding protein associated factor 10 |
| ENSMUSG00000026193 | 14268 | Fn1 | −0.547623298 | 0.018715895 | fibronectin 1 |
| ENSMUSG00000038143 | 71069 | Stox2 | −0.548035784 | 0.016371726 | storkhead box 2 |

TABLE 2-continued

| Ensembl | Entrez | Symbol | log2FoldChange | padj | Name |
|---|---|---|---|---|---|
| ENSMUSG00000033059 | 110078 | Pygb | −0.548233773 | 0.001239045 | brain glycogen phosphorylase |
| ENSMUSG00000045659 | 233765 | Plekha7 | −0.548295609 | 0.018715895 | pleckstrin homology domain containing, family A member 7 |
| ENSMUSG00000041841 | 67281 | Rpl37 | −0.548333221 | 0.001407851 | ribosomal protein L37 |
| ENSMUSG00000032187 | 20586 | Smarca4 | −0.548347351 | 0.007003141 | SWI/SNF related, matrix associated, actin dependent regulator of chromatin, subfamily a, member 4 |
| ENSMUSG00000038545 | 66515 | Cul7 | −0.548365061 | 0.04648534 | cullin 7 |
| ENSMUSG00000011832 | 213027 | Evi5l | −0.54842235 | 0.006972106 | ecotropic viral integration site 5 like |
| ENSMUSG00000005625 | 19185 | Psmd4 | −0.548422939 | 0.006167019 | proteasome (prosome, macropain) 26S subunit, non-ATPase, 4 |
| ENSMUSG00000018599 | 237781 | Mief2 | −0.548911736 | 0.009612715 | mitochondrial elongation factor 2 |
| ENSMUSG00000039911 | 74646 | Spsb1 | −0.54906238 | 0.003073692 | splA/ryanodine receptor domain and SOCS box containing 1 |
| ENSMUSG00000013584 | 19378 | Aldh1a2 | −0.549082866 | 0.039955709 | aldehyde dehydrogenase family 1, subfamily A2 |
| ENSMUSG00000026944 | 11305 | Abca2 | −0.549171015 | 0.018230406 | ATP-binding cassette, sub-family A (ABC1), member 2 |
| ENSMUSG00000051627 | 50709 | Hist1h1e | −0.549451374 | 0.013187769 | histone cluster 1, H1e |
| ENSMUSG00000070420 | 666311 | Zscan25 | −0.549524468 | 0.039345584 | zinc finger and SCAN domain containing 25 |
| ENSMUSG00000002486 | 77832 | Tchp | −0.549683759 | 0.024688022 | trichoplein, keratin filament binding |
| ENSMUSG00000028455 | 66592 | Stoml2 | −0.550172207 | 0.000608724 | stomatin (Epb7.2)-like 2 |
| ENSMUSG00000003299 | 66163 | Mrpl4 | −0.550276494 | 0.047849659 | mitochondrial ribosomal protein L4 |
| ENSMUSG00000060279 | 11771 | Ap2a1 | −0.550880162 | 0.016104543 | adaptor-related protein complex 2, alpha 1 subunit |
| ENSMUSG00000023118 | 68188 | Sympk | −0.551070302 | 0.00788099 | symplekin |
| ENSMUSG00000061477 | 20115 | Rps7 | −0.551133707 | 0.017512637 | ribosomal protein S7 |
| ENSMUSG00000060938 | 19941 | Rpl26 | −0.551492391 | 0.001658467 | ribosomal protein L26 |
| ENSMUSG00000030612 | 67308 | Mrpl46 | −0.551763154 | 0.002238309 | mitochondrial ribosomal protein L46 |
| ENSMUSG00000040712 | 216874 | Camta2 | −0.551884917 | 0.012319463 | calmodulin binding transcription activator 2 |
| ENSMUSG00000002983 | 19698 | Relb | −0.552095033 | 0.035654262 | avian reticuloendotheliosis viral (v-rel) oncogene related B |
| ENSMUSG00000026820 | 96979 | Ptges2 | −0.552322113 | 0.019796215 | prostaglandin E synthase 2 |
| ENSMUSG00000041164 | 52915 | Zmiz2 | −0.552707639 | 0.008949062 | zinc finger, MIZ-type containing 2 |
| ENSMUSG00000020827 | 50932 | Mink1 | −0.552730704 | 0.005001017 | misshapen-like kinase 1 (zebrafish) |
| ENSMUSG00000002345 | 72368 | Borcs8 | −0.552791418 | 0.013792464 | BLOC-1 related complex subunit 8 |
| ENSMUSG00000031503 | 12827 | Col4a2 | −0.55308674 | 0.043083007 | collagen, type IV, alpha 2 |
| ENSMUSG00000050711 | 20254 | Scg2 | −0.553257576 | 5.69E−05 | secretogranin II |
| ENSMUSG00000034245 | 232232 | Hdac11 | −0.553343251 | 0.005542314 | histone deacetylase 11 |
| ENSMUSG00000041241 | 68350 | Mul1 | −0.553588791 | 0.000773339 | mitochondrial ubiquitin ligase activator of NFKB 1 |
| ENSMUSG00000029465 | 56378 | Arpc3 | −0.553664732 | 0.01278908 | actin related protein 2/3 complex, subunit 3 |
| ENSMUSG00000025736 | 72106 | Jmjd8 | −0.553812328 | 0.017380866 | jumonji domain containing 8 |
| ENSMUSG00000037206 | 26968 | Islr | −0.554040915 | 0.01278908 | immunoglobulin superfamily containing leucine-rich repeat |
| ENSMUSG00000045246 | 66733 | Kcng4 | −0.554369645 | 0.029477001 | potassium voltage-gated channel, subfamily G, member 4 |
| ENSMUSG00000042109 | 105859 | Csdc2 | −0.554523887 | 0.01116783 | cold shock domain containing C2, RNA binding |
| ENSMUSG00000026277 | 59041 | Stk25 | −0.555124365 | 0.002356321 | serine/threonine kinase 25 (yeast) |
| ENSMUSG00000028433 | 68926 | Ubap2 | −0.555145793 | 0.026396678 | ubiquitin-associated protein 2 |
| ENSMUSG00000061451 | 381199 | Tmem151a | −0.555299705 | 0.002902043 | transmembrane protein 151A |
| ENSMUSG00000030747 | 67800 | Dgat2 | −0.555478931 | 1.92E−05 | diacylglycerol O-acyltransferase 2 |
| ENSMUSG00000053024 | 21367 | Cntn2 | −0.555787463 | 0.009746584 | contactin 2 |
| ENSMUSG00000031622 | 20467 | Sin3b | −0.55639997 | 0.003104002 | transcriptional regulator, SIN3B (yeast) |
| ENSMUSG00000050910 | 237988 | Cdr21 | −0.556654454 | 0.001405029 | cerebellar degeneration-related protein 2-like |
| ENSMUSG00000031825 | 78892 | Crispld2 | −0.556676623 | 0.031060625 | cysteine-rich secretory protein LCCL domain containing 2 |
| ENSMUSG00000003273 | 12348 | Car11 | −0.556829921 | 0.007008349 | carbonic anhydrase 11 |
| ENSMUSG00000069678 | 69837 | Pcgf1 | −0.556831248 | 0.001833082 | polycomb group ring finger 1 |
| ENSMUSG00000020785 | 55984 | Camkk1 | −0.556889989 | 2.76E−05 | calcium/calmodulin-dependent protein kinase kinase 1, alpha |
| ENSMUSG00000062381 | | | −0.556904168 | 0.002478562 | |
| ENSMUSG00000041528 | 84585 | Rnf123 | −0.557472438 | 0.027009464 | ring finger protein 123 |
| ENSMUSG00000024862 | 16594 | Klc2 | −0.557863804 | 0.013444742 | kinesin light chain 2 |
| ENSMUSG00000032294 | 18746 | Pkm | −0.558109804 | 0.02412924 | pyruvate kinase, muscle |
| ENSMUSG00000032867 | 231672 | Fbxw8 | −0.558529371 | 0.006705787 | F-box and WD-40 domain protein 8 |
| ENSMUSG00000030588 | 77254 | Yif1b | −0.558612927 | 0.047193031 | Yip1 interacting factor homolog B (S. cerevisiae) |
| ENSMUSG00000034793 | 68401 | G6pc3 | −0.558694765 | 0.020272645 | glucose 6 phosphatase, catalytic, 3 |
| ENSMUSG00000061306 | 72055 | Slc38a10 | −0.559219438 | 0.015500869 | solute carrier family 38, member 10 |

TABLE 2-continued

| Ensembl | Entrez | Symbol | log2FoldChange | padj | Name |
|---|---|---|---|---|---|
| ENSMUSG00000028059 | 16800 | Arhgef2 | −0.559844389 | 0.000772175 | rho/rac guanine nucleotide exchange factor (GEF) 2 |
| ENSMUSG00000007888 | 12931 | Crlf1 | −0.55991329 | 0.047193031 | cytokine receptor-like factor 1 |
| ENSMUSG00000050373 | 101113 | Snx21 | −0.559952595 | 0.016323268 | sorting nexin family member 21 |
| ENSMUSG00000068735 | 277414 | Trp53i11 | −0.560128151 | 0.001079007 | transformation related protein 53 inducible protein 11 |
| ENSMUSG00000042766 | 360213 | Trim46 | −0.560219871 | 0.024688022 | tripartite motif-containing 46 |
| ENSMUSG00000071074 | 28064 | Yipf3 | −0.560480362 | 0.036258437 | Yip1 domain family, member 3 |
| ENSMUSG00000027952 | 68603 | Pmvk | −0.56084126 | 0.020167127 | phosphomevalonate kinase |
| ENSMUSG00000019432 | 53817 | Ddx39b | −0.560909674 | 0.002591641 | DEAD (Asp-Glu-Ala-Asp) box polypeptide 39B |
| ENSMUSG00000043460 | 207393 | Elfn2 | −0.562401376 | 0.004702628 | leucine rich repeat and fibronectin type III, extracellular 2 |
| ENSMUSG00000040859 | 100383 | Bsdc1 | −0.562537517 | 0.000809039 | BSD domain containing 1 |
| ENSMUSG00000031217 | 13641 | Efnb1 | −0.562696897 | 0.029357419 | ephrin B1 |
| ENSMUSG00000029029 | 59002 | Wrap73 | −0.562974854 | 0.007776022 | WD repeat containing, antisense to Trp73 |
| ENSMUSG00000035671 | 212168 | Zswim4 | −0.562993928 | 0.034508425 | zinc finger SWIM-type containing 4 |
| ENSMUSG00000042870 | 21968 | Tom1 | −0.563022036 | 0.023857207 | target of myb1 trafficking protein |
| ENSMUSG00000040164 | 16538 | Kcns1 | −0.563063295 | 0.017790743 | K+ voltage-gated channel, subfamily S, 1 |
| ENSMUSG00000025555 | 223254 | Farp1 | −0.56355557 | 0.002911871 | FERM, RhoGEF (Arhgef) and pleckstrin domain protein 1 (chondrocyte-derived) |
| ENSMUSG00000025145 | 217366 | Lrrc45 | −0.563790996 | 0.040920033 | leucine rich repeat containing 45 |
| ENSMUSG00000028798 | 54709 | Eif3i | −0.564034411 | 0.006275636 | eukaryotic translation initiation factor 3, subunit I |
| ENSMUSG00000034707 | 75612 | Gns | −0.564196116 | 0.003310449 | glucosamine (N-acetyl)-6-sulfatase |
| ENSMUSG00000002803 | 399566 | Btbd6 | −0.564398092 | 0.000317383 | BTB (POZ) domain containing 6 |
| ENSMUSG00000021948 | 18753 | Prkcd | −0.564792623 | 0.001998408 | protein kinase C, delta |
| ENSMUSG00000038886 | 140481 | Man2a2 | −0.564865955 | 0.041221106 | mannosidase 2, alpha 2 |
| ENSMUSG00000064254 | 66071 | Ethe1 | −0.564957607 | 0.040368494 | ethylmalonic encephalopathy 1 |
| ENSMUSG00000041120 | 17965 | Nbl1 | −0.565005874 | 0.031595382 | neuroblastoma, suppression of tumorigenicity 1 |
| ENSMUSG00000027298 | 22174 | Tyro3 | −0.565197336 | 0.014642704 | TYRO3 protein tyrosine kinase 3 |
| ENSMUSG00000056413 | 231821 | Adap1 | −0.565259127 | 0.043328329 | ArfGAP with dual PH domains 1 |
| ENSMUSG00000030057 | 12785 | Cnbp | −0.565515357 | 0.018556154 | cellular nucleic acid binding protein |
| ENSMUSG00000029059 | 66469 | Fam213b | −0.566018451 | 0.023463949 | family with sequence similarity 213, member B |
| ENSMUSG00000058603 | | | −0.567062802 | 0.025357004 | |
| ENSMUSG00000038845 | 18673 | Phb | −0.567658713 | 0.009109437 | prohibitin |
| ENSMUSG00000068114 | 76457 | Ccdc134 | −0.567694179 | 0.017618704 | coiled-coil domain containing 134 |
| ENSMUSG00000025137 | 68671 | Pcyt2 | −0.568076544 | 0.002834919 | phosphate cytidylyltransferase 2, ethanolamine |
| ENSMUSG00000073640 | | | −0.568357946 | 0.000186491 | |
| ENSMUSG00000040136 | 20927 | Abcc8 | −0.568417003 | 0.031060625 | ATP-binding cassette, sub-family C (CFTR/MRP), member 8 |
| ENSMUSG00000006675 | 74443 | P4htm | −0.568424731 | 0.013947569 | prolyl 4-hydroxylase, transmembrane (endoplasmic reticulum) |
| ENSMUSG00000032812 | 69710 | Arap1 | −0.568955868 | 0.036713429 | ArfGAP with RhoGAP domain, ankyrin repeat and PH domain 1 |
| ENSMUSG00000062031 | 212974 | Pgghg | −0.569168028 | 0.029562552 | protein glucosylgalactosylhydroxylysine glucosidase |
| ENSMUSG00000036057 | 104831 | Ptpn23 | −0.569325571 | 0.015233442 | protein tyrosine phosphatase, non-receptor type 23 |
| ENSMUSG00000052911 | 16779 | Lamb2 | −0.569346769 | 0.034386122 | laminin, beta 2 |
| ENSMUSG00000018661 | 16834 | Cog1 | −0.569522447 | 0.0037729 | component of oligomeric golgi complex 1 |
| ENSMUSG00000061046 | 68977 | Haghl | −0.569698004 | 0.01436485 | hydroxyacylglutathione hydrolase-like |
| ENSMUSG00000036578 | 57780 | Fxyd7 | −0.569740085 | 0.043579121 | FXYD domain-containing ion transport regulator 7 |
| ENSMUSG00000027613 | 16418 | Eif6 | −0.569763765 | 0.003765637 | eukaryotic translation initiation factor 6 |
| ENSMUSG00000079304 | 71149 | 4933413G19Rik | −0.569982416 | 0.030432798 | RIKEN cDNA 4933413G19 gene |
| ENSMUSG00000062753 | 106672 | AI413582 | −0.570022514 | 0.031595382 | expressed sequence AI413582 |
| ENSMUSG00000022204 | 68966 | Ngdn | −0.570075525 | 0.007368041 | neuroguidin, EIF4E binding protein |
| ENSMUSG00000020211 | 20222 | Sf3a2 | −0.570077215 | 0.020538645 | splicing factor 3a, subunit 2 |
| ENSMUSG00000018574 | 11370 | Acadvl | −0.57033426 | 0.004154959 | acyl-Coenzyme A dehydrogenase, very long chain |
| ENSMUSG00000018040 | 74778 | Rrp7a | −0.570608349 | 0.015079436 | ribosomal RNA processing 7 homolog A (S. cerevisiae) |
| ENSMUSG00000056553 | 19276 | Ptprn2 | −0.570786058 | 0.043223052 | protein tyrosine phosphatase, receptor type, N polypeptide 2 |
| ENSMUSG00000025576 | 52897 | Rbfox3 | −0.571020395 | 0.002366821 | RNA binding protein, fox-1 homolog (C. elegans) 3 |
| ENSMUSG00000001472 | 66855 | Tcf25 | −0.571038536 | 0.001276768 | transcription factor 25 (basic helix-loop-helix) |
| ENSMUSG00000031708 | 106529 | Tecr | −0.571362939 | 0.04188267 | trans-2,3-enoyl-CoA reductase |
| ENSMUSG00000069744 | 26446 | Psmb3 | −0.571576615 | 0.002423477 | proteasome (prosome, macropain) subunit, beta type 3 |

TABLE 2-continued

| Ensembl | Entrez | Symbol | log2FoldChange | padj | Name |
|---|---|---|---|---|---|
| ENSMUSG00000069806 | 81904 | Cacng7 | −0.571633754 | 0.00154299 | calcium channel, voltage-dependent, gamma subunit 7 |
| ENSMUSG00000004035 | 68312 | Gstm7 | −0.571785486 | 0.001683662 | glutathione S-transferase, mu 7 |
| ENSMUSG00000025371 | 208092 | Chmp6 | −0.572288808 | 0.016376632 | charged multivesicular body protein 6 |
| ENSMUSG00000043439 | 103551 | E130012A19Rik | −0.572294018 | 0.022645506 | RIKEN cDNA E130012A19 gene |
| ENSMUSG00000024854 | 69745 | Pold4 | −0.572418579 | 0.032160015 | polymerase (DNA-directed), delta 4 |
| ENSMUSG00000042535 | 14904 | Gtpbp1 | −0.572791655 | 0.006192791 | GTP binding protein 1 |
| ENSMUSG00000036504 | 75454 | Phpt1 | −0.573172411 | 0.026558756 | phosphohistidine phosphatase 1 |
| ENSMUSG00000035024 | 78658 | Ncapd3 | −0.573314689 | 0.038187701 | non-SMC condensin II complex, subunit D3 |
| ENSMUSG00000012848 | 20103 | Rps5 | −0.5733714 | 0.0042042 | ribosomal protein S5 |
| ENSMUSG00000020057 | 71712 | Dram1 | −0.573805614 | 0.022323986 | DNA-damage regulated autophagy modulator 1 |
| ENSMUSG00000008153 | 232370 | Clstn3 | −0.573893925 | 0.003758628 | calsyntenin 3 |
| ENSMUSG00000020733 | 26941 | Slc9a3r1 | −0.573942456 | 0.000643185 | solute carrier family 9 (sodium/hydrogen exchanger), member 3 regulator 1 |
| ENSMUSG00000002985 | 11816 | Apoe | −0.574585737 | 0.006755243 | apolipoprotein E |
| ENSMUSG00000022091 | 20410 | Sorbs3 | −0.575196199 | 0.009303766 | sorbin and SH3 domain containing 3 |
| ENSMUSG00000030802 | 12041 | Bckdk | −0.575499645 | 0.001976899 | branched chain ketoacid dehydrogenase kinase |
| ENSMUSG00000084319 | | | −0.575544243 | 0.037076991 | |
| ENSMUSG00000019689 | 66117 | Fmc1 | −0.575587899 | 0.015293069 | formation of mitochondrial complex V assembly factor 1 |
| ENSMUSG00000031807 | 66171 | Pgls | −0.575940743 | 0.041620932 | 6-phosphogluconolactonase |
| ENSMUSG00000025218 | 56626 | Poll | −0.575957324 | 0.041535737 | polymerase (DNA directed), lambda |
| ENSMUSG00000046352 | 14619 | Gjb2 | −0.575974561 | 0.013315984 | gap junction protein, beta 2 |
| ENSMUSG00000028980 | 100198 | H6pd | −0.575999439 | 0.013870995 | hexose-6-phosphate dehydrogenase (glucose 1-dehydrogenase) |
| ENSMUSG00000000531 | 56149 | Grasp | −0.576082225 | 0.002485879 | GRP1 (general receptor for phosphoinositides 1)-associated scaffold protein |
| ENSMUSG00000063576 | 71765 | Klhdc3 | −0.576124748 | 0.015476946 | kelch domain containing 3 |
| ENSMUSG00000060862 | 230848 | Zbtb40 | −0.577473775 | 0.002483237 | zinc finger and BTB domain containing 40 |
| ENSMUSG00000024818 | 107375 | Slc25a45 | −0.577670624 | 0.032546234 | solute carrier family 25, member 45 |
| ENSMUSG00000039195 | 73737 | 1110008P14Rik | −0.577678172 | 0.005587517 | RIKEN cDNA 1110008P14 gene |
| ENSMUSG00000037579 | 16512 | Kcnh3 | −0.578137406 | 0.012390159 | potassium voltage-gated channel, subfamily H (eag-related), member 3 |
| ENSMUSG00000037014 | 20608 | Sstr4 | −0.579404635 | 0.019568593 | somatostatin receptor 4 |
| ENSMUSG00000043811 | 65079 | Rtn4r | −0.579482416 | 0.010154832 | reticulon 4 receptor |
| ENSMUSG00000063802 | 66245 | Hspbp1 | −0.579525188 | 0.032480156 | HSPA (heat shock 70kDa) binding protein, cytoplasmic cochaperone 1 |
| ENSMUSG00000019235 | 238323 | Rps6kl1 | −0.580351996 | 0.004304931 | ribosomal protein S6 kinase-like 1 |
| ENSMUSG00000020260 | 80294 | Pofut2 | −0.580453445 | 0.025337605 | protein O-fucosyltransferase 2 |
| ENSMUSG00000025876 | 107448 | Unc5a | −0.580454089 | 0.02636368 | unc-5 netrin receptor A |
| ENSMUSG00000049521 | 104445 | Cdc42ep1 | −0.581060808 | 0.038405912 | CDC42 effector protein (Rho GTPase binding) 1 |
| ENSMUSG00000013822 | 66126 | Elof1 | −0.581508109 | 0.016217471 | ELF1 homolog, elongation factor 1 |
| ENSMUSG00000027447 | 13010 | Cst3 | −0.581557586 | 0.001900142 | cystatin C |
| ENSMUSG00000044716 | 231134 | Dok7 | −0.582444851 | 0.026364678 | docking protein 7 |
| ENSMUSG00000024777 | 225849 | Ppp2r5b | −0.582466208 | 0.006167019 | protein phosphatase 2, regulatory subunit B', beta |
| ENSMUSG00000035681 | 268345 | Kcnc2 | −0.58253195 | 0.007447036 | potassium voltage gated channel, Shaw-related subfamily, member 2 |
| ENSMUSG00000075702 | 114679 | Selm | −0.582714474 | 0.017856266 | selenoprotein M |
| ENSMUSG00000034854 | 73822 | Mfsd12 | −0.582775806 | 0.013200056 | major facilitator superfamily domain containing 12 |
| ENSMUSG00000028971 | 12854 | Cort | −0.583113238 | 0.034008827 | cortistatin |
| ENSMUSG00000000732 | 50723 | Icosl | −0.58324884 | 0.019701573 | icos ligand |
| ENSMUSG00000027582 | 229007 | Zgpat | −0.583347389 | 0.010556984 | zinc finger, CCCH-type with G patch domain |
| ENSMUSG00000038274 | 14109 | Fau | −0.583404853 | 0.009783693 | Finkel-Biskis-Reilly murine sarcoma virus (FBR-MuSV) ubiquitously expressed (fox derived) |
| ENSMUSG00000062647 | 27176 | Rpl7a | −0.583974458 | 0.003207673 | ribosomal protein L7A |
| ENSMUSG00000029507 | 56361 | Pus1 | −0.584062314 | 0.024966049 | pseudouridine synthase 1 |
| ENSMUSG00000022562 | 75475 | Oplah | −0.584150857 | 0.019717711 | 5-oxoprolinase (ATP-hydrolysing) |
| ENSMUSG00000034220 | 14733 | Gpc1 | −0.584246677 | 0.007288939 | glypican 1 |
| ENSMUSG00000035686 | 21835 | Thrsp | −0.584466029 | 0.000942471 | thyroid hormone responsive |
| ENSMUSG00000000743 | 234852 | Chmp1a | −0.58459013 | 0.000605244 | charged multivesicular body protein 1A |
| ENSMUSG00000036186 | 56279 | Fam69b | −0.584692819 | 0.024672575 | family with sequence similarity 69, member B |
| ENSMUSG00000042558 | 100206 | Adprhl2 | −0.584853242 | 0.033978729 | ADP-ribosylhydrolase like 2 |
| ENSMUSG00000033287 | 72844 | Kctd17 | −0.584856825 | 0.00584403 | potassium channel tetramerisation domain containing 17 |
| ENSMUSG00000031862 | 170759 | Atp13a1 | −0.585083432 | 0.002080874 | ATPase type 13A1 |
| ENSMUSG00000074457 | 67860 | S100a16 | −0.585182439 | 5.35E−08 | S100 calcium binding protein A16 |
| ENSMUSG00000045790 | 100503884 | Ccdc149 | −0.585379757 | 0.001434658 | coiled-coil domain containing 149 |

TABLE 2-continued

| Ensembl | Entrez | Symbol | log2FoldChange | padj | Name |
|---|---|---|---|---|---|
| ENSMUSG00000018008 | 72318 | Cyth4 | −0.586061225 | 0.006594734 | cytohesin 4 |
| ENSMUSG00000024911 | 58249 | Fibp | −0.586165489 | 0.00601558 | fibroblast growth factor (acidic) intracellular binding protein |
| ENSMUSG00000030400 | 13871 | Ercc2 | −0.586212484 | 0.032103417 | excision repair cross-complementing rodent repair deficiency, complementation group 2 |
| ENSMUSG00000045045 | 225875 | Lrfn4 | −0.586302098 | 0.03772696 | leucine rich repeat and fibronectin type III domain containing 4 |
| ENSMUSG00000022175 | 65107 | Lrp10 | −0.586452723 | 0.014793089 | low-density lipoprotein receptor-related protein 10 |
| ENSMUSG00000026209 | 13437 | Dnpep | −0.586601264 | 0.010820876 | aspartyl aminopeptidase |
| ENSMUSG00000002210 | 71997 | Smg9 | −0.586603609 | 0.013155585 | smg-9 homolog, nonsense mediated mRNA decay factor (C. elegans) |
| ENSMUSG00000028051 | 15168 | Hcn3 | −0.586832314 | 0.033409508 | hyperpolarization-activated, cyclic nucleotide-gated K+ 3 |
| ENSMUSG00000005823 | 78308 | Gpr108 | −0.587264881 | 0.013912785 | G protein-coupled receptor 108 |
| ENSMUSG00000002319 | 75751 | Ipo4 | −0.587642494 | 0.001306557 | importin 4 |
| ENSMUSG00000073433 | 14570 | Arhgdig | −0.588029549 | 0.012723172 | Rho GDP dissociation inhibitor (GDI) gamma |
| ENSMUSG00000031788 | 16582 | Kifc3 | −0.588248768 | 0.031599635 | kinesin family member C3 |
| ENSMUSG00000031627 | 16363 | Irf2 | −0.588298418 | 0.004245189 | interferon regulatory factor 2 |
| ENSMUSG00000041859 | 17215 | Mcm3 | −0.589399787 | 0.031060625 | minichromosome maintenance complex component 3 |
| ENSMUSG00000028648 | 595136 | Ndufs5 | −0.589477317 | 0.000980908 | NADH dehydrogenase (ubiquinone) Fe-S protein 5 |
| ENSMUSG00000023019 | 14555 | Gpd1 | −0.589614881 | 0.004890059 | glycerol-3-phosphate dehydrogenase 1 (soluble) |
| ENSMUSG00000027646 | 20779 | Src | −0.589766548 | 0.014376971 | Rous sarcoma oncogene |
| ENSMUSG00000070284 | 331026 | Gmppb | −0.589863142 | 0.026648841 | GDP-mannose pyrophosphorylase B |
| ENSMUSG00000013787 | 110147 | Ehmt2 | −0.590225404 | 0.003623855 | euchromatic histone lysine N-methyltransferase 2 |
| ENSMUSG00000015095 | 30839 | Fbxw5 | −0.590326525 | 0.022286632 | F-box and WD-40 domain protein 5 |
| ENSMUSG00000003872 | 22342 | Lin7b | −0.59048979 | 0.036437189 | lin-7 homolog B (C. elegans) |
| ENSMUSG00000034445 | 225912 | Cyb561a3 | −0.590596272 | 0.013557723 | cytochrome b561 family, member A3 |
| ENSMUSG00000027944 | 23897 | Hax1 | −0.590812623 | 0.00499607 | HCLS1 associated X-1 |
| ENSMUSG00000022414 | 66513 | Tab1 | −0.59097964 | 0.024966049 | TGF-beta activated kinase 1/MAP3K7 binding protein 1 |
| ENSMUSG00000022556 | 15499 | Hsf1 | −0.591002199 | 0.010905565 | heat shock factor 1 |
| ENSMUSG00000018167 | 59045 | Stard3 | −0.591391547 | 0.017691061 | START domain containing 3 |
| ENSMUSG00000063160 | 18223 | Numbl | −0.591509091 | 0.006295462 | numb-like |
| ENSMUSG00000020811 | 216881 | Wscd1 | −0.591560661 | 0.003104002 | WSC domain containing 1 |
| ENSMUSG00000019039 | 67789 | Dalrd3 | −0.591860422 | 0.032645819 | DALR anticodon binding domain containing 3 |
| ENSMUSG00000030695 | 11674 | Aldoa | −0.592518808 | 0.019723205 | aldolase A, fructose-bisphosphate |
| ENSMUSG00000001248 | 52857 | Gramd1a | −0.5925324 | 0.034755427 | GRAM domain containing 1A |
| ENSMUSG00000051864 | 223754 | Tbc1d22a | −0.59290171 | 0.001383253 | TBC1 domain family, member 22a |
| ENSMUSG00000037679 | 70435 | Inf2 | −0.59305162 | 0.003887064 | inverted formin, FH2 and WH2 domain containing |
| ENSMUSG00000028849 | 245877 | Map7d1 | −0.593372882 | 0.002393361 | MAP7 domain containing 1 |
| ENSMUSG00000031930 | 66894 | Wwp2 | −0.593811075 | 0.007291454 | WW domain containing E3 ubiquitin protein ligase 2 |
| ENSMUSG00000075706 | 625249 | Gpx4 | −0.594169162 | 0.001913946 | glutathione peroxidase 4 |
| ENSMUSG00000005881 | 66366 | Ergic3 | −0.594254385 | 0.00892742 | ERGIC and golgi 3 |
| ENSMUSG00000047215 | 20005 | Rpl9 | −0.594573592 | 0.001254458 | ribosomal protein L9 |
| ENSMUSG00000008855 | 15184 | Hdac5 | −0.594677745 | 0.00852341 | histone deacetylase 5 |
| ENSMUSG00000090247 | 14533 | Bloc1s1 | −0.594831475 | 0.011338004 | biogenesis of lysosomal organelles complex-1, subunit 1 |
| ENSMUSG00000021913 | 239017 | Ogdhl | −0.594985492 | 0.000605244 | oxoglutarate dehydrogenase-like |
| ENSMUSG00000021904 | 218877 | Sema3g | −0.595476915 | 0.016005104 | sema domain, immunoglobulin domain (Ig), short basic domain, secreted, (semaphorin) 3G |
| ENSMUSG00000041168 | 74142 | Lonp1 | −0.595601683 | 0.003655288 | lon peptidase 1, mitochondrial |
| ENSMUSG00000035203 | 13854 | Epn1 | −0.595676374 | 0.033316859 | epsin 1 |
| ENSMUSG00000031833 | 546071 | Mast3 | −0.595798851 | 0.034725041 | microtubule associated serine/threonine kinase 3 |
| ENSMUSG00000024870 | 76308 | Rab1b | −0.595812083 | 0.003001153 | RAB1B, member RAS oncogene family |
| ENSMUSG00000040725 | 232989 | Hnrnpul1 | −0.595927712 | 1.69E−05 | heterogeneous nuclear ribonucleoprotein U-like 1 |
| ENSMUSG00000028851 | 18221 | Nudc | −0.596373429 | 0.00078832 | nudC nuclear distribution protein |
| ENSMUSG00000002812 | 14248 | Flii | −0.596433171 | 0.001166017 | flightless I actin binding protein |
| ENSMUSG00000087701 | | | −0.59662535 | 4.65E−06 | |
| ENSMUSG00000068220 | 16852 | Lgals1 | −0.596695304 | 0.033305696 | lectin, galactose binding, soluble 1 |
| ENSMUSG00000036138 | 113868 | Acaa1a | −0.597674183 | 0.013119359 | acetyl-Coenzyme A acyltransferase 1A |
| ENSMUSG00000056629 | 14227 | Fkbp2 | −0.597748135 | 0.012426596 | FK506 binding protein 2 |
| ENSMUSG00000058145 | 233332 | Adamts17 | −0.597909338 | 0.00971298 | a disintegrin-like and metallopeptidase (reprolysin type) with thrombospondin type 1 motif, 17 |
| ENSMUSG00000038463 | 320078 | Olfml2b | −0.597943313 | 0.000804537 | olfactomedin-like 2B |

TABLE 2-continued

| Ensembl | Entrez | Symbol | log2FoldChange | padj | Name |
|---|---|---|---|---|---|
| ENSMUSG00000038011 | 56087 | Dnah10 | −0.597994066 | 0.033742503 | dynein, axonemal, heavy chain 10 |
| ENSMUSG00000020668 | 16570 | Kif3c | −0.598711978 | 0.022343397 | kinesin family member 3C |
| ENSMUSG00000045625 | 239827 | Pigz | −0.598722718 | 0.015210303 | phosphatidylinositol glycan anchor biosynthesis, class Z |
| ENSMUSG00000027612 | 17391 | Mmp24 | −0.598757672 | 0.002238309 | matrix metallopeptidase 24 |
| ENSMUSG00000020520 | 171212 | Galnt10 | −0.599297284 | 0.024611757 | UDP-N-acetyl-alpha-D-galactosamine:polypeptide N-acetylgalactosaminyltransferase 10 |
| ENSMUSG00000052926 | 69724 | Rnaseh2a | −0.599350559 | 0.002777469 | ribonuclease H2, large subunit |
| ENSMUSG00000024170 | 71718 | Telo2 | −0.599446564 | 0.001998408 | telomere maintenance 2 |
| ENSMUSG00000044857 | 224640 | Lemd2 | −0.599688787 | 0.016494733 | LEM domain containing 2 |
| ENSMUSG00000024847 | 11632 | Aip | −0.599725621 | 0.02623425 | aryl-hydrocarbon receptor-interacting protein |
| ENSMUSG00000027649 | 66642 | Ctnnbl1 | −0.600135244 | 8.12E−05 | catenin, beta like 1 |
| ENSMUSG00000037761 | 109275 | Actr5 | −0.600393626 | 0.030957083 | ARP5 actin-related protein 5 |
| ENSMUSG00000050552 | 66096 | Lamtor4 | −0.600674391 | 0.009017867 | late endosomal/lysosomal adaptor, MAPK and MTOR activator 4 |
| ENSMUSG00000039936 | 18707 | Pik3cd | −0.600809954 | 0.01670801 | phosphatidylinositol 3-kinase catalytic delta polypeptide |
| ENSMUSG00000025204 | 67264 | Ndufb8 | −0.600856457 | 4.11E−06 | NADH dehydrogenase (ubiquinone) 1 beta subcomplex 8 |
| ENSMUSG00000053395 | 81905 | Cacng8 | −0.601293002 | 0.008378227 | calcium channel, voltage-dependent, gamma subunit 8 |
| ENSMUSG00000022174 | 13135 | Dad1 | −0.601295982 | 0.001338823 | defender against cell death 1 |
| ENSMUSG00000079442 | 20448 | St6galnac4 | −0.601440307 | 0.001575172 | ST6 (alpha-N-acetyl-neuraminyl-2,3-beta-galactosyl-1,3)-N-acetylgalactosaminide alpha-2,6-sialyltransferase 4 |
| ENSMUSG00000027859 | 18049 | Ngf | −0.60158719 | 0.030308838 | nerve growth factor |
| ENSMUSG00000047485 | 245683 | Klhl34 | −0.602890249 | 0.003016938 | kelch-like 34 |
| ENSMUSG00000037530 | 21345 | Tagln | −0.602908006 | 0.02432179 | transgelin |
| ENSMUSG00000019428 | 14232 | Fkbp8 | −0.60292571 | 0.005713467 | FK506 binding protein 8 |
| ENSMUSG00000075279 | | | −0.603020075 | 0.016426155 | |
| ENSMUSG00000074738 | 230991 | Fndc10 | −0.603048276 | 0.015293069 | fibronectin type III domain containing 10 |
| ENSMUSG00000019254 | 232807 | Ppp1r12c | −0.60321551 | 0.002437518 | protein phosphatase 1, regulatory (inhibitor) subunit 12C |
| ENSMUSG00000066621 | 70381 | Tecpr1 | −0.603892726 | 0.002356321 | tectonin beta-propeller repeat containing 1 |
| ENSMUSG00000028973 | 74610 | Abcb8 | −0.604221455 | 0.009349993 | ATP-binding cassette, sub-family B (MDR/TAP), member 8 |
| ENSMUSG00000025733 | 214952 | Rhot2 | −0.604397317 | 0.000310253 | ras homolog family member T2 |
| ENSMUSG00000028538 | 20441 | St3gal3 | −0.604401012 | 0.003210676 | ST3 beta-galactoside alpha-2,3-sialyltransferase 3 |
| ENSMUSG00000024112 | 58226 | Cacna1h | −0.604731533 | 0.006404251 | calcium channel, voltage-dependent, T type, alpha 1H subunit |
| ENSMUSG00000024327 | 14977 | Slc39a7 | −0.604938713 | 0.001418094 | solute carrier family 39 (zinc transporter), member 7 |
| ENSMUSG00000076441 | 11898 | Ass1 | −0.605111848 | 0.005686536 | argininosuccinate synthetase 1 |
| ENSMUSG00000092417 | 81845 | Gpank1 | −0.605335172 | 0.019103418 | G patch domain and ankyrin repeats 1 |
| ENSMUSG00000007783 | 78070 | Cpt1c | −0.605516753 | 0.004484016 | carnitine palmitoyltransferase 1c |
| ENSMUSG00000040472 | 56187 | Rabggta | −0.605555512 | 0.001968877 | Rab geranylgeranyl transferase, a subunit |
| ENSMUSG00000003072 | 66043 | Atp5d | −0.605649842 | 0.029269343 | ATP synthase, H+ transporting, mitochondrial F1 complex, delta subunit |
| ENSMUSG00000028444 | 12804 | Cntfr | −0.605768757 | 0.005176581 | ciliary neurotrophic factor receptor |
| ENSMUSG00000059518 | 70103 | Znhit1 | −0.6060308 | 0.016334183 | zinc finger, HIT domain containing 1 |
| ENSMUSG00000057342 | 56632 | Sphk2 | −0.606199965 | 0.00852341 | sphingosine kinase 2 |
| ENSMUSG00000026259 | 53972 | Ngef | −0.606450534 | 0.001662173 | neuronal guanine nucleotide exchange factor |
| ENSMUSG00000002768 | 17256 | Mea1 | −0.607076669 | 0.004370344 | male enhanced antigen 1 |
| ENSMUSG00000039615 | 56424 | Stub1 | −0.60729883 | 0.001801515 | STIP1 homology and U-Box containing protein 1 |
| ENSMUSG00000020473 | 11568 | Aebp1 | −0.607356466 | 0.02900422 | AE binding protein 1 |
| ENSMUSG00000028876 | 230735 | Epha10 | −0.607473775 | 0.004376521 | Eph receptor A10 |
| ENSMUSG00000037089 | 73836 | Slc35b2 | −0.607642371 | 0.005965958 | solute carrier family 35, member B2 |
| ENSMUSG00000021061 | 20741 | Sptb | −0.608022584 | 8.41E−05 | spectrin beta, erythrocytic |
| ENSMUSG00000078789 | 116905 | Dph1 | −0.608285394 | 0.0125064 | diphthamide biosynthesis 1 |
| ENSMUSG00000026179 | 56695 | Pnkd | −0.608911242 | 0.003761207 | paroxysmal nonkinesiogenic dyskinesia |
| ENSMUSG00000002524 | 67959 | Puf60 | −0.609586526 | 0.002391979 | poly-U binding splicing factor 60 |
| ENSMUSG00000008348 | 22190 | Ubc | −0.609611973 | 0.030906143 | ubiquitin C |
| ENSMUSG00000037563 | 20055 | Rps16 | −0.609667744 | 0.000291652 | ribosomal protein S16 |
| ENSMUSG00000058441 | 406218 | Panx2 | −0.609812365 | 0.023209714 | pannexin 2 |
| ENSMUSG00000001289 | 56612 | Pfdn5 | −0.610151803 | 0.000250755 | prefoldin 5 |
| ENSMUSG00000016344 | 66496 | Ppdpf | −0.610393992 | 0.005856448 | pancreatic progenitor cell differentiation and proliferation factor |
| ENSMUSG00000039660 | 227695 | Spout1 | −0.610446294 | 0.009746584 | SPOUT domain containing methyltransferase 1 |

TABLE 2-continued

| Ensembl | Entrez | Symbol | log2FoldChange | padj | Name |
|---|---|---|---|---|---|
| ENSMUSG00000055805 | 57778 | Fmnl1 | −0.610753826 | 0.012858283 | formin-like 1 |
| ENSMUSG00000023017 | 11419 | Asic1 | −0.610773963 | 0.001150495 | acid-sensing (proton-gated) ion channel 1 |
| ENSMUSG00000087408 | 14559 | Gdf1 | −0.610949998 | 0.026466237 | growth differentiation factor 1 |
| ENSMUSG00000029449 | 23912 | Rhof | −0.611271911 | 0.008593727 | ras homolog family member F (in filopodia) |
| ENSMUSG00000035754 | 216156 | Wdr18 | −0.611747268 | 0.003245063 | WD repeat domain 18 |
| ENSMUSG00000072620 | 20556 | Slfn2 | −0.612389825 | 0.006170952 | schlafen 2 |
| ENSMUSG00000043448 | 118454 | Gjc2 | −0.61269081 | 0.019275697 | gap junction protein, gamma 2 |
| ENSMUSG00000020133 | 66374 | 2310011J03Rik | −0.612805487 | 0.012977493 | RIKEN cDNA 2310011J03 gene |
| ENSMUSG00000024773 | 329015 | Atg2a | −0.61302723 | 0.023522014 | autophagy related 2A |
| ENSMUSG00000040097 | 224613 | Flywch1 | −0.614918609 | 0.011462086 | FLYWCH-type zinc finger 1 |
| ENSMUSG00000020591 | 18217 | Ntsr2 | −0.615127744 | 0.000186491 | neurotensin receptor 2 |
| ENSMUSG00000025175 | 63828 | Fn3k | −0.615580809 | 0.006235384 | fructosamine 3 kinase |
| ENSMUSG00000079677 | 68165 | Fdx1l | −0.615587705 | 0.018472842 | ferredoxin 1-like |
| ENSMUSG00000055044 | 54132 | Pdlim1 | −0.616584153 | 0.006967342 | PDZ and LIM domain 1 (elfin) |
| ENSMUSG00000024158 | 14651 | Hagh | −0.61737276 | 0.000998199 | hydroxyacyl glutathione hydrolase |
| ENSMUSG00000073879 | | | −0.617484874 | 0.012181426 | |
| ENSMUSG00000031328 | 192176 | Flna | −0.617750678 | 7.85E−05 | filamin, alpha |
| ENSMUSG00000047675 | 20116 | Rps8 | −0.617906605 | 0.002590106 | ribosomal protein S8 |
| ENSMUSG00000073434 | 106618 | Wdr90 | −0.618586587 | 0.014233443 | WD repeat domain 90 |
| ENSMUSG00000073422 | 14979 | H2-Ke6 | −0.618625085 | 0.018568298 | H2-K region expressed gene 6 |
| ENSMUSG00000011096 | 67605 | Akt1s1 | −0.618937093 | 0.009753505 | AKT1 substrate 1 (proline-rich) |
| ENSMUSG00000022551 | 66445 | Cyc1 | −0.619446316 | 0.007645477 | cytochrome c-1 |
| ENSMUSG00000013646 | 79566 | Sh3bp5l | −0.619538419 | 0.009351345 | SH3 binding domain protein 5 like |
| ENSMUSG00000001910 | 66830 | Nacc1 | −0.619906563 | 0.002080874 | nucleus accumbens associated 1, BEN and BTB (POZ) domain containing |
| ENSMUSG00000022558 | 223658 | Mroh1 | −0.620513964 | 0.003780714 | maestro heat-like repeat family member 1 |
| ENSMUSG00000039308 | 17423 | Ndst2 | −0.620629869 | 0.001181038 | N-deacetylase/N-sulfotransferase (heparan glucosaminyl) 2 |
| ENSMUSG00000029624 | 71799 | Ptcd1 | −0.620717352 | 0.012314063 | pentatricopeptide repeat domain 1 |
| ENSMUSG00000038690 | 57423 | Atp5j2 | −0.62099136 | 0.002126936 | ATP synthase, H+ transporting, mitochondrial F0 complex, subunit F2 |
| ENSMUSG00000051107 | | | −0.621168787 | 0.005714515 | |
| ENSMUSG00000029598 | 71772 | Plbd2 | −0.621639845 | 0.016059298 | phospholipase B domain containing 2 |
| ENSMUSG00000046330 | 19981 | Rpl37a | −0.621893661 | 0.001404895 | ribosomal protein L37a |
| ENSMUSG00000019054 | 66437 | Fis1 | −0.62189367 | 0.003036844 | fission, mitochondrial 1 |
| ENSMUSG00000004929 | 50492 | Thop1 | −0.621901784 | 0.027743402 | thimet oligopeptidase 1 |
| ENSMUSG00000030744 | 27050 | Rps3 | −0.62315274 | 0.001063449 | ribosomal protein S3 |
| ENSMUSG00000001227 | 20359 | Sema6b | −0.624554362 | 0.018129063 | sema domain, transmembrane domain (TM), and cytoplasmic domain, (semaphorin) 6B |
| ENSMUSG00000024736 | 98170 | Tmem132a | −0.624679251 | 0.011423699 | transmembrane protein 132A |
| ENSMUSG00000046480 | 399548 | Scn4b | −0.624944731 | 2.32E−05 | sodium channel, type IV, beta |
| ENSMUSG00000034595 | 76448 | Ppp1r18 | −0.625263187 | 0.023018223 | protein phosphatase 1, regulatory subunit 18 |
| ENSMUSG00000062906 | 170787 | Hdac10 | −0.625281494 | 0.022291905 | histone deacetylase 10 |
| ENSMUSG00000035228 | 232821 | Ccdc106 | −0.62543387 | 0.025965553 | coiled-coil domain containing 106 |
| ENSMUSG00000035674 | 66091 | Ndufa3 | −0.625682913 | 0.00574018 | NADH dehydrogenase (ubiquinone) 1 alpha subcomplex, 3 |
| ENSMUSG00000035863 | 18483 | Palm | −0.625800734 | 0.018707041 | paralemmin |
| ENSMUSG00000040759 | 67272 | Cmtm5 | −0.626261164 | 0.00445791 | CKLF-like MARVEL transmembrane domain containing 5 |
| ENSMUSG00000017417 | 72324 | Plxdc1 | −0.626350428 | 0.026648841 | plexin domain containing 1 |
| ENSMUSG00000017167 | 53321 | Cntnap1 | −0.626453113 | 0.001181038 | contactin associated protein-like 1 |
| ENSMUSG00000022551 | 20401 | Sh3bp1 | −0.626671085 | 0.024448559 | SH3-domain binding protein 1 |
| ENSMUSG00000027297 | 17005 | Ltk | −0.627128476 | 0.005774001 | leukocyte tyrosine kinase |
| ENSMUSG00000003813 | 19358 | Rad23a | −0.627999713 | 0.000869645 | RAD23 homolog A, nucleotide excision repair protein |
| ENSMUSG00000029723 | 78829 | Tsc22d4 | −0.628530138 | 0.017512637 | TSC22 domain family, member 4 |
| ENSMUSG00000027502 | 66404 | Rtfdc1 | −0.628592965 | 0.005001218 | replication termination factor 2 domain containing 1 |
| ENSMUSG00000066440 | 211978 | Zfyve26 | −0.629051643 | 0.005328626 | zinc finger, FYVE domain containing 26 |
| ENSMUSG00000037992 | 19401 | Rara | −0.629815844 | 0.024688022 | retinoic acid receptor, alpha |
| ENSMUSG00000002307 | 13163 | Daxx | −0.630024056 | 0.000541508 | Fas death domain-associated protein |
| ENSMUSG00000025651 | 22273 | Uqcrc1 | −0.630418801 | 0.022687539 | ubiquinol-cytochrome c reductase core protein 1 |
| ENSMUSG00000016349 | 13628 | Eef1a2 | −0.630634736 | 0.01775059 | eukaryotic translation elongation factor 1 alpha 2 |
| ENSMUSG00000033955 | 228140 | Tnks1bp1 | −0.630802165 | 0.0049917 | tankyrase 1 binding protein 1 |
| ENSMUSG00000020331 | 15166 | Hcn2 | −0.631099708 | 0.002238309 | hyperpolarization-activated, cyclic nucleotide-gated K+ 2 |
| ENSMUSG00000032556 | 107993 | Bfsp2 | −0.631318318 | 0.018672334 | beaded filament structural protein 2, phakinin |
| ENSMUSG00000050721 | 102595 | Plekho2 | −0.631455118 | 0.021670961 | pleckstrin homology domain containing, family O member 2 |
| ENSMUSG00000003346 | 216169 | Abhd17a | −0.631693066 | 0.025364617 | abhydrolase domain containing 17A |
| ENSMUSG00000028937 | 70025 | Acot7 | −0.631771962 | 0.005053643 | acyl-CoA thioesterase 7 |

TABLE 2-continued

| Ensembl | Entrez | Symbol | log2FoldChange | padj | Name |
|---|---|---|---|---|---|
| ENSMUSG00000050708 | 14325 | Ftl1 | −0.631878303 | 0.024169919 | ferritin light polypeptide 1 |
| ENSMUSG00000032185 | 59035 | Carm1 | −0.631935626 | 0.002200325 | coactivator-associated arginine methyltransferase 1 |
| ENSMUSG00000040323 | | | −0.632027363 | 0.020420753 | |
| ENSMUSG00000059734 | 225887 | Ndufs8 | −0.632232257 | 0.011706934 | NADH dehydrogenase (ubiquinone) Fe-S protein 8 |
| ENSMUSG00000060216 | 216869 | Arrb2 | −0.632290886 | 0.002743257 | arrestin, beta 2 |
| ENSMUSG00000050822 | 243328 | Slc29a4 | −0.632386317 | 0.006446155 | solute carrier family 29 (nucleoside transporters), member 4 |
| ENSMUSG00000022428 | 73739 | Cby1 | −0.632790976 | 0.008063658 | chibby homolog 1 (Drosophila) |
| ENSMUSG00000041378 | 12741 | Cldn5 | −0.633836987 | 0.022793857 | claudin 5 |
| ENSMUSG00000044628 | 68846 | Rnf208 | −0.634064897 | 0.024672575 | ring finger protein 208 |
| ENSMUSG00000003352 | 12297 | Cacnb3 | −0.634182033 | 0.006136465 | calcium channel, voltage-dependent, beta 3 subunit |
| ENSMUSG00000097006 | 638247 | 9530082P21Rik | −0.63422725 | 0.007916903 | RIKEN cDNA 9530082P21 gene |
| ENSMUSG00000053565 | 73830 | Eif3k | −0.634842192 | 0.005922988 | eukaryotic translation initiation factor 3, subunit K |
| ENSMUSG00000036199 | 67184 | Ndufa13 | −0.634997381 | 0.01946358 | NADH dehydrogenase (ubiquinone) 1 alpha subcomplex, 13 |
| ENSMUSG00000036073 | 14430 | Galt | −0.635010933 | 0.00376467 | galactose-1-phosphate uridyl transferase |
| ENSMUSG00000057789 | 12018 | Bak1 | −0.635551689 | 0.014455417 | BCL2-antagonist/killer 1 |
| ENSMUSG00000013367 | 210094 | Iglon5 | −0.635696369 | 0.015933498 | IgLON family member 5 |
| ENSMUSG00000011877 | 216963 | Git1 | −0.636339309 | 0.003682929 | G protein-coupled receptor kinase-interactor 1 |
| ENSMUSG00000080268 | 107392 | Brms1 | −0.63905559 | 0.015941294 | breast cancer metastasis-suppressor 1 |
| ENSMUSG00000035237 | 16816 | Lcat | −0.639140168 | 0.005081029 | lecithin cholesterol acyltransferase |
| ENSMUSG00000004056 | 11652 | Akt2 | −0.639506687 | 0.000186491 | thymoma viral proto-oncogene 2 |
| ENSMUSG00000020831 | 104457 | 0610010K14Rik | −0.63422725 | 0.007916903 | RIKEN cDNA 9530082P21 gene |
| ENSMUSG00000028664 | 13844 | Ephb2 | −0.641497793 | 0.011257904 | Eph receptor B2 |
| ENSMUSG00000036052 | 56323 | Dnajb5 | −0.641638513 | 0.001063449 | DnaJ heat shock protein family (Hsp40) member B5 |
| ENSMUSG00000002833 | 15193 | Hdgfrp2 | −0.641921398 | 0.001768632 | hepatoma-derived growth factor, related protein 2 |
| ENSMUSG00000034908 | 214597 | Sidt2 | −0.642345851 | 0.001026104 | SID1 transmembrane family, member 2 |
| ENSMUSG00000017754 | 18830 | Pltp | −0.642375392 | 0.006434883 | phospholipid transfer protein |
| ENSMUSG00000020087 | 71767 | Tysnd1 | −0.642688892 | 0.006172045 | trypsin domain containing 1 |
| ENSMUSG00000023707 | 66627 | Ogfod2 | −0.644066417 | 0.002934641 | 2-oxoglutarate and iron-dependent oxygenase domain containing 2 |
| ENSMUSG00000032480 | 72831 | Dhx30 | −0.644209389 | 0.018743104 | DEAH (Asp-Glu-Ala-His) box polypeptide 30 |
| ENSMUSG00000026799 | 68975 | Med27 | −0.644363918 | 0.001441714 | mediator complex subunit 27 |
| ENSMUSG00000062563 | 12879 | Cys1 | −0.644651751 | 0.001312062 | cystin 1 |
| ENSMUSG00000022564 | 66168 | Grina | −0.645637734 | 0.004568734 | glutamate receptor, ionotropic, N-methyl D-aspartate-associated protein 1 (glutamate binding) |
| ENSMUSG00000039838 | 242773 | Slc45a1 | −0.645653668 | 0.004198828 | solute carrier family 45, member 1 |
| ENSMUSG00000038393 | 56338 | Txnip | −0.645818648 | 3.88E−06 | thioredoxin interacting protein |
| ENSMUSG00000042729 | 107071 | Wdr74 | −0.645846206 | 0.001694389 | WD repeat domain 74 |
| ENSMUSG00000036748 | 67116 | Cuedc2 | −0.646259672 | 0.004307817 | CUE domain containing 2 |
| ENSMUSG00000024941 | 78891 | Scyl1 | −0.646404011 | 0.00826777 | SCY1-like 1 (S. cerevisiae) |
| ENSMUSG00000010057 | 56032 | Nprl2 | −0.647023089 | 0.006202355 | nitrogen permease regulator-like 2 |
| ENSMUSG00000022565 | 18810 | Plec | −0.647329975 | 0.003471695 | plectin |
| ENSMUSG00000072214 | 18951 | 5-Sep | −0.647714358 | 0.002845741 | septin 5 |
| ENSMUSG00000030410 | 13401 | Dmwd | −0.64788725 | 0.002163585 | dystrophia myotonica-containing WD repeat motif |
| ENSMUSG00000002660 | 53895 | Clpp | −0.648551911 | 0.002747619 | caseinolytic mitochondrial matrix peptidase proteolytic subunit |
| ENSMUSG00000031818 | 12857 | Cox4i1 | −0.648822521 | 0.001998408 | cytochrome c oxidase subunit IV isoform 1 |
| ENSMUSG00000035637 | 76238 | Grhpr | −0.649713183 | 0.005318466 | glyoxylate reductase/hydroxypyruvate reductase |
| ENSMUSG00000028758 | 16559 | Kif17 | −0.649862566 | 0.016699692 | kinesin family member 17 |
| ENSMUSG00000026307 | 50880 | Scly | −0.651113311 | 0.001417258 | selenocysteine lyase |
| ENSMUSG00000029166 | 100732 | Mapre3 | −0.651745093 | 0.004076949 | microtubule-associated protein, RP/EB family, member 3 |
| ENSMUSG00000056665 | 223626 | Them6 | −0.651909929 | 0.014878079 | thioesterase superfamily member 6 |
| ENSMUSG00000052146 | 67097 | Rps10 | −0.651940547 | 0.003210676 | ribosomal protein S10 |
| ENSMUSG00000040964 | 72754 | Arhgef10l | −0.652807628 | 0.000325542 | Rho guanine nucleotide exchange factor (GEF) 10-like |
| ENSMUSG00000002205 | 101568 | Vrk3 | −0.65303364 | 0.000368076 | vaccinia related kinase 3 |
| ENSMUSG00000020277 | 18641 | Pfkl | −0.653183293 | 0.002895288 | phosphofructokinase, liver, B-type |
| ENSMUSG00000030714 | 75565 | Sgf29 | −0.653283949 | 0.014879682 | SAGA complex associated factor 29 |
| ENSMUSG00000079598 | 665180 | Clec2l | −0.653318295 | 0.009648501 | C-type lectin domain family 2, member L |
| ENSMUSG00000020886 | 13385 | Dlg4 | −0.653750701 | 0.002391979 | discs, large homolog 4 (Drosophila) |
| ENSMUSG00000047417 | 66932 | Rexo1 | −0.654697039 | 0.016701264 | REX1, RNA exonuclease 1 |
| ENSMUSG00000024958 | 107173 | Gpr137 | −0.654883496 | 0.010229154 | G protein-coupled receptor 137 |

TABLE 2-continued

| Ensembl | Entrez | Symbol | log2FoldChange | padj | Name |
|---|---|---|---|---|---|
| ENSMUSG00000050821 | 78408 | Fam131a | −0.655280724 | 0.001345392 | family with sequence similarity 131, member A |
| ENSMUSG00000029603 | 14357 | Dtx1 | −0.655560092 | 0.013405766 | deltex 1, E3 ubiquitin ligase |
| ENSMUSG00000028917 | 69582 | Plekhm2 | −0.656010336 | 0.007447036 | pleckstrin homology domain containing, family M (with RUN domain) member 2 |
| ENSMUSG00000049482 | 66965 | Ctu2 | −0.656187473 | 0.020101173 | cytosolic thiouridylase subunit 2 |
| ENSMUSG00000034472 | 75141 | Rasd2 | −0.6570002 | 3.72E−08 | RASD family, member 2 |
| ENSMUSG00000028931 | 16498 | Kcnab2 | −0.657718304 | 0.000222519 | potassium voltage-gated channel, shaker-related subfamily, beta member 2 |
| ENSMUSG00000061111 | 192173 | Fam195b | −0.65832679 | 0.010725345 | family with sequence similarity 195, member B |
| ENSMUSG00000024570 | 68731 | Rbfa | −0.658634765 | 0.003811837 | ribosome binding factor A |
| ENSMUSG00000003546 | 74764 | Klc4 | −0.65878002 | 0.016392072 | kinesin light chain 4 |
| ENSMUSG00000074634 | 633640 | Tmem267 | −0.660912249 | 0.0125533 | transmembrane protein 267 |
| ENSMUSG00000004895 | 94315 | Prcc | −0.661535474 | 0.000950055 | papillary renal cell carcinoma (translocation-associated) |
| ENSMUSG00000004892 | 12032 | Bcan | −0.661667195 | 0.001301669 | brevican |
| ENSMUSG00000029712 | 83766 | Actl6b | −0.662011057 | 0.007291454 | actin-like 6B |
| ENSMUSG00000022557 | 12181 | Bop1 | −0.663032163 | 0.001306557 | block of proliferation 1 |
| ENSMUSG00000037916 | 17995 | Ndufv1 | −0.663228228 | 0.001340294 | NADH dehydrogenase (ubiquinone) flavoprotein 1 |
| ENSMUSG00000038521 | 50908 | C1s1 | −0.6636604 | 0.016699777 | complement component 1, s subcomponent 1 |
| ENSMUSG00000049760 | 224904 | 2410015M20Rik | −0.663663147 | 0.002296608 | RIKEN cDNA 2410015M20 gene |
| ENSMUSG00000006057 | 11951 | Atp5g1 | −0.663699041 | 0.012691029 | ATP synthase, H+ transporting, mitochondrial F0 complex, subunit C1 (subunit 9) |
| ENSMUSG00000006476 | 56876 | Nsmf | −0.664437408 | 0.000452634 | NMDA receptor synaptonuclear signaling and neuronal migration factor |
| ENSMUSG00000032796 | 16772 | Lama1 | −0.664621098 | 0.004360096 | laminin, alpha 1 |
| ENSMUSG00000030533 | 101869 | Unc45a | −0.665654615 | 0.010021535 | unc-45 myosin chaperone A |
| ENSMUSG00000000253 | 66355 | Gmpr | −0.665871519 | 0.001938468 | guanosine monophosphate reductase |
| ENSMUSG00000027763 | 56758 | Mbnl1 | −0.665999159 | 0.013444742 | muscleblind-like 1 (*Drosophila*) |
| ENSMUSG00000063904 | 75221 | Dpp3 | −0.666260679 | 0.004393496 | dipeptidylpeptidase 3 |
| ENSMUSG00000021957 | 21881 | Tkt | −0.666652033 | 0.003845974 | transketolase |
| ENSMUSG00000025737 | 268933 | Wdr24 | −0.668189749 | 0.012390159 | WD repeat domain 24 |
| ENSMUSG00000019370 | 12315 | Calm3 | −0.668238518 | 0.000418204 | calmodulin 3 |
| ENSMUSG00000057963 | 217837 | Itpk1 | −0.668389071 | 0.007160883 | inositol 1,3,4-triphosphate 5/6 kinase |
| ENSMUSG00000051067 | 237403 | Lingo3 | −0.668745473 | 3.83E−08 | leucine rich repeat and Ig domain containing 3 |
| ENSMUSG00000027932 | 26568 | Slc27a3 | −0.669546933 | 0.017512637 | solute carrier family 27 (fatty acid transporter), member 3 |
| ENSMUSG00000031848 | 50783 | Lsm4 | −0.669748952 | 0.01721585 | LSM4 homolog, U6 small nuclear RNA and mRNA degradation associated |
| ENSMUSG00000040414 | 246696 | Slc25a28 | −0.670100482 | 0.00560995 | solute carrier family 25, member 28 |
| ENSMUSG00000037032 | 11785 | Apbb1 | −0.670799313 | 0.015891051 | amyloid beta (A4) precursor protein-binding, family B, member 1 |
| ENSMUSG00000024914 | 66556 | Drap1 | −0.67217516 | 0.002947909 | Dr1 associated protein 1 (negative cofactor 2 alpha) |
| ENSMUSG00000053398 | 236539 | Phgdh | −0.672669677 | 0.000735754 | 3-phosphoglycerate dehydrogenase |
| ENSMUSG00000020755 | 57230 | Sap30bp | −0.673300922 | 8.96E−05 | SAP30 binding protein |
| ENSMUSG00000022443 | 17886 | Myh9 | −0.673995363 | 1.37E−06 | myosin, heavy polypeptide 9, non-muscle |
| ENSMUSG00000007950 | 64296 | Abhd8 | −0.674953625 | 0.015176592 | abhydrolase domain containing 8 |
| ENSMUSG00000002279 | 76483 | Lmf1 | −0.675191743 | 0.011256294 | lipase maturation factor 1 |
| ENSMUSG00000024608 | 20044 | Rps14 | −0.67568793 | 0.000665254 | ribosomal protein S14 |
| ENSMUSG00000039345 | 239706 | Mettl22 | −0.676058983 | 0.003481044 | methyltransferase like 22 |
| ENSMUSG00000038390 | 14788 | Gpr162 | −0.676621608 | 0.013546635 | G protein-coupled receptor 162 |
| ENSMUSG00000028857 | 52174 | Tmem222 | −0.676834652 | 0.00336981 | transmembrane protein 222 |
| ENSMUSG00000034685 | 217219 | Fam171a2 | −0.678148991 | 0.016376632 | family with sequence similarity 171, member A2 |
| ENSMUSG00000066724 | | | −0.678298566 | 0.008509909 | |
| ENSMUSG00000034994 | 13629 | Eef2 | −0.678980585 | 0.009303766 | eukaryotic translation elongation factor 2 |
| ENSMUSG00000027602 | 66734 | Map1lc3a | −0.680256141 | 0.01044046 | microtubule-associated protein 1 light chain 3 alpha |
| ENSMUSG00000030086 | 66098 | Chchd6 | −0.680706634 | 0.004877014 | coiled-coil-helix-coiled-coil-helix domain containing 6 |
| ENSMUSG00000029544 | 29867 | Cabp1 | −0.680832801 | 0.011630092 | calcium binding protein 1 |
| ENSMUSG00000022760 | 69009 | Thap7 | −0.681032519 | 0.002170917 | THAP domain containing 7 |
| ENSMUSG00000030741 | 73658 | Spns1 | −0.681243269 | 0.010090704 | spinster homolog 1 |
| ENSMUSG00000019659 | 72654 | Ccdc12 | −0.681736615 | 0.01594855 | coiled-coil domain containing 12 |
| ENSMUSG00000019470 | 67439 | Xab2 | −0.68183093 | 0.006755243 | XPA binding protein 2 |
| ENSMUSG00000018634 | 12921 | Crhr1 | −0.681962795 | 0.002365415 | corticotropin releasing hormone receptor 1 |

TABLE 2-continued

| Ensembl | Entrez | Symbol | log2FoldChange | padj | Name |
|---|---|---|---|---|---|
| ENSMUSG00000016554 | 55944 | Eif3d | −0.682435597 | 0.000694718 | eukaryotic translation initiation factor 3, subunit D |
| ENSMUSG00000003345 | 103236 | Csnk1g2 | −0.68367942 | 0.003780714 | casein kinase 1, gamma 2 |
| ENSMUSG00000024792 | 81909 | Zfpl1 | −0.684416986 | 0.00972421 | zinc finger like protein 1 |
| ENSMUSG00000028466 | 12913 | Creb3 | −0.685128638 | 0.000523977 | cAMP responsive element binding protein 3 |
| ENSMUSG00000040435 | 17872 | Ppp1r15a | −0.685304172 | 0.004568734 | protein phosphatase 1, regulatory (inhibitor) subunit 15A |
| ENSMUSG00000037204 | 68118 | Atg101 | −0.686631869 | 0.003641705 | autophagy related 101 |
| ENSMUSG00000067889 | 20743 | Sptbn2 | −0.686798854 | 0.000151612 | spectrin beta, non-erythrocytic 2 |
| ENSMUSG00000088789 | 100306943 | Scarna13 | −0.687471288 | 0.002590106 | small Cajal body-specific RNA 1 |
| ENSMUSG00000028796 | 54383 | Phc2 | −0.688145163 | 0.007569893 | polyhomeotic-like 2 (Drosophila) |
| ENSMUSG00000036599 | 59031 | Chst12 | −0.689019017 | 0.006708852 | carbohydrate sulfotransferase 12 |
| ENSMUSG00000028749 | 26971 | Pla2g2f | −0.689186532 | 0.014394062 | phospholipase A2, group IIF |
| ENSMUSG00000028833 | 26562 | Ncdn | −0.689219413 | 0.009551105 | neurochondrin |
| ENSMUSG00000020810 | 114886 | Cygb | −0.689320205 | 0.006608503 | cytoglobin |
| ENSMUSG00000056185 | 225861 | Snx32 | −0.689614085 | 0.004088241 | sorting nexin 32 |
| ENSMUSG00000002372 | 71810 | Ranbp3 | −0.689805749 | 0.006738514 | RAN binding protein 3 |
| ENSMUSG00000030007 | 12468 | Cct7 | −0.690317946 | 0.010643999 | chaperonin containing Tcp1, subunit 7 (eta) |
| ENSMUSG00000018974 | 53890 | Sart3 | −0.69117541 | 0.000222519 | squamous cell carcinoma antigen recognized by T cells 3 |
| ENSMUSG00000003808 | 66590 | Farsa | −0.692111324 | 0.000998199 | phenylalanyl-tRNA synthetase, alpha subunit |
| ENSMUSG00000005354 | 56551 | Txn2 | −0.692290517 | 0.001276768 | thioredoxin 2 |
| ENSMUSG00000032583 | 72825 | Mon1a | −0.692897386 | 0.014297364 | MON1 homolog A, secretory trafficking associated |
| ENSMUSG00000000753 | 20317 | Serpinf1 | −0.693304223 | 0.0015457 | serine (or cysteine) peptidase inhibitor, clade F, member 1 |
| ENSMUSG00000033594 | 78779 | Spata21 | −0.694167537 | 0.0037729 | spermatogenesis associated 2-like |
| ENSMUSG00000030584 | 29861 | Dpf1 | −0.695499807 | 0.005260245 | D4, zinc and double PHD fingers family 1 |
| ENSMUSG00000078619 | 83796 | Smarcd2 | −0.696646857 | 0.00125674 | SWI/SNF related, matrix associated, actin dependent regulator of chromatin, subfamily d, member 2 |
| ENSMUSG00000000530 | 11482 | Acvrl1 | −0.696976022 | 0.006423148 | activin A receptor, type II-like 1 |
| ENSMUSG00000021494 | 72935 | Ddx41 | −0.698073609 | 0.004331665 | DEAD (Asp-Glu-Ala-Asp) box polypeptide 41 |
| ENSMUSG00000017774 | 17913 | Myo1c | −0.698393716 | 0.000600147 | myosin IC |
| ENSMUSG00000006276 | 13859 | Eps15l1 | −0.698752812 | 0.011966178 | epidermal growth factor receptor pathway substrate 15-like 1 |
| ENSMUSG00000032060 | 12955 | Cryab | −0.699556083 | 0.001683662 | crystallin, alpha B |
| ENSMUSG00000036733 | 68035 | Rbm42 | −0.699704923 | 0.003780714 | RNA binding motif protein 42 |
| ENSMUSG00000025509 | 66853 | Pnpla2 | −0.699778459 | 0.012390159 | patatin-like phospholipase domain containing 2 |
| ENSMUSG00000027488 | 20648 | Snta1 | −0.70132101 | 0.001537324 | syntrophin, acidic 1 |
| ENSMUSG00000035783 | 11475 | Acta2 | −0.70133359 | 0.004187848 | actin, alpha 2, smooth muscle, aorta |
| ENSMUSG00000033006 | 20665 | Sox10 | −0.702590215 | 0.000556123 | SRY (sex determining region Y)-box 10 |
| ENSMUSG00000038354 | 213121 | Ankrd35 | −0.70387362 | 0.002044759 | ankyrin repeat domain 35 |
| ENSMUSG00000026697 | 17926 | Myoc | −0.7041283 | 0.000558417 | myocilin |
| ENSMUSG00000018459 | 114644 | Slc13a3 | −0.705044298 | 0.000407201 | solute carrier family 13 (sodium-dependent dicarboxylate transporter), member 3 |
| ENSMUSG00000021235 | 217707 | Coq6 | −0.706129644 | 0.002245385 | coenzyme Q6 monooxygenase |
| ENSMUSG00000009640 | 66233 | Dmap1 | −0.707204572 | 0.001999452 | DNA methyltransferase 1-associated protein 1 |
| ENSMUSG00000003549 | 13870 | Ercc1 | −0.707677588 | 0.009052603 | excision repair cross-complementing rodent repair deficiency, complementation group 1 |
| ENSMUSG00000003435 | 20924 | Supt5 | −0.707966508 | 0.011625189 | suppressor of Ty 5 |
| ENSMUSG00000029599 | 71990 | Ddx54 | −0.709450059 | 0.01155039 | DEAD (Asp-Glu-Ala-Asp) box polypeptide 54 |
| ENSMUSG00000014859 | 104394 | E2f4 | −0.71144034 | 0.01044046 | E2F transcription factor 4 |
| ENSMUSG00000051403 | 232947 | Ppp1r37 | −0.712532548 | 0.003845974 | protein phosphatase 1, regulatory subunit 37 |
| ENSMUSG00000038880 | 79044 | Mrps34 | −0.713621405 | 0.002365989 | mitochondrial ribosomal protein S34 |
| ENSMUSG00000036966 | 223918 | Spryd3 | −0.714182543 | 0.001751667 | SPRY domain containing 3 |
| ENSMUSG00000031827 | 72042 | Cotl1 | −0.714281952 | 0.004890059 | coactosin-like 1 (Dictyostelium) |
| ENSMUSG00000046719 | 104079 | Nxph3 | −0.715441544 | 0.009752335 | neurexophilin 3 |
| ENSMUSG00000092083 | 98741 | Kcnb2 | −0.716520282 | 0.001374059 | potassium voltage gated channel, Shab-related subfamily, member 2 |
| ENSMUSG00000024892 | 18563 | Pcx | −0.716521751 | 0.003481044 | pyruvate carboxylase |
| ENSMUSG00000034216 | 228545 | Vps18 | −0.717811491 | 0.000749687 | VPS18 CORVET/HOPS core subunit |
| ENSMUSG00000068329 | 64704 | Htra2 | −0.718738218 | 0.003885819 | HtrA serine peptidase 2 |
| ENSMUSG00000037907 | 268445 | Ankrd13b | −0.718795168 | 0.006473466 | ankyrin repeat domain 13b |
| ENSMUSG00000039771 | 20022 | Polr2j | −0.719840837 | 0.00196971 | polymerase (RNA) II (DNA directed) polypeptide J |

TABLE 2-continued

| Ensembl | Entrez | Symbol | log2FoldChange | padj | Name |
|---|---|---|---|---|---|
| ENSMUSG00000044986 | 22117 | Tst | −0.722887681 | 0.007055857 | thiosulfate sulfurtransferase, mitochondrial |
| ENSMUSG00000040813 | 21767 | Tex264 | −0.723970905 | 0.004413261 | testis expressed gene 264 |
| ENSMUSG00000072772 | 14790 | Grcc10 | −0.726236525 | 0.007057237 | gene rich cluster, C10 gene |
| ENSMUSG00000051768 | 22594 | Xrcc1 | −0.726721553 | 0.009052603 | X-ray repair complementing defective repair in Chinese hamster cells 1 |
| ENSMUSG00000070570 | 72961 | Slc17a7 | −0.726820552 | 0.00575267 | solute carrier family 17 (sodium-dependent inorganic phosphate cotransporter), member 7 |
| ENSMUSG00000038650 | 107702 | Rnh1 | −0.728017622 | 0.009752335 | ribonuclease/angiogenin inhibitor 1 |
| ENSMUSG00000039656 | 20182 | Rxrb | −0.72844985 | 0.000999986 | retinoid X receptor beta |
| ENSMUSG00000055681 | 59042 | Cope | −0.72891368 | 0.006403724 | coatomer protein complex, subunit epsilon |
| ENSMUSG00000039713 | 269608 | Plekhg5 | −0.729623554 | 0.002747619 | pleckstrin homology domain containing, family G (with RhoGef domain) member 5 |
| ENSMUSG00000025158 | 19719 | Rfng | −0.730797553 | 0.005812978 | RFNG O-fucosylpeptide 3-beta-N-acetylglucosaminyltransferase |
| ENSMUSG00000023224 | 12258 | Serping1 | −0.730902741 | 0.001179316 | serine (or cysteine) peptidase inhibitor, clade G, member 1 |
| ENSMUSG00000026688 | 66447 | Mgst3 | −0.732031182 | 0.002899047 | microsomal glutathione S-transferase 3 |
| ENSMUSG00000026860 | 227700 | Sh3glb2 | −0.732212311 | 0.003473018 | SH3-domain GRB2-like endophilin B2 |
| ENSMUSG00000042492 | 68449 | Tbc1d10b | −0.732351556 | 3.57E−05 | TBC1 domain family, member 10b |
| ENSMUSG00000026458 | 68507 | Ppfia4 | −0.733174428 | 0.006970524 | protein tyrosine phosphatase, receptor type, f polypeptide (PTPRF), interacting protein (liprin), alpha 4 |
| ENSMUSG00000078441 | 56214 | Scamp4 | −0.733253989 | 0.004754638 | secretory carrier membrane protein 4 |
| ENSMUSG00000002871 | 24100 | Tpra1 | −0.735924404 | 0.005647889 | transmembrane protein, adipocyte asscociated 1 |
| ENSMUSG00000090137 | 22186 | Uba52 | −0.736452474 | 0.001901327 | ubiquitin A-52 residue ribosomal protein fusion product 1 |
| ENSMUSG00000001270 | 12709 | Ckb | −0.738233346 | 0.000608724 | creatine kinase, brain |
| ENSMUSG00000040952 | 20085 | Rps19 | −0.738372882 | 0.00041893 | ribosomal protein S19 |
| ENSMUSG00000003200 | 20405 | Sh3gl1 | −0.739169416 | 0.006361553 | SH3-domain GRB2-like 1 |
| ENSMUSG00000091712 | 665119 | Sec14l5 | −0.739883804 | 0.00584403 | SEC14-like lipid binding 5 |
| ENSMUSG00000060260 | 101631 | Pwwp2b | −0.740350868 | 0.000652509 | PWWP domain containing 2B |
| ENSMUSG00000033327 | 81877 | Tnxb | −0.741649684 | 0.007996532 | tenascin XB |
| ENSMUSG00000088185 | | | −0.742163161 | 0.003544118 | |
| ENSMUSG00000042462 | 66422 | Dctpp1 | −0.742351618 | 0.007008349 | dCTP pyrophosphatase 1 |
| ENSMUSG00000026197 | 68818 | Zfand2b | −0.742483954 | 0.003919282 | zinc finger, AN1 type domain 2B |
| ENSMUSG00000004271 | 81703 | Jdp2 | −0.743587468 | 8.12E−05 | Jun dimerization protein 2 |
| ENSMUSG00000002343 | 76813 | Armc6 | −0.744088748 | 0.000659059 | armadillo repeat containing 6 |
| ENSMUSG00000006215 | 22642 | Zbtb17 | −0.747030813 | 0.00512457 | zinc finger and BTB domain containing 17 |
| ENSMUSG00000093674 | 67945 | Rpl41 | −0.747662654 | 0.001411939 | ribosomal protein L41 |
| ENSMUSG00000024835 | 23789 | Coro1b | −0.747669275 | 0.00017155 | coronin, actin binding protein 1B |
| ENSMUSG00000049739 | 233905 | Zfp646 | −0.747710853 | 0.001929017 | zinc finger protein 646 |
| ENSMUSG00000073838 | 233870 | Tufm | −0.748238729 | 0.000325542 | Tu translation elongation factor, mitochondrial |
| ENSMUSG00000020135 | 23805 | Apc2 | −0.750852897 | 0.002391979 | adenomatosis polyposis coli 2 |
| ENSMUSG00000006442 | 20810 | Srm | −0.751921478 | 0.003912983 | spermidine synthase |
| ENSMUSG00000028843 | 73723 | Sh3bgrl3 | −0.752138289 | 0.001600898 | SH3 domain binding glutamic acid-rich protein-like 3 |
| ENSMUSG00000028670 | 26394 | Lypla2 | −0.752307359 | 0.004996694 | lysophospholipase 2 |
| ENSMUSG00000048537 | 102693 | Phldb1 | −0.752732034 | 0.00037302 | pleckstrin homology like domain, family B, member 1 |
| ENSMUSG00000039640 | 56282 | Mrpl12 | −0.754273829 | 0.000608724 | mitochondrial ribosomal protein L12 |
| ENSMUSG00000020775 | 60441 | Mrpl38 | −0.757349677 | 0.002418557 | mitochondrial ribosomal protein L38 |
| ENSMUSG00000045268 | 195522 | Zfp691 | −0.759120388 | 0.006787952 | zinc finger protein 691 |
| ENSMUSG00000024039 | 12411 | Cbs | −0.760295179 | 0.000389211 | cystathionine beta-synthase |
| ENSMUSG00000052609 | 263406 | Plekhg3 | −0.761031641 | 0.006705787 | pleckstrin homology domain containing, family G (with RhoGef domain) member 3 |
| ENSMUSG00000013858 | 216157 | Tmem259 | −0.763388723 | 0.003868867 | transmembrane protein 259 |
| ENSMUSG00000016624 | 271305 | Phf21b | −0.763505199 | 0.006546749 | PHD finger protein 21B |
| ENSMUSG00000037820 | 21817 | Tgm2 | −0.765065898 | 0.004315106 | transglutaminase 2, C polypeptide |
| ENSMUSG00000028782 | 230775 | Adgrb2 | −0.765650679 | 0.000366557 | adhesion G protein-coupled receptor B2 |
| ENSMUSG00000022096 | 15460 | Hr | −0.766902534 | 0.002245385 | hairless |
| ENSMUSG00000060950 | 328162 | Trmt61a | −0.767407862 | 0.001833082 | tRNA methyltransferase 61A |
| ENSMUSG00000090291 | 278795 | Lrrc10b | −0.768261326 | 3.35E−05 | leucine rich repeat containing 10B |
| ENSMUSG00000004933 | 17179 | Matk | −0.77278843 | 0.001312062 | megakaryocyte-associated tyrosine kinase |
| ENSMUSG00000010936 | 234729 | Vac14 | −0.773788601 | 0.000389657 | Vac14 homolog (S. cerevisiae) |
| ENSMUSG00000036845 | 75660 | Lin37 | −0.774998935 | 0.001998408 | lin-37 homolog (C. elegans) |

TABLE 2-continued

| Ensembl | Entrez | Symbol | log2FoldChange | padj | Name |
|---|---|---|---|---|---|
| ENSMUSG00000029713 | 14693 | Gnb2 | −0.776106195 | 0.003073692 | guanine nucleotide binding protein (G protein), beta 2 |
| ENSMUSG00000033862 | 234854 | Cdk10 | −0.777734269 | 0.004591326 | cyclin-dependent kinase 10 |
| ENSMUSG00000023495 | 59092 | Pcbp4 | −0.77946645 | 0.005072478 | poly(rC) binding protein 4 |
| ENSMUSG00000038264 | 20361 | Sema7a | −0.782574914 | 1.56E−05 | sema domain, immunoglobulin domain (Ig), and GPI membrane anchor, (semaphorin) 7A |
| ENSMUSG00000034412 | 103724 | Tbc1d10a | −0.783099909 | 0.00437341 | TBC1 domain family, member 10a |
| ENSMUSG00000051851 | 72865 | Cxx1c | −0.783106525 | 0.004841802 | CAAX box 1C |
| ENSMUSG00000026354 | 226413 | Lct | −0.783330981 | 4.67E−06 | lactase |
| ENSMUSG00000008668 | 20084 | Rps18 | −0.785076034 | 0.000315513 | ribosomal protein S18 |
| ENSMUSG00000005237 | 327954 | Dnah2 | −0.785440111 | 0.002783667 | dynein, axonemal, heavy chain 2 |
| ENSMUSG00000033458 | 330554 | Fan1 | −0.785844832 | 0.000398698 | FANCD2/FANCI-associated nuclease 1 |
| ENSMUSG00000023192 | 108068 | Grm2 | −0.787481672 | 0.000412819 | glutamate receptor, metabotropic 2 |
| ENSMUSG00000030697 | 56420 | Ppp4c | −0.788985782 | 0.002743257 | protein phosphatase 4, catalytic subunit |
| ENSMUSG00000039714 | 235415 | Cplx3 | −0.789705212 | 0.001557476 | complexin 3 |
| ENSMUSG00000018476 | 216850 | Kdm6b | −0.791173174 | 0.003068704 | KDM1 lysine (K)-specific demethylase 6B |
| ENSMUSG00000032532 | 12424 | Cck | −0.79172782 | 0.005077667 | cholecystokinin |
| ENSMUSG00000003199 | 68047 | Mpnd | −0.792302898 | 0.001517648 | MPN domain containing |
| ENSMUSG00000002379 | 69875 | Ndufa11 | −0.795102524 | 0.004968841 | NADH dehydrogenase (ubiquinone) 1 alpha subcomplex 11 |
| ENSMUSG00000033730 | 13655 | Egr3 | −0.800844097 | 0.00410074 | early growth response 3 |
| ENSMUSG00000024201 | 193796 | Kdm4b | −0.803290754 | 0.002080874 | lysine (K)-specific demethylase 4B |
| ENSMUSG00000060376 | 12039 | Bckdha | −0.804525253 | 0.004293051 | branched chain ketoacid dehydrogenase E1, alpha polypeptide |
| ENSMUSG00000020150 | 14431 | Gamt | −0.808182888 | 0.00163991 | guanidinoacetate methyltransferase |
| ENSMUSG00000035559 | 234384 | Mpv17l2 | −0.808302472 | 0.002872529 | MPV17 mitochondrial membrane protein-like 2 |
| ENSMUSG00000039452 | 382083 | Snx22 | −0.809839327 | 0.002296608 | sorting nexin 22 |
| ENSMUSG00000025492 | 66141 | Ifitm3 | −0.809904293 | 0.002483237 | interferon induced transmembrane protein 3 |
| ENSMUSG00000078440 | 102115 | Dohh | −0.810129967 | 0.001467472 | deoxyhypusine hydroxylase/monooxygenase |
| ENSMUSG00000024395 | 225341 | Lims2 | −0.812725317 | 0.002747619 | LIM and senescent cell antigen like domains 2 |
| ENSMUSG00000030688 | 56018 | Stard10 | −0.814795313 | 0.000260636 | START domain containing 10 |
| ENSMUSG00000003970 | 26961 | Rpl8 | −0.817663867 | 0.00277665 | ribosomal protein L8 |
| ENSMUSG00000034930 | 20166 | Rtkn | −0.818029894 | 5.15E−05 | rhotekin |
| ENSMUSG00000060860 | 77891 | Ube2s | −0.818847315 | 0.003631611 | ubiquitin-conjugating enzyme E2S |
| ENSMUSG00000037570 | 51812 | Mcrs1 | −0.818973775 | 0.001815611 | microspherule protein 1 |
| ENSMUSG00000025348 | 16404 | Itga7 | −0.819498407 | 0.000517792 | integrin alpha 7 |
| ENSMUSG00000058586 | 68607 | Serhl | −0.82047299 | 0.000874286 | serine hydrolase-like |
| ENSMUSG00000031760 | 17751 | Mt3 | −0.823874073 | 0.003623855 | metallothionein 3 |
| ENSMUSG00000029554 | 17120 | Mad1l1 | −0.829306635 | 0.002002561 | MAD1 mitotic arrest deficient 1-like 1 |
| ENSMUSG00000026923 | 18128 | Notch1 | −0.830908953 | 0.002597492 | notch 1 |
| ENSMUSG00000025486 | 64384 | Sirt3 | −0.834205876 | 0.000642001 | sirtuin 3 |
| ENSMUSG00000001729 | 11651 | Akt1 | −0.835479712 | 0.000222519 | thymoma viral proto-oncogene 1 |
| ENSMUSG00000041556 | 230904 | Fbxo2 | −0.837174734 | 0.003034731 | F-box protein 2 |
| ENSMUSG00000015090 | 19215 | Ptgds | −0.845592451 | 0.002168825 | prostaglandin D2 synthase (brain) |
| ENSMUSG00000033216 | 65967 | Eefsec | −0.848635791 | 0.00063026 | eukaryotic elongation factor, selenocysteine-tRNA-specific |
| ENSMUSG00000039542 | 17967 | Ncam1 | −0.860588075 | 0.000840189 | neural cell adhesion molecule 1 |
| ENSMUSG00000025147 | 101513 | Mob2 | −0.87503202 | 0.000419257 | MOB kinase activator 2 |
| ENSMUSG00000003363 | 18807 | Pld3 | −0.885205603 | 0.000189211 | phospholipase D family, member 3 |
| ENSMUSG00000029054 | 14403 | Gabrd | −0.885481109 | 8.96E−05 | gamma-aminobutyric acid (GABA) A receptor, subunit delta |
| ENSMUSG00000082286 | | | −0.897476539 | 0.000535573 | |
| ENSMUSG00000052456 | 56495 | Asna1 | −0.906359021 | 0.00037302 | arsA arsenite transporter, ATP-binding, homolog 1 (bacterial) |
| ENSMUSG00000061032 | 18114 | Rrp1 | −0.908837668 | 1.21E−06 | ribosomal RNA processing 1 homolog (S. cerevisiae) |
| ENSMUSG00000050936 | | | −0.925459536 | 0.000638691 | |
| ENSMUSG00000029148 | 192292 | Nrbp1 | −0.927127341 | 0.000665254 | nuclear receptor binding protein 1 |
| ENSMUSG00000020836 | 216961 | Coro6 | −0.933192778 | 0.000608724 | coronin 6 |
| ENSMUSG00000040479 | 104418 | Dgkz | −0.942719889 | 1.46E−06 | diacylglycerol kinase zeta |
| ENSMUSG00000001418 | 56700 | Glmp | −0.946502535 | 0.000418385 | glycosylated lysosomal membrane protein |
| ENSMUSG00000030108 | 14412 | Slc6a13 | −0.953951709 | 0.000315513 | solute carrier family 6 (neurotransmitter transporter, GABA), member 13 |
| ENSMUSG00000006315 | 69804 | Tmem147 | −1.106417157 | 9.80E−05 | transmembrane protein 147 |
| ENSMUSG00000025366 | 23943 | Esyt1 | −1.303929003 | 2.14E−06 | extended synaptotagmin-like protein 1 |
| ENSMUSG00000002881 | 17936 | Nab1 | −1.794890701 | 6.14E−12 | Ngfi-A binding protein 1 |

TABLE 4

| Ensembl | Entrez | Symbol | log2FoldChange | padj | Name |
|---|---|---|---|---|---|
| ENSMUSG00000029372 | 57349 | Ppbp | 4.378971891 | 4.64E−06 | pro-platelet basic protein |
| ENSMUSG00000037035 | 16324 | Inhbb | 4.051835261 | 6.85E−07 | inhibin beta-B |
| ENSMUSG00000030159 | 56760 | Clec1b | 4.035825938 | 2.57E−05 | C-type lectin domain family 1, member b |
| ENSMUSG00000019947 | 71371 | Arid5b | 3.99058061 | 4.62E−05 | AT rich interactive domain 5B (MRF1-like) |
| ENSMUSG00000011008 | 68279 | Mcoln2 | 3.918354668 | 7.70E−05 | mucolipin 2 |
| ENSMUSG00000023341 | 17858 | Mx2 | 3.909527112 | 6.87E−05 | MX dynamin-like GTPase 2 |
| ENSMUSG00000038637 | 70552 | Lrrc56 | 3.825927365 | 4.64E−06 | leucine rich repeat containing 56 |
| ENSMUSG00000052477 | 620078 | C130026l21Rik | 3.779595382 | 1.25E−07 | RIKEN cDNA C130026l21 gene |
| ENSMUSG00000078847 | | | 3.718451758 | 0.000213003 | |
| ENSMUSG00000033429 | 73724 | Mcee | 3.715787309 | 1.16E−06 | methylmalonyl CoA epimerase |
| ENSMUSG00000090246 | | | 3.51008816 | 6.91E−07 | |
| ENSMUSG00000030310 | 232333 | Slc6a1 | 3.50263816 | 7.70E−05 | solute carrier family 6 (neurotransmitter transporter, GABA), member 1 |
| ENSMUSG00000053178 | 208595 | Mterf1b | 3.49153504 | 0.000712904 | mitochondrial transcription termination factor 1b |
| ENSMUSG00000026976 | 18510 | Pax8 | 3.423637498 | 0.000240115 | paired box 8 |
| ENSMUSG00000050533 | | | 3.41485259 | 8.76E−07 | |
| ENSMUSG00000059408 | 80978 | Mrgprh | 3.396337284 | 0.001087944 | MAS-related GPR, member H |
| ENSMUSG00000032252 | 93683 | Glce | 3.275067562 | 8.47E−05 | glucuronyl C5-epimerase |
| ENSMUSG00000029165 | 231093 | Agbl5 | 3.190478222 | 0.002503227 | ATP/GTP binding protein-like 5 |
| ENSMUSG00000021356 | 16364 | Irf4 | 3.174901716 | 0.000383524 | interferon regulatory factor 4 |
| ENSMUSG00000045775 | 217316 | Slc16a5 | 3.10726356 | 0.004168902 | solute carrier family 6 (monocarboxylic acid transporters), member 5 |
| ENSMUSG00000096833 | | | 3.093609253 | 0.004337696 | |
| ENSMUSG00000025153 | 14104 | Fasn | 3.086681846 | 3.89E−05 | fatty acid synthase |
| ENSMUSG00000032612 | 22258 | Usp4 | 3.0530175 | 0.001660736 | ubiquitin specific peptidase 4 (proto-oncogene) |
| ENSMUSG00000073409 | 15019 | H2-Q8 | 3.044951268 | 4.30E−09 | histocompatibility 2, Q region locus 8 |
| ENSMUSG00000038594 | 100038725 | Cep85l | 3.03966334 | 0.004131518 | centrosomal protein 85-like |
| ENSMUSG00000097582 | | | 3.035701368 | 0.005384185 | |
| ENSMUSG00000046463 | | | 3.034020588 | 0.005109906 | |
| ENSMUSG00000028528 | 72685 | Dnajc6 | 3.02873049 | 0.005214992 | DnaJ heat shock protein family (Hsp40) member C6 |
| ENSMUSG00000086191 | 432396 | Zfp652os | 2.997529194 | 0.006007451 | zinc finger protein 652, opposite strand |
| ENSMUSG00000010755 | 27267 | Cars | 2.970742162 | 2.59E−05 | cysteinyl-tRNA synthetase |
| ENSMUSG00000038888 | 233189 | Ctu1 | 2.96093014 | 0.00359675 | cytosolic thiouridylase subunit 1 |
| ENSMUSG00000025237 | 67287 | Parp6 | 2.936273336 | 0.007597903 | poly (ADP-ribose) polymerase family, member 6 |
| ENSMUSG00000087400 | | | 2.926059608 | 0.000955299 | |
| ENSMUSG00000029790 | 83922 | Cep41 | 2.923722302 | 0.001880617 | centrosomal protein 41 |
| ENSMUSG00000000094 | 21387 | Tbx4 | 2.923375614 | 0.002077384 | T-box 4 |
| ENSMUSG00000079457 | | | 2.91496531 | 7.39E−08 | |
| ENSMUSG00000097397 | 100503704 | Gm16861 | 2.88979551 | 0.000634534 | predicted gene, 16861 |
| ENSMUSG00000097558 | | | 2.880808739 | 0.005298803 | |
| ENSMUSG00000085039 | | | 2.864166205 | 0.009309582 | |
| ENSMUSG00000020549 | 68626 | Elac2 | 2.855157355 | 0.000240115 | elaC ribonuclease Z 2 |
| ENSMUSG00000093769 | 15077 | Hist2h3c1 | 2.850736795 | 0.005335917 | histone cluster 2, H3c1 |
| ENSMUSG00000028860 | 269589 | Sytl1 | 2.840828603 | 0.01102743 | synaptotagmin-like 1 |
| ENSMUSG00000091199 | | | 2.818989133 | 0.001084823 | |
| ENSMUSG00000024440 | 53601 | Pcdh12 | 2.810044861 | 2.01E−06 | protocadherin 12 |
| ENSMUSG00000097391 | 100040724 | Mirg | 2.782640889 | 0.007347559 | miRNA containing gene |
| ENSMUSG00000052429 | | | 2.756105326 | 0.01206718 | |
| ENSMUSG00000042010 | 100705 | Acacb | 2.752388644 | 7.70E−05 | acetyl-Coenzyme A carboxylase beta |
| ENSMUSG00000024670 | 12511 | Cd6 | 2.698231009 | 0.018907621 | CD6 antigen |
| ENSMUSG00000038583 | 18821 | Pln | 2.690958541 | 0.004856192 | phospholamban |
| ENSMUSG00000043340 | | | 2.685983124 | 0.00468024 | |
| ENSMUSG00000074219 | | | 2.668559792 | 0.014401825 | |
| ENSMUSG00000070691 | 12399 | Runx3 | 2.61962486 | 0.005408165 | runt related transcription factor 3 |
| ENSMUSG00000025498 | 54123 | Irf7 | 2.618142404 | 0.003733718 | interferon regulatory factor 7 |
| ENSMUSG00000038644 | 18971 | Pold1 | 2.600022241 | 0.003495189 | polymerase (DNA directed), delta 1, catalytic subunit |
| ENSMUSG00000014773 | 13388 | Dll1 | 2.585077394 | 0.007443127 | delta-like 1 (Drosophila) |
| ENSMUSG00000079362 | 100702 | Gbp6 | 2.57816577 | 0.000706817 | guanylate binding protein 6 |
| ENSMUSG00000048939 | 268878 | Atp13a5 | 2.572551126 | 0.027862243 | ATPase type 13A5 |
| ENSMUSG00000071342 | 380755 | Lsmem1 | 2.563073717 | 0.028611379 | leucine-rich single-pass membrane protein 1 |
| ENSMUSG00000024339 | 21355 | Tap2 | 2.53983116 | 0.000446886 | transporter 2, ATP-binding cassette, sub-family B (MDR/TAP) |
| ENSMUSG00000051457 | 20737 | Spn | 2.528900851 | 0.025677112 | sialophorin |
| ENSMUSG00000054588 | | | 2.511022253 | 0.005109906 | |

TABLE 4-continued

| Ensembl | Entrez | Symbol | log2FoldChange | padj | Name |
|---|---|---|---|---|---|
| ENSMUSG00000026686 | 110648 | Lmx1a | 2.510145757 | 0.01095587 | LIM homeobox transcription factor 1 alpha |
| ENSMUSG00000020641 | 58185 | Rsad2 | 2.507235647 | 3.87E−05 | radical S-adenosyl methionine domain containing 2 |
| ENSMUSG00000085558 | | | 2.504929227 | 0.009069647 | |
| ENSMUSG00000052776 | 246730 | Oas1a | 2.493178289 | 0.000300284 | 2′-5′ oligoadenylate synthetase 1A |
| ENSMUSG00000071716 | 666348 | Apol7e | 2.483870808 | 0.036393665 | apolipoprotein L 7e |
| ENSMUSG00000097746 | 633947 | Gm6225 | 2.471492716 | 0.02217361 | predicted gene 6225 |
| ENSMUSG00000035266 | 191578 | Helq | 2.465080964 | 0.005457978 | helicase, POLQ-like |
| ENSMUSG00000027859 | 18049 | Ngf | 2.460672316 | 0.039385129 | nerve growth factor |
| ENSMUSG00000083849 | | | 2.453193819 | 0.017083807 | |
| ENSMUSG00000050350 | 110168 | Gpr18 | 2.440422493 | 0.039769715 | G protein-coupled receptor 18 |
| ENSMUSG00000056735 | 109202 | A930024E05Rik | 2.43926444 | 0.042183071 | RIKEN cDNA A930024E05 gene |
| ENSMUSG00000044364 | 108832 | Tmem74b | 2.437019277 | 0.042311468 | transmembrane protein 74B |
| ENSMUSG00000004233 | 70560 | Wars2 | 2.430710372 | 0.003072021 | tryptophanyl tRNA synthetase 2 (mitochondrial) |
| ENSMUSG00000060550 | 15018 | H2-Q7 | 2.427501616 | 2.25E−09 | histocompatibility 2, Q region locus 7 |
| ENSMUSG00000084126 | | | 2.423399022 | 0.03711405 | |
| ENSMUSG00000038379 | 22137 | Ttk | 2.406773559 | 0.043383408 | Ttk protein kinase |
| ENSMUSG00000047037 | 233280 | Nipa1 | 2.403488755 | 0.002174787 | non imprinted in Prader-Willi/Angelman syndrome 1 homolog (human) |
| ENSMUSG00000079555 | 231123 | Haus3 | 2.397934247 | 0.018899557 | HAUS augmin-like complex, subunit 3 |
| ENSMUSG00000032643 | 14201 | Fhl3 | 2.383896278 | 8.47E−05 | four and a half LIM domains 3 |
| ENSMUSG00000007279 | 56788 | Scube2 | 2.383393027 | 0.003233893 | signal peptide, CUB domain, EGF-like 2 |
| ENSMUSG00000050211 | 329502 | Pla2g4e | 2.380299117 | 0.031152303 | phospholipase A2, group IVE |
| ENSMUSG00000044352 | 237761 | Sowaha | 2.376872372 | 0.035303173 | sosondowah ankyrin repeat domain family member A |
| ENSMUSG00000029575 | 77697 | Mmab | 2.372361443 | 0.002381472 | methylmalonic aciduria (cobalamin deficiency) cblB type homolog (human) |
| ENSMUSG00000042992 | 67774 | Borcs5 | 2.347522205 | 0.028869844 | BLOC-1 related complex subunit 5 |
| ENSMUSG00000046490 | 320040 | Rnf222 | 2.342213992 | 0.035303173 | ring finger protein 222 |
| ENSMUSG00000043822 | 66548 | Adamtsl5 | 2.336814641 | 0.030291219 | ADAMTS-like 5 |
| ENSMUSG00000043065 | 212514 | Spice1 | 2.320548192 | 0.000771599 | spindle and centriole associated protein 1 |
| ENSMUSG00000027080 | 381379 | Med19 | 2.319064126 | 0.010220409 | mediator complex subunit 19 |
| ENSMUSG00000000739 | 57429 | Sult5a1 | 2.309027747 | 0.00039023 | sulfotransferase family 5A, member 1 |
| ENSMUSG00000025270 | 11656 | Alas2 | 2.308732208 | 0.042183071 | aminolevulinic acid synthase 2, erythroid |
| ENSMUSG00000018750 | 75580 | Zbtb4 | 2.295989431 | 1.16E−06 | zinc finger and BTB domain containing 4 |
| ENSMUSG00000028051 | 15168 | Hcn3 | 2.294568531 | 0.032115868 | hyperpolarization-activated, cyclic nucleotide-gated K+ 3 |
| ENSMUSG00000072109 | | | 2.293832931 | 0.02129085 | |
| ENSMUSG00000028917 | 69582 | Plekhm2 | 2.284087936 | 0.000644318 | pleckstrin homology domain containing, family M (with RUN domain) member 2 |
| ENSMUSG00000039929 | 207932 | Urb1 | 2.282114502 | 0.002777374 | URB1 ribosome biogenesis 1 homolog (S. cerevisiae) |
| ENSMUSG00000044715 | 66787 | Gskip | 2.278623037 | 0.003491732 | GSK3B interacting protein |
| ENSMUSG00000034685 | 217219 | Fam171a2 | 2.276958777 | 0.012659524 | family with sequence similarity 171, member A2 |
| ENSMUSG00000045868 | 74558 | Gvin1 | 2.254871319 | 8.93E−08 | GTPase, very large interferon inducible 1 |
| ENSMUSG00000029725 | 69871 | Ppp1r35 | 2.247479427 | 0.046394819 | protein phosphatase 1, regulatory subunit 35 |
| ENSMUSG00000090150 | 102632 | Acad11 | 2.244052997 | 0.004116488 | acyl-Coenzyme A dehydrogenase family, member 11 |
| ENSMUSG00000079429 | 100040766 | Mroh2a | 2.231805995 | 0.000541021 | maestro heat-like repeat family member 2A |
| ENSMUSG00000084519 | | | 2.226701964 | 0.00485529 | |
| ENSMUSG00000071847 | 494504 | Apcdd1 | 2.224716424 | 0.032137325 | adenomatosis polyposis coli down-regulated 1 |
| ENSMUSG00000040734 | 333654 | Ppp1r13l | 2.222285037 | 0.03711405 | protein phosphatase 1, regulatory (inhibitor) subunit 13 like |
| ENSMUSG00000027985 | 16842 | Lef1 | 2.203367083 | 0.006129052 | lymphoid enhancer binding factor 1 |
| ENSMUSG00000054708 | 70615 | Ankrd24 | 2.195435044 | 0.028156387 | ankyrin repeat domain 24 |
| ENSMUSG00000073489 | 15951 | Ifi204 | 2.174152525 | 0.000116411 | interferon activated gene 204 |
| ENSMUSG00000036390 | 13197 | Gadd45a | 2.172733223 | 0.012398098 | growth arrest and DNA-damage-inducible 45 alpha |
| ENSMUSG00000038521 | 50908 | C1sl | 2.170138658 | 0.000254263 | complement component 1, s subcomponent 1 |

TABLE 4-continued

| Ensembl | Entrez | Symbol | log2FoldChange | padj | Name |
|---|---|---|---|---|---|
| ENSMUSG00000001131 | 21857 | Timp1 | 2.168400295 | 0.013400189 | tissue inhibitor of metalloproteinase 1 |
| ENSMUSG00000026697 | 17926 | Myoc | 2.164917077 | 0.002581374 | myocilin |
| ENSMUSG00000025731 | 68347 | Mettl26 | 2.162205447 | 0.031462879 | methyltransferase like 26 |
| ENSMUSG00000028334 | 94181 | Nans | 2.148802359 | 0.019029873 | N-acetylneuraminic acid synthase (sialic acid synthase) |
| ENSMUSG00000060397 | 243833 | Zfp128 | 2.14350543 | 0.02403498 | zinc finger protein 128 |
| ENSMUSG00000070031 | 434484 | Sp140 | 2.133227543 | 0.002220757 | Sp140 nuclear body protein |
| ENSMUSG00000006014 | 96875 | Prg4 | 2.13236769 | 0.006753139 | proteoglycan 4 (megakaryocyte stimulating factor, articular superficial zone protein) |
| ENSMUSG00000002814 | 21975 | Top3a | 2.132253772 | 0.01009259 | topoisomerase (DNA) III alpha |
| ENSMUSG00000027894 | 229706 | Slc6a17 | 2.112435065 | 0.001191906 | solute carrier family 6 (neurotransmitter transporter), member 17 |
| ENSMUSG00000031137 | 14168 | Fgf13 | 2.103493569 | 0.038078423 | fibroblast growth factor 13 |
| ENSMUSG00000015090 | 19215 | Ptgds | 2.093587478 | 3.50E−08 | prostaglandin D2 synthase (brain) |
| ENSMUSG00000020627 | 208439 | Klhl29 | 2.087458265 | 0.023987772 | kelch-like 29 |
| ENSMUSG00000028524 | 73094 | Sgip1 | 2.087231422 | 0.003760126 | SH3-domain GRB2-like (endophilin) interacting protein 1 |
| ENSMUSG00000029417 | 17329 | Cxcl9 | 2.076136316 | 0.019506204 | chemokine (C-X-C motif) ligand 9 |
| ENSMUSG00000021091 | 20716 | Serpina3n | 2.062644631 | 0.003790055 | serine (or cysteine) peptidase inhibitor, clade A, member 3N |
| ENSMUSG00000031877 | 72361 | Ces2g | 2.057949538 | 0.047587179 | carboxylesterase 2G |
| ENSMUSG00000039457 | 19041 | Ppl | 2.042762439 | 0.02117084 | periplakin |
| ENSMUSG00000089652 | | | 2.035098885 | 0.006769413 | |
| ENSMUSG00000033327 | 81877 | Tnxb | 2.031850859 | 3.65E−05 | tenascin XB |
| ENSMUSG00000053175 | 12051 | Bcl3 | 2.0226994 | 0.016098855 | B cell leukemia/lymphoma 3 |
| ENSMUSG00000041444 | 330914 | Arhgap32 | 2.020149575 | 5.48E−05 | Rho GTPase activating protein 32 |
| ENSMUSG00000023452 | 320951 | Pisd | 2.018542354 | 0.025765794 | phosphatidylserine decarboxylase |
| ENSMUSG00000036585 | 14164 | Fgf1 | 2.001564929 | 0.04760535 | fibroblast growth factor 1 |
| ENSMUSG00000052387 | 226025 | Trpm3 | 1.989643045 | 0.002390746 | transient receptor potential cation channel, subfamily M, member 3 |
| ENSMUSG00000041261 | 12319 | Car8 | 1.987951552 | 0.044730163 | carbonic anhydrase 8 |
| ENSMUSG00000057421 | 76130 | Las1l | 1.982053376 | 0.007954036 | LAS1-like (S. cerevisiae) |
| ENSMUSG00000001786 | 69754 | Fbxo7 | 1.978091536 | 0.005869678 | F-box protein 7 |
| ENSMUSG00000078921 | 100039796 | Tgtp2 | 1.976511392 | 0.000270412 | T cell specific GTPase 2 |
| ENSMUSG00000000827 | 66314 | Tpd52l2 | 1.966634422 | 7.70E−05 | tumor protein D52-like 2 |
| ENSMUSG00000016253 | 57314 | Nelfcd | 1.947294657 | 0.008590011 | negative elongation factor complex member C/D, Th1l |
| ENSMUSG00000026979 | 215632 | Psd4 | 1.941914974 | 0.02461081 | pleckstrin and Sec7 domain containing 4 |
| ENSMUSG00000037321 | 21354 | Tap1 | 1.935782086 | 0.013915452 | transporter 1, ATP-binding cassette, sub-family B (MDR/TAP) |
| ENSMUSG00000058396 | 11536 | Gpr182 | 1.908461752 | 8.54E−05 | G protein-coupled receptor 182 |
| ENSMUSG00000035772 | 118451 | Mrps2 | 1.906898002 | 0.026898506 | mitochondrial ribosomal protein S2 |
| ENSMUSG00000033955 | 228140 | Tnks1bp1 | 1.899991919 | 0.003336298 | tankyrase 1 binding protein 1 |
| ENSMUSG00000039480 | 319638 | Nt5dc1 | 1.888912846 | 0.020526065 | 5'-nucleotidase domain containing 1 |
| ENSMUSG00000056763 | 211660 | Cspp1 | 1.883699413 | 0.001142649 | centrosome and spindle pole associated protein 1 |
| ENSMUSG00000056025 | 12722 | Clca3a1 | 1.871377872 | 0.042183071 | chloride channel accessory 3A1 |
| ENSMUSG00000015747 | 22365 | Vps45 | 1.852897826 | 0.03800403 | vacuolar protein sorting 45 |
| ENSMUSG00000042208 | 71675 | 0610010F05Rik | 1.850346244 | 0.006737029 | RIKEN cDNA 0610010F05 gene |
| ENSMUSG00000025477 | 212111 | Inpp5a | 1.84464824 | 0.003233893 | inositol polyphosphate-5-phosphatase A |
| ENSMUSG00000038722 | 231889 | Bud31 | 1.841549376 | 0.031967862 | BUD31 homolog |
| ENSMUSG00000021102 | 73046 | Glrx5 | 1.836714752 | 0.036366217 | glutaredoxin 5 |
| ENSMUSG00000035168 | 66860 | Tanc1 | 1.83405303 | 3.45E−05 | tetratricopeptide repeat, ankyrin repeat and coiled-coil containing 1 |
| ENSMUSG00000056185 | 225861 | Snx32 | 1.821607979 | 0.030291219 | sorting nexin 32 |
| ENSMUSG00000063450 | 319565 | Syne2 | 1.817720842 | 8.47E−05 | spectrin repeat containing, nuclear envelope 2 |
| ENSMUSG00000046572 | 100515 | Zfp518b | 1.809228362 | 0.001200227 | zinc finger protein 518B |
| ENSMUSG00000032288 | 102462 | Imp3 | 1.800473443 | 0.041737067 | IMP3, U3 small nucleolar ribonucleoprotein |
| ENSMUSG00000003452 | 12121 | Bicd1 | 1.799551323 | 0.0435616 | bicaudal D homolog 1 (Drosophila) |
| ENSMUSG00000079017 | 76933 | Ifi27l2a | 1.796579172 | 0.006769413 | interferon, alpha-inducible protein 27 like 2A |
| ENSMUSG00000035305 | 26563 | Ror1 | 1.794001916 | 0.049743944 | receptor tyrosine kinase-like orphan receptor 1 |
| ENSMUSG00000085208 | 74038 | Brip1os | 1.792266048 | 0.00667546 | BRCA1 interacting protein C-terminal helicase 1, opposite strand |
| ENSMUSG00000025485 | 101489 | Ric8a | 1.790347284 | 0.013835717 | RIC8 guanine nucleotide exchange factor A |

TABLE 4-continued

| Ensembl | Entrez | Symbol | log2FoldChange | padj | Name |
|---|---|---|---|---|---|
| ENSMUSG00000040724 | 16490 | Kcna2 | 1.778314408 | 0.038502278 | potassium voltage-gated channel, shaker-related subfamily, member 2 |
| ENSMUSG00000034684 | 20350 | Sema3f | 1.776122555 | 0.011654863 | sema domain, immunoglobulin domain (Ig), short basic domain, secreted, (semaphorin) 3F |
| ENSMUSG00000034998 | 14236 | Foxn2 | 1.753448702 | 0.002777374 | forkhead box N2 |
| ENSMUSG00000041479 | 319508 | Syt15 | 1.73411285 | 0.047882922 | synaptotagmin XV |
| ENSMUSG00000032135 | 84004 | Mcam | 1.728606576 | 0.003495189 | melanoma cell adhesion molecule |
| ENSMUSG00000044197 | 80290 | Gpr146 | 1.724174994 | 0.000942971 | G protein-coupled receptor 146 |
| ENSMUSG00000032841 | 72446 | Prr5l | 1.711224294 | 0.024711215 | proline rich 5 like |
| ENSMUSG00000027314 | 54485 | Dll4 | 1.70770213 | 0.002077384 | delta-like 4 (Drosophila) |
| ENSMUSG00000018830 | 17880 | Myh11 | 1.697500262 | 0.000350675 | myosin, heavy polypeptide 11, smooth muscle |
| ENSMUSG00000024050 | 22404 | Wiz | 1.695945587 | 0.001978895 | widely-interspaced zinc finger motifs |
| ENSMUSG00000040018 | 226139 | Cox15 | 1.688689238 | 0.01102743 | cytochrome c oxidase assembly protein 15 |
| ENSMUSG00000030748 | 16190 | Il4ra | 1.687410003 | 0.033137405 | interleukin 4 receptor, alpha |
| ENSMUSG00000055204 | 81702 | Ankrd17 | 1.685921916 | 0.002267251 | ankyrin repeat domain 17 |
| ENSMUSG00000059173 | 18573 | Pde1a | 1.668593146 | 0.03711405 | phosphodiesterase 1A, calmodulin-dependent |
| ENSMUSG00000026127 | 27993 | Imp4 | 1.666841904 | 0.021170517 | IMP4, U3 small nucleolar ribonucleoprotein |
| ENSMUSG00000040584 | 18671 | Abcb1a | 1.666787226 | 0.003488379 | ATP-binding cassette, sub-family B (MDR/TAP), member 1A |
| ENSMUSG00000024456 | 13367 | Diaph1 | 1.661131123 | 0.01009259 | diaphanous related formin 1 |
| ENSMUSG00000020692 | 217011 | Nle1 | 1.654043688 | 0.041223379 | notchless homolog 1 (Drosophila) |
| ENSMUSG00000026858 | 108958 | Miga2 | 1.65218635 | 0.022292941 | mitoguardin 2 |
| ENSMUSG00000068452 | 214593 | Duox2 | 1.63071896 | 0.023335668 | dual oxidase 2 |
| ENSMUSG00000026580 | 20344 | Selp | 1.629698592 | 0.020374951 | selectin, platelet |
| ENSMUSG00000027514 | 58203 | Zbp1 | 1.624244651 | 0.01009259 | Z-DNA binding protein 1 |
| ENSMUSG00000017652 | 21939 | Cd40 | 1.61565528 | 0.030238921 | CD40 antigen |
| ENSMUSG00000026822 | 16819 | Lcn2 | 1.605113432 | 0.004498683 | lipocalin 2 |
| ENSMUSG00000050730 | 71544 | Arhgap42 | 1.560728869 | 0.037071292 | Rho GTPase activating protein 42 |
| ENSMUSG00000007097 | 98660 | Atp1a2 | 1.558869471 | 0.00304113 | ATPase, Na+/K+ transporting, alpha 2 polypeptide |
| ENSMUSG00000062169 | 98417 | Cnih4 | 1.538814097 | 0.01677015 | cornichon family AMPA receptor auxiliary protein 4 |
| ENSMUSG00000031762 | 17750 | Mt2 | 1.537401745 | 0.049736581 | metallothionein 2 |
| ENSMUSG00000001930 | 22371 | Vwf | 1.521976482 | 0.023375234 | Von Willebrand factor |
| ENSMUSG00000074918 | | | 1.516768896 | 0.021036389 | |
| ENSMUSG00000061232 | 14972 | H2-K1 | 1.505239248 | 0.000168757 | histocompatibility 2, K1, K region |
| ENSMUSG00000071454 | 13528 | Dtnb | 1.501967372 | 0.044491551 | dystrobrevin, beta |
| ENSMUSG00000028053 | 192195 | Ash1l | 1.470859688 | 0.042760235 | ash1 (absent, small, or homeotic)-like (Drosophila) |
| ENSMUSG00000028798 | 54709 | Eif3i | 1.46394621 | 0.022971923 | eukaryotic translation initiation factor 3, subunit I |
| ENSMUSG00000047307 | 93884 | Pcdhb13 | 1.46350674 | 0.049014464 | protocadherin beta 13 |
| ENSMUSG00000059810 | 50780 | Rgs3 | 1.461143277 | 0.004684154 | regulator of G-protein signaling 3 |
| ENSMUSG00000003721 | 72999 | Insig2 | 1.442890832 | 0.035303173 | insulin induced gene 2 |
| ENSMUSG00000022895 | 23872 | Ets2 | 1.442438767 | 0.003189169 | E26 avian leukemia oncogene 2, 3' domain |
| ENSMUSG00000028842 | 214150 | Ago3 | 1.440633706 | 0.00210609 | argonaute RISC catalytic subunit 3 |
| ENSMUSG00000055799 | 21415 | Tcf7l1 | 1.439225512 | 0.028097649 | transcription factor 7 like 1 (T cell specific, HMG box) |
| ENSMUSG00000078922 | 21822 | Tgtp1 | 1.405295578 | 0.014412709 | T cell specific GTPase 1 |
| ENSMUSG00000016831 | 268741 | Tox4 | 1.405015776 | 0.013281208 | TOX high mobility group box family member 4 |
| ENSMUSG00000035621 | 59090 | Midn | 1.389796916 | 0.002814653 | midnolin |
| ENSMUSG00000024858 | 110355 | Grk2 | 1.38234043 | 0.038238511 | G protein-coupled receptor kinase 2 |
| ENSMUSG00000050947 | 229715 | Amigo1 | 1.381643431 | 0.041085114 | adhesion molecule with Ig like domain 1 |
| ENSMUSG00000046718 | 69550 | Bst2 | 1.37207375 | 0.046394819 | bone marrow stromal cell antigen 2 |
| ENSMUSG00000000131 | 74204 | Xpo6 | 1.358701027 | 0.012117678 | exportin 6 |
| ENSMUSG00000029135 | 14284 | Fosl2 | 1.35388523 | 0.015309486 | fos-like antigen 2 |
| ENSMUSG00000042216 | 52850 | Sgsm1 | 1.345529107 | 0.024711215 | small G protein signaling modulator 1 |
| ENSMUSG00000044534 | 59289 | Ackr2 | 1.336338475 | 0.009980113 | atypical chemokine receptor 2 |
| ENSMUSG00000030249 | 20928 | Abcc9 | 1.332047653 | 0.035043172 | ATP-binding cassette, sub-family C (CFTR/MRP), member 9 |
| ENSMUSG00000063894 | 93681 | Zkscan8 | 1.277934894 | 0.023987772 | zinc finger with KRAB and SCAN domains 8 |
| ENSMUSG00000031985 | 14712 | Gnpat | 1.222732654 | 0.036795604 | glyceronephosphate O-acyltransferase |

TABLE 4-continued

| Ensembl | Entrez | Symbol | log2FoldChange | padj | Name |
|---|---|---|---|---|---|
| ENSMUSG00000096596 | 100041504 | LOC100041504 | 1.212781603 | 0.011737601 | C-C motif chemokine 21c |
| ENSMUSG00000095675 | 100041504 | LOC100041504 | 1.212609342 | 0.011737601 | C-C motif chemokine 21c |
| ENSMUSG00000028967 | 74155 | Errfi1 | 1.200291875 | 0.015150322 | ERBB receptor feedback inhibitor 1 |
| ENSMUSG00000025743 | 20970 | Sdc3 | 1.176560076 | 0.024953151 | syndecan 3 |
| ENSMUSG00000040451 | 208449 | Sgms1 | 1.175254208 | 0.03482516 | sphingomyelin synthase 1 |
| ENSMUSG00000017309 | 52685 | Cd300lg | 1.137986655 | 0.048686916 | CD300 molecule like family member G |
| ENSMUSG00000078606 | 100042856 | Gm4070 | 1.130512744 | 0.036395378 | predicted gene 4070 |
| ENSMUSG00000043079 | 104027 | Synpo | 1.118803716 | 0.025765794 | synaptopodin |
| ENSMUSG00000027074 | 58207 | Slc43a3 | 1.090650861 | 0.041085114 | solute carrier family 43, member 3 |
| ENSMUSG00000056342 | 17847 | Usp34 | 1.079876168 | 0.028560255 | ubiquitin specific peptidase 34 |
| ENSMUSG00000094065 | 65956 | Ccl21c | 1.021167342 | 0.018775811 | chemokine (C-C motif) ligand 21C (leucine) |
| ENSMUSG00000073411 | 14964 | H2-D1 | 1.018019345 | 0.028794346 | histocompatibility 2, D region locus 1 |
| ENSMUSG00000006932 | 12387 | Ctnnb1 | 0.997220145 | 0.048401129 | catenin (cadherin associated protein), beta 1 |
| ENSMUSG00000060802 | 12010 | B2m | 0.968857275 | 0.029729159 | beta-2 microglobulin |
| ENSMUSG00000006369 | 14114 | Fbln1 | -1.041880271 | 0.048401129 | fibulin 1 |
| ENSMUSG00000039671 | 228880 | Zmynd8 | -1.083159129 | 0.048452293 | zinc finger, MYND-type containing 8 |
| ENSMUSG00000036545 | 216725 | Adamts2 | -1.090588338 | 0.038936858 | a disintegrin-like and metallopeptidase (reprolysin type) with thrombospondin type 1 motif, 2 |
| ENSMUSG00000024621 | 12978 | Csf1r | -1.144219264 | 0.030436419 | colony stimulating factor 1 receptor |
| ENSMUSG00000004455 | 19047 | Ppp1cc | -1.169646842 | 0.023987772 | protein phosphatase 1, catalytic subunit, gamma isoform |
| ENSMUSG00000026043 | 12825 | Col3a1 | -1.173313854 | 0.016921368 | collagen, type III, alpha 1 |
| ENSMUSG00000028581 | 16792 | Laptm5 | -1.177869768 | 0.0182842 | lysosomal-associated protein transmembrane 5 |
| ENSMUSG00000057230 | 269774 | Aak1 | -1.178382075 | 0.016690277 | AP2 associated kinase 1 |
| ENSMUSG00000018547 | 108083 | Pip4k2b | -1.195951347 | 0.041187168 | phosphatidylinositol-5-phosphate 4-kinase, type II, beta |
| ENSMUSG00000018474 | 216848 | Chd3 | -1.279740637 | 0.03482516 | chromodomain helicase DNA binding protein 3 |
| ENSMUSG00000029581 | 14086 | Fscn1 | -1.301658925 | 0.024853918 | fascin actin-bundling protein 1 |
| ENSMUSG00000031012 | 12361 | Cask | -1.309575303 | 0.025567508 | calcium/calmodulin-dependent serine protein kinase (MAGUK family) |
| ENSMUSG00000039157 | 98952 | Fam102a | -1.326243917 | 0.045572341 | family with sequence similarity 102, member A |
| ENSMUSG00000023886 | 64074 | Smoc2 | -1.333467811 | 0.043125662 | SPARC related modular calcium binding 2 |
| ENSMUSG00000019899 | 16773 | Lama2 | -1.342782616 | 0.040361129 | laminin, alpha 2 |
| ENSMUSG00000020376 | 59044 | Rnf130 | -1.344586527 | 0.044855022 | ring finger protein 130 |
| ENSMUSG00000039084 | 12643 | Chad | -1.347545601 | 0.028063271 | chondroadherin |
| ENSMUSG00000029661 | 12843 | Col1a2 | -1.368139152 | 0.000446886 | collagen, type I, alpha 2 |
| ENSMUSG00000031665 | 58198 | Sall1 | -1.372713992 | 0.022729262 | sal-like 1 (Drosophila) |
| ENSMUSG00000026812 | 64930 | Tsc1 | -1.376875803 | 0.042183071 | tuberous sclerosis 1 |
| ENSMUSG00000093445 | 231798 | Lrch4 | -1.377821971 | 0.017429926 | leucine-rich repeats and calponin homology (CH) domain containing 4 |
| ENSMUSG00000027447 | 13010 | Cst3 | -1.390546093 | 0.000644318 | cystatin C |
| ENSMUSG00000001506 | 12842 | Col1a1 | -1.402205715 | 0.000725992 | collagen, type I, alpha 1 |
| ENSMUSG00000047146 | 52463 | Tet1 | -1.408731868 | 0.03711405 | tet methylcytosine dioxygenase 1 |
| ENSMUSG00000055254 | 18212 | Ntrk2 | -1.428507136 | 0.015414939 | neurotrophic tyrosine kinase, receptor, type 2 |
| ENSMUSG00000021112 | 56217 | Mpp5 | -1.431303682 | 0.048931536 | membrane protein, palmitoylated 5 (MAGUK p55 subfamily member 5) |
| ENSMUSG00000022148 | 23880 | Fyb | -1.431910062 | 0.030923641 | FYN binding protein |
| ENSMUSG00000015937 | 26914 | H2afy | -1.431993476 | 0.04547582 | H2A histone family, member Y |
| ENSMUSG00000052949 | 217340 | Rnf157 | -1.436509689 | 0.004400689 | ring finger protein 157 |
| ENSMUSG00000056427 | 20564 | Slit3 | -1.43767449 | 0.03237643 | slit homolog 3 (Drosophila) |
| ENSMUSG00000014361 | 17289 | Mertk | -1.439404531 | 0.017429926 | c-mer proto-oncogene tyrosine kinase |
| ENSMUSG00000002265 | 18616 | Peg3 | -1.444026769 | 0.003072021 | paternally expressed 3 |
| ENSMUSG00000043384 | 67298 | Gprasp1 | -1.448791307 | 0.025203574 | G protein-coupled receptor associated sorting protein 1 |
| ENSMUSG00000030560 | 13032 | Ctsc | -1.451378311 | 0.038882932 | cathepsin C |
| ENSMUSG00000027848 | 99543 | Olfml3 | -1.455264246 | 0.001804859 | olfactomedin-like 3 |
| ENSMUSG00000024370 | 52563 | Cdc23 | -1.458420627 | 0.04811549 | CDC23 cell division cycle 23 |
| ENSMUSG00000032712 | 67246 | 2810474O19Rik | -1.464730775 | 0.041085114 | RIKEN cDNA 2810474O19 gene |
| ENSMUSG00000024052 | 64898 | Lpin2 | -1.472360088 | 0.013915452 | lipin 2 |

TABLE 4-continued

| Ensembl | Entrez | Symbol | log2FoldChange | padj | Name |
|---|---|---|---|---|---|
| ENSMUSG00000051786 | 328580 | Tubgcp6 | −1.472883578 | 0.047882922 | tubulin, gamma complex associated protein 6 |
| ENSMUSG00000054675 | 231633 | Tmem119 | −1.479950513 | 0.003488379 | transmembrane protein 119 |
| ENSMUSG00000052336 | 13051 | Cx3cr1 | −1.48606313 | 0.002801478 | chemokine (C-X3-C motif) receptor 1 |
| ENSMUSG00000024076 | 74199 | Vit | −1.492682933 | 0.033567625 | vitrin |
| ENSMUSG00000079227 | 12774 | Ccr5 | −1.496543979 | 0.024711215 | chemokine (C-C motif) receptor 5 |
| ENSMUSG00000034024 | 12461 | Cct2 | −1.504302169 | 0.014364535 | chaperonin containing Tcp1, subunit 2 (beta) |
| ENSMUSG00000026042 | 12832 | Col5a2 | −1.515019098 | 0.016316844 | collagen, type V, alpha 2 |
| ENSMUSG00000036896 | 12262 | C1qc | −1.524013024 | 0.009398548 | complement component 1, q subcomponent, C chain |
| ENSMUSG00000007613 | 21812 | Tgfbr1 | −1.532018773 | 0.001464683 | transforming growth factor, beta receptor I |
| ENSMUSG00000021555 | 78689 | Naa35 | −1.55419992 | 0.030397423 | N(alpha)-acetyltransferase 35, NatC auxiliary subunit |
| ENSMUSG00000031613 | 15446 | Hpgd | −1.563134722 | 0.020947172 | hydroxyprostaglandin dehydrogenase 15 (NAD) |
| ENSMUSG00000027875 | 15360 | Hmgcs2 | −1.563139701 | 0.013232369 | 3-hydroxy-3-methylglutaryl-Coenzyme A synthase 2 |
| ENSMUSG00000028532 | 320508 | Cachd1 | −1.566660667 | 0.028156387 | cache domain containing 1 |
| ENSMUSG00000040943 | 214133 | Tet2 | −1.567655701 | 0.023649273 | tet methylcytosine dioxygenase 2 |
| ENSMUSG00000040325 | 321006 | Vprbp | −1.568814403 | 0.04188261 | Vpr (HIV-1) binding protein |
| ENSMUSG00000020354 | 24052 | Sgcd | −1.570610665 | 0.039051789 | sarcoglycan, delta (dystrophin-associated glycoprotein) |
| ENSMUSG00000028289 | 13841 | Epha7 | −1.577582935 | 0.025765794 | Eph receptor A7 |
| ENSMUSG00000036905 | 12260 | C1qb | −1.588624246 | 0.00199156 | complement component 1, q subcomponent, beta polypeptide |
| ENSMUSG00000044627 | 72931 | Swi5 | −1.591498694 | 0.030826405 | SWI5 recombination repair homolog (yeast) |
| ENSMUSG00000023243 | 16529 | Kcnk5 | −1.594670999 | 0.02549443 | potassium channel, subfamily K, member 5 |
| ENSMUSG00000026029 | 12370 | Casp8 | −1.59698672 | 0.034825631 | caspase 8 |
| ENSMUSG00000021665 | 15212 | Hexb | −1.60505426 | 8.69E−05 | hexosaminidase B |
| ENSMUSG00000026944 | 11305 | Abca2 | −1.618079797 | 0.03150425 | ATP-binding cassette, sub-family A (ABC1), member 2 |
| ENSMUSG00000030643 | 75985 | Rab30 | −1.618332572 | 0.021170517 | RAB30, member RAS oncogene family |
| ENSMUSG00000031740 | 17390 | Mmp2 | −1.627263598 | 0.006227627 | matrix metallopeptidase 2 |
| ENSMUSG00000005982 | 74763 | Naa60 | −1.632057188 | 0.009866751 | N(alpha)-acetyltransferase 60, NatF catalytic subunit |
| ENSMUSG00000032827 | 243725 | Ppp1r9a | −1.634855475 | 0.02400856 | protein phosphatase 1, regulatory (inhibitor) subunit 9A |
| ENSMUSG00000038738 | 243961 | Shank1 | −1.643386198 | 0.025523818 | SH3/ankyrin domain gene 1 |
| ENSMUSG00000037791 | 268448 | Phf12 | −1.652555819 | 0.025567508 | PHD finger protein 12 |
| ENSMUSG00000034211 | 66258 | Mrps17 | −1.673731573 | 0.025765794 | mitochondrial ribosomal protein S17 |
| ENSMUSG00000030246 | 16832 | Ldhb | −1.67848711 | 0.049323979 | lactate dehydrogenase B |
| ENSMUSG00000032913 | 269473 | Lrig2 | −1.68014098 | 0.04330508 | leucine-rich repeats and immunoglobulin-like domains 2 |
| ENSMUSG00000042699 | 13211 | Dhx9 | −1.685790919 | 0.020174985 | DEAH (Asp-Glu-Ala-His) box polypeptide 9 |
| ENSMUSG00000026360 | 19735 | Rgs2 | −1.688718788 | 0.009418413 | regulator of G-protein signaling 2 |
| ENSMUSG00000022106 | 105670 | Rcbtb2 | −1.690844747 | 0.01102743 | regulator of chromosome condensation (RCC1) and BTB (POZ) domain containing protein 2 |
| ENSMUSG00000025409 | 110962 | Mbd6 | 1.702382582 | 0.00951497 | methyl-CpG binding domain protein 6 |
| ENSMUSG00000000552 | 29813 | Zfp385a | −1.711402809 | 0.042254159 | zinc finger protein 385A |
| ENSMUSG00000046805 | 17476 | Mpeg1 | −1.712123845 | 0.000537482 | macrophage expressed gene 1 |
| ENSMUSG00000027253 | 228357 | Lrp4 | −1.713461508 | 0.008590011 | low density lipoprotein receptor-related protein 4 |
| ENSMUSG00000075232 | 11702 | Amd1 | −1.716535194 | 0.030291219 | S-adenosylmethionine decarboxylase 1 |
| ENSMUSG00000034910 | 72135 | Pygo1 | −1.728292729 | 0.049308217 | pygopus 1 |
| ENSMUSG00000073079 | 24067 | Srp54a | −1.738548426 | 0.047882922 | signal recognition particle 54A |
| ENSMUSG00000051504 | 233274 | Siglech | −1.741566146 | 0.002777374 | sialic acid binding Ig-like lectin H |
| ENSMUSG00000034300 | 66306 | Fam53c | −1.754100298 | 0.005612744 | family with sequence similarity 53, member C |
| ENSMUSG00000079469 | 55981 | Pigb | −1.761282012 | 0.017688708 | phosphatidylinositol glycan anchor biosynthesis, class B |
| ENSMUSG00000004105 | 26360 | Angptl2 | −1.766708124 | 0.035303173 | angiopoietin-like 2 |
| ENSMUSG00000032265 | 212943 | Fam46a | −1.772824144 | 0.022971923 | family with sequence similarity 46, member A |
| ENSMUSG00000028859 | 12986 | Csf3r | −1.783808017 | 0.00534762 | colony stimulating factor 3 receptor (granulocyte) |
| ENSMUSG00000074342 | 433638 | I830077J02Rik | −1.78647453 | 0.044855022 | RIKEN cDNA I830077J02 gene |
| ENSMUSG00000096862 | | | −1.790005872 | 0.023474918 | |

TABLE 4-continued

| Ensembl | Entrez | Symbol | log2FoldChange | padj | Name |
|---|---|---|---|---|---|
| ENSMUSG00000023830 | 16004 | Igf2 | −1.791235599 | 0.008911947 | insulin-like growth factor 2 receptor |
| ENSMUSG00000032123 | 13478 | Dpagt1 | −1.810513322 | 0.022978122 | dolichyl-phosphate (UDP-N-acetylglucosamine) acetylglucosaminephosphotransferase 1 (GlcNAc-1-P transferase) |
| ENSMUSG00000070972 | 72429 | Dnajc25 | −1.811954778 | 0.017327218 | DnaJ heat shock protein family (Hsp40) member C25 |
| ENSMUSG00000015852 | 80891 | Fcrls | −1.815721876 | 0.000942971 | Fc receptor-like S, scavenger receptor |
| ENSMUSG00000030980 | 66356 | Knop1 | −1.819709781 | 0.007649607 | lysine rich nucleolar protein 1 |
| ENSMUSG00000078851 | 319162 | Hist3h2a | −1.833274061 | 0.02240704 | histone cluster 3, H2a |
| ENSMUSG00000090626 | 21778 | Tex9 | −1.834577019 | 0.011690954 | testis expressed gene 9 |
| ENSMUSG00000022604 | 74201 | Cep97 | −1.841812572 | 0.041737067 | centrosomal protein 97 |
| ENSMUSG00000020253 | 67905 | Ppm1m | −1.854090439 | 0.042899028 | protein phosphatase 1M |
| ENSMUSG00000025381 | 56530 | Cnpy2 | −1.854895762 | 0.01426592 | canopy FGF signaling regulator 2 |
| ENSMUSG00000034126 | 217734 | Pomt2 | −1.855029855 | 0.016690277 | protein-O-mannosyltransferase 2 |
| ENSMUSG00000035133 | 11855 | Arhgap5 | −1.861315541 | 0.000891017 | Rho GTPase activating protein 5 |
| ENSMUSG00000039656 | 20182 | Rxrb | −1.862021963 | 0.021036389 | retinoid X receptor beta |
| ENSMUSG00000059498 | 14131 | Fcgr3 | −1.873391074 | 0.005549156 | Fc receptor, IgG, low affinity III |
| ENSMUSG00000018068 | 70422 | Ints2 | −1.873479502 | 0.002434212 | integrator complex subunit 2 |
| ENSMUSG00000024665 | 56473 | Fads2 | −1.876530099 | 0.026152588 | fatty acid desaturase 2 |
| ENSMUSG00000022032 | 71145 | Scara5 | −1.876584029 | 0.009866751 | scavenger receptor class A, member 5 |
| ENSMUSG00000094936 | 19653 | Rbm4 | −1.89316009 | 0.006836501 | RNA binding motif protein 4 |
| ENSMUSG00000003644 | 20111 | Rps6ka1 | −1.897290612 | 0.035869359 | ribosomal protein S6 kinase polypeptide 1 |
| ENSMUSG00000020818 | 69900 | Mfsd11 | −1.898366956 | 0.034014284 | major facilitator superfamily domain containing 11 |
| ENSMUSG00000003464 | 19298 | Pex19 | −1.904838599 | 0.014916778 | peroxisomal biogenesis factor 19 |
| ENSMUSG00000026288 | 16331 | Inpp5d | −1.905526687 | 0.000452959 | inositol polyphosphate-5-phosphatase D |
| ENSMUSG00000020903 | 55943 | Stx8 | −1.910202638 | 0.003488379 | syntaxin 8 |
| ENSMUSG00000051323 | 279653 | Pcdh19 | −1.911436198 | 0.04809685 | protocadherin 19 |
| ENSMUSG00000031561 | 23965 | Tenm3 | −1.922788934 | 0.001172773 | teneurin transmembrane protein 3 |
| ENSMUSG00000031398 | 18846 | Plxna3 | −1.925388576 | 0.049743944 | plexin A3 |
| ENSMUSG00000027508 | 94212 | Pag1 | −1.928682087 | 0.0009273 | phosphoprotein associated with glycosphingolipid microdomains 1 |
| ENSMUSG00000040229 | 23890 | Gpr34 | −1.933504447 | 0.020461846 | G protein-coupled receptor 34 |
| ENSMUSG00000029638 | 170772 | Glcci1 | −1.937285992 | 0.033303016 | glucocorticoid induced transcript 1 |
| ENSMUSG00000031834 | 18709 | Pik3r2 | −1.940223162 | 0.022212831 | phosphatidylinositol 3-kinase, regulatory subunit, polypeptide 2 (p85 beta) |
| ENSMUSG00000020032 | 77976 | Nuak1 | −1.950491465 | 0.013066229 | NUAK family, SNF1-like kinase, 1 |
| ENSMUSG00000043671 | 233115 | Dpy19l3 | −1.956180605 | 0.00280331 | dpy-19-like 3 (C. elegans) |
| ENSMUSG00000051506 | 545030 | Wdfy4 | −1.964063626 | 0.035303173 | WD repeat and FYVE domain containing 4 |
| ENSMUSG00000022793 | 56375 | B4galt4 | −1.964572155 | 0.044111702 | UDP-Gal:betaGlcNAc beta 1,4-galactosyltransferase, polypeptide 4 |
| ENSMUSG00000059921 | 22253 | Unc5c | −1.968445008 | 0.039316692 | unc-5 netrin receptor C |
| ENSMUSG00000048163 | 20345 | Selplg | −1.971682587 | 0.00015142 | selectin, platelet (p-selectin) ligand |
| ENSMUSG00000036206 | 98402 | Sh3bp4 | −1.97308679 | 0.049323979 | SH3-domain binding protein 4 |
| ENSMUSG00000031930 | 66894 | Wwp2 | −1.984857274 | 0.031075407 | WW domain containing E3 ubiquitin protein ligase 2 |
| ENSMUSG00000049764 | 64453 | Zfp280b | −1.988499853 | 0.047587179 | zinc finger protein 280B |
| ENSMUSG00000032340 | 18007 | Neo1 | −1.999586031 | 0.000157394 | neogenin |
| ENSMUSG00000033065 | 18642 | Pfkm | −2.001503866 | 0.047587179 | phosphofructokinase, muscle |
| ENSMUSG00000042496 | 382066 | Prdm10 | −2.004047624 | 0.03881884 | PR domain containing 10 |
| ENSMUSG00000032089 | 16154 | Il10ra | −2.004541519 | 0.023655468 | interleukin 10 receptor, alpha |
| ENSMUSG00000028683 | 108067 | Eif2b3 | −2.006295529 | 0.049378232 | eukaryotic translation initiation factor 2B, subunit 3 |
| ENSMUSG00000036596 | 242939 | Cpz | −2.006429682 | 0.000172533 | carboxypeptidase Z |
| ENSMUSG00000030844 | 67865 | Rgs10 | −2.007355139 | 0.010244243 | regulator of G-protein signalling 10 |
| ENSMUSG00000038463 | 320078 | Olfml2b | −2.008264699 | 0.005925803 | olfactomedin-like 2B |
| ENSMUSG00000044950 | 70802 | Pwwp2a | −2.008559886 | 0.003847158 | PWWP domain containing 2A |
| ENSMUSG00000021763 | 408066 | BC067074 | −2.00999696 | 0.027487655 | cDNA sequence BC067074 |
| ENSMUSG00000047875 | 269604 | Gpr157 | −2.010305195 | 0.036186814 | G protein-coupled receptor 157 |
| ENSMUSG00000030110 | 16768 | Lag3 | −2.015889678 | 0.016690277 | lymphocyte-activation gene 3 |
| ENSMUSG00000000290 | 16414 | Itgb2 | −2.016567354 | 0.005624239 | integrin beta 2 |
| ENSMUSG00000027122 | 212772 | Arl14ep | −2.021084139 | 0.000499676 | ADP-ribosylation factor-like 14 effector protein |
| ENSMUSG00000021457 | 20963 | Syk | −2.028998252 | 0.01009259 | spleen tyrosine kinase |
| ENSMUSG00000035735 | 269060 | Dagla | −2.029630592 | 0.020652488 | diacylglycerol lipase, alpha |
| ENSMUSG00000039795 | 66361 | Zfand1 | −2.030349124 | 0.017486032 | zinc finger, AN1-type domain 1 |
| ENSMUSG00000050288 | 57265 | Fzd2 | −2.03046892 | 0.002742877 | frizzled class receptor 2 |
| ENSMUSG00000020778 | 69535 | Ten1 | −2.031095782 | 0.030884553 | TEN1 telomerase capping complex subunit |

TABLE 4-continued

| Ensembl | Entrez | Symbol | log2FoldChange | padj | Name |
|---|---|---|---|---|---|
| ENSMUSG00000033068 | 12497 | Entpd6 | −2.034379642 | 0.03711405 | ectonucleoside triphosphate diphosphohydrolase 6 |
| ENSMUSG00000038765 | 16917 | Lmx1b | −2.045617421 | 0.008294045 | LIM homeobox transcription factor 1 beta |
| ENSMUSG00000025200 | 72502 | Cwf19l1 | −2.056672763 | 0.008911947 | CWF19-like 1, cell cycle control (S. pombe) |
| ENSMUSG00000031802 | 18689 | Phxr4 | −2.058006889 | 0.028560255 | per-hexamer repeat gene 4 |
| ENSMUSG00000060538 | 68742 | Tmem219 | −2.058892805 | 0.022729262 | transmembrane protein 219 |
| ENSMUSG00000020399 | 171285 | Havcr2 | −2.067686767 | 0.008911947 | hepatitis A virus cellular receptor 2 |
| ENSMUSG00000055541 | 52855 | Lair1 | −2.077392632 | 0.000123796 | leukocyte-associated Ig-like receptor 1 |
| ENSMUSG00000039263 | 228961 | Npepl1 | −2.078933088 | 0.004224924 | aminopeptidase-like 1 |
| ENSMUSG00000043061 | 211986 | Tmem18 | −2.08352673 | 0.016780537 | transmembrane protein 18 |
| ENSMUSG00000021624 | 17079 | Cd180 | −2.083547442 | 0.0005542 | CD180 antigen |
| ENSMUSG00000027996 | 20319 | Sfrp2 | −2.084051048 | 0.00485529 | secreted frizzled-related protein 2 |
| ENSMUSG00000025504 | 98845 | Eps8l2 | −2.084440214 | 0.034368655 | EPS8-like 2 |
| ENSMUSG00000029919 | 54486 | Hpgds | −2.085582617 | 0.006007451 | hematopoietic prostaglandin D synthase |
| ENSMUSG00000051185 | 67698 | Fam174a | −2.087420016 | 0.025765794 | family with sequence similarity 174, member A |
| ENSMUSG00000002981 | 56457 | Clptm1 | −2.088037345 | 0.022729262 | cleft lip and palate associated transmembrane protein 1 |
| ENSMUSG00000021948 | 18753 | Prkcd | −2.090858808 | 0.000197987 | protein kinase C, delta |
| ENSMUSG00000035941 | 108837 | Ibtk | −2.091182119 | 0.009621049 | inhibitor of Bruton agammaglobulinemia tyrosine kinase |
| ENSMUSG00000020697 | 16882 | Lig3 | −2.094358079 | 0.01395923 | ligase III, DNA, ATP-dependent |
| ENSMUSG00000032563 | 94062 | Mrpl3 | −2.098820248 | 0.0182842 | mitochondrial ribosomal protein L3 |
| ENSMUSG00000038831 | 241308 | Ralgps1 | −2.102872225 | 0.005280074 | Ral GEF with PH domain and SH3 binding motif 1 |
| ENSMUSG00000040537 | 11496 | Adam22 | −2.106864383 | 0.000233013 | a disintegrin and metallopeptidase domain 22 |
| ENSMUSG00000031711 | 30932 | Zfp330 | −2.112343724 | 0.035043172 | zinc finger protein 330 |
| ENSMUSG00000086580 | | | −2.120905757 | 0.018998499 | |
| ENSMUSG00000040054 | 116848 | Baz2a | −2.127565573 | 0.005144821 | bromodomain adjacent to zinc finger domain, 2A |
| ENSMUSG00000074238 | 211556 | Ap1ar | −2.138307179 | 0.006007451 | adaptor-related protein complex 1 associated regulatory protein |
| ENSMUSG00000078771 | 14017 | Evi2a | −2.138493987 | 0.005938634 | ecotropic viral integration site 2a |
| ENSMUSG00000040270 | 12014 | Bach2 | −2.143543199 | 0.002326924 | BTB and CNC homology, basic leucine zipper transcription factor 2 |
| ENSMUSG00000024644 | 66054 | Cndp2 | −2.146962012 | 0.016316844 | CNDP dipeptidase 2 (metallopeptidase M20 family) |
| ENSMUSG00000002266 | 22776 | Zim1 | −2.149551289 | 0.014437696 | zinc finger, imprinted 1 |
| ENSMUSG00000052974 | 13107 | Cyp2f2 | −2.168439072 | 0.010407269 | cytochrome P450, family 2, subfamily f, polypeptide 2 |
| ENSMUSG00000038331 | 212712 | Satb2 | −2.169140996 | 0.04380304 | special AT-rich sequence binding protein 2 |
| ENSMUSG00000083929 | | | −2.169821448 | 0.026719909 | |
| ENSMUSG00000016262 | 214791 | Sertad4 | −2.169858119 | 0.000309232 | SERTA domain containing 4 |
| ENSMUSG00000020120 | 56193 | Plek | −2.171422761 | 0.000537482 | pleckstrin |
| ENSMUSG00000038843 | 14537 | Gcnt1 | −2.173899045 | 0.004919583 | glucosaminyl (N-acetyl) transferase 1, core 2 |
| ENSMUSG00000039230 | 108903 | Tbcd | −2.176235998 | 0.00199156 | tubulin-specific chaperone d |
| ENSMUSG00000016356 | 73368 | Col20a1 | −2.178839725 | 0.044347476 | collagen, type XX, alpha 1 |
| ENSMUSG00000063663 | 382236 | Brwd3 | −2.198859581 | 0.0005542 | bromodomain and WD repeat domain containing 3 |
| ENSMUSG00000039908 | 268512 | Slc26a11 | −2.201837888 | 0.014401825 | solute carrier family 26, member 11 |
| ENSMUSG00000021276 | 67236 | Cinp | −2.202809578 | 0.047018179 | cyclin-dependent kinase 2 interacting protein |
| ENSMUSG00000039952 | 13138 | Dag1 | −2.211515325 | 0.016690277 | dystroglycan 1 |
| ENSMUSG00000030068 | | | −2.217378911 | 0.004272092 | |
| ENSMUSG00000058886 | 54006 | Deaf1 | −2.21994983 | 0.023003036 | deformed epidermal autoregulatory factor 1 (Drosophila) |
| ENSMUSG00000056091 | 20454 | St3gal5 | −2.228912313 | 0.000268156 | ST3 beta-galactoside alpha-2,3-sialyltransferase 5 |
| ENSMUSG00000074785 | 54712 | Plxnc1 | −2.231832701 | 0.005214992 | plexin C1 |
| ENSMUSG00000040586 | 237222 | Ofd1 | −2.242058859 | 0.026370037 | oral-facial-digital syndrome 1 gene homolog (human) |
| ENSMUSG00000029916 | 69923 | Agk | −2.258496573 | 0.018907621 | acylglycerol kinase |
| ENSMUSG00000083844 | 76508 | Ube2d-ps | −2.259738548 | 0.017744481 | ubiquitin-conjugating enzyme E2D, pseudogene |
| ENSMUSG00000027750 | 50706 | Postn | −2.26990927 | 0.000317875 | periostin, osteoblast specific factor |
| ENSMUSG00000070390 | 637515 | Nlrp1b | −2.277872062 | 0.040833024 | NLR family, pyrin domain containing 1B |

TABLE 4-continued

| Ensembl | Entrez | Symbol | log2FoldChange | padj | Name |
|---|---|---|---|---|---|
| ENSMUSG00000075596 | 320616 | B130006D01Rik | −2.28032127 | 0.046747394 | RIKEN cDNA B130006D01 gene |
| ENSMUSG00000021508 | 57266 | Cxcl14 | −2.280650794 | 0.006763469 | chemokine (C-X-C motif) ligand 14 |
| ENSMUSG00000070808 | 243842 | Gltscr1 | −2.281205777 | 0.005593356 | glioma tumor suppressor candidate region gene 1 |
| ENSMUSG00000045322 | 81897 | Tlr9 | −2.281690152 | 0.023474918 | toll-like receptor 9 |
| ENSMUSG00000021614 | 13003 | Vcan | −2.288481278 | 0.005909356 | versican |
| ENSMUSG00000036264 | 320027 | Fstl4 | −2.294855677 | 0.02372969 | follistatin-like 4 |
| ENSMUSG00000064294 | 71724 | Aox3 | −2.30155455 | 0.013915452 | aldehyde oxidase 3 |
| ENSMUSG00000038542 | 234069 | Pcid2 | −2.30408954 | 0.00309328 | PCI domain containing 2 |
| ENSMUSG00000023055 | 67488 | Calcoco1 | −2.307476169 | 0.000350675 | calcium binding and coiled coil domain 1 |
| ENSMUSG00000029199 | 79464 | Lias | −2.314430842 | 0.006049785 | lipoic acid synthetase |
| ENSMUSG00000057716 | 434008 | Tmem178b | −2.326293883 | 0.012530599 | transmembrane protein 178B |
| ENSMUSG00000059273 | 330474 | Zc3h4 | −2.33535063 | 0.035251873 | zinc finger CCCH-type containing 4 |
| ENSMUSG00000019467 | 52666 | Arhgef25 | −2.339699796 | 0.004600139 | Rho guanine nucleotide exchange factor (GEF) 25 |
| ENSMUSG00000012076 | 52592 | Brms1l | −2.345920786 | 0.007530725 | breast cancer metastasis-suppressor 1-like |
| ENSMUSG00000008496 | 18987 | Pou2f2 | −2.352769909 | 0.000383257 | POU domain, class 2, transcription factor 2 |
| ENSMUSG00000074129 | 22121 | Rpl13a | −2.352886739 | 0.002220757 | ribosomal protein L13A |
| ENSMUSG00000040820 | 110948 | Hlcs | −2.355241347 | 0.02837 | holocarboxylase synthetase (biotin-[propriony-Coenzyme A-carboxylase (ATP-hydrolysing)] ligase) |
| ENSMUSG00000097451 | | | −2.360785857 | 0.005018882 | |
| ENSMUSG00000043635 | 330119 | Adamts3 | −2.362426564 | 0.022319423 | a disintegrin-like and metallopeptidase (reprolysin type) with thrombospondin type 1 motif, 3 |
| ENSMUSG00000035062 | 245522 | Zc4h2 | −2.368462709 | 0.043894257 | zinc finger, C4H2 domain containing |
| ENSMUSG00000038095 | 243272 | Sbno1 | −2.36866356 | 2.62E−05 | strawberry notch homolog 1 (Drosophila) |
| ENSMUSG00000075600 | 223642 | Zc3h3 | −2.370529567 | 0.017626057 | zinc finger CCCH type containing 3 |
| ENSMUSG00000002963 | 59047 | Pnkp | −2.372943978 | 0.024711215 | polynucleotide kinase 3'-phosphatase |
| ENSMUSG00000022180 | 50934 | Slc7a8 | −2.37601576 | 3.49E−06 | solute carrier family 7 (cationic amino acid transporter, y+ system), member 8 |
| ENSMUSG00000031984 | 66523 | 2810004N23Rik | −2.376799169 | 0.014412709 | RIKEN cDNA 2810004N23 gene |
| ENSMUSG00000004266 | 15170 | Ptpn6 | −2.377465949 | 0.011790134 | protein tyrosine phosphatase, non-receptor type 6 |
| ENSMUSG00000019883 | 52665 | Echdc1 | −2.377622304 | 0.016316844 | enoyl Coenzyme A hydratase domain containing 1 |
| ENSMUSG00000046791 | 71952 | 2410016O06Rik | −2.381679602 | 0.041737067 | RIKEN cDNA 2410016O06 gene |
| ENSMUSG00000054252 | 14184 | Fgfr3 | −2.398538632 | 0.02895847 | fibroblast growth factor receptor 3 |
| ENSMUSG00000032965 | 73916 | Ift57 | −2.399652982 | 0.006007451 | intraflagellar transport 57 |
| ENSMUSG00000032852 | 228770 | Rspo4 | −2.399831122 | 0.045572341 | R-spondin 4 |
| ENSMUSG00000043795 | 677289 | Prr33 | −2.402401705 | 0.030173615 | proline rich 33 |
| ENSMUSG00000098112 | 668218 | Bin2 | −2.402649652 | 3.65E−05 | bridging integrator 2 |
| ENSMUSG00000031835 | 56453 | Mbtps1 | −2.407340058 | 0.00049455 | membrane-bound transcription factor peptidase, site 1 |
| ENSMUSG00000026837 | 12831 | Col5a1 | −2.409723722 | 0.000240115 | collagen, type V, alpha 1 |
| ENSMUSG00000023903 | 240047 | Mmp25 | −2.41083204 | 0.030291219 | matrix metallopeptidase 25 |
| ENSMUSG00000039828 | 545085 | Wdr70 | 2.411708751 | 0.000480315 | WD repeat domain 70 |
| ENSMUSG00000034509 | 66591 | Mad2l1bp | −2.417654671 | 0.041419561 | MAD2L1 binding protein |
| ENSMUSG00000026786 | 54519 | Apbb1ip | 2.424919895 | 0.000165104 | amyloid beta (A4) precursor protein-binding, family B, member 1 interacting protein |
| ENSMUSG00000020739 | 445007 | Nup85 | −2.42559156 | 0.003909466 | nucleoporin 85 |
| ENSMUSG00000028132 | 99887 | Tmem56 | −2.426389108 | 0.028465813 | transmembrane protein 56 |
| ENSMUSG00000043183 | 319719 | Simc1 | −2.430482906 | 0.00356383 | SUMO-interacting motifs containing 1 |
| ENSMUSG00000007682 | 13371 | Dio2 | −2.431012781 | 1.03E−06 | deiodinase, iodothyronine, type II |
| ENSMUSG00000001942 | 22619 | Siae | −2.437088207 | 0.024711215 | sialic acid acetylesterase |
| ENSMUSG00000039361 | 233489 | Picalm | −2.439839334 | 0.000794716 | phosphatidylinositol binding clathrin assembly protein |
| ENSMUSG00000040722 | 56807 | Scamp5 | −2.443518907 | 0.000512883 | secretory carrier membrane protein 5 |
| ENSMUSG00000060487 | 320825 | Samd5 | −2.443867874 | 0.005439383 | sterile alpha motif domain containing 5 |
| ENSMUSG00000038650 | 107702 | Rnh1 | −2.445998792 | 0.03711405 | ribonuclease/angiogenin inhibitor 1 |
| ENSMUSG00000061186 | 353282 | Sfmbt2 | −2.448674959 | 0.014401825 | Scm-like with four mbt domains 2 |

TABLE 4-continued

| Ensembl | Entrez | Symbol | log2FoldChange | padj | Name |
|---|---|---|---|---|---|
| ENSMUSG00000036564 | 234593 | Ndrg4 | −2.457034227 | 0.03800403 | N-myc downstream regulated gene 4 |
| ENSMUSG00000030263 | 16970 | Lrmp | −2.459927073 | 0.02344368 | lymphoid-restricted membrane protein |
| ENSMUSG00000029144 | | | −2.462204572 | 0.01789856 | |
| ENSMUSG00000035237 | 16816 | Lcat | −2.462715337 | 0.011985234 | lecithin cholesterol acyltransferase |
| ENSMUSG00000040797 | 243621 | Iqsec3 | −2.466771124 | 0.013066229 | IQ motif and Sec7 domain 3 |
| ENSMUSG00000031075 | 101772 | Ano1 | −2.47388378 | 0.024853918 | anoctamin 1, calcium activated chloride channel |
| ENSMUSG00000033222 | 74044 | Ttf2 | −2.474336506 | 0.013281208 | transcription termination factor, RNA polymerase II |
| ENSMUSG00000025854 | 80752 | Fam20c | −2.479183461 | 0.018899557 | family with sequence similarity 20, member C |
| ENSMUSG00000044006 | 68709 | Cilp2 | −2.480350278 | 0.00389975 | cartilage intermediate layer protein 2 |
| ENSMUSG00000002870 | 17216 | Mcm2 | −2.482728715 | 0.027727126 | minichromosome maintenance complex component 2 |
| ENSMUSG00000031903 | 192654 | Pla2g15 | −2.486596125 | 0.000254263 | phospholipase A2, group XV |
| ENSMUSG00000039936 | 18707 | Pik3cd | −2.490066458 | 0.002077384 | phosphatidylinositol 3-kinase catalytic delta polypeptide |
| ENSMUSG00000022211 | 268747 | Carmil3 | −2.496523899 | 0.035303173 | capping protein regulator and myosin 1 linker 3 |
| ENSMUSG00000032131 | 192663 | Abcg4 | −2.505417011 | 0.012398098 | ATP-binding cassette, sub-family G (WHITE), member 4 |
| ENSMUSG00000041707 | 69069 | 1810011H11Rik | −2.513701498 | 0.034014284 | RIKEN cDNA 1810011H11 gene |
| ENSMUSG00000037730 | 80732 | Mynn | −2.518386243 | 0.01206718 | myoneurin |
| ENSMUSG00000037020 | 233064 | Wdr62 | −2.531879464 | 0.007347559 | WD repeat domain 62 |
| ENSMUSG00000058486 | 101240 | Wdr91 | −2.534646367 | 0.009980113 | WD repeat domain 91 |
| ENSMUSG00000024565 | 20689 | Sall3 | −2.548946046 | 0.01696136 | sal-like 3 (Drosophila) |
| ENSMUSG00000010461 | 14051 | Eya4 | −2.550018067 | 0.015891784 | EYA transcriptional coactivator and phosphatase 4 |
| ENSMUSG00000000982 | 20302 | Ccl3 | −2.555213555 | 0.000233013 | chemokine (C-C motif) ligand 3 |
| ENSMUSG00000025486 | 64384 | Sirt3 | −2.560980412 | 0.02240704 | sirtuin 3 |
| ENSMUSG00000032122 | 56857 | Slc37a2 | −2.579890403 | 0.003146962 | solute carrier family 37 (glycerol-3-phosphate transporter), member 2 |
| ENSMUSG00000028629 | 73172 | Exo5 | −2.590515599 | 0.02344368 | exonuclease 5 |
| ENSMUSG00000041939 | 17855 | Mvk | −2.591010854 | 0.023987772 | mevalonate kinase |
| ENSMUSG00000037490 | 353169 | Slc2a12 | −2.596937475 | 0.020897851 | solute carrier family 2 (facilitated glucose transporter), member 12 |
| ENSMUSG00000036334 | 242050 | Igsf10 | −2.606747355 | 0.01677015 | immunoglobulin superfamily, member 10 |
| ENSMUSG00000036353 | 70839 | P2ry12 | −2.612023574 | 1.01E−05 | purinergic receptor P2Y, G-protein coupled 12 |
| ENSMUSG00000023992 | 83433 | Trem2 | −2.612399107 | 3.29E−05 | triggering receptor expressed on myeloid cells 2 |
| ENSMUSG00000033594 | 78779 | Spata2l | −2.618965331 | 0.00389975 | spermatogenesis associated 2-like |
| ENSMUSG00000093752 | 13480 | Dpm1 | −2.62740322 | 2.36E−05 | dolichol-phosphate (beta-D) mannosyltransferase 1 |
| ENSMUSG00000036362 | 74191 | P2ry13 | −2.629837998 | 4.64E−07 | purinergic receptor P2Y, G-protein coupled 13 |
| ENSMUSG00000001497 | 18511 | Pax9 | −2.630082191 | 0.022319423 | paired box 9 |
| ENSMUSG00000031264 | 12229 | Btk | −2.632253689 | 0.020374951 | Bruton agammaglobulinemia tyrosine kinase |
| ENSMUSG00000019539 | 52377 | Rcn3 | −2.633686781 | 0.000309232 | reticulocalbin 3, EF-hand calcium binding domain |
| ENSMUSG00000074505 | 270120 | Fat3 | −2.635138479 | 0.000479909 | FAT atypical cadherin 3 |
| ENSMUSG00000083405 | | | −2.636895888 | 0.000537482 | |
| ENSMUSG00000031099 | 93761 | Smarca1 | −2.637003844 | 0.000942971 | SWI/SNF related, matrix associated, actin dependent regulator of chromatin, subfamily a, member 1 |
| ENSMUSG00000086509 | 100313531 | Nkx2-2os | −2.639498064 | 0.021241849 | NK2 homeobox 2, opposite strand |
| ENSMUSG00000072915 | 108167848 | LOC108167848 | −2.644990972 | 0.005556103 | zinc finger protein 717-like |
| ENSMUSG00000079592 | 235312 | C1qtnf5 | −2.64663047 | 0.005117586 | C1q and tumor necrosis factor related protein 5 |
| ENSMUSG00000058542 | | | −2.647076853 | 0.01921403 | |
| ENSMUSG00000032076 | 54725 | Cadm1 | −2.667633841 | 0.00016808 | cell adhesion molecule 1 |
| ENSMUSG00000038195 | 280408 | Rilp | −2.667865746 | 0.018212287 | Rab interacting lysosomal protein |
| ENSMUSG00000032579 | 69536 | Hemk1 | −2.67912088 | 0.020080098 | HemK methyltransferase family member 1 |
| ENSMUSG00000030474 | 83382 | Siglece | −2.681578135 | 0.002012682 | sialic acid binding Ig-like lectin E |
| ENSMUSG00000027630 | 81004 | Tbl1xr1 | −2.685982993 | 1.68E−06 | transducin (beta)-like 1X-linked receptor 1 |
| ENSMUSG00000048351 | 69893 | Coa7 | −2.689739983 | 0.01009259 | cytochrome c oxidase assembly factor 7 |
| ENSMUSG00000038085 | 70873 | Cnbd2 | −2.690999409 | 0.019148821 | cyclic nucleotide binding domain containing 2 |

TABLE 4-continued

| Ensembl | Entrez | Symbol | log2FoldChange | padj | Name |
|---|---|---|---|---|---|
| ENSMUSG00000054545 | 94284 | Ugt1a6a | −2.708165632 | 0.0182842 | UDP glucuronosyltransferase 1 family, polypeptide A6A |
| ENSMUSG00000051212 | 321019 | Gpr183 | −2.714711106 | 0.003437917 | G protein-coupled receptor 183 |
| ENSMUSG00000042515 | 245631 | Mum1l1 | −2.717386375 | 0.009567714 | melanoma associated antigen (mutated) 1-like 1 |
| ENSMUSG00000038607 | 14700 | Gng10 | −2.718580943 | 0.000476418 | guanine nucleotide binding protein (G protein), gamma 10 |
| ENSMUSG00000087294 | | | −2.758999654 | 0.013281208 | |
| ENSMUSG00000020608 | 67241 | Smc6 | −2.761591713 | 7.70E−05 | structural maintenance of chromosomes 6 |
| ENSMUSG00000003423 | 68845 | Pih1d1 | −2.765095973 | 0.01009259 | PIH1 domain containing 1 |
| ENSMUSG00000045246 | 66733 | Kcng4 | −2.766500368 | 0.014602376 | potassium voltage-gated channel, subfamily G, member 4 |
| ENSMUSG00000061979 | 94254 | Wbscr16 | −2.771133056 | 0.010407269 | Williams-Beuren syndrome chromosome region 16 homolog (human) |
| ENSMUSG00000052031 | 380608 | Tagap1 | −2.771725986 | 0.005577885 | T cell activation GTPase activating protein 1 |
| ENSMUSG00000029061 | 26561 | Mmp23 | −2.785738205 | 0.002181521 | matrix metallopeptidase 23 |
| ENSMUSG00000009292 | 28240 | Trpm2 | −2.795856066 | 0.002169853 | transient receptor potential cation channel, subfamily M, member 2 |
| ENSMUSG00000075593 | 330217 | Gal3st4 | −2.807452663 | 0.00168761 | galactose-3-O-sulfotransferase 4 |
| ENSMUSG00000005501 | 227334 | Usp40 | −2.810843665 | 0.004047941 | ubiquitin specific peptidase 40 |
| ENSMUSG00000028459 | 12517 | Cd72 | −2.811378796 | 0.00063728 | CD72 antigen |
| ENSMUSG00000021918 | 23955 | Nek4 | −2.820196256 | 0.007021146 | NIMA (never in mitosis gene a)-related expressed kinase 4 |
| ENSMUSG00000002578 | 22781 | Ikzf4 | −2.829402069 | 0.006788957 | IKAROS family zinc finger 4 |
| ENSMUSG00000097060 | | | −2.839825021 | 0.000116951 | |
| ENSMUSG00000020658 | 668212 | Efr3b | −2.844407433 | 0.000508148 | EFR3 homolog B |
| ENSMUSG00000048895 | 12569 | Cdk5r1 | −2.855497556 | 0.008625532 | cyclin-dependent kinase 5, regulatory subunit 1 (p35) |
| ENSMUSG00000055733 | 54561 | Nap 113 | −2.858545341 | 0.007415434 | nucleosome assembly protein 1-like 3 |
| ENSMUSG00000094103 | 100101807 | 1700047l17Rik2 | −2.860858666 | 0.000361529 | RIKEN cDNA 1700047l17 gene 2 |
| ENSMUSG00000026069 | 17082 | Il1rl1 | −2.861271676 | 0.004788496 | interleukin 1 receptor-like 1 |
| ENSMUSG00000033948 | 74464 | Zswim5 | −2.867975426 | 0.008021591 | zinc finger SWIM-type containing 5 |
| ENSMUSG00000028976 | 56485 | Slc2a5 | −2.870939499 | 0.000214775 | solute carrier family 2 (facilitated glucose transporter), member 5 |
| ENSMUSG00000030774 | 18479 | Pak1 | −2.872095127 | 0.001087944 | p21 protein (Cdc42/Rac)-activated kinase 1 |
| ENSMUSG00000004446 | 12122 | Bid | −2.874737491 | 0.003603191 | BH3 interacting domain death agonist |
| ENSMUSG00000028024 | 13809 | Enpep | −2.877842193 | 0.000156109 | glutamyl aminopeptidase |
| ENSMUSG00000095440 | 668225 | Fignl2 | −2.8841811 | 0.002484667 | fidgetin-like 2 |
| ENSMUSG00000051256 | 67767 | Jagn1 | −2.888761528 | 0.000240115 | jagunal homolog 1 |
| ENSMUSG00000020988 | 217666 | L2hgdh | −2.913835223 | 0.000512883 | L-2-hydroxyglutarate dehydrogenase |
| ENSMUSG00000047497 | 239337 | Adamts12 | −2.925588715 | 0.003798719 | a disintegrin-like and metallopeptidase (reprolysin type) with thrombospondin type 1 motif, 12 |
| ENSMUSG00000026404 | 67997 | Ddx59 | −2.932911501 | 0.007443127 | DEAD (Asp-Glu-Ala-Asp) box polypeptide 59 |
| ENSMUSG00000083771 | | | −2.946244995 | 0.006007451 | |
| ENSMUSG00000060512 | 76261 | 0610040J01Rik | −2.954219499 | 0.004048799 | RIKEN cDNA 0610040J01 gene |
| ENSMUSG00000081929 | | | −2.978870586 | 0.004772036 | |
| ENSMUSG00000097993 | | | −3.032340138 | 5.43E−05 | |
| ENSMUSG00000033256 | 435684 | Shf | −3.038447155 | 0.002133136 | Src homology 2 domain containing F |
| ENSMUSG00000026941 | 381352 | Mamdc4 | −3.042103159 | 0.000537482 | MAM domain containing 4 |
| ENSMUSG00000034858 | 235493 | Fam214a | −3.043462814 | 7.10E−05 | family with sequence similarity 214, member A |
| ENSMUSG00000020829 | 52466 | Slc46a1 | −3.044100839 | 0.00304113 | solute carrier family 46, member 1 |
| ENSMUSG00000087347 | | | −3.050756079 | 0.00359675 | |
| ENSMUSG00000022439 | 64099 | Parvg | −3.070040951 | 0.00039023 | parvin, gamma |
| ENSMUSG00000040749 | 20438 | Siah1b | −3.085677882 | 0.002353823 | seven in absentia 1B |
| ENSMUSG00000037979 | 215707 | Ccdc92 | −3.096305097 | 0.000383524 | coiled-coil domain containing 92 |
| ENSMUSG00000030623 | | | −3.139601971 | 0.00199156 | |
| ENSMUSG00000042155 | 277396 | Klhl23 | −3.166208159 | 0.000590511 | kelch-like 23 |
| ENSMUSG00000073878 | 100041504 | LOC100041504 | −3.166235264 | 1.41E−09 | C-C motif chemokine 21c |
| ENSMUSG00000097147 | | | −3.177055818 | 0.002866659 | |
| ENSMUSG00000037513 | | | −3.212837261 | 6.02E−07 | |
| ENSMUSG00000020926 | 11488 | Adam11 | −3.237031168 | 1.03E−06 | a disintegrin and metallopeptidase domain 11 |

TABLE 4-continued

| Ensembl | Entrez | Symbol | log2FoldChange | padj | Name |
|---|---|---|---|---|---|
| ENSMUSG00000022231 | 20356 | Sema5a | −3.29158652 | 6.10E−05 | sema domain, seven thrombospondin repeats (type 1 and type 1-like), transmembrane domain (TM) and short cytoplasmic domain, (semaphorin) 5A |
| ENSMUSG00000037318 | 215243 | Traf3ip3 | −3.305297887 | 3.56E−05 | TRAF3 interacting protein 3 |
| ENSMUSG00000049092 | 70713 | Gpr137c | −3.310385524 | 0.001788429 | G protein-coupled receptor 137C |
| ENSMUSG00000045318 | 11553 | Adra2c | −3.314824177 | 0.000897945 | adrenergic receptor, alpha 2c |
| ENSMUSG00000048402 | 14633 | Gli2 | −3.354049163 | 0.000350675 | GLI-Kruppel family member GLI2 |
| ENSMUSG00000072770 | 54137 | Acrbp | −3.365894355 | 0.000157521 | proacrosin binding protein |
| ENSMUSG00000063506 | 239027 | Arhgap22 | −3.379771517 | 0.000361452 | Rho GTPase activating protein 22 |
| ENSMUSG00000031028 | 22141 | Tub | −3.402864154 | 3.02E−05 | tubby candidate gene |
| ENSMUSG00000074825 | 73338 | Itpripl1 | −3.405616 | 2.77E−06 | inositol 1,4,5-triphosphate receptor interacting protein-like 1 |
| ENSMUSG00000028480 | 384009 | Glipr2 | −3.420377468 | 0.000309232 | GLI pathogenesis-related 2 |
| ENSMUSG00000084803 | 641454 | 5830444B04Rik | −3.4390027 | 2.35E−05 | RIKEN cDNA 5830444B04 gene |
| ENSMUSG00000026587 | 11899 | Astn1 | −3.481863687 | 3.56E−05 | astrotactin 1 |
| ENSMUSG00000084010 | | | −3.488390758 | 0.000408936 | |
| ENSMUSG00000030443 | 213011 | Zfp583 | −3.507088063 | 0.000379733 | zinc finger protein 583 |
| ENSMUSG00000066975 | 12959 | Cryba4 | −3.519699133 | 0.000512883 | crystallin, beta A4 |
| ENSMUSG00000020474 | 54125 | Polm | −3.546052601 | 6.71E−06 | polymerase (DNA directed), mu |
| ENSMUSG00000063382 | 80288 | Bcl9l | −3.549409775 | 1.83E−05 | B cell CLL/lymphoma 9-like |
| ENSMUSG00000000308 | 12716 | Ckmt1 | −3.576697456 | 0.00039023 | creatine kinase, mitochondrial 1, ubiquitous |
| ENSMUSG00000031833 | 546071 | Mast3 | −3.618455518 | 8.68E−07 | microtubule associated serine/threonine kinase 3 |
| ENSMUSG00000015968 | 12289 | Cacna1d | −3.640841741 | 1.47E−05 | calcium channel, voltage-dependent, L type, alpha 1D subunit |
| ENSMUSG00000056536 | 27392 | Pign | −3.655573292 | 8.01E−05 | phosphatidylinositol glycan anchor biosynthesis, class N |
| ENSMUSG00000056204 | 66522 | Pgpep1 | −3.697337976 | 7.70E−05 | pyroglutamyl-peptidase I |
| ENSMUSG00000039774 | 230145 | Galnt12 | −3.711018497 | 0.000165104 | UDP-N-acetyl-alpha-D-galactosamine:polypeptide N-acetylgalactosaminyltransferase 12 |
| ENSMUSG00000073295 | 58242 | Nudt11 | −3.783407416 | 0.000169818 | nudix (nucleoside diphosphate linked moiety X)-type motif 11 |
| ENSMUSG00000050578 | 17386 | Mmp13 | −3.814852404 | 6.39E−05 | matrix metallopeptidase 13 |
| ENSMUSG00000029720 | 231798 | Lrch4 | −3.842799351 | 0.000123972 | leucine-rich repeats and calponin homology (CH) domain containing 4 |
| ENSMUSG00000035934 | 208076 | Pknox2 | −3.901952662 | 3.37E−06 | Pbx/knotted 1 homeobox 2 |
| ENSMUSG00000024013 | 26382 | Fgd2 | −3.946028448 | 1.08E−09 | FYVE, RhoGEF and PH domain containing 2 |
| ENSMUSG00000081564 | | | −4.130939636 | 1.74E−05 | |
| ENSMUSG00000075511 | | | −4.267141434 | 4.64E−06 | |
| ENSMUSG00000020573 | 30955 | Pik3cg | −4.272313986 | 1.14E−14 | phosphoinositide-3-kinase, catalytic, gamma polypeptide |
| ENSMUSG00000097272 | | | −4.421180244 | 4.43E−09 | |

What is claimed is:

1. A method of treating a subject afflicted with cognitive decline wherein the cognitive decline is a neurological disease, the method comprising:
   a) obtaining a biological sample from the subject, wherein the sample is from the meninges of the subject;
   b) determining the copy number, level of expression, or level of activity of FLT4 in the subject sample;
   c) comparing the copy number, level of expression, or level of activity of said FLT4 detected in steps b) to the copy number, level of expression, or level of activity of FLT4 in a control;
   wherein a significant decrease in the copy number, level of expression, or level of activity of FLT4 in the subject sample relative to the control copy number, level of expression, or level of activity of FLT4 indicates that the subject is afflicted with or is at risk for developing cognitive decline resulted from or is characterized by an aberrant decrease in meningeal lymphatic drainage and/or accumulated amyloid beta plaques; and
   d) administering to a meningeal space or the central nervous system of the subject in need an effective amount of an agent that increases the level of expression or level of activity of FLT4, wherein the agent comprises:
      (i) a nucleic acid molecule comprising a nucleotide sequence encoding FLT4;
      (ii) an expression vector comprising a nucleotide sequence encoding FLT4; or
      (iii) VEGF-C or VEGF-C156S;
      (iv) a nucleic acid molecule comprising a nucleotide sequence encoding VEGF-C or VEGF-C126S; or
      (v) an expression vector comprising a nucleotide sequence encoding VEGF-C or VEGF-C126S.

2. The method of claim 1, wherein the copy number, level of expression, or level of activity of FLT4 comprises the copy number, level of expression, or level of activity of FLT4 in the lymphatic endothelial cells (LECs).

3. The method of claim 1, wherein the control is an unaffected subject or member of the same species to which the subject belongs.

4. The method of claim 1, wherein the biological sample consists of or comprises fluid cerebral spinal fluid (CSF), interstitial fluid (ISF), or both, obtained from the subject.

5. The method of claim 1, wherein the copy number is assessed by microarray, quantitative PCR (qPCR), high-throughput sequencing, comparative genomic hybridization (CGH), or fluorescent in situ hybridization (FISH).

6. The method of claim 1, wherein the level of expression of FLT4 is assessed by detecting the presence in the samples of a protein of FLT4, a polypeptide, or protein fragment thereof.

7. The method of claim 1, wherein the diameter of the meningeal lymphatic vessel is increased by at least 20%.

8. The method of claim 1, wherein the central nervous system of the subject comprises amyloid-beta plaques, and wherein step d) results in increasing clearance of molecules and/or reducing the quantity of amyloid-beta plaques.

9. The method of claim 8, wherein the quantity of amyloid-beta plaques is reduced by at least 5%.

10. The method of claim 1, wherein the agent is administered selectively to the meningeal space of the subject.

11. The method of claim 1, wherein the neurological disease is selected from the group consisting of: AD, PD, cerebral edema, ALS, PANDAS, meningitis, hemorrhagic stroke, ASD, brain tumor, epilepsy, Down's syndrome, hereditary cerebral hemorrhage with amyloidosis-Dutch type (HCHWA-D), Familial Danish/British dementia, dementia with Lewy bodies (DLB), Lewy body (LB) variant of AD, multiple system atrophy (MSA), familial encephalopathy with neuroserpin inclusion bodies (FENIB), frontotemporal dementia (FTD), Huntington's disease (HD), Kennedy disease/spinobulbar muscular atrophy (SBMA), dentatorubropallidoluysian atrophy (DRPLA); spinocerebellar ataxia (SCA) type I, SCA2, SCA3 (Machado-Joseph disease), SCA6, SCA7, SCA17, Creutzfeldt-Jakob disease (CJD), Kuru, Gerstmann-Straussler-Scheinker syndrome (GSS), fatal familial insomnia (FFI), corticobasal degeneration (CBD), progressive supranuclear palsy (PSP), cerebral amyloid angiopathy (CAA), multiple sclerosis (MS), AIDS-related dementia complex, or a combination of two or more of any of the listed items.

12. The method of claim 1, wherein the agent is a VEGF-C.

13. The method of claim 1, wherein the cognitive decline is resulted from aging.

* * * * *